US007309594B1

(12) United States Patent
Brooun et al.

(10) Patent No.: US 7,309,594 B1
(45) Date of Patent: Dec. 18, 2007

(54) CRYSTALLIZATION OF PROTEIN KINASE Bα/AKT1

(75) Inventors: Alexei Brooun, San Diego, CA (US); Ellen Y. T. Chien, La Jolla, CA (US); Douglas R. Dougan, Calgary (CA); Andrew J. Jennings, La Jolla, CA (US); Michelle L. Kraus, Temecula, CA (US); Clifford D. Mol, San Diego, CA (US)

(73) Assignee: Takeda San Diego, Inc., San Diego, CA (US)

( * ) Notice: Subject to any disclaimer, the term of this patent is extended or adjusted under 35 U.S.C. 154(b) by 360 days.

(21) Appl. No.: 10/842,966

(22) Filed: May 10, 2004

(51) Int. Cl.
*C12N 9/12* (2006.01)
(52) U.S. Cl. .................................... 435/194
(58) Field of Classification Search ............. None
See application file for complete search history.

(56) References Cited

U.S. PATENT DOCUMENTS 6,054,285 A * 4/2000 Hemmings et al. .......... 435/15

OTHER PUBLICATIONS

Wiencek et al. New strategies for protein crystal growth. Ann. Rev. Biomed. Eng. 1999, 1, 505-534.*
Gilliland et al. Crystallization of biological molecules for X-ray diffraction studies. Current Opinion in Structure Biology 1996, 6, 595-603.*
Ke et al. Crystallization of RNA and RNA-protein complexes. Methods 34, 2004, 408-414.*
Brunger et al. "Crystallography & NMR System: A New Software Suite for Macromolecular Structure Determination" Acta Cryst. (1998). D54, 905-921.

* cited by examiner

*Primary Examiner*—Nashaat T. Nashed
(74) *Attorney, Agent, or Firm*—David J. Weitz

(57) ABSTRACT

Provided are crystals relating to Protein kinase Bα/AKT1 and its various uses.

4 Claims, 116 Drawing Sheets

FIGURE 1

Amino acid sequence for full-length human wild type AKT1 [SEQ. ID No. 1]

(Residues 138-480 are underlined)

```
  1 MSDVAIVKEG WLHKRGEYIK TWRPRYFLLK NDGTFIGYKE RPQDVDQREA PLNNFSVAQC
 61 QLMKTERPRP NTFIIRCLQW TTVIERTFHV ETPEEREEWT TAIQTVADGL KKQEEEEMDF
121 RSGSPSDNSG AEEMEVSLAK PKHRVTMNEF EYLKLLGKGT FGKVILVKEK ATGRYYAMKI
181 LKKEVIVAKD EVAHTLTENR VLQNSRHPFL TALKYSFQTH DRLCFVMEYA NGGELFFHLS
241 RERVFSEDRA RFYGAEIVSA LDYLHSEKNV VYRDLKLENL MLDKDGHIKI TDFGLCKEGI
301 KDGATMKTFC GTPEYLAPEV LEDNDYGRAV DWWGLGVVMY EMMCGRLPFY NQDHEKLFEL
361 ILMEEIRFPR TLGPEAKSLL SGLLKKDPKQ RLGGGSEDAK EIMQHRFFAG IVWQHVYEKK
421 LSPPFKPQVT SETDTRYFDE EFTAQMITIT PPDQDDSMEC VDSERRPHFP QFSYSASSTA
```

Human cDNA sequence encoding residues 138-480 of AKT1 [SEQ. ID No. 2]

```
   1 CTGGCCAAGC CCAAGCACCG CGTGACCATG AACGAGTTTG AGTACCTGAA GCTGCTGGGC
  61 AAGGGCACTT TCGGCAAGGT GATCCTGGTG AAGGAGAAGG CCACAGGCCG CTACTACGCC
 121 ATGAAGATCC TCAAGAAGGA AGTCATCGTG GCCAAGGACG AGGTGGCCCA CACACTCACC
 181 GAGAACCGCG TCCTGCAGAA CTCCAGGCAC CCCTTCCTCA CAGCCCTGAA GTACTCTTTC
 241 CAGACCCACG ACCGCCTCTG CTTTGTCATG GAGTACGCCA ACGGGGGCGA GCTGTTCTTC
 301 CACCTGTCCC GGGAACGTGT GTTCTCCGAG GACCGGGCCC GCTTCTATGG CGCTGAGATT
 361 GTGTCAGCCC TGGACTACCT GCACTCGGAG AAGAACGTGG TGTACCGGGA CCTCAAGCTG
 421 GAGAACCTCA TGCTGGACAA GGACGGGCAC ATTAAGATCA CAGACTTCGG GCTGTGCAAG
 481 GAGGGGATCA AGGACGGTGC CACCATGAAG ACCTTTTGCG GCACACCTGA GTACCTGGCC
 541 CCCGAGGTGC TGGAGGACAA TGACTACGGC CGTGCAGTGG ACTGGTGGGG GCTGGGCGTG
 601 GTCATGTACG AGATGATGTG CGGTCGCCTG CCCTTCTACA ACCAGGACCA TGAGAAGCTT
 661 TTTGAGCTCA TCCTCATGGA GGAGATCCGC TTCCCGCGCA CGCTTGGTCC CGAGGCCAAG
 721 TCCTTGCTTT CAGGGCTGCT CAAGAAGGAC CCCAAGCAGA GGCTTGGCGG GGGCTCCGAG
 781 GACGCCAAGG AGATCATGCA GCATCGCTTC TTTGCCGGTA TCGTGTGGCA GCACGTGTAC
 841 GAGAAGAAGC TCAGCCCACC CTTCAAGCCC CAGGTCACGT CGGAGACTGA CACCAGGTAT
 901 TTTGATGAGG AGTTCACGGC CCAGATGATC ACCATCACAC CACCTGACCA AGATGACAGC
 961 ATGGAGTGTG TGGACAGCGA GCGCAGGCCC CACTTCCCCC AGTTCTCCTA CTCGGCCAGC
1021 AGCACGGCCT GA
```

Amino acid sequence for residues 138-480 of AKT1 with a N-terminal 6x-histidine tag, spacer region and rTEV cleavage site [SEQ. ID No. 3]

(6x-histidine tag, spacer region, rTEV cleavage site, M446S, S473D, and (E267-K268-N269) to R267-D268 mutations are underlined)

```
  1 MSYYHHHHHH DYDIPTTENL YFQGAMGSLA KPKHRVTMNE FEYLKLLGKG TFGKVILVKE
 61 KATGRYYAMK ILKKEVIVAK DEVAHTLTEN RVLQNSRHPF LTALKYSFQT HDRLCFVMEY
121 ANGGELFFHL SRERVFSEDR ARFYGAEIVS ALDYLHSRDV VYRDLKLENL MLDKDGHIKI
181 TDFGLCKEGI KDGATMKTFC GTPEYLAPEV LEDNDYGRAV DWWGLGVVMY EMMCGRLPFY
241 NQDHEKLFEL ILMEEIRFPR TLGPEAKSLL SGLLKKDPKQ RLGGGSEDAK EIMQHRFFAG
301 IVWQHVYEKK LSPPFKPQVT SETDTRYFDE EFTAQSITIT PPDQDDSMEC VDSERRPHFP
361 QFDYSASSTA
```

FIGURE 1 (cont.)

Human cDNA sequence encoding SEQ. ID No. 5
[SEQ. ID No. 4]

```
  1 CGCGTGACCA TGAACGAGTT TGAGTACCTG AAGCTGCTGG GCAAGGGCAC TTTCGGCAAG
 61 GTGATCCTGG TGAAGGAGAA GGCCACAGGC CGCTACTACG CCATGAAGAT CCTCAAGAAG
121 GAAGTCATCG TGGCCAAGGA CGAGGTGGCC CACACACTCA CCGAGAACCG CGTCCTGCAG
181 AACTCCAGGC ACCCCTTCCT CACAGCCCTG AAGTACTCTT TCCAGACCCA CGACCGCCTC
241 TGCTTTGTCA TGGAGTACGC CAACGGGGGC GAGCTGTTCT TCCACCTGTC CCGGGAACGT
301 GTGTTCTCCG AGGACCGGGC CCGCTTCTAT GGCGCTGAGA TTGTGTCAGC CCTGGACTAC
361 CTGCACTCGG AGAAGAACGT GATGTACCGG GACCTCAAGC TGGAGAACCT CATGCTGGAC
421 AAGGACGGGC ACATTAAGAT CACAGACTTC GGGCTGTGCA AGGAGGGGAT CAAGGACGGT
481 GCCACCATGA AGACCTTTTG CGGCACACCT GAGTACCTGG CCCCCGAGGT GCTGGAGGAC
541 AATGACTACG GCCGTGCAGT GGACTGGTGG GGGCTGGGCG TGGTCATGTA CGAGATGATG
601 TGCGGTCGCC TGCCCTTCTA CAACCAGGAC CATGAGAAGC TTTTTGAGCT CATCCTCATG
661 GAGGAGATCC GCTTCCCGCG CACGCTTGGT CCCGAGGCCA AGTCCTTGCT TTCAGGGCTG
721 CTCAAGAAGG ACCCCAAGCA GAGGCTTGGC GGGGGCTCCG AGGACGCCAA GGAGATCATG
781 CAGCATCGCT TCTTTGCCGG TATCGTGTGG CAGCACGTGT ACGAGAAGAA GCTCAGCCCA
841 CCCTTCAAGC CCCAGGTCAC GTCGGAGACT GACACCAGGT ATTTTGATGA GGAGTTCACG
901 GCCCAGATGA TCACCATCAC ACCACCTGAC CAAGATGACA GCATGGAGTG TGTGGACAGC
961 GAGCGCGAGG AGCAGGAAAT GTTCAGAGAT TTTGACTACA TTGCTGATTG GTGA
```

Amino acid sequence with a N-terminal 6x-histidine tag, spacer region, rTEV cleavage site, and C-terminal PIFTIDE

[SEQ. ID No. 5]

(6x-histidine tag, spacer region, rTEV cleavage site, and PIFTIDE sequence are underlined)

```
  1 MSYYHHHHHH DYDIPTTENL YFQGAMGSRV TMNEFEYLKL LGKGTFGKVI LVKEKATGRY
 61 YAMKILKKEV IVAKDEVAHT LTENRVLQNS RHPFLTALKY SFQTHDRLCF VMEYANGGEL
121 FFHLSRERVF SEDRARFYGA EIVSALDYLH SEKNVVYRDL KLENLMLDKD GHIKITDFGL
181 CKEGIKDGAT MKTFCGTPEY LAPEVLEDND YGRAVDWWGL GVVMYEMMCG RLPFYNQDHE
241 KLFELILMEE IRFPRTLGPE AKSLLSGLLK KDPKQRLGGG SEDAKEIMQH RFFAGIVWQH
301 VYEKKLSPPF KPQVTSETDT RYFDEEFTAQ MITITPPDQD DSMECVDSER EEQEMFRDFD
361 YIADW
```

FIGURE 3

LEGEND

Column headings from left to right are (A)'Atom Number', (B)'Atom Type', (C)'Amino Acid', (D)'Chain Identifier', (E)'Amino Acid Number', (F)'X Coordinate', (G)'Y Coordinate', (H)'Z Coordinate', (I)'Occupancy' (OCC) and (J)'B factor'.

Molecule A

|      | A  | B   | C   | D | E   | F      | G       | H      | I    | J     |
|------|----|-----|-----|---|-----|--------|---------|--------|------|-------|
| ATOM | 1  | N   | ALA | A | 139 | 23.707 | -17.218 | 14.088 | 1.00 | 86.42 |
| ATOM | 2  | CA  | ALA | A | 139 | 24.409 | -15.913 | 14.293 | 1.00 | 87.20 |
| ATOM | 3  | CB  | ALA | A | 139 | 23.636 | -14.771 | 13.614 | 1.00 | 84.20 |
| ATOM | 4  | C   | ALA | A | 139 | 24.687 | -15.597 | 15.780 | 1.00 | 87.55 |
| ATOM | 5  | O   | ALA | A | 139 | 24.794 | -16.509 | 16.609 | 1.00 | 85.62 |
| ATOM | 6  | N   | LYS | A | 140 | 24.785 | -14.300 | 16.094 | 1.00 | 89.16 |
| ATOM | 7  | CA  | LYS | A | 140 | 25.305 | -13.788 | 17.374 | 1.00 | 89.75 |
| ATOM | 8  | CB  | LYS | A | 140 | 25.347 | -12.250 | 17.318 | 1.00 | 88.11 |
| ATOM | 9  | CG  | LYS | A | 140 | 26.307 | -11.575 | 18.308 | 1.00 | 89.92 |
| ATOM | 10 | CD  | LYS | A | 140 | 27.748 | -11.485 | 17.785 | 1.00 | 89.07 |
| ATOM | 11 | CE  | LYS | A | 140 | 28.207 | -10.043 | 17.570 | 1.00 | 89.81 |
| ATOM | 12 | NZ  | LYS | A | 140 | 28.761 | -9.428  | 18.811 | 1.00 | 90.51 |
| ATOM | 13 | C   | LYS | A | 140 | 24.527 | -14.256 | 18.617 | 1.00 | 91.23 |
| ATOM | 14 | O   | LYS | A | 140 | 23.305 | -14.395 | 18.553 | 1.00 | 95.47 |
| ATOM | 15 | N   | PRO | A | 141 | 25.217 | -14.515 | 19.736 | 1.00 | 91.45 |
| ATOM | 16 | CA  | PRO | A | 141 | 24.522 | -14.767 | 21.005 | 1.00 | 92.04 |
| ATOM | 17 | CB  | PRO | A | 141 | 25.627 | -15.313 | 21.919 | 1.00 | 89.78 |
| ATOM | 18 | CG  | PRO | A | 141 | 26.876 | -14.718 | 21.391 | 1.00 | 89.68 |
| ATOM | 19 | CD  | PRO | A | 141 | 26.680 | -14.601 | 19.899 | 1.00 | 90.79 |
| ATOM | 20 | C   | PRO | A | 141 | 23.947 | -13.454 | 21.549 | 1.00 | 93.36 |
| ATOM | 21 | O   | PRO | A | 141 | 24.467 | -12.363 | 21.248 | 1.00 | 92.03 |
| ATOM | 22 | N   | LYS | A | 142 | 22.868 | -13.566 | 22.323 | 1.00 | 94.37 |
| ATOM | 23 | CA  | LYS | A | 142 | 22.158 | -12.384 | 22.813 | 1.00 | 93.56 |
| ATOM | 24 | CB  | LYS | A | 142 | 20.706 | -12.696 | 23.236 | 1.00 | 96.03 |
| ATOM | 25 | CG  | LYS | A | 142 | 19.652 | -11.709 | 22.661 | 1.00 | 95.69 |
| ATOM | 26 | CD  | LYS | A | 142 | 19.201 | -12.082 | 21.224 | 1.00 | 96.14 |
| ATOM | 27 | CE  | LYS | A | 142 | 19.844 | -11.197 | 20.140 | 1.00 | 93.86 |
| ATOM | 28 | NZ  | LYS | A | 142 | 19.652 | -11.750 | 18.767 | 1.00 | 91.63 |
| ATOM | 29 | C   | LYS | A | 142 | 22.935 | -11.686 | 23.914 | 1.00 | 89.37 |
| ATOM | 30 | O   | LYS | A | 142 | 23.560 | -12.326 | 24.766 | 1.00 | 87.69 |
| ATOM | 31 | N   | HIS | A | 143 | 22.877 | -10.363 | 23.865 | 1.00 | 86.18 |
| ATOM | 32 | CA  | HIS | A | 143 | 23.729 | -9.505  | 24.663 | 1.00 | 84.00 |
| ATOM | 33 | CB  | HIS | A | 143 | 23.658 | -8.082  | 24.117 | 1.00 | 86.22 |
| ATOM | 34 | CG  | HIS | A | 143 | 24.802 | -7.233  | 24.550 | 1.00 | 89.75 |
| ATOM | 35 | ND1 | HIS | A | 143 | 24.643 | -6.129  | 25.359 | 1.00 | 90.66 |
| ATOM | 36 | CE1 | HIS | A | 143 | 25.826 | -5.588  | 25.591 | 1.00 | 92.24 |
| ATOM | 37 | NE2 | HIS | A | 143 | 26.745 | -6.306  | 24.970 | 1.00 | 93.33 |
| ATOM | 38 | CD2 | HIS | A | 143 | 26.131 | -7.346  | 24.316 | 1.00 | 91.07 |
| ATOM | 39 | C   | HIS | A | 143 | 23.441 | -9.514  | 26.173 | 1.00 | 80.49 |
| ATOM | 40 | O   | HIS | A | 143 | 22.351 | -9.139  | 26.616 | 1.00 | 83.46 |
| ATOM | 41 | N   | ARG | A | 144 | 24.430 | -9.956  | 26.948 | 1.00 | 72.33 |

FIGURE 3 (Cont.)

| | A | B | C | D | E | F | G | H | I | J |
|---|---|---|---|---|---|---|---|---|---|---|
| ATOM | 42 | CA | ARG | A | 144 | 24.422 | -9.825 | 28.402 | 1.00 | 63.95 |
| ATOM | 43 | CB | ARG | A | 144 | 25.702 | -10.451 | 28.977 | 1.00 | 65.42 |
| ATOM | 44 | CG | ARG | A | 144 | 25.639 | -10.874 | 30.443 | 1.00 | 66.69 |
| ATOM | 45 | CD | ARG | A | 144 | 25.071 | -12.278 | 30.680 | 1.00 | 67.92 |
| ATOM | 46 | NE | ARG | A | 144 | 24.818 | -12.569 | 32.098 | 1.00 | 68.78 |
| ATOM | 47 | CZ | ARG | A | 144 | 23.900 | -11.965 | 32.865 | 1.00 | 68.79 |
| ATOM | 48 | NH1 | ARG | A | 144 | 23.117 | -11.002 | 32.379 | 1.00 | 67.78 |
| ATOM | 49 | NH2 | ARG | A | 144 | 23.771 | -12.327 | 34.136 | 1.00 | 68.60 |
| ATOM | 50 | C | ARG | A | 144 | 24.341 | -8.329 | 28.747 | 1.00 | 58.11 |
| ATOM | 51 | O | ARG | A | 144 | 25.011 | -7.508 | 28.111 | 1.00 | 57.25 |
| ATOM | 52 | N | VAL | A | 145 | 23.508 | -7.972 | 29.725 | 1.00 | 51.20 |
| ATOM | 53 | CA | VAL | A | 145 | 23.340 | -6.565 | 30.112 | 1.00 | 43.35 |
| ATOM | 54 | CB | VAL | A | 145 | 21.856 | -6.091 | 30.054 | 1.00 | 39.00 |
| ATOM | 55 | CG1 | VAL | A | 145 | 21.753 | -4.628 | 30.406 | 1.00 | 36.52 |
| ATOM | 56 | CG2 | VAL | A | 145 | 21.261 | -6.313 | 28.676 | 1.00 | 36.94 |
| ATOM | 57 | C | VAL | A | 145 | 23.916 | -6.302 | 31.498 | 1.00 | 41.85 |
| ATOM | 58 | O | VAL | A | 145 | 23.728 | -7.102 | 32.423 | 1.00 | 40.86 |
| ATOM | 59 | N | THR | A | 146 | 24.640 | -5.190 | 31.623 | 1.00 | 40.26 |
| ATOM | 60 | CA | THR | A | 146 | 25.147 | -4.734 | 32.919 | 1.00 | 39.04 |
| ATOM | 61 | CB | THR | A | 146 | 26.656 | -5.063 | 33.120 | 1.00 | 38.33 |
| ATOM | 62 | OG1 | THR | A | 146 | 27.352 | -4.918 | 31.876 | 1.00 | 37.28 |
| ATOM | 63 | CG2 | THR | A | 146 | 26.872 | -6.541 | 33.536 | 1.00 | 37.14 |
| ATOM | 64 | C | THR | A | 146 | 24.930 | -3.246 | 33.121 | 1.00 | 36.55 |
| ATOM | 65 | O | THR | A | 146 | 24.695 | -2.497 | 32.171 | 1.00 | 36.01 |
| ATOM | 66 | N | MET | A | 147 | 25.020 | -2.849 | 34.387 | 1.00 | 34.58 |
| ATOM | 67 | CA | MET | A | 147 | 24.974 | -1.468 | 34.844 | 1.00 | 32.48 |
| ATOM | 68 | CB | MET | A | 147 | 25.687 | -1.391 | 36.199 | 1.00 | 34.06 |
| ATOM | 69 | CG | MET | A | 147 | 24.832 | -0.945 | 37.366 | 1.00 | 33.78 |
| ATOM | 70 | SD | MET | A | 147 | 23.464 | -2.046 | 37.760 | 1.00 | 35.32 |
| ATOM | 71 | CE | MET | A | 147 | 22.424 | -0.884 | 38.683 | 1.00 | 32.21 |
| ATOM | 72 | C | MET | A | 147 | 25.593 | -0.436 | 33.889 | 1.00 | 30.63 |
| ATOM | 73 | O | MET | A | 147 | 25.097 | 0.684 | 33.785 | 1.00 | 28.59 |
| ATOM | 74 | N | ASN | A | 148 | 26.667 | -0.819 | 33.198 | 1.00 | 30.76 |
| ATOM | 75 | CA | ASN | A | 148 | 27.484 | 0.137 | 32.447 | 1.00 | 30.78 |
| ATOM | 76 | CB | ASN | A | 148 | 28.944 | -0.355 | 32.295 | 1.00 | 33.81 |
| ATOM | 77 | CG | ASN | A | 148 | 29.099 | -1.506 | 31.296 | 1.00 | 35.58 |
| ATOM | 78 | OD1 | ASN | A | 148 | 29.451 | -1.293 | 30.131 | 1.00 | 36.67 |
| ATOM | 79 | ND2 | ASN | A | 148 | 28.879 | -2.731 | 31.764 | 1.00 | 34.81 |
| ATOM | 80 | C | ASN | A | 148 | 26.907 | 0.674 | 31.125 | 1.00 | 28.87 |
| ATOM | 81 | O | ASN | A | 148 | 27.374 | 1.691 | 30.621 | 1.00 | 28.97 |
| ATOM | 82 | N | GLU | A | 149 | 25.890 | 0.004 | 30.587 | 1.00 | 26.92 |
| ATOM | 83 | CA | GLU | A | 149 | 25.218 | 0.441 | 29.358 | 1.00 | 27.09 |
| ATOM | 84 | CB | GLU | A | 149 | 24.420 | -0.712 | 28.778 | 1.00 | 30.28 |
| ATOM | 85 | CG | GLU | A | 149 | 24.960 | -1.269 | 27.489 | 1.00 | 34.49 |
| ATOM | 86 | CD | GLU | A | 149 | 25.156 | -2.761 | 27.598 | 1.00 | 38.61 |
| ATOM | 87 | OE1 | GLU | A | 149 | 24.160 | -3.468 | 27.871 | 1.00 | 39.64 |
| ATOM | 88 | OE2 | GLU | A | 149 | 26.307 | -3.222 | 27.435 | 1.00 | 41.43 |
| ATOM | 89 | C | GLU | A | 149 | 24.259 | 1.629 | 29.542 | 1.00 | 25.11 |
| ATOM | 90 | O | GLU | A | 149 | 23.592 | 2.047 | 28.587 | 1.00 | 24.91 |
| ATOM | 91 | N | PHE | A | 150 | 24.179 | 2.152 | 30.763 | 1.00 | 20.96 |
| ATOM | 92 | CA | PHE | A | 150 | 23.248 | 3.222 | 31.098 | 1.00 | 17.83 |
| ATOM | 93 | CB | PHE | A | 150 | 22.115 | 2.695 | 31.980 | 1.00 | 15.40 |

FIGURE 3 (Cont.)

|      | A    | B   | C   | D | E   | F      | G      | H      | I    | J     |
|------|------|-----|-----|---|-----|--------|--------|--------|------|-------|
| ATOM | 94   | CG  | PHE | A | 150 | 21.375 | 1.547  | 31.379 | 1.00 | 13.62 |
| ATOM | 95   | CD1 | PHE | A | 150 | 20.236 | 1.767  | 30.615 | 1.00 | 12.86 |
| ATOM | 96   | CE1 | PHE | A | 150 | 19.550 | 0.713  | 30.042 | 1.00 | 11.67 |
| ATOM | 97   | CZ  | PHE | A | 150 | 20.007 | -0.577 | 30.225 | 1.00 | 13.56 |
| ATOM | 98   | CE2 | PHE | A | 150 | 21.155 | -0.811 | 30.988 | 1.00 | 12.96 |
| ATOM | 99   | CD2 | PHE | A | 150 | 21.825 | 0.246  | 31.558 | 1.00 | 12.00 |
| ATOM | 100  | C   | PHE | A | 150 | 23.958 | 4.327  | 31.837 | 1.00 | 19.17 |
| ATOM | 101  | O   | PHE | A | 150 | 24.892 | 4.073  | 32.591 | 1.00 | 20.74 |
| ATOM | 102  | N   | GLU | A | 151 | 23.526 | 5.559  | 31.598 | 1.00 | 20.45 |
| ATOM | 103  | CA  | GLU | A | 151 | 23.880 | 6.672  | 32.466 | 1.00 | 19.84 |
| ATOM | 104  | CB  | GLU | A | 151 | 24.109 | 7.965  | 31.667 | 1.00 | 23.27 |
| ATOM | 105  | CG  | GLU | A | 151 | 25.137 | 7.837  | 30.543 | 1.00 | 28.78 |
| ATOM | 106  | CD  | GLU | A | 151 | 25.531 | 9.166  | 29.893 | 1.00 | 32.74 |
| ATOM | 107  | OE1 | GLU | A | 151 | 26.638 | 9.227  | 29.290 | 1.00 | 33.48 |
| ATOM | 108  | OE2 | GLU | A | 151 | 24.743 | 10.145 | 29.966 | 1.00 | 33.06 |
| ATOM | 109  | C   | GLU | A | 151 | 22.731 | 6.803  | 33.466 | 1.00 | 16.14 |
| ATOM | 110  | O   | GLU | A | 151 | 21.612 | 6.360  | 33.200 | 1.00 | 14.06 |
| ATOM | 111  | N   | TYR | A | 152 | 23.017 | 7.378  | 34.625 | 1.00 | 13.34 |
| ATOM | 112  | CA  | TYR | A | 152 | 22.022 | 7.483  | 35.680 | 1.00 | 12.21 |
| ATOM | 113  | CB  | TYR | A | 152 | 22.472 | 6.684  | 36.906 | 1.00 | 12.73 |
| ATOM | 114  | CG  | TYR | A | 152 | 22.626 | 5.228  | 36.580 | 1.00 | 13.56 |
| ATOM | 115  | CD1 | TYR | A | 152 | 23.633 | 4.798  | 35.722 | 1.00 | 16.83 |
| ATOM | 116  | CE1 | TYR | A | 152 | 23.777 | 3.467  | 35.382 | 1.00 | 16.16 |
| ATOM | 117  | CZ  | TYR | A | 152 | 22.911 | 2.547  | 35.892 | 1.00 | 15.61 |
| ATOM | 118  | OH  | TYR | A | 152 | 23.085 | 1.244  | 35.537 | 1.00 | 17.29 |
| ATOM | 119  | CE2 | TYR | A | 152 | 21.887 | 2.933  | 36.743 | 1.00 | 16.68 |
| ATOM | 120  | CD2 | TYR | A | 152 | 21.750 | 4.282  | 37.085 | 1.00 | 14.83 |
| ATOM | 121  | C   | TYR | A | 152 | 21.719 | 8.940  | 36.003 | 1.00 | 12.75 |
| ATOM | 122  | O   | TYR | A | 152 | 22.472 | 9.605  | 36.717 | 1.00 | 14.73 |
| ATOM | 123  | N   | LEU | A | 153 | 20.597 | 9.415  | 35.467 | 1.00 | 13.16 |
| ATOM | 124  | CA  | LEU | A | 153 | 20.252 | 10.834 | 35.443 | 1.00 | 14.90 |
| ATOM | 125  | CB  | LEU | A | 153 | 19.361 | 11.122 | 34.236 | 1.00 | 19.30 |
| ATOM | 126  | CG  | LEU | A | 153 | 19.996 | 10.830 | 32.878 | 1.00 | 23.59 |
| ATOM | 127  | CD1 | LEU | A | 153 | 19.039 | 9.987  | 32.037 | 1.00 | 24.64 |
| ATOM | 128  | CD2 | LEU | A | 153 | 20.400 | 12.138 | 32.160 | 1.00 | 25.58 |
| ATOM | 129  | C   | LEU | A | 153 | 19.578 | 11.364 | 36.707 | 1.00 | 12.81 |
| ATOM | 130  | O   | LEU | A | 153 | 20.096 | 12.291 | 37.354 | 1.00 | 9.78  |
| ATOM | 131  | N   | LYS | A | 154 | 18.414 | 10.796 | 37.030 | 1.00 | 11.32 |
| ATOM | 132  | CA  | LYS | A | 154 | 17.596 | 11.258 | 38.155 | 1.00 | 9.86  |
| ATOM | 133  | CB  | LYS | A | 154 | 16.450 | 12.165 | 37.673 | 1.00 | 9.98  |
| ATOM | 134  | CG  | LYS | A | 154 | 16.867 | 13.507 | 37.061 | 1.00 | 10.31 |
| ATOM | 135  | CD  | LYS | A | 154 | 16.203 | 14.680 | 37.763 | 1.00 | 13.90 |
| ATOM | 136  | CE  | LYS | A | 154 | 16.783 | 16.023 | 37.298 | 1.00 | 18.24 |
| ATOM | 137  | NZ  | LYS | A | 154 | 16.054 | 17.218 | 37.853 | 1.00 | 19.19 |
| ATOM | 138  | C   | LYS | A | 154 | 17.020 | 10.092 | 38.951 | 1.00 | 7.31  |
| ATOM | 139  | O   | LYS | A | 154 | 16.674 | 9.045  | 38.382 | 1.00 | 4.70  |
| ATOM | 140  | N   | LEU | A | 155 | 16.928 | 10.281 | 40.268 | 1.00 | 5.43  |
| ATOM | 141  | CA  | LEU | A | 155 | 16.225 | 9.333  | 41.126 | 1.00 | 4.11  |
| ATOM | 142  | CB  | LEU | A | 155 | 16.721 | 9.384  | 42.570 | 1.00 | 3.10  |
| ATOM | 143  | CG  | LEU | A | 155 | 15.897 | 8.605  | 43.606 | 1.00 | 3.23  |
| ATOM | 144  | CD1 | LEU | A | 155 | 15.859 | 7.112  | 43.294 | 1.00 | 5.11  |
| ATOM | 145  | CD2 | LEU | A | 155 | 16.412 | 8.820  | 45.021 | 1.00 | 2.72  |

FIGURE 3 (Cont.)

|  | A | B | C | D | E | F | G | H | I | J |
|---|---|---|---|---|---|---|---|---|---|---|
| ATOM | 146 | C | LEU | A | 155 | 14.753 | 9.665 | 41.072 | 1.00 | 2.79 |
| ATOM | 147 | O | LEU | A | 155 | 14.353 | 10.770 | 41.398 | 1.00 | 2.00 |
| ATOM | 148 | N | LEU | A | 156 | 13.957 | 8.695 | 40.642 | 1.00 | 5.10 |
| ATOM | 149 | CA | LEU | A | 156 | 12.538 | 8.913 | 40.441 | 1.00 | 5.69 |
| ATOM | 150 | CB | LEU | A | 156 | 12.046 | 8.149 | 39.217 | 1.00 | 4.03 |
| ATOM | 151 | CG | LEU | A | 156 | 12.399 | 8.728 | 37.853 | 1.00 | 2.49 |
| ATOM | 152 | CD1 | LEU | A | 156 | 12.050 | 7.708 | 36.797 | 1.00 | 2.00 |
| ATOM | 153 | CD2 | LEU | A | 156 | 11.671 | 10.034 | 37.604 | 1.00 | 2.00 |
| ATOM | 154 | C | LEU | A | 156 | 11.743 | 8.481 | 41.648 | 1.00 | 8.44 |
| ATOM | 155 | O | LEU | A | 156 | 10.686 | 9.053 | 41.936 | 1.00 | 10.67 |
| ATOM | 156 | N | GLY | A | 157 | 12.244 | 7.474 | 42.355 | 1.00 | 9.99 |
| ATOM | 157 | CA | GLY | A | 157 | 11.471 | 6.891 | 43.431 | 1.00 | 18.79 |
| ATOM | 158 | C | GLY | A | 157 | 12.206 | 5.960 | 44.360 | 1.00 | 23.98 |
| ATOM | 159 | O | GLY | A | 157 | 13.180 | 5.315 | 43.967 | 1.00 | 24.19 |
| ATOM | 160 | N | LYS | A | 158 | 11.724 | 5.910 | 45.602 | 1.00 | 31.16 |
| ATOM | 161 | CA | LYS | A | 158 | 12.258 | 5.030 | 46.633 | 1.00 | 36.62 |
| ATOM | 162 | CB | LYS | A | 158 | 12.990 | 5.839 | 47.709 | 1.00 | 37.47 |
| ATOM | 163 | CG | LYS | A | 158 | 14.465 | 5.501 | 47.872 | 1.00 | 40.40 |
| ATOM | 164 | CD | LYS | A | 158 | 14.993 | 5.976 | 49.237 | 1.00 | 44.44 |
| ATOM | 165 | CE | LYS | A | 158 | 16.269 | 6.834 | 49.122 | 1.00 | 45.84 |
| ATOM | 166 | NZ | LYS | A | 158 | 17.494 | 6.052 | 48.729 | 1.00 | 44.09 |
| ATOM | 167 | C | LYS | A | 158 | 11.121 | 4.212 | 47.249 | 1.00 | 40.37 |
| ATOM | 168 | O | LYS | A | 158 | 10.151 | 4.768 | 47.774 | 1.00 | 40.54 |
| ATOM | 169 | N | GLY | A | 159 | 11.226 | 2.891 | 47.110 | 1.00 | 44.36 |
| ATOM | 170 | CA | GLY | A | 159 | 10.483 | 1.941 | 47.921 | 1.00 | 48.14 |
| ATOM | 171 | C | GLY | A | 159 | 11.455 | 1.512 | 49.011 | 1.00 | 52.03 |
| ATOM | 172 | O | GLY | A | 159 | 12.489 | 2.170 | 49.191 | 1.00 | 54.97 |
| ATOM | 173 | N | THR | A | 160 | 11.167 | 0.428 | 49.729 | 1.00 | 50.92 |
| ATOM | 174 | CA | THR | A | 160 | 12.011 | 0.075 | 50.881 | 1.00 | 49.58 |
| ATOM | 175 | CB | THR | A | 160 | 11.188 | -0.639 | 51.976 | 1.00 | 48.94 |
| ATOM | 176 | OG1 | THR | A | 160 | 10.014 | 0.133 | 52.258 | 1.00 | 49.13 |
| ATOM | 177 | CG2 | THR | A | 160 | 11.929 | -0.632 | 53.309 | 1.00 | 48.14 |
| ATOM | 178 | C | THR | A | 160 | 13.303 | -0.694 | 50.530 | 1.00 | 49.71 |
| ATOM | 179 | O | THR | A | 160 | 14.352 | -0.465 | 51.151 | 1.00 | 48.98 |
| ATOM | 180 | N | PHE | A | 161 | 13.228 | -1.585 | 49.538 | 1.00 | 47.64 |
| ATOM | 181 | CA | PHE | A | 161 | 14.389 | -2.385 | 49.129 | 1.00 | 44.58 |
| ATOM | 182 | CB | PHE | A | 161 | 14.029 | -3.874 | 48.980 | 1.00 | 40.85 |
| ATOM | 183 | CG | PHE | A | 161 | 12.952 | -4.340 | 49.910 | 1.00 | 39.69 |
| ATOM | 184 | CD1 | PHE | A | 161 | 11.780 | -4.880 | 49.408 | 1.00 | 39.80 |
| ATOM | 185 | CE1 | PHE | A | 161 | 10.766 | -5.309 | 50.263 | 1.00 | 40.55 |
| ATOM | 186 | CZ | PHE | A | 161 | 10.926 | -5.199 | 51.644 | 1.00 | 42.20 |
| ATOM | 187 | CE2 | PHE | A | 161 | 12.097 | -4.652 | 52.161 | 1.00 | 42.17 |
| ATOM | 188 | CD2 | PHE | A | 161 | 13.106 | -4.234 | 51.294 | 1.00 | 41.86 |
| ATOM | 189 | C | PHE | A | 161 | 14.979 | -1.871 | 47.826 | 1.00 | 44.47 |
| ATOM | 190 | O | PHE | A | 161 | 16.102 | -2.247 | 47.447 | 1.00 | 44.46 |
| ATOM | 191 | N | GLY | A | 162 | 14.227 | -0.998 | 47.155 | 1.00 | 43.18 |
| ATOM | 192 | CA | GLY | A | 162 | 14.510 | -0.674 | 45.770 | 1.00 | 42.43 |
| ATOM | 193 | C | GLY | A | 162 | 14.319 | 0.748 | 45.282 | 1.00 | 38.55 |
| ATOM | 194 | O | GLY | A | 162 | 13.238 | 1.330 | 45.405 | 1.00 | 38.14 |
| ATOM | 195 | N | LYS | A | 163 | 15.389 | 1.275 | 44.690 | 1.00 | 33.73 |
| ATOM | 196 | CA | LYS | A | 163 | 15.383 | 2.566 | 44.015 | 1.00 | 27.34 |
| ATOM | 197 | CB | LYS | A | 163 | 16.755 | 3.221 | 44.166 | 1.00 | 26.23 |

FIGURE 3 (Cont.)

|  | A | B | C | D | E | F | G | H | I | J |
|---|---|---|---|---|---|---|---|---|---|---|
| ATOM | 198 | CG  | LYS | A | 163 | 17.061 | 3.607  | 45.588 | 1.00 | 29.06 |
| ATOM | 199 | CD  | LYS | A | 163 | 18.023 | 2.641  | 46.260 | 1.00 | 30.29 |
| ATOM | 200 | CE  | LYS | A | 163 | 18.998 | 3.400  | 47.160 | 1.00 | 29.25 |
| ATOM | 201 | NZ  | LYS | A | 163 | 20.219 | 2.604  | 47.454 | 1.00 | 28.10 |
| ATOM | 202 | C   | LYS | A | 163 | 15.003 | 2.444  | 42.528 | 1.00 | 21.68 |
| ATOM | 203 | O   | LYS | A | 163 | 15.409 | 1.501  | 41.840 | 1.00 | 19.64 |
| ATOM | 204 | N   | VAL | A | 164 | 14.215 | 3.401  | 42.049 | 1.00 | 13.68 |
| ATOM | 205 | CA  | VAL | A | 164 | 13.906 | 3.515  | 40.638 | 1.00 | 9.22 |
| ATOM | 206 | CB  | VAL | A | 164 | 12.426 | 3.797  | 40.399 | 1.00 | 4.52 |
| ATOM | 207 | CG1 | VAL | A | 164 | 12.154 | 3.889  | 38.933 | 1.00 | 8.96 |
| ATOM | 208 | CG2 | VAL | A | 164 | 11.582 | 2.724  | 40.967 | 1.00 | 3.41 |
| ATOM | 209 | C   | VAL | A | 164 | 14.686 | 4.692  | 40.086 | 1.00 | 13.75 |
| ATOM | 210 | O   | VAL | A | 164 | 14.539 | 5.822  | 40.558 | 1.00 | 16.43 |
| ATOM | 211 | N   | ILE | A | 165 | 15.510 | 4.442  | 39.078 | 1.00 | 16.06 |
| ATOM | 212 | CA  | ILE | A | 165 | 16.264 | 5.528  | 38.467 | 1.00 | 17.85 |
| ATOM | 213 | CB  | ILE | A | 165 | 17.775 | 5.279  | 38.594 | 1.00 | 19.88 |
| ATOM | 214 | CG1 | ILE | A | 165 | 18.262 | 5.777  | 39.956 | 1.00 | 22.82 |
| ATOM | 215 | CD1 | ILE | A | 165 | 18.495 | 4.673  | 40.984 | 1.00 | 25.13 |
| ATOM | 216 | CG2 | ILE | A | 165 | 18.537 | 5.977  | 37.482 | 1.00 | 18.87 |
| ATOM | 217 | C   | ILE | A | 165 | 15.844 | 5.752  | 37.022 | 1.00 | 17.16 |
| ATOM | 218 | O   | ILE | A | 165 | 15.517 | 4.799  | 36.311 | 1.00 | 15.06 |
| ATOM | 219 | N   | LEU | A | 166 | 15.820 | 7.024  | 36.618 | 1.00 | 16.63 |
| ATOM | 220 | CA  | LEU | A | 166 | 15.517 | 7.404  | 35.244 | 1.00 | 13.27 |
| ATOM | 221 | CB  | LEU | A | 166 | 14.894 | 8.794  | 35.192 | 1.00 | 6.52 |
| ATOM | 222 | CG  | LEU | A | 166 | 15.059 | 9.491  | 33.852 | 1.00 | 4.74 |
| ATOM | 223 | CD1 | LEU | A | 166 | 13.853 | 9.260  | 32.971 | 1.00 | 4.78 |
| ATOM | 224 | CD2 | LEU | A | 166 | 15.311 | 10.955 | 34.068 | 1.00 | 4.92 |
| ATOM | 225 | C   | LEU | A | 166 | 16.817 | 7.378  | 34.466 | 1.00 | 15.72 |
| ATOM | 226 | O   | LEU | A | 166 | 17.671 | 8.246  | 34.629 | 1.00 | 20.64 |
| ATOM | 227 | N   | VAL | A | 167 | 16.964 | 6.366  | 33.627 | 1.00 | 16.96 |
| ATOM | 228 | CA  | VAL | A | 167 | 18.216 | 6.129  | 32.925 | 1.00 | 15.44 |
| ATOM | 229 | CB  | VAL | A | 167 | 18.657 | 4.630  | 33.001 | 1.00 | 16.81 |
| ATOM | 230 | CG1 | VAL | A | 167 | 18.901 | 4.192  | 34.442 | 1.00 | 14.89 |
| ATOM | 231 | CG2 | VAL | A | 167 | 17.636 | 3.713  | 32.328 | 1.00 | 16.18 |
| ATOM | 232 | C   | VAL | A | 167 | 18.113 | 6.542  | 31.469 | 1.00 | 13.87 |
| ATOM | 233 | O   | VAL | A | 167 | 17.017 | 6.743  | 30.933 | 1.00 | 13.52 |
| ATOM | 234 | N   | LYS | A | 168 | 19.273 | 6.680  | 30.847 | 1.00 | 12.62 |
| ATOM | 235 | CA  | LYS | A | 168 | 19.366 | 6.802  | 29.411 | 1.00 | 13.59 |
| ATOM | 236 | CB  | LYS | A | 168 | 20.009 | 8.139  | 29.032 | 1.00 | 10.75 |
| ATOM | 237 | CG  | LYS | A | 168 | 19.942 | 8.493  | 27.549 | 1.00 | 8.86 |
| ATOM | 238 | CD  | LYS | A | 168 | 21.315 | 8.906  | 27.006 | 1.00 | 10.25 |
| ATOM | 239 | CE  | LYS | A | 168 | 21.631 | 10.389 | 27.259 | 1.00 | 10.46 |
| ATOM | 240 | NZ  | LYS | A | 168 | 23.061 | 10.697 | 26.989 | 1.00 | 8.17 |
| ATOM | 241 | C   | LYS | A | 168 | 20.234 | 5.636  | 28.974 | 1.00 | 15.80 |
| ATOM | 242 | O   | LYS | A | 168 | 21.315 | 5.437  | 29.533 | 1.00 | 15.67 |
| ATOM | 243 | N   | GLU | A | 169 | 19.749 | 4.847  | 28.010 | 1.00 | 18.58 |
| ATOM | 244 | CA  | GLU | A | 169 | 20.546 | 3.763  | 27.413 | 1.00 | 19.15 |
| ATOM | 245 | CB  | GLU | A | 169 | 19.670 | 2.681  | 26.769 | 1.00 | 19.62 |
| ATOM | 246 | CG  | GLU | A | 169 | 20.341 | 1.312  | 26.715 | 1.00 | 20.43 |
| ATOM | 247 | CD  | GLU | A | 169 | 19.737 | 0.368  | 25.684 | 1.00 | 20.48 |
| ATOM | 248 | OE1 | GLU | A | 169 | 18.487 | 0.342  | 25.537 | 1.00 | 17.12 |
| ATOM | 249 | OE2 | GLU | A | 169 | 20.530 | -0.357 | 25.027 | 1.00 | 20.57 |

FIGURE 3 (Cont.)

| | A | B | C | D | E | F | G | H | I | J |
|---|---|---|---|---|---|---|---|---|---|---|
| ATOM | 250 | C | GLU | A | 169 | 21.491 | 4.337 | 26.380 | 1.00 | 18.92 |
| ATOM | 251 | O | GLU | A | 169 | 21.076 | 5.086 | 25.497 | 1.00 | 20.97 |
| ATOM | 252 | N | LYS | A | 170 | 22.762 | 3.973 | 26.496 | 1.00 | 20.03 |
| ATOM | 253 | CA | LYS | A | 170 | 23.825 | 4.573 | 25.691 | 1.00 | 18.18 |
| ATOM | 254 | CB | LYS | A | 170 | 25.190 | 4.254 | 26.303 | 1.00 | 17.20 |
| ATOM | 255 | CG | LYS | A | 170 | 25.527 | 5.100 | 27.530 | 1.00 | 17.46 |
| ATOM | 256 | CD | LYS | A | 170 | 26.050 | 4.233 | 28.670 | 1.00 | 18.36 |
| ATOM | 257 | CE | LYS | A | 170 | 27.353 | 4.764 | 29.245 | 1.00 | 20.45 |
| ATOM | 258 | NZ | LYS | A | 170 | 27.601 | 4.273 | 30.628 | 1.00 | 20.69 |
| ATOM | 259 | C | LYS | A | 170 | 23.768 | 4.169 | 24.216 | 1.00 | 17.61 |
| ATOM | 260 | O | LYS | A | 170 | 23.883 | 5.021 | 23.341 | 1.00 | 16.82 |
| ATOM | 261 | N | ALA | A | 171 | 23.565 | 2.878 | 23.954 | 1.00 | 19.42 |
| ATOM | 262 | CA | ALA | A | 171 | 23.522 | 2.340 | 22.591 | 1.00 | 20.18 |
| ATOM | 263 | CB | ALA | A | 171 | 23.588 | 0.795 | 22.616 | 1.00 | 18.65 |
| ATOM | 264 | C | ALA | A | 171 | 22.343 | 2.842 | 21.714 | 1.00 | 20.83 |
| ATOM | 265 | O | ALA | A | 171 | 22.541 | 3.125 | 20.524 | 1.00 | 21.41 |
| ATOM | 266 | N | THR | A | 172 | 21.140 | 2.956 | 22.288 | 1.00 | 20.00 |
| ATOM | 267 | CA | THR | A | 172 | 19.944 | 3.341 | 21.513 | 1.00 | 20.37 |
| ATOM | 268 | CB | THR | A | 172 | 18.711 | 2.448 | 21.857 | 1.00 | 20.64 |
| ATOM | 269 | OG1 | THR | A | 172 | 18.224 | 2.758 | 23.170 | 1.00 | 21.43 |
| ATOM | 270 | CG2 | THR | A | 172 | 19.093 | 0.968 | 21.948 | 1.00 | 20.65 |
| ATOM | 271 | C | THR | A | 172 | 19.561 | 4.825 | 21.618 | 1.00 | 21.49 |
| ATOM | 272 | O | THR | A | 172 | 18.977 | 5.397 | 20.686 | 1.00 | 21.89 |
| ATOM | 273 | N | GLY | A | 173 | 19.891 | 5.439 | 22.751 | 1.00 | 21.37 |
| ATOM | 274 | CA | GLY | A | 173 | 19.506 | 6.812 | 23.029 | 1.00 | 20.78 |
| ATOM | 275 | C | GLY | A | 173 | 18.256 | 6.852 | 23.887 | 1.00 | 21.56 |
| ATOM | 276 | O | GLY | A | 173 | 18.083 | 7.757 | 24.703 | 1.00 | 22.11 |
| ATOM | 277 | N | ARG | A | 174 | 17.401 | 5.847 | 23.703 | 1.00 | 21.59 |
| ATOM | 278 | CA | ARG | A | 174 | 16.112 | 5.711 | 24.390 | 1.00 | 22.43 |
| ATOM | 279 | CB | ARG | A | 174 | 15.480 | 4.364 | 24.000 | 1.00 | 23.24 |
| ATOM | 280 | CG | ARG | A | 174 | 15.195 | 4.192 | 22.490 | 1.00 | 24.28 |
| ATOM | 281 | CD | ARG | A | 174 | 13.704 | 4.148 | 22.107 | 1.00 | 25.73 |
| ATOM | 282 | NE | ARG | A | 174 | 12.955 | 5.251 | 22.719 | 1.00 | 29.66 |
| ATOM | 283 | CZ | ARG | A | 174 | 12.069 | 5.115 | 23.714 | 1.00 | 30.98 |
| ATOM | 284 | NH1 | ARG | A | 174 | 11.461 | 6.188 | 24.220 | 1.00 | 26.56 |
| ATOM | 285 | NH2 | ARG | A | 174 | 11.794 | 3.907 | 24.207 | 1.00 | 32.07 |
| ATOM | 286 | C | ARG | A | 174 | 16.151 | 5.885 | 25.937 | 1.00 | 22.05 |
| ATOM | 287 | O | ARG | A | 174 | 17.157 | 5.565 | 26.581 | 1.00 | 21.24 |
| ATOM | 288 | N | TYR | A | 175 | 15.062 | 6.407 | 26.518 | 1.00 | 21.57 |
| ATOM | 289 | CA | TYR | A | 175 | 14.968 | 6.627 | 27.976 | 1.00 | 19.36 |
| ATOM | 290 | CB | TYR | A | 175 | 14.478 | 8.040 | 28.302 | 1.00 | 18.70 |
| ATOM | 291 | CG | TYR | A | 175 | 15.492 | 9.115 | 28.007 | 1.00 | 18.35 |
| ATOM | 292 | CD1 | TYR | A | 175 | 15.481 | 9.794 | 26.783 | 1.00 | 16.50 |
| ATOM | 293 | CE1 | TYR | A | 175 | 16.412 | 10.774 | 26.505 | 1.00 | 16.96 |
| ATOM | 294 | CZ | TYR | A | 175 | 17.377 | 11.093 | 27.457 | 1.00 | 18.83 |
| ATOM | 295 | OH | TYR | A | 175 | 18.316 | 12.073 | 27.186 | 1.00 | 21.35 |
| ATOM | 296 | CE2 | TYR | A | 175 | 17.406 | 10.437 | 28.681 | 1.00 | 17.75 |
| ATOM | 297 | CD2 | TYR | A | 175 | 16.469 | 9.451 | 28.947 | 1.00 | 17.59 |
| ATOM | 298 | C | TYR | A | 175 | 14.059 | 5.625 | 28.661 | 1.00 | 17.75 |
| ATOM | 299 | O | TYR | A | 175 | 13.036 | 5.223 | 28.098 | 1.00 | 17.49 |
| ATOM | 300 | N | TYR | A | 176 | 14.443 | 5.227 | 29.874 | 1.00 | 15.48 |
| ATOM | 301 | CA | TYR | A | 176 | 13.700 | 4.237 | 30.652 | 1.00 | 13.76 |

FIGURE 3 (Cont.)

| | A | B | C | D | E | F | G | H | I | J |
|---|---|---|---|---|---|---|---|---|---|---|
| ATOM | 302 | CB | TYR | A | 176 | 14.235 | 2.819 | 30.395 | 1.00 | 16.36 |
| ATOM | 303 | CG | TYR | A | 176 | 14.354 | 2.417 | 28.932 | 1.00 | 17.80 |
| ATOM | 304 | CD1 | TYR | A | 176 | 15.534 | 2.620 | 28.231 | 1.00 | 16.73 |
| ATOM | 305 | CE1 | TYR | A | 176 | 15.643 | 2.270 | 26.906 | 1.00 | 18.79 |
| ATOM | 306 | CZ | TYR | A | 176 | 14.568 | 1.698 | 26.259 | 1.00 | 20.01 |
| ATOM | 307 | OH | TYR | A | 176 | 14.682 | 1.339 | 24.929 | 1.00 | 23.68 |
| ATOM | 308 | CE2 | TYR | A | 176 | 13.389 | 1.475 | 26.933 | 1.00 | 18.64 |
| ATOM | 309 | CD2 | TYR | A | 176 | 13.286 | 1.833 | 28.259 | 1.00 | 18.21 |
| ATOM | 310 | C | TYR | A | 176 | 13.828 | 4.551 | 32.131 | 1.00 | 12.19 |
| ATOM | 311 | O | TYR | A | 176 | 14.736 | 5.273 | 32.538 | 1.00 | 10.58 |
| ATOM | 312 | N | ALA | A | 177 | 12.908 | 4.017 | 32.930 | 1.00 | 12.05 |
| ATOM | 313 | CA | ALA | A | 177 | 13.089 | 3.970 | 34.383 | 1.00 | 12.59 |
| ATOM | 314 | CB | ALA | A | 177 | 11.777 | 4.239 | 35.100 | 1.00 | 9.41 |
| ATOM | 315 | C | ALA | A | 177 | 13.661 | 2.599 | 34.787 | 1.00 | 14.88 |
| ATOM | 316 | O | ALA | A | 177 | 13.148 | 1.554 | 34.367 | 1.00 | 16.84 |
| ATOM | 317 | N | MET | A | 178 | 14.733 | 2.601 | 35.577 | 1.00 | 14.52 |
| ATOM | 318 | CA | MET | A | 178 | 15.326 | 1.355 | 36.057 | 1.00 | 13.89 |
| ATOM | 319 | CB | MET | A | 178 | 16.825 | 1.325 | 35.781 | 1.00 | 14.22 |
| ATOM | 320 | CG | MET | A | 178 | 17.438 | -0.054 | 35.890 | 1.00 | 16.22 |
| ATOM | 321 | SD | MET | A | 178 | 19.209 | 0.012 | 36.148 | 1.00 | 20.29 |
| ATOM | 322 | CE | MET | A | 178 | 19.790 | 0.479 | 34.502 | 1.00 | 19.50 |
| ATOM | 323 | C | MET | A | 178 | 15.058 | 1.142 | 37.547 | 1.00 | 15.81 |
| ATOM | 324 | O | MET | A | 178 | 15.402 | 1.993 | 38.377 | 1.00 | 14.94 |
| ATOM | 325 | N | LYS | A | 179 | 14.421 | 0.010 | 37.867 | 1.00 | 16.16 |
| ATOM | 326 | CA | LYS | A | 179 | 14.197 | -0.421 | 39.245 | 1.00 | 12.04 |
| ATOM | 327 | CB | LYS | A | 179 | 12.907 | -1.224 | 39.379 | 1.00 | 7.71 |
| ATOM | 328 | CG | LYS | A | 179 | 12.197 | -0.962 | 40.684 | 1.00 | 5.94 |
| ATOM | 329 | CD | LYS | A | 179 | 11.652 | -2.220 | 41.295 | 1.00 | 6.24 |
| ATOM | 330 | CE | LYS | A | 179 | 10.145 | -2.119 | 41.529 | 1.00 | 8.12 |
| ATOM | 331 | NZ | LYS | A | 179 | 9.812 | -2.080 | 42.986 | 1.00 | 9.56 |
| ATOM | 332 | C | LYS | A | 179 | 15.364 | -1.275 | 39.667 | 1.00 | 12.03 |
| ATOM | 333 | O | LYS | A | 179 | 15.572 | -2.340 | 39.111 | 1.00 | 12.22 |
| ATOM | 334 | N | ILE | A | 180 | 16.126 | -0.786 | 40.639 | 1.00 | 16.15 |
| ATOM | 335 | CA | ILE | A | 180 | 17.341 | -1.446 | 41.119 | 1.00 | 17.67 |
| ATOM | 336 | CB | ILE | A | 180 | 18.482 | -0.408 | 41.257 | 1.00 | 18.26 |
| ATOM | 337 | CG1 | ILE | A | 180 | 19.039 | -0.070 | 39.875 | 1.00 | 20.33 |
| ATOM | 338 | CD1 | ILE | A | 180 | 18.931 | 1.393 | 39.514 | 1.00 | 21.55 |
| ATOM | 339 | CG2 | ILE | A | 180 | 19.603 | -0.907 | 42.165 | 1.00 | 17.80 |
| ATOM | 340 | C | ILE | A | 180 | 17.080 | -2.159 | 42.444 | 1.00 | 17.86 |
| ATOM | 341 | O | ILE | A | 180 | 16.541 | -1.567 | 43.391 | 1.00 | 14.98 |
| ATOM | 342 | N | LEU | A | 181 | 17.468 | -3.432 | 42.505 | 1.00 | 16.46 |
| ATOM | 343 | CA | LEU | A | 181 | 17.287 | -4.222 | 43.720 | 1.00 | 14.52 |
| ATOM | 344 | CB | LEU | A | 181 | 16.239 | -5.307 | 43.485 | 1.00 | 14.70 |
| ATOM | 345 | CG | LEU | A | 181 | 14.834 | -4.713 | 43.324 | 1.00 | 17.29 |
| ATOM | 346 | CD1 | LEU | A | 181 | 13.876 | -5.653 | 42.570 | 1.00 | 16.60 |
| ATOM | 347 | CD2 | LEU | A | 181 | 14.252 | -4.300 | 44.683 | 1.00 | 17.45 |
| ATOM | 348 | C | LEU | A | 181 | 18.590 | -4.816 | 44.261 | 1.00 | 11.71 |
| ATOM | 349 | O | LEU | A | 181 | 19.366 | -5.402 | 43.526 | 1.00 | 10.93 |
| ATOM | 350 | N | LYS | A | 182 | 18.836 | -4.639 | 45.552 | 1.00 | 10.51 |
| ATOM | 351 | CA | LYS | A | 182 | 19.983 | -5.277 | 46.179 | 1.00 | 11.01 |
| ATOM | 352 | CB | LYS | A | 182 | 20.457 | -4.495 | 47.416 | 1.00 | 14.23 |
| ATOM | 353 | CG | LYS | A | 182 | 20.959 | -3.063 | 47.158 | 1.00 | 15.69 |

FIGURE 3 (Cont.)

| | A | B | C | D | E | F | G | H | I | J |
|---|---|---|---|---|---|---|---|---|---|---|
| ATOM | 354 | CD | LYS | A | 182 | 22.464 | -3.022 | 46.878 | 1.00 | 18.93 |
| ATOM | 355 | CE | LYS | A | 182 | 23.173 | -1.966 | 47.725 | 1.00 | 22.93 |
| ATOM | 356 | NZ | LYS | A | 182 | 23.710 | -0.803 | 46.938 | 1.00 | 23.03 |
| ATOM | 357 | C | LYS | A | 182 | 19.579 | -6.702 | 46.550 | 1.00 | 10.11 |
| ATOM | 358 | O | LYS | A | 182 | 18.588 | -6.905 | 47.270 | 1.00 | 8.75 |
| ATOM | 359 | N | LYS | A | 183 | 20.322 | -7.688 | 46.037 | 1.00 | 8.75 |
| ATOM | 360 | CA | LYS | A | 183 | 19.984 | -9.093 | 46.275 | 1.00 | 4.08 |
| ATOM | 361 | CB | LYS | A | 183 | 20.852 | -10.052 | 45.469 | 1.00 | 2.00 |
| ATOM | 362 | CG | LYS | A | 183 | 20.735 | -9.936 | 43.985 | 1.00 | 2.00 |
| ATOM | 363 | CD | LYS | A | 183 | 21.924 | -10.618 | 43.345 | 1.00 | 2.00 |
| ATOM | 364 | CE | LYS | A | 183 | 21.627 | -11.110 | 41.940 | 1.00 | 2.00 |
| ATOM | 365 | NZ | LYS | A | 183 | 22.628 | -12.117 | 41.524 | 1.00 | 2.00 |
| ATOM | 366 | C | LYS | A | 183 | 20.162 | -9.388 | 47.737 | 1.00 | 3.32 |
| ATOM | 367 | O | LYS | A | 183 | 19.318 | -10.038 | 48.345 | 1.00 | 2.00 |
| ATOM | 368 | N | GLU | A | 184 | 21.257 | -8.886 | 48.305 | 1.00 | 6.85 |
| ATOM | 369 | CA | GLU | A | 184 | 21.595 | -9.167 | 49.704 | 1.00 | 11.76 |
| ATOM | 370 | CB | GLU | A | 184 | 22.810 | -8.347 | 50.160 | 1.00 | 16.12 |
| ATOM | 371 | CG | GLU | A | 184 | 22.943 | -6.983 | 49.479 | 1.00 | 21.94 |
| ATOM | 372 | CD | GLU | A | 184 | 23.841 | -6.020 | 50.248 | 1.00 | 24.70 |
| ATOM | 373 | OE1 | GLU | A | 184 | 24.907 | -6.473 | 50.728 | 1.00 | 25.05 |
| ATOM | 374 | OE2 | GLU | A | 184 | 23.490 | -4.814 | 50.371 | 1.00 | 24.23 |
| ATOM | 375 | C | GLU | A | 184 | 20.391 | -8.887 | 50.591 | 1.00 | 8.38 |
| ATOM | 376 | O | GLU | A | 184 | 20.163 | -9.576 | 51.586 | 1.00 | 7.73 |
| ATOM | 377 | N | VAL | A | 185 | 19.620 | -7.888 | 50.167 | 1.00 | 4.57 |
| ATOM | 378 | CA | VAL | A | 185 | 18.472 | -7.362 | 50.886 | 1.00 | 2.68 |
| ATOM | 379 | CB | VAL | A | 185 | 18.236 | -5.879 | 50.515 | 1.00 | 2.00 |
| ATOM | 380 | CG1 | VAL | A | 185 | 16.968 | -5.335 | 51.165 | 1.00 | 2.00 |
| ATOM | 381 | CG2 | VAL | A | 185 | 19.460 | -5.036 | 50.882 | 1.00 | 2.00 |
| ATOM | 382 | C | VAL | A | 185 | 17.221 | -8.174 | 50.594 | 1.00 | 3.44 |
| ATOM | 383 | O | VAL | A | 185 | 16.513 | -8.558 | 51.523 | 1.00 | 4.64 |
| ATOM | 384 | N | ILE | A | 186 | 16.952 | -8.417 | 49.308 | 1.00 | 2.66 |
| ATOM | 385 | CA | ILE | A | 186 | 15.844 | -9.266 | 48.864 | 1.00 | 2.00 |
| ATOM | 386 | CB | ILE | A | 186 | 15.896 | -9.428 | 47.333 | 1.00 | 2.77 |
| ATOM | 387 | CG1 | ILE | A | 186 | 15.614 | -8.082 | 46.643 | 1.00 | 7.73 |
| ATOM | 388 | CD1 | ILE | A | 186 | 14.133 | -7.577 | 46.692 | 1.00 | 10.02 |
| ATOM | 389 | CG2 | ILE | A | 186 | 14.982 | -10.569 | 46.852 | 1.00 | 2.00 |
| ATOM | 390 | C | ILE | A | 186 | 15.870 | -10.638 | 49.538 | 1.00 | 2.00 |
| ATOM | 391 | O | ILE | A | 186 | 14.838 | -11.153 | 49.967 | 1.00 | 2.00 |
| ATOM | 392 | N | VAL | A | 187 | 17.065 | -11.213 | 49.625 | 1.00 | 2.00 |
| ATOM | 393 | CA | VAL | A | 187 | 17.267 | -12.497 | 50.272 | 1.00 | 2.60 |
| ATOM | 394 | CB | VAL | A | 187 | 18.658 | -13.098 | 49.922 | 1.00 | 2.00 |
| ATOM | 395 | CG1 | VAL | A | 187 | 18.892 | -14.442 | 50.624 | 1.00 | 2.00 |
| ATOM | 396 | CG2 | VAL | A | 187 | 18.773 | -13.278 | 48.429 | 1.00 | 2.00 |
| ATOM | 397 | C | VAL | A | 187 | 17.045 | -12.376 | 51.785 | 1.00 | 5.41 |
| ATOM | 398 | O | VAL | A | 187 | 16.283 | -13.156 | 52.353 | 1.00 | 8.09 |
| ATOM | 399 | N | ALA | A | 188 | 17.677 | -11.388 | 52.423 | 1.00 | 5.56 |
| ATOM | 400 | CA | ALA | A | 188 | 17.570 | -11.217 | 53.868 | 1.00 | 6.01 |
| ATOM | 401 | CB | ALA | A | 188 | 18.652 | -10.290 | 54.382 | 1.00 | 7.78 |
| ATOM | 402 | C | ALA | A | 188 | 16.189 | -10.735 | 54.304 | 1.00 | 8.58 |
| ATOM | 403 | O | ALA | A | 188 | 15.713 | -11.098 | 55.374 | 1.00 | 12.33 |
| ATOM | 404 | N | LYS | A | 189 | 15.541 | -9.928 | 53.477 | 1.00 | 11.57 |
| ATOM | 405 | CA | LYS | A | 189 | 14.191 | -9.466 | 53.780 | 1.00 | 15.35 |

FIGURE 3 (Cont.)

|      | A    | B   | C   | D | E   | F      | G       | H      | I    | J     |
|------|------|-----|-----|---|-----|--------|---------|--------|------|-------|
| ATOM | 406  | CB  | LYS | A | 189 | 14.014 | -7.995  | 53.354 | 1.00 | 18.39 |
| ATOM | 407  | CG  | LYS | A | 189 | 12.845 | -7.255  | 54.036 | 1.00 | 21.90 |
| ATOM | 408  | CD  | LYS | A | 189 | 13.301 | -6.228  | 55.076 | 1.00 | 23.27 |
| ATOM | 409  | CE  | LYS | A | 189 | 12.113 | -5.688  | 55.872 | 1.00 | 22.64 |
| ATOM | 410  | NZ  | LYS | A | 189 | 11.746 | -6.598  | 57.000 | 1.00 | 21.10 |
| ATOM | 411  | C   | LYS | A | 189 | 13.112 | -10.382 | 53.171 | 1.00 | 15.74 |
| ATOM | 412  | O   | LYS | A | 189 | 11.922 | -10.080 | 53.233 | 1.00 | 18.80 |
| ATOM | 413  | N   | ASP | A | 190 | 13.531 | -11.497 | 52.577 | 1.00 | 16.29 |
| ATOM | 414  | CA  | ASP | A | 190 | 12.606 | -12.547 | 52.141 | 1.00 | 16.49 |
| ATOM | 415  | CB  | ASP | A | 190 | 11.788 | -13.026 | 53.336 | 1.00 | 17.12 |
| ATOM | 416  | CG  | ASP | A | 190 | 11.440 | -14.483 | 53.250 | 1.00 | 20.28 |
| ATOM | 417  | OD1 | ASP | A | 190 | 11.449 | -15.034 | 52.125 | 1.00 | 22.76 |
| ATOM | 418  | OD2 | ASP | A | 190 | 11.140 | -15.157 | 54.259 | 1.00 | 22.17 |
| ATOM | 419  | C   | ASP | A | 190 | 11.664 | -12.176 | 50.988 | 1.00 | 15.93 |
| ATOM | 420  | O   | ASP | A | 190 | 10.506 | -12.592 | 50.955 | 1.00 | 15.32 |
| ATOM | 421  | N   | GLU | A | 191 | 12.163 | -11.406 | 50.035 | 1.00 | 17.29 |
| ATOM | 422  | CA  | GLU | A | 191 | 11.321 | -10.935 | 48.940 | 1.00 | 19.49 |
| ATOM | 423  | CB  | GLU | A | 191 | 11.340 | -9.407  | 48.874 | 1.00 | 22.95 |
| ATOM | 424  | CG  | GLU | A | 191 | 10.635 | -8.724  | 50.042 | 1.00 | 29.33 |
| ATOM | 425  | CD  | GLU | A | 191 | 9.117  | -8.619  | 49.886 | 1.00 | 33.52 |
| ATOM | 426  | OE1 | GLU | A | 191 | 8.609  | -8.454  | 48.739 | 1.00 | 34.88 |
| ATOM | 427  | OE2 | GLU | A | 191 | 8.427  | -8.688  | 50.934 | 1.00 | 34.39 |
| ATOM | 428  | C   | GLU | A | 191 | 11.713 | -11.546 | 47.593 | 1.00 | 19.19 |
| ATOM | 429  | O   | GLU | A | 191 | 11.482 | -10.958 | 46.541 | 1.00 | 17.18 |
| ATOM | 430  | N   | VAL | A | 192 | 12.312 | -12.730 | 47.633 | 1.00 | 20.75 |
| ATOM | 431  | CA  | VAL | A | 192 | 12.689 | -13.438 | 46.418 | 1.00 | 17.59 |
| ATOM | 432  | CB  | VAL | A | 192 | 13.599 | -14.639 | 46.743 | 1.00 | 14.56 |
| ATOM | 433  | CG1 | VAL | A | 192 | 13.312 | -15.828 | 45.845 | 1.00 | 13.35 |
| ATOM | 434  | CG2 | VAL | A | 192 | 15.052 | -14.223 | 46.640 | 1.00 | 13.65 |
| ATOM | 435  | C   | VAL | A | 192 | 11.424 | -13.846 | 45.668 | 1.00 | 19.48 |
| ATOM | 436  | O   | VAL | A | 192 | 11.221 | -13.449 | 44.517 | 1.00 | 18.22 |
| ATOM | 437  | N   | ALA | A | 193 | 10.570 | -14.603 | 46.357 | 1.00 | 21.83 |
| ATOM | 438  | CA  | ALA | A | 193 | 9.301  | -15.093 | 45.831 | 1.00 | 22.50 |
| ATOM | 439  | CB  | ALA | A | 193 | 8.394  | -15.503 | 46.981 | 1.00 | 25.68 |
| ATOM | 440  | C   | ALA | A | 193 | 8.603  | -14.059 | 44.972 | 1.00 | 24.14 |
| ATOM | 441  | O   | ALA | A | 193 | 8.143  | -14.375 | 43.866 | 1.00 | 26.03 |
| ATOM | 442  | N   | HIS | A | 194 | 8.540  | -12.831 | 45.503 | 1.00 | 24.45 |
| ATOM | 443  | CA  | HIS | A | 194 | 7.865  | -11.688 | 44.876 | 1.00 | 22.28 |
| ATOM | 444  | CB  | HIS | A | 194 | 7.626  | -10.577 | 45.898 | 1.00 | 24.03 |
| ATOM | 445  | CG  | HIS | A | 194 | 6.735  | -10.992 | 47.024 | 1.00 | 26.41 |
| ATOM | 446  | ND1 | HIS | A | 194 | 7.211  | -11.266 | 48.287 | 1.00 | 26.89 |
| ATOM | 447  | CE1 | HIS | A | 194 | 6.204  | -11.621 | 49.064 | 1.00 | 28.79 |
| ATOM | 448  | NE2 | HIS | A | 194 | 5.094  | -11.593 | 48.348 | 1.00 | 27.91 |
| ATOM | 449  | CD2 | HIS | A | 194 | 5.400  | -11.215 | 47.065 | 1.00 | 26.28 |
| ATOM | 450  | C   | HIS | A | 194 | 8.637  | -11.140 | 43.703 | 1.00 | 19.15 |
| ATOM | 451  | O   | HIS | A | 194 | 8.085  | -11.033 | 42.616 | 1.00 | 21.49 |
| ATOM | 452  | N   | THR | A | 195 | 9.908  | -10.803 | 43.921 | 1.00 | 15.39 |
| ATOM | 453  | CA  | THR | A | 195 | 10.774 | -10.353 | 42.841 | 1.00 | 12.03 |
| ATOM | 454  | CB  | THR | A | 195 | 12.255 | -10.311 | 43.243 | 1.00 | 10.28 |
| ATOM | 455  | OG1 | THR | A | 195 | 12.420 | -9.673  | 44.507 | 1.00 | 10.64 |
| ATOM | 456  | CG2 | THR | A | 195 | 12.987 | -9.376  | 42.326 | 1.00 | 12.27 |
| ATOM | 457  | C   | THR | A | 195 | 10.645 | -11.256 | 41.630 | 1.00 | 13.09 |

FIGURE 3 (Cont.)

|      | A   | B   | C   | D | E   | F      | G       | H      | I    | J     |
|------|-----|-----|-----|---|-----|--------|---------|--------|------|-------|
| ATOM | 458 | O   | THR | A | 195 | 10.661 | -10.774 | 40.495 | 1.00 | 13.93 |
| ATOM | 459 | N   | LEU | A | 196 | 10.528 | -12.565 | 41.863 | 1.00 | 14.82 |
| ATOM | 460 | CA  | LEU | A | 196 | 10.453 | -13.524 | 40.757 | 1.00 | 15.21 |
| ATOM | 461 | CB  | LEU | A | 196 | 10.543 | -14.961 | 41.245 | 1.00 | 16.66 |
| ATOM | 462 | CG  | LEU | A | 196 | 11.962 | -15.511 | 41.277 | 1.00 | 19.79 |
| ATOM | 463 | CD1 | LEU | A | 196 | 11.910 | -17.015 | 41.514 | 1.00 | 20.37 |
| ATOM | 464 | CD2 | LEU | A | 196 | 12.729 | -15.148 | 39.985 | 1.00 | 21.48 |
| ATOM | 465 | C   | LEU | A | 196 | 9.179  | -13.325 | 39.993 | 1.00 | 13.40 |
| ATOM | 466 | O   | LEU | A | 196 | 9.192  | -13.236 | 38.775 | 1.00 | 17.14 |
| ATOM | 467 | N   | THR | A | 197 | 8.087  | -13.233 | 40.734 | 1.00 | 10.17 |
| ATOM | 468 | CA  | THR | A | 197 | 6.788  | -12.957 | 40.182 | 1.00 | 8.59  |
| ATOM | 469 | CB  | THR | A | 197 | 5.828  | -12.964 | 41.324 | 1.00 | 9.45  |
| ATOM | 470 | OG1 | THR | A | 197 | 5.492  | -14.321 | 41.605 | 1.00 | 15.47 |
| ATOM | 471 | CG2 | THR | A | 197 | 4.518  | -12.338 | 40.927 | 1.00 | 14.25 |
| ATOM | 472 | C   | THR | A | 197 | 6.763  | -11.614 | 39.456 | 1.00 | 11.50 |
| ATOM | 473 | O   | THR | A | 197 | 6.213  | -11.493 | 38.351 | 1.00 | 9.41  |
| ATOM | 474 | N   | GLU | A | 198 | 7.371  | -10.608 | 40.079 | 1.00 | 15.61 |
| ATOM | 475 | CA  | GLU | A | 198 | 7.375  | -9.257  | 39.538 | 1.00 | 17.76 |
| ATOM | 476 | CB  | GLU | A | 198 | 8.131  | -8.309  | 40.467 | 1.00 | 21.98 |
| ATOM | 477 | CG  | GLU | A | 198 | 8.596  | -7.030  | 39.790 | 1.00 | 34.80 |
| ATOM | 478 | CD  | GLU | A | 198 | 8.497  | -5.798  | 40.683 | 1.00 | 43.72 |
| ATOM | 479 | OE1 | GLU | A | 198 | 8.737  | -5.922  | 41.924 | 1.00 | 44.32 |
| ATOM | 480 | OE2 | GLU | A | 198 | 8.188  | -4.701  | 40.125 | 1.00 | 46.34 |
| ATOM | 481 | C   | GLU | A | 198 | 7.983  | -9.287  | 38.146 | 1.00 | 17.14 |
| ATOM | 482 | O   | GLU | A | 198 | 7.460  | -8.672  | 37.215 | 1.00 | 18.91 |
| ATOM | 483 | N   | ASN | A | 199 | 9.076  | -10.038 | 38.025 | 1.00 | 14.75 |
| ATOM | 484 | CA  | ASN | A | 199 | 9.786  | -10.254 | 36.775 | 1.00 | 11.16 |
| ATOM | 485 | CB  | ASN | A | 199 | 10.997 | -11.123 | 37.089 | 1.00 | 13.86 |
| ATOM | 486 | CG  | ASN | A | 199 | 11.863 | -11.387 | 35.892 | 1.00 | 18.38 |
| ATOM | 487 | OD1 | ASN | A | 199 | 11.906 | -10.592 | 34.946 | 1.00 | 21.95 |
| ATOM | 488 | ND2 | ASN | A | 199 | 12.577 | -12.518 | 35.924 | 1.00 | 17.30 |
| ATOM | 489 | C   | ASN | A | 199 | 8.867  | -10.944 | 35.778 | 1.00 | 10.73 |
| ATOM | 490 | O   | ASN | A | 199 | 8.544  | -10.409 | 34.717 | 1.00 | 7.56  |
| ATOM | 491 | N   | ARG | A | 200 | 8.412  | -12.123 | 36.176 | 1.00 | 11.36 |
| ATOM | 492 | CA  | ARG | A | 200 | 7.469  | -12.931 | 35.423 | 1.00 | 10.25 |
| ATOM | 493 | CB  | ARG | A | 200 | 6.995  | -14.103 | 36.294 | 1.00 | 13.72 |
| ATOM | 494 | CG  | ARG | A | 200 | 7.322  | -15.505 | 35.775 | 1.00 | 17.72 |
| ATOM | 495 | CD  | ARG | A | 200 | 6.773  | -16.628 | 36.642 | 1.00 | 19.49 |
| ATOM | 496 | NE  | ARG | A | 200 | 7.730  | -16.974 | 37.689 | 1.00 | 25.77 |
| ATOM | 497 | CZ  | ARG | A | 200 | 7.531  | -16.833 | 39.002 | 1.00 | 28.89 |
| ATOM | 498 | NH1 | ARG | A | 200 | 8.498  | -17.190 | 39.848 | 1.00 | 29.58 |
| ATOM | 499 | NH2 | ARG | A | 200 | 6.386  | -16.345 | 39.478 | 1.00 | 27.11 |
| ATOM | 500 | C   | ARG | A | 200 | 6.267  | -12.149 | 34.891 | 1.00 | 8.77  |
| ATOM | 501 | O   | ARG | A | 200 | 5.854  | -12.381 | 33.760 | 1.00 | 11.18 |
| ATOM | 502 | N   | VAL | A | 201 | 5.689  | -11.243 | 35.681 | 1.00 | 6.46  |
| ATOM | 503 | CA  | VAL | A | 201 | 4.491  | -10.550 | 35.198 | 1.00 | 9.17  |
| ATOM | 504 | CB  | VAL | A | 201 | 3.672  | -9.845  | 36.308 | 1.00 | 8.28  |
| ATOM | 505 | CG1 | VAL | A | 201 | 2.684  | -8.879  | 35.697 | 1.00 | 3.97  |
| ATOM | 506 | CG2 | VAL | A | 201 | 2.919  | -10.853 | 37.148 | 1.00 | 11.11 |
| ATOM | 507 | C   | VAL | A | 201 | 4.906  | -9.548  | 34.145 | 1.00 | 10.71 |
| ATOM | 508 | O   | VAL | A | 201 | 4.547  | -9.681  | 32.980 | 1.00 | 10.91 |
| ATOM | 509 | N   | LEU | A | 202 | 5.686  | -8.562  | 34.577 | 1.00 | 12.99 |

FIGURE 3 (Cont.)

| | A | B | C | D | E | F | G | H | I | J |
|---|---|---|---|---|---|---|---|---|---|---|
| ATOM | 510 | CA | LEU | A | 202 | 6.220 | -7.517 | 33.720 | 1.00 | 13.14 |
| ATOM | 511 | CB | LEU | A | 202 | 7.449 | -6.921 | 34.375 | 1.00 | 7.21 |
| ATOM | 512 | CG | LEU | A | 202 | 7.267 | -5.795 | 35.347 | 1.00 | 3.69 |
| ATOM | 513 | CD1 | LEU | A | 202 | 8.537 | -5.705 | 36.170 | 1.00 | 5.33 |
| ATOM | 514 | CD2 | LEU | A | 202 | 7.034 | -4.524 | 34.579 | 1.00 | 3.90 |
| ATOM | 515 | C | LEU | A | 202 | 6.658 | -8.080 | 32.380 | 1.00 | 15.64 |
| ATOM | 516 | O | LEU | A | 202 | 6.608 | -7.400 | 31.348 | 1.00 | 18.52 |
| ATOM | 517 | N | GLN | A | 203 | 7.112 | -9.325 | 32.422 | 1.00 | 12.64 |
| ATOM | 518 | CA | GLN | A | 203 | 7.701 | -9.952 | 31.274 | 1.00 | 13.55 |
| ATOM | 519 | CB | GLN | A | 203 | 8.468 | -11.178 | 31.725 | 1.00 | 11.38 |
| ATOM | 520 | CG | GLN | A | 203 | 9.929 | -11.095 | 31.488 | 1.00 | 7.78 |
| ATOM | 521 | CD | GLN | A | 203 | 10.594 | -12.400 | 31.741 | 1.00 | 6.69 |
| ATOM | 522 | OE1 | GLN | A | 203 | 10.422 | -13.363 | 30.979 | 1.00 | 4.01 |
| ATOM | 523 | NE2 | GLN | A | 203 | 11.354 | -12.458 | 32.824 | 1.00 | 8.36 |
| ATOM | 524 | C | GLN | A | 203 | 6.612 | -10.381 | 30.328 | 1.00 | 18.36 |
| ATOM | 525 | O | GLN | A | 203 | 6.735 | -10.221 | 29.113 | 1.00 | 22.07 |
| ATOM | 526 | N | ASN | A | 204 | 5.539 | -10.916 | 30.898 | 1.00 | 21.83 |
| ATOM | 527 | CA | ASN | A | 204 | 4.512 | -11.606 | 30.130 | 1.00 | 25.11 |
| ATOM | 528 | CB | ASN | A | 204 | 4.070 | -12.855 | 30.892 | 1.00 | 24.51 |
| ATOM | 529 | CG | ASN | A | 204 | 4.946 | -14.049 | 30.605 | 1.00 | 24.50 |
| ATOM | 530 | OD1 | ASN | A | 204 | 4.542 | -15.186 | 30.843 | 1.00 | 28.55 |
| ATOM | 531 | ND2 | ASN | A | 204 | 6.154 | -13.804 | 30.094 | 1.00 | 20.02 |
| ATOM | 532 | C | ASN | A | 204 | 3.292 | -10.751 | 29.786 | 1.00 | 27.01 |
| ATOM | 533 | O | ASN | A | 204 | 2.403 | -11.187 | 29.048 | 1.00 | 28.04 |
| ATOM | 534 | N | SER | A | 205 | 3.259 | -9.536 | 30.318 | 1.00 | 26.56 |
| ATOM | 535 | CA | SER | A | 205 | 2.043 | -8.755 | 30.310 | 1.00 | 25.06 |
| ATOM | 536 | CB | SER | A | 205 | 1.784 | -8.209 | 31.705 | 1.00 | 24.45 |
| ATOM | 537 | OG | SER | A | 205 | 1.453 | -9.274 | 32.576 | 1.00 | 23.55 |
| ATOM | 538 | C | SER | A | 205 | 2.111 | -7.649 | 29.280 | 1.00 | 27.77 |
| ATOM | 539 | O | SER | A | 205 | 2.896 | -6.701 | 29.411 | 1.00 | 35.42 |
| ATOM | 540 | N | ARG | A | 206 | 1.267 | -7.783 | 28.260 | 1.00 | 23.70 |
| ATOM | 541 | CA | ARG | A | 206 | 1.234 | -6.882 | 27.121 | 1.00 | 19.49 |
| ATOM | 542 | CB | ARG | A | 206 | 1.427 | -7.715 | 25.834 | 1.00 | 22.78 |
| ATOM | 543 | CG | ARG | A | 206 | 2.775 | -7.544 | 25.064 | 1.00 | 27.32 |
| ATOM | 544 | CD | ARG | A | 206 | 4.066 | -7.895 | 25.834 | 1.00 | 27.84 |
| ATOM | 545 | NE | ARG | A | 206 | 4.742 | -9.090 | 25.315 | 1.00 | 29.21 |
| ATOM | 546 | CZ | ARG | A | 206 | 5.945 | -9.516 | 25.712 | 1.00 | 29.95 |
| ATOM | 547 | NH1 | ARG | A | 206 | 6.636 | -8.845 | 26.622 | 1.00 | 31.56 |
| ATOM | 548 | NH2 | ARG | A | 206 | 6.467 | -10.622 | 25.203 | 1.00 | 29.69 |
| ATOM | 549 | C | ARG | A | 206 | -0.106 | -6.117 | 27.113 | 1.00 | 13.59 |
| ATOM | 550 | O | ARG | A | 206 | -1.107 | -6.619 | 26.623 | 1.00 | 17.68 |
| ATOM | 551 | N | HIS | A | 207 | -0.130 | -4.908 | 27.661 | 1.00 | 5.11 |
| ATOM | 552 | CA | HIS | A | 207 | -1.379 | -4.146 | 27.772 | 1.00 | 4.65 |
| ATOM | 553 | CB | HIS | A | 207 | -2.109 | -4.513 | 29.061 | 1.00 | 3.92 |
| ATOM | 554 | CG | HIS | A | 207 | -3.456 | -3.877 | 29.201 | 1.00 | 2.57 |
| ATOM | 555 | ND1 | HIS | A | 207 | -4.626 | -4.541 | 28.900 | 1.00 | 4.52 |
| ATOM | 556 | CE1 | HIS | A | 207 | -5.655 | -3.742 | 29.119 | 1.00 | 3.68 |
| ATOM | 557 | NE2 | HIS | A | 207 | -5.193 | -2.581 | 29.546 | 1.00 | 3.88 |
| ATOM | 558 | CD2 | HIS | A | 207 | -3.821 | -2.642 | 29.610 | 1.00 | 2.70 |
| ATOM | 559 | C | HIS | A | 207 | -1.108 | -2.646 | 27.752 | 1.00 | 7.08 |
| ATOM | 560 | O | HIS | A | 207 | -0.122 | -2.201 | 28.314 | 1.00 | 14.05 |
| ATOM | 561 | N | PRO | A | 208 | -1.966 | -1.851 | 27.118 | 1.00 | 8.27 |

FIGURE 3 (Cont.)

| | A | B | C | D | E | F | G | H | I | J |
|---|---|---|---|---|---|---|---|---|---|---|
| ATOM | 562 | CA | PRO | A | 208 | -1.694 | -0.420 | 26.977 | 1.00 | 9.24 |
| ATOM | 563 | CB | PRO | A | 208 | -2.946 | 0.086 | 26.269 | 1.00 | 8.40 |
| ATOM | 564 | CG | PRO | A | 208 | -3.974 | -0.939 | 26.571 | 1.00 | 6.67 |
| ATOM | 565 | CD | PRO | A | 208 | -3.238 | -2.216 | 26.469 | 1.00 | 8.30 |
| ATOM | 566 | C | PRO | A | 208 | -1.495 | 0.309 | 28.316 | 1.00 | 12.90 |
| ATOM | 567 | O | PRO | A | 208 | -0.768 | 1.306 | 28.345 | 1.00 | 14.64 |
| ATOM | 568 | N | PHE | A | 209 | -2.108 | -0.192 | 29.390 | 1.00 | 12.89 |
| ATOM | 569 | CA | PHE | A | 209 | -2.090 | 0.473 | 30.692 | 1.00 | 10.18 |
| ATOM | 570 | CB | PHE | A | 209 | -3.515 | 0.684 | 31.177 | 1.00 | 4.84 |
| ATOM | 571 | CG | PHE | A | 209 | -4.400 | 1.267 | 30.152 | 1.00 | 5.70 |
| ATOM | 572 | CD1 | PHE | A | 209 | -4.028 | 2.434 | 29.486 | 1.00 | 7.79 |
| ATOM | 573 | CE1 | PHE | A | 209 | -4.853 | 2.995 | 28.517 | 1.00 | 8.32 |
| ATOM | 574 | CZ | PHE | A | 209 | -6.076 | 2.372 | 28.204 | 1.00 | 9.16 |
| ATOM | 575 | CE2 | PHE | A | 209 | -6.452 | 1.196 | 28.864 | 1.00 | 7.28 |
| ATOM | 576 | CD2 | PHE | A | 209 | -5.606 | 0.652 | 29.828 | 1.00 | 7.12 |
| ATOM | 577 | C | PHE | A | 209 | -1.284 | -0.280 | 31.748 | 1.00 | 13.63 |
| ATOM | 578 | O | PHE | A | 209 | -1.406 | -0.030 | 32.958 | 1.00 | 19.21 |
| ATOM | 579 | N | LEU | A | 210 | -0.467 | -1.217 | 31.303 | 1.00 | 9.08 |
| ATOM | 580 | CA | LEU | A | 210 | 0.481 | -1.804 | 32.214 | 1.00 | 11.05 |
| ATOM | 581 | CB | LEU | A | 210 | 0.346 | -3.320 | 32.219 | 1.00 | 11.28 |
| ATOM | 582 | CG | LEU | A | 210 | -0.949 | -3.904 | 32.793 | 1.00 | 12.46 |
| ATOM | 583 | CD1 | LEU | A | 210 | -0.794 | -5.401 | 33.002 | 1.00 | 10.13 |
| ATOM | 584 | CD2 | LEU | A | 210 | -1.412 | -3.201 | 34.087 | 1.00 | 10.62 |
| ATOM | 585 | C | LEU | A | 210 | 1.871 | -1.367 | 31.793 | 1.00 | 15.31 |
| ATOM | 586 | O | LEU | A | 210 | 2.135 | -1.215 | 30.596 | 1.00 | 18.78 |
| ATOM | 587 | N | THR | A | 211 | 2.755 | -1.147 | 32.766 | 1.00 | 15.52 |
| ATOM | 588 | CA | THR | A | 211 | 4.130 | -0.768 | 32.462 | 1.00 | 17.90 |
| ATOM | 589 | CB | THR | A | 211 | 4.885 | -0.375 | 33.727 | 1.00 | 21.77 |
| ATOM | 590 | OG1 | THR | A | 211 | 3.995 | 0.317 | 34.605 | 1.00 | 26.09 |
| ATOM | 591 | CG2 | THR | A | 211 | 5.913 | 0.702 | 33.417 | 1.00 | 26.87 |
| ATOM | 592 | C | THR | A | 211 | 4.843 | -1.892 | 31.725 | 1.00 | 17.49 |
| ATOM | 593 | O | THR | A | 211 | 4.799 | -3.048 | 32.152 | 1.00 | 18.80 |
| ATOM | 594 | N | ALA | A | 212 | 5.462 | -1.539 | 30.598 | 1.00 | 15.19 |
| ATOM | 595 | CA | ALA | A | 212 | 6.134 | -2.490 | 29.719 | 1.00 | 12.51 |
| ATOM | 596 | CB | ALA | A | 212 | 6.055 | -2.012 | 28.286 | 1.00 | 10.74 |
| ATOM | 597 | C | ALA | A | 212 | 7.585 | -2.681 | 30.133 | 1.00 | 12.36 |
| ATOM | 598 | O | ALA | A | 212 | 8.287 | -1.709 | 30.414 | 1.00 | 9.72 |
| ATOM | 599 | N | LEU | A | 213 | 8.030 | -3.934 | 30.177 | 1.00 | 14.72 |
| ATOM | 600 | CA | LEU | A | 213 | 9.420 | -4.225 | 30.529 | 1.00 | 17.99 |
| ATOM | 601 | CB | LEU | A | 213 | 9.529 | -5.479 | 31.413 | 1.00 | 17.23 |
| ATOM | 602 | CG | LEU | A | 213 | 10.927 | -6.037 | 31.714 | 1.00 | 15.27 |
| ATOM | 603 | CD1 | LEU | A | 213 | 11.623 | -5.229 | 32.780 | 1.00 | 16.34 |
| ATOM | 604 | CD2 | LEU | A | 213 | 10.823 | -7.481 | 32.153 | 1.00 | 15.33 |
| ATOM | 605 | C | LEU | A | 213 | 10.276 | -4.358 | 29.276 | 1.00 | 20.60 |
| ATOM | 606 | O | LEU | A | 213 | 9.894 | -5.064 | 28.320 | 1.00 | 19.97 |
| ATOM | 607 | N | LYS | A | 214 | 11.418 | -3.658 | 29.294 | 1.00 | 22.83 |
| ATOM | 608 | CA | LYS | A | 214 | 12.379 | -3.630 | 28.180 | 1.00 | 23.96 |
| ATOM | 609 | CB | LYS | A | 214 | 12.905 | -2.207 | 27.940 | 1.00 | 22.99 |
| ATOM | 610 | CG | LYS | A | 214 | 14.133 | -2.124 | 27.033 | 1.00 | 25.04 |
| ATOM | 611 | CD | LYS | A | 214 | 13.750 | -2.032 | 25.539 | 1.00 | 26.92 |
| ATOM | 612 | CE | LYS | A | 214 | 14.865 | -2.523 | 24.612 | 1.00 | 23.84 |
| ATOM | 613 | NZ | LYS | A | 214 | 14.378 | -3.518 | 23.612 | 1.00 | 23.78 |

FIGURE 3 (Cont.)

|  | A | B | C | D | E | F | G | H | I | J |
|---|---|---|---|---|---|---|---|---|---|---|
| ATOM | 614 | C | LYS | A | 214 | 13.542 | -4.585 | 28.433 | 1.00 | 24.84 |
| ATOM | 615 | O | LYS | A | 214 | 13.805 | -5.481 | 27.622 | 1.00 | 25.03 |
| ATOM | 616 | N | TYR | A | 215 | 14.239 | -4.369 | 29.549 | 1.00 | 23.99 |
| ATOM | 617 | CA | TYR | A | 215 | 15.278 | -5.276 | 30.018 | 1.00 | 21.25 |
| ATOM | 618 | CB | TYR | A | 215 | 16.672 | -4.652 | 29.911 | 1.00 | 19.04 |
| ATOM | 619 | CG | TYR | A | 215 | 17.087 | -4.151 | 28.557 | 1.00 | 18.19 |
| ATOM | 620 | CD1 | TYR | A | 215 | 17.022 | -4.966 | 27.434 | 1.00 | 18.49 |
| ATOM | 621 | CE1 | TYR | A | 215 | 17.418 | -4.497 | 26.184 | 1.00 | 19.88 |
| ATOM | 622 | CZ | TYR | A | 215 | 17.899 | -3.203 | 26.060 | 1.00 | 20.21 |
| ATOM | 623 | OH | TYR | A | 215 | 18.293 | -2.729 | 24.830 | 1.00 | 22.62 |
| ATOM | 624 | CE2 | TYR | A | 215 | 17.988 | -2.383 | 27.166 | 1.00 | 20.01 |
| ATOM | 625 | CD2 | TYR | A | 215 | 17.586 | -2.862 | 28.408 | 1.00 | 18.95 |
| ATOM | 626 | C | TYR | A | 215 | 15.055 | -5.613 | 31.481 | 1.00 | 21.19 |
| ATOM | 627 | O | TYR | A | 215 | 14.675 | -4.752 | 32.280 | 1.00 | 20.20 |
| ATOM | 628 | N | SER | A | 216 | 15.310 | -6.869 | 31.823 | 1.00 | 18.31 |
| ATOM | 629 | CA | SER | A | 216 | 15.540 | -7.242 | 33.200 | 1.00 | 16.18 |
| ATOM | 630 | CB | SER | A | 216 | 14.377 | -8.055 | 33.739 | 1.00 | 16.79 |
| ATOM | 631 | OG | SER | A | 216 | 14.590 | -9.434 | 33.548 | 1.00 | 18.82 |
| ATOM | 632 | C | SER | A | 216 | 16.837 | -8.032 | 33.232 | 1.00 | 17.13 |
| ATOM | 633 | O | SER | A | 216 | 16.990 | -8.993 | 32.496 | 1.00 | 17.99 |
| ATOM | 634 | N | PHE | A | 217 | 17.782 | -7.603 | 34.064 | 1.00 | 19.20 |
| ATOM | 635 | CA | PHE | A | 217 | 19.101 | -8.240 | 34.144 | 1.00 | 16.30 |
| ATOM | 636 | CB | PHE | A | 217 | 20.106 | -7.498 | 33.262 | 1.00 | 12.42 |
| ATOM | 637 | CG | PHE | A | 217 | 20.371 | -6.083 | 33.699 | 1.00 | 11.83 |
| ATOM | 638 | CD1 | PHE | A | 217 | 19.562 | -5.042 | 33.261 | 1.00 | 11.69 |
| ATOM | 639 | CE1 | PHE | A | 217 | 19.808 | -3.725 | 33.658 | 1.00 | 11.93 |
| ATOM | 640 | CZ | PHE | A | 217 | 20.876 | -3.441 | 34.504 | 1.00 | 12.79 |
| ATOM | 641 | CE2 | PHE | A | 217 | 21.695 | -4.474 | 34.951 | 1.00 | 12.87 |
| ATOM | 642 | CD2 | PHE | A | 217 | 21.440 | -5.788 | 34.543 | 1.00 | 12.76 |
| ATOM | 643 | C | PHE | A | 217 | 19.598 | -8.313 | 35.594 | 1.00 | 16.91 |
| ATOM | 644 | O | PHE | A | 217 | 18.994 | -7.690 | 36.497 | 1.00 | 17.16 |
| ATOM | 645 | N | GLN | A | 218 | 20.674 | -9.079 | 35.817 | 1.00 | 10.91 |
| ATOM | 646 | CA | GLN | A | 218 | 21.285 | -9.165 | 37.146 | 1.00 | 6.42 |
| ATOM | 647 | CB | GLN | A | 218 | 20.864 | -10.433 | 37.899 | 1.00 | 4.74 |
| ATOM | 648 | CG | GLN | A | 218 | 21.708 | -11.683 | 37.621 | 1.00 | 3.09 |
| ATOM | 649 | CD | GLN | A | 218 | 21.054 | -12.964 | 38.116 | 1.00 | 2.00 |
| ATOM | 650 | OE1 | GLN | A | 218 | 21.044 | -13.246 | 39.312 | 1.00 | 2.00 |
| ATOM | 651 | NE2 | GLN | A | 218 | 20.506 | -13.733 | 37.200 | 1.00 | 2.00 |
| ATOM | 652 | C | GLN | A | 218 | 22.794 | -9.047 | 37.097 | 1.00 | 7.78 |
| ATOM | 653 | O | GLN | A | 218 | 23.440 | -9.568 | 36.185 | 1.00 | 7.07 |
| ATOM | 654 | N | THR | A | 219 | 23.327 | -8.329 | 38.085 | 1.00 | 10.09 |
| ATOM | 655 | CA | THR | A | 219 | 24.760 | -8.150 | 38.293 | 1.00 | 12.25 |
| ATOM | 656 | CB | THR | A | 219 | 25.076 | -6.691 | 38.709 | 1.00 | 13.22 |
| ATOM | 657 | OG1 | THR | A | 219 | 24.258 | -6.322 | 39.824 | 1.00 | 13.71 |
| ATOM | 658 | CG2 | THR | A | 219 | 24.667 | -5.701 | 37.635 | 1.00 | 14.64 |
| ATOM | 659 | C | THR | A | 219 | 25.176 | -9.103 | 39.409 | 1.00 | 12.92 |
| ATOM | 660 | O | THR | A | 219 | 24.410 | -10.002 | 39.765 | 1.00 | 11.32 |
| ATOM | 661 | N | HIS | A | 220 | 26.376 | -8.914 | 39.960 | 1.00 | 14.53 |
| ATOM | 662 | CA | HIS | A | 220 | 26.773 | -9.654 | 41.159 | 1.00 | 18.28 |
| ATOM | 663 | CB | HIS | A | 220 | 28.267 | -9.468 | 41.522 | 1.00 | 24.00 |
| ATOM | 664 | CG | HIS | A | 220 | 28.893 | -8.199 | 41.005 | 1.00 | 31.28 |
| ATOM | 665 | ND1 | HIS | A | 220 | 30.108 | -8.184 | 40.348 | 1.00 | 35.42 |

FIGURE 3 (Cont.)

| | A | B | C | D | E | F | G | H | I | J |
|---|---|---|---|---|---|---|---|---|---|---|
| ATOM | 666 | CE1 | HIS | A | 220 | 30.424 | -6.940 | 40.028 | 1.00 | 34.54 |
| ATOM | 667 | NE2 | HIS | A | 220 | 29.464 | -6.143 | 40.463 | 1.00 | 33.64 |
| ATOM | 668 | CD2 | HIS | A | 220 | 28.500 | -6.903 | 41.086 | 1.00 | 32.64 |
| ATOM | 669 | C | HIS | A | 220 | 25.857 | -9.355 | 42.366 | 1.00 | 16.57 |
| ATOM | 670 | O | HIS | A | 220 | 25.497 | -10.263 | 43.121 | 1.00 | 14.27 |
| ATOM | 671 | N | ASP | A | 221 | 25.457 | -8.092 | 42.514 | 1.00 | 15.94 |
| ATOM | 672 | CA | ASP | A | 221 | 24.796 | -7.620 | 43.732 | 1.00 | 16.25 |
| ATOM | 673 | CB | ASP | A | 221 | 25.626 | -6.527 | 44.431 | 1.00 | 22.55 |
| ATOM | 674 | CG | ASP | A | 221 | 26.212 | -5.498 | 43.461 | 1.00 | 28.05 |
| ATOM | 675 | OD1 | ASP | A | 221 | 25.601 | -5.230 | 42.395 | 1.00 | 30.06 |
| ATOM | 676 | OD2 | ASP | A | 221 | 27.290 | -4.899 | 43.697 | 1.00 | 29.84 |
| ATOM | 677 | C | ASP | A | 221 | 23.388 | -7.108 | 43.522 | 1.00 | 13.08 |
| ATOM | 678 | O | ASP | A | 221 | 22.632 | -6.955 | 44.483 | 1.00 | 12.33 |
| ATOM | 679 | N | ARG | A | 222 | 23.036 | -6.840 | 42.272 | 1.00 | 10.45 |
| ATOM | 680 | CA | ARG | A | 222 | 21.752 | -6.219 | 41.991 | 1.00 | 10.85 |
| ATOM | 681 | CB | ARG | A | 222 | 21.940 | -4.794 | 41.443 | 1.00 | 13.32 |
| ATOM | 682 | CG | ARG | A | 222 | 22.544 | -3.772 | 42.417 | 1.00 | 12.17 |
| ATOM | 683 | CD | ARG | A | 222 | 23.394 | -2.739 | 41.708 | 1.00 | 12.56 |
| ATOM | 684 | NE | ARG | A | 222 | 24.347 | -2.060 | 42.578 | 1.00 | 13.85 |
| ATOM | 685 | CZ | ARG | A | 222 | 24.225 | -0.797 | 42.974 | 1.00 | 15.21 |
| ATOM | 686 | NH1 | ARG | A | 222 | 23.176 | -0.072 | 42.600 | 1.00 | 16.45 |
| ATOM | 687 | NH2 | ARG | A | 222 | 25.146 | -0.256 | 43.755 | 1.00 | 15.42 |
| ATOM | 688 | C | ARG | A | 222 | 20.878 | -7.015 | 41.037 | 1.00 | 9.25 |
| ATOM | 689 | O | ARG | A | 222 | 21.371 | -7.707 | 40.150 | 1.00 | 11.73 |
| ATOM | 690 | N | LEU | A | 223 | 19.571 | -6.920 | 41.255 | 1.00 | 7.95 |
| ATOM | 691 | CA | LEU | A | 223 | 18.582 | -7.266 | 40.250 | 1.00 | 5.79 |
| ATOM | 692 | CB | LEU | A | 223 | 17.430 | -8.055 | 40.845 | 1.00 | 2.99 |
| ATOM | 693 | CG | LEU | A | 223 | 17.876 | -9.270 | 41.625 | 1.00 | 2.31 |
| ATOM | 694 | CD1 | LEU | A | 223 | 16.745 | -9.689 | 42.514 | 1.00 | 5.68 |
| ATOM | 695 | CD2 | LEU | A | 223 | 18.288 | -10.382 | 40.691 | 1.00 | 2.00 |
| ATOM | 696 | C | LEU | A | 223 | 18.067 | -5.966 | 39.693 | 1.00 | 6.90 |
| ATOM | 697 | O | LEU | A | 223 | 17.958 | -4.972 | 40.423 | 1.00 | 3.04 |
| ATOM | 698 | N | CYS | A | 224 | 17.754 | -5.984 | 38.398 | 1.00 | 10.76 |
| ATOM | 699 | CA | CYS | A | 224 | 17.418 | -4.771 | 37.675 | 1.00 | 13.46 |
| ATOM | 700 | CB | CYS | A | 224 | 18.636 | -4.265 | 36.934 | 1.00 | 15.09 |
| ATOM | 701 | SG | CYS | A | 224 | 19.705 | -3.287 | 37.982 | 1.00 | 23.17 |
| ATOM | 702 | C | CYS | A | 224 | 16.303 | -4.940 | 36.683 | 1.00 | 13.74 |
| ATOM | 703 | O | CYS | A | 224 | 16.427 | -5.721 | 35.742 | 1.00 | 16.00 |
| ATOM | 704 | N | PHE | A | 225 | 15.222 | -4.195 | 36.891 | 1.00 | 12.21 |
| ATOM | 705 | CA | PHE | A | 225 | 14.208 | -4.033 | 35.868 | 1.00 | 11.81 |
| ATOM | 706 | CB | PHE | A | 225 | 12.826 | -4.147 | 36.459 | 1.00 | 14.09 |
| ATOM | 707 | CG | PHE | A | 225 | 12.565 | -5.423 | 37.169 | 1.00 | 14.19 |
| ATOM | 708 | CD1 | PHE | A | 225 | 12.423 | -5.440 | 38.548 | 1.00 | 14.88 |
| ATOM | 709 | CE1 | PHE | A | 225 | 12.144 | -6.615 | 39.230 | 1.00 | 13.51 |
| ATOM | 710 | CZ | PHE | A | 225 | 11.986 | -7.782 | 38.532 | 1.00 | 14.88 |
| ATOM | 711 | CE2 | PHE | A | 225 | 12.113 | -7.778 | 37.140 | 1.00 | 16.65 |
| ATOM | 712 | CD2 | PHE | A | 225 | 12.392 | -6.593 | 36.467 | 1.00 | 15.37 |
| ATOM | 713 | C | PHE | A | 225 | 14.326 | -2.663 | 35.186 | 1.00 | 12.12 |
| ATOM | 714 | O | PHE | A | 225 | 14.347 | -1.615 | 35.847 | 1.00 | 5.03 |
| ATOM | 715 | N | VAL | A | 226 | 14.402 | -2.697 | 33.854 | 1.00 | 12.07 |
| ATOM | 716 | CA | VAL | A | 226 | 14.371 | -1.506 | 33.020 | 1.00 | 8.03 |
| ATOM | 717 | CB | VAL | A | 226 | 15.458 | -1.549 | 31.972 | 1.00 | 5.66 |

FIGURE 3 (Cont.)

|      | A    | B   | C   | D | E   | F      | G       | H      | I    | J     |
|------|------|-----|-----|---|-----|--------|---------|--------|------|-------|
| ATOM | 718  | CG1 | VAL | A | 226 | 15.666 | -0.168  | 31.393 | 1.00 | 5.17  |
| ATOM | 719  | CG2 | VAL | A | 226 | 16.743 | -2.103  | 32.562 | 1.00 | 5.62  |
| ATOM | 720  | C   | VAL | A | 226 | 13.033 | -1.458  | 32.312 | 1.00 | 9.28  |
| ATOM | 721  | O   | VAL | A | 226 | 12.806 | -2.173  | 31.337 | 1.00 | 8.28  |
| ATOM | 722  | N   | MET | A | 227 | 12.135 | -0.634  | 32.825 | 1.00 | 12.05 |
| ATOM | 723  | CA  | MET | A | 227 | 10.811 | -0.525  | 32.244 | 1.00 | 16.06 |
| ATOM | 724  | CB  | MET | A | 227 | 9.721  | -0.903  | 33.249 | 1.00 | 21.27 |
| ATOM | 725  | CG  | MET | A | 227 | 9.591  | 0.001   | 34.446 | 1.00 | 24.93 |
| ATOM | 726  | SD  | MET | A | 227 | 9.527  | -1.061  | 35.855 | 1.00 | 31.99 |
| ATOM | 727  | CE  | MET | A | 227 | 9.029  | 0.085   | 37.161 | 1.00 | 29.11 |
| ATOM | 728  | C   | MET | A | 227 | 10.571 | 0.853   | 31.667 | 1.00 | 15.33 |
| ATOM | 729  | O   | MET | A | 227 | 11.422 | 1.747   | 31.790 | 1.00 | 13.47 |
| ATOM | 730  | N   | GLU | A | 228 | 9.414  | 1.017   | 31.030 | 1.00 | 14.08 |
| ATOM | 731  | CA  | GLU | A | 228 | 9.165  | 2.225   | 30.282 | 1.00 | 15.90 |
| ATOM | 732  | CB  | GLU | A | 228 | 8.082  | 2.025   | 29.218 | 1.00 | 22.01 |
| ATOM | 733  | CG  | GLU | A | 228 | 6.649  | 2.246   | 29.686 | 1.00 | 34.10 |
| ATOM | 734  | CD  | GLU | A | 228 | 5.629  | 1.562   | 28.785 | 1.00 | 41.38 |
| ATOM | 735  | OE1 | GLU | A | 228 | 5.738  | 1.713   | 27.546 | 1.00 | 42.83 |
| ATOM | 736  | OE2 | GLU | A | 228 | 4.719  | 0.864   | 29.310 | 1.00 | 44.92 |
| ATOM | 737  | C   | GLU | A | 228 | 8.828  | 3.307   | 31.263 | 1.00 | 12.11 |
| ATOM | 738  | O   | GLU | A | 228 | 7.907  | 3.158   | 32.047 | 1.00 | 13.79 |
| ATOM | 739  | N   | TYR | A | 229 | 9.626  | 4.371   | 31.227 | 1.00 | 11.73 |
| ATOM | 740  | CA  | TYR | A | 229 | 9.421  | 5.603   | 31.994 | 1.00 | 13.35 |
| ATOM | 741  | CB  | TYR | A | 229 | 10.469 | 6.610   | 31.541 | 1.00 | 13.11 |
| ATOM | 742  | CG  | TYR | A | 229 | 10.439 | 7.970   | 32.209 | 1.00 | 13.35 |
| ATOM | 743  | CD1 | TYR | A | 229 | 10.270 | 8.111   | 33.587 | 1.00 | 12.43 |
| ATOM | 744  | CE1 | TYR | A | 229 | 10.266 | 9.373   | 34.180 | 1.00 | 12.97 |
| ATOM | 745  | CZ  | TYR | A | 229 | 10.449 | 10.502  | 33.392 | 1.00 | 12.63 |
| ATOM | 746  | OH  | TYR | A | 229 | 10.462 | 11.759  | 33.939 | 1.00 | 12.80 |
| ATOM | 747  | CE2 | TYR | A | 229 | 10.619 | 10.382  | 32.038 | 1.00 | 13.97 |
| ATOM | 748  | CD2 | TYR | A | 229 | 10.621 | 9.122   | 31.453 | 1.00 | 14.34 |
| ATOM | 749  | C   | TYR | A | 229 | 8.040  | 6.241   | 31.825 | 1.00 | 13.03 |
| ATOM | 750  | O   | TYR | A | 229 | 7.563  | 6.434   | 30.711 | 1.00 | 15.41 |
| ATOM | 751  | N   | ALA | A | 230 | 7.409  | 6.604   | 32.927 | 1.00 | 11.02 |
| ATOM | 752  | CA  | ALA | A | 230 | 6.122  | 7.273   | 32.836 | 1.00 | 14.49 |
| ATOM | 753  | CB  | ALA | A | 230 | 5.132  | 6.562   | 33.707 | 1.00 | 14.72 |
| ATOM | 754  | C   | ALA | A | 230 | 6.197  | 8.786   | 33.175 | 1.00 | 18.02 |
| ATOM | 755  | O   | ALA | A | 230 | 5.917  | 9.197   | 34.306 | 1.00 | 22.60 |
| ATOM | 756  | N   | ASN | A | 231 | 6.566  | 9.594   | 32.178 | 1.00 | 16.28 |
| ATOM | 757  | CA  | ASN | A | 231 | 6.748  | 11.042  | 32.298 | 1.00 | 15.09 |
| ATOM | 758  | CB  | ASN | A | 231 | 6.626  | 11.692  | 30.917 | 1.00 | 22.58 |
| ATOM | 759  | CG  | ASN | A | 231 | 7.770  | 11.328  | 29.980 | 1.00 | 29.16 |
| ATOM | 760  | OD1 | ASN | A | 231 | 8.741  | 12.089  | 29.832 | 1.00 | 31.83 |
| ATOM | 761  | ND2 | ASN | A | 231 | 7.648  | 10.175  | 29.315 | 1.00 | 30.67 |
| ATOM | 762  | C   | ASN | A | 231 | 5.806  | 11.792  | 33.249 | 1.00 | 15.62 |
| ATOM | 763  | O   | ASN | A | 231 | 6.221  | 12.776  | 33.889 | 1.00 | 16.15 |
| ATOM | 764  | N   | GLY | A | 232 | 4.550  | 11.342  | 33.328 | 1.00 | 13.50 |
| ATOM | 765  | CA  | GLY | A | 232 | 3.486  | 12.078  | 34.001 | 1.00 | 13.31 |
| ATOM | 766  | C   | GLY | A | 232 | 3.313  | 11.864  | 35.497 | 1.00 | 15.07 |
| ATOM | 767  | O   | GLY | A | 232 | 2.338  | 12.348  | 36.087 | 1.00 | 16.07 |
| ATOM | 768  | N   | GLY | A | 233 | 4.240  | 11.133  | 36.112 | 1.00 | 12.98 |
| ATOM | 769  | CA  | GLY | A | 233 | 4.255  | 10.975  | 37.554 | 1.00 | 14.96 |

FIGURE 3 (Cont.)

|  | A | B | C | D | E | F | G | H | I | J |
|---|---|---|---|---|---|---|---|---|---|---|
| ATOM | 770 | C | GLY | A | 233 | 3.155 | 10.090 | 38.089 | 1.00 | 16.36 |
| ATOM | 771 | O | GLY | A | 233 | 2.380 | 9.532 | 37.315 | 1.00 | 17.11 |
| ATOM | 772 | N | GLU | A | 234 | 3.095 | 9.945 | 39.413 | 1.00 | 16.83 |
| ATOM | 773 | CA | GLU | A | 234 | 2.067 | 9.111 | 40.031 | 1.00 | 14.46 |
| ATOM | 774 | CB | GLU | A | 234 | 2.517 | 8.542 | 41.364 | 1.00 | 15.78 |
| ATOM | 775 | CG | GLU | A | 234 | 4.009 | 8.550 | 41.626 | 1.00 | 19.92 |
| ATOM | 776 | CD | GLU | A | 234 | 4.294 | 8.254 | 43.088 | 1.00 | 22.18 |
| ATOM | 777 | OE1 | GLU | A | 234 | 4.054 | 9.154 | 43.923 | 1.00 | 25.14 |
| ATOM | 778 | OE2 | GLU | A | 234 | 4.730 | 7.125 | 43.412 | 1.00 | 20.01 |
| ATOM | 779 | C | GLU | A | 234 | 0.783 | 9.888 | 40.241 | 1.00 | 12.81 |
| ATOM | 780 | O | GLU | A | 234 | 0.801 | 11.115 | 40.343 | 1.00 | 12.19 |
| ATOM | 781 | N | LEU | A | 235 | -0.336 | 9.174 | 40.304 | 1.00 | 10.87 |
| ATOM | 782 | CA | LEU | A | 235 | -1.612 | 9.834 | 40.515 | 1.00 | 8.65 |
| ATOM | 783 | CB | LEU | A | 235 | -2.779 | 8.853 | 40.438 | 1.00 | 4.06 |
| ATOM | 784 | CG | LEU | A | 235 | -3.327 | 8.660 | 39.022 | 1.00 | 2.00 |
| ATOM | 785 | CD1 | LEU | A | 235 | -4.546 | 7.765 | 39.018 | 1.00 | 2.00 |
| ATOM | 786 | CD2 | LEU | A | 235 | -3.660 | 9.994 | 38.368 | 1.00 | 2.00 |
| ATOM | 787 | C | LEU | A | 235 | -1.574 | 10.540 | 41.849 | 1.00 | 10.95 |
| ATOM | 788 | O | LEU | A | 235 | -2.066 | 11.657 | 41.956 | 1.00 | 12.05 |
| ATOM | 789 | N | PHE | A | 236 | -0.950 | 9.892 | 42.842 | 1.00 | 13.16 |
| ATOM | 790 | CA | PHE | A | 236 | -0.726 | 10.459 | 44.178 | 1.00 | 10.40 |
| ATOM | 791 | CB | PHE | A | 236 | 0.233 | 9.585 | 44.996 | 1.00 | 14.94 |
| ATOM | 792 | CG | PHE | A | 236 | 0.599 | 10.166 | 46.355 | 1.00 | 17.86 |
| ATOM | 793 | CD1 | PHE | A | 236 | -0.291 | 10.106 | 47.423 | 1.00 | 19.44 |
| ATOM | 794 | CE1 | PHE | A | 236 | 0.044 | 10.636 | 48.668 | 1.00 | 20.09 |
| ATOM | 795 | CZ | PHE | A | 236 | 1.284 | 11.227 | 48.859 | 1.00 | 19.46 |
| ATOM | 796 | CE2 | PHE | A | 236 | 2.186 | 11.287 | 47.809 | 1.00 | 19.27 |
| ATOM | 797 | CD2 | PHE | A | 236 | 1.841 | 10.759 | 46.565 | 1.00 | 19.97 |
| ATOM | 798 | C | PHE | A | 236 | -0.156 | 11.852 | 44.099 | 1.00 | 6.28 |
| ATOM | 799 | O | PHE | A | 236 | -0.570 | 12.726 | 44.840 | 1.00 | 8.31 |
| ATOM | 800 | N | PHE | A | 237 | 0.799 | 12.052 | 43.204 | 1.00 | 3.82 |
| ATOM | 801 | CA | PHE | A | 237 | 1.404 | 13.353 | 43.026 | 1.00 | 2.00 |
| ATOM | 802 | CB | PHE | A | 237 | 2.431 | 13.302 | 41.927 | 1.00 | 2.00 |
| ATOM | 803 | CG | PHE | A | 237 | 3.076 | 14.617 | 41.658 | 1.00 | 5.97 |
| ATOM | 804 | CD1 | PHE | A | 237 | 4.224 | 14.995 | 42.347 | 1.00 | 7.67 |
| ATOM | 805 | CE1 | PHE | A | 237 | 4.842 | 16.202 | 42.088 | 1.00 | 5.23 |
| ATOM | 806 | CZ | PHE | A | 237 | 4.310 | 17.058 | 41.146 | 1.00 | 4.52 |
| ATOM | 807 | CE2 | PHE | A | 237 | 3.166 | 16.702 | 40.461 | 1.00 | 5.86 |
| ATOM | 808 | CD2 | PHE | A | 237 | 2.547 | 15.487 | 40.719 | 1.00 | 5.21 |
| ATOM | 809 | C | PHE | A | 237 | 0.372 | 14.413 | 42.695 | 1.00 | 2.00 |
| ATOM | 810 | O | PHE | A | 237 | 0.288 | 15.421 | 43.379 | 1.00 | 2.15 |
| ATOM | 811 | N | HIS | A | 238 | -0.403 | 14.176 | 41.642 | 1.00 | 4.82 |
| ATOM | 812 | CA | HIS | A | 238 | -1.428 | 15.114 | 41.174 | 1.00 | 8.42 |
| ATOM | 813 | CB | HIS | A | 238 | -2.038 | 14.593 | 39.882 | 1.00 | 8.32 |
| ATOM | 814 | CG | HIS | A | 238 | -1.036 | 14.438 | 38.794 | 1.00 | 9.16 |
| ATOM | 815 | ND1 | HIS | A | 238 | -0.527 | 15.513 | 38.102 | 1.00 | 11.04 |
| ATOM | 816 | CE1 | HIS | A | 238 | 0.358 | 15.085 | 37.219 | 1.00 | 10.69 |
| ATOM | 817 | NE2 | HIS | A | 238 | 0.454 | 13.772 | 37.327 | 1.00 | 10.36 |
| ATOM | 818 | CD2 | HIS | A | 238 | -0.399 | 13.344 | 38.316 | 1.00 | 11.22 |
| ATOM | 819 | C | HIS | A | 238 | -2.523 | 15.362 | 42.196 | 1.00 | 8.33 |
| ATOM | 820 | O | HIS | A | 238 | -2.751 | 16.482 | 42.620 | 1.00 | 9.16 |
| ATOM | 821 | N | LEU | A | 239 | -3.196 | 14.296 | 42.585 | 1.00 | 12.07 |

FIGURE 3 (Cont.)

|      | A    | B   | C   | D | E   | F       | G      | H      | I    | J     |
|------|------|-----|-----|---|-----|---------|--------|--------|------|-------|
| ATOM | 822  | CA  | LEU | A | 239 | -4.176  | 14.325 | 43.656 | 1.00 | 13.95 |
| ATOM | 823  | CB  | LEU | A | 239 | -4.564  | 12.887 | 44.008 | 1.00 | 12.97 |
| ATOM | 824  | CG  | LEU | A | 239 | -6.041  | 12.617 | 44.265 | 1.00 | 13.93 |
| ATOM | 825  | CD1 | LEU | A | 239 | -6.956  | 13.590 | 43.540 | 1.00 | 10.64 |
| ATOM | 826  | CD2 | LEU | A | 239 | -6.333  | 11.202 | 43.852 | 1.00 | 16.40 |
| ATOM | 827  | C   | LEU | A | 239 | -3.751  | 15.077 | 44.930 | 1.00 | 13.76 |
| ATOM | 828  | O   | LEU | A | 239 | -4.594  | 15.384 | 45.760 | 1.00 | 18.08 |
| ATOM | 829  | N   | SER | A | 240 | -2.461  | 15.352 | 45.102 | 1.00 | 11.93 |
| ATOM | 830  | CA  | SER | A | 240 | -2.009  | 16.191 | 46.210 | 1.00 | 13.43 |
| ATOM | 831  | CB  | SER | A | 240 | -0.529  | 15.952 | 46.513 | 1.00 | 18.66 |
| ATOM | 832  | OG  | SER | A | 240 | -0.283  | 14.620 | 46.909 | 1.00 | 24.83 |
| ATOM | 833  | C   | SER | A | 240 | -2.200  | 17.664 | 45.867 | 1.00 | 12.02 |
| ATOM | 834  | O   | SER | A | 240 | -2.536  | 18.469 | 46.732 | 1.00 | 10.52 |
| ATOM | 835  | N   | ARG | A | 241 | -1.967  | 17.983 | 44.594 | 1.00 | 10.21 |
| ATOM | 836  | CA  | ARG | A | 241 | -1.998  | 19.328 | 44.057 | 1.00 | 9.84  |
| ATOM | 837  | CB  | ARG | A | 241 | -1.076  | 19.410 | 42.844 | 1.00 | 12.11 |
| ATOM | 838  | CG  | ARG | A | 241 | 0.381   | 19.716 | 43.172 | 1.00 | 17.30 |
| ATOM | 839  | CD  | ARG | A | 241 | 1.402   | 18.766 | 42.527 | 1.00 | 20.90 |
| ATOM | 840  | NE  | ARG | A | 241 | 2.154   | 17.955 | 43.500 | 1.00 | 19.01 |
| ATOM | 841  | CZ  | ARG | A | 241 | 3.309   | 18.320 | 44.059 | 1.00 | 19.63 |
| ATOM | 842  | NH1 | ARG | A | 241 | 3.883   | 19.494 | 43.752 | 1.00 | 19.40 |
| ATOM | 843  | NH2 | ARG | A | 241 | 3.897   | 17.500 | 44.920 | 1.00 | 18.01 |
| ATOM | 844  | C   | ARG | A | 241 | -3.403  | 19.756 | 43.655 | 1.00 | 14.03 |
| ATOM | 845  | O   | ARG | A | 241 | -3.767  | 20.911 | 43.832 | 1.00 | 14.10 |
| ATOM | 846  | N   | GLU | A | 242 | -4.186  | 18.832 | 43.101 | 1.00 | 19.47 |
| ATOM | 847  | CA  | GLU | A | 242 | -5.552  | 19.135 | 42.669 | 1.00 | 22.54 |
| ATOM | 848  | CB  | GLU | A | 242 | -5.892  | 18.440 | 41.363 | 1.00 | 30.13 |
| ATOM | 849  | CG  | GLU | A | 242 | -4.730  | 18.361 | 40.393 | 1.00 | 42.01 |
| ATOM | 850  | CD  | GLU | A | 242 | -4.881  | 19.313 | 39.233 | 1.00 | 48.30 |
| ATOM | 851  | OE1 | GLU | A | 242 | -5.932  | 20.000 | 39.171 | 1.00 | 50.47 |
| ATOM | 852  | OE2 | GLU | A | 242 | -3.950  | 19.361 | 38.387 | 1.00 | 53.05 |
| ATOM | 853  | C   | GLU | A | 242 | -6.555  | 18.731 | 43.722 | 1.00 | 20.62 |
| ATOM | 854  | O   | GLU | A | 242 | -7.710  | 19.133 | 43.664 | 1.00 | 26.70 |
| ATOM | 855  | N   | ARG | A | 243 | -6.111  | 17.924 | 44.672 | 1.00 | 15.81 |
| ATOM | 856  | CA  | ARG | A | 243 | -6.871  | 17.622 | 45.882 | 1.00 | 14.63 |
| ATOM | 857  | CB  | ARG | A | 243 | -7.189  | 18.882 | 46.684 | 1.00 | 16.82 |
| ATOM | 858  | CG  | ARG | A | 243 | -6.375  | 18.997 | 47.982 | 1.00 | 22.96 |
| ATOM | 859  | CD  | ARG | A | 243 | -5.385  | 20.163 | 48.033 | 1.00 | 21.92 |
| ATOM | 860  | NE  | ARG | A | 243 | -5.356  | 20.849 | 49.332 | 1.00 | 24.97 |
| ATOM | 861  | CZ  | ARG | A | 243 | -5.929  | 22.033 | 49.580 | 1.00 | 27.07 |
| ATOM | 862  | NH1 | ARG | A | 243 | -6.595  | 22.668 | 48.619 | 1.00 | 29.02 |
| ATOM | 863  | NH2 | ARG | A | 243 | -5.838  | 22.593 | 50.786 | 1.00 | 24.52 |
| ATOM | 864  | C   | ARG | A | 243 | -8.108  | 16.762 | 45.703 | 1.00 | 13.45 |
| ATOM | 865  | O   | ARG | A | 243 | -8.341  | 15.892 | 46.531 | 1.00 | 21.66 |
| ATOM | 866  | N   | VAL | A | 244 | -8.880  | 16.971 | 44.637 | 1.00 | 8.26  |
| ATOM | 867  | CA  | VAL | A | 244 | -10.011 | 16.088 | 44.277 | 1.00 | 5.77  |
| ATOM | 868  | CB  | VAL | A | 244 | -11.286 | 16.455 | 45.077 | 1.00 | 2.00  |
| ATOM | 869  | CG1 | VAL | A | 244 | -11.374 | 17.915 | 45.227 | 1.00 | 4.93  |
| ATOM | 870  | CG2 | VAL | A | 244 | -12.541 | 15.963 | 44.399 | 1.00 | 4.11  |
| ATOM | 871  | C   | VAL | A | 244 | -10.286 | 16.096 | 42.748 | 1.00 | 6.46  |
| ATOM | 872  | O   | VAL | A | 244 | -10.305 | 17.172 | 42.139 | 1.00 | 7.16  |
| ATOM | 873  | N   | PHE | A | 245 | -10.480 | 14.918 | 42.135 | 1.00 | 2.00  |

FIGURE 3 (Cont.)

| | A | B | C | D | E | F | G | H | I | J |
|---|---|---|---|---|---|---|---|---|---|---|
| ATOM | 874 | CA | PHE | A | 245 | -10.780 | 14.833 | 40.699 | 1.00 | 2.00 |
| ATOM | 875 | CB | PHE | A | 245 | -10.310 | 13.508 | 40.105 | 1.00 | 2.00 |
| ATOM | 876 | CG | PHE | A | 245 | -8.821 | 13.357 | 40.026 | 1.00 | 2.09 |
| ATOM | 877 | CD1 | PHE | A | 245 | -7.966 | 14.448 | 40.238 | 1.00 | 2.13 |
| ATOM | 878 | CE1 | PHE | A | 245 | -6.571 | 14.303 | 40.166 | 1.00 | 2.00 |
| ATOM | 879 | CZ | PHE | A | 245 | -6.030 | 13.054 | 39.879 | 1.00 | 2.35 |
| ATOM | 880 | CE2 | PHE | A | 245 | -6.874 | 11.948 | 39.649 | 1.00 | 2.11 |
| ATOM | 881 | CD2 | PHE | A | 245 | -8.260 | 12.106 | 39.729 | 1.00 | 3.36 |
| ATOM | 882 | C | PHE | A | 245 | -12.271 | 14.998 | 40.372 | 1.00 | 4.17 |
| ATOM | 883 | O | PHE | A | 245 | -13.155 | 14.592 | 41.146 | 1.00 | 5.50 |
| ATOM | 884 | N | SER | A | 246 | -12.554 | 15.582 | 39.211 | 1.00 | 2.00 |
| ATOM | 885 | CA | SER | A | 246 | -13.912 | 15.586 | 38.715 | 1.00 | 2.00 |
| ATOM | 886 | CB | SER | A | 246 | -14.002 | 16.351 | 37.416 | 1.00 | 3.48 |
| ATOM | 887 | OG | SER | A | 246 | -13.388 | 15.626 | 36.369 | 1.00 | 6.69 |
| ATOM | 888 | C | SER | A | 246 | -14.239 | 14.154 | 38.459 | 1.00 | 3.42 |
| ATOM | 889 | O | SER | A | 246 | -13.352 | 13.378 | 38.120 | 1.00 | 8.90 |
| ATOM | 890 | N | GLU | A | 247 | -15.501 | 13.790 | 38.623 | 1.00 | 8.83 |
| ATOM | 891 | CA | GLU | A | 247 | -15.931 | 12.424 | 38.336 | 1.00 | 11.81 |
| ATOM | 892 | CB | GLU | A | 247 | -17.428 | 12.265 | 38.534 | 1.00 | 14.51 |
| ATOM | 893 | CG | GLU | A | 247 | -17.818 | 12.126 | 39.992 | 1.00 | 20.39 |
| ATOM | 894 | CD | GLU | A | 247 | -19.195 | 12.685 | 40.300 | 1.00 | 22.98 |
| ATOM | 895 | OE1 | GLU | A | 247 | -20.079 | 12.623 | 39.409 | 1.00 | 24.75 |
| ATOM | 896 | OE2 | GLU | A | 247 | -19.388 | 13.173 | 41.443 | 1.00 | 23.79 |
| ATOM | 897 | C | GLU | A | 247 | -15.542 | 12.043 | 36.923 | 1.00 | 13.67 |
| ATOM | 898 | O | GLU | A | 247 | -15.065 | 10.945 | 36.693 | 1.00 | 11.40 |
| ATOM | 899 | N | ASP | A | 248 | -15.710 | 12.972 | 35.986 | 1.00 | 20.80 |
| ATOM | 900 | CA | ASP | A | 248 | -15.310 | 12.735 | 34.603 | 1.00 | 27.14 |
| ATOM | 901 | CB | ASP | A | 248 | -15.789 | 13.862 | 33.678 | 1.00 | 33.47 |
| ATOM | 902 | CG | ASP | A | 248 | -16.577 | 13.336 | 32.468 | 1.00 | 41.51 |
| ATOM | 903 | OD1 | ASP | A | 248 | -17.114 | 14.184 | 31.709 | 1.00 | 44.30 |
| ATOM | 904 | OD2 | ASP | A | 248 | -16.712 | 12.104 | 32.195 | 1.00 | 42.84 |
| ATOM | 905 | C | ASP | A | 248 | -13.804 | 12.457 | 34.438 | 1.00 | 26.38 |
| ATOM | 906 | O | ASP | A | 248 | -13.402 | 11.775 | 33.492 | 1.00 | 27.22 |
| ATOM | 907 | N | ARG | A | 249 | -12.982 | 12.973 | 35.356 | 1.00 | 23.02 |
| ATOM | 908 | CA | ARG | A | 249 | -11.557 | 12.671 | 35.338 | 1.00 | 18.30 |
| ATOM | 909 | CB | ARG | A | 249 | -10.719 | 13.771 | 35.989 | 1.00 | 21.33 |
| ATOM | 910 | CG | ARG | A | 249 | -9.210 | 13.504 | 35.948 | 1.00 | 26.93 |
| ATOM | 911 | CD | ARG | A | 249 | -8.307 | 14.713 | 36.270 | 1.00 | 30.97 |
| ATOM | 912 | NE | ARG | A | 249 | -6.894 | 14.318 | 36.364 | 1.00 | 31.18 |
| ATOM | 913 | CZ | ARG | A | 249 | -5.902 | 15.117 | 36.763 | 1.00 | 33.25 |
| ATOM | 914 | NH1 | ARG | A | 249 | -6.139 | 16.376 | 37.124 | 1.00 | 32.63 |
| ATOM | 915 | NH2 | ARG | A | 249 | -4.657 | 14.653 | 36.797 | 1.00 | 33.88 |
| ATOM | 916 | C | ARG | A | 249 | -11.310 | 11.341 | 36.014 | 1.00 | 15.86 |
| ATOM | 917 | O | ARG | A | 249 | -10.461 | 10.582 | 35.566 | 1.00 | 17.48 |
| ATOM | 918 | N | ALA | A | 250 | -12.049 | 11.046 | 37.081 | 1.00 | 11.34 |
| ATOM | 919 | CA | ALA | A | 250 | -11.860 | 9.773 | 37.779 | 1.00 | 10.56 |
| ATOM | 920 | CB | ALA | A | 250 | -12.478 | 9.796 | 39.150 | 1.00 | 7.55 |
| ATOM | 921 | C | ALA | A | 250 | -12.433 | 8.641 | 36.960 | 1.00 | 12.21 |
| ATOM | 922 | O | ALA | A | 250 | -11.911 | 7.536 | 36.975 | 1.00 | 13.09 |
| ATOM | 923 | N | ARG | A | 251 | -13.513 | 8.934 | 36.243 | 1.00 | 16.78 |
| ATOM | 924 | CA | ARG | A | 251 | -14.131 | 7.984 | 35.326 | 1.00 | 18.77 |
| ATOM | 925 | CB | ARG | A | 251 | -15.262 | 8.657 | 34.547 | 1.00 | 20.30 |

FIGURE 3 (Cont.)

| | A | B | C | D | E | F | G | H | I | J |
|---|---|---|---|---|---|---|---|---|---|---|
| ATOM | 926 | CG | ARG | A | 251 | -16.267 | 7.733 | 33.894 | 1.00 | 21.32 |
| ATOM | 927 | CD | ARG | A | 251 | -17.293 | 8.481 | 33.035 | 1.00 | 26.36 |
| ATOM | 928 | NE | ARG | A | 251 | -17.956 | 9.566 | 33.763 | 1.00 | 29.99 |
| ATOM | 929 | CZ | ARG | A | 251 | -18.696 | 9.404 | 34.869 | 1.00 | 32.84 |
| ATOM | 930 | NH1 | ARG | A | 251 | -18.877 | 8.187 | 35.382 | 1.00 | 31.79 |
| ATOM | 931 | NH2 | ARG | A | 251 | -19.257 | 10.463 | 35.470 | 1.00 | 31.78 |
| ATOM | 932 | C | ARG | A | 251 | -13.046 | 7.514 | 34.381 | 1.00 | 18.69 |
| ATOM | 933 | O | ARG | A | 251 | -12.886 | 6.313 | 34.179 | 1.00 | 21.73 |
| ATOM | 934 | N | PHE | A | 252 | -12.277 | 8.465 | 33.848 | 1.00 | 14.28 |
| ATOM | 935 | CA | PHE | A | 252 | -11.204 | 8.152 | 32.919 | 1.00 | 11.87 |
| ATOM | 936 | CB | PHE | A | 252 | -10.573 | 9.414 | 32.341 | 1.00 | 13.19 |
| ATOM | 937 | CG | PHE | A | 252 | -9.379 | 9.132 | 31.496 | 1.00 | 15.31 |
| ATOM | 938 | CD1 | PHE | A | 252 | -9.521 | 8.802 | 30.164 | 1.00 | 19.60 |
| ATOM | 939 | CE1 | PHE | A | 252 | -8.410 | 8.506 | 29.385 | 1.00 | 22.22 |
| ATOM | 940 | CZ | PHE | A | 252 | -7.143 | 8.528 | 29.947 | 1.00 | 20.67 |
| ATOM | 941 | CE2 | PHE | A | 252 | -6.997 | 8.842 | 31.271 | 1.00 | 20.37 |
| ATOM | 942 | CD2 | PHE | A | 252 | -8.115 | 9.132 | 32.042 | 1.00 | 17.82 |
| ATOM | 943 | C | PHE | A | 252 | -10.099 | 7.253 | 33.491 | 1.00 | 10.80 |
| ATOM | 944 | O | PHE | A | 252 | -9.635 | 6.349 | 32.805 | 1.00 | 13.98 |
| ATOM | 945 | N | TYR | A | 253 | -9.653 | 7.507 | 34.717 | 1.00 | 5.62 |
| ATOM | 946 | CA | TYR | A | 253 | -8.592 | 6.691 | 35.278 | 1.00 | 2.59 |
| ATOM | 947 | CB | TYR | A | 253 | -7.932 | 7.381 | 36.459 | 1.00 | 2.00 |
| ATOM | 948 | CG | TYR | A | 253 | -7.201 | 8.630 | 36.052 | 1.00 | 2.22 |
| ATOM | 949 | CD1 | TYR | A | 253 | -6.435 | 8.667 | 34.884 | 1.00 | 2.00 |
| ATOM | 950 | CE1 | TYR | A | 253 | -5.774 | 9.820 | 34.490 | 1.00 | 2.00 |
| ATOM | 951 | CZ | TYR | A | 253 | -5.877 | 10.966 | 35.260 | 1.00 | 4.68 |
| ATOM | 952 | OH | TYR | A | 253 | -5.219 | 12.119 | 34.887 | 1.00 | 5.21 |
| ATOM | 953 | CE2 | TYR | A | 253 | -6.634 | 10.961 | 36.432 | 1.00 | 7.42 |
| ATOM | 954 | CD2 | TYR | A | 253 | -7.290 | 9.790 | 36.820 | 1.00 | 5.43 |
| ATOM | 955 | C | TYR | A | 253 | -9.128 | 5.326 | 35.660 | 1.00 | 6.96 |
| ATOM | 956 | O | TYR | A | 253 | -8.486 | 4.304 | 35.397 | 1.00 | 9.53 |
| ATOM | 957 | N | GLY | A | 254 | -10.324 | 5.317 | 36.248 | 1.00 | 9.33 |
| ATOM | 958 | CA | GLY | A | 254 | -10.981 | 4.100 | 36.693 | 1.00 | 7.25 |
| ATOM | 959 | C | GLY | A | 254 | -11.173 | 3.127 | 35.555 | 1.00 | 8.88 |
| ATOM | 960 | O | GLY | A | 254 | -10.852 | 1.945 | 35.693 | 1.00 | 7.60 |
| ATOM | 961 | N | ALA | A | 255 | -11.675 | 3.639 | 34.428 | 1.00 | 10.17 |
| ATOM | 962 | CA | ALA | A | 255 | -11.881 | 2.850 | 33.206 | 1.00 | 7.78 |
| ATOM | 963 | CB | ALA | A | 255 | -12.416 | 3.713 | 32.084 | 1.00 | 3.52 |
| ATOM | 964 | C | ALA | A | 255 | -10.594 | 2.178 | 32.778 | 1.00 | 7.86 |
| ATOM | 965 | O | ALA | A | 255 | -10.574 | 0.972 | 32.517 | 1.00 | 8.42 |
| ATOM | 966 | N | GLU | A | 256 | -9.512 | 2.950 | 32.733 | 1.00 | 7.56 |
| ATOM | 967 | CA | GLU | A | 256 | -8.230 | 2.377 | 32.353 | 1.00 | 10.01 |
| ATOM | 968 | CB | GLU | A | 256 | -7.199 | 3.457 | 32.059 | 1.00 | 11.01 |
| ATOM | 969 | CG | GLU | A | 256 | -7.545 | 4.199 | 30.781 | 1.00 | 19.08 |
| ATOM | 970 | CD | GLU | A | 256 | -6.481 | 5.175 | 30.310 | 1.00 | 24.92 |
| ATOM | 971 | OE1 | GLU | A | 256 | -5.593 | 5.559 | 31.111 | 1.00 | 28.83 |
| ATOM | 972 | OE2 | GLU | A | 256 | -6.545 | 5.565 | 29.121 | 1.00 | 25.17 |
| ATOM | 973 | C | GLU | A | 256 | -7.744 | 1.345 | 33.368 | 1.00 | 9.76 |
| ATOM | 974 | O | GLU | A | 256 | -7.340 | 0.257 | 32.988 | 1.00 | 13.11 |
| ATOM | 975 | N | ILE | A | 257 | -7.828 | 1.653 | 34.653 | 1.00 | 7.54 |
| ATOM | 976 | CA | ILE | A | 257 | -7.418 | 0.691 | 35.662 | 1.00 | 7.64 |
| ATOM | 977 | CB | ILE | A | 257 | -7.542 | 1.315 | 37.059 | 1.00 | 11.05 |

FIGURE 3 (Cont.)

| | A | B | C | D | E | F | G | H | I | J |
|---|---|---|---|---|---|---|---|---|---|---|
| ATOM | 978 | CG1 | ILE | A | 257 | -6.443 | 2.378 | 37.227 | 1.00 | 12.52 |
| ATOM | 979 | CD1 | ILE | A | 257 | -6.872 | 3.595 | 37.959 | 1.00 | 10.73 |
| ATOM | 980 | CG2 | ILE | A | 257 | -7.479 | 0.239 | 38.153 | 1.00 | 8.70 |
| ATOM | 981 | C | ILE | A | 257 | -8.216 | -0.606 | 35.528 | 1.00 | 8.16 |
| ATOM | 982 | O | ILE | A | 257 | -7.633 | -1.696 | 35.466 | 1.00 | 7.37 |
| ATOM | 983 | N | VAL | A | 258 | -9.541 | -0.477 | 35.441 | 1.00 | 9.01 |
| ATOM | 984 | CA | VAL | A | 258 | -10.429 | -1.631 | 35.268 | 1.00 | 7.18 |
| ATOM | 985 | CB | VAL | A | 258 | -11.902 | -1.241 | 35.119 | 1.00 | 2.93 |
| ATOM | 986 | CG1 | VAL | A | 258 | -12.702 | -2.442 | 34.690 | 1.00 | 2.00 |
| ATOM | 987 | CG2 | VAL | A | 258 | -12.443 | -0.704 | 36.420 | 1.00 | 2.00 |
| ATOM | 988 | C | VAL | A | 258 | -10.025 | -2.461 | 34.061 | 1.00 | 8.66 |
| ATOM | 989 | O | VAL | A | 258 | -9.829 | -3.673 | 34.189 | 1.00 | 10.98 |
| ATOM | 990 | N | SER | A | 259 | -9.895 | -1.811 | 32.905 | 1.00 | 6.46 |
| ATOM | 991 | CA | SER | A | 259 | -9.383 | -2.479 | 31.713 | 1.00 | 8.54 |
| ATOM | 992 | CB | SER | A | 259 | -9.007 | -1.478 | 30.620 | 1.00 | 11.72 |
| ATOM | 993 | OG | SER | A | 259 | -8.323 | -2.138 | 29.557 | 1.00 | 14.31 |
| ATOM | 994 | C | SER | A | 259 | -8.160 | -3.321 | 32.036 | 1.00 | 7.89 |
| ATOM | 995 | O | SER | A | 259 | -8.147 | -4.516 | 31.797 | 1.00 | 11.33 |
| ATOM | 996 | N | ALA | A | 260 | -7.142 | -2.687 | 32.594 | 1.00 | 6.11 |
| ATOM | 997 | CA | ALA | A | 260 | -5.876 | -3.338 | 32.824 | 1.00 | 5.59 |
| ATOM | 998 | CB | ALA | A | 260 | -4.876 | -2.352 | 33.368 | 1.00 | 5.91 |
| ATOM | 999 | C | ALA | A | 260 | -6.031 | -4.520 | 33.759 | 1.00 | 8.69 |
| ATOM | 1000 | O | ALA | A | 260 | -5.489 | -5.595 | 33.464 | 1.00 | 10.96 |
| ATOM | 1001 | N | LEU | A | 261 | -6.767 | -4.328 | 34.863 | 1.00 | 5.59 |
| ATOM | 1002 | CA | LEU | A | 261 | -6.969 | -5.387 | 35.856 | 1.00 | 7.05 |
| ATOM | 1003 | CB | LEU | A | 261 | -7.781 | -4.889 | 37.047 | 1.00 | 7.02 |
| ATOM | 1004 | CG | LEU | A | 261 | -7.135 | -3.979 | 38.088 | 1.00 | 9.71 |
| ATOM | 1005 | CD1 | LEU | A | 261 | -8.208 | -3.459 | 39.027 | 1.00 | 8.51 |
| ATOM | 1006 | CD2 | LEU | A | 261 | -6.009 | -4.660 | 38.872 | 1.00 | 7.95 |
| ATOM | 1007 | C | LEU | A | 261 | -7.723 | -6.547 | 35.235 | 1.00 | 9.57 |
| ATOM | 1008 | O | LEU | A | 261 | -7.393 | -7.722 | 35.440 | 1.00 | 10.43 |
| ATOM | 1009 | N | ASP | A | 262 | -8.756 | -6.200 | 34.478 | 1.00 | 10.73 |
| ATOM | 1010 | CA | ASP | A | 262 | -9.573 | -7.188 | 33.799 | 1.00 | 12.07 |
| ATOM | 1011 | CB | ASP | A | 262 | -10.561 | -6.493 | 32.856 | 1.00 | 11.69 |
| ATOM | 1012 | CG | ASP | A | 262 | -11.169 | -7.440 | 31.858 | 1.00 | 11.58 |
| ATOM | 1013 | OD1 | ASP | A | 262 | -11.173 | -7.117 | 30.646 | 1.00 | 9.76 |
| ATOM | 1014 | OD2 | ASP | A | 262 | -11.654 | -8.537 | 32.206 | 1.00 | 14.40 |
| ATOM | 1015 | C | ASP | A | 262 | -8.671 | -8.135 | 33.022 | 1.00 | 11.58 |
| ATOM | 1016 | O | ASP | A | 262 | -8.883 | -9.349 | 33.023 | 1.00 | 13.83 |
| ATOM | 1017 | N | TYR | A | 263 | -7.660 | -7.562 | 32.372 | 1.00 | 9.31 |
| ATOM | 1018 | CA | TYR | A | 263 | -6.749 | -8.306 | 31.519 | 1.00 | 6.69 |
| ATOM | 1019 | CB | TYR | A | 263 | -5.926 | -7.343 | 30.663 | 1.00 | 5.18 |
| ATOM | 1020 | CG | TYR | A | 263 | -4.620 | -7.885 | 30.157 | 1.00 | 5.20 |
| ATOM | 1021 | CD1 | TYR | A | 263 | -4.578 | -8.776 | 29.104 | 1.00 | 3.18 |
| ATOM | 1022 | CE1 | TYR | A | 263 | -3.378 | -9.273 | 28.640 | 1.00 | 3.93 |
| ATOM | 1023 | CZ | TYR | A | 263 | -2.198 | -8.865 | 29.219 | 1.00 | 5.10 |
| ATOM | 1024 | OH | TYR | A | 263 | -1.002 | -9.365 | 28.762 | 1.00 | 8.97 |
| ATOM | 1025 | CE2 | TYR | A | 263 | -2.207 | -7.972 | 30.259 | 1.00 | 6.12 |
| ATOM | 1026 | CD2 | TYR | A | 263 | -3.416 | -7.489 | 30.729 | 1.00 | 8.30 |
| ATOM | 1027 | C | TYR | A | 263 | -5.877 | -9.195 | 32.380 | 1.00 | 7.87 |
| ATOM | 1028 | O | TYR | A | 263 | -5.690 | -10.357 | 32.063 | 1.00 | 11.02 |
| ATOM | 1029 | N | LEU | A | 264 | -5.373 | -8.653 | 33.483 | 1.00 | 6.46 |

FIGURE 3 (Cont.)

| | A | B | C | D | E | F | G | H | I | J |
|---|---|---|---|---|---|---|---|---|---|---|
| ATOM | 1030 | CA  | LEU | A | 264 | -4.626 | -9.437  | 34.455 | 1.00 | 3.11 |
| ATOM | 1031 | CB  | LEU | A | 264 | -4.174 | -8.559  | 35.623 | 1.00 | 3.56 |
| ATOM | 1032 | CG  | LEU | A | 264 | -3.016 | -7.591  | 35.355 | 1.00 | 3.38 |
| ATOM | 1033 | CD1 | LEU | A | 264 | -2.798 | -6.686  | 36.564 | 1.00 | 2.00 |
| ATOM | 1034 | CD2 | LEU | A | 264 | -1.741 | -8.350  | 34.956 | 1.00 | 2.00 |
| ATOM | 1035 | C   | LEU | A | 264 | -5.460 | -10.606 | 34.968 | 1.00 | 3.11 |
| ATOM | 1036 | O   | LEU | A | 264 | -5.038 | -11.766 | 34.874 | 1.00 | 5.05 |
| ATOM | 1037 | N   | HIS | A | 265 | -6.646 | -10.310 | 35.493 | 1.00 | 2.00 |
| ATOM | 1038 | CA  | HIS | A | 265 | -7.544 | -11.354 | 35.989 | 1.00 | 2.00 |
| ATOM | 1039 | CB  | HIS | A | 265 | -8.853 | -10.736 | 36.443 | 1.00 | 3.27 |
| ATOM | 1040 | CG  | HIS | A | 265 | -8.749 | -9.974  | 37.722 | 1.00 | 7.09 |
| ATOM | 1041 | ND1 | HIS | A | 265 | -9.858 | -9.550  | 38.424 | 1.00 | 7.78 |
| ATOM | 1042 | CE1 | HIS | A | 265 | -9.466 | -8.906  | 39.509 | 1.00 | 8.06 |
| ATOM | 1043 | NE2 | HIS | A | 265 | -8.144 | -8.889  | 39.532 | 1.00 | 8.28 |
| ATOM | 1044 | CD2 | HIS | A | 265 | -7.671 | -9.560  | 38.431 | 1.00 | 7.75 |
| ATOM | 1045 | C   | HIS | A | 265 | -7.810 | -12.430 | 34.932 | 1.00 | 2.00 |
| ATOM | 1046 | O   | HIS | A | 265 | -7.794 | -13.618 | 35.218 | 1.00 | 2.00 |
| ATOM | 1047 | N   | SER | A | 266 | -8.037 | -11.981 | 33.704 | 1.00 | 3.00 |
| ATOM | 1048 | CA  | SER | A | 266 | -8.193 | -12.842 | 32.545 | 1.00 | 3.05 |
| ATOM | 1049 | CB  | SER | A | 266 | -8.362 | -11.975 | 31.300 | 1.00 | 2.18 |
| ATOM | 1050 | OG  | SER | A | 266 | -7.309 | -12.193 | 30.382 | 1.00 | 2.00 |
| ATOM | 1051 | C   | SER | A | 266 | -7.026 | -13.816 | 32.350 | 1.00 | 4.19 |
| ATOM | 1052 | O   | SER | A | 266 | -7.239 | -14.954 | 31.946 | 1.00 | 2.17 |
| ATOM | 1053 | N   | ARG | A | 267 | -5.804 | -13.348 | 32.619 | 1.00 | 7.93 |
| ATOM | 1054 | CA  | ARG | A | 267 | -4.597 | -14.168 | 32.520 | 1.00 | 9.33 |
| ATOM | 1055 | CB  | ARG | A | 267 | -3.456 | -13.402 | 31.863 | 1.00 | 7.77 |
| ATOM | 1056 | CG  | ARG | A | 267 | -3.908 | -12.468 | 30.772 | 1.00 | 15.83 |
| ATOM | 1057 | CD  | ARG | A | 267 | -3.423 | -12.808 | 29.368 | 1.00 | 22.54 |
| ATOM | 1058 | NE  | ARG | A | 267 | -2.002 | -12.512 | 29.248 | 1.00 | 27.49 |
| ATOM | 1059 | CZ  | ARG | A | 267 | -1.127 | -13.290 | 28.631 | 1.00 | 31.28 |
| ATOM | 1060 | NH1 | ARG | A | 267 | -1.519 | -14.419 | 28.036 | 1.00 | 31.45 |
| ATOM | 1061 | NH2 | ARG | A | 267 |  0.150 | -12.933 | 28.607 | 1.00 | 33.16 |
| ATOM | 1062 | C   | ARG | A | 267 | -4.184 | -14.677 | 33.898 | 1.00 | 13.33 |
| ATOM | 1063 | O   | ARG | A | 267 | -3.032 | -15.060 | 34.112 | 1.00 | 17.32 |
| ATOM | 1064 | N   | ASP | A | 268 | -5.137 | -14.673 | 34.828 | 1.00 | 13.39 |
| ATOM | 1065 | CA  | ASP | A | 268 | -5.019 | -15.386 | 36.101 | 1.00 | 14.93 |
| ATOM | 1066 | CB  | ASP | A | 268 | -4.564 | -16.836 | 35.883 | 1.00 | 17.33 |
| ATOM | 1067 | CG  | ASP | A | 268 | -5.612 | -17.689 | 35.166 | 1.00 | 22.64 |
| ATOM | 1068 | OD1 | ASP | A | 268 | -6.561 | -17.127 | 34.576 | 1.00 | 24.96 |
| ATOM | 1069 | OD2 | ASP | A | 268 | -5.560 | -18.940 | 35.129 | 1.00 | 24.99 |
| ATOM | 1070 | C   | ASP | A | 268 | -4.139 | -14.714 | 37.151 | 1.00 | 15.41 |
| ATOM | 1071 | O   | ASP | A | 268 | -3.770 | -15.340 | 38.150 | 1.00 | 18.69 |
| ATOM | 1072 | N   | VAL | A | 269 | -3.833 | -13.437 | 36.945 | 1.00 | 10.02 |
| ATOM | 1073 | CA  | VAL | A | 269 | -2.963 | -12.720 | 37.858 | 1.00 | 6.59 |
| ATOM | 1074 | CB  | VAL | A | 269 | -1.947 | -11.853 | 37.103 | 1.00 | 7.45 |
| ATOM | 1075 | CG1 | VAL | A | 269 | -1.006 | -11.136 | 38.078 | 1.00 | 7.11 |
| ATOM | 1076 | CG2 | VAL | A | 269 | -1.162 | -12.686 | 36.073 | 1.00 | 5.78 |
| ATOM | 1077 | C   | VAL | A | 269 | -3.820 | -11.807 | 38.673 | 1.00 | 7.01 |
| ATOM | 1078 | O   | VAL | A | 269 | -4.675 | -11.128 | 38.117 | 1.00 | 7.24 |
| ATOM | 1079 | N   | VAL | A | 270 | -3.600 | -11.793 | 39.989 | 1.00 | 9.82 |
| ATOM | 1080 | CA  | VAL | A | 270 | -4.199 | -10.778 | 40.865 | 1.00 | 10.76 |
| ATOM | 1081 | CB  | VAL | A | 270 | -4.728 | -11.355 | 42.156 | 1.00 | 9.09 |

FIGURE 3 (Cont.)

| | A | B | C | D | E | F | G | H | I | J |
|---|---|---|---|---|---|---|---|---|---|---|
| ATOM | 1082 | CG1 | VAL | A | 270 | -5.448 | -10.269 | 42.923 | 1.00 | 6.31 |
| ATOM | 1083 | CG2 | VAL | A | 270 | -5.645 | -12.506 | 41.876 | 1.00 | 10.51 |
| ATOM | 1084 | C | VAL | A | 270 | -3.165 | -9.747 | 41.259 | 1.00 | 13.99 |
| ATOM | 1085 | O | VAL | A | 270 | -2.072 | -10.109 | 41.701 | 1.00 | 17.06 |
| ATOM | 1086 | N | TYR | A | 271 | -3.520 | -8.469 | 41.130 | 1.00 | 15.45 |
| ATOM | 1087 | CA | TYR | A | 271 | -2.553 | -7.386 | 41.287 | 1.00 | 15.75 |
| ATOM | 1088 | CB | TYR | A | 271 | -3.044 | -6.104 | 40.651 | 1.00 | 15.96 |
| ATOM | 1089 | CG | TYR | A | 271 | -2.044 | -4.990 | 40.763 | 1.00 | 17.33 |
| ATOM | 1090 | CD1 | TYR | A | 271 | -0.853 | -5.020 | 40.032 | 1.00 | 16.87 |
| ATOM | 1091 | CE1 | TYR | A | 271 | 0.069 | -3.999 | 40.135 | 1.00 | 17.14 |
| ATOM | 1092 | CZ | TYR | A | 271 | -0.195 | -2.929 | 40.982 | 1.00 | 19.63 |
| ATOM | 1093 | OH | TYR | A | 271 | 0.712 | -1.897 | 41.097 | 1.00 | 22.51 |
| ATOM | 1094 | CE2 | TYR | A | 271 | -1.366 | -2.879 | 41.713 | 1.00 | 18.04 |
| ATOM | 1095 | CD2 | TYR | A | 271 | -2.280 | -3.907 | 41.604 | 1.00 | 18.02 |
| ATOM | 1096 | C | TYR | A | 271 | -2.180 | -7.139 | 42.733 | 1.00 | 16.74 |
| ATOM | 1097 | O | TYR | A | 271 | -1.011 | -7.237 | 43.090 | 1.00 | 20.28 |
| ATOM | 1098 | N | ARG | A | 272 | -3.168 | -6.801 | 43.552 | 1.00 | 17.70 |
| ATOM | 1099 | CA | ARG | A | 272 | -3.025 | -6.850 | 45.013 | 1.00 | 19.65 |
| ATOM | 1100 | CB | ARG | A | 272 | -2.211 | -8.071 | 45.457 | 1.00 | 16.16 |
| ATOM | 1101 | CG | ARG | A | 272 | -2.992 | -9.362 | 45.456 | 1.00 | 14.21 |
| ATOM | 1102 | CD | ARG | A | 272 | -2.515 | -10.347 | 46.493 | 1.00 | 12.14 |
| ATOM | 1103 | NE | ARG | A | 272 | -1.206 | -10.902 | 46.150 | 1.00 | 8.20 |
| ATOM | 1104 | CZ | ARG | A | 272 | -0.507 | -11.709 | 46.933 | 1.00 | 4.92 |
| ATOM | 1105 | NH1 | ARG | A | 272 | -0.983 | -12.049 | 48.125 | 1.00 | 5.63 |
| ATOM | 1106 | NH2 | ARG | A | 272 | 0.668 | -12.175 | 46.528 | 1.00 | 2.00 |
| ATOM | 1107 | C | ARG | A | 272 | -2.440 | -5.629 | 45.682 | 1.00 | 21.67 |
| ATOM | 1108 | O | ARG | A | 272 | -2.510 | -5.522 | 46.896 | 1.00 | 27.94 |
| ATOM | 1109 | N | ASP | A | 273 | -1.863 | -4.708 | 44.924 | 1.00 | 21.64 |
| ATOM | 1110 | CA | ASP | A | 273 | -1.301 | -3.528 | 45.556 | 1.00 | 22.15 |
| ATOM | 1111 | CB | ASP | A | 273 | 0.222 | -3.565 | 45.499 | 1.00 | 28.08 |
| ATOM | 1112 | CG | ASP | A | 273 | 0.876 | -2.895 | 46.720 | 1.00 | 32.52 |
| ATOM | 1113 | OD1 | ASP | A | 273 | 0.151 | -2.595 | 47.702 | 1.00 | 29.10 |
| ATOM | 1114 | OD2 | ASP | A | 273 | 2.109 | -2.631 | 46.770 | 1.00 | 34.26 |
| ATOM | 1115 | C | ASP | A | 273 | -1.826 | -2.217 | 44.995 | 1.00 | 21.77 |
| ATOM | 1116 | O | ASP | A | 273 | -1.147 | -1.197 | 45.045 | 1.00 | 27.34 |
| ATOM | 1117 | N | LEU | A | 274 | -3.045 | -2.228 | 44.481 | 1.00 | 17.73 |
| ATOM | 1118 | CA | LEU | A | 274 | -3.610 | -1.039 | 43.857 | 1.00 | 13.92 |
| ATOM | 1119 | CB | LEU | A | 274 | -5.030 | -1.340 | 43.422 | 1.00 | 9.76 |
| ATOM | 1120 | CG | LEU | A | 274 | -5.506 | -0.521 | 42.242 | 1.00 | 9.33 |
| ATOM | 1121 | CD1 | LEU | A | 274 | -5.396 | -1.276 | 40.910 | 1.00 | 8.23 |
| ATOM | 1122 | CD2 | LEU | A | 274 | -6.916 | -0.159 | 42.533 | 1.00 | 7.44 |
| ATOM | 1123 | C | LEU | A | 274 | -3.574 | 0.191 | 44.770 | 1.00 | 14.88 |
| ATOM | 1124 | O | LEU | A | 274 | -4.129 | 0.173 | 45.866 | 1.00 | 19.59 |
| ATOM | 1125 | N | LYS | A | 275 | -2.885 | 1.242 | 44.338 | 1.00 | 13.47 |
| ATOM | 1126 | CA | LYS | A | 275 | -2.859 | 2.502 | 45.089 | 1.00 | 13.09 |
| ATOM | 1127 | CB | LYS | A | 275 | -1.982 | 2.409 | 46.341 | 1.00 | 11.39 |
| ATOM | 1128 | CG | LYS | A | 275 | -0.514 | 2.086 | 46.149 | 1.00 | 14.33 |
| ATOM | 1129 | CD | LYS | A | 275 | 0.214 | 2.351 | 47.509 | 1.00 | 18.51 |
| ATOM | 1130 | CE | LYS | A | 275 | 1.668 | 1.825 | 47.603 | 1.00 | 15.35 |
| ATOM | 1131 | NZ | LYS | A | 275 | 1.714 | 0.330 | 47.725 | 1.00 | 12.90 |
| ATOM | 1132 | C | LYS | A | 275 | -2.466 | 3.691 | 44.228 | 1.00 | 12.82 |
| ATOM | 1133 | O | LYS | A | 275 | -2.066 | 3.530 | 43.087 | 1.00 | 14.18 |

FIGURE 3 (Cont.)

|   | A | B | C | D | E | F | G | H | I | J |
|---|---|---|---|---|---|---|---|---|---|---|
| ATOM | 1134 | N | LEU | A | 276 | -2.581 | 4.891 | 44.773 | 1.00 | 12.66 |
| ATOM | 1135 | CA | LEU | A | 276 | -2.217 | 6.086 | 44.018 | 1.00 | 13.20 |
| ATOM | 1136 | CB | LEU | A | 276 | -2.515 | 7.339 | 44.833 | 1.00 | 13.28 |
| ATOM | 1137 | CG | LEU | A | 276 | -3.996 | 7.426 | 45.204 | 1.00 | 15.59 |
| ATOM | 1138 | CD1 | LEU | A | 276 | -4.274 | 8.695 | 45.946 | 1.00 | 17.83 |
| ATOM | 1139 | CD2 | LEU | A | 276 | -4.859 | 7.352 | 43.966 | 1.00 | 16.71 |
| ATOM | 1140 | C | LEU | A | 276 | -0.760 | 6.066 | 43.572 | 1.00 | 12.67 |
| ATOM | 1141 | O | LEU | A | 276 | -0.423 | 6.524 | 42.480 | 1.00 | 14.01 |
| ATOM | 1142 | N | GLU | A | 277 | 0.091 | 5.502 | 44.415 | 1.00 | 11.30 |
| ATOM | 1143 | CA | GLU | A | 277 | 1.515 | 5.512 | 44.187 | 1.00 | 12.17 |
| ATOM | 1144 | CB | GLU | A | 277 | 2.255 | 5.088 | 45.453 | 1.00 | 17.18 |
| ATOM | 1145 | CG | GLU | A | 277 | 2.294 | 6.164 | 46.524 | 1.00 | 21.52 |
| ATOM | 1146 | CD | GLU | A | 277 | 1.163 | 6.032 | 47.528 | 1.00 | 26.98 |
| ATOM | 1147 | OE1 | GLU | A | 277 | 0.005 | 5.717 | 47.132 | 1.00 | 31.14 |
| ATOM | 1148 | OE2 | GLU | A | 277 | 1.427 | 6.249 | 48.729 | 1.00 | 28.95 |
| ATOM | 1149 | C | GLU | A | 277 | 1.886 | 4.588 | 43.062 | 1.00 | 12.72 |
| ATOM | 1150 | O | GLU | A | 277 | 2.935 | 4.737 | 42.463 | 1.00 | 16.01 |
| ATOM | 1151 | N | ASN | A | 278 | 1.044 | 3.612 | 42.778 | 1.00 | 14.09 |
| ATOM | 1152 | CA | ASN | A | 278 | 1.409 | 2.626 | 41.777 | 1.00 | 16.17 |
| ATOM | 1153 | CB | ASN | A | 278 | 1.057 | 1.195 | 42.242 | 1.00 | 18.41 |
| ATOM | 1154 | CG | ASN | A | 278 | 1.947 | 0.682 | 43.398 | 1.00 | 19.23 |
| ATOM | 1155 | OD1 | ASN | A | 278 | 2.901 | 1.333 | 43.827 | 1.00 | 24.41 |
| ATOM | 1156 | ND2 | ASN | A | 278 | 1.630 | -0.503 | 43.890 | 1.00 | 16.64 |
| ATOM | 1157 | C | ASN | A | 278 | 0.728 | 2.954 | 40.460 | 1.00 | 17.72 |
| ATOM | 1158 | O | ASN | A | 278 | 0.825 | 2.188 | 39.505 | 1.00 | 26.88 |
| ATOM | 1159 | N | LEU | A | 279 | 0.022 | 4.081 | 40.406 | 1.00 | 12.26 |
| ATOM | 1160 | CA | LEU | A | 279 | -0.675 | 4.457 | 39.188 | 1.00 | 7.30 |
| ATOM | 1161 | CB | LEU | A | 279 | -2.116 | 4.815 | 39.480 | 1.00 | 2.00 |
| ATOM | 1162 | CG | LEU | A | 279 | -2.939 | 3.709 | 40.111 | 1.00 | 2.00 |
| ATOM | 1163 | CD1 | LEU | A | 279 | -4.289 | 4.233 | 40.586 | 1.00 | 4.54 |
| ATOM | 1164 | CD2 | LEU | A | 279 | -3.121 | 2.567 | 39.158 | 1.00 | 2.00 |
| ATOM | 1165 | C | LEU | A | 279 | 0.020 | 5.630 | 38.547 | 1.00 | 12.00 |
| ATOM | 1166 | O | LEU | A | 279 | -0.048 | 6.754 | 39.054 | 1.00 | 15.43 |
| ATOM | 1167 | N | MET | A | 280 | 0.684 | 5.364 | 37.428 | 1.00 | 11.29 |
| ATOM | 1168 | CA | MET | A | 280 | 1.426 | 6.383 | 36.702 | 1.00 | 10.05 |
| ATOM | 1169 | CB | MET | A | 280 | 2.675 | 5.771 | 36.076 | 1.00 | 15.79 |
| ATOM | 1170 | CG | MET | A | 280 | 3.545 | 4.985 | 37.024 | 1.00 | 21.72 |
| ATOM | 1171 | SD | MET | A | 280 | 3.754 | 5.819 | 38.584 | 1.00 | 27.06 |
| ATOM | 1172 | CE | MET | A | 280 | 5.330 | 6.743 | 38.254 | 1.00 | 25.39 |
| ATOM | 1173 | C | MET | A | 280 | 0.611 | 7.012 | 35.592 | 1.00 | 8.61 |
| ATOM | 1174 | O | MET | A | 280 | -0.538 | 6.633 | 35.345 | 1.00 | 11.31 |
| ATOM | 1175 | N | LEU | A | 281 | 1.239 | 7.974 | 34.925 | 1.00 | 5.78 |
| ATOM | 1176 | CA | LEU | A | 281 | 0.717 | 8.629 | 33.740 | 1.00 | 2.07 |
| ATOM | 1177 | CB | LEU | A | 281 | 0.226 | 10.043 | 34.084 | 1.00 | 2.00 |
| ATOM | 1178 | CG | LEU | A | 281 | -0.979 | 10.338 | 34.991 | 1.00 | 2.00 |
| ATOM | 1179 | CD1 | LEU | A | 281 | -1.417 | 11.771 | 34.784 | 1.00 | 2.87 |
| ATOM | 1180 | CD2 | LEU | A | 281 | -2.153 | 9.397 | 34.746 | 1.00 | 2.12 |
| ATOM | 1181 | C | LEU | A | 281 | 1.840 | 8.722 | 32.707 | 1.00 | 3.99 |
| ATOM | 1182 | O | LEU | A | 281 | 2.905 | 9.292 | 32.969 | 1.00 | 2.00 |
| ATOM | 1183 | N | ASP | A | 282 | 1.606 | 8.154 | 31.530 | 1.00 | 7.30 |
| ATOM | 1184 | CA | ASP | A | 282 | 2.572 | 8.239 | 30.438 | 1.00 | 8.52 |
| ATOM | 1185 | CB | ASP | A | 282 | 2.296 | 7.167 | 29.383 | 1.00 | 13.73 |

FIGURE 3 (Cont.)

|      | A    | B    | C   | D | E   | F      | G      | H      | I    | J     |
|------|------|------|-----|---|-----|--------|--------|--------|------|-------|
| ATOM | 1186 | CG   | ASP | A | 282 | 0.896  | 7.247  | 28.818 | 1.00 | 16.68 |
| ATOM | 1187 | OD1  | ASP | A | 282 | 0.155  | 8.168  | 29.231 | 1.00 | 18.36 |
| ATOM | 1188 | OD2  | ASP | A | 282 | 0.459  | 6.438  | 27.958 | 1.00 | 18.90 |
| ATOM | 1189 | C    | ASP | A | 282 | 2.582  | 9.624  | 29.806 | 1.00 | 5.65  |
| ATOM | 1190 | O    | ASP | A | 282 | 1.868  | 10.521 | 30.254 | 1.00 | 2.00  |
| ATOM | 1191 | N    | LYS | A | 283 | 3.397  | 9.783  | 28.764 | 1.00 | 8.25  |
| ATOM | 1192 | CA   | LYS | A | 283 | 3.570  | 11.088 | 28.116 | 1.00 | 13.57 |
| ATOM | 1193 | CB   | LYS | A | 283 | 4.632  | 11.042 | 27.001 | 1.00 | 16.92 |
| ATOM | 1194 | CG   | LYS | A | 283 | 4.568  | 9.841  | 26.044 | 1.00 | 20.42 |
| ATOM | 1195 | CD   | LYS | A | 283 | 5.386  | 10.106 | 24.759 | 1.00 | 22.50 |
| ATOM | 1196 | CE   | LYS | A | 283 | 6.739  | 9.370  | 24.746 | 1.00 | 22.07 |
| ATOM | 1197 | NZ   | LYS | A | 283 | 7.521  | 9.612  | 23.497 | 1.00 | 20.59 |
| ATOM | 1198 | C    | LYS | A | 283 | 2.261  | 11.702 | 27.606 | 1.00 | 12.66 |
| ATOM | 1199 | O    | LYS | A | 283 | 2.051  | 12.912 | 27.694 | 1.00 | 13.40 |
| ATOM | 1200 | N    | ASP | A | 284 | 1.375  | 10.861 | 27.098 | 1.00 | 11.64 |
| ATOM | 1201 | CA   | ASP | A | 284 | 0.130  | 11.348 | 26.551 | 1.00 | 13.33 |
| ATOM | 1202 | CB   | ASP | A | 284 | -0.238 | 10.561 | 25.282 | 1.00 | 18.18 |
| ATOM | 1203 | CG   | ASP | A | 284 | 0.540  | 11.050 | 24.035 | 1.00 | 22.64 |
| ATOM | 1204 | OD1  | ASP | A | 284 | 0.433  | 12.255 | 23.684 | 1.00 | 22.92 |
| ATOM | 1205 | OD2  | ASP | A | 284 | 1.287  | 10.309 | 23.347 | 1.00 | 22.09 |
| ATOM | 1206 | C    | ASP | A | 284 | -1.007 | 11.408 | 27.577 | 1.00 | 12.90 |
| ATOM | 1207 | O    | ASP | A | 284 | -2.085 | 11.877 | 27.258 | 1.00 | 17.88 |
| ATOM | 1208 | N    | GLY | A | 285 | -0.768 | 10.948 | 28.803 | 1.00 | 12.91 |
| ATOM | 1209 | CA   | GLY | A | 285 | -1.712 | 11.141 | 29.897 | 1.00 | 10.52 |
| ATOM | 1210 | C    | GLY | A | 285 | -2.604 | 9.978  | 30.304 | 1.00 | 11.06 |
| ATOM | 1211 | O    | GLY | A | 285 | -3.496 | 10.150 | 31.133 | 1.00 | 10.20 |
| ATOM | 1212 | N    | HIS | A | 286 | -2.374 | 8.803  | 29.723 | 1.00 | 11.24 |
| ATOM | 1213 | CA   | HIS | A | 286 | -3.127 | 7.586  | 30.060 | 1.00 | 9.81  |
| ATOM | 1214 | CB   | HIS | A | 286 | -3.158 | 6.608  | 28.870 | 1.00 | 11.11 |
| ATOM | 1215 | CG   | HIS | A | 286 | -3.807 | 7.171  | 27.641 | 1.00 | 11.60 |
| ATOM | 1216 | ND1  | HIS | A | 286 | -5.100 | 6.858  | 27.269 | 1.00 | 11.62 |
| ATOM | 1217 | CE1  | HIS | A | 286 | -5.409 | 7.508  | 26.163 | 1.00 | 7.93  |
| ATOM | 1218 | NE2  | HIS | A | 286 | -4.363 | 8.228  | 25.800 | 1.00 | 9.43  |
| ATOM | 1219 | CD2  | HIS | A | 286 | -3.351 | 8.042  | 26.712 | 1.00 | 9.35  |
| ATOM | 1220 | C    | HIS | A | 286 | -2.525 | 6.886  | 31.267 | 1.00 | 8.93  |
| ATOM | 1221 | O    | HIS | A | 286 | -1.361 | 7.099  | 31.610 | 1.00 | 9.27  |
| ATOM | 1222 | N    | ILE | A | 287 | -3.313 | 6.032  | 31.902 | 1.00 | 7.87  |
| ATOM | 1223 | CA   | ILE | A | 287 | -2.827 | 5.302  | 33.051 | 1.00 | 8.76  |
| ATOM | 1224 | CB   | ILE | A | 287 | -3.968 | 4.595  | 33.752 | 1.00 | 10.57 |
| ATOM | 1225 | CG1  | ILE | A | 287 | -4.696 | 5.589  | 34.672 | 1.00 | 13.11 |
| ATOM | 1226 | CD1  | ILE | A | 287 | -4.281 | 5.553  | 36.135 | 1.00 | 11.59 |
| ATOM | 1227 | CG2  | ILE | A | 287 | -3.458 | 3.343  | 34.507 | 1.00 | 12.90 |
| ATOM | 1228 | C    | ILE | A | 287 | -1.743 | 4.313  | 32.685 | 1.00 | 9.76  |
| ATOM | 1229 | O    | ILE | A | 287 | -1.724 | 3.757  | 31.594 | 1.00 | 12.23 |
| ATOM | 1230 | N    | LYS | A | 288 | -0.821 | 4.133  | 33.616 | 1.00 | 13.88 |
| ATOM | 1231 | CA   | LYS | A | 288 | 0.144  | 3.058  | 33.578 | 1.00 | 15.36 |
| ATOM | 1232 | CB   | LYS | A | 288 | 1.514  | 3.603  | 33.215 | 1.00 | 16.11 |
| ATOM | 1233 | CG   | LYS | A | 288 | 1.690  | 3.861  | 31.735 | 1.00 | 23.75 |
| ATOM | 1234 | CD   | LYS | A | 288 | 1.420  | 2.607  | 30.903 | 1.00 | 27.10 |
| ATOM | 1235 | CE   | LYS | A | 288 | 1.929  | 2.776  | 29.473 | 1.00 | 28.84 |
| ATOM | 1236 | NZ   | LYS | A | 288 | 1.853  | 1.488  | 28.709 | 1.00 | 30.01 |
| ATOM | 1237 | C    | LYS | A | 288 | 0.171  | 2.512  | 34.982 | 1.00 | 17.26 |

FIGURE 3 (Cont.)

| | A | B | C | D | E | F | G | H | I | J |
|---|---|---|---|---|---|---|---|---|---|---|
| ATOM | 1238 | O | LYS | A | 288 | 0.488 | 3.255 | 35.918 | 1.00 | 21.27 |
| ATOM | 1239 | N | ILE | A | 289 | -0.202 | 1.246 | 35.156 | 1.00 | 13.63 |
| ATOM | 1240 | CA | ILE | A | 289 | 0.007 | 0.593 | 36.446 | 1.00 | 10.47 |
| ATOM | 1241 | CB | ILE | A | 289 | -0.947 | -0.574 | 36.627 | 1.00 | 9.99 |
| ATOM | 1242 | CG1 | ILE | A | 289 | -2.383 | -0.088 | 36.750 | 1.00 | 12.51 |
| ATOM | 1243 | CD1 | ILE | A | 289 | -3.384 | -1.240 | 36.977 | 1.00 | 15.02 |
| ATOM | 1244 | CG2 | ILE | A | 289 | -0.558 | -1.394 | 37.835 | 1.00 | 6.59 |
| ATOM | 1245 | C | ILE | A | 289 | 1.434 | 0.073 | 36.493 | 1.00 | 8.91 |
| ATOM | 1246 | O | ILE | A | 289 | 1.844 | -0.672 | 35.617 | 1.00 | 11.53 |
| ATOM | 1247 | N | THR | A | 290 | 2.192 | 0.468 | 37.504 | 1.00 | 7.24 |
| ATOM | 1248 | CA | THR | A | 290 | 3.470 | -0.173 | 37.783 | 1.00 | 11.92 |
| ATOM | 1249 | CB | THR | A | 290 | 4.590 | 0.856 | 37.617 | 1.00 | 13.73 |
| ATOM | 1250 | OG1 | THR | A | 290 | 5.845 | 0.292 | 38.048 | 1.00 | 19.87 |
| ATOM | 1251 | CG2 | THR | A | 290 | 4.352 | 2.029 | 38.545 | 1.00 | 13.69 |
| ATOM | 1252 | C | THR | A | 290 | 3.523 | -0.875 | 39.177 | 1.00 | 13.06 |
| ATOM | 1253 | O | THR | A | 290 | 2.631 | -0.696 | 40.015 | 1.00 | 13.14 |
| ATOM | 1254 | N | ASP | A | 291 | 4.558 | -1.682 | 39.408 | 1.00 | 10.41 |
| ATOM | 1255 | CA | ASP | A | 291 | 4.841 | -2.217 | 40.743 | 1.00 | 10.96 |
| ATOM | 1256 | CB | ASP | A | 291 | 4.495 | -1.194 | 41.837 | 1.00 | 8.28 |
| ATOM | 1257 | CG | ASP | A | 291 | 5.087 | -1.540 | 43.199 | 1.00 | 6.40 |
| ATOM | 1258 | OD1 | ASP | A | 291 | 6.051 | -2.329 | 43.278 | 1.00 | 5.88 |
| ATOM | 1259 | OD2 | ASP | A | 291 | 4.644 | -1.052 | 44.259 | 1.00 | 4.36 |
| ATOM | 1260 | C | ASP | A | 291 | 4.139 | -3.543 | 40.973 | 1.00 | 13.95 |
| ATOM | 1261 | O | ASP | A | 291 | 3.074 | -3.604 | 41.581 | 1.00 | 19.80 |
| ATOM | 1262 | N | PHE | A | 292 | 4.765 | -4.613 | 40.498 | 1.00 | 14.16 |
| ATOM | 1263 | CA | PHE | A | 292 | 4.135 | -5.924 | 40.494 | 1.00 | 11.92 |
| ATOM | 1264 | CB | PHE | A | 292 | 4.229 | -6.536 | 39.090 | 1.00 | 9.29 |
| ATOM | 1265 | CG | PHE | A | 292 | 3.561 | -5.704 | 38.042 | 1.00 | 8.89 |
| ATOM | 1266 | CD1 | PHE | A | 292 | 4.306 | -4.918 | 37.185 | 1.00 | 8.76 |
| ATOM | 1267 | CE1 | PHE | A | 292 | 3.683 | -4.130 | 36.216 | 1.00 | 7.86 |
| ATOM | 1268 | CZ | PHE | A | 292 | 2.302 | -4.106 | 36.115 | 1.00 | 6.05 |
| ATOM | 1269 | CE2 | PHE | A | 292 | 1.546 | -4.871 | 36.979 | 1.00 | 9.27 |
| ATOM | 1270 | CD2 | PHE | A | 292 | 2.175 | -5.665 | 37.944 | 1.00 | 9.42 |
| ATOM | 1271 | C | PHE | A | 292 | 4.707 | -6.838 | 41.560 | 1.00 | 11.39 |
| ATOM | 1272 | O | PHE | A | 292 | 4.599 | -8.065 | 41.468 | 1.00 | 13.14 |
| ATOM | 1273 | N | GLY | A | 293 | 5.314 | -6.228 | 42.575 | 1.00 | 11.27 |
| ATOM | 1274 | CA | GLY | A | 293 | 5.857 | -6.954 | 43.716 | 1.00 | 11.03 |
| ATOM | 1275 | C | GLY | A | 293 | 4.880 | -7.961 | 44.300 | 1.00 | 9.86 |
| ATOM | 1276 | O | GLY | A | 293 | 5.222 | -9.117 | 44.496 | 1.00 | 10.07 |
| ATOM | 1277 | N | LEU | A | 294 | 3.641 | -7.537 | 44.513 | 1.00 | 10.59 |
| ATOM | 1278 | CA | LEU | A | 294 | 2.691 | -8.381 | 45.194 | 1.00 | 12.73 |
| ATOM | 1279 | CB | LEU | A | 294 | 1.968 | -7.568 | 46.264 | 1.00 | 11.55 |
| ATOM | 1280 | CG | LEU | A | 294 | 2.833 | -6.822 | 47.275 | 1.00 | 9.66 |
| ATOM | 1281 | CD1 | LEU | A | 294 | 1.913 | -6.303 | 48.321 | 1.00 | 11.57 |
| ATOM | 1282 | CD2 | LEU | A | 294 | 3.887 | -7.701 | 47.908 | 1.00 | 9.53 |
| ATOM | 1283 | C | LEU | A | 294 | 1.695 | -9.144 | 44.308 | 1.00 | 18.57 |
| ATOM | 1284 | O | LEU | A | 294 | 0.727 | -9.711 | 44.818 | 1.00 | 24.42 |
| ATOM | 1285 | N | CYS | A | 295 | 1.928 | -9.189 | 42.999 | 1.00 | 20.56 |
| ATOM | 1286 | CA | CYS | A | 295 | 1.118 | -10.034 | 42.114 | 1.00 | 19.93 |
| ATOM | 1287 | CB | CYS | A | 295 | 1.634 | -9.957 | 40.696 | 1.00 | 23.56 |
| ATOM | 1288 | SG | CYS | A | 295 | 1.191 | -8.392 | 39.972 | 1.00 | 39.04 |
| ATOM | 1289 | C | CYS | A | 295 | 1.120 | -11.488 | 42.527 | 1.00 | 16.76 |

FIGURE 3 (Cont.)

|      | A    | B   | C   | D | E   | F       | G       | H      | I    | J     |
|------|------|-----|-----|---|-----|---------|---------|--------|------|-------|
| ATOM | 1290 | O   | CYS | A | 295 | 2.152   | -12.019 | 42.918 | 1.00 | 19.03 |
| ATOM | 1291 | N   | LYS | A | 296 | -0.038  | -12.130 | 42.445 | 1.00 | 12.42 |
| ATOM | 1292 | CA  | LYS | A | 296 | -0.096  | -13.576 | 42.572 | 1.00 | 10.90 |
| ATOM | 1293 | CB  | LYS | A | 296 | -0.924  | -13.993 | 43.790 | 1.00 | 8.32  |
| ATOM | 1294 | CG  | LYS | A | 296 | -0.928  | -15.496 | 44.071 | 1.00 | 5.48  |
| ATOM | 1295 | CD  | LYS | A | 296 | 0.337   | -15.957 | 44.762 | 1.00 | 3.51  |
| ATOM | 1296 | CE  | LYS | A | 296 | 0.193   | -17.388 | 45.229 | 1.00 | 7.63  |
| ATOM | 1297 | NZ  | LYS | A | 296 | 1.418   | -18.219 | 44.994 | 1.00 | 7.61  |
| ATOM | 1298 | C   | LYS | A | 296 | -0.663  | -14.168 | 41.292 | 1.00 | 13.40 |
| ATOM | 1299 | O   | LYS | A | 296 | -1.756  | -13.779 | 40.851 | 1.00 | 15.65 |
| ATOM | 1300 | N   | GLU | A | 297 | 0.091   | -15.088 | 40.690 | 1.00 | 13.26 |
| ATOM | 1301 | CA  | GLU | A | 297 | -0.369  | -15.778 | 39.486 | 1.00 | 16.11 |
| ATOM | 1302 | CB  | GLU | A | 297 | 0.771   | -16.015 | 38.494 | 1.00 | 20.74 |
| ATOM | 1303 | CG  | GLU | A | 297 | 1.824   | -14.919 | 38.412 | 1.00 | 27.12 |
| ATOM | 1304 | CD  | GLU | A | 297 | 3.235   | -15.473 | 38.531 | 1.00 | 32.35 |
| ATOM | 1305 | OE1 | GLU | A | 297 | 3.668   | -16.234 | 37.625 | 1.00 | 35.73 |
| ATOM | 1306 | OE2 | GLU | A | 297 | 3.910   | -15.165 | 39.541 | 1.00 | 34.30 |
| ATOM | 1307 | C   | GLU | A | 297 | -1.040  | -17.105 | 39.830 | 1.00 | 13.64 |
| ATOM | 1308 | O   | GLU | A | 297 | -1.010  | -17.546 | 40.979 | 1.00 | 12.09 |
| ATOM | 1309 | N   | GLY | A | 298 | -1.659  | -17.725 | 38.831 | 1.00 | 12.65 |
| ATOM | 1310 | CA  | GLY | A | 298 | -2.257  | -19.041 | 38.994 | 1.00 | 17.89 |
| ATOM | 1311 | C   | GLY | A | 298 | -3.592  | -19.077 | 39.715 | 1.00 | 20.28 |
| ATOM | 1312 | O   | GLY | A | 298 | -4.111  | -20.154 | 40.006 | 1.00 | 19.05 |
| ATOM | 1313 | N   | ILE | A | 299 | -4.144  | -17.900 | 39.993 | 1.00 | 25.39 |
| ATOM | 1314 | CA  | ILE | A | 299 | -5.447  | -17.761 | 40.635 | 1.00 | 30.72 |
| ATOM | 1315 | CB  | ILE | A | 299 | -5.470  | -16.472 | 41.517 | 1.00 | 33.04 |
| ATOM | 1316 | CG1 | ILE | A | 299 | -4.323  | -16.460 | 42.547 | 1.00 | 34.26 |
| ATOM | 1317 | CD1 | ILE | A | 299 | -4.164  | -17.736 | 43.394 | 1.00 | 36.04 |
| ATOM | 1318 | CG2 | ILE | A | 299 | -6.846  | -16.261 | 42.177 | 1.00 | 34.45 |
| ATOM | 1319 | C   | ILE | A | 299 | -6.536  | -17.684 | 39.571 | 1.00 | 32.52 |
| ATOM | 1320 | O   | ILE | A | 299 | -6.548  | -16.754 | 38.767 | 1.00 | 31.64 |
| ATOM | 1321 | N   | SER | A | 300 | -7.450  | -18.650 | 39.570 | 1.00 | 37.14 |
| ATOM | 1322 | CA  | SER | A | 300 | -8.537  | -18.669 | 38.583 | 1.00 | 45.21 |
| ATOM | 1323 | CB  | SER | A | 300 | -8.220  | -19.646 | 37.428 | 1.00 | 43.01 |
| ATOM | 1324 | OG  | SER | A | 300 | -8.321  | -21.010 | 37.817 | 1.00 | 41.17 |
| ATOM | 1325 | C   | SER | A | 300 | -9.905  | -18.973 | 39.219 | 1.00 | 51.19 |
| ATOM | 1326 | O   | SER | A | 300 | -9.996  | -19.864 | 40.071 | 1.00 | 56.49 |
| ATOM | 1327 | N   | ASP | A | 301 | -10.945 | -18.226 | 38.809 | 1.00 | 54.32 |
| ATOM | 1328 | CA  | ASP | A | 301 | -12.360 | -18.433 | 39.227 | 1.00 | 56.18 |
| ATOM | 1329 | CB  | ASP | A | 301 | -12.817 | -19.892 | 38.985 | 1.00 | 58.07 |
| ATOM | 1330 | CG  | ASP | A | 301 | -13.440 | -20.100 | 37.610 | 1.00 | 59.00 |
| ATOM | 1331 | OD1 | ASP | A | 301 | -14.664 | -20.350 | 37.550 | 1.00 | 58.53 |
| ATOM | 1332 | OD2 | ASP | A | 301 | -12.785 | -20.046 | 36.542 | 1.00 | 58.87 |
| ATOM | 1333 | C   | ASP | A | 301 | -12.704 | -17.987 | 40.671 | 1.00 | 55.93 |
| ATOM | 1334 | O   | ASP | A | 301 | -13.116 | -16.845 | 40.902 | 1.00 | 56.42 |
| ATOM | 1335 | N   | GLY | A | 302 | -12.569 | -18.912 | 41.621 | 1.00 | 55.03 |
| ATOM | 1336 | CA  | GLY | A | 302 | -12.685 | -18.617 | 43.040 | 1.00 | 54.04 |
| ATOM | 1337 | C   | GLY | A | 302 | -11.393 | -18.961 | 43.772 | 1.00 | 53.74 |
| ATOM | 1338 | O   | GLY | A | 302 | -10.863 | -18.115 | 44.506 | 1.00 | 53.95 |
| ATOM | 1339 | N   | ALA | A | 303 | -10.897 | -20.192 | 43.550 | 1.00 | 50.75 |
| ATOM | 1340 | CA  | ALA | A | 303 | -9.658  | -20.733 | 44.153 | 1.00 | 45.71 |
| ATOM | 1341 | CB  | ALA | A | 303 | -8.966  | -21.741 | 43.203 | 1.00 | 43.99 |

FIGURE 3 (Cont.)

|      | A | B | C | D | E | F | G | H | I | J |
|---|---|---|---|---|---|---|---|---|---|---|
| ATOM | 1342 | C   | ALA | A | 303 | -8.679  | -19.655 | 44.655 | 1.00 | 40.94 |
| ATOM | 1343 | O   | ALA | A | 303 | -8.212  | -18.807 | 43.889 | 1.00 | 38.19 |
| ATOM | 1344 | N   | THR | A | 304 | -8.381  | -19.727 | 45.954 | 1.00 | 36.35 |
| ATOM | 1345 | CA  | THR | A | 304 | -7.928  | -18.585 | 46.748 | 1.00 | 29.90 |
| ATOM | 1346 | CB  | THR | A | 304 | -8.765  | -18.488 | 48.033 | 1.00 | 29.06 |
| ATOM | 1347 | OG1 | THR | A | 304 | -8.877  | -19.788 | 48.627 | 1.00 | 28.06 |
| ATOM | 1348 | CG2 | THR | A | 304 | -10.211 | -18.077 | 47.727 | 1.00 | 29.14 |
| ATOM | 1349 | C   | THR | A | 304 | -6.455  | -18.602 | 47.137 | 1.00 | 26.61 |
| ATOM | 1350 | O   | THR | A | 304 | -5.756  | -19.589 | 46.919 | 1.00 | 27.47 |
| ATOM | 1351 | N   | MET | A | 305 | -6.022  | -17.497 | 47.744 | 1.00 | 21.67 |
| ATOM | 1352 | CA  | MET | A | 305 | -4.636  | -17.269 | 48.122 | 1.00 | 20.81 |
| ATOM | 1353 | CB  | MET | A | 305 | -4.018  | -16.234 | 47.189 | 1.00 | 19.97 |
| ATOM | 1354 | CG  | MET | A | 305 | -4.730  | -14.905 | 47.169 | 1.00 | 16.09 |
| ATOM | 1355 | SD  | MET | A | 305 | -4.325  | -13.994 | 45.692 | 1.00 | 17.08 |
| ATOM | 1356 | CE  | MET | A | 305 | -5.913  | -13.322 | 45.257 | 1.00 | 15.14 |
| ATOM | 1357 | C   | MET | A | 305 | -4.480  | -16.820 | 49.585 | 1.00 | 22.96 |
| ATOM | 1358 | O   | MET | A | 305 | -5.350  | -16.133 | 50.128 | 1.00 | 23.37 |
| ATOM | 1359 | N   | LYS | A | 306 | -3.338  | -17.173 | 50.185 | 1.00 | 24.44 |
| ATOM | 1360 | CA  | LYS | A | 306 | -3.127  | -17.144 | 51.643 | 1.00 | 22.17 |
| ATOM | 1361 | CB  | LYS | A | 306 | -2.407  | -18.436 | 52.075 | 1.00 | 22.43 |
| ATOM | 1362 | CG  | LYS | A | 306 | -3.315  | -19.566 | 52.582 | 1.00 | 23.73 |
| ATOM | 1363 | CD  | LYS | A | 306 | -2.582  | -20.926 | 52.603 | 1.00 | 25.27 |
| ATOM | 1364 | CE  | LYS | A | 306 | -2.006  | -21.281 | 53.986 | 1.00 | 23.74 |
| ATOM | 1365 | NZ  | LYS | A | 306 | -2.976  | -22.017 | 54.847 | 1.00 | 22.13 |
| ATOM | 1366 | C   | LYS | A | 306 | -2.372  | -15.934 | 52.241 | 1.00 | 20.52 |
| ATOM | 1367 | O   | LYS | A | 306 | -2.592  | -15.594 | 53.402 | 1.00 | 23.31 |
| ATOM | 1368 | N   | TPO | A | 307 | -1.487  | -15.303 | 51.471 | 1.00 | 15.84 |
| ATOM | 1369 | CA  | TPO | A | 307 | -0.529  | -14.349 | 52.010 | 1.00 | 12.48 |
| ATOM | 1370 | CB  | TPO | A | 307 | 0.428   | -13.943 | 50.889 | 1.00 | 13.73 |
| ATOM | 1371 | CG2 | TPO | A | 307 | 1.578   | -13.043 | 51.340 | 1.00 | 13.62 |
| ATOM | 1372 | OG1 | TPO | A | 307 | 0.965   | -15.105 | 50.270 | 1.00 | 13.91 |
| ATOM | 1373 | P   | TPO | A | 307 | 0.929   | -15.315 | 48.673 | 1.00 | 10.79 |
| ATOM | 1374 | O1P | TPO | A | 307 | 2.301   | -14.780 | 48.073 | 1.00 | 6.15  |
| ATOM | 1375 | O3P | TPO | A | 307 | 0.650   | -16.863 | 48.393 | 1.00 | 7.66  |
| ATOM | 1376 | O2P | TPO | A | 307 | -0.267  | -14.495 | 48.033 | 1.00 | 14.09 |
| ATOM | 1377 | C   | TPO | A | 307 | -1.207  | -13.102 | 52.470 | 1.00 | 14.73 |
| ATOM | 1378 | O   | TPO | A | 307 | -1.927  | -12.479 | 51.700 | 1.00 | 17.22 |
| ATOM | 1379 | N   | PHE | A | 308 | -0.967  | -12.719 | 53.723 | 1.00 | 14.16 |
| ATOM | 1380 | CA  | PHE | A | 308 | -1.412  | -11.417 | 54.240 | 1.00 | 11.06 |
| ATOM | 1381 | CB  | PHE | A | 308 | -1.603  | -11.481 | 55.767 | 1.00 | 9.57  |
| ATOM | 1382 | CG  | PHE | A | 308 | -1.814  | -10.143 | 56.418 | 1.00 | 9.80  |
| ATOM | 1383 | CD1 | PHE | A | 308 | -0.840  | -9.599  | 57.246 | 1.00 | 8.38  |
| ATOM | 1384 | CE1 | PHE | A | 308 | -1.039  | -8.340  | 57.856 | 1.00 | 8.52  |
| ATOM | 1385 | CZ  | PHE | A | 308 | -2.227  | -7.623  | 57.635 | 1.00 | 5.08  |
| ATOM | 1386 | CE2 | PHE | A | 308 | -3.207  | -8.162  | 56.823 | 1.00 | 5.15  |
| ATOM | 1387 | CD2 | PHE | A | 308 | -3.000  | -9.423  | 56.215 | 1.00 | 9.95  |
| ATOM | 1388 | C   | PHE | A | 308 | -0.385  | -10.355 | 53.814 | 1.00 | 9.19  |
| ATOM | 1389 | O   | PHE | A | 308 | 0.780   | -10.412 | 54.213 | 1.00 | 8.70  |
| ATOM | 1390 | N   | CYS | A | 309 | -0.815  | -9.411  | 52.977 | 1.00 | 8.03  |
| ATOM | 1391 | CA  | CYS | A | 309 | 0.117   | -8.506  | 52.286 | 1.00 | 6.30  |
| ATOM | 1392 | CB  | CYS | A | 309 | 0.953   | -9.303  | 51.294 | 1.00 | 5.84  |
| ATOM | 1393 | SG  | CYS | A | 309 | 0.076   | -9.585  | 49.739 | 1.00 | 6.28  |

FIGURE 3 (Cont.)

|      | A    | B   | C   | D | E   | F      | G      | H      | I    | J     |
|------|------|-----|-----|---|-----|--------|--------|--------|------|-------|
| ATOM | 1394 | C   | CYS | A | 309 | -0.584 | -7.396 | 51.508 | 1.00 | 4.40  |
| ATOM | 1395 | O   | CYS | A | 309 | -1.752 | -7.541 | 51.107 | 1.00 | 4.55  |
| ATOM | 1396 | N   | GLY | A | 310 | 0.130  | -6.301 | 51.258 | 1.00 | 2.00  |
| ATOM | 1397 | CA  | GLY | A | 310 | -0.455 | -5.220 | 50.478 | 1.00 | 3.38  |
| ATOM | 1398 | C   | GLY | A | 310 | -0.116 | -3.855 | 51.003 | 1.00 | 4.67  |
| ATOM | 1399 | O   | GLY | A | 310 | 1.047  | -3.568 | 51.277 | 1.00 | 2.00  |
| ATOM | 1400 | N   | THR | A | 311 | -1.121 | -2.997 | 51.137 | 1.00 | 8.60  |
| ATOM | 1401 | CA  | THR | A | 311 | -0.856 | -1.690 | 51.733 | 1.00 | 14.76 |
| ATOM | 1402 | CB  | THR | A | 311 | -0.720 | -0.594 | 50.676 | 1.00 | 16.15 |
| ATOM | 1403 | OG1 | THR | A | 311 | 0.253  | -1.001 | 49.709 | 1.00 | 22.33 |
| ATOM | 1404 | CG2 | THR | A | 311 | -0.064 | 0.624  | 51.275 | 1.00 | 15.85 |
| ATOM | 1405 | C   | THR | A | 311 | -1.863 | -1.315 | 52.810 | 1.00 | 17.96 |
| ATOM | 1406 | O   | THR | A | 311 | -3.054 | -1.168 | 52.522 | 1.00 | 20.47 |
| ATOM | 1407 | N   | PRO | A | 312 | -1.359 | -1.153 | 54.042 | 1.00 | 18.77 |
| ATOM | 1408 | CA  | PRO | A | 312 | -2.187 | -0.999 | 55.243 | 1.00 | 17.39 |
| ATOM | 1409 | CB  | PRO | A | 312 | -1.266 | -0.236 | 56.200 | 1.00 | 21.08 |
| ATOM | 1410 | CG  | PRO | A | 312 | 0.119  | -0.139 | 55.502 | 1.00 | 19.52 |
| ATOM | 1411 | CD  | PRO | A | 312 | 0.078  | -1.093 | 54.374 | 1.00 | 19.18 |
| ATOM | 1412 | C   | PRO | A | 312 | -3.469 | -0.215 | 55.009 | 1.00 | 17.23 |
| ATOM | 1413 | O   | PRO | A | 312 | -4.549 | -0.694 | 55.343 | 1.00 | 21.66 |
| ATOM | 1414 | N   | GLU | A | 313 | -3.357 | 0.963  | 54.414 | 1.00 | 13.05 |
| ATOM | 1415 | CA  | GLU | A | 313 | -4.528 | 1.773  | 54.131 | 1.00 | 12.09 |
| ATOM | 1416 | CB  | GLU | A | 313 | -4.110 | 3.179  | 53.696 | 1.00 | 16.47 |
| ATOM | 1417 | CG  | GLU | A | 313 | -3.482 | 4.024  | 54.811 | 1.00 | 23.06 |
| ATOM | 1418 | CD  | GLU | A | 313 | -1.960 | 3.870  | 54.947 | 1.00 | 25.49 |
| ATOM | 1419 | OE1 | GLU | A | 313 | -1.369 | 2.922  | 54.356 | 1.00 | 26.10 |
| ATOM | 1420 | OE2 | GLU | A | 313 | -1.350 | 4.710  | 55.658 | 1.00 | 25.03 |
| ATOM | 1421 | C   | GLU | A | 313 | -5.460 | 1.154  | 53.096 | 1.00 | 9.65  |
| ATOM | 1422 | O   | GLU | A | 313 | -6.647 | 1.463  | 53.090 | 1.00 | 13.08 |
| ATOM | 1423 | N   | TYR | A | 314 | -4.939 | 0.285  | 52.234 | 1.00 | 6.62  |
| ATOM | 1424 | CA  | TYR | A | 314 | -5.689 | -0.165 | 51.057 | 1.00 | 10.22 |
| ATOM | 1425 | CB  | TYR | A | 314 | -4.833 | -0.064 | 49.796 | 1.00 | 10.80 |
| ATOM | 1426 | CG  | TYR | A | 314 | -4.593 | 1.328  | 49.275 | 1.00 | 11.28 |
| ATOM | 1427 | CD1 | TYR | A | 314 | -3.476 | 2.041  | 49.658 | 1.00 | 13.10 |
| ATOM | 1428 | CE1 | TYR | A | 314 | -3.239 | 3.317  | 49.177 | 1.00 | 15.53 |
| ATOM | 1429 | CZ  | TYR | A | 314 | -4.115 | 3.893  | 48.285 | 1.00 | 13.24 |
| ATOM | 1430 | OH  | TYR | A | 314 | -3.851 | 5.168  | 47.805 | 1.00 | 11.46 |
| ATOM | 1431 | CE2 | TYR | A | 314 | -5.227 | 3.189  | 47.880 | 1.00 | 12.73 |
| ATOM | 1432 | CD2 | TYR | A | 314 | -5.459 | 1.915  | 48.375 | 1.00 | 11.10 |
| ATOM | 1433 | C   | TYR | A | 314 | -6.181 | -1.598 | 51.168 | 1.00 | 14.85 |
| ATOM | 1434 | O   | TYR | A | 314 | -6.773 | -2.131 | 50.216 | 1.00 | 14.13 |
| ATOM | 1435 | N   | LEU | A | 315 | -5.927 | -2.226 | 52.317 | 1.00 | 16.85 |
| ATOM | 1436 | CA  | LEU | A | 315 | -6.239 | -3.645 | 52.505 | 1.00 | 16.59 |
| ATOM | 1437 | CB  | LEU | A | 315 | -5.567 | -4.182 | 53.763 | 1.00 | 17.38 |
| ATOM | 1438 | CG  | LEU | A | 315 | -4.045 | -4.146 | 53.817 | 1.00 | 18.06 |
| ATOM | 1439 | CD1 | LEU | A | 315 | -3.586 | -4.489 | 55.218 | 1.00 | 18.85 |
| ATOM | 1440 | CD2 | LEU | A | 315 | -3.463 | -5.101 | 52.804 | 1.00 | 18.81 |
| ATOM | 1441 | C   | LEU | A | 315 | -7.731 | -3.946 | 52.566 | 1.00 | 17.42 |
| ATOM | 1442 | O   | LEU | A | 315 | -8.526 | -3.155 | 53.091 | 1.00 | 20.19 |
| ATOM | 1443 | N   | ALA | A | 316 | -8.094 | -5.103 | 52.025 | 1.00 | 17.44 |
| ATOM | 1444 | CA  | ALA | A | 316 | -9.475 | -5.574 | 52.029 | 1.00 | 16.43 |
| ATOM | 1445 | CB  | ALA | A | 316 | -9.701 | -6.541 | 50.879 | 1.00 | 17.27 |

FIGURE 3 (Cont.)

|  | A | B | C | D | E | F | G | H | I | J |
|---|---|---|---|---|---|---|---|---|---|---|
| ATOM | 1446 | C | ALA | A | 316 | -9.846 | -6.235 | 53.353 | 1.00 | 14.45 |
| ATOM | 1447 | O | ALA | A | 316 | -9.022 | -6.938 | 53.962 | 1.00 | 11.13 |
| ATOM | 1448 | N | PRO | A | 317 | -11.086 | -6.005 | 53.797 | 1.00 | 13.89 |
| ATOM | 1449 | CA | PRO | A | 317 | -11.632 | -6.702 | 54.961 | 1.00 | 11.20 |
| ATOM | 1450 | CB | PRO | A | 317 | -13.137 | -6.511 | 54.786 | 1.00 | 5.63 |
| ATOM | 1451 | CG | PRO | A | 317 | -13.250 | -5.195 | 54.207 | 1.00 | 4.89 |
| ATOM | 1452 | CD | PRO | A | 317 | -12.068 | -5.047 | 53.254 | 1.00 | 10.86 |
| ATOM | 1453 | C | PRO | A | 317 | -11.246 | -8.185 | 55.000 | 1.00 | 12.09 |
| ATOM | 1454 | O | PRO | A | 317 | -10.768 | -8.621 | 56.041 | 1.00 | 15.68 |
| ATOM | 1455 | N | GLU | A | 318 | -11.405 | -8.930 | 53.908 | 1.00 | 10.93 |
| ATOM | 1456 | CA | GLU | A | 318 | -11.122 | -10.368 | 53.941 | 1.00 | 12.09 |
| ATOM | 1457 | CB | GLU | A | 318 | -11.528 | -11.089 | 52.642 | 1.00 | 14.71 |
| ATOM | 1458 | CG | GLU | A | 318 | -10.907 | -10.534 | 51.365 | 1.00 | 21.18 |
| ATOM | 1459 | CD | GLU | A | 318 | -11.728 | -9.434 | 50.694 | 1.00 | 24.13 |
| ATOM | 1460 | OE1 | GLU | A | 318 | -12.181 | -8.487 | 51.384 | 1.00 | 24.60 |
| ATOM | 1461 | OE2 | GLU | A | 318 | -11.903 | -9.503 | 49.456 | 1.00 | 25.49 |
| ATOM | 1462 | C | GLU | A | 318 | -9.670 | -10.627 | 54.301 | 1.00 | 11.22 |
| ATOM | 1463 | O | GLU | A | 318 | -9.402 | -11.409 | 55.199 | 1.00 | 15.25 |
| ATOM | 1464 | N | VAL | A | 319 | -8.745 | -9.941 | 53.636 | 1.00 | 9.45 |
| ATOM | 1465 | CA | VAL | A | 319 | -7.324 | -10.070 | 53.932 | 1.00 | 8.20 |
| ATOM | 1466 | CB | VAL | A | 319 | -6.472 | -9.065 | 53.117 | 1.00 | 7.43 |
| ATOM | 1467 | CG1 | VAL | A | 319 | -4.976 | -9.411 | 53.172 | 1.00 | 4.93 |
| ATOM | 1468 | CG2 | VAL | A | 319 | -6.945 | -9.013 | 51.672 | 1.00 | 9.50 |
| ATOM | 1469 | C | VAL | A | 319 | -7.089 | -9.857 | 55.424 | 1.00 | 10.41 |
| ATOM | 1470 | O | VAL | A | 319 | -6.281 | -10.563 | 56.035 | 1.00 | 9.70 |
| ATOM | 1471 | N | LEU | A | 320 | -7.815 | -8.899 | 56.005 | 1.00 | 12.04 |
| ATOM | 1472 | CA | LEU | A | 320 | -7.639 | -8.541 | 57.414 | 1.00 | 13.27 |
| ATOM | 1473 | CB | LEU | A | 320 | -8.149 | -7.126 | 57.706 | 1.00 | 7.97 |
| ATOM | 1474 | CG | LEU | A | 320 | -7.085 | -6.040 | 57.511 | 1.00 | 8.68 |
| ATOM | 1475 | CD1 | LEU | A | 320 | -7.639 | -4.659 | 57.754 | 1.00 | 10.30 |
| ATOM | 1476 | CD2 | LEU | A | 320 | -5.876 | -6.262 | 58.384 | 1.00 | 8.93 |
| ATOM | 1477 | C | LEU | A | 320 | -8.234 | -9.540 | 58.393 | 1.00 | 19.44 |
| ATOM | 1478 | O | LEU | A | 320 | -7.848 | -9.568 | 59.554 | 1.00 | 22.61 |
| ATOM | 1479 | N | GLU | A | 321 | -9.177 | -10.357 | 57.943 | 1.00 | 27.14 |
| ATOM | 1480 | CA | GLU | A | 321 | -9.545 | -11.538 | 58.706 | 1.00 | 34.83 |
| ATOM | 1481 | CB | GLU | A | 321 | -10.963 | -11.974 | 58.380 | 1.00 | 36.15 |
| ATOM | 1482 | CG | GLU | A | 321 | -11.996 | -11.232 | 59.200 | 1.00 | 42.19 |
| ATOM | 1483 | CD | GLU | A | 321 | -13.255 | -10.940 | 58.415 | 1.00 | 46.01 |
| ATOM | 1484 | OE1 | GLU | A | 321 | -14.349 | -11.328 | 58.885 | 1.00 | 47.07 |
| ATOM | 1485 | OE2 | GLU | A | 321 | -13.150 | -10.328 | 57.328 | 1.00 | 49.35 |
| ATOM | 1486 | C | GLU | A | 321 | -8.541 | -12.580 | 58.264 | 1.00 | 39.85 |
| ATOM | 1487 | O | GLU | A | 321 | -7.323 | -12.357 | 58.349 | 1.00 | 41.58 |
| ATOM | 1488 | N | ASP | A | 322 | -9.033 | -13.712 | 57.785 | 1.00 | 42.30 |
| ATOM | 1489 | CA | ASP | A | 322 | -8.217 | -14.531 | 56.913 | 1.00 | 45.72 |
| ATOM | 1490 | CB | ASP | A | 322 | -7.074 | -15.244 | 57.655 | 1.00 | 50.04 |
| ATOM | 1491 | CG | ASP | A | 322 | -6.075 | -15.907 | 56.695 | 1.00 | 55.00 |
| ATOM | 1492 | OD1 | ASP | A | 322 | -5.624 | -15.225 | 55.738 | 1.00 | 57.17 |
| ATOM | 1493 | OD2 | ASP | A | 322 | -5.697 | -17.101 | 56.813 | 1.00 | 54.91 |
| ATOM | 1494 | C | ASP | A | 322 | -9.065 | -15.517 | 56.161 | 1.00 | 46.88 |
| ATOM | 1495 | O | ASP | A | 322 | -9.687 | -15.168 | 55.143 | 1.00 | 45.15 |
| ATOM | 1496 | N | ASN | A | 323 | -9.098 | -16.737 | 56.703 | 1.00 | 47.64 |
| ATOM | 1497 | CA | ASN | A | 323 | -9.403 | -17.953 | 55.952 | 1.00 | 47.91 |

FIGURE 3 (Cont.)

|      |      | A    | B   | C   | D | E   | F       | G       | H      | I    | J     |
|------|------|------|-----|-----|---|-----|---------|---------|--------|------|-------|
| ATOM | 1498 | CB   | ASN | A   | 323 |   | -10.602 | -18.704 | 56.552 | 1.00 | 49.15 |
| ATOM | 1499 | CG   | ASN | A   | 323 |   | -10.180 | -19.975 | 57.293 | 1.00 | 52.25 |
| ATOM | 1500 | OD1  | ASN | A   | 323 |   |  -9.600 | -20.896 | 56.702 | 1.00 | 53.16 |
| ATOM | 1501 | ND2  | ASN | A   | 323 |   | -10.467 | -20.028 | 58.592 | 1.00 | 53.36 |
| ATOM | 1502 | C    | ASN | A   | 323 |   |  -9.494 | -17.788 | 54.418 | 1.00 | 46.92 |
| ATOM | 1503 | O    | ASN | A   | 323 |   | -10.518 | -18.102 | 53.801 | 1.00 | 48.98 |
| ATOM | 1504 | N    | ASP | A   | 324 |   |  -8.415 | -17.255 | 53.836 | 1.00 | 41.86 |
| ATOM | 1505 | CA   | ASP | A   | 324 |   |  -8.139 | -17.358 | 52.408 | 1.00 | 37.08 |
| ATOM | 1506 | CB   | ASP | A   | 324 |   |  -8.090 | -18.837 | 51.988 | 1.00 | 42.15 |
| ATOM | 1507 | CG   | ASP | A   | 324 |   |  -7.272 | -19.700 | 52.964 | 1.00 | 46.60 |
| ATOM | 1508 | OD1  | ASP | A   | 324 |   |  -6.531 | -19.120 | 53.795 | 1.00 | 49.52 |
| ATOM | 1509 | OD2  | ASP | A   | 324 |   |  -7.307 | -20.955 | 52.986 | 1.00 | 48.00 |
| ATOM | 1510 | C    | ASP | A   | 324 |   |  -9.059 | -16.534 | 51.507 | 1.00 | 32.79 |
| ATOM | 1511 | O    | ASP | A   | 324 |   | -10.148 | -16.969 | 51.132 | 1.00 | 32.67 |
| ATOM | 1512 | N    | TYR | A   | 325 |   |  -8.579 | -15.347 | 51.154 | 1.00 | 28.14 |
| ATOM | 1513 | CA   | TYR | A   | 325 |   |  -9.261 | -14.422 | 50.258 | 1.00 | 22.60 |
| ATOM | 1514 | CB   | TYR | A   | 325 |   |  -8.852 | -12.992 | 50.599 | 1.00 | 24.02 |
| ATOM | 1515 | CG   | TYR | A   | 325 |   |  -7.376 | -12.682 | 50.391 | 1.00 | 22.91 |
| ATOM | 1516 | CD1  | TYR | A   | 325 |   |  -6.910 | -12.194 | 49.175 | 1.00 | 23.11 |
| ATOM | 1517 | CE1  | TYR | A   | 325 |   |  -5.578 | -11.897 | 48.978 | 1.00 | 23.04 |
| ATOM | 1518 | CZ   | TYR | A   | 325 |   |  -4.684 | -12.093 | 50.008 | 1.00 | 25.86 |
| ATOM | 1519 | OH   | TYR | A   | 325 |   |  -3.349 | -11.802 | 49.816 | 1.00 | 29.42 |
| ATOM | 1520 | CE2  | TYR | A   | 325 |   |  -5.119 | -12.577 | 51.230 | 1.00 | 24.57 |
| ATOM | 1521 | CD2  | TYR | A   | 325 |   |  -6.456 | -12.862 | 51.417 | 1.00 | 23.79 |
| ATOM | 1522 | C    | TYR | A   | 325 |   |  -8.881 | -14.687 | 48.819 | 1.00 | 20.02 |
| ATOM | 1523 | O    | TYR | A   | 325 |   |  -7.921 | -15.399 | 48.558 | 1.00 | 18.90 |
| ATOM | 1524 | N    | GLY | A   | 326 |   |  -9.610 | -14.070 | 47.889 | 1.00 | 21.15 |
| ATOM | 1525 | CA   | GLY | A   | 326 |   |  -9.350 | -14.229 | 46.467 | 1.00 | 21.96 |
| ATOM | 1526 | C    | GLY | A   | 326 |   |  -9.438 | -12.975 | 45.604 | 1.00 | 22.94 |
| ATOM | 1527 | O    | GLY | A   | 326 |   |  -9.273 | -11.855 | 46.081 | 1.00 | 24.00 |
| ATOM | 1528 | N    | ARG | A   | 327 |   |  -9.723 | -13.191 | 44.322 | 1.00 | 22.49 |
| ATOM | 1529 | CA   | ARG | A   | 327 |   |  -9.660 | -12.188 | 43.253 | 1.00 | 18.40 |
| ATOM | 1530 | CB   | ARG | A   | 327 |   | -10.276 | -12.799 | 42.002 | 1.00 | 20.86 |
| ATOM | 1531 | CG   | ARG | A   | 327 |   |  -9.761 | -12.273 | 40.692 | 1.00 | 22.09 |
| ATOM | 1532 | CD   | ARG | A   | 327 |   | -10.362 | -13.013 | 39.526 | 1.00 | 25.00 |
| ATOM | 1533 | NE   | ARG | A   | 327 |   | -11.808 | -13.124 | 39.691 | 1.00 | 27.42 |
| ATOM | 1534 | CZ   | ARG | A   | 327 |   | -12.576 | -13.948 | 38.999 | 1.00 | 30.21 |
| ATOM | 1535 | NH1  | ARG | A   | 327 |   | -12.024 | -14.742 | 38.095 | 1.00 | 33.39 |
| ATOM | 1536 | NH2  | ARG | A   | 327 |   | -13.893 | -13.985 | 39.204 | 1.00 | 29.71 |
| ATOM | 1537 | C    | ARG | A   | 327 |   | -10.349 | -10.856 | 43.516 | 1.00 | 16.87 |
| ATOM | 1538 | O    | ARG | A   | 327 |   |  -9.988 |  -9.844 | 42.918 | 1.00 | 17.74 |
| ATOM | 1539 | N    | ALA | A   | 328 |   | -11.346 | -10.858 | 44.395 | 1.00 | 15.65 |
| ATOM | 1540 | CA   | ALA | A   | 328 |   | -12.162 |  -9.672 | 44.644 | 1.00 | 12.90 |
| ATOM | 1541 | CB   | ALA | A   | 328 |   | -13.395 | -10.052 | 45.411 | 1.00 | 12.66 |
| ATOM | 1542 | C    | ALA | A   | 328 |   | -11.423 |  -8.546 | 45.366 | 1.00 | 14.00 |
| ATOM | 1543 | O    | ALA | A   | 328 |   | -11.915 |  -7.425 | 45.430 | 1.00 | 17.90 |
| ATOM | 1544 | N    | VAL | A   | 329 |   | -10.248 |  -8.837 | 45.910 | 1.00 | 14.94 |
| ATOM | 1545 | CA   | VAL | A   | 329 |   |  -9.480 |  -7.827 | 46.632 | 1.00 | 14.02 |
| ATOM | 1546 | CB   | VAL | A   | 329 |   |  -8.318 |  -8.436 | 47.445 | 1.00 |  9.86 |
| ATOM | 1547 | CG1  | VAL | A   | 329 |   |  -8.842 |  -9.487 | 48.371 | 1.00 | 10.74 |
| ATOM | 1548 | CG2  | VAL | A   | 329 |   |  -7.272 |  -9.022 | 46.554 | 1.00 |  6.17 |
| ATOM | 1549 | C    | VAL | A   | 329 |   |  -8.984 |  -6.703 | 45.720 | 1.00 | 17.59 |

FIGURE 3 (Cont.)

|  | A | B | C | D | E | F | G | H | I | J |
|---|---|---|---|---|---|---|---|---|---|---|
| ATOM | 1550 | O | VAL | A | 329 | -8.807 | -5.564 | 46.170 | 1.00 | 18.03 |
| ATOM | 1551 | N | ASP | A | 330 | -8.783 | -7.006 | 44.440 | 1.00 | 20.06 |
| ATOM | 1552 | CA | ASP | A | 330 | -8.391 | -5.966 | 43.502 | 1.00 | 22.43 |
| ATOM | 1553 | CB | ASP | A | 330 | -7.993 | -6.555 | 42.156 | 1.00 | 24.76 |
| ATOM | 1554 | CG | ASP | A | 330 | -6.584 | -7.110 | 42.160 | 1.00 | 29.26 |
| ATOM | 1555 | OD1 | ASP | A | 330 | -5.930 | -7.128 | 43.222 | 1.00 | 31.26 |
| ATOM | 1556 | OD2 | ASP | A | 330 | -6.039 | -7.572 | 41.143 | 1.00 | 33.33 |
| ATOM | 1557 | C | ASP | A | 330 | -9.524 | -4.969 | 43.345 | 1.00 | 23.04 |
| ATOM | 1558 | O | ASP | A | 330 | -9.292 | -3.785 | 43.111 | 1.00 | 24.61 |
| ATOM | 1559 | N | TRP | A | 331 | -10.756 | -5.445 | 43.507 | 1.00 | 21.27 |
| ATOM | 1560 | CA | TRP | A | 331 | -11.915 | -4.572 | 43.336 | 1.00 | 16.46 |
| ATOM | 1561 | CB | TRP | A | 331 | -13.129 | -5.360 | 42.848 | 1.00 | 13.86 |
| ATOM | 1562 | CG | TRP | A | 331 | -12.882 | -6.126 | 41.553 | 1.00 | 12.21 |
| ATOM | 1563 | CD1 | TRP | A | 331 | -13.138 | -7.445 | 41.336 | 1.00 | 15.09 |
| ATOM | 1564 | NE1 | TRP | A | 331 | -12.801 | -7.799 | 40.050 | 1.00 | 15.16 |
| ATOM | 1565 | CE2 | TRP | A | 331 | -12.314 | -6.700 | 39.398 | 1.00 | 12.76 |
| ATOM | 1566 | CD2 | TRP | A | 331 | -12.350 | -5.621 | 40.312 | 1.00 | 11.92 |
| ATOM | 1567 | CE3 | TRP | A | 331 | -11.910 | -4.369 | 39.874 | 1.00 | 13.68 |
| ATOM | 1568 | CZ3 | TRP | A | 331 | -11.454 | -4.238 | 38.562 | 1.00 | 13.91 |
| ATOM | 1569 | CH2 | TRP | A | 331 | -11.421 | -5.331 | 37.693 | 1.00 | 12.57 |
| ATOM | 1570 | CZ2 | TRP | A | 331 | -11.849 | -6.567 | 38.088 | 1.00 | 11.93 |
| ATOM | 1571 | C | TRP | A | 331 | -12.200 | -3.693 | 44.563 | 1.00 | 12.65 |
| ATOM | 1572 | O | TRP | A | 331 | -12.629 | -2.546 | 44.429 | 1.00 | 9.35 |
| ATOM | 1573 | N | TRP | A | 332 | -11.923 | -4.213 | 45.751 | 1.00 | 11.41 |
| ATOM | 1574 | CA | TRP | A | 332 | -11.787 | -3.347 | 46.919 | 1.00 | 14.38 |
| ATOM | 1575 | CB | TRP | A | 332 | -11.267 | -4.130 | 48.110 | 1.00 | 12.68 |
| ATOM | 1576 | CG | TRP | A | 332 | -11.080 | -3.292 | 49.319 | 1.00 | 10.70 |
| ATOM | 1577 | CD1 | TRP | A | 332 | -9.926 | -2.735 | 49.755 | 1.00 | 11.77 |
| ATOM | 1578 | NE1 | TRP | A | 332 | -10.142 | -2.038 | 50.920 | 1.00 | 15.20 |
| ATOM | 1579 | CE2 | TRP | A | 332 | -11.467 | -2.144 | 51.254 | 1.00 | 14.27 |
| ATOM | 1580 | CD2 | TRP | A | 332 | -12.086 | -2.927 | 50.263 | 1.00 | 12.80 |
| ATOM | 1581 | CE3 | TRP | A | 332 | -13.461 | -3.180 | 50.371 | 1.00 | 13.51 |
| ATOM | 1582 | CZ3 | TRP | A | 332 | -14.147 | -2.664 | 51.440 | 1.00 | 13.25 |
| ATOM | 1583 | CH2 | TRP | A | 332 | -13.501 | -1.887 | 52.413 | 1.00 | 12.67 |
| ATOM | 1584 | CZ2 | TRP | A | 332 | -12.168 | -1.612 | 52.335 | 1.00 | 13.72 |
| ATOM | 1585 | C | TRP | A | 332 | -10.791 | -2.229 | 46.643 | 1.00 | 16.64 |
| ATOM | 1586 | O | TRP | A | 332 | -11.116 | -1.046 | 46.753 | 1.00 | 17.97 |
| ATOM | 1587 | N | GLY | A | 333 | -9.567 | -2.625 | 46.294 | 1.00 | 17.74 |
| ATOM | 1588 | CA | GLY | A | 333 | -8.495 | -1.684 | 46.064 | 1.00 | 15.88 |
| ATOM | 1589 | C | GLY | A | 333 | -9.022 | -0.588 | 45.174 | 1.00 | 17.44 |
| ATOM | 1590 | O | GLY | A | 333 | -8.918 | 0.596 | 45.515 | 1.00 | 15.19 |
| ATOM | 1591 | N | LEU | A | 334 | -9.629 | -1.008 | 44.053 | 1.00 | 18.58 |
| ATOM | 1592 | CA | LEU | A | 334 | -10.057 | -0.108 | 42.983 | 1.00 | 16.11 |
| ATOM | 1593 | CB | LEU | A | 334 | -10.790 | -0.876 | 41.872 | 1.00 | 12.43 |
| ATOM | 1594 | CG | LEU | A | 334 | -11.631 | -0.033 | 40.901 | 1.00 | 11.62 |
| ATOM | 1595 | CD1 | LEU | A | 334 | -10.773 | 0.878 | 40.048 | 1.00 | 9.04 |
| ATOM | 1596 | CD2 | LEU | A | 334 | -12.507 | -0.904 | 40.030 | 1.00 | 9.65 |
| ATOM | 1597 | C | LEU | A | 334 | -10.935 | 0.960 | 43.589 | 1.00 | 16.13 |
| ATOM | 1598 | O | LEU | A | 334 | -10.750 | 2.152 | 43.330 | 1.00 | 15.68 |
| ATOM | 1599 | N | GLY | A | 335 | -11.847 | 0.493 | 44.439 | 1.00 | 13.78 |
| ATOM | 1600 | CA | GLY | A | 335 | -12.798 | 1.323 | 45.142 | 1.00 | 13.31 |
| ATOM | 1601 | C | GLY | A | 335 | -12.181 | 2.285 | 46.118 | 1.00 | 13.20 |

FIGURE 3 (Cont.)

| | A | B | C | D | E | F | G | H | I | J |
|---|---|---|---|---|---|---|---|---|---|---|
| ATOM | 1602 | O | GLY | A | 335 | -12.675 | 3.394 | 46.246 | 1.00 | 19.17 |
| ATOM | 1603 | N | VAL | A | 336 | -11.120 | 1.879 | 46.808 | 1.00 | 11.90 |
| ATOM | 1604 | CA | VAL | A | 336 | -10.365 | 2.818 | 47.639 | 1.00 | 10.30 |
| ATOM | 1605 | CB | VAL | A | 336 | -9.250 | 2.123 | 48.407 | 1.00 | 5.00 |
| ATOM | 1606 | CG1 | VAL | A | 336 | -8.512 | 3.107 | 49.260 | 1.00 | 2.00 |
| ATOM | 1607 | CG2 | VAL | A | 336 | -9.825 | 1.050 | 49.253 | 1.00 | 7.28 |
| ATOM | 1608 | C | VAL | A | 336 | -9.771 | 3.926 | 46.757 | 1.00 | 13.19 |
| ATOM | 1609 | O | VAL | A | 336 | -10.030 | 5.115 | 46.971 | 1.00 | 15.21 |
| ATOM | 1610 | N | VAL | A | 337 | -9.000 | 3.516 | 45.754 | 1.00 | 13.29 |
| ATOM | 1611 | CA | VAL | A | 337 | -8.400 | 4.429 | 44.782 | 1.00 | 13.05 |
| ATOM | 1612 | CB | VAL | A | 337 | -7.611 | 3.619 | 43.731 | 1.00 | 11.85 |
| ATOM | 1613 | CG1 | VAL | A | 337 | -7.521 | 4.315 | 42.387 | 1.00 | 7.08 |
| ATOM | 1614 | CG2 | VAL | A | 337 | -6.229 | 3.330 | 44.277 | 1.00 | 14.96 |
| ATOM | 1615 | C | VAL | A | 337 | -9.427 | 5.399 | 44.160 | 1.00 | 14.21 |
| ATOM | 1616 | O | VAL | A | 337 | -9.225 | 6.617 | 44.141 | 1.00 | 12.98 |
| ATOM | 1617 | N | MET | A | 338 | -10.545 | 4.863 | 43.695 | 1.00 | 13.70 |
| ATOM | 1618 | CA | MET | A | 338 | -11.588 | 5.701 | 43.147 | 1.00 | 13.96 |
| ATOM | 1619 | CB | MET | A | 338 | -12.711 | 4.847 | 42.611 | 1.00 | 17.57 |
| ATOM | 1620 | CG | MET | A | 338 | -12.255 | 3.989 | 41.496 | 1.00 | 23.12 |
| ATOM | 1621 | SD | MET | A | 338 | -12.444 | 4.883 | 40.013 | 1.00 | 26.77 |
| ATOM | 1622 | CE | MET | A | 338 | -13.722 | 3.901 | 39.305 | 1.00 | 24.75 |
| ATOM | 1623 | C | MET | A | 338 | -12.126 | 6.660 | 44.184 | 1.00 | 14.27 |
| ATOM | 1624 | O | MET | A | 338 | -12.302 | 7.842 | 43.892 | 1.00 | 19.25 |
| ATOM | 1625 | N | TYR | A | 339 | -12.378 | 6.160 | 45.391 | 1.00 | 10.05 |
| ATOM | 1626 | CA | TYR | A | 339 | -12.918 | 6.990 | 46.466 | 1.00 | 9.15 |
| ATOM | 1627 | CB | TYR | A | 339 | -13.059 | 6.152 | 47.732 | 1.00 | 7.31 |
| ATOM | 1628 | CG | TYR | A | 339 | -13.783 | 6.840 | 48.864 | 1.00 | 7.19 |
| ATOM | 1629 | CD1 | TYR | A | 339 | -13.150 | 7.804 | 49.645 | 1.00 | 6.57 |
| ATOM | 1630 | CE1 | TYR | A | 339 | -13.813 | 8.426 | 50.685 | 1.00 | 6.77 |
| ATOM | 1631 | CZ | TYR | A | 339 | -15.120 | 8.068 | 50.963 | 1.00 | 6.13 |
| ATOM | 1632 | OH | TYR | A | 339 | -15.812 | 8.671 | 51.995 | 1.00 | 7.61 |
| ATOM | 1633 | CE2 | TYR | A | 339 | -15.747 | 7.104 | 50.211 | 1.00 | 4.44 |
| ATOM | 1634 | CD2 | TYR | A | 339 | -15.087 | 6.504 | 49.172 | 1.00 | 4.23 |
| ATOM | 1635 | C | TYR | A | 339 | -11.968 | 8.159 | 46.727 | 1.00 | 9.95 |
| ATOM | 1636 | O | TYR | A | 339 | -12.362 | 9.333 | 46.881 | 1.00 | 4.09 |
| ATOM | 1637 | N | GLU | A | 340 | -10.695 | 7.808 | 46.763 | 1.00 | 8.87 |
| ATOM | 1638 | CA | GLU | A | 340 | -9.678 | 8.770 | 47.021 | 1.00 | 8.82 |
| ATOM | 1639 | CB | GLU | A | 340 | -8.339 | 8.092 | 47.060 | 1.00 | 13.95 |
| ATOM | 1640 | CG | GLU | A | 340 | -7.805 | 7.904 | 48.455 | 1.00 | 17.74 |
| ATOM | 1641 | CD | GLU | A | 340 | -6.506 | 7.144 | 48.427 | 1.00 | 23.24 |
| ATOM | 1642 | OE1 | GLU | A | 340 | -5.524 | 7.647 | 49.014 | 1.00 | 29.67 |
| ATOM | 1643 | OE2 | GLU | A | 340 | -6.464 | 6.060 | 47.802 | 1.00 | 22.69 |
| ATOM | 1644 | C | GLU | A | 340 | -9.702 | 9.829 | 45.959 | 1.00 | 7.56 |
| ATOM | 1645 | O | GLU | A | 340 | -9.693 | 10.992 | 46.311 | 1.00 | 14.77 |
| ATOM | 1646 | N | MET | A | 341 | -9.756 | 9.441 | 44.681 | 1.00 | 3.16 |
| ATOM | 1647 | CA | MET | A | 341 | -9.778 | 10.408 | 43.578 | 1.00 | 2.20 |
| ATOM | 1648 | CB | MET | A | 341 | -9.800 | 9.715 | 42.233 | 1.00 | 2.13 |
| ATOM | 1649 | CG | MET | A | 341 | -8.514 | 9.029 | 41.882 | 1.00 | 8.20 |
| ATOM | 1650 | SD | MET | A | 341 | -8.502 | 8.404 | 40.209 | 1.00 | 15.10 |
| ATOM | 1651 | CE | MET | A | 341 | -9.632 | 6.925 | 40.303 | 1.00 | 11.05 |
| ATOM | 1652 | C | MET | A | 341 | -10.964 | 11.349 | 43.634 | 1.00 | 5.59 |
| ATOM | 1653 | O | MET | A | 341 | -10.848 | 12.537 | 43.297 | 1.00 | 5.28 |

FIGURE 3 (Cont.)

|      | A    | B    | C   | D | E   | F       | G      | H      | I    | J     |
|------|------|------|-----|---|-----|---------|--------|--------|------|-------|
| ATOM | 1654 | N    | MET | A | 342 | -12.099 | 10.824 | 44.086 | 1.00 | 9.81  |
| ATOM | 1655 | CA   | MET | A | 342 | -13.366 | 11.541 | 44.002 | 1.00 | 9.64  |
| ATOM | 1656 | CB   | MET | A | 342 | -14.455 | 10.599 | 43.542 | 1.00 | 7.76  |
| ATOM | 1657 | CG   | MET | A | 342 | -14.436 | 10.382 | 42.073 | 1.00 | 6.50  |
| ATOM | 1658 | SD   | MET | A | 342 | -15.918 | 9.558  | 41.619 | 1.00 | 8.48  |
| ATOM | 1659 | CE   | MET | A | 342 | -15.483 | 7.811  | 42.026 | 1.00 | 10.33 |
| ATOM | 1660 | C    | MET | A | 342 | -13.821 | 12.247 | 45.259 | 1.00 | 11.25 |
| ATOM | 1661 | O    | MET | A | 342 | -14.480 | 13.274 | 45.169 | 1.00 | 14.95 |
| ATOM | 1662 | N    | CYS | A | 343 | -13.509 | 11.699 | 46.425 | 1.00 | 14.53 |
| ATOM | 1663 | CA   | CYS | A | 343 | -13.929 | 12.341 | 47.666 | 1.00 | 19.16 |
| ATOM | 1664 | CB   | CYS | A | 343 | -14.331 | 11.312 | 48.708 | 1.00 | 26.83 |
| ATOM | 1665 | SG   | CYS | A | 343 | -15.377 | 9.974  | 48.085 | 1.00 | 39.83 |
| ATOM | 1666 | C    | CYS | A | 343 | -12.826 | 13.208 | 48.221 | 1.00 | 17.73 |
| ATOM | 1667 | O    | CYS | A | 343 | -13.092 | 14.092 | 49.042 | 1.00 | 16.70 |
| ATOM | 1668 | N    | GLY | A | 344 | -11.600 | 12.936 | 47.759 | 1.00 | 15.57 |
| ATOM | 1669 | CA   | GLY | A | 344 | -10.393 | 13.618 | 48.200 | 1.00 | 13.42 |
| ATOM | 1670 | C    | GLY | A | 344 | -9.715  | 13.028 | 49.433 | 1.00 | 12.80 |
| ATOM | 1671 | O    | GLY | A | 344 | -8.841  | 13.654 | 50.028 | 1.00 | 14.05 |
| ATOM | 1672 | N    | ARG | A | 345 | -10.127 | 11.835 | 49.841 | 1.00 | 11.01 |
| ATOM | 1673 | CA   | ARG | A | 345 | -9.500  | 11.169 | 50.974 | 1.00 | 10.21 |
| ATOM | 1674 | CB   | ARG | A | 345 | -9.975  | 11.749 | 52.297 | 1.00 | 8.41  |
| ATOM | 1675 | CG   | ARG | A | 345 | -11.437 | 12.047 | 52.366 | 1.00 | 11.04 |
| ATOM | 1676 | CD   | ARG | A | 345 | -11.752 | 13.263 | 53.234 | 1.00 | 18.32 |
| ATOM | 1677 | NE   | ARG | A | 345 | -10.682 | 13.587 | 54.192 | 1.00 | 20.21 |
| ATOM | 1678 | CZ   | ARG | A | 345 | -10.214 | 14.820 | 54.437 | 1.00 | 21.73 |
| ATOM | 1679 | NH1  | ARG | A | 345 | -10.703 | 15.891 | 53.801 | 1.00 | 19.40 |
| ATOM | 1680 | NH2  | ARG | A | 345 | -9.239  | 14.979 | 55.325 | 1.00 | 22.31 |
| ATOM | 1681 | C    | ARG | A | 345 | -9.699  | 9.660  | 50.984 | 1.00 | 12.42 |
| ATOM | 1682 | O    | ARG | A | 345 | -10.582 | 9.118  | 50.315 | 1.00 | 16.50 |
| ATOM | 1683 | N    | LEU | A | 346 | -8.857  | 8.981  | 51.748 | 1.00 | 9.34  |
| ATOM | 1684 | CA   | LEU | A | 346 | -9.034  | 7.578  | 51.967 | 1.00 | 8.96  |
| ATOM | 1685 | CB   | LEU | A | 346 | -7.916  | 7.084  | 52.851 | 1.00 | 9.30  |
| ATOM | 1686 | CG   | LEU | A | 346 | -6.570  | 6.708  | 52.267 | 1.00 | 10.30 |
| ATOM | 1687 | CD1  | LEU | A | 346 | -5.658  | 6.426  | 53.448 | 1.00 | 13.78 |
| ATOM | 1688 | CD2  | LEU | A | 346 | -6.687  | 5.475  | 51.401 | 1.00 | 11.35 |
| ATOM | 1689 | C    | LEU | A | 346 | -10.368 | 7.401  | 52.688 | 1.00 | 13.73 |
| ATOM | 1690 | O    | LEU | A | 346 | -10.718 | 8.204  | 53.569 | 1.00 | 17.37 |
| ATOM | 1691 | N    | PRO | A | 347 | -11.107 | 6.351  | 52.346 | 1.00 | 12.75 |
| ATOM | 1692 | CA   | PRO | A | 347 | -12.399 | 6.097  | 52.980 | 1.00 | 11.53 |
| ATOM | 1693 | CB   | PRO | A | 347 | -12.947 | 4.929  | 52.172 | 1.00 | 11.57 |
| ATOM | 1694 | CG   | PRO | A | 347 | -11.732 | 4.222  | 51.711 | 1.00 | 14.66 |
| ATOM | 1695 | CD   | PRO | A | 347 | -10.751 | 5.301  | 51.381 | 1.00 | 13.94 |
| ATOM | 1696 | C    | PRO | A | 347 | -12.179 | 5.701  | 54.437 | 1.00 | 13.65 |
| ATOM | 1697 | O    | PRO | A | 347 | -13.024 | 5.956  | 55.297 | 1.00 | 17.03 |
| ATOM | 1698 | N    | PHE | A | 348 | -11.036 | 5.087  | 54.718 | 1.00 | 14.13 |
| ATOM | 1699 | CA   | PHE | A | 348 | -10.684 | 4.781  | 56.096 | 1.00 | 14.35 |
| ATOM | 1700 | CB   | PHE | A | 348 | -10.895 | 3.301  | 56.379 | 1.00 | 11.20 |
| ATOM | 1701 | CG   | PHE | A | 348 | -12.149 | 2.760  | 55.800 | 1.00 | 6.24  |
| ATOM | 1702 | CD1  | PHE | A | 348 | -13.318 | 2.791  | 56.525 | 1.00 | 2.00  |
| ATOM | 1703 | CE1  | PHE | A | 348 | -14.482 | 2.286  | 56.007 | 1.00 | 2.00  |
| ATOM | 1704 | CZ   | PHE | A | 348 | -14.493 | 1.757  | 54.734 | 1.00 | 5.53  |
| ATOM | 1705 | CE2  | PHE | A | 348 | -13.319 | 1.727  | 53.979 | 1.00 | 7.16  |

FIGURE 3 (Cont.)

| | A | B | C | D | E | F | G | H | I | J |
|---|---|---|---|---|---|---|---|---|---|---|
| ATOM | 1706 | CD2 | PHE | A | 348 | -12.158 | 2.223 | 54.519 | 1.00 | 6.89 |
| ATOM | 1707 | C | PHE | A | 348 | -9.245 | 5.174 | 56.382 | 1.00 | 15.09 |
| ATOM | 1708 | O | PHE | A | 348 | -8.346 | 4.818 | 55.624 | 1.00 | 15.00 |
| ATOM | 1709 | N | TYR | A | 349 | -9.034 | 5.917 | 57.468 | 1.00 | 14.03 |
| ATOM | 1710 | CA | TYR | A | 349 | -7.688 | 6.293 | 57.841 | 1.00 | 14.44 |
| ATOM | 1711 | CB | TYR | A | 349 | -7.213 | 7.517 | 57.060 | 1.00 | 20.39 |
| ATOM | 1712 | CG | TYR | A | 349 | -5.807 | 7.917 | 57.435 | 1.00 | 25.69 |
| ATOM | 1713 | CD1 | TYR | A | 349 | -4.712 | 7.255 | 56.892 | 1.00 | 26.63 |
| ATOM | 1714 | CE1 | TYR | A | 349 | -3.418 | 7.607 | 57.253 | 1.00 | 28.83 |
| ATOM | 1715 | CZ | TYR | A | 349 | -3.211 | 8.622 | 58.171 | 1.00 | 28.13 |
| ATOM | 1716 | OH | TYR | A | 349 | -1.925 | 8.967 | 58.517 | 1.00 | 31.56 |
| ATOM | 1717 | CE2 | TYR | A | 349 | -4.280 | 9.287 | 58.736 | 1.00 | 27.43 |
| ATOM | 1718 | CD2 | TYR | A | 349 | -5.573 | 8.929 | 58.370 | 1.00 | 27.30 |
| ATOM | 1719 | C | TYR | A | 349 | -7.464 | 6.534 | 59.317 | 1.00 | 12.98 |
| ATOM | 1720 | O | TYR | A | 349 | -8.288 | 7.122 | 60.007 | 1.00 | 16.82 |
| ATOM | 1721 | N | ASN | A | 350 | -6.323 | 6.045 | 59.780 | 1.00 | 10.92 |
| ATOM | 1722 | CA | ASN | A | 350 | -5.714 | 6.456 | 61.025 | 1.00 | 6.69 |
| ATOM | 1723 | CB | ASN | A | 350 | -6.198 | 5.630 | 62.203 | 1.00 | 2.00 |
| ATOM | 1724 | CG | ASN | A | 350 | -5.876 | 6.289 | 63.524 | 1.00 | 3.96 |
| ATOM | 1725 | OD1 | ASN | A | 350 | -5.679 | 5.626 | 64.533 | 1.00 | 6.29 |
| ATOM | 1726 | ND2 | ASN | A | 350 | -5.800 | 7.610 | 63.520 | 1.00 | 3.04 |
| ATOM | 1727 | C | ASN | A | 350 | -4.220 | 6.317 | 60.861 | 1.00 | 8.60 |
| ATOM | 1728 | O | ASN | A | 350 | -3.758 | 5.714 | 59.903 | 1.00 | 10.62 |
| ATOM | 1729 | N | GLN | A | 351 | -3.452 | 6.903 | 61.765 | 1.00 | 11.60 |
| ATOM | 1730 | CA | GLN | A | 351 | -2.011 | 6.718 | 61.720 | 1.00 | 14.45 |
| ATOM | 1731 | CB | GLN | A | 351 | -1.268 | 7.922 | 62.317 | 1.00 | 13.31 |
| ATOM | 1732 | CG | GLN | A | 351 | -1.726 | 8.365 | 63.698 | 1.00 | 12.80 |
| ATOM | 1733 | CD | GLN | A | 351 | -2.971 | 9.231 | 63.681 | 1.00 | 11.44 |
| ATOM | 1734 | OE1 | GLN | A | 351 | -3.714 | 9.257 | 62.700 | 1.00 | 6.37 |
| ATOM | 1735 | NE2 | GLN | A | 351 | -3.206 | 9.938 | 64.782 | 1.00 | 13.56 |
| ATOM | 1736 | C | GLN | A | 351 | -1.677 | 5.406 | 62.422 | 1.00 | 18.19 |
| ATOM | 1737 | O | GLN | A | 351 | -0.907 | 4.595 | 61.903 | 1.00 | 19.31 |
| ATOM | 1738 | N | ASP | A | 352 | -2.303 | 5.206 | 63.582 | 1.00 | 21.04 |
| ATOM | 1739 | CA | ASP | A | 352 | -2.230 | 3.977 | 64.359 | 1.00 | 24.13 |
| ATOM | 1740 | CB | ASP | A | 352 | -2.973 | 4.194 | 65.682 | 1.00 | 30.24 |
| ATOM | 1741 | CG | ASP | A | 352 | -2.908 | 2.992 | 66.611 | 1.00 | 37.40 |
| ATOM | 1742 | OD1 | ASP | A | 352 | -3.359 | 1.901 | 66.196 | 1.00 | 41.72 |
| ATOM | 1743 | OD2 | ASP | A | 352 | -2.450 | 3.049 | 67.780 | 1.00 | 38.87 |
| ATOM | 1744 | C | ASP | A | 352 | -2.831 | 2.814 | 63.556 | 1.00 | 24.61 |
| ATOM | 1745 | O | ASP | A | 352 | -4.044 | 2.751 | 63.341 | 1.00 | 26.63 |
| ATOM | 1746 | N | HIS | A | 353 | -1.968 | 1.903 | 63.110 | 1.00 | 23.40 |
| ATOM | 1747 | CA | HIS | A | 353 | -2.355 | 0.819 | 62.208 | 1.00 | 20.40 |
| ATOM | 1748 | CB | HIS | A | 353 | -1.134 | -0.021 | 61.813 | 1.00 | 23.22 |
| ATOM | 1749 | CG | HIS | A | 353 | -0.332 | 0.555 | 60.683 | 1.00 | 27.71 |
| ATOM | 1750 | ND1 | HIS | A | 353 | 0.904 | 1.141 | 60.867 | 1.00 | 29.44 |
| ATOM | 1751 | CE1 | HIS | A | 353 | 1.377 | 1.545 | 59.699 | 1.00 | 28.89 |
| ATOM | 1752 | NE2 | HIS | A | 353 | 0.498 | 1.232 | 58.762 | 1.00 | 26.91 |
| ATOM | 1753 | CD2 | HIS | A | 353 | -0.581 | 0.615 | 59.351 | 1.00 | 27.75 |
| ATOM | 1754 | C | HIS | A | 353 | -3.443 | -0.077 | 62.789 | 1.00 | 17.83 |
| ATOM | 1755 | O | HIS | A | 353 | -4.261 | -0.594 | 62.039 | 1.00 | 17.31 |
| ATOM | 1756 | N | GLU | A | 354 | -3.456 | -0.257 | 64.113 | 1.00 | 18.43 |
| ATOM | 1757 | CA | GLU | A | 354 | -4.460 | -1.106 | 64.776 | 1.00 | 18.97 |

FIGURE 3 (Cont.)

| | A | B | C | D | E | F | G | H | I | J |
|---|---|---|---|---|---|---|---|---|---|---|
| ATOM | 1758 | CB | GLU | A | 354 | -4.233 | -1.226 | 66.293 | 1.00 | 22.59 |
| ATOM | 1759 | CG | GLU | A | 354 | -2.918 | -1.860 | 66.739 | 1.00 | 31.68 |
| ATOM | 1760 | CD | GLU | A | 354 | -2.741 | -1.848 | 68.266 | 1.00 | 38.26 |
| ATOM | 1761 | OE1 | GLU | A | 354 | -2.741 | -0.745 | 68.875 | 1.00 | 38.41 |
| ATOM | 1762 | OE2 | GLU | A | 354 | -2.596 | -2.945 | 68.869 | 1.00 | 40.21 |
| ATOM | 1763 | C | GLU | A | 354 | -5.837 | -0.518 | 64.534 | 1.00 | 15.95 |
| ATOM | 1764 | O | GLU | A | 354 | -6.786 | -1.249 | 64.254 | 1.00 | 15.29 |
| ATOM | 1765 | N | LYS | A | 355 | -5.920 | 0.810 | 64.632 | 1.00 | 11.89 |
| ATOM | 1766 | CA | LYS | A | 355 | -7.175 | 1.541 | 64.523 | 1.00 | 8.73 |
| ATOM | 1767 | CB | LYS | A | 355 | -7.056 | 2.928 | 65.151 | 1.00 | 11.05 |
| ATOM | 1768 | CG | LYS | A | 355 | -6.776 | 2.924 | 66.659 | 1.00 | 15.63 |
| ATOM | 1769 | CD | LYS | A | 355 | -7.456 | 4.096 | 67.380 | 1.00 | 16.06 |
| ATOM | 1770 | CE | LYS | A | 355 | -7.555 | 3.837 | 68.875 | 1.00 | 16.05 |
| ATOM | 1771 | NZ | LYS | A | 355 | -7.529 | 2.378 | 69.172 | 1.00 | 13.84 |
| ATOM | 1772 | C | LYS | A | 355 | -7.590 | 1.669 | 63.080 | 1.00 | 7.48 |
| ATOM | 1773 | O | LYS | A | 355 | -8.771 | 1.653 | 62.766 | 1.00 | 8.66 |
| ATOM | 1774 | N | LEU | A | 356 | -6.613 | 1.807 | 62.194 | 1.00 | 8.54 |
| ATOM | 1775 | CA | LEU | A | 356 | -6.880 | 1.771 | 60.766 | 1.00 | 4.66 |
| ATOM | 1776 | CB | LEU | A | 356 | -5.583 | 1.889 | 59.989 | 1.00 | 2.00 |
| ATOM | 1777 | CG | LEU | A | 356 | -5.772 | 1.542 | 58.527 | 1.00 | 2.00 |
| ATOM | 1778 | CD1 | LEU | A | 356 | -6.488 | 2.715 | 57.863 | 1.00 | 2.00 |
| ATOM | 1779 | CD2 | LEU | A | 356 | -4.419 | 1.206 | 57.891 | 1.00 | 2.00 |
| ATOM | 1780 | C | LEU | A | 356 | -7.619 | 0.477 | 60.406 | 1.00 | 6.08 |
| ATOM | 1781 | O | LEU | A | 356 | -8.701 | 0.529 | 59.839 | 1.00 | 9.14 |
| ATOM | 1782 | N | PHE | A | 357 | -7.048 | -0.672 | 60.767 | 1.00 | 5.80 |
| ATOM | 1783 | CA | PHE | A | 357 | -7.694 | -1.969 | 60.564 | 1.00 | 6.03 |
| ATOM | 1784 | CB | PHE | A | 357 | -6.784 | -3.099 | 61.048 | 1.00 | 3.68 |
| ATOM | 1785 | CG | PHE | A | 357 | -5.474 | -3.206 | 60.303 | 1.00 | 3.15 |
| ATOM | 1786 | CD1 | PHE | A | 357 | -4.402 | -3.893 | 60.865 | 1.00 | 4.03 |
| ATOM | 1787 | CE1 | PHE | A | 357 | -3.189 | -4.004 | 60.193 | 1.00 | 2.00 |
| ATOM | 1788 | CZ | PHE | A | 357 | -3.039 | -3.431 | 58.952 | 1.00 | 2.00 |
| ATOM | 1789 | CE2 | PHE | A | 357 | -4.093 | -2.751 | 58.378 | 1.00 | 2.00 |
| ATOM | 1790 | CD2 | PHE | A | 357 | -5.306 | -2.641 | 59.049 | 1.00 | 2.68 |
| ATOM | 1791 | C | PHE | A | 357 | -9.080 | -2.078 | 61.235 | 1.00 | 9.65 |
| ATOM | 1792 | O | PHE | A | 357 | -10.027 | -2.571 | 60.632 | 1.00 | 10.22 |
| ATOM | 1793 | N | GLU | A | 358 | -9.196 | -1.623 | 62.480 | 1.00 | 15.70 |
| ATOM | 1794 | CA | GLU | A | 358 | -10.487 | -1.586 | 63.168 | 1.00 | 19.55 |
| ATOM | 1795 | CB | GLU | A | 358 | -10.393 | -0.751 | 64.457 | 1.00 | 24.82 |
| ATOM | 1796 | CG | GLU | A | 358 | -11.227 | -1.254 | 65.626 | 1.00 | 34.95 |
| ATOM | 1797 | CD | GLU | A | 358 | -10.439 | -1.360 | 66.942 | 1.00 | 43.24 |
| ATOM | 1798 | OE1 | GLU | A | 358 | -11.079 | -1.444 | 68.022 | 1.00 | 45.63 |
| ATOM | 1799 | OE2 | GLU | A | 358 | -9.180 | -1.371 | 66.918 | 1.00 | 45.90 |
| ATOM | 1800 | C | GLU | A | 358 | -11.542 | -1.003 | 62.222 | 1.00 | 18.14 |
| ATOM | 1801 | O | GLU | A | 358 | -12.608 | -1.592 | 62.038 | 1.00 | 19.53 |
| ATOM | 1802 | N | LEU | A | 359 | -11.210 | 0.132 | 61.598 | 1.00 | 14.04 |
| ATOM | 1803 | CA | LEU | A | 359 | -12.130 | 0.880 | 60.744 | 1.00 | 8.74 |
| ATOM | 1804 | CB | LEU | A | 359 | -11.541 | 2.227 | 60.365 | 1.00 | 6.14 |
| ATOM | 1805 | CG | LEU | A | 359 | -11.467 | 3.286 | 61.446 | 1.00 | 5.96 |
| ATOM | 1806 | CD1 | LEU | A | 359 | -10.567 | 4.398 | 60.965 | 1.00 | 5.93 |
| ATOM | 1807 | CD2 | LEU | A | 359 | -12.852 | 3.809 | 61.727 | 1.00 | 9.82 |
| ATOM | 1808 | C | LEU | A | 359 | -12.475 | 0.139 | 59.476 | 1.00 | 9.26 |
| ATOM | 1809 | O | LEU | A | 359 | -13.611 | 0.162 | 59.055 | 1.00 | 12.21 |

FIGURE 3 (Cont.)

|  | A | B | C | D | E | F | G | H | I | J |
|---|---|---|---|---|---|---|---|---|---|---|
| ATOM | 1810 | N | ILE | A | 360 | -11.493 | -0.516 | 58.869 | 1.00 | 11.43 |
| ATOM | 1811 | CA | ILE | A | 360 | -11.698 | -1.250 | 57.620 | 1.00 | 10.30 |
| ATOM | 1812 | CB | ILE | A | 360 | -10.347 | -1.634 | 57.007 | 1.00 | 7.27 |
| ATOM | 1813 | CG1 | ILE | A | 360 | -9.638 | -0.374 | 56.521 | 1.00 | 8.60 |
| ATOM | 1814 | CD1 | ILE | A | 360 | -8.114 | -0.476 | 56.529 | 1.00 | 11.30 |
| ATOM | 1815 | CG2 | ILE | A | 360 | -10.526 | -2.597 | 55.856 | 1.00 | 7.20 |
| ATOM | 1816 | C | ILE | A | 360 | -12.623 | -2.467 | 57.754 | 1.00 | 11.77 |
| ATOM | 1817 | O | ILE | A | 360 | -13.270 | -2.855 | 56.789 | 1.00 | 15.18 |
| ATOM | 1818 | N | LEU | A | 361 | -12.699 | -3.065 | 58.935 | 1.00 | 12.28 |
| ATOM | 1819 | CA | LEU | A | 361 | -13.555 | -4.229 | 59.108 | 1.00 | 15.34 |
| ATOM | 1820 | CB | LEU | A | 361 | -12.917 | -5.243 | 60.056 | 1.00 | 15.41 |
| ATOM | 1821 | CG | LEU | A | 361 | -11.561 | -5.857 | 59.742 | 1.00 | 15.18 |
| ATOM | 1822 | CD1 | LEU | A | 361 | -10.597 | -5.492 | 60.845 | 1.00 | 13.37 |
| ATOM | 1823 | CD2 | LEU | A | 361 | -11.700 | -7.367 | 59.621 | 1.00 | 15.77 |
| ATOM | 1824 | C | LEU | A | 361 | -14.917 | -3.861 | 59.665 | 1.00 | 19.43 |
| ATOM | 1825 | O | LEU | A | 361 | -15.832 | -4.679 | 59.630 | 1.00 | 23.44 |
| ATOM | 1826 | N | MET | A | 362 | -15.059 | -2.649 | 60.198 | 1.00 | 21.97 |
| ATOM | 1827 | CA | MET | A | 362 | -16.203 | -2.356 | 61.067 | 1.00 | 21.82 |
| ATOM | 1828 | CB | MET | A | 362 | -15.799 | -2.549 | 62.532 | 1.00 | 26.07 |
| ATOM | 1829 | CG | MET | A | 362 | -15.409 | -3.979 | 62.881 | 1.00 | 29.84 |
| ATOM | 1830 | SD | MET | A | 362 | -15.264 | -4.285 | 64.654 | 1.00 | 39.13 |
| ATOM | 1831 | CE | MET | A | 362 | -14.784 | -2.629 | 65.364 | 1.00 | 36.73 |
| ATOM | 1832 | C | MET | A | 362 | -16.910 | -1.009 | 60.897 | 1.00 | 17.65 |
| ATOM | 1833 | O | MET | A | 362 | -18.030 | -0.831 | 61.386 | 1.00 | 16.77 |
| ATOM | 1834 | N | GLU | A | 363 | -16.266 | -0.055 | 60.242 | 1.00 | 13.74 |
| ATOM | 1835 | CA | GLU | A | 363 | -16.931 | 1.210 | 60.001 | 1.00 | 15.51 |
| ATOM | 1836 | CB | GLU | A | 363 | -15.966 | 2.398 | 59.973 | 1.00 | 18.68 |
| ATOM | 1837 | CG | GLU | A | 363 | -16.561 | 3.663 | 60.593 | 1.00 | 31.01 |
| ATOM | 1838 | CD | GLU | A | 363 | -17.452 | 3.422 | 61.856 | 1.00 | 35.93 |
| ATOM | 1839 | OE1 | GLU | A | 363 | -16.941 | 3.569 | 63.002 | 1.00 | 33.27 |
| ATOM | 1840 | OE2 | GLU | A | 363 | -18.679 | 3.116 | 61.719 | 1.00 | 36.28 |
| ATOM | 1841 | C | GLU | A | 363 | -17.708 | 1.115 | 58.722 | 1.00 | 14.52 |
| ATOM | 1842 | O | GLU | A | 363 | -17.162 | 0.701 | 57.713 | 1.00 | 16.89 |
| ATOM | 1843 | N | GLU | A | 364 | -18.992 | 1.469 | 58.779 | 1.00 | 15.11 |
| ATOM | 1844 | CA | GLU | A | 364 | -19.842 | 1.498 | 57.597 | 1.00 | 13.83 |
| ATOM | 1845 | CB | GLU | A | 364 | -21.301 | 1.639 | 57.994 | 1.00 | 19.07 |
| ATOM | 1846 | CG | GLU | A | 364 | -22.261 | 1.741 | 56.819 | 1.00 | 27.20 |
| ATOM | 1847 | CD | GLU | A | 364 | -23.493 | 0.882 | 57.022 | 1.00 | 35.18 |
| ATOM | 1848 | OE1 | GLU | A | 364 | -23.525 | -0.246 | 56.461 | 1.00 | 38.36 |
| ATOM | 1849 | OE2 | GLU | A | 364 | -24.418 | 1.325 | 57.756 | 1.00 | 36.57 |
| ATOM | 1850 | C | GLU | A | 364 | -19.427 | 2.684 | 56.744 | 1.00 | 9.11 |
| ATOM | 1851 | O | GLU | A | 364 | -19.415 | 3.820 | 57.241 | 1.00 | 8.00 |
| ATOM | 1852 | N | ILE | A | 365 | -19.087 | 2.399 | 55.480 | 1.00 | 2.46 |
| ATOM | 1853 | CA | ILE | A | 365 | -18.591 | 3.383 | 54.519 | 1.00 | 2.00 |
| ATOM | 1854 | CB | ILE | A | 365 | -18.508 | 2.771 | 53.104 | 1.00 | 2.00 |
| ATOM | 1855 | CG1 | ILE | A | 365 | -18.004 | 3.797 | 52.107 | 1.00 | 2.00 |
| ATOM | 1856 | CD1 | ILE | A | 365 | -16.534 | 3.631 | 51.825 | 1.00 | 7.55 |
| ATOM | 1857 | CG2 | ILE | A | 365 | -19.829 | 2.211 | 52.623 | 1.00 | 2.00 |
| ATOM | 1858 | C | ILE | A | 365 | -19.394 | 4.678 | 54.488 | 1.00 | 6.75 |
| ATOM | 1859 | O | ILE | A | 365 | -20.624 | 4.660 | 54.565 | 1.00 | 10.34 |
| ATOM | 1860 | N | ARG | A | 366 | -18.708 | 5.810 | 54.381 | 1.00 | 8.02 |
| ATOM | 1861 | CA | ARG | A | 366 | -19.431 | 7.071 | 54.286 | 1.00 | 7.06 |

FIGURE 3 (Cont.)

|      | A    | B   | C   | D | E   | F       | G      | H      | I    | J     |
|------|------|-----|-----|---|-----|---------|--------|--------|------|-------|
| ATOM | 1862 | CB  | ARG | A | 366 | -19.236 | 7.880  | 55.555 | 1.00 | 8.35  |
| ATOM | 1863 | CG  | ARG | A | 366 | -19.736 | 7.175  | 56.794 | 1.00 | 12.15 |
| ATOM | 1864 | CD  | ARG | A | 366 | -19.268 | 7.803  | 58.083 | 1.00 | 15.18 |
| ATOM | 1865 | NE  | ARG | A | 366 | -17.854 | 8.135  | 57.999 | 1.00 | 16.46 |
| ATOM | 1866 | CZ  | ARG | A | 366 | -17.181 | 8.835  | 58.895 | 1.00 | 16.58 |
| ATOM | 1867 | NH1 | ARG | A | 366 | -17.781 | 9.308  | 59.978 | 1.00 | 14.84 |
| ATOM | 1868 | NH2 | ARG | A | 366 | -15.891 | 9.064  | 58.699 | 1.00 | 18.16 |
| ATOM | 1869 | C   | ARG | A | 366 | -19.029 | 7.868  | 53.046 | 1.00 | 7.11  |
| ATOM | 1870 | O   | ARG | A | 366 | -17.892 | 7.755  | 52.579 | 1.00 | 8.22  |
| ATOM | 1871 | N   | PHE | A | 367 | -19.964 | 8.656  | 52.511 | 1.00 | 2.00  |
| ATOM | 1872 | CA  | PHE | A | 367 | -19.679 | 9.482  | 51.348 | 1.00 | 2.00  |
| ATOM | 1873 | CB  | PHE | A | 367 | -20.386 | 8.974  | 50.107 | 1.00 | 2.00  |
| ATOM | 1874 | CG  | PHE | A | 367 | -20.239 | 7.526  | 49.902 | 1.00 | 2.00  |
| ATOM | 1875 | CD1 | PHE | A | 367 | -19.098 | 7.025  | 49.351 | 1.00 | 2.00  |
| ATOM | 1876 | CE1 | PHE | A | 367 | -18.945 | 5.682  | 49.180 | 1.00 | 6.88  |
| ATOM | 1877 | CZ  | PHE | A | 367 | -19.962 | 4.826  | 49.551 | 1.00 | 8.38  |
| ATOM | 1878 | CE2 | PHE | A | 367 | -21.117 | 5.330  | 50.095 | 1.00 | 3.01  |
| ATOM | 1879 | CD2 | PHE | A | 367 | -21.246 | 6.662  | 50.270 | 1.00 | 2.00  |
| ATOM | 1880 | C   | PHE | A | 367 | -20.068 | 10.914 | 51.575 | 1.00 | 2.00  |
| ATOM | 1881 | O   | PHE | A | 367 | -21.084 | 11.177 | 52.202 | 1.00 | 2.00  |
| ATOM | 1882 | N   | PRO | A | 368 | -19.215 | 11.818 | 51.073 | 1.00 | 4.91  |
| ATOM | 1883 | CA  | PRO | A | 368 | -19.438 | 13.259 | 51.105 | 1.00 | 2.00  |
| ATOM | 1884 | CB  | PRO | A | 368 | -18.320 | 13.797 | 50.230 | 1.00 | 2.29  |
| ATOM | 1885 | CG  | PRO | A | 368 | -17.240 | 12.835 | 50.409 | 1.00 | 6.63  |
| ATOM | 1886 | CD  | PRO | A | 368 | -17.917 | 11.495 | 50.445 | 1.00 | 7.01  |
| ATOM | 1887 | C   | PRO | A | 368 | -20.729 | 13.579 | 50.443 | 1.00 | 2.99  |
| ATOM | 1888 | O   | PRO | A | 368 | -20.998 | 13.116 | 49.325 | 1.00 | 2.00  |
| ATOM | 1889 | N   | ARG | A | 369 | -21.509 | 14.396 | 51.141 | 1.00 | 5.03  |
| ATOM | 1890 | CA  | ARG | A | 369 | -22.850 | 14.733 | 50.739 | 1.00 | 3.72  |
| ATOM | 1891 | CB  | ARG | A | 369 | -23.365 | 15.888 | 51.579 | 1.00 | 7.65  |
| ATOM | 1892 | CG  | ARG | A | 369 | -24.719 | 15.626 | 52.204 | 1.00 | 9.47  |
| ATOM | 1893 | CD  | ARG | A | 369 | -25.829 | 15.484 | 51.201 | 1.00 | 9.66  |
| ATOM | 1894 | NE  | ARG | A | 369 | -26.866 | 16.473 | 51.426 | 1.00 | 9.67  |
| ATOM | 1895 | CZ  | ARG | A | 369 | -28.026 | 16.187 | 51.978 | 1.00 | 10.71 |
| ATOM | 1896 | NH1 | ARG | A | 369 | -28.276 | 14.934 | 52.347 | 1.00 | 11.69 |
| ATOM | 1897 | NH2 | ARG | A | 369 | -28.934 | 17.143 | 52.163 | 1.00 | 10.99 |
| ATOM | 1898 | C   | ARG | A | 369 | -22.873 | 15.091 | 49.280 | 1.00 | 6.32  |
| ATOM | 1899 | O   | ARG | A | 369 | -23.819 | 14.757 | 48.595 | 1.00 | 10.60 |
| ATOM | 1900 | N   | THR | A | 370 | -21.809 | 15.743 | 48.813 | 1.00 | 9.67  |
| ATOM | 1901 | CA  | THR | A | 370 | -21.677 | 16.193 | 47.423 | 1.00 | 9.89  |
| ATOM | 1902 | CB  | THR | A | 370 | -20.444 | 17.099 | 47.254 | 1.00 | 12.56 |
| ATOM | 1903 | OG1 | THR | A | 370 | -19.264 | 16.420 | 47.730 | 1.00 | 12.80 |
| ATOM | 1904 | CG2 | THR | A | 370 | -20.580 | 18.342 | 48.147 | 1.00 | 12.18 |
| ATOM | 1905 | C   | THR | A | 370 | -21.642 | 15.055 | 46.418 | 1.00 | 6.63  |
| ATOM | 1906 | O   | THR | A | 370 | -22.650 | 14.763 | 45.821 | 1.00 | 12.38 |
| ATOM | 1907 | N   | LEU | A | 371 | -20.494 | 14.423 | 46.235 | 1.00 | 6.19  |
| ATOM | 1908 | CA  | LEU | A | 371 | -20.316 | 13.310 | 45.285 | 1.00 | 10.00 |
| ATOM | 1909 | CB  | LEU | A | 371 | -19.373 | 12.274 | 45.890 | 1.00 | 9.60  |
| ATOM | 1910 | CG  | LEU | A | 371 | -19.355 | 10.867 | 45.314 | 1.00 | 5.30  |
| ATOM | 1911 | CD1 | LEU | A | 371 | -17.944 | 10.607 | 44.839 | 1.00 | 5.99  |
| ATOM | 1912 | CD2 | LEU | A | 371 | -19.795 | 9.859  | 46.361 | 1.00 | 3.04  |
| ATOM | 1913 | C   | LEU | A | 371 | -21.587 | 12.606 | 44.819 | 1.00 | 10.68 |

FIGURE 3 (Cont.)

|  | A | B | C | D | E | F | G | H | I | J |
|---|---|---|---|---|---|---|---|---|---|---|
| ATOM | 1914 | O | LEU | A | 371 | -22.356 | 12.131 | 45.648 | 1.00 | 14.90 |
| ATOM | 1915 | N | GLY | A | 372 | -21.755 | 12.495 | 43.496 | 1.00 | 12.62 |
| ATOM | 1916 | CA | GLY | A | 372 | -22.994 | 12.057 | 42.854 | 1.00 | 14.23 |
| ATOM | 1917 | C | GLY | A | 372 | -23.426 | 10.584 | 42.918 | 1.00 | 17.99 |
| ATOM | 1918 | O | GLY | A | 372 | -22.618 | 9.682 | 43.214 | 1.00 | 13.97 |
| ATOM | 1919 | N | PRO | A | 373 | -24.706 | 10.347 | 42.593 | 1.00 | 18.71 |
| ATOM | 1920 | CA | PRO | A | 373 | -25.390 | 9.062 | 42.820 | 1.00 | 19.50 |
| ATOM | 1921 | CB | PRO | A | 373 | -26.781 | 9.319 | 42.242 | 1.00 | 16.42 |
| ATOM | 1922 | CG | PRO | A | 373 | -26.583 | 10.417 | 41.270 | 1.00 | 14.30 |
| ATOM | 1923 | CD | PRO | A | 373 | -25.606 | 11.314 | 41.940 | 1.00 | 17.57 |
| ATOM | 1924 | C | PRO | A | 373 | -24.752 | 7.833 | 42.143 | 1.00 | 21.10 |
| ATOM | 1925 | O | PRO | A | 373 | -24.542 | 6.826 | 42.820 | 1.00 | 20.43 |
| ATOM | 1926 | N | GLU | A | 374 | -24.485 | 7.917 | 40.839 | 1.00 | 22.94 |
| ATOM | 1927 | CA | GLU | A | 374 | -23.759 | 6.884 | 40.108 | 1.00 | 23.93 |
| ATOM | 1928 | CB | GLU | A | 374 | -23.542 | 7.282 | 38.636 | 1.00 | 29.70 |
| ATOM | 1929 | CG | GLU | A | 374 | -23.741 | 8.774 | 38.304 | 1.00 | 41.13 |
| ATOM | 1930 | CD | GLU | A | 374 | -22.653 | 9.710 | 38.883 | 1.00 | 47.03 |
| ATOM | 1931 | OE1 | GLU | A | 374 | -21.468 | 9.659 | 38.436 | 1.00 | 48.15 |
| ATOM | 1932 | OE2 | GLU | A | 374 | -22.986 | 10.519 | 39.789 | 1.00 | 46.39 |
| ATOM | 1933 | C | GLU | A | 374 | -22.430 | 6.548 | 40.816 | 1.00 | 23.18 |
| ATOM | 1934 | O | GLU | A | 374 | -22.226 | 5.403 | 41.210 | 1.00 | 27.76 |
| ATOM | 1935 | N | ALA | A | 375 | -21.549 | 7.534 | 41.014 | 1.00 | 19.13 |
| ATOM | 1936 | CA | ALA | A | 375 | -20.269 | 7.314 | 41.719 | 1.00 | 15.51 |
| ATOM | 1937 | CB | ALA | A | 375 | -19.458 | 8.576 | 41.731 | 1.00 | 16.49 |
| ATOM | 1938 | C | ALA | A | 375 | -20.432 | 6.797 | 43.148 | 1.00 | 13.68 |
| ATOM | 1939 | O | ALA | A | 375 | -19.704 | 5.902 | 43.583 | 1.00 | 7.47 |
| ATOM | 1940 | N | LYS | A | 376 | -21.401 | 7.375 | 43.866 | 1.00 | 15.49 |
| ATOM | 1941 | CA | LYS | A | 376 | -21.757 | 6.928 | 45.213 | 1.00 | 13.73 |
| ATOM | 1942 | CB | LYS | A | 376 | -22.922 | 7.737 | 45.786 | 1.00 | 10.52 |
| ATOM | 1943 | CG | LYS | A | 376 | -22.830 | 7.940 | 47.288 | 1.00 | 10.89 |
| ATOM | 1944 | CD | LYS | A | 376 | -24.037 | 8.668 | 47.842 | 1.00 | 14.93 |
| ATOM | 1945 | CE | LYS | A | 376 | -23.665 | 9.986 | 48.489 | 1.00 | 16.52 |
| ATOM | 1946 | NZ | LYS | A | 376 | -24.387 | 11.112 | 47.840 | 1.00 | 19.42 |
| ATOM | 1947 | C | LYS | A | 376 | -22.094 | 5.455 | 45.214 | 1.00 | 13.09 |
| ATOM | 1948 | O | LYS | A | 376 | -21.755 | 4.752 | 46.154 | 1.00 | 14.09 |
| ATOM | 1949 | N | SER | A | 377 | -22.743 | 5.004 | 44.141 | 1.00 | 14.13 |
| ATOM | 1950 | CA | SER | A | 377 | -23.130 | 3.607 | 43.950 | 1.00 | 15.25 |
| ATOM | 1951 | CB | SER | A | 377 | -24.243 | 3.511 | 42.894 | 1.00 | 14.83 |
| ATOM | 1952 | OG | SER | A | 377 | -24.388 | 2.201 | 42.373 | 1.00 | 16.34 |
| ATOM | 1953 | C | SER | A | 377 | -21.943 | 2.708 | 43.577 | 1.00 | 16.37 |
| ATOM | 1954 | O | SER | A | 377 | -21.725 | 1.657 | 44.198 | 1.00 | 14.21 |
| ATOM | 1955 | N | LEU | A | 378 | -21.178 | 3.116 | 42.567 | 1.00 | 16.17 |
| ATOM | 1956 | CA | LEU | A | 378 | -20.029 | 2.326 | 42.160 | 1.00 | 17.04 |
| ATOM | 1957 | CB | LEU | A | 378 | -19.255 | 2.989 | 41.025 | 1.00 | 14.67 |
| ATOM | 1958 | CG | LEU | A | 378 | -17.890 | 2.364 | 40.736 | 1.00 | 11.76 |
| ATOM | 1959 | CD1 | LEU | A | 378 | -18.033 | 1.024 | 40.038 | 1.00 | 11.34 |
| ATOM | 1960 | CD2 | LEU | A | 378 | -17.072 | 3.292 | 39.901 | 1.00 | 12.30 |
| ATOM | 1961 | C | LEU | A | 378 | -19.119 | 2.079 | 43.351 | 1.00 | 17.65 |
| ATOM | 1962 | O | LEU | A | 378 | -18.641 | 0.954 | 43.542 | 1.00 | 18.82 |
| ATOM | 1963 | N | LEU | A | 379 | -18.917 | 3.126 | 44.153 | 1.00 | 14.53 |
| ATOM | 1964 | CA | LEU | A | 379 | -18.048 | 3.051 | 45.320 | 1.00 | 14.73 |
| ATOM | 1965 | CB | LEU | A | 379 | -17.826 | 4.434 | 45.916 | 1.00 | 16.09 |

FIGURE 3 (Cont.)

|   | A | B | C | D | E | F | G | H | I | J |
|---|---|---|---|---|---|---|---|---|---|---|
| ATOM | 1966 | CG | LEU | A | 379 | -16.878 | 5.318 | 45.098 | 1.00 | 20.41 |
| ATOM | 1967 | CD1 | LEU | A | 379 | -16.374 | 6.478 | 45.938 | 1.00 | 21.62 |
| ATOM | 1968 | CD2 | LEU | A | 379 | -15.706 | 4.530 | 44.482 | 1.00 | 19.01 |
| ATOM | 1969 | C | LEU | A | 379 | -18.612 | 2.111 | 46.357 | 1.00 | 13.13 |
| ATOM | 1970 | O | LEU | A | 379 | -18.013 | 1.083 | 46.669 | 1.00 | 12.02 |
| ATOM | 1971 | N | SER | A | 380 | -19.786 | 2.467 | 46.860 | 1.00 | 14.58 |
| ATOM | 1972 | CA | SER | A | 380 | -20.576 | 1.617 | 47.741 | 1.00 | 14.20 |
| ATOM | 1973 | CB | SER | A | 380 | -22.035 | 2.076 | 47.758 | 1.00 | 8.63 |
| ATOM | 1974 | OG | SER | A | 380 | -22.568 | 1.963 | 49.063 | 1.00 | 8.09 |
| ATOM | 1975 | C | SER | A | 380 | -20.512 | 0.156 | 47.329 | 1.00 | 16.32 |
| ATOM | 1976 | O | SER | A | 380 | -20.367 | -0.713 | 48.190 | 1.00 | 18.70 |
| ATOM | 1977 | N | GLY | A | 381 | -20.613 | -0.096 | 46.018 | 1.00 | 16.95 |
| ATOM | 1978 | CA | GLY | A | 381 | -20.575 | -1.437 | 45.458 | 1.00 | 15.44 |
| ATOM | 1979 | C | GLY | A | 381 | -19.194 | -2.036 | 45.586 | 1.00 | 18.09 |
| ATOM | 1980 | O | GLY | A | 381 | -19.023 | -3.159 | 46.077 | 1.00 | 21.76 |
| ATOM | 1981 | N | LEU | A | 382 | -18.192 | -1.265 | 45.178 | 1.00 | 16.17 |
| ATOM | 1982 | CA | LEU | A | 382 | -16.829 | -1.757 | 45.177 | 1.00 | 8.34 |
| ATOM | 1983 | CB | LEU | A | 382 | -15.913 | -0.816 | 44.416 | 1.00 | 3.25 |
| ATOM | 1984 | CG | LEU | A | 382 | -16.022 | -0.733 | 42.890 | 1.00 | 3.54 |
| ATOM | 1985 | CD1 | LEU | A | 382 | -15.416 | 0.566 | 42.395 | 1.00 | 3.71 |
| ATOM | 1986 | CD2 | LEU | A | 382 | -15.353 | -1.916 | 42.220 | 1.00 | 2.00 |
| ATOM | 1987 | C | LEU | A | 382 | -16.326 | -1.901 | 46.575 | 1.00 | 10.35 |
| ATOM | 1988 | O | LEU | A | 382 | -15.334 | -2.563 | 46.788 | 1.00 | 19.95 |
| ATOM | 1989 | N | LEU | A | 383 | -16.981 | -1.277 | 47.542 | 1.00 | 11.20 |
| ATOM | 1990 | CA | LEU | A | 383 | -16.438 | -1.292 | 48.906 | 1.00 | 13.21 |
| ATOM | 1991 | CB | LEU | A | 383 | -16.120 | 0.129 | 49.416 | 1.00 | 8.87 |
| ATOM | 1992 | CG | LEU | A | 383 | -14.894 | 0.790 | 48.798 | 1.00 | 6.84 |
| ATOM | 1993 | CD1 | LEU | A | 383 | -15.057 | 2.269 | 48.787 | 1.00 | 7.23 |
| ATOM | 1994 | CD2 | LEU | A | 383 | -13.639 | 0.417 | 49.544 | 1.00 | 11.95 |
| ATOM | 1995 | C | LEU | A | 383 | -17.287 | -2.081 | 49.910 | 1.00 | 15.85 |
| ATOM | 1996 | O | LEU | A | 383 | -17.208 | -1.863 | 51.128 | 1.00 | 16.68 |
| ATOM | 1997 | N | LYS | A | 384 | -18.087 | -3.013 | 49.404 | 1.00 | 15.31 |
| ATOM | 1998 | CA | LYS | A | 384 | -18.679 | -4.008 | 50.281 | 1.00 | 14.09 |
| ATOM | 1999 | CB | LYS | A | 384 | -19.651 | -4.879 | 49.502 | 1.00 | 12.53 |
| ATOM | 2000 | CG | LYS | A | 384 | -21.080 | -4.475 | 49.721 | 1.00 | 14.38 |
| ATOM | 2001 | CD | LYS | A | 384 | -21.640 | -3.759 | 48.507 | 1.00 | 17.18 |
| ATOM | 2002 | CE | LYS | A | 384 | -23.140 | -4.038 | 48.328 | 1.00 | 18.85 |
| ATOM | 2003 | NZ | LYS | A | 384 | -23.973 | -3.410 | 49.387 | 1.00 | 19.04 |
| ATOM | 2004 | C | LYS | A | 384 | -17.574 | -4.840 | 50.982 | 1.00 | 13.85 |
| ATOM | 2005 | O | LYS | A | 384 | -16.525 | -5.158 | 50.390 | 1.00 | 13.11 |
| ATOM | 2006 | N | LYS | A | 385 | -17.802 | -5.150 | 52.253 | 1.00 | 11.59 |
| ATOM | 2007 | CA | LYS | A | 385 | -16.804 | -5.826 | 53.068 | 1.00 | 12.04 |
| ATOM | 2008 | CB | LYS | A | 385 | -17.063 | -5.581 | 54.545 | 1.00 | 9.30 |
| ATOM | 2009 | CG | LYS | A | 385 | -17.188 | -4.138 | 54.885 | 1.00 | 7.03 |
| ATOM | 2010 | CD | LYS | A | 385 | -16.208 | -3.764 | 55.946 | 1.00 | 5.61 |
| ATOM | 2011 | CE | LYS | A | 385 | -16.613 | -2.461 | 56.584 | 1.00 | 6.56 |
| ATOM | 2012 | NZ | LYS | A | 385 | -15.998 | -1.321 | 55.843 | 1.00 | 9.18 |
| ATOM | 2013 | C | LYS | A | 385 | -16.749 | -7.318 | 52.793 | 1.00 | 17.00 |
| ATOM | 2014 | O | LYS | A | 385 | -15.660 | -7.897 | 52.731 | 1.00 | 19.47 |
| ATOM | 2015 | N | ASP | A | 386 | -17.910 | -7.955 | 52.652 | 1.00 | 20.71 |
| ATOM | 2016 | CA | ASP | A | 386 | -17.920 | -9.340 | 52.208 | 1.00 | 25.16 |
| ATOM | 2017 | CB | ASP | A | 386 | -19.183 | -10.083 | 52.624 | 1.00 | 29.20 |

FIGURE 3 (Cont.)

|      | A    | B   | C   | D | E   | F       | G       | H      | I    | J     |
|------|------|-----|-----|---|-----|---------|---------|--------|------|-------|
| ATOM | 2018 | CG  | ASP | A | 386 | -19.322 | -11.411 | 51.895 | 1.00 | 33.93 |
| ATOM | 2019 | OD1 | ASP | A | 386 | -19.802 | -11.386 | 50.742 | 1.00 | 34.87 |
| ATOM | 2020 | OD2 | ASP | A | 386 | -18.939 | -12.513 | 52.366 | 1.00 | 36.62 |
| ATOM | 2021 | C   | ASP | A | 386 | -17.742 | -9.406  | 50.689 | 1.00 | 25.90 |
| ATOM | 2022 | O   | ASP | A | 386 | -18.517 | -8.803  | 49.943 | 1.00 | 26.86 |
| ATOM | 2023 | N   | PRO | A | 387 | -16.742 | -10.162 | 50.236 | 1.00 | 25.68 |
| ATOM | 2024 | CA  | PRO | A | 387 | -16.328 | -10.140 | 48.832 | 1.00 | 24.61 |
| ATOM | 2025 | CB  | PRO | A | 387 | -15.070 | -10.995 | 48.831 | 1.00 | 25.30 |
| ATOM | 2026 | CG  | PRO | A | 387 | -14.684 | -11.112 | 50.264 | 1.00 | 26.40 |
| ATOM | 2027 | CD  | PRO | A | 387 | -15.949 | -11.118 | 51.028 | 1.00 | 26.16 |
| ATOM | 2028 | C   | PRO | A | 387 | -17.370 | -10.770 | 47.928 | 1.00 | 26.24 |
| ATOM | 2029 | O   | PRO | A | 387 | -17.449 | -10.407 | 46.750 | 1.00 | 29.56 |
| ATOM | 2030 | N   | LYS | A | 388 | -18.170 | -11.685 | 48.475 | 1.00 | 23.34 |
| ATOM | 2031 | CA  | LYS | A | 388 | -19.192 | -12.370 | 47.687 | 1.00 | 20.87 |
| ATOM | 2032 | CB  | LYS | A | 388 | -19.858 | -13.498 | 48.488 | 1.00 | 20.71 |
| ATOM | 2033 | CG  | LYS | A | 388 | -18.910 | -14.284 | 49.395 | 1.00 | 22.88 |
| ATOM | 2034 | CD  | LYS | A | 388 | -19.416 | -15.682 | 49.674 | 1.00 | 25.38 |
| ATOM | 2035 | CE  | LYS | A | 388 | -18.912 | -16.664 | 48.623 | 1.00 | 29.08 |
| ATOM | 2036 | NZ  | LYS | A | 388 | -19.845 | -17.822 | 48.432 | 1.00 | 32.58 |
| ATOM | 2037 | C   | LYS | A | 388 | -20.228 | -11.376 | 47.157 | 1.00 | 18.56 |
| ATOM | 2038 | O   | LYS | A | 388 | -20.881 | -11.635 | 46.146 | 1.00 | 21.02 |
| ATOM | 2039 | N   | GLN | A | 389 | -20.347 | -10.233 | 47.832 | 1.00 | 14.34 |
| ATOM | 2040 | CA  | GLN | A | 389 | -21.299 | -9.191  | 47.450 | 1.00 | 10.32 |
| ATOM | 2041 | CB  | GLN | A | 389 | -22.126 | -8.760  | 48.647 | 1.00 | 6.71  |
| ATOM | 2042 | CG  | GLN | A | 389 | -22.820 | -9.868  | 49.349 | 1.00 | 8.49  |
| ATOM | 2043 | CD  | GLN | A | 389 | -24.087 | -9.400  | 49.982 | 1.00 | 13.62 |
| ATOM | 2044 | OE1 | GLN | A | 389 | -24.245 | -8.207  | 50.273 | 1.00 | 17.67 |
| ATOM | 2045 | NE2 | GLN | A | 389 | -25.014 | -10.323 | 50.191 | 1.00 | 16.98 |
| ATOM | 2046 | C   | GLN | A | 389 | -20.606 | -7.968  | 46.869 | 1.00 | 9.84  |
| ATOM | 2047 | O   | GLN | A | 389 | -21.260 | -6.979  | 46.550 | 1.00 | 9.03  |
| ATOM | 2048 | N   | ARG | A | 390 | -19.288 | -8.023  | 46.738 | 1.00 | 8.38  |
| ATOM | 2049 | CA  | ARG | A | 390 | -18.570 | -6.907  | 46.157 | 1.00 | 10.59 |
| ATOM | 2050 | CB  | ARG | A | 390 | -17.084 | -7.002  | 46.462 | 1.00 | 12.48 |
| ATOM | 2051 | CG  | ARG | A | 390 | -16.373 | -5.667  | 46.362 | 1.00 | 14.11 |
| ATOM | 2052 | CD  | ARG | A | 390 | -14.951 | -5.667  | 46.908 | 1.00 | 13.49 |
| ATOM | 2053 | NE  | ARG | A | 390 | -14.894 | -6.129  | 48.282 | 1.00 | 12.63 |
| ATOM | 2054 | CZ  | ARG | A | 390 | -14.009 | -7.009  | 48.726 | 1.00 | 16.63 |
| ATOM | 2055 | NH1 | ARG | A | 390 | -13.083 | -7.512  | 47.905 | 1.00 | 13.48 |
| ATOM | 2056 | NH2 | ARG | A | 390 | -14.041 | -7.378  | 50.002 | 1.00 | 17.94 |
| ATOM | 2057 | C   | ARG | A | 390 | -18.780 | -6.866  | 44.659 | 1.00 | 12.58 |
| ATOM | 2058 | O   | ARG | A | 390 | -18.759 | -7.899  | 43.994 | 1.00 | 16.45 |
| ATOM | 2059 | N   | LEU | A | 391 | -18.989 | -5.669  | 44.132 | 1.00 | 14.13 |
| ATOM | 2060 | CA  | LEU | A | 391 | -19.121 | -5.480  | 42.695 | 1.00 | 15.13 |
| ATOM | 2061 | CB  | LEU | A | 391 | -19.425 | -4.008  | 42.386 | 1.00 | 15.53 |
| ATOM | 2062 | CG  | LEU | A | 391 | -19.725 | -3.569  | 40.953 | 1.00 | 17.60 |
| ATOM | 2063 | CD1 | LEU | A | 391 | -21.190 | -3.692  | 40.671 | 1.00 | 20.74 |
| ATOM | 2064 | CD2 | LEU | A | 391 | -19.305 | -2.130  | 40.762 | 1.00 | 20.61 |
| ATOM | 2065 | C   | LEU | A | 391 | -17.843 | -5.970  | 41.998 | 1.00 | 15.47 |
| ATOM | 2066 | O   | LEU | A | 391 | -16.769 | -5.392  | 42.155 | 1.00 | 14.75 |
| ATOM | 2067 | N   | GLY | A | 392 | -17.967 | -7.066  | 41.262 | 1.00 | 15.12 |
| ATOM | 2068 | CA  | GLY | A | 392 | -16.828 | -7.660  | 40.587 | 1.00 | 17.84 |
| ATOM | 2069 | C   | GLY | A | 392 | -16.357 | -8.910  | 41.303 | 1.00 | 20.98 |

FIGURE 3 (Cont.)

| | A | B | C | D | E | F | G | H | I | J |
|---|---|---|---|---|---|---|---|---|---|---|
| ATOM | 2070 | O | GLY | A | 392 | -15.473 | -9.630 | 40.818 | 1.00 | 22.43 |
| ATOM | 2071 | N | GLY | A | 393 | -16.959 | -9.167 | 42.463 | 1.00 | 20.09 |
| ATOM | 2072 | CA | GLY | A | 393 | -16.612 | -10.312 | 43.283 | 1.00 | 16.71 |
| ATOM | 2073 | C | GLY | A | 393 | -17.370 | -11.560 | 42.908 | 1.00 | 14.93 |
| ATOM | 2074 | O | GLY | A | 393 | -17.251 | -12.571 | 43.594 | 1.00 | 12.93 |
| ATOM | 2075 | N | GLY | A | 394 | -18.143 | -11.473 | 41.824 | 1.00 | 16.03 |
| ATOM | 2076 | CA | GLY | A | 394 | -18.918 | -12.584 | 41.301 | 1.00 | 17.57 |
| ATOM | 2077 | C | GLY | A | 394 | -18.175 | -13.308 | 40.196 | 1.00 | 19.56 |
| ATOM | 2078 | O | GLY | A | 394 | -17.091 | -12.888 | 39.788 | 1.00 | 18.92 |
| ATOM | 2079 | N | SER | A | 395 | -18.758 | -14.400 | 39.704 | 1.00 | 24.04 |
| ATOM | 2080 | CA | SER | A | 395 | -18.100 | -15.238 | 38.692 | 1.00 | 25.88 |
| ATOM | 2081 | CB | SER | A | 395 | -18.886 | -16.531 | 38.449 | 1.00 | 23.26 |
| ATOM | 2082 | OG | SER | A | 395 | -19.769 | -16.385 | 37.356 | 1.00 | 20.98 |
| ATOM | 2083 | C | SER | A | 395 | -17.892 | -14.471 | 37.389 | 1.00 | 26.74 |
| ATOM | 2084 | O | SER | A | 395 | -17.107 | -14.869 | 36.534 | 1.00 | 29.07 |
| ATOM | 2085 | N | GLU | A | 396 | -18.602 | -13.360 | 37.263 | 1.00 | 28.31 |
| ATOM | 2086 | CA | GLU | A | 396 | -18.481 | -12.484 | 36.109 | 1.00 | 28.63 |
| ATOM | 2087 | CB | GLU | A | 396 | -19.735 | -11.603 | 35.983 | 1.00 | 32.93 |
| ATOM | 2088 | CG | GLU | A | 396 | -20.983 | -12.323 | 35.479 | 1.00 | 33.78 |
| ATOM | 2089 | CD | GLU | A | 396 | -20.770 | -13.049 | 34.157 | 1.00 | 35.89 |
| ATOM | 2090 | OE1 | GLU | A | 396 | -19.819 | -12.700 | 33.417 | 1.00 | 36.68 |
| ATOM | 2091 | OE2 | GLU | A | 396 | -21.560 | -13.974 | 33.852 | 1.00 | 36.45 |
| ATOM | 2092 | C | GLU | A | 396 | -17.215 | -11.623 | 36.154 | 1.00 | 24.68 |
| ATOM | 2093 | O | GLU | A | 396 | -16.606 | -11.364 | 35.126 | 1.00 | 24.78 |
| ATOM | 2094 | N | ASP | A | 397 | -16.835 | -11.177 | 37.345 | 1.00 | 22.19 |
| ATOM | 2095 | CA | ASP | A | 397 | -15.623 | -10.382 | 37.543 | 1.00 | 20.91 |
| ATOM | 2096 | CB | ASP | A | 397 | -14.378 | -11.115 | 37.003 | 1.00 | 19.88 |
| ATOM | 2097 | CG | ASP | A | 397 | -13.075 | -10.575 | 37.582 | 1.00 | 19.17 |
| ATOM | 2098 | OD1 | ASP | A | 397 | -12.996 | -10.330 | 38.805 | 1.00 | 18.63 |
| ATOM | 2099 | OD2 | ASP | A | 397 | -12.073 | -10.355 | 36.879 | 1.00 | 19.50 |
| ATOM | 2100 | C | ASP | A | 397 | -15.738 | -8.955 | 36.990 | 1.00 | 20.29 |
| ATOM | 2101 | O | ASP | A | 397 | -16.717 | -8.263 | 37.251 | 1.00 | 21.60 |
| ATOM | 2102 | N | ALA | A | 398 | -14.730 | -8.527 | 36.235 | 1.00 | 17.86 |
| ATOM | 2103 | CA | ALA | A | 398 | -14.608 | -7.157 | 35.758 | 1.00 | 13.23 |
| ATOM | 2104 | CB | ALA | A | 398 | -13.297 | -6.997 | 35.003 | 1.00 | 12.08 |
| ATOM | 2105 | C | ALA | A | 398 | -15.781 | -6.692 | 34.886 | 1.00 | 15.62 |
| ATOM | 2106 | O | ALA | A | 398 | -16.081 | -5.496 | 34.835 | 1.00 | 14.95 |
| ATOM | 2107 | N | LYS | A | 399 | -16.432 | -7.626 | 34.189 | 1.00 | 16.02 |
| ATOM | 2108 | CA | LYS | A | 399 | -17.551 | -7.273 | 33.334 | 1.00 | 13.91 |
| ATOM | 2109 | CB | LYS | A | 399 | -18.051 | -8.479 | 32.547 | 1.00 | 17.50 |
| ATOM | 2110 | CG | LYS | A | 399 | -19.096 | -8.158 | 31.458 | 1.00 | 25.65 |
| ATOM | 2111 | CD | LYS | A | 399 | -18.517 | -7.314 | 30.303 | 1.00 | 29.81 |
| ATOM | 2112 | CE | LYS | A | 399 | -19.613 | -6.624 | 29.472 | 1.00 | 31.23 |
| ATOM | 2113 | NZ | LYS | A | 399 | -19.138 | -5.328 | 28.890 | 1.00 | 30.95 |
| ATOM | 2114 | C | LYS | A | 399 | -18.657 | -6.633 | 34.181 | 1.00 | 13.96 |
| ATOM | 2115 | O | LYS | A | 399 | -19.251 | -5.638 | 33.775 | 1.00 | 17.10 |
| ATOM | 2116 | N | GLU | A | 400 | -18.890 | -7.175 | 35.372 | 1.00 | 11.25 |
| ATOM | 2117 | CA | GLU | A | 400 | -19.871 | -6.629 | 36.308 | 1.00 | 10.44 |
| ATOM | 2118 | CB | GLU | A | 400 | -19.843 | -7.433 | 37.609 | 1.00 | 15.28 |
| ATOM | 2119 | CG | GLU | A | 400 | -20.876 | -7.011 | 38.644 | 1.00 | 21.17 |
| ATOM | 2120 | CD | GLU | A | 400 | -21.075 | -8.047 | 39.740 | 1.00 | 24.54 |
| ATOM | 2121 | OE1 | GLU | A | 400 | -20.243 | -9.001 | 39.849 | 1.00 | 24.52 |

FIGURE 3 (Cont.)

|  | A | B | C | D | E | F | G | H | I | J |
|---|---|---|---|---|---|---|---|---|---|---|
| ATOM | 2122 | OE2 | GLU | A | 400 | -22.075 | -7.894 | 40.489 | 1.00 | 24.68 |
| ATOM | 2123 | C | GLU | A | 400 | -19.675 | -5.130 | 36.588 | 1.00 | 7.48 |
| ATOM | 2124 | O | GLU | A | 400 | -20.627 | -4.350 | 36.521 | 1.00 | 8.69 |
| ATOM | 2125 | N | ILE | A | 401 | -18.439 | -4.749 | 36.898 | 1.00 | 4.25 |
| ATOM | 2126 | CA | ILE | A | 401 | -18.050 | -3.364 | 37.112 | 1.00 | 2.00 |
| ATOM | 2127 | CB | ILE | A | 401 | -16.592 | -3.292 | 37.537 | 1.00 | 2.00 |
| ATOM | 2128 | CG1 | ILE | A | 401 | -16.424 | -3.713 | 38.982 | 1.00 | 2.00 |
| ATOM | 2129 | CD1 | ILE | A | 401 | -14.981 | -3.785 | 39.366 | 1.00 | 2.00 |
| ATOM | 2130 | CG2 | ILE | A | 401 | -16.035 | -1.900 | 37.324 | 1.00 | 2.00 |
| ATOM | 2131 | C | ILE | A | 401 | -18.181 | -2.562 | 35.837 | 1.00 | 3.17 |
| ATOM | 2132 | O | ILE | A | 401 | -18.612 | -1.412 | 35.870 | 1.00 | 8.59 |
| ATOM | 2133 | N | MET | A | 402 | -17.775 | -3.146 | 34.716 | 1.00 | 2.00 |
| ATOM | 2134 | CA | MET | A | 402 | -17.805 | -2.418 | 33.457 | 1.00 | 5.25 |
| ATOM | 2135 | CB | MET | A | 402 | -17.162 | -3.219 | 32.340 | 1.00 | 8.13 |
| ATOM | 2136 | CG | MET | A | 402 | -15.688 | -3.489 | 32.519 | 1.00 | 12.00 |
| ATOM | 2137 | SD | MET | A | 402 | -15.070 | -4.549 | 31.204 | 1.00 | 13.70 |
| ATOM | 2138 | CE | MET | A | 402 | -13.342 | -4.323 | 31.370 | 1.00 | 18.16 |
| ATOM | 2139 | C | MET | A | 402 | -19.224 | -2.056 | 33.065 | 1.00 | 7.97 |
| ATOM | 2140 | O | MET | A | 402 | -19.457 | -0.980 | 32.524 | 1.00 | 12.30 |
| ATOM | 2141 | N | GLN | A | 403 | -20.181 | -2.936 | 33.340 | 1.00 | 10.04 |
| ATOM | 2142 | CA | GLN | A | 403 | -21.560 | -2.632 | 32.984 | 1.00 | 14.71 |
| ATOM | 2143 | CB | GLN | A | 403 | -22.295 | -3.868 | 32.436 | 1.00 | 17.30 |
| ATOM | 2144 | CG | GLN | A | 403 | -22.528 | -5.003 | 33.437 | 1.00 | 21.10 |
| ATOM | 2145 | CD | GLN | A | 403 | -22.767 | -6.365 | 32.777 | 1.00 | 21.02 |
| ATOM | 2146 | OE1 | GLN | A | 403 | -22.443 | -6.568 | 31.600 | 1.00 | 21.82 |
| ATOM | 2147 | NE2 | GLN | A | 403 | -23.321 | -7.301 | 33.544 | 1.00 | 20.17 |
| ATOM | 2148 | C | GLN | A | 403 | -22.332 | -1.897 | 34.092 | 1.00 | 16.89 |
| ATOM | 2149 | O | GLN | A | 403 | -23.555 | -1.809 | 34.048 | 1.00 | 19.63 |
| ATOM | 2150 | N | HIS | A | 404 | -21.608 | -1.346 | 35.066 | 1.00 | 20.40 |
| ATOM | 2151 | CA | HIS | A | 404 | -22.199 | -0.470 | 36.086 | 1.00 | 20.49 |
| ATOM | 2152 | CB | HIS | A | 404 | -21.240 | -0.253 | 37.258 | 1.00 | 19.20 |
| ATOM | 2153 | CG | HIS | A | 404 | -21.867 | 0.439 | 38.434 | 1.00 | 23.38 |
| ATOM | 2154 | ND1 | HIS | A | 404 | -22.411 | 1.706 | 38.355 | 1.00 | 22.39 |
| ATOM | 2155 | CE1 | HIS | A | 404 | -22.873 | 2.060 | 39.541 | 1.00 | 22.77 |
| ATOM | 2156 | NE2 | HIS | A | 404 | -22.650 | 1.071 | 40.389 | 1.00 | 24.02 |
| ATOM | 2157 | CD2 | HIS | A | 404 | -22.024 | 0.043 | 39.722 | 1.00 | 24.27 |
| ATOM | 2158 | C | HIS | A | 404 | -22.582 | 0.870 | 35.478 | 1.00 | 19.31 |
| ATOM | 2159 | O | HIS | A | 404 | -21.863 | 1.379 | 34.609 | 1.00 | 18.03 |
| ATOM | 2160 | N | ARG | A | 405 | -23.705 | 1.431 | 35.948 | 1.00 | 20.12 |
| ATOM | 2161 | CA | ARG | A | 405 | -24.279 | 2.667 | 35.380 | 1.00 | 19.49 |
| ATOM | 2162 | CB | ARG | A | 405 | -25.522 | 3.208 | 36.154 | 1.00 | 26.30 |
| ATOM | 2163 | CG | ARG | A | 405 | -26.203 | 2.287 | 37.226 | 1.00 | 34.75 |
| ATOM | 2164 | CD | ARG | A | 405 | -26.704 | 3.019 | 38.529 | 1.00 | 40.05 |
| ATOM | 2165 | NE | ARG | A | 405 | -27.325 | 2.125 | 39.534 | 1.00 | 45.09 |
| ATOM | 2166 | CZ | ARG | A | 405 | -27.555 | 2.427 | 40.831 | 1.00 | 46.58 |
| ATOM | 2167 | NH1 | ARG | A | 405 | -27.225 | 3.614 | 41.335 | 1.00 | 47.07 |
| ATOM | 2168 | NH2 | ARG | A | 405 | -28.139 | 1.536 | 41.631 | 1.00 | 45.92 |
| ATOM | 2169 | C | ARG | A | 405 | -23.203 | 3.741 | 35.252 | 1.00 | 13.15 |
| ATOM | 2170 | O | ARG | A | 405 | -23.203 | 4.510 | 34.296 | 1.00 | 7.53 |
| ATOM | 2171 | N | PHE | A | 406 | -22.274 | 3.751 | 36.206 | 1.00 | 8.31 |
| ATOM | 2172 | CA | PHE | A | 406 | -21.176 | 4.711 | 36.247 | 1.00 | 8.69 |
| ATOM | 2173 | CB | PHE | A | 406 | -20.263 | 4.375 | 37.411 | 1.00 | 7.28 |

FIGURE 3 (Cont.)

|      | A    | B    | C   | D | E   | F       | G      | H      | I    | J     |
|------|------|------|-----|---|-----|---------|--------|--------|------|-------|
| ATOM | 2174 | CG   | PHE | A | 406 | -19.132 | 5.342  | 37.614 | 1.00 | 8.21  |
| ATOM | 2175 | CD1  | PHE | A | 406 | -19.304 | 6.486  | 38.397 | 1.00 | 7.87  |
| ATOM | 2176 | CE1  | PHE | A | 406 | -18.250 | 7.368  | 38.631 | 1.00 | 6.30  |
| ATOM | 2177 | CZ   | PHE | A | 406 | -17.013 | 7.130  | 38.086 | 1.00 | 4.86  |
| ATOM | 2178 | CE2  | PHE | A | 406 | -16.822 | 5.992  | 37.301 | 1.00 | 11.39 |
| ATOM | 2179 | CD2  | PHE | A | 406 | -17.880 | 5.090  | 37.077 | 1.00 | 7.66  |
| ATOM | 2180 | C    | PHE | A | 406 | -20.359 | 4.782  | 34.957 | 1.00 | 10.86 |
| ATOM | 2181 | O    | PHE | A | 406 | -20.048 | 5.878  | 34.487 | 1.00 | 15.89 |
| ATOM | 2182 | N    | PHE | A | 407 | -19.997 | 3.629  | 34.401 | 1.00 | 9.05  |
| ATOM | 2183 | CA   | PHE | A | 407 | -19.290 | 3.592  | 33.126 | 1.00 | 10.03 |
| ATOM | 2184 | CB   | PHE | A | 407 | -18.272 | 2.455  | 33.100 | 1.00 | 9.81  |
| ATOM | 2185 | CG   | PHE | A | 407 | -17.283 | 2.492  | 34.218 | 1.00 | 11.46 |
| ATOM | 2186 | CD1  | PHE | A | 407 | -17.313 | 1.523  | 35.214 | 1.00 | 12.13 |
| ATOM | 2187 | CE1  | PHE | A | 407 | -16.390 | 1.552  | 36.260 | 1.00 | 12.46 |
| ATOM | 2188 | CZ   | PHE | A | 407 | -15.409 | 2.548  | 36.300 | 1.00 | 10.97 |
| ATOM | 2189 | CE2  | PHE | A | 407 | -15.359 | 3.508  | 35.310 | 1.00 | 9.95  |
| ATOM | 2190 | CD2  | PHE | A | 407 | -16.297 | 3.480  | 34.271 | 1.00 | 12.99 |
| ATOM | 2191 | C    | PHE | A | 407 | -20.321 | 3.449  | 31.993 | 1.00 | 13.09 |
| ATOM | 2192 | O    | PHE | A | 407 | -20.269 | 2.527  | 31.146 | 1.00 | 13.19 |
| ATOM | 2193 | N    | ALA | A | 408 | -21.262 | 4.384  | 31.988 | 1.00 | 12.26 |
| ATOM | 2194 | CA   | ALA | A | 408 | -22.454 | 4.246  | 31.178 | 1.00 | 13.45 |
| ATOM | 2195 | CB   | ALA | A | 408 | -23.487 | 5.232  | 31.613 | 1.00 | 17.35 |
| ATOM | 2196 | C    | ALA | A | 408 | -22.171 | 4.400  | 29.703 | 1.00 | 12.66 |
| ATOM | 2197 | O    | ALA | A | 408 | -22.472 | 3.510  | 28.914 | 1.00 | 13.17 |
| ATOM | 2198 | N    | GLY | A | 409 | -21.596 | 5.534  | 29.332 | 1.00 | 12.46 |
| ATOM | 2199 | CA   | GLY | A | 409 | -21.367 | 5.820  | 27.932 | 1.00 | 15.37 |
| ATOM | 2200 | C    | GLY | A | 409 | -20.243 | 5.002  | 27.346 | 1.00 | 15.57 |
| ATOM | 2201 | O    | GLY | A | 409 | -20.086 | 4.931  | 26.122 | 1.00 | 18.02 |
| ATOM | 2202 | N    | ILE | A | 410 | -19.498 | 4.356  | 28.240 | 1.00 | 14.24 |
| ATOM | 2203 | CA   | ILE | A | 410 | -18.184 | 3.798  | 27.952 | 1.00 | 10.40 |
| ATOM | 2204 | CB   | ILE | A | 410 | -17.421 | 3.577  | 29.293 | 1.00 | 8.70  |
| ATOM | 2205 | CG1  | ILE | A | 410 | -17.453 | 4.838  | 30.163 | 1.00 | 8.11  |
| ATOM | 2206 | CD1  | ILE | A | 410 | -17.234 | 6.165  | 29.419 | 1.00 | 10.58 |
| ATOM | 2207 | CG2  | ILE | A | 410 | -15.992 | 3.152  | 29.054 | 1.00 | 7.34  |
| ATOM | 2208 | C    | ILE | A | 410 | -18.268 | 2.509  | 27.149 | 1.00 | 8.15  |
| ATOM | 2209 | O    | ILE | A | 410 | -18.843 | 1.523  | 27.617 | 1.00 | 7.91  |
| ATOM | 2210 | N    | VAL | A | 411 | -17.701 | 2.541  | 25.942 | 1.00 | 5.79  |
| ATOM | 2211 | CA   | VAL | A | 411 | -17.562 | 1.365  | 25.081 | 1.00 | 7.84  |
| ATOM | 2212 | CB   | VAL | A | 411 | -17.639 | 1.771  | 23.594 | 1.00 | 6.79  |
| ATOM | 2213 | CG1  | VAL | A | 411 | -16.876 | 0.792  | 22.704 | 1.00 | 5.60  |
| ATOM | 2214 | CG2  | VAL | A | 411 | -19.088 | 1.904  | 23.154 | 1.00 | 7.51  |
| ATOM | 2215 | C    | VAL | A | 411 | -16.190 | 0.774  | 25.376 | 1.00 | 10.04 |
| ATOM | 2216 | O    | VAL | A | 411 | -15.176 | 1.431  | 25.146 | 1.00 | 14.94 |
| ATOM | 2217 | N    | TRP | A | 412 | -16.132 | -0.449 | 25.887 | 1.00 | 8.39  |
| ATOM | 2218 | CA   | TRP | A | 412 | -14.870 | -0.906 | 26.468 | 1.00 | 7.36  |
| ATOM | 2219 | CB   | TRP | A | 412 | -15.102 | -2.010 | 27.489 | 1.00 | 7.46  |
| ATOM | 2220 | CG   | TRP | A | 412 | -15.767 | -1.441 | 28.681 | 1.00 | 6.78  |
| ATOM | 2221 | CD1  | TRP | A | 412 | -17.106 | -1.290 | 28.878 | 1.00 | 6.79  |
| ATOM | 2222 | NE1  | TRP | A | 412 | -17.344 | -0.688 | 30.089 | 1.00 | 4.22  |
| ATOM | 2223 | CE2  | TRP | A | 412 | -16.147 | -0.422 | 30.691 | 1.00 | 5.59  |
| ATOM | 2224 | CD2  | TRP | A | 412 | -15.130 | -0.878 | 29.821 | 1.00 | 5.75  |
| ATOM | 2225 | CE3  | TRP | A | 412 | -13.796 | -0.721 | 30.208 | 1.00 | 4.31  |

FIGURE 3 (Cont.)

|      | A    | B    | C   | D | E   | F       | G      | H      | I    | J     |
|------|------|------|-----|---|-----|---------|--------|--------|------|-------|
| ATOM | 2226 | CZ3  | TRP | A | 412 | -13.523 | -0.130 | 31.428 | 1.00 | 6.57  |
| ATOM | 2227 | CH2  | TRP | A | 412 | -14.562 | 0.316  | 32.273 | 1.00 | 7.77  |
| ATOM | 2228 | CZ2  | TRP | A | 412 | -15.876 | 0.175  | 31.921 | 1.00 | 6.37  |
| ATOM | 2229 | C    | TRP | A | 412 | -13.779 | -1.253 | 25.472 | 1.00 | 7.76  |
| ATOM | 2230 | O    | TRP | A | 412 | -12.604 | -1.069 | 25.760 | 1.00 | 5.78  |
| ATOM | 2231 | N    | GLN | A | 413 | -14.179 | -1.711 | 24.289 | 1.00 | 12.61 |
| ATOM | 2232 | CA   | GLN | A | 413 | -13.245 | -1.960 | 23.192 | 1.00 | 13.87 |
| ATOM | 2233 | CB   | GLN | A | 413 | -14.018 | -2.428 | 21.948 | 1.00 | 15.66 |
| ATOM | 2234 | CG   | GLN | A | 413 | -13.170 | -3.026 | 20.811 | 1.00 | 19.47 |
| ATOM | 2235 | CD   | GLN | A | 413 | -12.166 | -4.066 | 21.293 | 1.00 | 21.00 |
| ATOM | 2236 | OE1  | GLN | A | 413 | -12.549 | -5.179 | 21.656 | 1.00 | 22.65 |
| ATOM | 2237 | NE2  | GLN | A | 413 | -10.882 | -3.708 | 21.292 | 1.00 | 19.40 |
| ATOM | 2238 | C    | GLN | A | 413 | -12.418 | -0.698 | 22.903 | 1.00 | 14.24 |
| ATOM | 2239 | O    | GLN | A | 413 | -11.291 | -0.776 | 22.411 | 1.00 | 11.50 |
| ATOM | 2240 | N    | HIS | A | 414 | -12.991 | 0.455  | 23.248 | 1.00 | 16.94 |
| ATOM | 2241 | CA   | HIS | A | 414 | -12.385 | 1.766  | 23.022 | 1.00 | 17.62 |
| ATOM | 2242 | CB   | HIS | A | 414 | -13.468 | 2.848  | 23.006 | 1.00 | 19.87 |
| ATOM | 2243 | CG   | HIS | A | 414 | -14.076 | 3.082  | 21.663 | 1.00 | 20.19 |
| ATOM | 2244 | ND1  | HIS | A | 414 | -13.908 | 2.215  | 20.604 | 1.00 | 20.96 |
| ATOM | 2245 | CE1  | HIS | A | 414 | -14.552 | 2.681  | 19.551 | 1.00 | 21.64 |
| ATOM | 2246 | NE2  | HIS | A | 414 | -15.132 | 3.820  | 19.888 | 1.00 | 22.51 |
| ATOM | 2247 | CD2  | HIS | A | 414 | -14.849 | 4.093  | 21.205 | 1.00 | 20.49 |
| ATOM | 2248 | C    | HIS | A | 414 | -11.349 | 2.119  | 24.084 | 1.00 | 16.49 |
| ATOM | 2249 | O    | HIS | A | 414 | -10.235 | 2.546  | 23.749 | 1.00 | 17.52 |
| ATOM | 2250 | N    | VAL | A | 415 | -11.729 | 1.960  | 25.355 | 1.00 | 12.06 |
| ATOM | 2251 | CA   | VAL | A | 415 | -10.839 | 2.235  | 26.479 | 1.00 | 10.57 |
| ATOM | 2252 | CB   | VAL | A | 415 | -11.373 | 1.604  | 27.781 | 1.00 | 11.67 |
| ATOM | 2253 | CG1  | VAL | A | 415 | -10.326 | 1.615  | 28.882 | 1.00 | 12.86 |
| ATOM | 2254 | CG2  | VAL | A | 415 | -12.597 | 2.324  | 28.246 | 1.00 | 13.26 |
| ATOM | 2255 | C    | VAL | A | 415 | -9.486  | 1.645  | 26.156 | 1.00 | 10.82 |
| ATOM | 2256 | O    | VAL | A | 415 | -8.478  | 2.346  | 26.185 | 1.00 | 10.89 |
| ATOM | 2257 | N    | TYR | A | 416 | -9.505  | 0.357  | 25.813 | 1.00 | 11.93 |
| ATOM | 2258 | CA   | TYR | A | 416 | -8.336  | -0.425 | 25.444 | 1.00 | 14.80 |
| ATOM | 2259 | CB   | TYR | A | 416 | -8.768  | -1.857 | 25.112 | 1.00 | 17.60 |
| ATOM | 2260 | CG   | TYR | A | 416 | -7.634  | -2.783 | 24.736 | 1.00 | 20.78 |
| ATOM | 2261 | CD1  | TYR | A | 416 | -6.969  | -3.524 | 25.712 | 1.00 | 22.95 |
| ATOM | 2262 | CE1  | TYR | A | 416 | -5.927  | -4.369 | 25.381 | 1.00 | 27.08 |
| ATOM | 2263 | CZ   | TYR | A | 416 | -5.535  | -4.484 | 24.053 | 1.00 | 29.57 |
| ATOM | 2264 | OH   | TYR | A | 416 | -4.497  | -5.330 | 23.726 | 1.00 | 34.35 |
| ATOM | 2265 | CE2  | TYR | A | 416 | -6.181  | -3.758 | 23.058 | 1.00 | 25.68 |
| ATOM | 2266 | CD2  | TYR | A | 416 | -7.224  | -2.917 | 23.406 | 1.00 | 21.99 |
| ATOM | 2267 | C    | TYR | A | 416 | -7.576  | 0.161  | 24.262 | 1.00 | 16.68 |
| ATOM | 2268 | O    | TYR | A | 416 | -6.349  | 0.264  | 24.284 | 1.00 | 16.33 |
| ATOM | 2269 | N    | GLU | A | 417 | -8.303  | 0.541  | 23.222 | 1.00 | 20.09 |
| ATOM | 2270 | CA   | GLU | A | 417 | -7.653  | 1.034  | 22.024 | 1.00 | 24.16 |
| ATOM | 2271 | CB   | GLU | A | 417 | -8.603  | 0.959  | 20.823 | 1.00 | 28.25 |
| ATOM | 2272 | CG   | GLU | A | 417 | -8.317  | -0.235 | 19.916 | 1.00 | 34.46 |
| ATOM | 2273 | CD   | GLU | A | 417 | -9.559  | -0.843 | 19.265 | 1.00 | 38.53 |
| ATOM | 2274 | OE1  | GLU | A | 417 | -10.606 | -0.153 | 19.176 | 1.00 | 41.35 |
| ATOM | 2275 | OE2  | GLU | A | 417 | -9.479  | -2.018 | 18.823 | 1.00 | 38.88 |
| ATOM | 2276 | C    | GLU | A | 417 | -7.064  | 2.433  | 22.220 | 1.00 | 24.63 |
| ATOM | 2277 | O    | GLU | A | 417 | -6.575  | 3.030  | 21.263 | 1.00 | 27.05 |

FIGURE 3 (Cont.)

| | A | B | C | D | E | F | G | H | I | J |
|---|---|---|---|---|---|---|---|---|---|---|
| ATOM | 2278 | N   | LYS | A | 418 | -7.085  | 2.926  | 23.463 | 1.00 | 24.74 |
| ATOM | 2279 | CA  | LYS | A | 418 | -6.534  | 4.239  | 23.839 | 1.00 | 24.89 |
| ATOM | 2280 | CB  | LYS | A | 418 | -5.022  | 4.324  | 23.550 | 1.00 | 27.02 |
| ATOM | 2281 | CG  | LYS | A | 418 | -4.111  | 3.705  | 24.604 | 1.00 | 29.36 |
| ATOM | 2282 | CD  | LYS | A | 418 | -2.970  | 4.658  | 25.001 | 1.00 | 31.86 |
| ATOM | 2283 | CE  | LYS | A | 418 | -1.603  | 3.970  | 25.020 | 1.00 | 32.41 |
| ATOM | 2284 | NZ  | LYS | A | 418 | -0.820  | 4.259  | 23.782 | 1.00 | 34.20 |
| ATOM | 2285 | C   | LYS | A | 418 | -7.275  | 5.360  | 23.110 | 1.00 | 23.86 |
| ATOM | 2286 | O   | LYS | A | 418 | -6.665  | 6.246  | 22.500 | 1.00 | 23.82 |
| ATOM | 2287 | N   | LYS | A | 419 | -8.598  | 5.313  | 23.162 | 1.00 | 21.27 |
| ATOM | 2288 | CA  | LYS | A | 419 | -9.382  | 6.235  | 22.365 | 1.00 | 20.30 |
| ATOM | 2289 | CB  | LYS | A | 419 | -10.243 | 5.491  | 21.335 | 1.00 | 21.32 |
| ATOM | 2290 | CG  | LYS | A | 419 | -9.764  | 5.665  | 19.889 | 1.00 | 22.89 |
| ATOM | 2291 | CD  | LYS | A | 419 | -9.481  | 4.318  | 19.199 | 1.00 | 24.64 |
| ATOM | 2292 | CE  | LYS | A | 419 | -9.389  | 4.457  | 17.670 | 1.00 | 26.40 |
| ATOM | 2293 | NZ  | LYS | A | 419 | -9.932  | 3.266  | 16.942 | 1.00 | 26.48 |
| ATOM | 2294 | C   | LYS | A | 419 | -10.212 | 7.159  | 23.225 | 1.00 | 19.91 |
| ATOM | 2295 | O   | LYS | A | 419 | -10.781 | 8.119  | 22.715 | 1.00 | 24.88 |
| ATOM | 2296 | N   | LEU | A | 420 | -10.287 | 6.879  | 24.522 | 1.00 | 17.22 |
| ATOM | 2297 | CA  | LEU | A | 420 | -10.801 | 7.860  | 25.468 | 1.00 | 16.76 |
| ATOM | 2298 | CB  | LEU | A | 420 | -10.765 | 7.300  | 26.882 | 1.00 | 16.60 |
| ATOM | 2299 | CG  | LEU | A | 420 | -12.082 | 6.922  | 27.553 | 1.00 | 17.80 |
| ATOM | 2300 | CD1 | LEU | A | 420 | -11.811 | 5.953  | 28.688 | 1.00 | 18.43 |
| ATOM | 2301 | CD2 | LEU | A | 420 | -12.811 | 8.152  | 28.074 | 1.00 | 20.69 |
| ATOM | 2302 | C   | LEU | A | 420 | -9.874  | 9.066  | 25.384 | 1.00 | 17.86 |
| ATOM | 2303 | O   | LEU | A | 420 | -8.698  | 8.910  | 25.049 | 1.00 | 19.46 |
| ATOM | 2304 | N   | SER | A | 421 | -10.380 | 10.264 | 25.652 | 1.00 | 17.80 |
| ATOM | 2305 | CA  | SER | A | 421 | -9.490  | 11.423 | 25.671 | 1.00 | 19.78 |
| ATOM | 2306 | CB  | SER | A | 421 | -10.115 | 12.642 | 25.001 | 1.00 | 21.15 |
| ATOM | 2307 | OG  | SER | A | 421 | -9.183  | 13.712 | 24.998 | 1.00 | 22.32 |
| ATOM | 2308 | C   | SER | A | 421 | -9.052  | 11.759 | 27.091 | 1.00 | 17.99 |
| ATOM | 2309 | O   | SER | A | 421 | -9.904  | 11.967 | 27.958 | 1.00 | 21.61 |
| ATOM | 2310 | N   | PRO | A | 422 | -7.733  | 11.828 | 27.316 | 1.00 | 14.82 |
| ATOM | 2311 | CA  | PRO | A | 422 | -7.161  | 11.975 | 28.667 | 1.00 | 12.99 |
| ATOM | 2312 | CB  | PRO | A | 422 | -5.661  | 11.729 | 28.451 | 1.00 | 11.78 |
| ATOM | 2313 | CG  | PRO | A | 422 | -5.559  | 11.175 | 27.066 | 1.00 | 12.55 |
| ATOM | 2314 | CD  | PRO | A | 422 | -6.679  | 11.793 | 26.290 | 1.00 | 14.08 |
| ATOM | 2315 | C   | PRO | A | 422 | -7.388  | 13.364 | 29.243 | 1.00 | 10.04 |
| ATOM | 2316 | O   | PRO | A | 422 | -7.011  | 14.357 | 28.622 | 1.00 | 13.43 |
| ATOM | 2317 | N   | PRO | A | 423 | -7.998  | 13.420 | 30.419 | 1.00 | 5.22 |
| ATOM | 2318 | CA  | PRO | A | 423 | -8.457  | 14.673 | 31.026 | 1.00 | 3.86 |
| ATOM | 2319 | CB  | PRO | A | 423 | -9.195  | 14.190 | 32.255 | 1.00 | 5.07 |
| ATOM | 2320 | CG  | PRO | A | 423 | -8.527  | 12.914 | 32.578 | 1.00 | 5.83 |
| ATOM | 2321 | CD  | PRO | A | 423 | -8.292  | 12.256 | 31.261 | 1.00 | 3.68 |
| ATOM | 2322 | C   | PRO | A | 423 | -7.323  | 15.605 | 31.442 | 1.00 | 6.00 |
| ATOM | 2323 | O   | PRO | A | 423 | -7.570  | 16.813 | 31.541 | 1.00 | 5.41 |
| ATOM | 2324 | N   | PHE | A | 424 | -6.128  | 15.057 | 31.692 | 1.00 | 6.47 |
| ATOM | 2325 | CA  | PHE | A | 424 | -4.916  | 15.864 | 31.898 | 1.00 | 6.25 |
| ATOM | 2326 | CB  | PHE | A | 424 | -4.600  | 16.013 | 33.388 | 1.00 | 4.23 |
| ATOM | 2327 | CG  | PHE | A | 424 | -3.158  | 16.291 | 33.670 | 1.00 | 3.18 |
| ATOM | 2328 | CD1 | PHE | A | 424 | -2.670  | 17.588 | 33.635 | 1.00 | 2.66 |
| ATOM | 2329 | CE1 | PHE | A | 424 | -1.324  | 17.860 | 33.875 | 1.00 | 2.00 |

FIGURE 3 (Cont.)

|  | A | B | C | D | E | F | G | H | I | J |
|---|---|---|---|---|---|---|---|---|---|---|
| ATOM | 2330 | CZ | PHE | A | 424 | -0.460 | 16.831 | 34.144 | 1.00 | 2.52 |
| ATOM | 2331 | CE2 | PHE | A | 424 | -0.935 | 15.510 | 34.176 | 1.00 | 5.37 |
| ATOM | 2332 | CD2 | PHE | A | 424 | -2.277 | 15.252 | 33.945 | 1.00 | 4.69 |
| ATOM | 2333 | C | PHE | A | 424 | -3.689 | 15.311 | 31.153 | 1.00 | 8.77 |
| ATOM | 2334 | O | PHE | A | 424 | -3.235 | 14.198 | 31.448 | 1.00 | 11.40 |
| ATOM | 2335 | N | LYS | A | 425 | -3.150 | 16.093 | 30.207 | 1.00 | 10.06 |
| ATOM | 2336 | CA | LYS | A | 425 | -1.941 | 15.708 | 29.461 | 1.00 | 12.05 |
| ATOM | 2337 | CB | LYS | A | 425 | -2.044 | 16.089 | 27.975 | 1.00 | 13.73 |
| ATOM | 2338 | CG | LYS | A | 425 | -0.799 | 15.726 | 27.126 | 1.00 | 17.23 |
| ATOM | 2339 | CD | LYS | A | 425 | -0.807 | 16.424 | 25.744 | 1.00 | 19.83 |
| ATOM | 2340 | CE | LYS | A | 425 | 0.395 | 16.019 | 24.861 | 1.00 | 19.75 |
| ATOM | 2341 | NZ | LYS | A | 425 | 0.140 | 14.829 | 23.972 | 1.00 | 15.66 |
| ATOM | 2342 | C | LYS | A | 425 | -0.688 | 16.328 | 30.077 | 1.00 | 12.47 |
| ATOM | 2343 | O | LYS | A | 425 | -0.617 | 17.548 | 30.216 | 1.00 | 12.89 |
| ATOM | 2344 | N | PRO | A | 426 | 0.293 | 15.498 | 30.445 | 1.00 | 13.17 |
| ATOM | 2345 | CA | PRO | A | 426 | 1.544 | 15.985 | 31.032 | 1.00 | 12.94 |
| ATOM | 2346 | CB | PRO | A | 426 | 2.363 | 14.709 | 31.235 | 1.00 | 11.47 |
| ATOM | 2347 | CG | PRO | A | 426 | 1.390 | 13.649 | 31.300 | 1.00 | 13.23 |
| ATOM | 2348 | CD | PRO | A | 426 | 0.291 | 14.030 | 30.336 | 1.00 | 14.38 |
| ATOM | 2349 | C | PRO | A | 426 | 2.270 | 16.928 | 30.085 | 1.00 | 15.53 |
| ATOM | 2350 | O | PRO | A | 426 | 2.402 | 16.673 | 28.877 | 1.00 | 15.98 |
| ATOM | 2351 | N | GLN | A | 427 | 2.731 | 18.031 | 30.655 | 1.00 | 17.00 |
| ATOM | 2352 | CA | GLN | A | 427 | 3.370 | 19.077 | 29.888 | 1.00 | 19.77 |
| ATOM | 2353 | CB | GLN | A | 427 | 2.754 | 20.437 | 30.255 | 1.00 | 21.17 |
| ATOM | 2354 | CG | GLN | A | 427 | 1.258 | 20.538 | 29.937 | 1.00 | 21.21 |
| ATOM | 2355 | CD | GLN | A | 427 | 1.001 | 20.967 | 28.507 | 1.00 | 21.46 |
| ATOM | 2356 | OE1 | GLN | A | 427 | 1.154 | 22.144 | 28.188 | 1.00 | 25.85 |
| ATOM | 2357 | NE2 | GLN | A | 427 | 0.627 | 20.022 | 27.641 | 1.00 | 17.80 |
| ATOM | 2358 | C | GLN | A | 427 | 4.855 | 19.026 | 30.182 | 1.00 | 18.92 |
| ATOM | 2359 | O | GLN | A | 427 | 5.305 | 19.557 | 31.192 | 1.00 | 18.67 |
| ATOM | 2360 | N | VAL | A | 428 | 5.612 | 18.374 | 29.305 | 1.00 | 20.29 |
| ATOM | 2361 | CA | VAL | A | 428 | 7.032 | 18.124 | 29.573 | 1.00 | 22.77 |
| ATOM | 2362 | CB | VAL | A | 428 | 7.332 | 16.607 | 29.687 | 1.00 | 22.73 |
| ATOM | 2363 | CG1 | VAL | A | 428 | 7.250 | 16.164 | 31.129 | 1.00 | 21.19 |
| ATOM | 2364 | CG2 | VAL | A | 428 | 6.375 | 15.788 | 28.810 | 1.00 | 25.01 |
| ATOM | 2365 | C | VAL | A | 428 | 7.998 | 18.768 | 28.569 | 1.00 | 22.85 |
| ATOM | 2366 | O | VAL | A | 428 | 7.976 | 18.424 | 27.385 | 1.00 | 22.93 |
| ATOM | 2367 | N | THR | A | 429 | 8.841 | 19.688 | 29.054 | 1.00 | 21.94 |
| ATOM | 2368 | CA | THR | A | 429 | 9.901 | 20.294 | 28.239 | 1.00 | 22.99 |
| ATOM | 2369 | CB | THR | A | 429 | 10.802 | 21.281 | 29.057 | 1.00 | 22.41 |
| ATOM | 2370 | OG1 | THR | A | 429 | 10.960 | 20.820 | 30.401 | 1.00 | 21.36 |
| ATOM | 2371 | CG2 | THR | A | 429 | 10.129 | 22.630 | 29.230 | 1.00 | 24.23 |
| ATOM | 2372 | C | THR | A | 429 | 10.767 | 19.230 | 27.560 | 1.00 | 23.72 |
| ATOM | 2373 | O | THR | A | 429 | 10.651 | 19.010 | 26.354 | 1.00 | 24.52 |
| ATOM | 2374 | N | SER | A | 430 | 11.618 | 18.570 | 28.342 | 1.00 | 24.66 |
| ATOM | 2375 | CA | SER | A | 430 | 12.521 | 17.542 | 27.827 | 1.00 | 26.61 |
| ATOM | 2376 | CB | SER | A | 430 | 13.908 | 17.648 | 28.493 | 1.00 | 27.85 |
| ATOM | 2377 | OG | SER | A | 430 | 13.836 | 18.114 | 29.835 | 1.00 | 27.62 |
| ATOM | 2378 | C | SER | A | 430 | 11.936 | 16.131 | 27.982 | 1.00 | 26.95 |
| ATOM | 2379 | O | SER | A | 430 | 10.785 | 15.972 | 28.386 | 1.00 | 29.17 |
| ATOM | 2380 | N | GLU | A | 431 | 12.722 | 15.118 | 27.625 | 1.00 | 27.55 |
| ATOM | 2381 | CA | GLU | A | 431 | 12.372 | 13.727 | 27.896 | 1.00 | 28.48 |

FIGURE 3 (Cont.)

| | A | B | C | D | E | F | G | H | I | J |
|---|---|---|---|---|---|---|---|---|---|---|
| ATOM | 2382 | CB  | GLU | A | 431 | 12.876 | 12.808 | 26.772 | 1.00 | 34.87 |
| ATOM | 2383 | CG  | GLU | A | 431 | 11.797 | 12.315 | 25.807 | 1.00 | 41.73 |
| ATOM | 2384 | CD  | GLU | A | 431 | 10.501 | 11.912 | 26.507 | 1.00 | 46.70 |
| ATOM | 2385 | OE1 | GLU | A | 431 | 10.511 | 10.885 | 27.250 | 1.00 | 46.51 |
| ATOM | 2386 | OE2 | GLU | A | 431 |  9.480 | 12.634 | 26.314 | 1.00 | 47.10 |
| ATOM | 2387 | C   | GLU | A | 431 | 12.974 | 13.315 | 29.238 | 1.00 | 24.07 |
| ATOM | 2388 | O   | GLU | A | 431 | 12.554 | 12.339 | 29.855 | 1.00 | 22.58 |
| ATOM | 2389 | N   | THR | A | 432 | 13.968 | 14.081 | 29.669 | 1.00 | 20.65 |
| ATOM | 2390 | CA  | THR | A | 432 | 14.663 | 13.861 | 30.924 | 1.00 | 17.87 |
| ATOM | 2391 | CB  | THR | A | 432 | 16.121 | 14.357 | 30.805 | 1.00 | 18.34 |
| ATOM | 2392 | OG1 | THR | A | 432 | 16.836 | 14.016 | 31.993 | 1.00 | 19.58 |
| ATOM | 2393 | CG2 | THR | A | 432 | 16.198 | 15.892 | 30.794 | 1.00 | 18.90 |
| ATOM | 2394 | C   | THR | A | 432 | 13.958 | 14.597 | 32.046 | 1.00 | 17.44 |
| ATOM | 2395 | O   | THR | A | 432 | 14.330 | 14.461 | 33.211 | 1.00 | 18.21 |
| ATOM | 2396 | N   | ASP | A | 433 | 12.943 | 15.377 | 31.675 | 1.00 | 17.27 |
| ATOM | 2397 | CA  | ASP | A | 433 | 12.202 | 16.253 | 32.589 | 1.00 | 16.24 |
| ATOM | 2398 | CB  | ASP | A | 433 | 11.390 | 17.277 | 31.780 | 1.00 | 15.83 |
| ATOM | 2399 | CG  | ASP | A | 433 | 10.417 | 18.084 | 32.631 | 1.00 | 15.05 |
| ATOM | 2400 | OD1 | ASP | A | 433 | 10.656 | 18.266 | 33.846 | 1.00 | 16.45 |
| ATOM | 2401 | OD2 | ASP | A | 433 |  9.382 | 18.592 | 32.154 | 1.00 | 13.26 |
| ATOM | 2402 | C   | ASP | A | 433 | 11.304 | 15.488 | 33.569 | 1.00 | 15.99 |
| ATOM | 2403 | O   | ASP | A | 433 | 10.463 | 14.668 | 33.167 | 1.00 | 15.55 |
| ATOM | 2404 | N   | THR | A | 434 | 11.494 | 15.789 | 34.854 | 1.00 | 15.25 |
| ATOM | 2405 | CA  | THR | A | 434 | 10.842 | 15.079 | 35.956 | 1.00 | 15.02 |
| ATOM | 2406 | CB  | THR | A | 434 | 11.889 | 14.363 | 36.833 | 1.00 | 13.94 |
| ATOM | 2407 | OG1 | THR | A | 434 | 13.013 | 15.232 | 37.035 | 1.00 | 13.12 |
| ATOM | 2408 | CG2 | THR | A | 434 | 12.472 | 13.169 | 36.112 | 1.00 | 14.82 |
| ATOM | 2409 | C   | THR | A | 434 | 10.095 | 16.058 | 36.836 | 1.00 | 13.54 |
| ATOM | 2410 | O   | THR | A | 434 | 10.347 | 16.128 | 38.044 | 1.00 | 15.37 |
| ATOM | 2411 | N   | ARG | A | 435 |  9.178 | 16.806 | 36.235 | 1.00 |  9.54 |
| ATOM | 2412 | CA  | ARG | A | 435 |  8.452 | 17.836 | 36.953 | 1.00 |  7.55 |
| ATOM | 2413 | CB  | ARG | A | 435 |  8.043 | 18.938 | 35.996 | 1.00 |  6.94 |
| ATOM | 2414 | CG  | ARG | A | 435 |  6.838 | 18.596 | 35.163 | 1.00 |  8.64 |
| ATOM | 2415 | CD  | ARG | A | 435 |  6.246 | 19.788 | 34.446 | 1.00 | 12.25 |
| ATOM | 2416 | NE  | ARG | A | 435 |  7.084 | 20.172 | 33.320 | 1.00 | 11.98 |
| ATOM | 2417 | CZ  | ARG | A | 435 |  7.706 | 21.325 | 33.213 | 1.00 | 10.79 |
| ATOM | 2418 | NH1 | ARG | A | 435 |  7.581 | 22.243 | 34.160 | 1.00 | 10.79 |
| ATOM | 2419 | NH2 | ARG | A | 435 |  8.453 | 21.559 | 32.146 | 1.00 | 12.40 |
| ATOM | 2420 | C   | ARG | A | 435 |  7.232 | 17.285 | 37.669 | 1.00 | 11.60 |
| ATOM | 2421 | O   | ARG | A | 435 |  6.531 | 18.030 | 38.352 | 1.00 | 14.72 |
| ATOM | 2422 | N   | TYR | A | 436 |  6.980 | 15.984 | 37.505 | 1.00 | 14.41 |
| ATOM | 2423 | CA  | TYR | A | 436 |  5.857 | 15.305 | 38.154 | 1.00 | 13.00 |
| ATOM | 2424 | CB  | TYR | A | 436 |  4.899 | 14.750 | 37.101 | 1.00 | 12.31 |
| ATOM | 2425 | CG  | TYR | A | 436 |  4.318 | 15.802 | 36.176 | 1.00 | 12.72 |
| ATOM | 2426 | CD1 | TYR | A | 436 |  4.672 | 15.846 | 34.827 | 1.00 | 11.97 |
| ATOM | 2427 | CE1 | TYR | A | 436 |  4.141 | 16.806 | 33.971 | 1.00 | 11.68 |
| ATOM | 2428 | CZ  | TYR | A | 436 |  3.238 | 17.741 | 34.459 | 1.00 | 14.36 |
| ATOM | 2429 | OH  | TYR | A | 436 |  2.695 | 18.702 | 33.613 | 1.00 | 14.60 |
| ATOM | 2430 | CE2 | TYR | A | 436 |  2.871 | 17.717 | 35.802 | 1.00 | 15.32 |
| ATOM | 2431 | CD2 | TYR | A | 436 |  3.414 | 16.750 | 36.648 | 1.00 | 13.69 |
| ATOM | 2432 | C   | TYR | A | 436 |  6.332 | 14.204 | 39.114 | 1.00 | 15.33 |
| ATOM | 2433 | O   | TYR | A | 436 |  5.645 | 13.192 | 39.338 | 1.00 | 17.52 |

FIGURE 3 (Cont.)

|      | A    | B    | C   | D | E   | F      | G      | H      | I    | J     |
|------|------|------|-----|---|-----|--------|--------|--------|------|-------|
| ATOM | 2434 | N    | PHE | A | 437 | 7.516  | 14.411 | 39.688 | 1.00 | 14.74 |
| ATOM | 2435 | CA   | PHE | A | 437 | 8.053  | 13.495 | 40.683 | 1.00 | 15.01 |
| ATOM | 2436 | CB   | PHE | A | 437 | 9.177  | 12.652 | 40.088 | 1.00 | 9.23  |
| ATOM | 2437 | CG   | PHE | A | 437 | 8.707  | 11.668 | 39.026 | 1.00 | 8.11  |
| ATOM | 2438 | CD1  | PHE | A | 437 | 8.532  | 12.071 | 37.698 | 1.00 | 5.58  |
| ATOM | 2439 | CE1  | PHE | A | 437 | 8.114  | 11.169 | 36.727 | 1.00 | 2.86  |
| ATOM | 2440 | CZ   | PHE | A | 437 | 7.863  | 9.841  | 37.061 | 1.00 | 2.00  |
| ATOM | 2441 | CE2  | PHE | A | 437 | 8.037  | 9.420  | 38.364 | 1.00 | 4.31  |
| ATOM | 2442 | CD2  | PHE | A | 437 | 8.454  | 10.336 | 39.349 | 1.00 | 6.23  |
| ATOM | 2443 | C    | PHE | A | 437 | 8.516  | 14.296 | 41.885 | 1.00 | 18.53 |
| ATOM | 2444 | O    | PHE | A | 437 | 9.058  | 15.387 | 41.717 | 1.00 | 20.02 |
| ATOM | 2445 | N    | ASP | A | 438 | 8.268  | 13.765 | 43.088 | 1.00 | 23.47 |
| ATOM | 2446 | CA   | ASP | A | 438 | 8.584  | 14.449 | 44.352 | 1.00 | 26.09 |
| ATOM | 2447 | CB   | ASP | A | 438 | 8.203  | 13.586 | 45.576 | 1.00 | 33.71 |
| ATOM | 2448 | CG   | ASP | A | 438 | 6.727  | 13.763 | 46.016 | 1.00 | 42.00 |
| ATOM | 2449 | OD1  | ASP | A | 438 | 5.954  | 12.763 | 45.994 | 1.00 | 46.17 |
| ATOM | 2450 | OD2  | ASP | A | 438 | 6.249  | 14.853 | 46.417 | 1.00 | 43.62 |
| ATOM | 2451 | C    | ASP | A | 438 | 10.065 | 14.819 | 44.403 | 1.00 | 23.94 |
| ATOM | 2452 | O    | ASP | A | 438 | 10.940 | 13.982 | 44.155 | 1.00 | 21.39 |
| ATOM | 2453 | N    | GLU | A | 439 | 10.334 | 16.083 | 44.705 | 1.00 | 22.31 |
| ATOM | 2454 | CA   | GLU | A | 439 | 11.696 | 16.568 | 44.843 | 1.00 | 21.57 |
| ATOM | 2455 | CB   | GLU | A | 439 | 11.698 | 18.076 | 45.063 | 1.00 | 25.90 |
| ATOM | 2456 | CG   | GLU | A | 439 | 11.832 | 18.898 | 43.793 | 1.00 | 31.12 |
| ATOM | 2457 | CD   | GLU | A | 439 | 11.707 | 20.389 | 44.062 | 1.00 | 35.66 |
| ATOM | 2458 | OE1  | GLU | A | 439 | 10.769 | 20.784 | 44.793 | 1.00 | 37.72 |
| ATOM | 2459 | OE2  | GLU | A | 439 | 12.543 | 21.172 | 43.551 | 1.00 | 38.40 |
| ATOM | 2460 | C    | GLU | A | 439 | 12.448 | 15.858 | 45.977 | 1.00 | 19.40 |
| ATOM | 2461 | O    | GLU | A | 439 | 13.677 | 15.817 | 45.979 | 1.00 | 18.71 |
| ATOM | 2462 | N    | GLU | A | 440 | 11.717 | 15.300 | 46.938 | 1.00 | 17.67 |
| ATOM | 2463 | CA   | GLU | A | 440 | 12.311 | 14.379 | 47.906 | 1.00 | 18.42 |
| ATOM | 2464 | CB   | GLU | A | 440 | 11.219 | 13.697 | 48.746 | 1.00 | 23.20 |
| ATOM | 2465 | CG   | GLU | A | 440 | 11.666 | 13.189 | 50.121 | 1.00 | 28.72 |
| ATOM | 2466 | CD   | GLU | A | 440 | 11.089 | 11.819 | 50.505 | 1.00 | 31.66 |
| ATOM | 2467 | OE1  | GLU | A | 440 | 9.896  | 11.554 | 50.212 | 1.00 | 32.34 |
| ATOM | 2468 | OE2  | GLU | A | 440 | 11.828 | 11.002 | 51.120 | 1.00 | 32.38 |
| ATOM | 2469 | C    | GLU | A | 440 | 13.180 | 13.324 | 47.196 | 1.00 | 17.00 |
| ATOM | 2470 | O    | GLU | A | 440 | 14.143 | 12.818 | 47.765 | 1.00 | 15.43 |
| ATOM | 2471 | N    | PHE | A | 441 | 12.849 | 13.010 | 45.946 | 1.00 | 18.63 |
| ATOM | 2472 | CA   | PHE | A | 441 | 13.579 | 11.987 | 45.196 | 1.00 | 17.87 |
| ATOM | 2473 | CB   | PHE | A | 441 | 12.622 | 10.924 | 44.659 | 1.00 | 15.69 |
| ATOM | 2474 | CG   | PHE | A | 441 | 11.676 | 10.409 | 45.687 | 1.00 | 17.75 |
| ATOM | 2475 | CD1  | PHE | A | 441 | 10.315 | 10.672 | 45.587 | 1.00 | 19.74 |
| ATOM | 2476 | CE1  | PHE | A | 441 | 9.421  | 10.208 | 46.553 | 1.00 | 19.46 |
| ATOM | 2477 | CZ   | PHE | A | 441 | 9.892  | 9.480  | 47.632 | 1.00 | 20.42 |
| ATOM | 2478 | CE2  | PHE | A | 441 | 11.263 | 9.217  | 47.749 | 1.00 | 20.77 |
| ATOM | 2479 | CD2  | PHE | A | 441 | 12.143 | 9.685  | 46.780 | 1.00 | 18.84 |
| ATOM | 2480 | C    | PHE | A | 441 | 14.469 | 12.543 | 44.087 | 1.00 | 18.41 |
| ATOM | 2481 | O    | PHE | A | 441 | 15.668 | 12.266 | 44.069 | 1.00 | 20.18 |
| ATOM | 2482 | N    | THR | A | 442 | 13.894 | 13.324 | 43.175 | 1.00 | 16.17 |
| ATOM | 2483 | CA   | THR | A | 442 | 14.655 | 13.854 | 42.044 | 1.00 | 14.82 |
| ATOM | 2484 | CB   | THR | A | 442 | 13.771 | 14.728 | 41.153 | 1.00 | 15.66 |
| ATOM | 2485 | OG1  | THR | A | 442 | 13.033 | 15.654 | 41.963 | 1.00 | 18.46 |

FIGURE 3 (Cont.)

|  | A | B | C | D | E | F | G | H | I | J |
|---|---|---|---|---|---|---|---|---|---|---|
| ATOM | 2486 | CG2 | THR | A | 442 | 12.697 | 13.874 | 40.496 | 1.00 | 15.68 |
| ATOM | 2487 | C | THR | A | 442 | 15.904 | 14.609 | 42.492 | 1.00 | 13.47 |
| ATOM | 2488 | O | THR | A | 442 | 17.020 | 14.289 | 42.063 | 1.00 | 11.96 |
| ATOM | 2489 | N | ALA | A | 443 | 15.696 | 15.581 | 43.380 | 1.00 | 12.58 |
| ATOM | 2490 | CA | ALA | A | 443 | 16.750 | 16.443 | 43.911 | 1.00 | 11.64 |
| ATOM | 2491 | CB | ALA | A | 443 | 16.172 | 17.421 | 44.922 | 1.00 | 11.16 |
| ATOM | 2492 | C | ALA | A | 443 | 17.925 | 15.684 | 44.519 | 1.00 | 11.90 |
| ATOM | 2493 | O | ALA | A | 443 | 19.050 | 16.139 | 44.409 | 1.00 | 11.09 |
| ATOM | 2494 | N | GLN | A | 444 | 17.656 | 14.535 | 45.144 | 1.00 | 15.91 |
| ATOM | 2495 | CA | GLN | A | 444 | 18.688 | 13.666 | 45.735 | 1.00 | 16.93 |
| ATOM | 2496 | CB | GLN | A | 444 | 18.089 | 12.333 | 46.216 | 1.00 | 17.44 |
| ATOM | 2497 | CG | GLN | A | 444 | 17.500 | 12.346 | 47.635 | 1.00 | 17.93 |
| ATOM | 2498 | CD | GLN | A | 444 | 17.325 | 10.948 | 48.230 | 1.00 | 17.80 |
| ATOM | 2499 | OE1 | GLN | A | 444 | 16.255 | 10.610 | 48.747 | 1.00 | 16.82 |
| ATOM | 2500 | NE2 | GLN | A | 444 | 18.379 | 10.140 | 48.168 | 1.00 | 18.55 |
| ATOM | 2501 | C | GLN | A | 444 | 19.785 | 13.371 | 44.733 | 1.00 | 17.83 |
| ATOM | 2502 | O | GLN | A | 444 | 19.510 | 13.175 | 43.552 | 1.00 | 17.46 |
| ATOM | 2503 | N | SER | A | 445 | 21.023 | 13.353 | 45.214 | 1.00 | 21.82 |
| ATOM | 2504 | CA | SER | A | 445 | 22.190 | 13.069 | 44.388 | 1.00 | 26.42 |
| ATOM | 2505 | CB | SER | A | 445 | 23.411 | 13.782 | 44.964 | 1.00 | 25.97 |
| ATOM | 2506 | OG | SER | A | 445 | 24.454 | 13.839 | 44.012 | 1.00 | 25.89 |
| ATOM | 2507 | C | SER | A | 445 | 22.419 | 11.562 | 44.360 | 1.00 | 30.03 |
| ATOM | 2508 | O | SER | A | 445 | 21.937 | 10.857 | 45.245 | 1.00 | 31.67 |
| ATOM | 2509 | N | ILE | A | 446 | 23.128 | 11.061 | 43.345 | 1.00 | 34.17 |
| ATOM | 2510 | CA | ILE | A | 446 | 23.424 | 9.617 | 43.253 | 1.00 | 37.93 |
| ATOM | 2511 | CB | ILE | A | 446 | 22.569 | 8.897 | 42.163 | 1.00 | 35.13 |
| ATOM | 2512 | CG1 | ILE | A | 446 | 21.328 | 9.708 | 41.777 | 1.00 | 32.91 |
| ATOM | 2513 | CD1 | ILE | A | 446 | 21.164 | 9.894 | 40.291 | 1.00 | 30.52 |
| ATOM | 2514 | CG2 | ILE | A | 446 | 22.170 | 7.509 | 42.650 | 1.00 | 34.99 |
| ATOM | 2515 | C | ILE | A | 446 | 24.907 | 9.287 | 43.042 | 1.00 | 42.06 |
| ATOM | 2516 | O | ILE | A | 446 | 25.633 | 10.044 | 42.400 | 1.00 | 41.40 |
| ATOM | 2517 | N | THR | A | 447 | 25.337 | 8.143 | 43.581 | 1.00 | 48.62 |
| ATOM | 2518 | CA | THR | A | 447 | 26.705 | 7.641 | 43.393 | 1.00 | 54.23 |
| ATOM | 2519 | CB | THR | A | 447 | 27.181 | 6.806 | 44.630 | 1.00 | 54.12 |
| ATOM | 2520 | OG1 | THR | A | 447 | 26.172 | 6.805 | 45.651 | 1.00 | 52.75 |
| ATOM | 2521 | CG2 | THR | A | 447 | 28.386 | 7.470 | 45.306 | 1.00 | 52.75 |
| ATOM | 2522 | C | THR | A | 447 | 26.854 | 6.835 | 42.079 | 1.00 | 57.41 |
| ATOM | 2523 | O | THR | A | 447 | 26.590 | 5.620 | 42.044 | 1.00 | 57.99 |
| ATOM | 2524 | N | ILE | A | 448 | 27.271 | 7.530 | 41.011 | 1.00 | 58.95 |
| ATOM | 2525 | CA | ILE | A | 448 | 27.457 | 6.943 | 39.671 | 1.00 | 58.60 |
| ATOM | 2526 | CB | ILE | A | 448 | 27.233 | 8.021 | 38.532 | 1.00 | 59.46 |
| ATOM | 2527 | CG1 | ILE | A | 448 | 26.874 | 7.352 | 37.188 | 1.00 | 58.50 |
| ATOM | 2528 | CD1 | ILE | A | 448 | 26.212 | 8.285 | 36.155 | 1.00 | 55.93 |
| ATOM | 2529 | CG2 | ILE | A | 448 | 28.448 | 8.978 | 38.402 | 1.00 | 59.54 |
| ATOM | 2530 | C | ILE | A | 448 | 28.822 | 6.264 | 39.533 | 1.00 | 56.94 |
| ATOM | 2531 | O | ILE | A | 448 | 29.744 | 6.536 | 40.303 | 1.00 | 54.73 |
| TER | 2531 |  | ILE | A | 448 |  |  |  |  |  |
| ATOM | 2532 | N | VAL | A | 462 | 32.330 | -14.621 | 42.822 | 1.00 | 29.03 |
| ATOM | 2533 | CA | VAL | A | 462 | 30.967 | -14.453 | 42.328 | 1.00 | 31.88 |
| ATOM | 2534 | CB | VAL | A | 462 | 30.926 | -14.299 | 40.778 | 1.00 | 32.80 |
| ATOM | 2535 | CG1 | VAL | A | 462 | 29.568 | -13.712 | 40.321 | 1.00 | 32.01 |
| ATOM | 2536 | CG2 | VAL | A | 462 | 32.119 | -13.448 | 40.260 | 1.00 | 32.03 |

FIGURE 3 (Cont.)

|      | A    | B   | C   | D | E   | F      | G       | H      | I    | J     |
|------|------|-----|-----|---|-----|--------|---------|--------|------|-------|
| ATOM | 2537 | C   | VAL | A | 462 | 30.056 | -15.612 | 42.776 | 1.00 | 32.81 |
| ATOM | 2538 | O   | VAL | A | 462 | 30.437 | -16.786 | 42.649 | 1.00 | 35.61 |
| ATOM | 2539 | N   | ASP | A | 463 | 28.866 | -15.262 | 43.290 | 1.00 | 30.73 |
| ATOM | 2540 | CA  | ASP | A | 463 | 27.848 | -16.204 | 43.814 | 1.00 | 28.18 |
| ATOM | 2541 | CB  | ASP | A | 463 | 27.822 | -17.527 | 43.033 | 1.00 | 25.67 |
| ATOM | 2542 | CG  | ASP | A | 463 | 27.038 | -17.431 | 41.732 | 1.00 | 23.77 |
| ATOM | 2543 | OD1 | ASP | A | 463 | 27.172 | -16.426 | 40.995 | 1.00 | 23.24 |
| ATOM | 2544 | OD2 | ASP | A | 463 | 26.261 | -18.328 | 41.361 | 1.00 | 22.28 |
| ATOM | 2545 | C   | ASP | A | 463 | 27.989 | -16.446 | 45.327 | 1.00 | 28.40 |
| ATOM | 2546 | O   | ASP | A | 463 | 28.787 | -17.291 | 45.767 | 1.00 | 27.70 |
| ATOM | 2547 | N   | SER | A | 464 | 27.171 | -15.727 | 46.103 | 1.00 | 27.89 |
| ATOM | 2548 | CA  | SER | A | 464 | 27.475 | -15.425 | 47.510 | 1.00 | 26.48 |
| ATOM | 2549 | CB  | SER | A | 464 | 27.780 | -13.917 | 47.648 | 1.00 | 27.28 |
| ATOM | 2550 | OG  | SER | A | 464 | 28.436 | -13.593 | 48.867 | 1.00 | 27.64 |
| ATOM | 2551 | C   | SER | A | 464 | 26.441 | -15.853 | 48.563 | 1.00 | 23.91 |
| ATOM | 2552 | O   | SER | A | 464 | 26.620 | -15.558 | 49.747 | 1.00 | 24.37 |
| ATOM | 2553 | N   | GLU | A | 465 | 25.381 | -16.546 | 48.141 | 1.00 | 22.01 |
| ATOM | 2554 | CA  | GLU | A | 465 | 24.335 | -17.068 | 49.049 | 1.00 | 22.71 |
| ATOM | 2555 | CB  | GLU | A | 465 | 24.930 | -17.880 | 50.208 | 1.00 | 24.14 |
| ATOM | 2556 | CG  | GLU | A | 465 | 23.903 | -18.670 | 50.999 | 1.00 | 25.75 |
| ATOM | 2557 | CD  | GLU | A | 465 | 23.477 | -17.964 | 52.271 | 1.00 | 26.73 |
| ATOM | 2558 | OE1 | GLU | A | 465 | 24.287 | -17.933 | 53.226 | 1.00 | 26.40 |
| ATOM | 2559 | OE2 | GLU | A | 465 | 22.334 | -17.449 | 52.311 | 1.00 | 25.81 |
| ATOM | 2560 | C   | GLU | A | 465 | 23.357 | -16.007 | 49.570 | 1.00 | 22.06 |
| ATOM | 2561 | O   | GLU | A | 465 | 22.144 | -16.142 | 49.395 | 1.00 | 22.79 |
| ATOM | 2562 | N   | ARG | A | 466 | 23.875 | -14.968 | 50.225 | 1.00 | 21.00 |
| ATOM | 2563 | CA  | ARG | A | 466 | 23.090 | -13.744 | 50.429 | 1.00 | 19.59 |
| ATOM | 2564 | CB  | ARG | A | 466 | 23.668 | -12.844 | 51.540 | 1.00 | 20.63 |
| ATOM | 2565 | CG  | ARG | A | 466 | 25.102 | -12.317 | 51.322 | 1.00 | 20.37 |
| ATOM | 2566 | CD  | ARG | A | 466 | 25.853 | -11.926 | 52.610 | 1.00 | 18.99 |
| ATOM | 2567 | NE  | ARG | A | 466 | 25.547 | -12.813 | 53.736 | 1.00 | 18.72 |
| ATOM | 2568 | CZ  | ARG | A | 466 | 25.981 | -14.072 | 53.859 | 1.00 | 19.56 |
| ATOM | 2569 | NH1 | ARG | A | 466 | 25.635 | -14.786 | 54.922 | 1.00 | 18.24 |
| ATOM | 2570 | NH2 | ARG | A | 466 | 26.759 | -14.624 | 52.929 | 1.00 | 19.52 |
| ATOM | 2571 | C   | ARG | A | 466 | 22.945 | -12.988 | 49.100 | 1.00 | 16.56 |
| ATOM | 2572 | O   | ARG | A | 466 | 21.963 | -12.289 | 48.899 | 1.00 | 15.33 |
| ATOM | 2573 | N   | ARG | A | 467 | 23.932 | -13.153 | 48.211 | 1.00 | 14.83 |
| ATOM | 2574 | CA  | ARG | A | 467 | 23.877 | -12.704 | 46.815 | 1.00 | 11.72 |
| ATOM | 2575 | CB  | ARG | A | 467 | 24.960 | -11.654 | 46.510 | 1.00 | 14.84 |
| ATOM | 2576 | CG  | ARG | A | 467 | 25.629 | -10.995 | 47.694 | 1.00 | 20.60 |
| ATOM | 2577 | CD  | ARG | A | 467 | 26.962 | -10.343 | 47.339 | 1.00 | 27.04 |
| ATOM | 2578 | NE  | ARG | A | 467 | 27.371 | -9.341  | 48.325 | 1.00 | 32.91 |
| ATOM | 2579 | CZ  | ARG | A | 467 | 27.067 | -8.042  | 48.266 | 1.00 | 35.36 |
| ATOM | 2580 | NH1 | ARG | A | 467 | 26.344 | -7.558  | 47.265 | 1.00 | 36.83 |
| ATOM | 2581 | NH2 | ARG | A | 467 | 27.490 | -7.218  | 49.217 | 1.00 | 36.43 |
| ATOM | 2582 | C   | ARG | A | 467 | 24.014 | -13.866 | 45.804 | 1.00 | 8.55  |
| ATOM | 2583 | O   | ARG | A | 467 | 25.040 | -13.979 | 45.117 | 1.00 | 7.15  |
| ATOM | 2584 | N   | PRO | A | 468 | 22.979 | -14.698 | 45.675 | 1.00 | 5.25  |
| ATOM | 2585 | CA  | PRO | A | 468 | 23.043 | -15.872 | 44.798 | 1.00 | 4.79  |
| ATOM | 2586 | CB  | PRO | A | 468 | 21.948 | -16.772 | 45.365 | 1.00 | 4.41  |
| ATOM | 2587 | CG  | PRO | A | 468 | 20.929 | -15.815 | 45.880 | 1.00 | 4.60  |
| ATOM | 2588 | CD  | PRO | A | 468 | 21.657 | -14.571 | 46.313 | 1.00 | 3.51  |

FIGURE 3 (Cont.)

| | A | B | C | D | E | F | G | H | I | J |
|---|---|---|---|---|---|---|---|---|---|---|
| ATOM | 2589 | C | PRO | A | 468 | 22.726 | -15.516 | 43.344 | 1.00 | 4.93 |
| ATOM | 2590 | O | PRO | A | 468 | 22.462 | -14.355 | 43.036 | 1.00 | 7.95 |
| ATOM | 2591 | N | HIS | A | 469 | 22.765 | -16.507 | 42.460 | 1.00 | 2.40 |
| ATOM | 2592 | CA | HIS | A | 469 | 22.336 | -16.327 | 41.082 | 1.00 | 2.00 |
| ATOM | 2593 | CB | HIS | A | 469 | 22.892 | -17.446 | 40.223 | 1.00 | 2.00 |
| ATOM | 2594 | CG | HIS | A | 469 | 22.596 | -17.304 | 38.766 | 1.00 | 2.00 |
| ATOM | 2595 | ND1 | HIS | A | 469 | 22.981 | -16.204 | 38.031 | 1.00 | 2.00 |
| ATOM | 2596 | CE1 | HIS | A | 469 | 22.605 | -16.365 | 36.775 | 1.00 | 2.27 |
| ATOM | 2597 | NE2 | HIS | A | 469 | 21.994 | -17.531 | 36.669 | 1.00 | 2.42 |
| ATOM | 2598 | CD2 | HIS | A | 469 | 21.981 | -18.141 | 37.898 | 1.00 | 2.00 |
| ATOM | 2599 | C | HIS | A | 469 | 20.848 | -16.454 | 41.088 | 1.00 | 3.01 |
| ATOM | 2600 | O | HIS | A | 469 | 20.291 | -17.126 | 41.952 | 1.00 | 8.45 |
| ATOM | 2601 | N | PHE | A | 470 | 20.189 | -15.799 | 40.143 | 1.00 | 3.70 |
| ATOM | 2602 | CA | PHE | A | 470 | 18.764 | -16.017 | 39.940 | 1.00 | 2.31 |
| ATOM | 2603 | CB | PHE | A | 470 | 18.002 | -14.697 | 39.995 | 1.00 | 2.00 |
| ATOM | 2604 | CG | PHE | A | 470 | 17.943 | -14.083 | 41.373 | 1.00 | 2.00 |
| ATOM | 2605 | CD1 | PHE | A | 470 | 16.731 | -13.955 | 42.040 | 1.00 | 2.82 |
| ATOM | 2606 | CE1 | PHE | A | 470 | 16.659 | -13.393 | 43.293 | 1.00 | 2.00 |
| ATOM | 2607 | CZ | PHE | A | 470 | 17.796 | -12.954 | 43.907 | 1.00 | 2.00 |
| ATOM | 2608 | CE2 | PHE | A | 470 | 19.013 | -13.071 | 43.267 | 1.00 | 2.75 |
| ATOM | 2609 | CD2 | PHE | A | 470 | 19.085 | -13.625 | 42.000 | 1.00 | 2.00 |
| ATOM | 2610 | C | PHE | A | 470 | 18.637 | -16.696 | 38.587 | 1.00 | 3.26 |
| ATOM | 2611 | O | PHE | A | 470 | 18.889 | -16.079 | 37.561 | 1.00 | 7.10 |
| ATOM | 2612 | N | PRO | A | 471 | 18.346 | -17.991 | 38.583 | 1.00 | 2.89 |
| ATOM | 2613 | CA | PRO | A | 471 | 18.218 | -18.740 | 37.333 | 1.00 | 3.97 |
| ATOM | 2614 | CB | PRO | A | 471 | 17.851 | -20.153 | 37.812 | 1.00 | 6.10 |
| ATOM | 2615 | CG | PRO | A | 471 | 18.398 | -20.231 | 39.201 | 1.00 | 4.25 |
| ATOM | 2616 | CD | PRO | A | 471 | 18.171 | -18.856 | 39.763 | 1.00 | 4.21 |
| ATOM | 2617 | C | PRO | A | 471 | 17.121 | -18.182 | 36.437 | 1.00 | 4.41 |
| ATOM | 2618 | O | PRO | A | 471 | 16.034 | -17.864 | 36.935 | 1.00 | 2.00 |
| ATOM | 2619 | N | GLN | A | 472 | 17.428 | -18.056 | 35.142 | 1.00 | 6.75 |
| ATOM | 2620 | CA | GLN | A | 472 | 16.458 | -17.674 | 34.109 | 1.00 | 10.11 |
| ATOM | 2621 | CB | GLN | A | 472 | 15.492 | -18.834 | 33.778 | 1.00 | 14.63 |
| ATOM | 2622 | CG | GLN | A | 472 | 16.071 | -20.254 | 33.857 | 1.00 | 18.29 |
| ATOM | 2623 | CD | GLN | A | 472 | 16.974 | -20.597 | 32.678 | 1.00 | 20.73 |
| ATOM | 2624 | OE1 | GLN | A | 472 | 18.198 | -20.435 | 32.753 | 1.00 | 22.50 |
| ATOM | 2625 | NE2 | GLN | A | 472 | 16.376 | -21.077 | 31.592 | 1.00 | 21.17 |
| ATOM | 2626 | C | GLN | A | 472 | 15.670 | -16.426 | 34.512 | 1.00 | 10.43 |
| ATOM | 2627 | O | GLN | A | 472 | 14.431 | -16.428 | 34.542 | 1.00 | 11.93 |
| ATOM | 2628 | N | PHE | A | 473 | 16.403 | -15.363 | 34.823 | 1.00 | 8.38 |
| ATOM | 2629 | CA | PHE | A | 473 | 15.822 | -14.135 | 35.341 | 1.00 | 6.25 |
| ATOM | 2630 | CB | PHE | A | 473 | 16.553 | -13.749 | 36.626 | 1.00 | 4.31 |
| ATOM | 2631 | CG | PHE | A | 473 | 16.182 | -12.414 | 37.189 | 1.00 | 5.05 |
| ATOM | 2632 | CD1 | PHE | A | 473 | 15.150 | -12.300 | 38.110 | 1.00 | 6.22 |
| ATOM | 2633 | CE1 | PHE | A | 473 | 14.822 | -11.059 | 38.665 | 1.00 | 6.94 |
| ATOM | 2634 | CZ | PHE | A | 473 | 15.538 | -9.922 | 38.303 | 1.00 | 6.54 |
| ATOM | 2635 | CE2 | PHE | A | 473 | 16.588 | -10.023 | 37.386 | 1.00 | 5.98 |
| ATOM | 2636 | CD2 | PHE | A | 473 | 16.910 | -11.268 | 36.847 | 1.00 | 6.62 |
| ATOM | 2637 | C | PHE | A | 473 | 15.943 | -13.073 | 34.259 | 1.00 | 8.33 |
| ATOM | 2638 | O | PHE | A | 473 | 14.999 | -12.330 | 34.002 | 1.00 | 8.66 |
| ATOM | 2639 | N | ASP | A | 474 | 17.093 | -13.038 | 33.596 | 1.00 | 10.32 |
| ATOM | 2640 | CA | ASP | A | 474 | 17.351 | -12.049 | 32.556 | 1.00 | 13.73 |

FIGURE 3 (Cont.)

| | A | B | C | D | E | F | G | H | I | J |
|---|---|---|---|---|---|---|---|---|---|---|
| ATOM | 2641 | CB | ASP | A | 474 | 18.824 | -12.079 | 32.147 | 1.00 | 19.99 |
| ATOM | 2642 | CG | ASP | A | 474 | 19.756 | -11.804 | 33.322 | 1.00 | 25.09 |
| ATOM | 2643 | OD1 | ASP | A | 474 | 19.758 | -12.626 | 34.267 | 1.00 | 27.20 |
| ATOM | 2644 | OD2 | ASP | A | 474 | 20.508 | -10.800 | 33.400 | 1.00 | 26.77 |
| ATOM | 2645 | C | ASP | A | 474 | 16.434 | -12.183 | 31.342 | 1.00 | 11.65 |
| ATOM | 2646 | O | ASP | A | 474 | 16.105 | -13.282 | 30.921 | 1.00 | 12.33 |
| ATOM | 2647 | N | TYR | A | 475 | 16.027 | -11.043 | 30.797 | 1.00 | 10.82 |
| ATOM | 2648 | CA | TYR | A | 475 | 15.051 | -10.982 | 29.724 | 1.00 | 10.43 |
| ATOM | 2649 | CB | TYR | A | 475 | 13.643 | -11.008 | 30.316 | 1.00 | 9.78 |
| ATOM | 2650 | CG | TYR | A | 475 | 12.552 | -10.481 | 29.404 | 1.00 | 8.52 |
| ATOM | 2651 | CD1 | TYR | A | 475 | 11.808 | -11.347 | 28.607 | 1.00 | 8.82 |
| ATOM | 2652 | CE1 | TYR | A | 475 | 10.810 | -10.878 | 27.772 | 1.00 | 9.06 |
| ATOM | 2653 | CZ | TYR | A | 475 | 10.539 | -9.525 | 27.730 | 1.00 | 9.88 |
| ATOM | 2654 | OH | TYR | A | 475 | 9.536 | -9.060 | 26.906 | 1.00 | 12.39 |
| ATOM | 2655 | CE2 | TYR | A | 475 | 11.257 | -8.642 | 28.517 | 1.00 | 9.17 |
| ATOM | 2656 | CD2 | TYR | A | 475 | 12.255 | -9.123 | 29.349 | 1.00 | 8.01 |
| ATOM | 2657 | C | TYR | A | 475 | 15.221 | -9.708 | 28.910 | 1.00 | 14.83 |
| ATOM | 2658 | O | TYR | A | 475 | 15.369 | -8.619 | 29.473 | 1.00 | 15.48 |
| ATOM | 2659 | N | SER | A | 476 | 15.177 | -9.854 | 27.586 | 1.00 | 19.52 |
| ATOM | 2660 | CA | SER | A | 476 | 15.089 | -8.715 | 26.668 | 1.00 | 22.51 |
| ATOM | 2661 | CB | SER | A | 476 | 16.444 | -8.450 | 26.012 | 1.00 | 23.32 |
| ATOM | 2662 | OG | SER | A | 476 | 17.410 | -8.139 | 27.001 | 1.00 | 24.41 |
| ATOM | 2663 | C | SER | A | 476 | 13.977 | -8.894 | 25.617 | 1.00 | 23.84 |
| ATOM | 2664 | O | SER | A | 476 | 13.631 | -10.021 | 25.249 | 1.00 | 23.58 |
| ATOM | 2665 | N | ALA | A | 477 | 13.419 | -7.778 | 25.151 | 1.00 | 25.99 |
| ATOM | 2666 | CA | ALA | A | 477 | 12.286 | -7.797 | 24.228 | 1.00 | 29.87 |
| ATOM | 2667 | CB | ALA | A | 477 | 11.243 | -6.792 | 24.669 | 1.00 | 31.38 |
| ATOM | 2668 | C | ALA | A | 477 | 12.698 | -7.538 | 22.783 | 1.00 | 32.99 |
| ATOM | 2669 | O | ALA | A | 477 | 13.846 | -7.193 | 22.512 | 1.00 | 31.52 |
| ATOM | 2670 | N | SER | A | 478 | 11.742 | -7.678 | 21.867 | 1.00 | 39.23 |
| ATOM | 2671 | CA | SER | A | 478 | 12.006 | -7.640 | 20.422 | 1.00 | 46.05 |
| ATOM | 2672 | CB | SER | A | 478 | 10.852 | -8.300 | 19.651 | 1.00 | 45.56 |
| ATOM | 2673 | OG | SER | A | 478 | 10.801 | -9.695 | 19.899 | 1.00 | 44.26 |
| ATOM | 2674 | C | SER | A | 478 | 12.338 | -6.259 | 19.815 | 1.00 | 51.01 |
| ATOM | 2675 | O | SER | A | 478 | 12.290 | -6.100 | 18.587 | 1.00 | 50.93 |
| ATOM | 2676 | N | SER | A | 479 | 12.660 | -5.281 | 20.674 | 1.00 | 56.07 |
| ATOM | 2677 | CA | SER | A | 479 | 13.231 | -3.970 | 20.285 | 1.00 | 60.50 |
| ATOM | 2678 | CB | SER | A | 479 | 13.264 | -3.758 | 18.760 | 1.00 | 59.31 |
| ATOM | 2679 | OG | SER | A | 479 | 14.507 | -4.167 | 18.209 | 1.00 | 57.46 |
| ATOM | 2680 | C | SER | A | 479 | 12.581 | -2.758 | 20.966 | 1.00 | 64.42 |
| ATOM | 2681 | O | SER | A | 479 | 13.285 | -1.844 | 21.415 | 1.00 | 66.04 |
| ATOM | 2682 | N | THR | A | 480 | 11.249 | -2.744 | 21.029 | 1.00 | 68.01 |
| ATOM | 2683 | CA | THR | A | 480 | 10.518 | -1.591 | 21.569 | 1.00 | 70.48 |
| ATOM | 2684 | CB | THR | A | 480 | 9.611 | -0.907 | 20.477 | 1.00 | 71.90 |
| ATOM | 2685 | OG1 | THR | A | 480 | 8.389 | -1.644 | 20.317 | 1.00 | 73.01 |
| ATOM | 2686 | CG2 | THR | A | 480 | 10.254 | -0.962 | 19.073 | 1.00 | 71.50 |
| ATOM | 2687 | C | THR | A | 480 | 9.702 | -1.954 | 22.814 | 1.00 | 70.06 |
| ATOM | 2688 | O | THR | A | 480 | 8.828 | -2.825 | 22.766 | 1.00 | 70.83 |
| ATOM | 2689 | N | ALA | A | 481 | 10.012 | -1.293 | 23.927 | 1.00 | 68.83 |
| ATOM | 2690 | CA | ALA | A | 481 | 9.262 | -1.452 | 25.171 | 1.00 | 67.76 |
| ATOM | 2691 | CB | ALA | A | 481 | 9.639 | -2.741 | 25.876 | 1.00 | 65.66 |
| ATOM | 2692 | C | ALA | A | 481 | 9.496 | -0.254 | 26.081 | 1.00 | 69.28 |

FIGURE 3 (Cont.)

| | A | B | C | D | E | F | G | H | I | J |
|---|---|---|---|---|---|---|---|---|---|---|
| ATOM | 2693 | O | ALA | A | 481 | 9.867 | 0.826 | 25.618 | 1.00 | 71.43 |
| TER PEPTIDE A | | | | | | | | | | |
| ATOM | 2694 | N | GLY | A | 3 | -2.454 | 15.839 | 53.220 | 1.00 | 59.77 |
| ATOM | 2695 | CA | GLY | A | 3 | -3.404 | 14.806 | 52.720 | 1.00 | 63.34 |
| ATOM | 2696 | C | GLY | A | 3 | -2.775 | 13.431 | 52.602 | 1.00 | 65.23 |
| ATOM | 2697 | O | GLY | A | 3 | -2.205 | 13.082 | 51.558 | 1.00 | 68.14 |
| ATOM | 2698 | N | ARG | A | 4 | -2.905 | 12.652 | 53.676 | 1.00 | 64.00 |
| ATOM | 2699 | CA | ARG | A | 4 | -2.278 | 11.329 | 53.831 | 1.00 | 61.26 |
| ATOM | 2700 | CB | ARG | A | 4 | -3.188 | 10.206 | 53.324 | 1.00 | 57.91 |
| ATOM | 2701 | CG | ARG | A | 4 | -3.107 | 9.935 | 51.850 | 1.00 | 56.34 |
| ATOM | 2702 | CD | ARG | A | 4 | -3.517 | 8.535 | 51.482 | 1.00 | 53.99 |
| ATOM | 2703 | NE | ARG | A | 4 | -2.387 | 7.755 | 51.012 | 1.00 | 51.59 |
| ATOM | 2704 | CZ | ARG | A | 4 | -2.022 | 7.650 | 49.746 | 1.00 | 51.26 |
| ATOM | 2705 | NH1 | ARG | A | 4 | -2.695 | 8.269 | 48.792 | 1.00 | 51.55 |
| ATOM | 2706 | NH2 | ARG | A | 4 | -0.974 | 6.919 | 49.429 | 1.00 | 53.20 |
| ATOM | 2707 | C | ARG | A | 4 | -0.825 | 11.159 | 53.329 | 1.00 | 60.21 |
| ATOM | 2708 | O | ARG | A | 4 | -0.520 | 11.333 | 52.133 | 1.00 | 59.47 |
| ATOM | 2709 | N | PRO | A | 5 | 0.055 | 10.809 | 54.268 | 1.00 | 56.58 |
| ATOM | 2710 | CA | PRO | A | 5 | 1.437 | 10.453 | 53.966 | 1.00 | 53.20 |
| ATOM | 2711 | CB | PRO | A | 5 | 1.967 | 10.013 | 55.330 | 1.00 | 55.07 |
| ATOM | 2712 | CG | PRO | A | 5 | 0.736 | 9.598 | 56.070 | 1.00 | 56.56 |
| ATOM | 2713 | CD | PRO | A | 5 | -0.212 | 10.707 | 55.712 | 1.00 | 56.60 |
| ATOM | 2714 | C | PRO | A | 5 | 1.517 | 9.272 | 53.014 | 1.00 | 51.17 |
| ATOM | 2715 | O | PRO | A | 5 | 0.730 | 8.327 | 53.097 | 1.00 | 52.66 |
| ATOM | 2716 | N | ARG | A | 6 | 2.480 | 9.351 | 52.113 | 1.00 | 49.43 |
| ATOM | 2717 | CA | ARG | A | 6 | 2.923 | 8.231 | 51.305 | 1.00 | 49.47 |
| ATOM | 2718 | CB | ARG | A | 6 | 4.294 | 8.566 | 50.762 | 1.00 | 45.72 |
| ATOM | 2719 | CG | ARG | A | 6 | 4.819 | 7.592 | 49.784 | 1.00 | 49.30 |
| ATOM | 2720 | CD | ARG | A | 6 | 5.554 | 8.271 | 48.692 | 1.00 | 52.59 |
| ATOM | 2721 | NE | ARG | A | 6 | 5.891 | 7.368 | 47.610 | 1.00 | 54.37 |
| ATOM | 2722 | CZ | ARG | A | 6 | 6.057 | 7.781 | 46.376 | 1.00 | 57.39 |
| ATOM | 2723 | NH1 | ARG | A | 6 | 5.899 | 9.077 | 46.104 | 1.00 | 58.86 |
| ATOM | 2724 | NH2 | ARG | A | 6 | 6.375 | 6.915 | 45.420 | 1.00 | 58.53 |
| ATOM | 2725 | C | ARG | A | 6 | 3.004 | 6.909 | 52.084 | 1.00 | 53.73 |
| ATOM | 2726 | O | ARG | A | 6 | 3.533 | 6.858 | 53.202 | 1.00 | 56.89 |
| ATOM | 2727 | N | THR | A | 7 | 2.487 | 5.846 | 51.469 | 1.00 | 54.48 |
| ATOM | 2728 | CA | THR | A | 7 | 2.452 | 4.511 | 52.059 | 1.00 | 53.43 |
| ATOM | 2729 | CB | THR | A | 7 | 1.040 | 3.922 | 51.913 | 1.00 | 54.97 |
| ATOM | 2730 | OG1 | THR | A | 7 | 0.805 | 3.582 | 50.538 | 1.00 | 55.62 |
| ATOM | 2731 | CG2 | THR | A | 7 | -0.017 | 4.977 | 52.190 | 1.00 | 54.48 |
| ATOM | 2732 | C | THR | A | 7 | 3.437 | 3.602 | 51.343 | 1.00 | 52.28 |
| ATOM | 2733 | O | THR | A | 7 | 3.782 | 3.861 | 50.185 | 1.00 | 54.07 |
| ATOM | 2734 | N | THR | A | 8 | 3.893 | 2.549 | 52.025 | 1.00 | 49.53 |
| ATOM | 2735 | CA | THR | A | 8 | 4.673 | 1.494 | 51.366 | 1.00 | 51.75 |
| ATOM | 2736 | CB | THR | A | 8 | 6.169 | 1.497 | 51.773 | 1.00 | 55.90 |
| ATOM | 2737 | OG1 | THR | A | 8 | 6.272 | 1.356 | 53.195 | 1.00 | 59.32 |
| ATOM | 2738 | CG2 | THR | A | 8 | 6.879 | 2.860 | 51.437 | 1.00 | 57.69 |
| ATOM | 2739 | C | THR | A | 8 | 4.060 | 0.150 | 51.685 | 1.00 | 48.28 |
| ATOM | 2740 | O | THR | A | 8 | 3.385 | 0.014 | 52.698 | 1.00 | 53.43 |
| ATOM | 2741 | N | SER | A | 9 | 4.312 | -0.837 | 50.828 | 1.00 | 42.88 |
| ATOM | 2742 | CA | SER | A | 9 | 3.671 | -2.141 | 50.918 | 1.00 | 37.85 |
| ATOM | 2743 | CB | SER | A | 9 | 3.649 | -2.790 | 49.541 | 1.00 | 39.65 |

FIGURE 3 (Cont.)

| | A | B | C | D | E | F | G | H | I | J |
|---|---|---|---|---|---|---|---|---|---|---|
| ATOM | 2744 | OG | SER | A | 9 | 4.938 | -3.228 | 49.167 | 1.00 | 41.04 |
| ATOM | 2745 | C | SER | A | 9 | 4.350 | -3.069 | 51.920 | 1.00 | 36.94 |
| ATOM | 2746 | O | SER | A | 9 | 5.337 | -2.705 | 52.543 | 1.00 | 35.22 |
| ATOM | 2747 | N | PHE | A | 10 | 3.823 | -4.277 | 52.070 | 1.00 | 37.43 |
| ATOM | 2748 | CA | PHE | A | 10 | 4.352 | -5.198 | 53.054 | 1.00 | 41.36 |
| ATOM | 2749 | CB | PHE | A | 10 | 3.849 | -4.798 | 54.449 | 1.00 | 43.51 |
| ATOM | 2750 | CG | PHE | A | 10 | 2.418 | -5.165 | 54.699 | 1.00 | 47.05 |
| ATOM | 2751 | CD1 | PHE | A | 10 | 2.088 | -6.411 | 55.240 | 1.00 | 49.04 |
| ATOM | 2752 | CE1 | PHE | A | 10 | 0.756 | -6.773 | 55.446 | 1.00 | 50.01 |
| ATOM | 2753 | CZ | PHE | A | 10 | -0.263 | -5.882 | 55.116 | 1.00 | 49.88 |
| ATOM | 2754 | CE2 | PHE | A | 10 | 0.054 | -4.633 | 54.577 | 1.00 | 48.79 |
| ATOM | 2755 | CD2 | PHE | A | 10 | 1.392 | -4.284 | 54.372 | 1.00 | 48.20 |
| ATOM | 2756 | C | PHE | A | 10 | 3.929 | -6.625 | 52.720 | 1.00 | 46.07 |
| ATOM | 2757 | O | PHE | A | 10 | 2.993 | -6.808 | 51.924 | 1.00 | 41.79 |
| ATOM | 2758 | N | ALA | A | 11 | 4.615 | -7.609 | 53.337 | 1.00 | 52.65 |
| ATOM | 2759 | CA | ALA | A | 11 | 4.234 | -9.042 | 53.308 | 1.00 | 57.70 |
| ATOM | 2760 | CB | ALA | A | 11 | 4.770 | -9.730 | 52.049 | 1.00 | 55.58 |
| ATOM | 2761 | C | ALA | A | 11 | 4.631 | -9.858 | 54.562 | 1.00 | 62.68 |
| ATOM | 2762 | O | ALA | A | 11 | 5.822 | -10.062 | 54.839 | 1.00 | 63.97 |
| ATOM | 2763 | N | GLU | A | 12 | 3.620 | -10.333 | 55.297 | 1.00 | 67.34 |
| ATOM | 2764 | CA | GLU | A | 12 | 3.793 | -11.258 | 56.425 | 1.00 | 68.21 |
| ATOM | 2765 | CB | GLU | A | 12 | 2.461 | -11.451 | 57.184 | 1.00 | 72.49 |
| ATOM | 2766 | CG | GLU | A | 12 | 2.570 | -11.968 | 58.629 | 1.00 | 79.61 |
| ATOM | 2767 | CD | GLU | A | 12 | 1.320 | -12.729 | 59.136 | 1.00 | 84.11 |
| ATOM | 2768 | OE1 | GLU | A | 12 | 0.656 | -12.247 | 60.096 | 1.00 | 83.62 |
| ATOM | 2769 | OE2 | GLU | A | 12 | 1.000 | -13.827 | 58.599 | 1.00 | 86.05 |
| ATOM | 2770 | C | GLU | A | 12 | 4.277 | -12.593 | 55.874 | 1.00 | 67.02 |
| ATOM | 2771 | O | GLU | A | 12 | 3.586 | -13.230 | 55.074 | 1.00 | 65.82 |
| TER Nucleotide A | | | | | | | | | | |
| ATOM | 2772 | O1A | ANP | A | 490 | 7.746 | -0.022 | 41.698 | 1.00 | 35.93 |
| ATOM | 2773 | PA | ANP | A | 490 | 7.806 | 0.868 | 43.030 | 1.00 | 35.16 |
| ATOM | 2774 | O2A | ANP | A | 490 | 6.367 | 1.219 | 43.604 | 1.00 | 35.78 |
| ATOM | 2775 | O3A | ANP | A | 490 | 8.781 | 0.266 | 44.165 | 1.00 | 38.17 |
| ATOM | 2776 | PB | ANP | A | 490 | 8.219 | -0.290 | 45.557 | 1.00 | 39.61 |
| ATOM | 2777 | O1B | ANP | A | 490 | 9.354 | -0.331 | 46.671 | 1.00 | 40.09 |
| ATOM | 2778 | O2B | ANP | A | 490 | 7.590 | -1.715 | 45.264 | 1.00 | 36.29 |
| ATOM | 2779 | N3B | ANP | A | 490 | 6.945 | 0.666 | 46.231 | 1.00 | 40.41 |
| ATOM | 2780 | PG | ANP | A | 490 | 5.885 | -0.321 | 47.201 | 1.00 | 38.25 |
| ATOM | 2781 | O3G | ANP | A | 490 | 6.411 | -0.345 | 48.702 | 1.00 | 40.92 |
| ATOM | 2782 | O2G | ANP | A | 490 | 4.430 | 0.307 | 47.167 | 1.00 | 41.75 |
| ATOM | 2783 | O1G | ANP | A | 490 | 5.861 | -1.782 | 46.588 | 1.00 | 36.72 |
| ATOM | 2784 | O5* | ANP | A | 490 | 8.626 | 2.195 | 42.741 | 1.00 | 31.73 |
| ATOM | 2785 | C5* | ANP | A | 490 | 8.678 | 3.206 | 43.722 | 1.00 | 31.76 |
| ATOM | 2786 | C4* | ANP | A | 490 | 8.277 | 4.427 | 42.929 | 1.00 | 34.78 |
| ATOM | 2787 | O4* | ANP | A | 490 | 9.086 | 4.561 | 41.750 | 1.00 | 32.89 |
| ATOM | 2788 | C1* | ANP | A | 490 | 8.359 | 5.295 | 40.754 | 1.00 | 33.06 |
| ATOM | 2789 | C2* | ANP | A | 490 | 6.957 | 5.486 | 41.331 | 1.00 | 34.08 |
| ATOM | 2790 | O2* | ANP | A | 490 | 6.908 | 6.784 | 41.926 | 1.00 | 33.18 |
| ATOM | 2791 | C3* | ANP | A | 490 | 6.856 | 4.368 | 42.365 | 1.00 | 34.86 |
| ATOM | 2792 | O3* | ANP | A | 490 | 5.811 | 4.487 | 43.339 | 1.00 | 34.01 |
| ATOM | 2793 | N9 | ANP | A | 490 | 8.269 | 4.512 | 39.496 | 1.00 | 29.79 |
| ATOM | 2794 | C8 | ANP | A | 490 | 8.077 | 3.187 | 39.400 | 1.00 | 30.79 |

FIGURE 3 (Cont.)

|      | A    | B  | C   | D | E   | F       | G       | H      | I    | J     |
|------|------|----|-----|---|-----|---------|---------|--------|------|-------|
| ATOM | 2795 | N7 | ANP | A | 490 | 8.014   | 2.738   | 38.116 | 1.00 | 30.51 |
| ATOM | 2796 | C5 | ANP | A | 490 | 8.175   | 3.806   | 37.348 | 1.00 | 31.16 |
| ATOM | 2797 | C6 | ANP | A | 490 | 8.219   | 4.114   | 35.903 | 1.00 | 35.88 |
| ATOM | 2798 | N6 | ANP | A | 490 | 8.072   | 3.103   | 35.010 | 1.00 | 40.38 |
| ATOM | 2799 | C4 | ANP | A | 490 | 8.330   | 4.917   | 38.249 | 1.00 | 28.69 |
| ATOM | 2800 | N3 | ANP | A | 490 | 8.504   | 6.239   | 37.747 | 1.00 | 30.51 |
| ATOM | 2801 | C2 | ANP | A | 490 | 8.528   | 6.395   | 36.411 | 1.00 | 35.81 |
| ATOM | 2802 | N1 | ANP | A | 490 | 8.399   | 5.394   | 35.509 | 1.00 | 34.95 |
| ATOM | 2803 | MN | MN  | A | 491 | 4.819   | 1.152   | 44.653 | 1.00 | 35.84 |
| ATOM | 2804 | MN | MN  | A | 492 | 5.692   | -2.995  | 45.330 | 1.00 | 52.47 |
| TER  |      |    |     |   |     |         |         |        |      |       |
| ATOM | 2805 | O  | HOH | A | 500 | 4.426   | 12.104  | 51.909 | 1.00 | 42.36 |
| ATOM | 2806 | O  | HOH | A | 501 | 5.627   | -13.477 | 51.544 | 1.00 | 35.43 |
| ATOM | 2807 | O  | HOH | A | 502 | 11.354  | -15.784 | 49.503 | 1.00 | 38.30 |
| ATOM | 2808 | O  | HOH | A | 503 | -2.804  | 12.308  | 48.376 | 1.00 | 27.45 |
| ATOM | 2809 | O  | HOH | A | 504 | 0.959   | 1.839   | 63.849 | 1.00 | 31.25 |
| ATOM | 2810 | O  | HOH | A | 505 | -16.543 | -0.308  | 53.597 | 1.00 | 29.80 |
| ATOM | 2811 | O  | HOH | A | 506 | 2.705   | -16.629 | 29.426 | 1.00 | 65.56 |
| ATOM | 2812 | O  | HOH | A | 507 | -5.035  | 12.206  | 32.492 | 1.00 | 37.82 |
| ATOM | 2813 | O  | HOH | A | 508 | 20.328  | -18.653 | 33.701 | 1.00 | 31.39 |
| ATOM | 2814 | O  | HOH | A | 509 | 7.557   | -11.808 | 52.321 | 1.00 | 49.98 |
| ATOM | 2815 | O  | HOH | A | 510 | 6.457   | -5.738  | 48.691 | 1.00 | 32.48 |
| ATOM | 2816 | O  | HOH | A | 511 | 2.515   | -14.181 | 34.209 | 1.00 | 52.27 |
| ATOM | 2817 | O  | HOH | A | 512 | 0.867   | 3.100   | 56.892 | 1.00 | 51.11 |
| ATOM | 2818 | O  | HOH | A | 513 | 7.998   | 10.436  | 43.186 | 1.00 | 51.40 |
| ATOM | 2819 | O  | HOH | A | 514 | -6.287  | -4.147  | 48.669 | 1.00 | 42.79 |
| ATOM | 2820 | O  | HOH | A | 515 | -7.047  | 10.124  | 53.539 | 1.00 | 16.21 |
| ATOM | 2821 | O  | HOH | A | 516 | -14.864 | 14.377  | 52.119 | 1.00 | 27.95 |
| ATOM | 2822 | O  | HOH | A | 517 | -20.995 | -0.876  | 51.272 | 1.00 | 41.50 |
| ATOM | 2823 | O  | HOH | A | 518 | 7.067   | -2.676  | 38.556 | 1.00 | 52.19 |

FIGURE 3 (Cont.)

Molecule B

|      | A    | B  | C   | D | E   | F      | G      | H       | I    | J     |
|------|------|----|-----|---|-----|--------|--------|---------|------|-------|
| ATOM | 2824 | N  | PRO | B | 141 | 55.967 | 72.234 | -24.377 | 1.00 | 25.65 |
| ATOM | 2825 | CA | PRO | B | 141 | 55.049 | 72.260 | -23.201 | 1.00 | 26.88 |
| ATOM | 2826 | CB | PRO | B | 141 | 55.076 | 73.733 | -22.789 | 1.00 | 25.75 |
| ATOM | 2827 | CG | PRO | B | 141 | 56.468 | 74.185 | -23.160 | 1.00 | 25.49 |
| ATOM | 2828 | CD | PRO | B | 141 | 56.930 | 73.348 | -24.341 | 1.00 | 25.20 |
| ATOM | 2829 | C  | PRO | B | 141 | 53.621 | 71.815 | -23.540 | 1.00 | 28.46 |
| ATOM | 2830 | O  | PRO | B | 141 | 53.285 | 71.695 | -24.722 | 1.00 | 27.28 |
| ATOM | 2831 | N  | LYS | B | 142 | 52.822 | 71.561 | -22.497 | 1.00 | 30.99 |
| ATOM | 2832 | CA | LYS | B | 142 | 51.411 | 71.127 | -22.581 | 1.00 | 33.92 |
| ATOM | 2833 | CB | LYS | B | 142 | 50.752 | 71.575 | -23.898 | 1.00 | 34.19 |
| ATOM | 2834 | CG | LYS | B | 142 | 49.419 | 72.286 | -23.721 | 1.00 | 34.83 |
| ATOM | 2835 | CD | LYS | B | 142 | 48.260 | 71.431 | -24.227 | 1.00 | 35.69 |
| ATOM | 2836 | CE | LYS | B | 142 | 47.565 | 70.663 | -23.100 | 1.00 | 36.71 |
| ATOM | 2837 | NZ | LYS | B | 142 | 47.239 | 69.250 | -23.472 | 1.00 | 36.54 |

FIGURE 3 (Cont.)

|  | A | B | C | D | E | F | G | H | I | J |
|---|---|---|---|---|---|---|---|---|---|---|
| ATOM | 2838 | C | LYS | B | 142 | 51.214 | 69.613 | -22.350 | 1.00 | 35.24 |
| ATOM | 2839 | O | LYS | B | 142 | 51.927 | 68.800 | -22.945 | 1.00 | 34.48 |
| ATOM | 2840 | N | HIS | B | 143 | 50.253 | 69.245 | -21.490 | 1.00 | 37.31 |
| ATOM | 2841 | CA | HIS | B | 143 | 49.964 | 67.826 | -21.194 | 1.00 | 39.24 |
| ATOM | 2842 | CB | HIS | B | 143 | 50.710 | 67.363 | -19.932 | 1.00 | 41.24 |
| ATOM | 2843 | CG | HIS | B | 143 | 51.251 | 65.965 | -20.025 | 1.00 | 44.44 |
| ATOM | 2844 | ND1 | HIS | B | 143 | 51.391 | 65.144 | -18.924 | 1.00 | 46.18 |
| ATOM | 2845 | CE1 | HIS | B | 143 | 51.892 | 63.981 | -19.302 | 1.00 | 46.30 |
| ATOM | 2846 | NE2 | HIS | B | 143 | 52.082 | 64.015 | -20.610 | 1.00 | 45.69 |
| ATOM | 2847 | CD2 | HIS | B | 143 | 51.690 | 65.243 | -21.086 | 1.00 | 44.97 |
| ATOM | 2848 | C | HIS | B | 143 | 48.476 | 67.433 | -21.098 | 1.00 | 38.35 |
| ATOM | 2849 | O | HIS | B | 143 | 47.621 | 68.271 | -20.809 | 1.00 | 38.18 |
| ATOM | 2850 | N | ARG | B | 144 | 48.200 | 66.147 | -21.346 | 1.00 | 37.37 |
| ATOM | 2851 | CA | ARG | B | 144 | 46.856 | 65.548 | -21.278 | 1.00 | 36.93 |
| ATOM | 2852 | CB | ARG | B | 144 | 46.766 | 64.340 | -22.219 | 1.00 | 36.20 |
| ATOM | 2853 | CG | ARG | B | 144 | 47.820 | 63.253 | -21.961 | 1.00 | 35.57 |
| ATOM | 2854 | CD | ARG | B | 144 | 47.789 | 62.084 | -22.941 | 1.00 | 35.98 |
| ATOM | 2855 | NE | ARG | B | 144 | 48.217 | 62.478 | -24.286 | 1.00 | 37.34 |
| ATOM | 2856 | CZ | ARG | B | 144 | 48.164 | 61.698 | -25.366 | 1.00 | 36.61 |
| ATOM | 2857 | NH1 | ARG | B | 144 | 47.699 | 60.456 | -25.285 | 1.00 | 36.43 |
| ATOM | 2858 | NH2 | ARG | B | 144 | 48.581 | 62.163 | -26.537 | 1.00 | 35.98 |
| ATOM | 2859 | C | ARG | B | 144 | 46.519 | 65.118 | -19.848 | 1.00 | 38.00 |
| ATOM | 2860 | O | ARG | B | 144 | 47.303 | 65.382 | -18.933 | 1.00 | 38.83 |
| ATOM | 2861 | N | VAL | B | 145 | 45.375 | 64.448 | -19.650 | 1.00 | 37.99 |
| ATOM | 2862 | CA | VAL | B | 145 | 44.955 | 64.046 | -18.293 | 1.00 | 37.66 |
| ATOM | 2863 | CB | VAL | B | 145 | 44.719 | 65.320 | -17.391 | 1.00 | 37.43 |
| ATOM | 2864 | CG1 | VAL | B | 145 | 43.250 | 65.763 | -17.377 | 1.00 | 36.42 |
| ATOM | 2865 | CG2 | VAL | B | 145 | 45.284 | 65.120 | -15.979 | 1.00 | 37.58 |
| ATOM | 2866 | C | VAL | B | 145 | 43.778 | 63.042 | -18.151 | 1.00 | 37.36 |
| ATOM | 2867 | O | VAL | B | 145 | 43.537 | 62.531 | -17.056 | 1.00 | 36.86 |
| ATOM | 2868 | N | THR | B | 146 | 43.078 | 62.732 | -19.242 | 1.00 | 38.07 |
| ATOM | 2869 | CA | THR | B | 146 | 41.789 | 62.018 | -19.153 | 1.00 | 38.65 |
| ATOM | 2870 | CB | THR | B | 146 | 40.933 | 62.183 | -20.456 | 1.00 | 41.17 |
| ATOM | 2871 | OG1 | THR | B | 146 | 41.544 | 63.128 | -21.350 | 1.00 | 42.20 |
| ATOM | 2872 | CG2 | THR | B | 146 | 39.577 | 62.826 | -20.128 | 1.00 | 41.16 |
| ATOM | 2873 | C | THR | B | 146 | 41.845 | 60.545 | -18.702 | 1.00 | 37.11 |
| ATOM | 2874 | O | THR | B | 146 | 42.919 | 59.946 | -18.627 | 1.00 | 34.40 |
| ATOM | 2875 | N | MET | B | 147 | 40.656 | 59.984 | -18.460 | 1.00 | 38.23 |
| ATOM | 2876 | CA | MET | B | 147 | 40.422 | 58.784 | -17.632 | 1.00 | 39.19 |
| ATOM | 2877 | CB | MET | B | 147 | 38.932 | 58.715 | -17.230 | 1.00 | 41.33 |
| ATOM | 2878 | CG | MET | B | 147 | 38.504 | 57.476 | -16.419 | 1.00 | 43.05 |
| ATOM | 2879 | SD | MET | B | 147 | 38.486 | 57.722 | -14.614 | 1.00 | 45.63 |
| ATOM | 2880 | CE | MET | B | 147 | 36.884 | 57.098 | -14.165 | 1.00 | 44.48 |
| ATOM | 2881 | C | MET | B | 147 | 40.892 | 57.404 | -18.125 | 1.00 | 37.93 |
| ATOM | 2882 | O | MET | B | 147 | 41.692 | 56.757 | -17.446 | 1.00 | 38.55 |
| ATOM | 2883 | N | ASN | B | 148 | 40.377 | 56.934 | -19.262 | 1.00 | 35.19 |
| ATOM | 2884 | CA | ASN | B | 148 | 40.535 | 55.519 | -19.627 | 1.00 | 32.46 |
| ATOM | 2885 | CB | ASN | B | 148 | 39.451 | 55.070 | -20.624 | 1.00 | 31.08 |
| ATOM | 2886 | CG | ASN | B | 148 | 39.757 | 55.477 | -22.053 | 1.00 | 30.50 |
| ATOM | 2887 | OD1 | ASN | B | 148 | 40.143 | 54.647 | -22.877 | 1.00 | 28.96 |
| ATOM | 2888 | ND2 | ASN | B | 148 | 39.579 | 56.756 | -22.356 | 1.00 | 30.60 |
| ATOM | 2889 | C | ASN | B | 148 | 41.947 | 55.081 | -20.053 | 1.00 | 31.76 |

FIGURE 3 (Cont.)

|  | A | B | C | D | E | F | G | H | I | J |
|---|---|---|---|---|---|---|---|---|---|---|
| ATOM | 2890 | O | ASN | B | 148 | 42.118 | 54.069 | -20.737 | 1.00 | 31.62 |
| ATOM | 2891 | N | GLU | B | 149 | 42.952 | 55.840 | -19.620 | 1.00 | 31.55 |
| ATOM | 2892 | CA | GLU | B | 149 | 44.352 | 55.446 | -19.761 | 1.00 | 32.79 |
| ATOM | 2893 | CB | GLU | B | 149 | 45.245 | 56.683 | -19.860 | 1.00 | 34.53 |
| ATOM | 2894 | CG | GLU | B | 149 | 46.360 | 56.547 | -20.886 | 1.00 | 38.42 |
| ATOM | 2895 | CD | GLU | B | 149 | 46.896 | 57.887 | -21.354 | 1.00 | 40.44 |
| ATOM | 2896 | OE1 | GLU | B | 149 | 47.234 | 58.008 | -22.560 | 1.00 | 39.02 |
| ATOM | 2897 | OE2 | GLU | B | 149 | 46.979 | 58.816 | -20.512 | 1.00 | 41.25 |
| ATOM | 2898 | C | GLU | B | 149 | 44.795 | 54.547 | -18.596 | 1.00 | 32.34 |
| ATOM | 2899 | O | GLU | B | 149 | 45.989 | 54.428 | -18.296 | 1.00 | 32.04 |
| ATOM | 2900 | N | PHE | B | 150 | 43.815 | 53.920 | -17.946 | 1.00 | 31.13 |
| ATOM | 2901 | CA | PHE | B | 150 | 44.045 | 53.030 | -16.816 | 1.00 | 29.14 |
| ATOM | 2902 | CB | PHE | B | 150 | 43.658 | 53.726 | -15.513 | 1.00 | 26.42 |
| ATOM | 2903 | CG | PHE | B | 150 | 44.526 | 54.897 | -15.165 | 1.00 | 24.27 |
| ATOM | 2904 | CD1 | PHE | B | 150 | 45.637 | 54.732 | -14.342 | 1.00 | 24.17 |
| ATOM | 2905 | CE1 | PHE | B | 150 | 46.443 | 55.818 | -14.009 | 1.00 | 23.48 |
| ATOM | 2906 | CZ | PHE | B | 150 | 46.135 | 57.086 | -14.502 | 1.00 | 22.82 |
| ATOM | 2907 | CE2 | PHE | B | 150 | 45.022 | 57.260 | -15.318 | 1.00 | 21.75 |
| ATOM | 2908 | CD2 | PHE | B | 150 | 44.224 | 56.169 | -15.640 | 1.00 | 22.24 |
| ATOM | 2909 | C | PHE | B | 150 | 43.204 | 51.770 | -16.966 | 1.00 | 30.40 |
| ATOM | 2910 | O | PHE | B | 150 | 42.017 | 51.850 | -17.292 | 1.00 | 30.97 |
| ATOM | 2911 | N | GLU | B | 151 | 43.820 | 50.612 | -16.738 | 1.00 | 32.16 |
| ATOM | 2912 | CA | GLU | B | 151 | 43.083 | 49.346 | -16.645 | 1.00 | 33.17 |
| ATOM | 2913 | CB | GLU | B | 151 | 43.803 | 48.197 | -17.380 | 1.00 | 33.04 |
| ATOM | 2914 | CG | GLU | B | 151 | 45.164 | 47.805 | -16.816 | 1.00 | 32.26 |
| ATOM | 2915 | CD | GLU | B | 151 | 45.949 | 46.896 | -17.739 | 1.00 | 31.33 |
| ATOM | 2916 | OE1 | GLU | B | 151 | 46.934 | 47.366 | -18.347 | 1.00 | 30.58 |
| ATOM | 2917 | OE2 | GLU | B | 151 | 45.581 | 45.708 | -17.852 | 1.00 | 31.56 |
| ATOM | 2918 | C | GLU | B | 151 | 42.789 | 48.999 | -15.175 | 1.00 | 32.79 |
| ATOM | 2919 | O | GLU | B | 151 | 43.661 | 49.116 | -14.304 | 1.00 | 31.86 |
| ATOM | 2920 | N | TYR | B | 152 | 41.546 | 48.599 | -14.912 | 1.00 | 31.61 |
| ATOM | 2921 | CA | TYR | B | 152 | 41.065 | 48.387 | -13.549 | 1.00 | 29.61 |
| ATOM | 2922 | CB | TYR | B | 152 | 39.673 | 49.013 | -13.354 | 1.00 | 27.68 |
| ATOM | 2923 | CG | TYR | B | 152 | 39.522 | 50.419 | -13.917 | 1.00 | 25.99 |
| ATOM | 2924 | CD1 | TYR | B | 152 | 40.629 | 51.256 | -14.072 | 1.00 | 26.09 |
| ATOM | 2925 | CE1 | TYR | B | 152 | 40.507 | 52.533 | -14.590 | 1.00 | 25.95 |
| ATOM | 2926 | CZ | TYR | B | 152 | 39.265 | 53.006 | -14.953 | 1.00 | 26.19 |
| ATOM | 2927 | OH | TYR | B | 152 | 39.171 | 54.281 | -15.462 | 1.00 | 26.39 |
| ATOM | 2928 | CE2 | TYR | B | 152 | 38.136 | 52.205 | -14.806 | 1.00 | 25.84 |
| ATOM | 2929 | CD2 | TYR | B | 152 | 38.272 | 50.914 | -14.290 | 1.00 | 25.38 |
| ATOM | 2930 | C | TYR | B | 152 | 41.059 | 46.897 | -13.230 | 1.00 | 29.35 |
| ATOM | 2931 | O | TYR | B | 152 | 40.402 | 46.105 | -13.913 | 1.00 | 30.27 |
| ATOM | 2932 | N | LEU | B | 153 | 41.802 | 46.528 | -12.190 | 1.00 | 27.64 |
| ATOM | 2933 | CA | LEU | B | 153 | 42.066 | 45.129 | -11.874 | 1.00 | 25.68 |
| ATOM | 2934 | CB | LEU | B | 153 | 43.546 | 44.947 | -11.524 | 1.00 | 25.67 |
| ATOM | 2935 | CG | LEU | B | 153 | 44.573 | 44.871 | -12.656 | 1.00 | 24.65 |
| ATOM | 2936 | CD1 | LEU | B | 153 | 44.915 | 46.246 | -13.211 | 1.00 | 23.31 |
| ATOM | 2937 | CD2 | LEU | B | 153 | 45.830 | 44.181 | -12.146 | 1.00 | 26.63 |
| ATOM | 2938 | C | LEU | B | 153 | 41.190 | 44.609 | -10.734 | 1.00 | 24.16 |
| ATOM | 2939 | O | LEU | B | 153 | 40.482 | 43.608 | -10.887 | 1.00 | 23.10 |
| ATOM | 2940 | N | LYS | B | 154 | 41.250 | 45.293 | -9.592 | 1.00 | 21.85 |
| ATOM | 2941 | CA | LYS | B | 154 | 40.504 | 44.889 | -8.404 | 1.00 | 18.64 |

FIGURE 3 (Cont.)

|      | A    | B    | C   | D   | E   | F      | G      | H      | I    | J     |
|------|------|------|-----|-----|-----|--------|--------|--------|------|-------|
| ATOM | 2942 | CB   | LYS | B   | 154 | 41.378 | 44.013 | -7.495 | 1.00 | 18.98 |
| ATOM | 2943 | CG   | LYS | B   | 154 | 41.555 | 42.579 | -7.970 | 1.00 | 18.54 |
| ATOM | 2944 | CD   | LYS | B   | 154 | 42.147 | 41.711 | -6.880 | 1.00 | 18.55 |
| ATOM | 2945 | CE   | LYS | B   | 154 | 43.487 | 41.140 | -7.301 | 1.00 | 19.63 |
| ATOM | 2946 | NZ   | LYS | B   | 154 | 43.445 | 39.657 | -7.416 | 1.00 | 20.51 |
| ATOM | 2947 | C    | LYS | B   | 154 | 39.965 | 46.084 | -7.614 | 1.00 | 15.97 |
| ATOM | 2948 | O    | LYS | B   | 154 | 40.506 | 47.199 | -7.680 | 1.00 | 12.31 |
| ATOM | 2949 | N    | LEU | B   | 155 | 38.884 | 45.837 | -6.880 | 1.00 | 14.81 |
| ATOM | 2950 | CA   | LEU | B   | 155 | 38.377 | 46.794 | -5.908 | 1.00 | 14.24 |
| ATOM | 2951 | CB   | LEU | B   | 155 | 36.856 | 46.699 | -5.789 | 1.00 | 12.61 |
| ATOM | 2952 | CG   | LEU | B   | 155 | 36.196 | 47.636 | -4.775 | 1.00 | 11.77 |
| ATOM | 2953 | CD1  | LEU | B   | 155 | 36.154 | 49.071 | -5.302 | 1.00 | 11.09 |
| ATOM | 2954 | CD2  | LEU | B   | 155 | 34.808 | 47.145 | -4.401 | 1.00 | 11.76 |
| ATOM | 2955 | C    | LEU | B   | 155 | 39.041 | 46.564 | -4.548 | 1.00 | 14.26 |
| ATOM | 2956 | O    | LEU | B   | 155 | 39.190 | 45.419 | -4.101 | 1.00 | 10.85 |
| ATOM | 2957 | N    | LEU | B   | 156 | 39.438 | 47.670 | -3.915 | 1.00 | 15.80 |
| ATOM | 2958 | CA   | LEU | B   | 156 | 40.138 | 47.663 | -2.629 | 1.00 | 18.23 |
| ATOM | 2959 | CB   | LEU | B   | 156 | 41.414 | 48.506 | -2.701 | 1.00 | 17.38 |
| ATOM | 2960 | CG   | LEU | B   | 156 | 42.311 | 48.370 | -3.926 | 1.00 | 17.09 |
| ATOM | 2961 | CD1  | LEU | B   | 156 | 42.840 | 49.740 | -4.332 | 1.00 | 16.63 |
| ATOM | 2962 | CD2  | LEU | B   | 156 | 43.448 | 47.393 | -3.654 | 1.00 | 17.25 |
| ATOM | 2963 | C    | LEU | B   | 156 | 39.261 | 48.172 | -1.482 | 1.00 | 20.43 |
| ATOM | 2964 | O    | LEU | B   | 156 | 39.554 | 47.921 | -0.304 | 1.00 | 21.20 |
| ATOM | 2965 | N    | GLY | B   | 157 | 38.198 | 48.893 | -1.826 | 1.00 | 20.49 |
| ATOM | 2966 | CA   | GLY | B   | 157 | 37.266 | 49.365 | -0.830 | 1.00 | 24.58 |
| ATOM | 2967 | C    | GLY | B   | 157 | 36.560 | 50.620 | -1.251 | 1.00 | 28.95 |
| ATOM | 2968 | O    | GLY | B   | 157 | 37.093 | 51.391 | -2.042 | 1.00 | 29.72 |
| ATOM | 2969 | N    | LYS | B   | 158 | 35.353 | 50.808 | -0.723 | 1.00 | 34.92 |
| ATOM | 2970 | CA   | LYS | B   | 158 | 34.592 | 52.039 | -0.929 | 1.00 | 40.31 |
| ATOM | 2971 | CB   | LYS | B   | 158 | 33.322 | 51.795 | -1.769 | 1.00 | 39.42 |
| ATOM | 2972 | CG   | LYS | B   | 158 | 32.725 | 50.392 | -1.706 | 1.00 | 40.69 |
| ATOM | 2973 | CD   | LYS | B   | 158 | 31.565 | 50.256 | -2.706 | 1.00 | 42.09 |
| ATOM | 2974 | CE   | LYS | B   | 158 | 30.898 | 48.879 | -2.649 | 1.00 | 41.38 |
| ATOM | 2975 | NZ   | LYS | B   | 158 | 29.410 | 48.973 | -2.590 | 1.00 | 39.96 |
| ATOM | 2976 | C    | LYS | B   | 158 | 34.254 | 52.772 | 0.383  | 1.00 | 44.49 |
| ATOM | 2977 | O    | LYS | B   | 158 | 34.478 | 52.258 | 1.490  | 1.00 | 45.65 |
| ATOM | 2978 | N    | GLY | B   | 159 | 33.746 | 53.993 | 0.225  | 1.00 | 47.89 |
| ATOM | 2979 | CA   | GLY | B   | 159 | 33.221 | 54.813 | 1.307  | 1.00 | 49.52 |
| ATOM | 2980 | C    | GLY | B   | 159 | 32.291 | 55.862 | 0.710  | 1.00 | 51.26 |
| ATOM | 2981 | O    | GLY | B   | 159 | 32.573 | 56.400 | -0.372 | 1.00 | 53.43 |
| ATOM | 2982 | N    | THR | B   | 160 | 31.193 | 56.145 | 1.416  | 1.00 | 50.37 |
| ATOM | 2983 | CA   | THR | B   | 160 | 30.089 | 57.021 | 0.961  | 1.00 | 49.09 |
| ATOM | 2984 | CB   | THR | B   | 160 | 29.831 | 58.176 | 1.987  | 1.00 | 49.54 |
| ATOM | 2985 | OG1  | THR | B   | 160 | 30.600 | 57.960 | 3.181  | 1.00 | 49.35 |
| ATOM | 2986 | CG2  | THR | B   | 160 | 28.381 | 58.146 | 2.489  | 1.00 | 48.18 |
| ATOM | 2987 | C    | THR | B   | 160 | 30.108 | 57.566 | -0.491 | 1.00 | 47.74 |
| ATOM | 2988 | O    | THR | B   | 160 | 29.157 | 57.354 | -1.244 | 1.00 | 46.68 |
| ATOM | 2989 | N    | PHE | B   | 161 | 31.181 | 58.256 | -0.874 | 1.00 | 47.18 |
| ATOM | 2990 | CA   | PHE | B   | 161 | 31.228 | 58.982 | -2.147 | 1.00 | 47.38 |
| ATOM | 2991 | CB   | PHE | B   | 161 | 32.199 | 60.165 | -2.050 | 1.00 | 50.56 |
| ATOM | 2992 | CG   | PHE | B   | 161 | 31.926 | 61.076 | -0.881 | 1.00 | 53.82 |
| ATOM | 2993 | CD1  | PHE | B   | 161 | 32.666 | 60.957 | 0.300  | 1.00 | 55.99 |

FIGURE 3 (Cont.)

| | A | B | C | D | E | F | G | H | I | J |
|---|---|---|---|---|---|---|---|---|---|---|
| ATOM | 2994 | CE1 | PHE | B | 161 | 32.418 | 61.794 | 1.395 | 1.00 | 56.48 |
| ATOM | 2995 | CZ | PHE | B | 161 | 31.414 | 62.757 | 1.310 | 1.00 | 56.78 |
| ATOM | 2996 | CE2 | PHE | B | 161 | 30.663 | 62.881 | 0.131 | 1.00 | 55.40 |
| ATOM | 2997 | CD2 | PHE | B | 161 | 30.923 | 62.042 | -0.953 | 1.00 | 54.09 |
| ATOM | 2998 | C | PHE | B | 161 | 31.555 | 58.123 | -3.367 | 1.00 | 44.90 |
| ATOM | 2999 | O | PHE | B | 161 | 30.964 | 58.309 | -4.436 | 1.00 | 42.47 |
| ATOM | 3000 | N | GLY | B | 162 | 32.498 | 57.195 | -3.204 | 1.00 | 43.68 |
| ATOM | 3001 | CA | GLY | B | 162 | 32.929 | 56.332 | -4.295 | 1.00 | 40.50 |
| ATOM | 3002 | C | GLY | B | 162 | 33.958 | 55.267 | -3.933 | 1.00 | 37.19 |
| ATOM | 3003 | O | GLY | B | 162 | 34.288 | 55.058 | -2.756 | 1.00 | 38.92 |
| ATOM | 3004 | N | LYS | B | 163 | 34.485 | 54.614 | -4.966 | 1.00 | 30.26 |
| ATOM | 3005 | CA | LYS | B | 163 | 35.339 | 53.436 | -4.811 | 1.00 | 24.46 |
| ATOM | 3006 | CB | LYS | B | 163 | 35.023 | 52.437 | -5.931 | 1.00 | 25.68 |
| ATOM | 3007 | CG | LYS | B | 163 | 33.544 | 52.038 | -6.035 | 1.00 | 26.84 |
| ATOM | 3008 | CD | LYS | B | 163 | 32.951 | 52.293 | -7.428 | 1.00 | 25.06 |
| ATOM | 3009 | CE | LYS | B | 163 | 31.425 | 52.207 | -7.399 | 1.00 | 23.84 |
| ATOM | 3010 | NZ | LYS | B | 163 | 30.861 | 51.757 | -8.698 | 1.00 | 22.80 |
| ATOM | 3011 | C | LYS | B | 163 | 36.844 | 53.752 | -4.786 | 1.00 | 19.56 |
| ATOM | 3012 | O | LYS | B | 163 | 37.265 | 54.860 | -5.119 | 1.00 | 16.54 |
| ATOM | 3013 | N | VAL | B | 164 | 37.648 | 52.776 | -4.370 | 1.00 | 15.92 |
| ATOM | 3014 | CA | VAL | B | 164 | 39.100 | 52.863 | -4.506 | 1.00 | 15.88 |
| ATOM | 3015 | CB | VAL | B | 164 | 39.838 | 53.061 | -3.150 | 1.00 | 19.18 |
| ATOM | 3016 | CG1 | VAL | B | 164 | 41.352 | 53.009 | -3.331 | 1.00 | 19.31 |
| ATOM | 3017 | CG2 | VAL | B | 164 | 39.460 | 54.385 | -2.512 | 1.00 | 21.61 |
| ATOM | 3018 | C | VAL | B | 164 | 39.580 | 51.598 | -5.196 | 1.00 | 14.60 |
| ATOM | 3019 | O | VAL | B | 164 | 39.533 | 50.511 | -4.621 | 1.00 | 11.90 |
| ATOM | 3020 | N | ILE | B | 165 | 40.037 | 51.763 | -6.437 | 1.00 | 16.31 |
| ATOM | 3021 | CA | ILE | B | 165 | 40.376 | 50.649 | -7.324 | 1.00 | 14.66 |
| ATOM | 3022 | CB | ILE | B | 165 | 39.550 | 50.745 | -8.627 | 1.00 | 12.90 |
| ATOM | 3023 | CG1 | ILE | B | 165 | 38.107 | 50.325 | -8.357 | 1.00 | 12.23 |
| ATOM | 3024 | CD1 | ILE | B | 165 | 37.081 | 51.296 | -8.886 | 1.00 | 11.23 |
| ATOM | 3025 | CG2 | ILE | B | 165 | 40.161 | 49.897 | -9.746 | 1.00 | 11.95 |
| ATOM | 3026 | C | ILE | B | 165 | 41.868 | 50.588 | -7.640 | 1.00 | 15.08 |
| ATOM | 3027 | O | ILE | B | 165 | 42.523 | 51.627 | -7.837 | 1.00 | 12.74 |
| ATOM | 3028 | N | LEU | B | 166 | 42.387 | 49.358 | -7.676 | 1.00 | 14.35 |
| ATOM | 3029 | CA | LEU | B | 166 | 43.763 | 49.103 | -8.079 | 1.00 | 13.67 |
| ATOM | 3030 | CB | LEU | B | 166 | 44.236 | 47.727 | -7.608 | 1.00 | 12.75 |
| ATOM | 3031 | CG | LEU | B | 166 | 45.637 | 47.253 | -8.014 | 1.00 | 11.73 |
| ATOM | 3032 | CD1 | LEU | B | 166 | 46.682 | 48.340 | -7.858 | 1.00 | 10.66 |
| ATOM | 3033 | CD2 | LEU | B | 166 | 46.023 | 46.052 | -7.182 | 1.00 | 12.31 |
| ATOM | 3034 | C | LEU | B | 166 | 43.846 | 49.197 | -9.586 | 1.00 | 13.54 |
| ATOM | 3035 | O | LEU | B | 166 | 43.140 | 48.483 | -10.305 | 1.00 | 12.39 |
| ATOM | 3036 | N | VAL | B | 167 | 44.710 | 50.096 | -10.044 | 1.00 | 13.67 |
| ATOM | 3037 | CA | VAL | B | 167 | 44.867 | 50.381 | -11.464 | 1.00 | 14.12 |
| ATOM | 3038 | CB | VAL | B | 167 | 44.504 | 51.858 | -11.806 | 1.00 | 15.23 |
| ATOM | 3039 | CG1 | VAL | B | 167 | 43.017 | 52.096 | -11.623 | 1.00 | 16.85 |
| ATOM | 3040 | CG2 | VAL | B | 167 | 45.304 | 52.850 | -10.965 | 1.00 | 14.24 |
| ATOM | 3041 | C | VAL | B | 167 | 46.275 | 50.051 | -11.949 | 1.00 | 13.34 |
| ATOM | 3042 | O | VAL | B | 167 | 47.185 | 49.820 | -11.155 | 1.00 | 13.13 |
| ATOM | 3043 | N | LYS | B | 168 | 46.444 | 50.015 | -13.260 | 1.00 | 12.42 |
| ATOM | 3044 | CA | LYS | B | 168 | 47.757 | 49.823 | -13.833 | 1.00 | 14.47 |
| ATOM | 3045 | CB | LYS | B | 168 | 47.987 | 48.347 | -14.181 | 1.00 | 14.07 |

FIGURE 3 (Cont.)

| | A | B | C | D | E | F | G | H | I | J |
|---|---|---|---|---|---|---|---|---|---|---|
| ATOM | 3046 | CG | LYS | B | 168 | 49.353 | 48.034 | -14.789 | 1.00 | 13.75 |
| ATOM | 3047 | CD | LYS | B | 168 | 49.213 | 47.397 | -16.173 | 1.00 | 13.02 |
| ATOM | 3048 | CE | LYS | B | 168 | 50.510 | 46.765 | -16.644 | 1.00 | 12.06 |
| ATOM | 3049 | NZ | LYS | B | 168 | 50.951 | 45.675 | -15.728 | 1.00 | 11.53 |
| ATOM | 3050 | C | LYS | B | 168 | 47.871 | 50.714 | -15.058 | 1.00 | 17.72 |
| ATOM | 3051 | O | LYS | B | 168 | 47.286 | 50.424 | -16.108 | 1.00 | 20.51 |
| ATOM | 3052 | N | GLU | B | 169 | 48.600 | 51.817 | -14.911 | 1.00 | 18.76 |
| ATOM | 3053 | CA | GLU | B | 169 | 48.909 | 52.694 | -16.037 | 1.00 | 18.96 |
| ATOM | 3054 | CB | GLU | B | 169 | 49.931 | 53.757 | -15.609 | 1.00 | 19.22 |
| ATOM | 3055 | CG | GLU | B | 169 | 49.482 | 55.199 | -15.808 | 1.00 | 19.70 |
| ATOM | 3056 | CD | GLU | B | 169 | 50.398 | 55.991 | -16.729 | 1.00 | 19.27 |
| ATOM | 3057 | OE1 | GLU | B | 169 | 51.433 | 56.495 | -16.242 | 1.00 | 20.27 |
| ATOM | 3058 | OE2 | GLU | B | 169 | 50.079 | 56.118 | -17.933 | 1.00 | 16.81 |
| ATOM | 3059 | C | GLU | B | 169 | 49.451 | 51.851 | -17.202 | 1.00 | 18.66 |
| ATOM | 3060 | O | GLU | B | 169 | 50.395 | 51.078 | -17.027 | 1.00 | 20.15 |
| ATOM | 3061 | N | LYS | B | 170 | 48.833 | 51.966 | -18.376 | 1.00 | 17.08 |
| ATOM | 3062 | CA | LYS | B | 170 | 49.329 | 51.257 | -19.556 | 1.00 | 13.85 |
| ATOM | 3063 | CB | LYS | B | 170 | 48.256 | 51.153 | -20.642 | 1.00 | 10.29 |
| ATOM | 3064 | CG | LYS | B | 170 | 47.578 | 49.788 | -20.689 | 1.00 | 7.02 |
| ATOM | 3065 | CD | LYS | B | 170 | 46.286 | 49.817 | -21.489 | 1.00 | 4.66 |
| ATOM | 3066 | CE | LYS | B | 170 | 45.100 | 50.230 | -20.636 | 1.00 | 2.49 |
| ATOM | 3067 | NZ | LYS | B | 170 | 44.443 | 51.441 | -21.193 | 1.00 | 2.00 |
| ATOM | 3068 | C | LYS | B | 170 | 50.599 | 51.915 | -20.088 | 1.00 | 14.36 |
| ATOM | 3069 | O | LYS | B | 170 | 51.599 | 51.236 | -20.302 | 1.00 | 13.75 |
| ATOM | 3070 | N | ALA | B | 171 | 50.558 | 53.239 | -20.255 | 1.00 | 16.89 |
| ATOM | 3071 | CA | ALA | B | 171 | 51.691 | 54.032 | -20.757 | 1.00 | 19.89 |
| ATOM | 3072 | CB | ALA | B | 171 | 51.303 | 55.515 | -20.861 | 1.00 | 19.72 |
| ATOM | 3073 | C | ALA | B | 171 | 53.013 | 53.870 | -19.978 | 1.00 | 21.78 |
| ATOM | 3074 | O | ALA | B | 171 | 54.096 | 54.010 | -20.558 | 1.00 | 20.72 |
| ATOM | 3075 | N | THR | B | 172 | 52.926 | 53.591 | -18.676 | 1.00 | 24.55 |
| ATOM | 3076 | CA | THR | B | 172 | 54.122 | 53.310 | -17.868 | 1.00 | 26.35 |
| ATOM | 3077 | CB | THR | B | 172 | 54.290 | 54.312 | -16.669 | 1.00 | 26.26 |
| ATOM | 3078 | OG1 | THR | B | 172 | 53.073 | 54.406 | -15.920 | 1.00 | 26.87 |
| ATOM | 3079 | CG2 | THR | B | 172 | 54.537 | 55.747 | -17.156 | 1.00 | 25.39 |
| ATOM | 3080 | C | THR | B | 172 | 54.205 | 51.851 | -17.383 | 1.00 | 27.04 |
| ATOM | 3081 | O | THR | B | 172 | 55.265 | 51.403 | -16.944 | 1.00 | 27.20 |
| ATOM | 3082 | N | GLY | B | 173 | 53.096 | 51.116 | -17.469 | 1.00 | 27.89 |
| ATOM | 3083 | CA | GLY | B | 173 | 53.049 | 49.732 | -17.017 | 1.00 | 29.84 |
| ATOM | 3084 | C | GLY | B | 173 | 53.130 | 49.562 | -15.504 | 1.00 | 32.31 |
| ATOM | 3085 | O | GLY | B | 173 | 53.339 | 48.447 | -15.015 | 1.00 | 33.58 |
| ATOM | 3086 | N | ARG | B | 174 | 52.965 | 50.662 | -14.765 | 1.00 | 32.20 |
| ATOM | 3087 | CA | ARG | B | 174 | 53.067 | 50.655 | -13.306 | 1.00 | 31.81 |
| ATOM | 3088 | CB | ARG | B | 174 | 53.850 | 51.879 | -12.818 | 1.00 | 32.79 |
| ATOM | 3089 | CG | ARG | B | 174 | 55.361 | 51.729 | -12.926 | 1.00 | 33.41 |
| ATOM | 3090 | CD | ARG | B | 174 | 56.140 | 52.267 | -11.729 | 1.00 | 33.86 |
| ATOM | 3091 | NE | ARG | B | 174 | 57.584 | 52.129 | -11.922 | 1.00 | 33.77 |
| ATOM | 3092 | CZ | ARG | B | 174 | 58.389 | 53.082 | -12.393 | 1.00 | 33.88 |
| ATOM | 3093 | NH1 | ARG | B | 174 | 57.913 | 54.281 | -12.729 | 1.00 | 32.54 |
| ATOM | 3094 | NH2 | ARG | B | 174 | 59.684 | 52.833 | -12.532 | 1.00 | 34.39 |
| ATOM | 3095 | C | ARG | B | 174 | 51.688 | 50.596 | -12.648 | 1.00 | 31.62 |
| ATOM | 3096 | O | ARG | B | 174 | 50.675 | 50.833 | -13.309 | 1.00 | 31.31 |
| ATOM | 3097 | N | TYR | B | 175 | 51.661 | 50.281 | -11.350 | 1.00 | 30.75 |

FIGURE 3 (Cont.)

|  | A | B | C | D | E | F | G | H | I | J |
|---|---|---|---|---|---|---|---|---|---|---|
| ATOM | 3098 | CA | TYR | B | 175 | 50.414 | 50.076 | -10.609 | 1.00 | 28.48 |
| ATOM | 3099 | CB | TYR | B | 175 | 50.467 | 48.755 | -9.834 | 1.00 | 28.93 |
| ATOM | 3100 | CG | TYR | B | 175 | 50.536 | 47.515 | -10.703 | 1.00 | 30.55 |
| ATOM | 3101 | CD1 | TYR | B | 175 | 51.766 | 46.953 | -11.057 | 1.00 | 31.60 |
| ATOM | 3102 | CE1 | TYR | B | 175 | 51.837 | 45.808 | -11.863 | 1.00 | 32.41 |
| ATOM | 3103 | CZ | TYR | B | 175 | 50.666 | 45.215 | -12.318 | 1.00 | 32.43 |
| ATOM | 3104 | OH | TYR | B | 175 | 50.731 | 44.088 | -13.108 | 1.00 | 31.58 |
| ATOM | 3105 | CE2 | TYR | B | 175 | 49.431 | 45.754 | -11.976 | 1.00 | 32.14 |
| ATOM | 3106 | CD2 | TYR | B | 175 | 49.373 | 46.898 | -11.170 | 1.00 | 31.36 |
| ATOM | 3107 | C | TYR | B | 175 | 50.160 | 51.219 | -9.638 | 1.00 | 27.23 |
| ATOM | 3108 | O | TYR | B | 175 | 51.102 | 51.746 | -9.058 | 1.00 | 29.24 |
| ATOM | 3109 | N | TYR | B | 176 | 48.892 | 51.601 | -9.471 | 1.00 | 26.33 |
| ATOM | 3110 | CA | TYR | B | 176 | 48.479 | 52.591 | -8.456 | 1.00 | 24.31 |
| ATOM | 3111 | CB | TYR | B | 176 | 48.531 | 54.021 | -9.008 | 1.00 | 25.59 |
| ATOM | 3112 | CG | TYR | B | 176 | 49.875 | 54.435 | -9.556 | 1.00 | 26.87 |
| ATOM | 3113 | CD1 | TYR | B | 176 | 50.141 | 54.351 | -10.922 | 1.00 | 27.53 |
| ATOM | 3114 | CE1 | TYR | B | 176 | 51.373 | 54.726 | -11.440 | 1.00 | 29.97 |
| ATOM | 3115 | CZ | TYR | B | 176 | 52.364 | 55.192 | -10.586 | 1.00 | 30.78 |
| ATOM | 3116 | OH | TYR | B | 176 | 53.588 | 55.564 | -11.109 | 1.00 | 30.86 |
| ATOM | 3117 | CE2 | TYR | B | 176 | 52.122 | 55.283 | -9.216 | 1.00 | 29.84 |
| ATOM | 3118 | CD2 | TYR | B | 176 | 50.881 | 54.904 | -8.712 | 1.00 | 27.21 |
| ATOM | 3119 | C | TYR | B | 176 | 47.085 | 52.330 | -7.873 | 1.00 | 21.31 |
| ATOM | 3120 | O | TYR | B | 176 | 46.367 | 51.428 | -8.305 | 1.00 | 19.62 |
| ATOM | 3121 | N | ALA | B | 177 | 46.716 | 53.125 | -6.877 | 1.00 | 19.77 |
| ATOM | 3122 | CA | ALA | B | 177 | 45.393 | 53.031 | -6.273 | 1.00 | 18.79 |
| ATOM | 3123 | CB | ALA | B | 177 | 45.492 | 53.020 | -4.750 | 1.00 | 17.23 |
| ATOM | 3124 | C | ALA | B | 177 | 44.578 | 54.216 | -6.745 | 1.00 | 16.22 |
| ATOM | 3125 | O | ALA | B | 177 | 45.040 | 55.356 | -6.657 | 1.00 | 16.95 |
| ATOM | 3126 | N | MET | B | 178 | 43.381 | 53.958 | -7.264 | 1.00 | 11.19 |
| ATOM | 3127 | CA | MET | B | 178 | 42.548 | 55.053 | -7.727 | 1.00 | 8.24 |
| ATOM | 3128 | CB | MET | B | 178 | 42.176 | 54.904 | -9.194 | 1.00 | 10.55 |
| ATOM | 3129 | CG | MET | B | 178 | 41.649 | 56.199 | -9.816 | 1.00 | 9.81 |
| ATOM | 3130 | SD | MET | B | 178 | 41.668 | 56.172 | -11.623 | 1.00 | 10.61 |
| ATOM | 3131 | CE | MET | B | 178 | 40.404 | 54.917 | -11.993 | 1.00 | 8.01 |
| ATOM | 3132 | C | MET | B | 178 | 41.304 | 55.236 | -6.904 | 1.00 | 6.62 |
| ATOM | 3133 | O | MET | B | 178 | 40.388 | 54.420 | -6.948 | 1.00 | 5.81 |
| ATOM | 3134 | N | LYS | B | 179 | 41.290 | 56.325 | -6.149 | 1.00 | 6.16 |
| ATOM | 3135 | CA | LYS | B | 179 | 40.093 | 56.777 | -5.478 | 1.00 | 5.71 |
| ATOM | 3136 | CB | LYS | B | 179 | 40.448 | 57.681 | -4.294 | 1.00 | 8.85 |
| ATOM | 3137 | CG | LYS | B | 179 | 39.254 | 58.071 | -3.420 | 1.00 | 11.61 |
| ATOM | 3138 | CD | LYS | B | 179 | 39.664 | 58.954 | -2.245 | 1.00 | 13.48 |
| ATOM | 3139 | CE | LYS | B | 179 | 38.491 | 59.218 | -1.302 | 1.00 | 13.08 |
| ATOM | 3140 | NZ | LYS | B | 179 | 38.953 | 59.602 | 0.065 | 1.00 | 12.82 |
| ATOM | 3141 | C | LYS | B | 179 | 39.293 | 57.535 | -6.518 | 1.00 | 4.26 |
| ATOM | 3142 | O | LYS | B | 179 | 39.775 | 58.508 | -7.095 | 1.00 | 5.59 |
| ATOM | 3143 | N | ILE | B | 180 | 38.084 | 57.055 | -6.775 | 1.00 | 3.99 |
| ATOM | 3144 | CA | ILE | B | 180 | 37.161 | 57.669 | -7.726 | 1.00 | 3.85 |
| ATOM | 3145 | CB | ILE | B | 180 | 36.579 | 56.590 | -8.694 | 1.00 | 2.03 |
| ATOM | 3146 | CG1 | ILE | B | 180 | 37.665 | 56.013 | -9.598 | 1.00 | 2.00 |
| ATOM | 3147 | CD1 | ILE | B | 180 | 38.046 | 54.594 | -9.232 | 1.00 | 2.00 |
| ATOM | 3148 | CG2 | ILE | B | 180 | 35.413 | 57.119 | -9.517 | 1.00 | 2.00 |
| ATOM | 3149 | C | ILE | B | 180 | 36.043 | 58.293 | -6.909 | 1.00 | 6.25 |

FIGURE 3 (Cont.)

| | A | B | C | D | E | F | G | H | I | J |
|---|---|---|---|---|---|---|---|---|---|---|
| ATOM | 3150 | O | ILE | B | 180 | 35.517 | 57.678 | -5.974 | 1.00 | 5.92 |
| ATOM | 3151 | N | LEU | B | 181 | 35.681 | 59.519 | -7.246 | 1.00 | 8.25 |
| ATOM | 3152 | CA | LEU | B | 181 | 34.531 | 60.137 | -6.614 | 1.00 | 12.38 |
| ATOM | 3153 | CB | LEU | B | 181 | 34.945 | 61.375 | -5.821 | 1.00 | 11.67 |
| ATOM | 3154 | CG | LEU | B | 181 | 36.354 | 61.423 | -5.230 | 1.00 | 12.56 |
| ATOM | 3155 | CD1 | LEU | B | 181 | 36.761 | 62.852 | -4.962 | 1.00 | 13.98 |
| ATOM | 3156 | CD2 | LEU | B | 181 | 36.437 | 60.607 | -3.958 | 1.00 | 14.82 |
| ATOM | 3157 | C | LEU | B | 181 | 33.543 | 60.506 | -7.700 | 1.00 | 15.82 |
| ATOM | 3158 | O | LEU | B | 181 | 33.953 | 60.842 | -8.811 | 1.00 | 16.82 |
| ATOM | 3159 | N | LYS | B | 182 | 32.250 | 60.413 | -7.390 | 1.00 | 17.80 |
| ATOM | 3160 | CA | LYS | B | 182 | 31.205 | 60.888 | -8.294 | 1.00 | 18.83 |
| ATOM | 3161 | CB | LYS | B | 182 | 29.913 | 60.081 | -8.123 | 1.00 | 20.70 |
| ATOM | 3162 | CG | LYS | B | 182 | 29.485 | 59.293 | -9.361 | 1.00 | 22.58 |
| ATOM | 3163 | CD | LYS | B | 182 | 28.383 | 58.287 | -9.032 | 1.00 | 24.37 |
| ATOM | 3164 | CE | LYS | B | 182 | 28.941 | 57.022 | -8.378 | 1.00 | 24.69 |
| ATOM | 3165 | NZ | LYS | B | 182 | 29.450 | 56.050 | -9.388 | 1.00 | 26.49 |
| ATOM | 3166 | C | LYS | B | 182 | 30.959 | 62.368 | -8.016 | 1.00 | 18.52 |
| ATOM | 3167 | O | LYS | B | 182 | 30.591 | 62.751 | -6.901 | 1.00 | 18.92 |
| ATOM | 3168 | N | LYS | B | 183 | 31.176 | 63.198 | -9.032 | 1.00 | 17.38 |
| ATOM | 3169 | CA | LYS | B | 183 | 31.010 | 64.640 | -8.894 | 1.00 | 16.72 |
| ATOM | 3170 | CB | LYS | B | 183 | 31.362 | 65.342 | -10.208 | 1.00 | 16.79 |
| ATOM | 3171 | CG | LYS | B | 183 | 32.870 | 65.489 | -10.445 | 1.00 | 16.98 |
| ATOM | 3172 | CD | LYS | B | 183 | 33.218 | 65.631 | -11.923 | 1.00 | 16.75 |
| ATOM | 3173 | CE | LYS | B | 183 | 33.622 | 67.058 | -12.288 | 1.00 | 16.29 |
| ATOM | 3174 | NZ | LYS | B | 183 | 33.600 | 67.290 | -13.766 | 1.00 | 15.14 |
| ATOM | 3175 | C | LYS | B | 183 | 29.596 | 64.991 | -8.429 | 1.00 | 16.79 |
| ATOM | 3176 | O | LYS | B | 183 | 29.403 | 65.932 | -7.658 | 1.00 | 16.80 |
| ATOM | 3177 | N | GLU | B | 184 | 28.624 | 64.205 | -8.890 | 1.00 | 18.36 |
| ATOM | 3178 | CA | GLU | B | 184 | 27.229 | 64.303 | -8.467 | 1.00 | 20.14 |
| ATOM | 3179 | CB | GLU | B | 184 | 26.403 | 63.186 | -9.124 | 1.00 | 21.73 |
| ATOM | 3180 | CG | GLU | B | 184 | 24.893 | 63.312 | -8.959 | 1.00 | 23.96 |
| ATOM | 3181 | CD | GLU | B | 184 | 24.176 | 63.631 | -10.265 | 1.00 | 26.46 |
| ATOM | 3182 | OE1 | GLU | B | 184 | 22.961 | 63.935 | -10.221 | 1.00 | 27.52 |
| ATOM | 3183 | OE2 | GLU | B | 184 | 24.816 | 63.582 | -11.339 | 1.00 | 26.92 |
| ATOM | 3184 | C | GLU | B | 184 | 27.099 | 64.224 | -6.945 | 1.00 | 20.17 |
| ATOM | 3185 | O | GLU | B | 184 | 26.534 | 65.124 | -6.316 | 1.00 | 21.28 |
| ATOM | 3186 | N | VAL | B | 185 | 27.638 | 63.152 | -6.367 | 1.00 | 18.26 |
| ATOM | 3187 | CA | VAL | B | 185 | 27.503 | 62.880 | -4.938 | 1.00 | 17.96 |
| ATOM | 3188 | CB | VAL | B | 185 | 28.036 | 61.455 | -4.556 | 1.00 | 20.09 |
| ATOM | 3189 | CG1 | VAL | B | 185 | 27.886 | 61.172 | -3.051 | 1.00 | 19.56 |
| ATOM | 3190 | CG2 | VAL | B | 185 | 27.334 | 60.367 | -5.373 | 1.00 | 19.88 |
| ATOM | 3191 | C | VAL | B | 185 | 28.173 | 63.970 | -4.097 | 1.00 | 15.76 |
| ATOM | 3192 | O | VAL | B | 185 | 27.611 | 64.411 | -3.089 | 1.00 | 16.87 |
| ATOM | 3193 | N | ILE | B | 186 | 29.354 | 64.417 | -4.520 | 1.00 | 11.10 |
| ATOM | 3194 | CA | ILE | B | 186 | 30.087 | 65.428 | -3.770 | 1.00 | 7.49 |
| ATOM | 3195 | CB | ILE | B | 186 | 31.469 | 65.690 | -4.396 | 1.00 | 6.65 |
| ATOM | 3196 | CG1 | ILE | B | 186 | 32.498 | 64.768 | -3.763 | 1.00 | 6.43 |
| ATOM | 3197 | CD1 | ILE | B | 186 | 33.450 | 64.209 | -4.755 | 1.00 | 8.66 |
| ATOM | 3198 | CG2 | ILE | B | 186 | 31.930 | 67.127 | -4.195 | 1.00 | 6.46 |
| ATOM | 3199 | C | ILE | B | 186 | 29.249 | 66.685 | -3.669 | 1.00 | 6.95 |
| ATOM | 3200 | O | ILE | B | 186 | 29.222 | 67.338 | -2.630 | 1.00 | 6.39 |
| ATOM | 3201 | N | VAL | B | 187 | 28.538 | 66.997 | -4.744 | 1.00 | 7.91 |

FIGURE 3 (Cont.)

| | A | B | C | D | E | F | G | H | I | J |
|---|---|---|---|---|---|---|---|---|---|---|
| ATOM | 3202 | CA | VAL | B | 187 | 27.676 | 68.166 | -4.767 | 1.00 | 11.34 |
| ATOM | 3203 | CB | VAL | B | 187 | 27.341 | 68.583 | -6.221 | 1.00 | 11.96 |
| ATOM | 3204 | CG1 | VAL | B | 187 | 26.043 | 69.397 | -6.295 | 1.00 | 12.18 |
| ATOM | 3205 | CG2 | VAL | B | 187 | 28.505 | 69.365 | -6.820 | 1.00 | 11.81 |
| ATOM | 3206 | C | VAL | B | 187 | 26.420 | 67.910 | -3.936 | 1.00 | 12.90 |
| ATOM | 3207 | O | VAL | B | 187 | 26.027 | 68.753 | -3.123 | 1.00 | 12.41 |
| ATOM | 3208 | N | ALA | B | 188 | 25.820 | 66.736 | -4.131 | 1.00 | 15.25 |
| ATOM | 3209 | CA | ALA | B | 188 | 24.571 | 66.366 | -3.465 | 1.00 | 17.66 |
| ATOM | 3210 | CB | ALA | B | 188 | 24.034 | 65.041 | -4.010 | 1.00 | 17.54 |
| ATOM | 3211 | C | ALA | B | 188 | 24.713 | 66.313 | -1.947 | 1.00 | 19.31 |
| ATOM | 3212 | O | ALA | B | 188 | 23.905 | 66.903 | -1.238 | 1.00 | 20.34 |
| ATOM | 3213 | N | LYS | B | 189 | 25.738 | 65.616 | -1.456 | 1.00 | 21.45 |
| ATOM | 3214 | CA | LYS | B | 189 | 26.007 | 65.556 | -0.018 | 1.00 | 24.50 |
| ATOM | 3215 | CB | LYS | B | 189 | 26.655 | 64.216 | 0.380 | 1.00 | 26.28 |
| ATOM | 3216 | CG | LYS | B | 189 | 26.008 | 63.531 | 1.607 | 1.00 | 28.54 |
| ATOM | 3217 | CD | LYS | B | 189 | 26.634 | 63.998 | 2.932 | 1.00 | 30.44 |
| ATOM | 3218 | CE | LYS | B | 189 | 25.610 | 64.074 | 4.068 | 1.00 | 31.09 |
| ATOM | 3219 | NZ | LYS | B | 189 | 26.298 | 64.060 | 5.396 | 1.00 | 32.57 |
| ATOM | 3220 | C | LYS | B | 189 | 26.841 | 66.754 | 0.466 | 1.00 | 25.18 |
| ATOM | 3221 | O | LYS | B | 189 | 27.235 | 66.821 | 1.640 | 1.00 | 27.28 |
| ATOM | 3222 | N | ASP | B | 190 | 27.104 | 67.692 | -0.448 | 1.00 | 23.16 |
| ATOM | 3223 | CA | ASP | B | 190 | 27.708 | 68.991 | -0.127 | 1.00 | 21.54 |
| ATOM | 3224 | CB | ASP | B | 190 | 26.884 | 69.711 | 0.950 | 1.00 | 21.28 |
| ATOM | 3225 | CG | ASP | B | 190 | 27.256 | 71.172 | 1.094 | 1.00 | 22.63 |
| ATOM | 3226 | OD1 | ASP | B | 190 | 27.936 | 71.512 | 2.083 | 1.00 | 23.67 |
| ATOM | 3227 | OD2 | ASP | B | 190 | 26.919 | 72.054 | 0.274 | 1.00 | 23.72 |
| ATOM | 3228 | C | ASP | B | 190 | 29.203 | 68.981 | 0.245 | 1.00 | 21.17 |
| ATOM | 3229 | O | ASP | B | 190 | 29.801 | 70.043 | 0.430 | 1.00 | 20.90 |
| ATOM | 3230 | N | GLU | B | 191 | 29.812 | 67.800 | 0.329 | 1.00 | 22.04 |
| ATOM | 3231 | CA | GLU | B | 191 | 31.225 | 67.698 | 0.720 | 1.00 | 23.15 |
| ATOM | 3232 | CB | GLU | B | 191 | 31.563 | 66.296 | 1.262 | 1.00 | 26.18 |
| ATOM | 3233 | CG | GLU | B | 191 | 31.707 | 66.218 | 2.784 | 1.00 | 29.43 |
| ATOM | 3234 | CD | GLU | B | 191 | 30.753 | 67.155 | 3.523 | 1.00 | 32.38 |
| ATOM | 3235 | OE1 | GLU | B | 191 | 31.238 | 68.167 | 4.088 | 1.00 | 32.81 |
| ATOM | 3236 | OE2 | GLU | B | 191 | 29.519 | 66.889 | 3.530 | 1.00 | 32.22 |
| ATOM | 3237 | C | GLU | B | 191 | 32.168 | 68.112 | -0.405 | 1.00 | 20.16 |
| ATOM | 3238 | O | GLU | B | 191 | 32.860 | 67.284 | -0.998 | 1.00 | 20.39 |
| ATOM | 3239 | N | VAL | B | 192 | 32.200 | 69.413 | -0.667 | 1.00 | 17.94 |
| ATOM | 3240 | CA | VAL | B | 192 | 32.862 | 69.946 | -1.846 | 1.00 | 17.27 |
| ATOM | 3241 | CB | VAL | B | 192 | 31.997 | 71.017 | -2.545 | 1.00 | 17.63 |
| ATOM | 3242 | CG1 | VAL | B | 192 | 32.745 | 71.618 | -3.720 | 1.00 | 17.42 |
| ATOM | 3243 | CG2 | VAL | B | 192 | 30.661 | 70.434 | -2.994 | 1.00 | 16.82 |
| ATOM | 3244 | C | VAL | B | 192 | 34.209 | 70.546 | -1.497 | 1.00 | 16.16 |
| ATOM | 3245 | O | VAL | B | 192 | 35.208 | 70.240 | -2.150 | 1.00 | 16.58 |
| ATOM | 3246 | N | ALA | B | 193 | 34.225 | 71.407 | -0.481 | 1.00 | 14.30 |
| ATOM | 3247 | CA | ALA | B | 193 | 35.441 | 72.107 | -0.073 | 1.00 | 13.95 |
| ATOM | 3248 | CB | ALA | B | 193 | 35.112 | 73.211 | 0.922 | 1.00 | 12.65 |
| ATOM | 3249 | C | ALA | B | 193 | 36.506 | 71.156 | 0.490 | 1.00 | 14.42 |
| ATOM | 3250 | O | ALA | B | 193 | 37.708 | 71.389 | 0.321 | 1.00 | 13.33 |
| ATOM | 3251 | N | HIS | B | 194 | 36.050 | 70.087 | 1.147 | 1.00 | 16.49 |
| ATOM | 3252 | CA | HIS | B | 194 | 36.920 | 69.046 | 1.710 | 1.00 | 16.55 |
| ATOM | 3253 | CB | HIS | B | 194 | 36.127 | 68.098 | 2.625 | 1.00 | 16.77 |

FIGURE 3 (Cont.)

|      | A    | B   | C   | D | E   | F      | G      | H      | I    | J     |
|------|------|-----|-----|---|-----|--------|--------|--------|------|-------|
| ATOM | 3254 | CG  | HIS | B | 194 | 35.531 | 68.758 | 3.826  | 1.00 | 15.93 |
| ATOM | 3255 | ND1 | HIS | B | 194 | 34.179 | 68.728 | 4.091  | 1.00 | 15.23 |
| ATOM | 3256 | CE1 | HIS | B | 194 | 33.941 | 69.395 | 5.206  | 1.00 | 18.34 |
| ATOM | 3257 | NE2 | HIS | B | 194 | 35.090 | 69.844 | 5.681  | 1.00 | 18.34 |
| ATOM | 3258 | CD2 | HIS | B | 194 | 36.101 | 69.457 | 4.836  | 1.00 | 17.07 |
| ATOM | 3259 | C   | HIS | B | 194 | 37.556 | 68.221 | 0.599  | 1.00 | 15.40 |
| ATOM | 3260 | O   | HIS | B | 194 | 38.731 | 67.853 | 0.674  | 1.00 | 15.53 |
| ATOM | 3261 | N   | THR | B | 195 | 36.751 | 67.918 | -0.416 | 1.00 | 13.68 |
| ATOM | 3262 | CA  | THR | B | 195 | 37.193 | 67.183 | -1.591 | 1.00 | 12.68 |
| ATOM | 3263 | CB  | THR | B | 195 | 35.980 | 66.953 | -2.538 | 1.00 | 9.64  |
| ATOM | 3264 | OG1 | THR | B | 195 | 35.635 | 65.563 | -2.545 | 1.00 | 4.08  |
| ATOM | 3265 | CG2 | THR | B | 195 | 36.321 | 67.239 | -3.986 | 1.00 | 10.67 |
| ATOM | 3266 | C   | THR | B | 195 | 38.369 | 67.914 | -2.267 | 1.00 | 14.58 |
| ATOM | 3267 | O   | THR | B | 195 | 39.315 | 67.278 | -2.755 | 1.00 | 16.73 |
| ATOM | 3268 | N   | LEU | B | 196 | 38.318 | 69.246 | -2.258 | 1.00 | 13.55 |
| ATOM | 3269 | CA  | LEU | B | 196 | 39.424 | 70.067 | -2.741 | 1.00 | 12.15 |
| ATOM | 3270 | CB  | LEU | B | 196 | 38.976 | 71.504 | -3.002 | 1.00 | 12.80 |
| ATOM | 3271 | CG  | LEU | B | 196 | 38.218 | 71.782 | -4.293 | 1.00 | 11.62 |
| ATOM | 3272 | CD1 | LEU | B | 196 | 37.301 | 72.963 | -4.054 | 1.00 | 11.32 |
| ATOM | 3273 | CD2 | LEU | B | 196 | 39.178 | 72.046 | -5.453 | 1.00 | 12.64 |
| ATOM | 3274 | C   | LEU | B | 196 | 40.556 | 70.064 | -1.731 | 1.00 | 10.37 |
| ATOM | 3275 | O   | LEU | B | 196 | 41.690 | 69.735 | -2.080 | 1.00 | 11.36 |
| ATOM | 3276 | N   | THR | B | 197 | 40.242 | 70.434 | -0.488 | 1.00 | 8.25  |
| ATOM | 3277 | CA  | THR | B | 197 | 41.204 | 70.393 | 0.612  | 1.00 | 6.50  |
| ATOM | 3278 | CB  | THR | B | 197 | 40.490 | 70.438 | 1.983  | 1.00 | 7.68  |
| ATOM | 3279 | OG1 | THR | B | 197 | 39.753 | 71.659 | 2.114  | 1.00 | 10.07 |
| ATOM | 3280 | CG2 | THR | B | 197 | 41.496 | 70.549 | 3.093  | 1.00 | 8.76  |
| ATOM | 3281 | C   | THR | B | 197 | 42.036 | 69.130 | 0.502  | 1.00 | 4.18  |
| ATOM | 3282 | O   | THR | B | 197 | 43.247 | 69.180 | 0.646  | 1.00 | 2.00  |
| ATOM | 3283 | N   | GLU | B | 198 | 41.372 | 68.009 | 0.224  | 1.00 | 7.75  |
| ATOM | 3284 | CA  | GLU | B | 198 | 42.038 | 66.727 | 0.007  | 1.00 | 13.36 |
| ATOM | 3285 | CB  | GLU | B | 198 | 41.025 | 65.618 | -0.297 | 1.00 | 17.07 |
| ATOM | 3286 | CG  | GLU | B | 198 | 41.572 | 64.208 | -0.078 | 1.00 | 22.09 |
| ATOM | 3287 | CD  | GLU | B | 198 | 40.549 | 63.102 | -0.327 | 1.00 | 25.19 |
| ATOM | 3288 | OE1 | GLU | B | 198 | 39.496 | 63.362 | -0.966 | 1.00 | 26.00 |
| ATOM | 3289 | OE2 | GLU | B | 198 | 40.807 | 61.956 | 0.118  | 1.00 | 26.31 |
| ATOM | 3290 | C   | GLU | B | 198 | 43.080 | 66.822 | -1.102 | 1.00 | 15.54 |
| ATOM | 3291 | O   | GLU | B | 198 | 44.284 | 66.737 | -0.834 | 1.00 | 16.05 |
| ATOM | 3292 | N   | ASN | B | 199 | 42.617 | 67.011 | -2.339 | 1.00 | 17.68 |
| ATOM | 3293 | CA  | ASN | B | 199 | 43.513 | 67.213 | -3.475 | 1.00 | 17.06 |
| ATOM | 3294 | CB  | ASN | B | 199 | 42.756 | 67.766 | -4.677 | 1.00 | 19.03 |
| ATOM | 3295 | CG  | ASN | B | 199 | 43.647 | 67.937 | -5.894 | 1.00 | 21.41 |
| ATOM | 3296 | OD1 | ASN | B | 199 | 43.935 | 69.056 | -6.315 | 1.00 | 23.88 |
| ATOM | 3297 | ND2 | ASN | B | 199 | 44.098 | 66.825 | -6.459 | 1.00 | 21.67 |
| ATOM | 3298 | C   | ASN | B | 199 | 44.697 | 68.120 | -3.142 | 1.00 | 15.66 |
| ATOM | 3299 | O   | ASN | B | 199 | 45.836 | 67.751 | -3.384 | 1.00 | 16.09 |
| ATOM | 3300 | N   | ARG | B | 200 | 44.416 | 69.290 | -2.573 | 1.00 | 13.84 |
| ATOM | 3301 | CA  | ARG | B | 200 | 45.449 | 70.221 | -2.128 | 1.00 | 13.10 |
| ATOM | 3302 | CB  | ARG | B | 200 | 44.806 | 71.410 | -1.417 | 1.00 | 13.13 |
| ATOM | 3303 | CG  | ARG | B | 200 | 45.640 | 72.669 | -1.415 | 1.00 | 14.66 |
| ATOM | 3304 | CD  | ARG | B | 200 | 44.979 | 73.840 | -2.118 | 1.00 | 17.08 |
| ATOM | 3305 | NE  | ARG | B | 200 | 44.169 | 74.657 | -1.214 | 1.00 | 19.01 |

FIGURE 3 (Cont.)

| | A | B | C | D | E | F | G | H | I | J |
|---|---|---|---|---|---|---|---|---|---|---|
| ATOM | 3306 | CZ | ARG | B | 200 | 42.902 | 74.407 | -0.882 | 1.00 | 20.18 |
| ATOM | 3307 | NH1 | ARG | B | 200 | 42.268 | 75.226 | -0.054 | 1.00 | 21.81 |
| ATOM | 3308 | NH2 | ARG | B | 200 | 42.262 | 73.348 | -1.364 | 1.00 | 19.24 |
| ATOM | 3309 | C | ARG | B | 200 | 46.519 | 69.568 | -1.228 | 1.00 | 13.83 |
| ATOM | 3310 | O | ARG | B | 200 | 47.717 | 69.638 | -1.536 | 1.00 | 17.02 |
| ATOM | 3311 | N | VAL | B | 201 | 46.097 | 68.939 | -0.130 | 1.00 | 9.96 |
| ATOM | 3312 | CA | VAL | B | 201 | 47.046 | 68.292 | 0.777 | 1.00 | 5.98 |
| ATOM | 3313 | CB | VAL | B | 201 | 46.367 | 67.724 | 2.055 | 1.00 | 2.72 |
| ATOM | 3314 | CG1 | VAL | B | 201 | 47.366 | 66.966 | 2.922 | 1.00 | 2.00 |
| ATOM | 3315 | CG2 | VAL | B | 201 | 45.733 | 68.834 | 2.858 | 1.00 | 2.00 |
| ATOM | 3316 | C | VAL | B | 201 | 47.765 | 67.202 | -0.005 | 1.00 | 7.60 |
| ATOM | 3317 | O | VAL | B | 201 | 48.992 | 67.206 | -0.090 | 1.00 | 7.95 |
| ATOM | 3318 | N | LEU | B | 202 | 46.986 | 66.312 | -0.615 | 1.00 | 8.97 |
| ATOM | 3319 | CA | LEU | B | 202 | 47.499 | 65.235 | -1.462 | 1.00 | 13.56 |
| ATOM | 3320 | CB | LEU | B | 202 | 46.370 | 64.640 | -2.306 | 1.00 | 10.35 |
| ATOM | 3321 | CG | LEU | B | 202 | 45.740 | 63.337 | -1.826 | 1.00 | 9.87 |
| ATOM | 3322 | CD1 | LEU | B | 202 | 44.575 | 62.972 | -2.723 | 1.00 | 8.92 |
| ATOM | 3323 | CD2 | LEU | B | 202 | 46.749 | 62.196 | -1.777 | 1.00 | 10.04 |
| ATOM | 3324 | C | LEU | B | 202 | 48.697 | 65.591 | -2.376 | 1.00 | 19.28 |
| ATOM | 3325 | O | LEU | B | 202 | 49.604 | 64.765 | -2.548 | 1.00 | 22.90 |
| ATOM | 3326 | N | GLN | B | 203 | 48.705 | 66.789 | -2.970 | 1.00 | 20.31 |
| ATOM | 3327 | CA | GLN | B | 203 | 49.865 | 67.208 | -3.766 | 1.00 | 20.11 |
| ATOM | 3328 | CB | GLN | B | 203 | 49.501 | 67.955 | -5.069 | 1.00 | 20.67 |
| ATOM | 3329 | CG | GLN | B | 203 | 48.030 | 68.019 | -5.470 | 1.00 | 19.67 |
| ATOM | 3330 | CD | GLN | B | 203 | 47.634 | 69.363 | -6.095 | 1.00 | 18.61 |
| ATOM | 3331 | OE1 | GLN | B | 203 | 48.314 | 70.379 | -5.909 | 1.00 | 17.21 |
| ATOM | 3332 | NE2 | GLN | B | 203 | 46.527 | 69.364 | -6.827 | 1.00 | 18.03 |
| ATOM | 3333 | C | GLN | B | 203 | 50.879 | 68.021 | -2.958 | 1.00 | 20.30 |
| ATOM | 3334 | O | GLN | B | 203 | 52.082 | 67.749 | -3.007 | 1.00 | 20.81 |
| ATOM | 3335 | N | ASN | B | 204 | 50.402 | 69.010 | -2.212 | 1.00 | 19.66 |
| ATOM | 3336 | CA | ASN | B | 204 | 51.317 | 69.919 | -1.530 | 1.00 | 22.16 |
| ATOM | 3337 | CB | ASN | B | 204 | 50.617 | 71.231 | -1.188 | 1.00 | 20.11 |
| ATOM | 3338 | CG | ASN | B | 204 | 50.676 | 72.204 | -2.321 | 1.00 | 20.95 |
| ATOM | 3339 | OD1 | ASN | B | 204 | 51.691 | 72.869 | -2.525 | 1.00 | 22.09 |
| ATOM | 3340 | ND2 | ASN | B | 204 | 49.600 | 72.276 | -3.098 | 1.00 | 21.15 |
| ATOM | 3341 | C | ASN | B | 204 | 52.038 | 69.320 | -0.314 | 1.00 | 24.57 |
| ATOM | 3342 | O | ASN | B | 204 | 52.479 | 70.044 | 0.585 | 1.00 | 27.00 |
| ATOM | 3343 | N | SER | B | 205 | 52.175 | 67.996 | -0.308 | 1.00 | 23.83 |
| ATOM | 3344 | CA | SER | B | 205 | 52.816 | 67.285 | 0.796 | 1.00 | 22.84 |
| ATOM | 3345 | CB | SER | B | 205 | 51.768 | 66.650 | 1.720 | 1.00 | 20.77 |
| ATOM | 3346 | OG | SER | B | 205 | 50.927 | 67.649 | 2.276 | 1.00 | 18.07 |
| ATOM | 3347 | C | SER | B | 205 | 53.812 | 66.243 | 0.290 | 1.00 | 22.23 |
| ATOM | 3348 | O | SER | B | 205 | 53.831 | 65.905 | -0.898 | 1.00 | 21.65 |
| ATOM | 3349 | N | ARG | B | 206 | 54.635 | 65.753 | 1.213 | 1.00 | 19.78 |
| ATOM | 3350 | CA | ARG | B | 206 | 55.770 | 64.893 | 0.912 | 1.00 | 17.79 |
| ATOM | 3351 | CB | ARG | B | 206 | 56.790 | 65.621 | 0.027 | 1.00 | 20.24 |
| ATOM | 3352 | CG | ARG | B | 206 | 56.739 | 65.227 | -1.437 | 1.00 | 23.99 |
| ATOM | 3353 | CD | ARG | B | 206 | 57.007 | 66.375 | -2.404 | 1.00 | 26.62 |
| ATOM | 3354 | NE | ARG | B | 206 | 55.770 | 67.008 | -2.854 | 1.00 | 29.11 |
| ATOM | 3355 | CZ | ARG | B | 206 | 55.708 | 68.165 | -3.504 | 1.00 | 31.55 |
| ATOM | 3356 | NH1 | ARG | B | 206 | 54.528 | 68.653 | -3.869 | 1.00 | 32.36 |
| ATOM | 3357 | NH2 | ARG | B | 206 | 56.820 | 68.840 | -3.793 | 1.00 | 31.99 |

FIGURE 3 (Cont.)

|      | A    | B    | C   | D | E   | F      | G      | H      | I    | J     |
|------|------|------|-----|---|-----|--------|--------|--------|------|-------|
| ATOM | 3358 | C    | ARG | B | 206 | 56.410 | 64.489 | 2.237  | 1.00 | 13.72 |
| ATOM | 3359 | O    | ARG | B | 206 | 57.137 | 65.259 | 2.866  | 1.00 | 14.06 |
| ATOM | 3360 | N    | HIS | B | 207 | 56.109 | 63.275 | 2.659  | 1.00 | 7.72  |
| ATOM | 3361 | CA   | HIS | B | 207 | 56.562 | 62.746 | 3.925  | 1.00 | 4.20  |
| ATOM | 3362 | CB   | HIS | B | 207 | 55.678 | 63.286 | 5.052  | 1.00 | 2.00  |
| ATOM | 3363 | CG   | HIS | B | 207 | 56.146 | 62.919 | 6.422  | 1.00 | 2.00  |
| ATOM | 3364 | ND1  | HIS | B | 207 | 56.694 | 63.836 | 7.289  | 1.00 | 2.00  |
| ATOM | 3365 | CE1  | HIS | B | 207 | 57.014 | 63.235 | 8.421  | 1.00 | 2.00  |
| ATOM | 3366 | NE2  | HIS | B | 207 | 56.689 | 61.958 | 8.320  | 1.00 | 2.00  |
| ATOM | 3367 | CD2  | HIS | B | 207 | 56.142 | 61.734 | 7.080  | 1.00 | 2.00  |
| ATOM | 3368 | C    | HIS | B | 207 | 56.402 | 61.235 | 3.740  | 1.00 | 4.66  |
| ATOM | 3369 | O    | HIS | B | 207 | 55.416 | 60.803 | 3.136  | 1.00 | 6.44  |
| ATOM | 3370 | N    | PRO | B | 208 | 57.371 | 60.441 | 4.195  | 1.00 | 2.15  |
| ATOM | 3371 | CA   | PRO | B | 208 | 57.394 | 58.998 | 3.909  | 1.00 | 2.00  |
| ATOM | 3372 | CB   | PRO | B | 208 | 58.703 | 58.539 | 4.539  | 1.00 | 2.00  |
| ATOM | 3373 | CG   | PRO | B | 208 | 59.506 | 59.778 | 4.680  | 1.00 | 2.36  |
| ATOM | 3374 | CD   | PRO | B | 208 | 58.547 | 60.869 | 4.972  | 1.00 | 2.00  |
| ATOM | 3375 | C    | PRO | B | 208 | 56.237 | 58.173 | 4.466  | 1.00 | 3.08  |
| ATOM | 3376 | O    | PRO | B | 208 | 56.101 | 57.023 | 4.045  | 1.00 | 4.07  |
| ATOM | 3377 | N    | PHE | B | 209 | 55.438 | 58.719 | 5.383  | 1.00 | 6.28  |
| ATOM | 3378 | CA   | PHE | B | 209 | 54.255 | 57.999 | 5.901  | 1.00 | 9.54  |
| ATOM | 3379 | CB   | PHE | B | 209 | 54.385 | 57.703 | 7.408  | 1.00 | 10.16 |
| ATOM | 3380 | CG   | PHE | B | 209 | 55.790 | 57.367 | 7.832  | 1.00 | 12.18 |
| ATOM | 3381 | CD1  | PHE | B | 209 | 56.473 | 56.298 | 7.248  | 1.00 | 11.99 |
| ATOM | 3382 | CE1  | PHE | B | 209 | 57.772 | 56.003 | 7.611  | 1.00 | 8.61  |
| ATOM | 3383 | CZ   | PHE | B | 209 | 58.403 | 56.773 | 8.564  | 1.00 | 8.44  |
| ATOM | 3384 | CE2  | PHE | B | 209 | 57.746 | 57.840 | 9.148  | 1.00 | 9.66  |
| ATOM | 3385 | CD2  | PHE | B | 209 | 56.448 | 58.140 | 8.777  | 1.00 | 11.74 |
| ATOM | 3386 | C    | PHE | B | 209 | 52.935 | 58.699 | 5.562  | 1.00 | 10.55 |
| ATOM | 3387 | O    | PHE | B | 209 | 51.904 | 58.450 | 6.173  | 1.00 | 12.81 |
| ATOM | 3388 | N    | LEU | B | 210 | 53.000 | 59.587 | 4.576  | 1.00 | 10.78 |
| ATOM | 3389 | CA   | LEU | B | 210 | 51.830 | 60.166 | 3.938  | 1.00 | 8.21  |
| ATOM | 3390 | CB   | LEU | B | 210 | 51.943 | 61.695 | 3.914  | 1.00 | 4.33  |
| ATOM | 3391 | CG   | LEU | B | 210 | 52.009 | 62.451 | 5.241  | 1.00 | 2.22  |
| ATOM | 3392 | CD1  | LEU | B | 210 | 51.877 | 63.949 | 5.029  | 1.00 | 2.00  |
| ATOM | 3393 | CD2  | LEU | B | 210 | 50.944 | 61.942 | 6.204  | 1.00 | 3.54  |
| ATOM | 3394 | C    | LEU | B | 210 | 51.783 | 59.635 | 2.512  | 1.00 | 8.78  |
| ATOM | 3395 | O    | LEU | B | 210 | 52.806 | 59.621 | 1.825  | 1.00 | 8.97  |
| ATOM | 3396 | N    | THR | B | 211 | 50.610 | 59.195 | 2.062  | 1.00 | 9.14  |
| ATOM | 3397 | CA   | THR | B | 211 | 50.460 | 58.767 | 0.674  | 1.00 | 9.56  |
| ATOM | 3398 | CB   | THR | B | 211 | 49.028 | 58.304 | 0.376  | 1.00 | 9.73  |
| ATOM | 3399 | OG1  | THR | B | 211 | 48.541 | 57.521 | 1.470  | 1.00 | 14.21 |
| ATOM | 3400 | CG2  | THR | B | 211 | 49.026 | 57.307 | -0.757 | 1.00 | 8.12  |
| ATOM | 3401 | C    | THR | B | 211 | 50.846 | 59.903 | -0.259 | 1.00 | 11.00 |
| ATOM | 3402 | O    | THR | B | 211 | 50.470 | 61.058 | -0.038 | 1.00 | 11.02 |
| ATOM | 3403 | N    | ALA | B | 212 | 51.627 | 59.566 | -1.282 | 1.00 | 12.18 |
| ATOM | 3404 | CA   | ALA | B | 212 | 52.005 | 60.519 | -2.318 | 1.00 | 12.85 |
| ATOM | 3405 | CB   | ALA | B | 212 | 53.461 | 60.319 | -2.725 | 1.00 | 12.10 |
| ATOM | 3406 | C    | ALA | B | 212 | 51.078 | 60.402 | -3.532 | 1.00 | 13.78 |
| ATOM | 3407 | O    | ALA | B | 212 | 50.625 | 59.309 | -3.887 | 1.00 | 12.07 |
| ATOM | 3408 | N    | LEU | B | 213 | 50.802 | 61.545 | -4.156 | 1.00 | 15.82 |
| ATOM | 3409 | CA   | LEU | B | 213 | 49.935 | 61.620 | -5.325 | 1.00 | 15.71 |

FIGURE 3 (Cont.)

|      | A    | B    | C   | D | E   | F      | G      | H       | I    | J     |
|------|------|------|-----|---|-----|--------|--------|---------|------|-------|
| ATOM | 3410 | CB   | LEU | B | 213 | 49.039 | 62.857 | -5.233  | 1.00 | 13.93 |
| ATOM | 3411 | CG   | LEU | B | 213 | 47.861 | 63.017 | -6.193  | 1.00 | 12.55 |
| ATOM | 3412 | CD1  | LEU | B | 213 | 46.823 | 61.925 | -5.995  | 1.00 | 12.37 |
| ATOM | 3413 | CD2  | LEU | B | 213 | 47.242 | 64.382 | -5.980  | 1.00 | 11.68 |
| ATOM | 3414 | C    | LEU | B | 213 | 50.755 | 61.670 | -6.605  | 1.00 | 17.99 |
| ATOM | 3415 | O    | LEU | B | 213 | 51.598 | 62.553 | -6.781  | 1.00 | 18.02 |
| ATOM | 3416 | N    | LYS | B | 214 | 50.515 | 60.702 | -7.486  | 1.00 | 20.78 |
| ATOM | 3417 | CA   | LYS | B | 214 | 51.087 | 60.715 | -8.825  | 1.00 | 20.72 |
| ATOM | 3418 | CB   | LYS | B | 214 | 51.331 | 59.292 | -9.348  | 1.00 | 20.15 |
| ATOM | 3419 | CG   | LYS | B | 214 | 51.802 | 59.215 | -10.796 | 1.00 | 20.99 |
| ATOM | 3420 | CD   | LYS | B | 214 | 53.276 | 58.835 | -10.909 | 1.00 | 22.86 |
| ATOM | 3421 | CE   | LYS | B | 214 | 53.753 | 58.847 | -12.366 | 1.00 | 22.87 |
| ATOM | 3422 | NZ   | LYS | B | 214 | 55.060 | 59.553 | -12.527 | 1.00 | 22.08 |
| ATOM | 3423 | C    | LYS | B | 214 | 50.132 | 61.491 | -9.721  | 1.00 | 21.98 |
| ATOM | 3424 | O    | LYS | B | 214 | 50.454 | 62.602 | -10.143 | 1.00 | 25.32 |
| ATOM | 3425 | N    | TYR | B | 215 | 48.953 | 60.934 | -9.987  | 1.00 | 22.06 |
| ATOM | 3426 | CA   | TYR | B | 215 | 47.995 | 61.604 | -10.865 | 1.00 | 24.71 |
| ATOM | 3427 | CB   | TYR | B | 215 | 47.602 | 60.726 | -12.070 | 1.00 | 24.65 |
| ATOM | 3428 | CG   | TYR | B | 215 | 48.755 | 60.297 | -12.968 | 1.00 | 25.07 |
| ATOM | 3429 | CD1  | TYR | B | 215 | 49.532 | 61.235 | -13.648 | 1.00 | 24.49 |
| ATOM | 3430 | CE1  | TYR | B | 215 | 50.592 | 60.836 | -14.469 | 1.00 | 24.75 |
| ATOM | 3431 | CZ   | TYR | B | 215 | 50.873 | 59.484 | -14.619 | 1.00 | 25.14 |
| ATOM | 3432 | OH   | TYR | B | 215 | 51.913 | 59.076 | -15.423 | 1.00 | 25.97 |
| ATOM | 3433 | CE2  | TYR | B | 215 | 50.113 | 58.535 | -13.961 | 1.00 | 25.56 |
| ATOM | 3434 | CD2  | TYR | B | 215 | 49.058 | 58.944 | -13.143 | 1.00 | 25.71 |
| ATOM | 3435 | C    | TYR | B | 215 | 46.750 | 62.088 | -10.130 | 1.00 | 25.72 |
| ATOM | 3436 | O    | TYR | B | 215 | 46.250 | 61.425 | -9.218  | 1.00 | 25.47 |
| ATOM | 3437 | N    | SER | B | 216 | 46.278 | 63.263 | -10.542 | 1.00 | 27.13 |
| ATOM | 3438 | CA   | SER | B | 216 | 44.990 | 63.810 | -10.127 | 1.00 | 27.09 |
| ATOM | 3439 | CB   | SER | B | 216 | 45.186 | 64.894 | -9.075  | 1.00 | 26.03 |
| ATOM | 3440 | OG   | SER | B | 216 | 43.940 | 65.456 | -8.716  | 1.00 | 26.14 |
| ATOM | 3441 | C    | SER | B | 216 | 44.269 | 64.385 | -11.350 | 1.00 | 27.91 |
| ATOM | 3442 | O    | SER | B | 216 | 44.854 | 65.159 | -12.117 | 1.00 | 31.31 |
| ATOM | 3443 | N    | PHE | B | 217 | 43.006 | 64.004 | -11.535 | 1.00 | 25.40 |
| ATOM | 3444 | CA   | PHE | B | 217 | 42.244 | 64.414 | -12.714 | 1.00 | 22.13 |
| ATOM | 3445 | CB   | PHE | B | 217 | 42.733 | 63.662 | -13.955 | 1.00 | 22.21 |
| ATOM | 3446 | CG   | PHE | B | 217 | 42.442 | 62.190 | -13.930 | 1.00 | 23.35 |
| ATOM | 3447 | CD1  | PHE | B | 217 | 43.357 | 61.297 | -13.382 | 1.00 | 23.90 |
| ATOM | 3448 | CE1  | PHE | B | 217 | 43.096 | 59.931 | -13.358 | 1.00 | 23.73 |
| ATOM | 3449 | CZ   | PHE | B | 217 | 41.911 | 59.446 | -13.887 | 1.00 | 24.33 |
| ATOM | 3450 | CE2  | PHE | B | 217 | 40.986 | 60.331 | -14.440 | 1.00 | 25.02 |
| ATOM | 3451 | CD2  | PHE | B | 217 | 41.257 | 61.691 | -14.464 | 1.00 | 23.98 |
| ATOM | 3452 | C    | PHE | B | 217 | 40.743 | 64.213 | -12.540 | 1.00 | 21.34 |
| ATOM | 3453 | O    | PHE | B | 217 | 40.271 | 63.891 | -11.450 | 1.00 | 22.92 |
| ATOM | 3454 | N    | GLN | B | 218 | 40.005 | 64.387 | -13.634 | 1.00 | 19.79 |
| ATOM | 3455 | CA   | GLN | B | 218 | 38.547 | 64.322 | -13.623 | 1.00 | 18.96 |
| ATOM | 3456 | CB   | GLN | B | 218 | 37.970 | 65.679 | -13.196 | 1.00 | 17.85 |
| ATOM | 3457 | CG   | GLN | B | 218 | 38.334 | 66.843 | -14.128 | 1.00 | 16.69 |
| ATOM | 3458 | CD   | GLN | B | 218 | 38.074 | 68.205 | -13.523 | 1.00 | 15.21 |
| ATOM | 3459 | OE1  | GLN | B | 218 | 36.941 | 68.527 | -13.161 | 1.00 | 15.00 |
| ATOM | 3460 | NE2  | GLN | B | 218 | 39.119 | 69.017 | -13.427 | 1.00 | 14.27 |
| ATOM | 3461 | C    | GLN | B | 218 | 37.969 | 63.925 | -14.988 | 1.00 | 19.16 |

FIGURE 3 (Cont.)

|      | A    | B   | C   | D | E   | F      | G      | H       | I    | J     |
|------|------|-----|-----|---|-----|--------|--------|---------|------|-------|
| ATOM | 3462 | O   | GLN | B | 218 | 38.573 | 64.193 | -16.032 | 1.00 | 21.40 |
| ATOM | 3463 | N   | THR | B | 219 | 36.806 | 63.278 | -14.969 | 1.00 | 17.52 |
| ATOM | 3464 | CA  | THR | B | 219 | 35.989 | 63.129 | -16.171 | 1.00 | 14.96 |
| ATOM | 3465 | CB  | THR | B | 219 | 35.439 | 61.672 | -16.356 | 1.00 | 11.54 |
| ATOM | 3466 | OG1 | THR | B | 219 | 34.249 | 61.487 | -15.582 | 1.00 | 6.79  |
| ATOM | 3467 | CG2 | THR | B | 219 | 36.390 | 60.637 | -15.794 | 1.00 | 9.95  |
| ATOM | 3468 | C   | THR | B | 219 | 34.859 | 64.155 | -16.109 | 1.00 | 17.47 |
| ATOM | 3469 | O   | THR | B | 219 | 34.877 | 65.058 | -15.270 | 1.00 | 16.56 |
| ATOM | 3470 | N   | HIS | B | 220 | 33.890 | 64.020 | -17.011 | 1.00 | 22.23 |
| ATOM | 3471 | CA  | HIS | B | 220 | 32.696 | 64.868 | -17.040 | 1.00 | 24.44 |
| ATOM | 3472 | CB  | HIS | B | 220 | 31.836 | 64.514 | -18.263 | 1.00 | 23.54 |
| ATOM | 3473 | CG  | HIS | B | 220 | 31.614 | 63.043 | -18.428 | 1.00 | 24.02 |
| ATOM | 3474 | ND1 | HIS | B | 220 | 32.637 | 62.163 | -18.714 | 1.00 | 24.07 |
| ATOM | 3475 | CE1 | HIS | B | 220 | 32.155 | 60.934 | -18.774 | 1.00 | 24.52 |
| ATOM | 3476 | NE2 | HIS | B | 220 | 30.856 | 60.986 | -18.537 | 1.00 | 25.10 |
| ATOM | 3477 | CD2 | HIS | B | 220 | 30.494 | 62.293 | -18.313 | 1.00 | 24.34 |
| ATOM | 3478 | C   | HIS | B | 220 | 31.878 | 64.754 | -15.738 | 1.00 | 25.13 |
| ATOM | 3479 | O   | HIS | B | 220 | 31.328 | 65.750 | -15.264 | 1.00 | 25.10 |
| ATOM | 3480 | N   | ASP | B | 221 | 31.823 | 63.549 | -15.161 | 1.00 | 26.39 |
| ATOM | 3481 | CA  | ASP | B | 221 | 31.053 | 63.291 | -13.929 | 1.00 | 27.34 |
| ATOM | 3482 | CB  | ASP | B | 221 | 29.705 | 62.598 | -14.253 | 1.00 | 28.05 |
| ATOM | 3483 | CG  | ASP | B | 221 | 29.857 | 61.118 | -14.609 | 1.00 | 28.22 |
| ATOM | 3484 | OD1 | ASP | B | 221 | 29.853 | 60.277 | -13.684 | 1.00 | 28.41 |
| ATOM | 3485 | OD2 | ASP | B | 221 | 29.964 | 60.702 | -15.784 | 1.00 | 28.02 |
| ATOM | 3486 | C   | ASP | B | 221 | 31.821 | 62.569 | -12.784 | 1.00 | 26.18 |
| ATOM | 3487 | O   | ASP | B | 221 | 31.269 | 62.325 | -11.702 | 1.00 | 25.24 |
| ATOM | 3488 | N   | ARG | B | 222 | 33.093 | 62.255 | -13.020 | 1.00 | 24.14 |
| ATOM | 3489 | CA  | ARG | B | 222 | 33.907 | 61.551 | -12.038 | 1.00 | 22.59 |
| ATOM | 3490 | CB  | ARG | B | 222 | 34.354 | 60.200 | -12.600 | 1.00 | 22.44 |
| ATOM | 3491 | CG  | ARG | B | 222 | 33.722 | 59.003 | -11.922 | 1.00 | 23.64 |
| ATOM | 3492 | CD  | ARG | B | 222 | 32.672 | 58.286 | -12.746 | 1.00 | 23.94 |
| ATOM | 3493 | NE  | ARG | B | 222 | 33.190 | 57.049 | -13.322 | 1.00 | 25.81 |
| ATOM | 3494 | CZ  | ARG | B | 222 | 33.432 | 56.860 | -14.619 | 1.00 | 28.20 |
| ATOM | 3495 | NH1 | ARG | B | 222 | 33.205 | 57.827 | -15.505 | 1.00 | 29.58 |
| ATOM | 3496 | NH2 | ARG | B | 222 | 33.905 | 55.694 | -15.039 | 1.00 | 29.09 |
| ATOM | 3497 | C   | ARG | B | 222 | 35.125 | 62.365 | -11.604 | 1.00 | 23.12 |
| ATOM | 3498 | O   | ARG | B | 222 | 35.822 | 62.940 | -12.437 | 1.00 | 23.43 |
| ATOM | 3499 | N   | LEU | B | 223 | 35.366 | 62.422 | -10.295 | 1.00 | 23.95 |
| ATOM | 3500 | CA  | LEU | B | 223 | 36.604 | 62.984 | -9.750  | 1.00 | 22.51 |
| ATOM | 3501 | CB  | LEU | B | 223 | 36.334 | 63.850 | -8.516  | 1.00 | 21.97 |
| ATOM | 3502 | CG  | LEU | B | 223 | 36.196 | 65.376 | -8.607  | 1.00 | 22.19 |
| ATOM | 3503 | CD1 | LEU | B | 223 | 36.734 | 66.019 | -7.341  | 1.00 | 21.37 |
| ATOM | 3504 | CD2 | LEU | B | 223 | 36.866 | 65.985 | -9.832  | 1.00 | 22.54 |
| ATOM | 3505 | C   | LEU | B | 223 | 37.546 | 61.843 | -9.395  | 1.00 | 21.59 |
| ATOM | 3506 | O   | LEU | B | 223 | 37.108 | 60.786 | -8.925  | 1.00 | 18.49 |
| ATOM | 3507 | N   | CYS | B | 224 | 38.839 | 62.063 | -9.619  | 1.00 | 22.66 |
| ATOM | 3508 | CA  | CYS | B | 224 | 39.822 | 60.995 | -9.490  | 1.00 | 24.10 |
| ATOM | 3509 | CB  | CYS | B | 224 | 40.166 | 60.425 | -10.862 | 1.00 | 25.39 |
| ATOM | 3510 | SG  | CYS | B | 224 | 39.348 | 58.863 | -11.221 | 1.00 | 29.27 |
| ATOM | 3511 | C   | CYS | B | 224 | 41.104 | 61.396 | -8.784  | 1.00 | 23.67 |
| ATOM | 3512 | O   | CYS | B | 224 | 41.647 | 62.483 | -8.994  | 1.00 | 24.47 |
| ATOM | 3513 | N   | PHE | B | 225 | 41.575 | 60.484 | -7.945  | 1.00 | 22.95 |

FIGURE 3 (Cont.)

| | A | B | C | D | E | F | G | H | I | J |
|---|---|---|---|---|---|---|---|---|---|---|
| ATOM | 3514 | CA | PHE | B | 225 | 42.872 | 60.593 | -7.315 | 1.00 | 21.39 |
| ATOM | 3515 | CB | PHE | B | 225 | 42.710 | 60.808 | -5.824 | 1.00 | 22.81 |
| ATOM | 3516 | CG | PHE | B | 225 | 42.062 | 62.102 | -5.466 | 1.00 | 23.36 |
| ATOM | 3517 | CD1 | PHE | B | 225 | 40.862 | 62.115 | -4.767 | 1.00 | 23.31 |
| ATOM | 3518 | CE1 | PHE | B | 225 | 40.263 | 63.313 | -4.415 | 1.00 | 23.94 |
| ATOM | 3519 | CZ | PHE | B | 225 | 40.866 | 64.513 | -4.759 | 1.00 | 23.79 |
| ATOM | 3520 | CE2 | PHE | B | 225 | 42.065 | 64.507 | -5.457 | 1.00 | 23.30 |
| ATOM | 3521 | CD2 | PHE | B | 225 | 42.657 | 63.309 | -5.806 | 1.00 | 22.68 |
| ATOM | 3522 | C | PHE | B | 225 | 43.596 | 59.290 | -7.554 | 1.00 | 20.16 |
| ATOM | 3523 | O | PHE | B | 225 | 43.082 | 58.214 | -7.233 | 1.00 | 19.70 |
| ATOM | 3524 | N | VAL | B | 226 | 44.781 | 59.385 | -8.141 | 1.00 | 18.07 |
| ATOM | 3525 | CA | VAL | B | 226 | 45.586 | 58.204 | -8.397 | 1.00 | 17.13 |
| ATOM | 3526 | CB | VAL | B | 226 | 45.880 | 58.015 | -9.896 | 1.00 | 15.53 |
| ATOM | 3527 | CG1 | VAL | B | 226 | 46.529 | 56.668 | -10.132 | 1.00 | 16.08 |
| ATOM | 3528 | CG2 | VAL | B | 226 | 44.609 | 58.129 | -10.711 | 1.00 | 13.03 |
| ATOM | 3529 | C | VAL | B | 226 | 46.875 | 58.304 | -7.592 | 1.00 | 17.83 |
| ATOM | 3530 | O | VAL | B | 226 | 47.845 | 58.924 | -8.027 | 1.00 | 19.87 |
| ATOM | 3531 | N | MET | B | 227 | 46.856 | 57.704 | -6.405 | 1.00 | 17.36 |
| ATOM | 3532 | CA | MET | B | 227 | 47.985 | 57.740 | -5.477 | 1.00 | 16.79 |
| ATOM | 3533 | CB | MET | B | 227 | 47.542 | 58.220 | -4.087 | 1.00 | 16.52 |
| ATOM | 3534 | CG | MET | B | 227 | 46.365 | 57.459 | -3.469 | 1.00 | 14.52 |
| ATOM | 3535 | SD | MET | B | 227 | 44.982 | 58.543 | -3.094 | 1.00 | 11.06 |
| ATOM | 3536 | CE | MET | B | 227 | 44.157 | 57.589 | -1.812 | 1.00 | 15.09 |
| ATOM | 3537 | C | MET | B | 227 | 48.614 | 56.365 | -5.386 | 1.00 | 17.36 |
| ATOM | 3538 | O | MET | B | 227 | 48.024 | 55.384 | -5.851 | 1.00 | 19.57 |
| ATOM | 3539 | N | GLU | B | 228 | 49.801 | 56.294 | -4.788 | 1.00 | 17.38 |
| ATOM | 3540 | CA | GLU | B | 228 | 50.559 | 55.046 | -4.732 | 1.00 | 20.06 |
| ATOM | 3541 | CB | GLU | B | 228 | 51.976 | 55.265 | -4.177 | 1.00 | 23.13 |
| ATOM | 3542 | CG | GLU | B | 228 | 52.089 | 56.324 | -3.092 | 1.00 | 29.42 |
| ATOM | 3543 | CD | GLU | B | 228 | 52.791 | 55.816 | -1.840 | 1.00 | 33.76 |
| ATOM | 3544 | OE1 | GLU | B | 228 | 54.034 | 55.938 | -1.781 | 1.00 | 35.59 |
| ATOM | 3545 | OE2 | GLU | B | 228 | 52.106 | 55.297 | -0.916 | 1.00 | 35.91 |
| ATOM | 3546 | C | GLU | B | 228 | 49.814 | 53.958 | -3.961 | 1.00 | 18.82 |
| ATOM | 3547 | O | GLU | B | 228 | 49.501 | 54.117 | -2.787 | 1.00 | 19.18 |
| ATOM | 3548 | N | TYR | B | 229 | 49.510 | 52.866 | -4.649 | 1.00 | 20.12 |
| ATOM | 3549 | CA | TYR | B | 229 | 48.837 | 51.734 | -4.038 | 1.00 | 24.76 |
| ATOM | 3550 | CB | TYR | B | 229 | 48.491 | 50.696 | -5.119 | 1.00 | 26.14 |
| ATOM | 3551 | CG | TYR | B | 229 | 48.325 | 49.259 | -4.647 | 1.00 | 28.17 |
| ATOM | 3552 | CD1 | TYR | B | 229 | 47.262 | 48.887 | -3.821 | 1.00 | 28.49 |
| ATOM | 3553 | CE1 | TYR | B | 229 | 47.111 | 47.566 | -3.396 | 1.00 | 29.29 |
| ATOM | 3554 | CZ | TYR | B | 229 | 48.022 | 46.601 | -3.803 | 1.00 | 28.67 |
| ATOM | 3555 | OH | TYR | B | 229 | 47.866 | 45.303 | -3.380 | 1.00 | 29.35 |
| ATOM | 3556 | CE2 | TYR | B | 229 | 49.079 | 46.940 | -4.629 | 1.00 | 27.97 |
| ATOM | 3557 | CD2 | TYR | B | 229 | 49.226 | 48.265 | -5.049 | 1.00 | 28.17 |
| ATOM | 3558 | C | TYR | B | 229 | 49.713 | 51.146 | -2.919 | 1.00 | 28.17 |
| ATOM | 3559 | O | TYR | B | 229 | 50.873 | 50.788 | -3.147 | 1.00 | 31.19 |
| ATOM | 3560 | N | ALA | B | 230 | 49.160 | 51.081 | -1.708 | 1.00 | 27.08 |
| ATOM | 3561 | CA | ALA | B | 230 | 49.859 | 50.512 | -0.562 | 1.00 | 23.43 |
| ATOM | 3562 | CB | ALA | B | 230 | 49.444 | 51.222 | 0.698 | 1.00 | 22.72 |
| ATOM | 3563 | C | ALA | B | 230 | 49.554 | 49.024 | -0.471 | 1.00 | 23.03 |
| ATOM | 3564 | O | ALA | B | 230 | 48.402 | 48.633 | -0.313 | 1.00 | 23.44 |
| ATOM | 3565 | N | ASN | B | 231 | 50.594 | 48.202 | -0.570 | 1.00 | 24.43 |

FIGURE 3 (Cont.)

|      | A    | B    | C   | D | E   | F      | G      | H      | I    | J     |
|------|------|------|-----|---|-----|--------|--------|--------|------|-------|
| ATOM | 3566 | CA   | ASN | B | 231 | 50.446 | 46.747 | -0.700 | 1.00 | 25.46 |
| ATOM | 3567 | CB   | ASN | B | 231 | 51.751 | 46.122 | -1.224 | 1.00 | 29.96 |
| ATOM | 3568 | CG   | ASN | B | 231 | 51.898 | 46.251 | -2.746 | 1.00 | 33.44 |
| ATOM | 3569 | OD1  | ASN | B | 231 | 51.525 | 45.346 | -3.511 | 1.00 | 33.53 |
| ATOM | 3570 | ND2  | ASN | B | 231 | 52.441 | 47.381 | -3.189 | 1.00 | 35.04 |
| ATOM | 3571 | C    | ASN | B | 231 | 49.948 | 45.981 | 0.535  | 1.00 | 22.34 |
| ATOM | 3572 | O    | ASN | B | 231 | 49.330 | 44.925 | 0.398  | 1.00 | 21.90 |
| ATOM | 3573 | N    | GLY | B | 232 | 50.205 | 46.515 | 1.726  | 1.00 | 20.16 |
| ATOM | 3574 | CA   | GLY | B | 232 | 49.874 | 45.831 | 2.967  | 1.00 | 17.91 |
| ATOM | 3575 | C    | GLY | B | 232 | 48.495 | 46.116 | 3.535  | 1.00 | 18.47 |
| ATOM | 3576 | O    | GLY | B | 232 | 48.199 | 45.733 | 4.673  | 1.00 | 17.38 |
| ATOM | 3577 | N    | GLY | B | 233 | 47.655 | 46.798 | 2.757  | 1.00 | 19.34 |
| ATOM | 3578 | CA   | GLY | B | 233 | 46.279 | 47.074 | 3.149  | 1.00 | 21.72 |
| ATOM | 3579 | C    | GLY | B | 233 | 46.132 | 48.004 | 4.340  | 1.00 | 22.37 |
| ATOM | 3580 | O    | GLY | B | 233 | 47.109 | 48.589 | 4.803  | 1.00 | 23.78 |
| ATOM | 3581 | N    | GLU | B | 234 | 44.904 | 48.157 | 4.826  | 1.00 | 22.76 |
| ATOM | 3582 | CA   | GLU | B | 234 | 44.651 | 48.983 | 6.009  | 1.00 | 20.83 |
| ATOM | 3583 | CB   | GLU | B | 234 | 43.159 | 49.326 | 6.183  | 1.00 | 26.19 |
| ATOM | 3584 | CG   | GLU | B | 234 | 42.202 | 48.705 | 5.164  | 1.00 | 32.46 |
| ATOM | 3585 | CD   | GLU | B | 234 | 40.778 | 48.562 | 5.691  | 1.00 | 35.07 |
| ATOM | 3586 | OE1  | GLU | B | 234 | 40.331 | 47.406 | 5.904  | 1.00 | 36.60 |
| ATOM | 3587 | OE2  | GLU | B | 234 | 40.101 | 49.600 | 5.891  | 1.00 | 35.06 |
| ATOM | 3588 | C    | GLU | B | 234 | 45.168 | 48.288 | 7.249  | 1.00 | 16.25 |
| ATOM | 3589 | O    | GLU | B | 234 | 45.318 | 47.069 | 7.282  | 1.00 | 15.37 |
| ATOM | 3590 | N    | LEU | B | 235 | 45.455 | 49.083 | 8.268  | 1.00 | 14.75 |
| ATOM | 3591 | CA   | LEU | B | 235 | 45.927 | 48.567 | 9.545  | 1.00 | 11.98 |
| ATOM | 3592 | CB   | LEU | B | 235 | 46.388 | 49.712 | 10.443 | 1.00 | 8.14  |
| ATOM | 3593 | CG   | LEU | B | 235 | 47.555 | 49.400 | 11.369 | 1.00 | 7.64  |
| ATOM | 3594 | CD1  | LEU | B | 235 | 48.578 | 48.519 | 10.684 | 1.00 | 9.85  |
| ATOM | 3595 | CD2  | LEU | B | 235 | 48.204 | 50.688 | 11.821 | 1.00 | 8.88  |
| ATOM | 3596 | C    | LEU | B | 235 | 44.798 | 47.819 | 10.198 | 1.00 | 10.94 |
| ATOM | 3597 | O    | LEU | B | 235 | 45.011 | 46.847 | 10.904 | 1.00 | 12.43 |
| ATOM | 3598 | N    | PHE | B | 236 | 43.588 | 48.289 | 9.933  | 1.00 | 10.87 |
| ATOM | 3599 | CA   | PHE | B | 236 | 42.389 | 47.666 | 10.425 | 1.00 | 11.40 |
| ATOM | 3600 | CB   | PHE | B | 236 | 41.166 | 48.437 | 9.937  | 1.00 | 12.84 |
| ATOM | 3601 | CG   | PHE | B | 236 | 39.863 | 47.761 | 10.249 | 1.00 | 16.04 |
| ATOM | 3602 | CD1  | PHE | B | 236 | 39.486 | 47.520 | 11.571 | 1.00 | 19.00 |
| ATOM | 3603 | CE1  | PHE | B | 236 | 38.290 | 46.892 | 11.867 | 1.00 | 19.86 |
| ATOM | 3604 | CZ   | PHE | B | 236 | 37.454 | 46.491 | 10.832 | 1.00 | 21.31 |
| ATOM | 3605 | CE2  | PHE | B | 236 | 37.828 | 46.716 | 9.506  | 1.00 | 18.80 |
| ATOM | 3606 | CD2  | PHE | B | 236 | 39.023 | 47.348 | 9.226  | 1.00 | 16.34 |
| ATOM | 3607 | C    | PHE | B | 236 | 42.324 | 46.213 | 9.972  | 1.00 | 12.66 |
| ATOM | 3608 | O    | PHE | B | 236 | 41.777 | 45.362 | 10.674 | 1.00 | 14.17 |
| ATOM | 3609 | N    | PHE | B | 237 | 42.879 | 45.919 | 8.802  | 1.00 | 12.25 |
| ATOM | 3610 | CA   | PHE | B | 237 | 42.913 | 44.536 | 8.352  | 1.00 | 11.35 |
| ATOM | 3611 | CB   | PHE | B | 237 | 43.495 | 44.417 | 6.949  | 1.00 | 7.11  |
| ATOM | 3612 | CG   | PHE | B | 237 | 43.428 | 43.032 | 6.377  | 1.00 | 4.35  |
| ATOM | 3613 | CD1  | PHE | B | 237 | 42.292 | 42.596 | 5.709  | 1.00 | 3.73  |
| ATOM | 3614 | CE1  | PHE | B | 237 | 42.233 | 41.329 | 5.161  | 1.00 | 2.00  |
| ATOM | 3615 | CZ   | PHE | B | 237 | 43.311 | 40.474 | 5.281  | 1.00 | 3.10  |
| ATOM | 3616 | CE2  | PHE | B | 237 | 44.452 | 40.895 | 5.940  | 1.00 | 4.74  |
| ATOM | 3617 | CD2  | PHE | B | 237 | 44.505 | 42.170 | 6.487  | 1.00 | 4.37  |

FIGURE 3 (Cont.)

| | A | B | C | D | E | F | G | H | I | J |
|---|---|---|---|---|---|---|---|---|---|---|
| ATOM | 3618 | C | PHE | B | 237 | 43.743 | 43.748 | 9.347 | 1.00 | 12.10 |
| ATOM | 3619 | O | PHE | B | 237 | 43.235 | 42.847 | 10.005 | 1.00 | 15.18 |
| ATOM | 3620 | N | HIS | B | 238 | 45.005 | 44.131 | 9.486 | 1.00 | 12.48 |
| ATOM | 3621 | CA | HIS | B | 238 | 45.932 | 43.436 | 10.362 | 1.00 | 12.30 |
| ATOM | 3622 | CB | HIS | B | 238 | 47.300 | 44.080 | 10.286 | 1.00 | 13.34 |
| ATOM | 3623 | CG | HIS | B | 238 | 47.932 | 43.934 | 8.950 | 1.00 | 16.34 |
| ATOM | 3624 | ND1 | HIS | B | 238 | 48.172 | 42.702 | 8.380 | 1.00 | 17.77 |
| ATOM | 3625 | CE1 | HIS | B | 238 | 48.718 | 42.877 | 7.191 | 1.00 | 19.98 |
| ATOM | 3626 | NE2 | HIS | B | 238 | 48.826 | 44.176 | 6.966 | 1.00 | 20.31 |
| ATOM | 3627 | CD2 | HIS | B | 238 | 48.331 | 44.859 | 8.048 | 1.00 | 18.37 |
| ATOM | 3628 | C | HIS | B | 238 | 45.470 | 43.392 | 11.795 | 1.00 | 12.20 |
| ATOM | 3629 | O | HIS | B | 238 | 45.637 | 42.375 | 12.467 | 1.00 | 12.69 |
| ATOM | 3630 | N | LEU | B | 239 | 44.893 | 44.490 | 12.271 | 1.00 | 12.45 |
| ATOM | 3631 | CA | LEU | B | 239 | 44.407 | 44.502 | 13.632 | 1.00 | 12.24 |
| ATOM | 3632 | CB | LEU | B | 239 | 44.053 | 45.898 | 14.119 | 1.00 | 13.26 |
| ATOM | 3633 | CG | LEU | B | 239 | 44.026 | 46.021 | 15.657 | 1.00 | 18.81 |
| ATOM | 3634 | CD1 | LEU | B | 239 | 45.123 | 45.221 | 16.397 | 1.00 | 17.71 |
| ATOM | 3635 | CD2 | LEU | B | 239 | 44.059 | 47.473 | 16.107 | 1.00 | 20.71 |
| ATOM | 3636 | C | LEU | B | 239 | 43.242 | 43.555 | 13.767 | 1.00 | 12.24 |
| ATOM | 3637 | O | LEU | B | 239 | 43.148 | 42.859 | 14.758 | 1.00 | 15.41 |
| ATOM | 3638 | N | SER | B | 240 | 42.393 | 43.476 | 12.750 | 1.00 | 13.36 |
| ATOM | 3639 | CA | SER | B | 240 | 41.257 | 42.568 | 12.802 | 1.00 | 13.98 |
| ATOM | 3640 | CB | SER | B | 240 | 40.257 | 42.886 | 11.705 | 1.00 | 14.45 |
| ATOM | 3641 | OG | SER | B | 240 | 39.239 | 43.717 | 12.234 | 1.00 | 17.74 |
| ATOM | 3642 | C | SER | B | 240 | 41.672 | 41.106 | 12.759 | 1.00 | 17.75 |
| ATOM | 3643 | O | SER | B | 240 | 41.177 | 40.299 | 13.546 | 1.00 | 18.66 |
| ATOM | 3644 | N | ARG | B | 241 | 42.592 | 40.781 | 11.853 | 1.00 | 23.18 |
| ATOM | 3645 | CA | ARG | B | 241 | 43.134 | 39.428 | 11.704 | 1.00 | 25.44 |
| ATOM | 3646 | CB | ARG | B | 241 | 44.011 | 39.350 | 10.445 | 1.00 | 28.42 |
| ATOM | 3647 | CG | ARG | B | 241 | 43.611 | 38.290 | 9.401 | 1.00 | 34.89 |
| ATOM | 3648 | CD | ARG | B | 241 | 42.112 | 37.968 | 9.317 | 1.00 | 38.95 |
| ATOM | 3649 | NE | ARG | B | 241 | 41.447 | 38.556 | 8.148 | 1.00 | 41.44 |
| ATOM | 3650 | CZ | ARG | B | 241 | 41.003 | 39.814 | 8.069 | 1.00 | 40.91 |
| ATOM | 3651 | NH1 | ARG | B | 241 | 41.153 | 40.654 | 9.087 | 1.00 | 41.21 |
| ATOM | 3652 | NH2 | ARG | B | 241 | 40.401 | 40.234 | 6.963 | 1.00 | 39.49 |
| ATOM | 3653 | C | ARG | B | 241 | 43.927 | 38.961 | 12.934 | 1.00 | 25.59 |
| ATOM | 3654 | O | ARG | B | 241 | 43.706 | 37.862 | 13.438 | 1.00 | 24.73 |
| ATOM | 3655 | N | GLU | B | 242 | 44.831 | 39.809 | 13.422 | 1.00 | 27.86 |
| ATOM | 3656 | CA | GLU | B | 242 | 45.775 | 39.423 | 14.472 | 1.00 | 29.22 |
| ATOM | 3657 | CB | GLU | B | 242 | 47.192 | 39.939 | 14.132 | 1.00 | 32.42 |
| ATOM | 3658 | CG | GLU | B | 242 | 48.074 | 38.930 | 13.379 | 1.00 | 38.65 |
| ATOM | 3659 | CD | GLU | B | 242 | 48.236 | 39.197 | 11.867 | 1.00 | 43.26 |
| ATOM | 3660 | OE1 | GLU | B | 242 | 48.752 | 40.283 | 11.484 | 1.00 | 45.59 |
| ATOM | 3661 | OE2 | GLU | B | 242 | 47.884 | 38.303 | 11.047 | 1.00 | 41.56 |
| ATOM | 3662 | C | GLU | B | 242 | 45.312 | 39.811 | 15.893 | 1.00 | 26.73 |
| ATOM | 3663 | O | GLU | B | 242 | 46.004 | 39.540 | 16.879 | 1.00 | 25.63 |
| ATOM | 3664 | N | ARG | B | 243 | 44.133 | 40.428 | 15.982 | 1.00 | 25.04 |
| ATOM | 3665 | CA | ARG | B | 243 | 43.449 | 40.724 | 17.257 | 1.00 | 26.42 |
| ATOM | 3666 | CB | ARG | B | 243 | 43.157 | 39.430 | 18.031 | 1.00 | 33.23 |
| ATOM | 3667 | CG | ARG | B | 243 | 42.671 | 39.588 | 19.479 | 1.00 | 40.89 |
| ATOM | 3668 | CD | ARG | B | 243 | 43.052 | 38.398 | 20.393 | 1.00 | 45.42 |
| ATOM | 3669 | NE | ARG | B | 243 | 44.511 | 38.250 | 20.512 | 1.00 | 46.45 |

FIGURE 3 (Cont.)

| | A | B | C | D | E | F | G | H | I | J |
|---|---|---|---|---|---|---|---|---|---|---|
| ATOM | 3670 | CZ  | ARG | B | 243 | 45.163 | 37.098 | 20.654 | 1.00 | 43.99 |
| ATOM | 3671 | NH1 | ARG | B | 243 | 44.505 | 35.943 | 20.705 | 1.00 | 42.91 |
| ATOM | 3672 | NH2 | ARG | B | 243 | 46.486 | 37.110 | 20.751 | 1.00 | 43.20 |
| ATOM | 3673 | C   | ARG | B | 243 | 44.087 | 41.817 | 18.145 | 1.00 | 23.60 |
| ATOM | 3674 | O   | ARG | B | 243 | 43.430 | 42.823 | 18.456 | 1.00 | 20.86 |
| ATOM | 3675 | N   | VAL | B | 244 | 45.347 | 41.640 | 18.549 | 1.00 | 20.80 |
| ATOM | 3676 | CA  | VAL | B | 244 | 46.065 | 42.714 | 19.275 | 1.00 | 17.32 |
| ATOM | 3677 | CB  | VAL | B | 244 | 45.764 | 42.675 | 20.788 | 1.00 | 13.75 |
| ATOM | 3678 | CG1 | VAL | B | 244 | 45.957 | 41.277 | 21.334 | 1.00 | 14.89 |
| ATOM | 3679 | CG2 | VAL | B | 244 | 46.627 | 43.651 | 21.519 | 1.00 | 14.53 |
| ATOM | 3680 | C   | VAL | B | 244 | 47.594 | 42.798 | 19.016 | 1.00 | 12.92 |
| ATOM | 3681 | O   | VAL | B | 244 | 48.306 | 41.813 | 19.148 | 1.00 | 12.72 |
| ATOM | 3682 | N   | PHE | B | 245 | 48.077 | 43.978 | 18.640 | 1.00 | 8.85 |
| ATOM | 3683 | CA  | PHE | B | 245 | 49.492 | 44.176 | 18.359 | 1.00 | 7.43 |
| ATOM | 3684 | CB  | PHE | B | 245 | 49.733 | 45.523 | 17.693 | 1.00 | 6.03 |
| ATOM | 3685 | CG  | PHE | B | 245 | 49.151 | 45.643 | 16.329 | 1.00 | 7.92 |
| ATOM | 3686 | CD1 | PHE | B | 245 | 48.698 | 44.516 | 15.636 | 1.00 | 8.46 |
| ATOM | 3687 | CE1 | PHE | B | 245 | 48.147 | 44.639 | 14.357 | 1.00 | 8.66 |
| ATOM | 3688 | CZ  | PHE | B | 245 | 48.049 | 45.907 | 13.764 | 1.00 | 10.44 |
| ATOM | 3689 | CE2 | PHE | B | 245 | 48.505 | 47.042 | 14.453 | 1.00 | 10.03 |
| ATOM | 3690 | CD2 | PHE | B | 245 | 49.051 | 46.898 | 15.726 | 1.00 | 9.11 |
| ATOM | 3691 | C   | PHE | B | 245 | 50.298 | 44.154 | 19.635 | 1.00 | 8.25 |
| ATOM | 3692 | O   | PHE | B | 245 | 49.844 | 44.657 | 20.658 | 1.00 | 10.25 |
| ATOM | 3693 | N   | SER | B | 246 | 51.496 | 43.574 | 19.565 | 1.00 | 9.03 |
| ATOM | 3694 | CA  | SER | B | 246 | 52.469 | 43.687 | 20.636 | 1.00 | 10.64 |
| ATOM | 3695 | CB  | SER | B | 246 | 53.743 | 42.933 | 20.275 | 1.00 | 12.32 |
| ATOM | 3696 | OG  | SER | B | 246 | 54.700 | 43.797 | 19.673 | 1.00 | 11.12 |
| ATOM | 3697 | C   | SER | B | 246 | 52.789 | 45.163 | 20.829 | 1.00 | 12.93 |
| ATOM | 3698 | O   | SER | B | 246 | 52.749 | 45.943 | 19.875 | 1.00 | 11.65 |
| ATOM | 3699 | N   | GLU | B | 247 | 53.116 | 45.535 | 22.062 | 1.00 | 16.52 |
| ATOM | 3700 | CA  | GLU | B | 247 | 53.413 | 46.926 | 22.403 | 1.00 | 18.36 |
| ATOM | 3701 | CB  | GLU | B | 247 | 53.854 | 47.031 | 23.862 | 1.00 | 20.57 |
| ATOM | 3702 | CG  | GLU | B | 247 | 52.992 | 47.959 | 24.689 | 1.00 | 24.45 |
| ATOM | 3703 | CD  | GLU | B | 247 | 53.340 | 47.917 | 26.168 | 1.00 | 29.43 |
| ATOM | 3704 | OE1 | GLU | B | 247 | 54.418 | 48.466 | 26.545 | 1.00 | 29.97 |
| ATOM | 3705 | OE2 | GLU | B | 247 | 52.531 | 47.337 | 26.946 | 1.00 | 28.87 |
| ATOM | 3706 | C   | GLU | B | 247 | 54.452 | 47.578 | 21.485 | 1.00 | 19.59 |
| ATOM | 3707 | O   | GLU | B | 247 | 54.296 | 48.735 | 21.107 | 1.00 | 20.59 |
| ATOM | 3708 | N   | ASP | B | 248 | 55.506 | 46.845 | 21.132 | 1.00 | 22.07 |
| ATOM | 3709 | CA  | ASP | B | 248 | 56.562 | 47.392 | 20.286 | 1.00 | 25.41 |
| ATOM | 3710 | CB  | ASP | B | 248 | 57.833 | 46.533 | 20.315 | 1.00 | 31.95 |
| ATOM | 3711 | CG  | ASP | B | 248 | 58.297 | 46.200 | 21.738 | 1.00 | 38.78 |
| ATOM | 3712 | OD1 | ASP | B | 248 | 59.536 | 46.143 | 21.969 | 1.00 | 41.91 |
| ATOM | 3713 | OD2 | ASP | B | 248 | 57.500 | 45.961 | 22.682 | 1.00 | 41.40 |
| ATOM | 3714 | C   | ASP | B | 248 | 56.043 | 47.545 | 18.864 | 1.00 | 25.21 |
| ATOM | 3715 | O   | ASP | B | 248 | 56.320 | 48.553 | 18.209 | 1.00 | 27.38 |
| ATOM | 3716 | N   | ARG | B | 249 | 55.272 | 46.562 | 18.392 | 1.00 | 21.04 |
| ATOM | 3717 | CA  | ARG | B | 249 | 54.624 | 46.687 | 17.094 | 1.00 | 16.48 |
| ATOM | 3718 | CB  | ARG | B | 249 | 53.726 | 45.491 | 16.787 | 1.00 | 20.73 |
| ATOM | 3719 | CG  | ARG | B | 249 | 52.761 | 45.695 | 15.606 | 1.00 | 24.52 |
| ATOM | 3720 | CD  | ARG | B | 249 | 53.272 | 45.179 | 14.265 | 1.00 | 26.01 |
| ATOM | 3721 | NE  | ARG | B | 249 | 52.216 | 44.631 | 13.412 | 1.00 | 26.55 |

FIGURE 3 (Cont.)

| | A | B | C | D | E | F | G | H | I | J |
|---|---|---|---|---|---|---|---|---|---|---|
| ATOM | 3722 | CZ | ARG | B | 249 | 52.005 | 43.331 | 13.232 | 1.00 | 29.09 |
| ATOM | 3723 | NH1 | ARG | B | 249 | 52.769 | 42.434 | 13.853 | 1.00 | 29.90 |
| ATOM | 3724 | NH2 | ARG | B | 249 | 51.029 | 42.921 | 12.429 | 1.00 | 28.91 |
| ATOM | 3725 | C | ARG | B | 249 | 53.828 | 47.977 | 17.090 | 1.00 | 12.59 |
| ATOM | 3726 | O | ARG | B | 249 | 53.955 | 48.773 | 16.172 | 1.00 | 15.67 |
| ATOM | 3727 | N | ALA | B | 250 | 53.035 | 48.198 | 18.133 | 1.00 | 9.24 |
| ATOM | 3728 | CA | ALA | B | 250 | 52.304 | 49.456 | 18.270 | 1.00 | 6.86 |
| ATOM | 3729 | CB | ALA | B | 250 | 51.380 | 49.434 | 19.470 | 1.00 | 3.36 |
| ATOM | 3730 | C | ALA | B | 250 | 53.245 | 50.649 | 18.334 | 1.00 | 6.78 |
| ATOM | 3731 | O | ALA | B | 250 | 53.075 | 51.600 | 17.577 | 1.00 | 9.97 |
| ATOM | 3732 | N | ARG | B | 251 | 54.249 | 50.595 | 19.206 | 1.00 | 6.67 |
| ATOM | 3733 | CA | ARG | B | 251 | 55.145 | 51.736 | 19.385 | 1.00 | 9.26 |
| ATOM | 3734 | CB | ARG | B | 251 | 56.273 | 51.427 | 20.379 | 1.00 | 8.88 |
| ATOM | 3735 | CG | ARG | B | 251 | 57.471 | 52.401 | 20.316 | 1.00 | 7.32 |
| ATOM | 3736 | CD | ARG | B | 251 | 58.390 | 52.375 | 21.528 | 1.00 | 8.86 |
| ATOM | 3737 | NE | ARG | B | 251 | 58.726 | 51.014 | 21.939 | 1.00 | 10.26 |
| ATOM | 3738 | CZ | ARG | B | 251 | 58.267 | 50.425 | 23.040 | 1.00 | 9.71 |
| ATOM | 3739 | NH1 | ARG | B | 251 | 57.448 | 51.073 | 23.862 | 1.00 | 11.36 |
| ATOM | 3740 | NH2 | ARG | B | 251 | 58.624 | 49.180 | 23.322 | 1.00 | 7.85 |
| ATOM | 3741 | C | ARG | B | 251 | 55.712 | 52.188 | 18.044 | 1.00 | 10.47 |
| ATOM | 3742 | O | ARG | B | 251 | 55.872 | 53.388 | 17.806 | 1.00 | 10.48 |
| ATOM | 3743 | N | PHE | B | 252 | 55.992 | 51.215 | 17.177 | 1.00 | 10.75 |
| ATOM | 3744 | CA | PHE | B | 252 | 56.560 | 51.477 | 15.860 | 1.00 | 12.79 |
| ATOM | 3745 | CB | PHE | B | 252 | 56.930 | 50.160 | 15.173 | 1.00 | 13.58 |
| ATOM | 3746 | CG | PHE | B | 252 | 57.263 | 50.304 | 13.716 | 1.00 | 15.85 |
| ATOM | 3747 | CD1 | PHE | B | 252 | 58.586 | 50.358 | 13.300 | 1.00 | 16.32 |
| ATOM | 3748 | CE1 | PHE | B | 252 | 58.906 | 50.487 | 11.959 | 1.00 | 15.62 |
| ATOM | 3749 | CZ | PHE | B | 252 | 57.894 | 50.554 | 11.011 | 1.00 | 16.06 |
| ATOM | 3750 | CE2 | PHE | B | 252 | 56.567 | 50.498 | 11.412 | 1.00 | 17.32 |
| ATOM | 3751 | CD2 | PHE | B | 252 | 56.256 | 50.368 | 12.757 | 1.00 | 16.07 |
| ATOM | 3752 | C | PHE | B | 252 | 55.569 | 52.267 | 15.018 | 1.00 | 13.87 |
| ATOM | 3753 | O | PHE | B | 252 | 55.872 | 53.378 | 14.578 | 1.00 | 15.18 |
| ATOM | 3754 | N | TYR | B | 253 | 54.386 | 51.686 | 14.814 | 1.00 | 11.93 |
| ATOM | 3755 | CA | TYR | B | 253 | 53.319 | 52.332 | 14.066 | 1.00 | 11.73 |
| ATOM | 3756 | CB | TYR | B | 253 | 52.051 | 51.451 | 14.022 | 1.00 | 12.04 |
| ATOM | 3757 | CG | TYR | B | 253 | 52.191 | 50.173 | 13.204 | 1.00 | 11.95 |
| ATOM | 3758 | CD1 | TYR | B | 253 | 52.843 | 50.170 | 11.976 | 1.00 | 13.55 |
| ATOM | 3759 | CE1 | TYR | B | 253 | 52.984 | 49.008 | 11.224 | 1.00 | 15.10 |
| ATOM | 3760 | CZ | TYR | B | 253 | 52.459 | 47.821 | 11.692 | 1.00 | 16.33 |
| ATOM | 3761 | OH | TYR | B | 253 | 52.595 | 46.660 | 10.933 | 1.00 | 16.01 |
| ATOM | 3762 | CE2 | TYR | B | 253 | 51.796 | 47.804 | 12.914 | 1.00 | 14.88 |
| ATOM | 3763 | CD2 | TYR | B | 253 | 51.669 | 48.974 | 13.660 | 1.00 | 11.99 |
| ATOM | 3764 | C | TYR | B | 253 | 53.031 | 53.723 | 14.639 | 1.00 | 10.93 |
| ATOM | 3765 | O | TYR | B | 253 | 52.960 | 54.700 | 13.892 | 1.00 | 11.26 |
| ATOM | 3766 | N | GLY | B | 254 | 52.910 | 53.811 | 15.962 | 1.00 | 9.60 |
| ATOM | 3767 | CA | GLY | B | 254 | 52.648 | 55.075 | 16.626 | 1.00 | 8.49 |
| ATOM | 3768 | C | GLY | B | 254 | 53.728 | 56.102 | 16.331 | 1.00 | 9.75 |
| ATOM | 3769 | O | GLY | B | 254 | 53.448 | 57.268 | 16.086 | 1.00 | 7.16 |
| ATOM | 3770 | N | ALA | B | 255 | 54.976 | 55.660 | 16.342 | 1.00 | 11.39 |
| ATOM | 3771 | CA | ALA | B | 255 | 56.088 | 56.566 | 16.140 | 1.00 | 13.46 |
| ATOM | 3772 | CB | ALA | B | 255 | 57.407 | 55.840 | 16.346 | 1.00 | 16.28 |
| ATOM | 3773 | C | ALA | B | 255 | 56.015 | 57.167 | 14.749 | 1.00 | 16.98 |

FIGURE 3 (Cont.)

|  | A | B | C | D | E | F | G | H | I | J |
|---|---|---|---|---|---|---|---|---|---|---|
| ATOM | 3774 | O | ALA | B | 255 | 56.149 | 58.387 | 14.595 | 1.00 | 19.71 |
| ATOM | 3775 | N | GLU | B | 256 | 55.789 | 56.317 | 13.741 | 1.00 | 16.99 |
| ATOM | 3776 | CA | GLU | B | 256 | 55.700 | 56.782 | 12.356 | 1.00 | 15.53 |
| ATOM | 3777 | CB | GLU | B | 256 | 55.694 | 55.631 | 11.346 | 1.00 | 16.03 |
| ATOM | 3778 | CG | GLU | B | 256 | 56.682 | 54.518 | 11.667 | 1.00 | 21.98 |
| ATOM | 3779 | CD | GLU | B | 256 | 57.471 | 54.020 | 10.461 | 1.00 | 24.51 |
| ATOM | 3780 | OE1 | GLU | B | 256 | 56.871 | 53.325 | 9.606 | 1.00 | 24.45 |
| ATOM | 3781 | OE2 | GLU | B | 256 | 58.699 | 54.298 | 10.380 | 1.00 | 25.10 |
| ATOM | 3782 | C | GLU | B | 256 | 54.476 | 57.668 | 12.193 | 1.00 | 15.45 |
| ATOM | 3783 | O | GLU | B | 256 | 54.541 | 58.671 | 11.490 | 1.00 | 17.96 |
| ATOM | 3784 | N | ILE | B | 257 | 53.377 | 57.314 | 12.861 | 1.00 | 11.95 |
| ATOM | 3785 | CA | ILE | B | 257 | 52.176 | 58.148 | 12.858 | 1.00 | 11.20 |
| ATOM | 3786 | CB | ILE | B | 257 | 51.000 | 57.455 | 13.613 | 1.00 | 10.84 |
| ATOM | 3787 | CG1 | ILE | B | 257 | 50.575 | 56.177 | 12.892 | 1.00 | 12.72 |
| ATOM | 3788 | CD1 | ILE | B | 257 | 49.644 | 55.301 | 13.704 | 1.00 | 13.50 |
| ATOM | 3789 | CG2 | ILE | B | 257 | 49.789 | 58.376 | 13.747 | 1.00 | 5.24 |
| ATOM | 3790 | C | ILE | B | 257 | 52.499 | 59.522 | 13.453 | 1.00 | 11.67 |
| ATOM | 3791 | O | ILE | B | 257 | 52.212 | 60.557 | 12.829 | 1.00 | 12.09 |
| ATOM | 3792 | N | VAL | B | 258 | 53.109 | 59.516 | 14.642 | 1.00 | 10.87 |
| ATOM | 3793 | CA | VAL | B | 258 | 53.482 | 60.737 | 15.355 | 1.00 | 11.46 |
| ATOM | 3794 | CB | VAL | B | 258 | 54.181 | 60.448 | 16.717 | 1.00 | 13.08 |
| ATOM | 3795 | CG1 | VAL | B | 258 | 54.782 | 61.725 | 17.320 | 1.00 | 11.32 |
| ATOM | 3796 | CG2 | VAL | B | 258 | 53.233 | 59.788 | 17.712 | 1.00 | 11.37 |
| ATOM | 3797 | C | VAL | B | 258 | 54.428 | 61.537 | 14.485 | 1.00 | 13.06 |
| ATOM | 3798 | O | VAL | B | 258 | 54.381 | 62.768 | 14.476 | 1.00 | 17.71 |
| ATOM | 3799 | N | SER | B | 259 | 55.281 | 60.842 | 13.741 | 1.00 | 11.90 |
| ATOM | 3800 | CA | SER | B | 259 | 56.160 | 61.528 | 12.805 | 1.00 | 13.92 |
| ATOM | 3801 | CB | SER | B | 259 | 57.045 | 60.539 | 12.056 | 1.00 | 14.45 |
| ATOM | 3802 | OG | SER | B | 259 | 57.933 | 61.235 | 11.202 | 1.00 | 15.85 |
| ATOM | 3803 | C | SER | B | 259 | 55.367 | 62.379 | 11.812 | 1.00 | 13.33 |
| ATOM | 3804 | O | SER | B | 259 | 55.593 | 63.586 | 11.707 | 1.00 | 13.14 |
| ATOM | 3805 | N | ALA | B | 260 | 54.421 | 61.734 | 11.125 | 1.00 | 12.38 |
| ATOM | 3806 | CA | ALA | B | 260 | 53.659 | 62.324 | 10.025 | 1.00 | 9.41 |
| ATOM | 3807 | CB | ALA | B | 260 | 52.852 | 61.253 | 9.321 | 1.00 | 8.75 |
| ATOM | 3808 | C | ALA | B | 260 | 52.751 | 63.449 | 10.475 | 1.00 | 10.35 |
| ATOM | 3809 | O | ALA | B | 260 | 52.697 | 64.497 | 9.821 | 1.00 | 4.53 |
| ATOM | 3810 | N | LEU | B | 261 | 52.034 | 63.208 | 11.580 | 1.00 | 13.29 |
| ATOM | 3811 | CA | LEU | B | 261 | 51.186 | 64.213 | 12.230 | 1.00 | 16.38 |
| ATOM | 3812 | CB | LEU | B | 261 | 50.461 | 63.620 | 13.437 | 1.00 | 20.28 |
| ATOM | 3813 | CG | LEU | B | 261 | 49.305 | 62.650 | 13.190 | 1.00 | 24.47 |
| ATOM | 3814 | CD1 | LEU | B | 261 | 49.069 | 61.799 | 14.433 | 1.00 | 25.71 |
| ATOM | 3815 | CD2 | LEU | B | 261 | 48.028 | 63.383 | 12.807 | 1.00 | 25.27 |
| ATOM | 3816 | C | LEU | B | 261 | 51.968 | 65.452 | 12.674 | 1.00 | 16.26 |
| ATOM | 3817 | O | LEU | B | 261 | 51.479 | 66.580 | 12.556 | 1.00 | 15.70 |
| ATOM | 3818 | N | ASP | B | 262 | 53.177 | 65.248 | 13.186 | 1.00 | 16.35 |
| ATOM | 3819 | CA | ASP | B | 262 | 54.037 | 66.377 | 13.481 | 1.00 | 19.99 |
| ATOM | 3820 | CB | ASP | B | 262 | 55.360 | 65.929 | 14.103 | 1.00 | 26.16 |
| ATOM | 3821 | CG | ASP | B | 262 | 56.248 | 67.112 | 14.487 | 1.00 | 33.46 |
| ATOM | 3822 | OD1 | ASP | B | 262 | 57.440 | 67.125 | 14.103 | 1.00 | 36.25 |
| ATOM | 3823 | OD2 | ASP | B | 262 | 55.834 | 68.092 | 15.154 | 1.00 | 36.48 |
| ATOM | 3824 | C | ASP | B | 262 | 54.285 | 67.221 | 12.220 | 1.00 | 18.68 |
| ATOM | 3825 | O | ASP | B | 262 | 54.294 | 68.453 | 12.283 | 1.00 | 18.21 |

FIGURE 3 (Cont.)

| | A | B | C | D | E | F | G | H | I | J |
|---|---|---|---|---|---|---|---|---|---|---|
| ATOM | 3826 | N | TYR | B | 263 | 54.464 | 66.551 | 11.081 | 1.00 | 17.48 |
| ATOM | 3827 | CA | TYR | B | 263 | 54.758 | 67.219 | 9.809 | 1.00 | 15.05 |
| ATOM | 3828 | CB | TYR | B | 263 | 55.132 | 66.190 | 8.738 | 1.00 | 15.69 |
| ATOM | 3829 | CG | TYR | B | 263 | 55.120 | 66.690 | 7.301 | 1.00 | 14.80 |
| ATOM | 3830 | CD1 | TYR | B | 263 | 56.275 | 67.195 | 6.704 | 1.00 | 15.24 |
| ATOM | 3831 | CE1 | TYR | B | 263 | 56.272 | 67.636 | 5.373 | 1.00 | 13.92 |
| ATOM | 3832 | CZ | TYR | B | 263 | 55.102 | 67.565 | 4.636 | 1.00 | 12.27 |
| ATOM | 3833 | OH | TYR | B | 263 | 55.075 | 67.993 | 3.334 | 1.00 | 9.40 |
| ATOM | 3834 | CE2 | TYR | B | 263 | 53.949 | 67.061 | 5.207 | 1.00 | 13.72 |
| ATOM | 3835 | CD2 | TYR | B | 263 | 53.964 | 66.620 | 6.527 | 1.00 | 14.46 |
| ATOM | 3836 | C | TYR | B | 263 | 53.603 | 68.086 | 9.336 | 1.00 | 11.49 |
| ATOM | 3837 | O | TYR | B | 263 | 53.830 | 69.195 | 8.866 | 1.00 | 10.76 |
| ATOM | 3838 | N | LEU | B | 264 | 52.381 | 67.565 | 9.461 | 1.00 | 7.44 |
| ATOM | 3839 | CA | LEU | B | 264 | 51.177 | 68.272 | 9.047 | 1.00 | 6.41 |
| ATOM | 3840 | CB | LEU | B | 264 | 49.980 | 67.324 | 8.965 | 1.00 | 5.17 |
| ATOM | 3841 | CG | LEU | B | 264 | 50.126 | 66.107 | 8.047 | 1.00 | 4.42 |
| ATOM | 3842 | CD1 | LEU | B | 264 | 49.436 | 64.900 | 8.658 | 1.00 | 4.41 |
| ATOM | 3843 | CD2 | LEU | B | 264 | 49.581 | 66.396 | 6.659 | 1.00 | 2.79 |
| ATOM | 3844 | C | LEU | B | 264 | 50.866 | 69.424 | 9.986 | 1.00 | 9.34 |
| ATOM | 3845 | O | LEU | B | 264 | 50.503 | 70.514 | 9.530 | 1.00 | 8.84 |
| ATOM | 3846 | N | HIS | B | 265 | 51.021 | 69.192 | 11.291 | 1.00 | 12.24 |
| ATOM | 3847 | CA | HIS | B | 265 | 50.812 | 70.253 | 12.279 | 1.00 | 15.69 |
| ATOM | 3848 | CB | HIS | B | 265 | 50.942 | 69.724 | 13.693 | 1.00 | 15.73 |
| ATOM | 3849 | CG | HIS | B | 265 | 49.743 | 68.976 | 14.166 | 1.00 | 18.99 |
| ATOM | 3850 | ND1 | HIS | B | 265 | 49.481 | 68.762 | 15.502 | 1.00 | 19.56 |
| ATOM | 3851 | CE1 | HIS | B | 265 | 48.364 | 68.065 | 15.620 | 1.00 | 21.56 |
| ATOM | 3852 | NE2 | HIS | B | 265 | 47.891 | 67.821 | 14.410 | 1.00 | 21.71 |
| ATOM | 3853 | CD2 | HIS | B | 265 | 48.736 | 68.380 | 13.482 | 1.00 | 20.73 |
| ATOM | 3854 | C | HIS | B | 265 | 51.761 | 71.424 | 12.095 | 1.00 | 17.80 |
| ATOM | 3855 | O | HIS | B | 265 | 51.413 | 72.551 | 12.429 | 1.00 | 18.90 |
| ATOM | 3856 | N | SER | B | 266 | 52.953 | 71.146 | 11.571 | 1.00 | 20.25 |
| ATOM | 3857 | CA | SER | B | 266 | 53.938 | 72.182 | 11.261 | 1.00 | 22.04 |
| ATOM | 3858 | CB | SER | B | 266 | 55.338 | 71.591 | 11.155 | 1.00 | 22.97 |
| ATOM | 3859 | OG | SER | B | 266 | 55.662 | 70.896 | 12.340 | 1.00 | 26.79 |
| ATOM | 3860 | C | SER | B | 266 | 53.607 | 72.911 | 9.975 | 1.00 | 22.21 |
| ATOM | 3861 | O | SER | B | 266 | 53.963 | 74.076 | 9.830 | 1.00 | 22.23 |
| ATOM | 3862 | N | ARG | B | 267 | 52.948 | 72.218 | 9.043 | 1.00 | 22.84 |
| ATOM | 3863 | CA | ARG | B | 267 | 52.465 | 72.837 | 7.803 | 1.00 | 24.70 |
| ATOM | 3864 | CB | ARG | B | 267 | 52.504 | 71.861 | 6.612 | 1.00 | 24.20 |
| ATOM | 3865 | CG | ARG | B | 267 | 53.859 | 71.205 | 6.320 | 1.00 | 24.57 |
| ATOM | 3866 | CD | ARG | B | 267 | 54.696 | 71.860 | 5.223 | 1.00 | 26.75 |
| ATOM | 3867 | NE | ARG | B | 267 | 54.068 | 71.823 | 3.902 | 1.00 | 28.96 |
| ATOM | 3868 | CZ | ARG | B | 267 | 54.688 | 72.117 | 2.755 | 1.00 | 31.17 |
| ATOM | 3869 | NH1 | ARG | B | 267 | 55.974 | 72.466 | 2.738 | 1.00 | 31.08 |
| ATOM | 3870 | NH2 | ARG | B | 267 | 54.018 | 72.061 | 1.612 | 1.00 | 31.93 |
| ATOM | 3871 | C | ARG | B | 267 | 51.050 | 73.401 | 8.002 | 1.00 | 26.83 |
| ATOM | 3872 | O | ARG | B | 267 | 50.373 | 73.790 | 7.037 | 1.00 | 26.30 |
| ATOM | 3873 | N | ASP | B | 268 | 50.616 | 73.431 | 9.264 | 1.00 | 28.62 |
| ATOM | 3874 | CA | ASP | B | 268 | 49.358 | 74.064 | 9.677 | 1.00 | 29.79 |
| ATOM | 3875 | CB | ASP | B | 268 | 49.197 | 75.445 | 9.025 | 1.00 | 31.20 |
| ATOM | 3876 | CG | ASP | B | 268 | 50.113 | 76.491 | 9.635 | 1.00 | 33.22 |
| ATOM | 3877 | OD1 | ASP | B | 268 | 50.358 | 76.424 | 10.861 | 1.00 | 33.13 |

FIGURE 3 (Cont.)

| | A | B | C | D | E | F | G | H | I | J |
|---|---|---|---|---|---|---|---|---|---|---|
| ATOM | 3878 | OD2 | ASP | B | 268 | 50.626 | 77.422 | 8.966 | 1.00 | 35.06 |
| ATOM | 3879 | C | ASP | B | 268 | 48.113 | 73.215 | 9.428 | 1.00 | 28.67 |
| ATOM | 3880 | O | ASP | B | 268 | 46.992 | 73.643 | 9.715 | 1.00 | 29.73 |
| ATOM | 3881 | N | VAL | B | 269 | 48.317 | 72.013 | 8.901 | 1.00 | 25.09 |
| ATOM | 3882 | CA | VAL | B | 269 | 47.216 | 71.121 | 8.585 | 1.00 | 21.13 |
| ATOM | 3883 | CB | VAL | B | 269 | 47.597 | 70.122 | 7.480 | 1.00 | 20.59 |
| ATOM | 3884 | CG1 | VAL | B | 269 | 46.391 | 69.296 | 7.064 | 1.00 | 20.48 |
| ATOM | 3885 | CG2 | VAL | B | 269 | 48.187 | 70.846 | 6.280 | 1.00 | 21.56 |
| ATOM | 3886 | C | VAL | B | 269 | 46.835 | 70.344 | 9.824 | 1.00 | 20.15 |
| ATOM | 3887 | O | VAL | B | 269 | 47.710 | 69.838 | 10.530 | 1.00 | 23.42 |
| ATOM | 3888 | N | VAL | B | 270 | 45.536 | 70.253 | 10.093 | 1.00 | 16.48 |
| ATOM | 3889 | CA | VAL | B | 270 | 45.034 | 69.315 | 11.095 | 1.00 | 14.10 |
| ATOM | 3890 | CB | VAL | B | 270 | 44.104 | 69.999 | 12.100 | 1.00 | 12.84 |
| ATOM | 3891 | CG1 | VAL | B | 270 | 43.569 | 68.993 | 13.113 | 1.00 | 11.27 |
| ATOM | 3892 | CG2 | VAL | B | 270 | 44.849 | 71.116 | 12.802 | 1.00 | 11.59 |
| ATOM | 3893 | C | VAL | B | 270 | 44.351 | 68.148 | 10.372 | 1.00 | 13.41 |
| ATOM | 3894 | O | VAL | B | 270 | 43.500 | 68.371 | 9.496 | 1.00 | 13.88 |
| ATOM | 3895 | N | TYR | B | 271 | 44.743 | 66.916 | 10.717 | 1.00 | 8.60 |
| ATOM | 3896 | CA | TYR | B | 271 | 44.361 | 65.769 | 9.911 | 1.00 | 6.61 |
| ATOM | 3897 | CB | TYR | B | 271 | 45.191 | 64.555 | 10.211 | 1.00 | 6.33 |
| ATOM | 3898 | CG | TYR | B | 271 | 44.714 | 63.318 | 9.478 | 1.00 | 9.70 |
| ATOM | 3899 | CD1 | TYR | B | 271 | 44.680 | 63.271 | 8.082 | 1.00 | 8.67 |
| ATOM | 3900 | CE1 | TYR | B | 271 | 44.250 | 62.128 | 7.417 | 1.00 | 9.99 |
| ATOM | 3901 | CZ | TYR | B | 271 | 43.857 | 61.013 | 8.154 | 1.00 | 10.62 |
| ATOM | 3902 | OH | TYR | B | 271 | 43.435 | 59.873 | 7.516 | 1.00 | 11.89 |
| ATOM | 3903 | CE2 | TYR | B | 271 | 43.887 | 61.030 | 9.534 | 1.00 | 9.27 |
| ATOM | 3904 | CD2 | TYR | B | 271 | 44.306 | 62.178 | 10.187 | 1.00 | 11.18 |
| ATOM | 3905 | C | TYR | B | 271 | 42.920 | 65.442 | 10.110 | 1.00 | 8.64 |
| ATOM | 3906 | O | TYR | B | 271 | 42.176 | 65.317 | 9.136 | 1.00 | 14.24 |
| ATOM | 3907 | N | ARG | B | 272 | 42.540 | 65.276 | 11.369 | 1.00 | 8.63 |
| ATOM | 3908 | CA | ARG | B | 272 | 41.139 | 65.364 | 11.771 | 1.00 | 10.79 |
| ATOM | 3909 | CB | ARG | B | 272 | 40.489 | 66.581 | 11.112 | 1.00 | 8.64 |
| ATOM | 3910 | CG | ARG | B | 272 | 39.812 | 67.526 | 12.048 | 1.00 | 8.05 |
| ATOM | 3911 | CD | ARG | B | 272 | 38.499 | 68.043 | 11.508 | 1.00 | 8.63 |
| ATOM | 3912 | NE | ARG | B | 272 | 38.660 | 68.690 | 10.208 | 1.00 | 7.20 |
| ATOM | 3913 | CZ | ARG | B | 272 | 38.070 | 69.825 | 9.846 | 1.00 | 5.40 |
| ATOM | 3914 | NH1 | ARG | B | 272 | 37.255 | 70.463 | 10.680 | 1.00 | 3.22 |
| ATOM | 3915 | NH2 | ARG | B | 272 | 38.295 | 70.322 | 8.635 | 1.00 | 4.22 |
| ATOM | 3916 | C | ARG | B | 272 | 40.297 | 64.133 | 11.491 | 1.00 | 13.52 |
| ATOM | 3917 | O | ARG | B | 272 | 39.080 | 64.217 | 11.497 | 1.00 | 17.96 |
| ATOM | 3918 | N | ASP | B | 273 | 40.928 | 62.997 | 11.239 | 1.00 | 18.21 |
| ATOM | 3919 | CA | ASP | B | 273 | 40.179 | 61.755 | 11.076 | 1.00 | 26.05 |
| ATOM | 3920 | CB | ASP | B | 273 | 39.440 | 61.725 | 9.729 | 1.00 | 27.64 |
| ATOM | 3921 | CG | ASP | B | 273 | 38.417 | 60.588 | 9.645 | 1.00 | 32.74 |
| ATOM | 3922 | OD1 | ASP | B | 273 | 37.912 | 60.147 | 10.709 | 1.00 | 34.89 |
| ATOM | 3923 | OD2 | ASP | B | 273 | 38.074 | 60.059 | 8.559 | 1.00 | 34.29 |
| ATOM | 3924 | C | ASP | B | 273 | 41.030 | 60.484 | 11.280 | 1.00 | 30.86 |
| ATOM | 3925 | O | ASP | B | 273 | 40.929 | 59.512 | 10.511 | 1.00 | 31.97 |
| ATOM | 3926 | N | LEU | B | 274 | 41.856 | 60.476 | 12.325 | 1.00 | 29.70 |
| ATOM | 3927 | CA | LEU | B | 274 | 42.631 | 59.281 | 12.616 | 1.00 | 25.23 |
| ATOM | 3928 | CB | LEU | B | 274 | 43.540 | 59.501 | 13.832 | 1.00 | 24.15 |
| ATOM | 3929 | CG | LEU | B | 274 | 44.972 | 59.912 | 13.465 | 1.00 | 23.29 |

FIGURE 3 (Cont.)

| | A | B | C | D | E | F | G | H | I | J |
|---|---|---|---|---|---|---|---|---|---|---|
| ATOM | 3930 | CD1 | LEU | B | 274 | 45.547 | 60.841 | 14.484 | 1.00 | 24.64 |
| ATOM | 3931 | CD2 | LEU | B | 274 | 45.870 | 58.716 | 13.324 | 1.00 | 23.16 |
| ATOM | 3932 | C | LEU | B | 274 | 41.687 | 58.074 | 12.785 | 1.00 | 23.84 |
| ATOM | 3933 | O | LEU | B | 274 | 40.551 | 58.215 | 13.272 | 1.00 | 23.21 |
| ATOM | 3934 | N | LYS | B | 275 | 42.149 | 56.917 | 12.312 | 1.00 | 19.54 |
| ATOM | 3935 | CA | LYS | B | 275 | 41.452 | 55.635 | 12.440 | 1.00 | 14.94 |
| ATOM | 3936 | CB | LYS | B | 275 | 40.013 | 55.687 | 11.915 | 1.00 | 15.47 |
| ATOM | 3937 | CG | LYS | B | 275 | 39.860 | 55.855 | 10.423 | 1.00 | 13.62 |
| ATOM | 3938 | CD | LYS | B | 275 | 38.728 | 56.806 | 10.129 | 1.00 | 13.95 |
| ATOM | 3939 | CE | LYS | B | 275 | 37.932 | 56.339 | 8.928 | 1.00 | 13.96 |
| ATOM | 3940 | NZ | LYS | B | 275 | 36.602 | 55.797 | 9.294 | 1.00 | 13.42 |
| ATOM | 3941 | C | LYS | B | 275 | 42.222 | 54.580 | 11.691 | 1.00 | 13.50 |
| ATOM | 3942 | O | LYS | B | 275 | 42.942 | 54.889 | 10.751 | 1.00 | 14.43 |
| ATOM | 3943 | N | LEU | B | 276 | 42.061 | 53.331 | 12.102 | 1.00 | 13.70 |
| ATOM | 3944 | CA | LEU | B | 276 | 42.824 | 52.244 | 11.517 | 1.00 | 13.52 |
| ATOM | 3945 | CB | LEU | B | 276 | 42.473 | 50.926 | 12.183 | 1.00 | 16.85 |
| ATOM | 3946 | CG | LEU | B | 276 | 42.570 | 50.910 | 13.698 | 1.00 | 18.11 |
| ATOM | 3947 | CD1 | LEU | B | 276 | 41.902 | 49.639 | 14.204 | 1.00 | 20.40 |
| ATOM | 3948 | CD2 | LEU | B | 276 | 44.031 | 51.012 | 14.134 | 1.00 | 15.92 |
| ATOM | 3949 | C | LEU | B | 276 | 42.524 | 52.161 | 10.050 | 1.00 | 11.42 |
| ATOM | 3950 | O | LEU | B | 276 | 43.427 | 52.129 | 9.237 | 1.00 | 11.05 |
| ATOM | 3951 | N | GLU | B | 277 | 41.237 | 52.141 | 9.732 | 1.00 | 12.97 |
| ATOM | 3952 | CA | GLU | B | 277 | 40.746 | 52.189 | 8.365 | 1.00 | 13.31 |
| ATOM | 3953 | CB | GLU | B | 277 | 39.334 | 52.774 | 8.347 | 1.00 | 15.76 |
| ATOM | 3954 | CG | GLU | B | 277 | 38.255 | 51.811 | 8.785 | 1.00 | 20.20 |
| ATOM | 3955 | CD | GLU | B | 277 | 38.079 | 51.761 | 10.288 | 1.00 | 26.93 |
| ATOM | 3956 | OE1 | GLU | B | 277 | 38.930 | 52.316 | 11.033 | 1.00 | 31.26 |
| ATOM | 3957 | OE2 | GLU | B | 277 | 37.077 | 51.155 | 10.731 | 1.00 | 30.26 |
| ATOM | 3958 | C | GLU | B | 277 | 41.632 | 53.047 | 7.491 | 1.00 | 11.94 |
| ATOM | 3959 | O | GLU | B | 277 | 41.923 | 52.668 | 6.355 | 1.00 | 10.81 |
| ATOM | 3960 | N | ASN | B | 278 | 42.059 | 54.190 | 8.037 | 1.00 | 9.53 |
| ATOM | 3961 | CA | ASN | B | 278 | 42.783 | 55.206 | 7.280 | 1.00 | 11.45 |
| ATOM | 3962 | CB | ASN | B | 278 | 42.370 | 56.614 | 7.720 | 1.00 | 12.57 |
| ATOM | 3963 | CG | ASN | B | 278 | 41.105 | 57.114 | 7.012 | 1.00 | 15.14 |
| ATOM | 3964 | OD1 | ASN | B | 278 | 40.489 | 56.394 | 6.211 | 1.00 | 18.84 |
| ATOM | 3965 | ND2 | ASN | B | 278 | 40.713 | 58.356 | 7.303 | 1.00 | 11.94 |
| ATOM | 3966 | C | ASN | B | 278 | 44.308 | 55.072 | 7.261 | 1.00 | 14.22 |
| ATOM | 3967 | O | ASN | B | 278 | 44.950 | 55.585 | 6.356 | 1.00 | 21.17 |
| ATOM | 3968 | N | LEU | B | 279 | 44.897 | 54.393 | 8.239 | 1.00 | 14.52 |
| ATOM | 3969 | CA | LEU | B | 279 | 46.334 | 54.117 | 8.189 | 1.00 | 14.22 |
| ATOM | 3970 | CB | LEU | B | 279 | 46.900 | 53.880 | 9.591 | 1.00 | 14.21 |
| ATOM | 3971 | CG | LEU | B | 279 | 46.348 | 54.817 | 10.671 | 1.00 | 16.90 |
| ATOM | 3972 | CD1 | LEU | B | 279 | 46.535 | 54.220 | 12.044 | 1.00 | 17.27 |
| ATOM | 3973 | CD2 | LEU | B | 279 | 46.961 | 56.214 | 10.610 | 1.00 | 18.37 |
| ATOM | 3974 | C | LEU | B | 279 | 46.626 | 52.926 | 7.282 | 1.00 | 15.24 |
| ATOM | 3975 | O | LEU | B | 279 | 46.070 | 51.847 | 7.470 | 1.00 | 18.52 |
| ATOM | 3976 | N | MET | B | 280 | 47.495 | 53.126 | 6.299 | 1.00 | 14.57 |
| ATOM | 3977 | CA | MET | B | 280 | 47.873 | 52.060 | 5.370 | 1.00 | 16.22 |
| ATOM | 3978 | CB | MET | B | 280 | 47.746 | 52.563 | 3.937 | 1.00 | 19.44 |
| ATOM | 3979 | CG | MET | B | 280 | 46.373 | 53.065 | 3.572 | 1.00 | 21.86 |
| ATOM | 3980 | SD | MET | B | 280 | 45.226 | 51.715 | 3.443 | 1.00 | 25.77 |
| ATOM | 3981 | CE | MET | B | 280 | 46.062 | 50.624 | 2.357 | 1.00 | 25.16 |

FIGURE 3 (Cont.)

| | A | B | C | D | E | F | G | H | I | J |
|---|---|---|---|---|---|---|---|---|---|---|
| ATOM | 3982 | C | MET | B | 280 | 49.292 | 51.502 | 5.589 | 1.00 | 15.01 |
| ATOM | 3983 | O | MET | B | 280 | 50.141 | 52.143 | 6.208 | 1.00 | 16.82 |
| ATOM | 3984 | N | LEU | B | 281 | 49.540 | 50.305 | 5.070 | 1.00 | 11.33 |
| ATOM | 3985 | CA | LEU | B | 281 | 50.876 | 49.735 | 5.090 | 1.00 | 10.44 |
| ATOM | 3986 | CB | LEU | B | 281 | 50.875 | 48.366 | 5.775 | 1.00 | 11.60 |
| ATOM | 3987 | CG | LEU | B | 281 | 50.898 | 48.260 | 7.304 | 1.00 | 12.47 |
| ATOM | 3988 | CD1 | LEU | B | 281 | 51.413 | 46.885 | 7.740 | 1.00 | 11.32 |
| ATOM | 3989 | CD2 | LEU | B | 281 | 51.720 | 49.371 | 7.941 | 1.00 | 13.97 |
| ATOM | 3990 | C | LEU | B | 281 | 51.404 | 49.610 | 3.669 | 1.00 | 11.00 |
| ATOM | 3991 | O | LEU | B | 281 | 50.699 | 49.133 | 2.776 | 1.00 | 7.94 |
| ATOM | 3992 | N | ASP | B | 282 | 52.645 | 50.048 | 3.462 | 1.00 | 13.47 |
| ATOM | 3993 | CA | ASP | B | 282 | 53.280 | 49.940 | 2.154 | 1.00 | 15.45 |
| ATOM | 3994 | CB | ASP | B | 282 | 54.068 | 51.220 | 1.784 | 1.00 | 18.66 |
| ATOM | 3995 | CG | ASP | B | 282 | 55.308 | 51.445 | 2.651 | 1.00 | 21.95 |
| ATOM | 3996 | OD1 | ASP | B | 282 | 55.692 | 50.533 | 3.419 | 1.00 | 23.53 |
| ATOM | 3997 | OD2 | ASP | B | 282 | 55.973 | 52.513 | 2.614 | 1.00 | 21.81 |
| ATOM | 3998 | C | ASP | B | 282 | 54.106 | 48.653 | 2.032 | 1.00 | 15.47 |
| ATOM | 3999 | O | ASP | B | 282 | 54.371 | 47.980 | 3.031 | 1.00 | 11.94 |
| ATOM | 4000 | N | LYS | B | 283 | 54.495 | 48.323 | 0.800 | 1.00 | 18.41 |
| ATOM | 4001 | CA | LYS | B | 283 | 55.125 | 47.038 | 0.470 | 1.00 | 20.20 |
| ATOM | 4002 | CB | LYS | B | 283 | 55.541 | 47.002 | -1.012 | 1.00 | 22.65 |
| ATOM | 4003 | CG | LYS | B | 283 | 56.903 | 47.637 | -1.330 | 1.00 | 25.28 |
| ATOM | 4004 | CD | LYS | B | 283 | 56.853 | 49.169 | -1.290 | 1.00 | 27.19 |
| ATOM | 4005 | CE | LYS | B | 283 | 57.721 | 49.778 | -2.380 | 1.00 | 28.25 |
| ATOM | 4006 | NZ | LYS | B | 283 | 58.863 | 50.544 | -1.807 | 1.00 | 28.78 |
| ATOM | 4007 | C | LYS | B | 283 | 56.304 | 46.651 | 1.365 | 1.00 | 18.36 |
| ATOM | 4008 | O | LYS | B | 283 | 56.758 | 45.512 | 1.324 | 1.00 | 17.22 |
| ATOM | 4009 | N | ASP | B | 284 | 56.787 | 47.596 | 2.164 | 1.00 | 17.64 |
| ATOM | 4010 | CA | ASP | B | 284 | 57.940 | 47.361 | 3.023 | 1.00 | 20.57 |
| ATOM | 4011 | CB | ASP | B | 284 | 58.921 | 48.542 | 2.949 | 1.00 | 22.45 |
| ATOM | 4012 | CG | ASP | B | 284 | 60.009 | 48.355 | 1.881 | 1.00 | 24.12 |
| ATOM | 4013 | OD1 | ASP | B | 284 | 60.380 | 47.199 | 1.562 | 1.00 | 24.05 |
| ATOM | 4014 | OD2 | ASP | B | 284 | 60.559 | 49.323 | 1.308 | 1.00 | 24.11 |
| ATOM | 4015 | C | ASP | B | 284 | 57.550 | 47.080 | 4.477 | 1.00 | 21.72 |
| ATOM | 4016 | O | ASP | B | 284 | 58.292 | 46.418 | 5.206 | 1.00 | 25.04 |
| ATOM | 4017 | N | GLY | B | 285 | 56.389 | 47.572 | 4.896 | 1.00 | 19.99 |
| ATOM | 4018 | CA | GLY | B | 285 | 55.974 | 47.458 | 6.281 | 1.00 | 16.00 |
| ATOM | 4019 | C | GLY | B | 285 | 55.768 | 48.820 | 6.910 | 1.00 | 14.30 |
| ATOM | 4020 | O | GLY | B | 285 | 55.392 | 48.926 | 8.080 | 1.00 | 13.46 |
| ATOM | 4021 | N | HIS | B | 286 | 56.000 | 49.863 | 6.120 | 1.00 | 14.12 |
| ATOM | 4022 | CA | HIS | B | 286 | 55.938 | 51.236 | 6.613 | 1.00 | 14.76 |
| ATOM | 4023 | CB | HIS | B | 286 | 57.035 | 52.107 | 5.988 | 1.00 | 14.04 |
| ATOM | 4024 | CG | HIS | B | 286 | 58.404 | 51.778 | 6.493 | 1.00 | 13.46 |
| ATOM | 4025 | ND1 | HIS | B | 286 | 58.970 | 52.412 | 7.576 | 1.00 | 13.99 |
| ATOM | 4026 | CE1 | HIS | B | 286 | 60.165 | 51.903 | 7.809 | 1.00 | 12.21 |
| ATOM | 4027 | NE2 | HIS | B | 286 | 60.388 | 50.949 | 6.924 | 1.00 | 12.71 |
| ATOM | 4028 | CD2 | HIS | B | 286 | 59.300 | 50.848 | 6.093 | 1.00 | 12.57 |
| ATOM | 4029 | C | HIS | B | 286 | 54.567 | 51.875 | 6.460 | 1.00 | 14.95 |
| ATOM | 4030 | O | HIS | B | 286 | 53.808 | 51.599 | 5.529 | 1.00 | 14.87 |
| ATOM | 4031 | N | ILE | B | 287 | 54.266 | 52.727 | 7.420 | 1.00 | 15.50 |
| ATOM | 4032 | CA | ILE | B | 287 | 52.984 | 53.368 | 7.512 | 1.00 | 16.67 |
| ATOM | 4033 | CB | ILE | B | 287 | 52.923 | 54.114 | 8.860 | 1.00 | 17.31 |

FIGURE 3 (Cont.)

|   | A | B | C | D | E | F | G | H | I | J |
|---|---|---|---|---|---|---|---|---|---|---|
| ATOM | 4034 | CG1 | ILE | B | 287 | 52.628 | 53.124 | 9.997 | 1.00 | 16.61 |
| ATOM | 4035 | CD1 | ILE | B | 287 | 51.155 | 52.943 | 10.339 | 1.00 | 19.28 |
| ATOM | 4036 | CG2 | ILE | B | 287 | 51.969 | 55.328 | 8.809 | 1.00 | 19.59 |
| ATOM | 4037 | C | ILE | B | 287 | 52.812 | 54.311 | 6.338 | 1.00 | 18.26 |
| ATOM | 4038 | O | ILE | B | 287 | 53.778 | 54.893 | 5.848 | 1.00 | 21.65 |
| ATOM | 4039 | N | LYS | B | 288 | 51.582 | 54.408 | 5.859 | 1.00 | 18.75 |
| ATOM | 4040 | CA | LYS | B | 288 | 51.164 | 55.522 | 5.026 | 1.00 | 20.21 |
| ATOM | 4041 | CB | LYS | B | 288 | 51.024 | 55.100 | 3.558 | 1.00 | 21.22 |
| ATOM | 4042 | CG | LYS | B | 288 | 52.327 | 54.753 | 2.847 | 1.00 | 22.42 |
| ATOM | 4043 | CD | LYS | B | 288 | 53.173 | 55.987 | 2.622 | 1.00 | 22.79 |
| ATOM | 4044 | CE | LYS | B | 288 | 54.265 | 55.706 | 1.619 | 1.00 | 24.52 |
| ATOM | 4045 | NZ | LYS | B | 288 | 54.815 | 56.972 | 1.038 | 1.00 | 25.89 |
| ATOM | 4046 | C | LYS | B | 288 | 49.820 | 55.981 | 5.569 | 1.00 | 19.61 |
| ATOM | 4047 | O | LYS | B | 288 | 48.972 | 55.153 | 5.903 | 1.00 | 20.57 |
| ATOM | 4048 | N | ILE | B | 289 | 49.618 | 57.286 | 5.692 | 1.00 | 17.64 |
| ATOM | 4049 | CA | ILE | B | 289 | 48.271 | 57.772 | 5.946 | 1.00 | 14.96 |
| ATOM | 4050 | CB | ILE | B | 289 | 48.247 | 59.031 | 6.818 | 1.00 | 12.67 |
| ATOM | 4051 | CG1 | ILE | B | 289 | 49.121 | 58.861 | 8.052 | 1.00 | 13.19 |
| ATOM | 4052 | CD1 | ILE | B | 289 | 49.475 | 60.180 | 8.710 | 1.00 | 15.81 |
| ATOM | 4053 | CG2 | ILE | B | 289 | 46.816 | 59.337 | 7.243 | 1.00 | 11.80 |
| ATOM | 4054 | C | ILE | B | 289 | 47.620 | 58.060 | 4.604 | 1.00 | 15.91 |
| ATOM | 4055 | O | ILE | B | 289 | 48.262 | 58.595 | 3.699 | 1.00 | 15.73 |
| ATOM | 4056 | N | THR | B | 290 | 46.355 | 57.676 | 4.483 | 1.00 | 14.99 |
| ATOM | 4057 | CA | THR | B | 290 | 45.519 | 58.087 | 3.374 | 1.00 | 17.72 |
| ATOM | 4058 | CB | THR | B | 290 | 45.120 | 56.873 | 2.530 | 1.00 | 21.24 |
| ATOM | 4059 | OG1 | THR | B | 290 | 44.450 | 57.320 | 1.334 | 1.00 | 25.71 |
| ATOM | 4060 | CG2 | THR | B | 290 | 44.070 | 56.019 | 3.261 | 1.00 | 21.21 |
| ATOM | 4061 | C | THR | B | 290 | 44.282 | 58.821 | 3.896 | 1.00 | 17.37 |
| ATOM | 4062 | O | THR | B | 290 | 44.150 | 59.036 | 5.095 | 1.00 | 20.44 |
| ATOM | 4063 | N | ASP | B | 291 | 43.397 | 59.213 | 2.981 | 1.00 | 16.74 |
| ATOM | 4064 | CA | ASP | B | 291 | 42.109 | 59.819 | 3.300 | 1.00 | 12.53 |
| ATOM | 4065 | CB | ASP | B | 291 | 41.218 | 58.819 | 4.021 | 1.00 | 8.46 |
| ATOM | 4066 | CG | ASP | B | 291 | 39.751 | 59.126 | 3.863 | 1.00 | 7.11 |
| ATOM | 4067 | OD1 | ASP | B | 291 | 39.346 | 59.579 | 2.777 | 1.00 | 6.11 |
| ATOM | 4068 | OD2 | ASP | B | 291 | 38.914 | 58.940 | 4.773 | 1.00 | 5.63 |
| ATOM | 4069 | C | ASP | B | 291 | 42.220 | 61.138 | 4.065 | 1.00 | 15.34 |
| ATOM | 4070 | O | ASP | B | 291 | 41.889 | 61.228 | 5.245 | 1.00 | 14.83 |
| ATOM | 4071 | N | PHE | B | 292 | 42.693 | 62.160 | 3.357 | 1.00 | 21.28 |
| ATOM | 4072 | CA | PHE | B | 292 | 42.773 | 63.527 | 3.866 | 1.00 | 23.85 |
| ATOM | 4073 | CB | PHE | B | 292 | 43.940 | 64.265 | 3.214 | 1.00 | 24.42 |
| ATOM | 4074 | CG | PHE | B | 292 | 45.255 | 63.587 | 3.387 | 1.00 | 28.01 |
| ATOM | 4075 | CD1 | PHE | B | 292 | 45.650 | 62.576 | 2.520 | 1.00 | 30.07 |
| ATOM | 4076 | CE1 | PHE | B | 292 | 46.881 | 61.947 | 2.679 | 1.00 | 32.33 |
| ATOM | 4077 | CZ | PHE | B | 292 | 47.735 | 62.334 | 3.717 | 1.00 | 31.47 |
| ATOM | 4078 | CE2 | PHE | B | 292 | 47.351 | 63.346 | 4.581 | 1.00 | 30.21 |
| ATOM | 4079 | CD2 | PHE | B | 292 | 46.112 | 63.965 | 4.412 | 1.00 | 29.79 |
| ATOM | 4080 | C | PHE | B | 292 | 41.490 | 64.299 | 3.575 | 1.00 | 24.92 |
| ATOM | 4081 | O | PHE | B | 292 | 41.480 | 65.529 | 3.622 | 1.00 | 25.78 |
| ATOM | 4082 | N | GLY | B | 293 | 40.409 | 63.576 | 3.287 | 1.00 | 25.90 |
| ATOM | 4083 | CA | GLY | B | 293 | 39.165 | 64.182 | 2.841 | 1.00 | 26.17 |
| ATOM | 4084 | C | GLY | B | 293 | 38.466 | 65.055 | 3.861 | 1.00 | 25.59 |
| ATOM | 4085 | O | GLY | B | 293 | 37.377 | 65.551 | 3.605 | 1.00 | 25.62 |

FIGURE 3 (Cont.)

| | A | B | C | D | E | F | G | H | I | J |
|---|---|---|---|---|---|---|---|---|---|---|
| ATOM | 4086 | N | LEU | B | 294 | 39.097 | 65.234 | 5.017 | 1.00 | 26.69 |
| ATOM | 4087 | CA | LEU | B | 294 | 38.504 | 65.951 | 6.136 | 1.00 | 27.18 |
| ATOM | 4088 | CB | LEU | B | 294 | 37.788 | 64.968 | 7.073 | 1.00 | 27.17 |
| ATOM | 4089 | CG | LEU | B | 294 | 36.843 | 63.981 | 6.376 | 1.00 | 27.36 |
| ATOM | 4090 | CD1 | LEU | B | 294 | 37.255 | 62.528 | 6.618 | 1.00 | 25.96 |
| ATOM | 4091 | CD2 | LEU | B | 294 | 35.385 | 64.248 | 6.742 | 1.00 | 26.88 |
| ATOM | 4092 | C | LEU | B | 294 | 39.589 | 66.716 | 6.881 | 1.00 | 27.27 |
| ATOM | 4093 | O | LEU | B | 294 | 39.498 | 66.940 | 8.083 | 1.00 | 28.32 |
| ATOM | 4094 | N | CYS | B | 295 | 40.623 | 67.110 | 6.152 | 1.00 | 28.61 |
| ATOM | 4095 | CA | CYS | B | 295 | 41.716 | 67.875 | 6.729 | 1.00 | 30.95 |
| ATOM | 4096 | CB | CYS | B | 295 | 42.960 | 67.762 | 5.856 | 1.00 | 33.50 |
| ATOM | 4097 | SG | CYS | B | 295 | 43.930 | 66.270 | 6.153 | 1.00 | 39.30 |
| ATOM | 4098 | C | CYS | B | 295 | 41.312 | 69.326 | 6.817 | 1.00 | 29.29 |
| ATOM | 4099 | O | CYS | B | 295 | 40.406 | 69.757 | 6.112 | 1.00 | 31.89 |
| ATOM | 4100 | N | LYS | B | 296 | 41.972 | 70.075 | 7.691 | 1.00 | 26.61 |
| ATOM | 4101 | CA | LYS | B | 296 | 41.807 | 71.518 | 7.703 | 1.00 | 24.06 |
| ATOM | 4102 | CB | LYS | B | 296 | 41.115 | 72.003 | 8.976 | 1.00 | 20.64 |
| ATOM | 4103 | CG | LYS | B | 296 | 40.703 | 73.472 | 8.923 | 1.00 | 18.81 |
| ATOM | 4104 | CD | LYS | B | 296 | 39.201 | 73.650 | 8.771 | 1.00 | 17.08 |
| ATOM | 4105 | CE | LYS | B | 296 | 38.845 | 75.045 | 8.266 | 1.00 | 14.88 |
| ATOM | 4106 | NZ | LYS | B | 296 | 37.760 | 75.011 | 7.242 | 1.00 | 11.00 |
| ATOM | 4107 | C | LYS | B | 296 | 43.160 | 72.175 | 7.537 | 1.00 | 25.69 |
| ATOM | 4108 | O | LYS | B | 296 | 44.066 | 71.959 | 8.342 | 1.00 | 27.64 |
| ATOM | 4109 | N | GLU | B | 297 | 43.280 | 72.959 | 6.468 | 1.00 | 27.06 |
| ATOM | 4110 | CA | GLU | B | 297 | 44.476 | 73.732 | 6.158 | 1.00 | 27.73 |
| ATOM | 4111 | CB | GLU | B | 297 | 44.527 | 74.032 | 4.651 | 1.00 | 30.44 |
| ATOM | 4112 | CG | GLU | B | 297 | 45.335 | 73.045 | 3.810 | 1.00 | 33.05 |
| ATOM | 4113 | CD | GLU | B | 297 | 45.751 | 73.610 | 2.453 | 1.00 | 34.35 |
| ATOM | 4114 | OE1 | GLU | B | 297 | 46.973 | 73.746 | 2.194 | 1.00 | 33.32 |
| ATOM | 4115 | OE2 | GLU | B | 297 | 44.853 | 73.911 | 1.638 | 1.00 | 35.78 |
| ATOM | 4116 | C | GLU | B | 297 | 44.448 | 75.046 | 6.928 | 1.00 | 26.90 |
| ATOM | 4117 | O | GLU | B | 297 | 43.383 | 75.516 | 7.327 | 1.00 | 27.34 |
| ATOM | 4118 | N | GLY | B | 298 | 45.621 | 75.633 | 7.138 | 1.00 | 26.49 |
| ATOM | 4119 | CA | GLY | B | 298 | 45.710 | 76.994 | 7.640 | 1.00 | 28.04 |
| ATOM | 4120 | C | GLY | B | 298 | 45.461 | 77.194 | 9.125 | 1.00 | 28.16 |
| ATOM | 4121 | O | GLY | B | 298 | 45.290 | 78.332 | 9.577 | 1.00 | 26.15 |
| ATOM | 4122 | N | ILE | B | 299 | 45.441 | 76.097 | 9.881 | 1.00 | 28.82 |
| ATOM | 4123 | CA | ILE | B | 299 | 45.351 | 76.169 | 11.337 | 1.00 | 30.02 |
| ATOM | 4124 | CB | ILE | B | 299 | 44.813 | 74.829 | 11.918 | 1.00 | 28.71 |
| ATOM | 4125 | CG1 | ILE | B | 299 | 43.393 | 74.548 | 11.413 | 1.00 | 28.14 |
| ATOM | 4126 | CD1 | ILE | B | 299 | 42.433 | 75.726 | 11.512 | 1.00 | 27.71 |
| ATOM | 4127 | CG2 | ILE | B | 299 | 44.870 | 74.801 | 13.456 | 1.00 | 28.80 |
| ATOM | 4128 | C | ILE | B | 299 | 46.726 | 76.535 | 11.907 | 1.00 | 32.40 |
| ATOM | 4129 | O | ILE | B | 299 | 47.582 | 75.667 | 12.097 | 1.00 | 34.75 |
| ATOM | 4130 | N | LYS | B | 300 | 46.940 | 77.827 | 12.155 | 1.00 | 33.00 |
| ATOM | 4131 | CA | LYS | B | 300 | 48.208 | 78.306 | 12.699 | 1.00 | 34.66 |
| ATOM | 4132 | CB | LYS | B | 300 | 48.442 | 79.771 | 12.301 | 1.00 | 33.37 |
| ATOM | 4133 | CG | LYS | B | 300 | 49.212 | 79.954 | 10.994 | 1.00 | 31.98 |
| ATOM | 4134 | CD | LYS | B | 300 | 49.691 | 81.392 | 10.827 | 1.00 | 30.75 |
| ATOM | 4135 | CE | LYS | B | 300 | 49.703 | 81.822 | 9.361 | 1.00 | 29.78 |
| ATOM | 4136 | NZ | LYS | B | 300 | 50.639 | 82.964 | 9.100 | 1.00 | 27.39 |
| ATOM | 4137 | C | LYS | B | 300 | 48.249 | 78.130 | 14.224 | 1.00 | 37.69 |

FIGURE 3 (Cont.)

| | A | B | C | D | E | F | G | H | I | J |
|---|---|---|---|---|---|---|---|---|---|---|
| ATOM | 4138 | O | LYS | B | 300 | 47.430 | 77.397 | 14.785 | 1.00 | 37.82 |
| ATOM | 4139 | N | ASP | B | 301 | 49.225 | 78.778 | 14.868 | 1.00 | 41.28 |
| ATOM | 4140 | CA | ASP | B | 301 | 49.314 | 78.931 | 16.336 | 1.00 | 42.05 |
| ATOM | 4141 | CB | ASP | B | 301 | 48.979 | 80.386 | 16.733 | 1.00 | 42.76 |
| ATOM | 4142 | CG | ASP | B | 301 | 50.214 | 81.265 | 16.883 | 1.00 | 42.64 |
| ATOM | 4143 | OD1 | ASP | B | 301 | 50.670 | 81.463 | 18.031 | 1.00 | 42.06 |
| ATOM | 4144 | OD2 | ASP | B | 301 | 50.782 | 81.818 | 15.916 | 1.00 | 42.92 |
| ATOM | 4145 | C | ASP | B | 301 | 48.434 | 77.961 | 17.141 | 1.00 | 41.09 |
| ATOM | 4146 | O | ASP | B | 301 | 48.868 | 76.873 | 17.519 | 1.00 | 39.01 |
| ATOM | 4147 | N | GLY | B | 302 | 47.197 | 78.383 | 17.396 | 1.00 | 40.84 |
| ATOM | 4148 | CA | GLY | B | 302 | 46.216 | 77.577 | 18.093 | 1.00 | 40.09 |
| ATOM | 4149 | C | GLY | B | 302 | 44.827 | 77.730 | 17.497 | 1.00 | 39.23 |
| ATOM | 4150 | O | GLY | B | 302 | 43.904 | 77.038 | 17.932 | 1.00 | 41.07 |
| ATOM | 4151 | N | ALA | B | 303 | 44.695 | 78.617 | 16.501 | 1.00 | 35.74 |
| ATOM | 4152 | CA | ALA | B | 303 | 43.420 | 78.938 | 15.832 | 1.00 | 33.12 |
| ATOM | 4153 | CB | ALA | B | 303 | 43.676 | 79.655 | 14.514 | 1.00 | 33.92 |
| ATOM | 4154 | C | ALA | B | 303 | 42.496 | 77.736 | 15.614 | 1.00 | 30.93 |
| ATOM | 4155 | O | ALA | B | 303 | 42.942 | 76.656 | 15.227 | 1.00 | 31.89 |
| ATOM | 4156 | N | THR | B | 304 | 41.203 | 77.948 | 15.847 | 1.00 | 28.15 |
| ATOM | 4157 | CA | THR | B | 304 | 40.247 | 76.853 | 16.035 | 1.00 | 25.09 |
| ATOM | 4158 | CB | THR | B | 304 | 39.228 | 77.240 | 17.126 | 1.00 | 24.05 |
| ATOM | 4159 | OG1 | THR | B | 304 | 39.291 | 78.651 | 17.370 | 1.00 | 20.65 |
| ATOM | 4160 | CG2 | THR | B | 304 | 39.625 | 76.628 | 18.466 | 1.00 | 25.55 |
| ATOM | 4161 | C | THR | B | 304 | 39.499 | 76.405 | 14.782 | 1.00 | 24.59 |
| ATOM | 4162 | O | THR | B | 304 | 39.200 | 77.215 | 13.901 | 1.00 | 28.47 |
| ATOM | 4163 | N | MET | B | 305 | 39.191 | 75.112 | 14.717 | 1.00 | 21.30 |
| ATOM | 4164 | CA | MET | B | 305 | 38.301 | 74.582 | 13.685 | 1.00 | 21.40 |
| ATOM | 4165 | CB | MET | B | 305 | 38.683 | 73.154 | 13.327 | 1.00 | 25.58 |
| ATOM | 4166 | CG | MET | B | 305 | 39.904 | 73.025 | 12.450 | 1.00 | 29.28 |
| ATOM | 4167 | SD | MET | B | 305 | 40.799 | 71.510 | 12.828 | 1.00 | 33.34 |
| ATOM | 4168 | CE | MET | B | 305 | 41.805 | 72.106 | 14.169 | 1.00 | 35.80 |
| ATOM | 4169 | C | MET | B | 305 | 36.854 | 74.609 | 14.169 | 1.00 | 17.85 |
| ATOM | 4170 | O | MET | B | 305 | 36.603 | 74.754 | 15.361 | 1.00 | 16.79 |
| ATOM | 4171 | N | LYS | B | 306 | 35.904 | 74.461 | 13.250 | 1.00 | 15.67 |
| ATOM | 4172 | CA | LYS | B | 306 | 34.493 | 74.577 | 13.610 | 1.00 | 13.80 |
| ATOM | 4173 | CB | LYS | B | 306 | 33.920 | 75.908 | 13.112 | 1.00 | 15.58 |
| ATOM | 4174 | CG | LYS | B | 306 | 34.359 | 77.130 | 13.927 | 1.00 | 14.93 |
| ATOM | 4175 | CD | LYS | B | 306 | 33.222 | 78.134 | 14.093 | 1.00 | 13.99 |
| ATOM | 4176 | CE | LYS | B | 306 | 33.349 | 78.925 | 15.397 | 1.00 | 13.21 |
| ATOM | 4177 | NZ | LYS | B | 306 | 32.097 | 78.914 | 16.214 | 1.00 | 11.81 |
| ATOM | 4178 | C | LYS | B | 306 | 33.613 | 73.403 | 13.165 | 1.00 | 13.20 |
| ATOM | 4179 | O | LYS | B | 306 | 32.654 | 73.072 | 13.852 | 1.00 | 12.73 |
| ATOM | 4180 | N | TPO | B | 307 | 33.949 | 72.771 | 12.038 | 1.00 | 13.75 |
| ATOM | 4181 | CA | TPO | B | 307 | 33.158 | 71.664 | 11.474 | 1.00 | 13.74 |
| ATOM | 4182 | CB | TPO | B | 307 | 33.732 | 71.229 | 10.114 | 1.00 | 13.15 |
| ATOM | 4183 | CG2 | TPO | B | 307 | 32.815 | 70.259 | 9.372 | 1.00 | 14.66 |
| ATOM | 4184 | OG1 | TPO | B | 307 | 33.938 | 72.346 | 9.253 | 1.00 | 10.91 |
| ATOM | 4185 | P | TPO | B | 307 | 35.420 | 72.802 | 8.842 | 1.00 | 9.53 |
| ATOM | 4186 | O1P | TPO | B | 307 | 36.207 | 71.536 | 8.300 | 1.00 | 6.89 |
| ATOM | 4187 | O3P | TPO | B | 307 | 35.357 | 73.859 | 7.649 | 1.00 | 11.73 |
| ATOM | 4188 | O2P | TPO | B | 307 | 36.108 | 73.496 | 10.100 | 1.00 | 7.85 |
| ATOM | 4189 | C | TPO | B | 307 | 33.049 | 70.458 | 12.388 | 1.00 | 14.07 |

FIGURE 3 (Cont.)

| | A | B | C | D | E | F | G | H | I | J |
|---|---|---|---|---|---|---|---|---|---|---|
| ATOM | 4190 | O | TPO | B | 307 | 34.050 | 69.936 | 12.863 | 1.00 | 12.48 |
| ATOM | 4191 | N | PHE | B | 308 | 31.811 | 70.019 | 12.627 | 1.00 | 14.74 |
| ATOM | 4192 | CA | PHE | B | 308 | 31.527 | 68.786 | 13.368 | 1.00 | 14.01 |
| ATOM | 4193 | CB | PHE | B | 308 | 30.113 | 68.827 | 13.954 | 1.00 | 14.29 |
| ATOM | 4194 | CG | PHE | B | 308 | 29.626 | 67.514 | 14.528 | 1.00 | 14.25 |
| ATOM | 4195 | CD1 | PHE | B | 308 | 28.531 | 66.861 | 13.969 | 1.00 | 13.68 |
| ATOM | 4196 | CE1 | PHE | B | 308 | 28.052 | 65.660 | 14.501 | 1.00 | 11.04 |
| ATOM | 4197 | CZ | PHE | B | 308 | 28.653 | 65.112 | 15.606 | 1.00 | 9.76 |
| ATOM | 4198 | CE2 | PHE | B | 308 | 29.732 | 65.754 | 16.188 | 1.00 | 12.82 |
| ATOM | 4199 | CD2 | PHE | B | 308 | 30.214 | 66.957 | 15.652 | 1.00 | 14.98 |
| ATOM | 4200 | C | PHE | B | 308 | 31.680 | 67.654 | 12.381 | 1.00 | 13.56 |
| ATOM | 4201 | O | PHE | B | 308 | 30.901 | 67.529 | 11.437 | 1.00 | 14.83 |
| ATOM | 4202 | N | CYS | B | 309 | 32.721 | 66.860 | 12.581 | 1.00 | 13.32 |
| ATOM | 4203 | CA | CYS | B | 309 | 33.156 | 65.895 | 11.586 | 1.00 | 14.09 |
| ATOM | 4204 | CB | CYS | B | 309 | 33.565 | 66.593 | 10.283 | 1.00 | 11.67 |
| ATOM | 4205 | SG | CYS | B | 309 | 35.302 | 67.070 | 10.197 | 1.00 | 10.79 |
| ATOM | 4206 | C | CYS | B | 309 | 34.307 | 65.054 | 12.110 | 1.00 | 16.69 |
| ATOM | 4207 | O | CYS | B | 309 | 35.035 | 65.450 | 13.032 | 1.00 | 17.81 |
| ATOM | 4208 | N | GLY | B | 310 | 34.475 | 63.900 | 11.485 | 1.00 | 18.08 |
| ATOM | 4209 | CA | GLY | B | 310 | 35.425 | 62.907 | 11.924 | 1.00 | 20.86 |
| ATOM | 4210 | C | GLY | B | 310 | 34.756 | 61.575 | 11.705 | 1.00 | 22.42 |
| ATOM | 4211 | O | GLY | B | 310 | 34.030 | 61.400 | 10.725 | 1.00 | 23.61 |
| ATOM | 4212 | N | THR | B | 311 | 35.003 | 60.641 | 12.613 | 1.00 | 22.53 |
| ATOM | 4213 | CA | THR | B | 311 | 34.352 | 59.342 | 12.585 | 1.00 | 21.84 |
| ATOM | 4214 | CB | THR | B | 311 | 35.352 | 58.275 | 12.150 | 1.00 | 23.59 |
| ATOM | 4215 | OG1 | THR | B | 311 | 35.755 | 58.539 | 10.800 | 1.00 | 24.41 |
| ATOM | 4216 | CG2 | THR | B | 311 | 34.685 | 56.919 | 12.048 | 1.00 | 24.94 |
| ATOM | 4217 | C | THR | B | 311 | 33.857 | 59.110 | 14.000 | 1.00 | 21.08 |
| ATOM | 4218 | O | THR | B | 311 | 34.608 | 59.335 | 14.950 | 1.00 | 23.66 |
| ATOM | 4219 | N | PRO | B | 312 | 32.594 | 58.704 | 14.151 | 1.00 | 19.37 |
| ATOM | 4220 | CA | PRO | B | 312 | 31.945 | 58.698 | 15.467 | 1.00 | 17.05 |
| ATOM | 4221 | CB | PRO | B | 312 | 30.672 | 57.870 | 15.240 | 1.00 | 16.77 |
| ATOM | 4222 | CG | PRO | B | 312 | 30.808 | 57.292 | 13.879 | 1.00 | 19.01 |
| ATOM | 4223 | CD | PRO | B | 312 | 31.682 | 58.231 | 13.098 | 1.00 | 19.81 |
| ATOM | 4224 | C | PRO | B | 312 | 32.820 | 58.117 | 16.583 | 1.00 | 15.80 |
| ATOM | 4225 | O | PRO | B | 312 | 33.066 | 58.840 | 17.544 | 1.00 | 16.07 |
| ATOM | 4226 | N | GLU | B | 313 | 33.319 | 56.891 | 16.435 | 1.00 | 11.78 |
| ATOM | 4227 | CA | GLU | B | 313 | 34.069 | 56.226 | 17.496 | 1.00 | 10.83 |
| ATOM | 4228 | CB | GLU | B | 313 | 34.235 | 54.752 | 17.166 | 1.00 | 17.06 |
| ATOM | 4229 | CG | GLU | B | 313 | 32.925 | 54.014 | 16.950 | 1.00 | 25.85 |
| ATOM | 4230 | CD | GLU | B | 313 | 32.535 | 53.899 | 15.485 | 1.00 | 28.53 |
| ATOM | 4231 | OE1 | GLU | B | 313 | 32.964 | 54.764 | 14.693 | 1.00 | 29.32 |
| ATOM | 4232 | OE2 | GLU | B | 313 | 31.790 | 52.947 | 15.132 | 1.00 | 31.09 |
| ATOM | 4233 | C | GLU | B | 313 | 35.437 | 56.835 | 17.801 | 1.00 | 10.32 |
| ATOM | 4234 | O | GLU | B | 313 | 36.081 | 56.458 | 18.771 | 1.00 | 8.56 |
| ATOM | 4235 | N | TYR | B | 314 | 35.876 | 57.781 | 16.980 | 1.00 | 12.37 |
| ATOM | 4236 | CA | TYR | B | 314 | 37.155 | 58.465 | 17.197 | 1.00 | 14.09 |
| ATOM | 4237 | CB | TYR | B | 314 | 38.044 | 58.356 | 15.947 | 1.00 | 12.21 |
| ATOM | 4238 | CG | TYR | B | 314 | 38.491 | 56.961 | 15.583 | 1.00 | 11.23 |
| ATOM | 4239 | CD1 | TYR | B | 314 | 37.640 | 56.081 | 14.924 | 1.00 | 12.44 |
| ATOM | 4240 | CE1 | TYR | B | 314 | 38.063 | 54.800 | 14.570 | 1.00 | 13.78 |
| ATOM | 4241 | CZ | TYR | B | 314 | 39.354 | 54.388 | 14.879 | 1.00 | 14.18 |

FIGURE 3 (Cont.)

|      | A    | B    | C   | D | E   | F      | G      | H      | I    | J     |
|------|------|------|-----|---|-----|--------|--------|--------|------|-------|
| ATOM | 4242 | OH   | TYR | B | 314 | 39.786 | 53.116 | 14.528 | 1.00 | 15.73 |
| ATOM | 4243 | CE2  | TYR | B | 314 | 40.215 | 55.256 | 15.519 | 1.00 | 13.25 |
| ATOM | 4244 | CD2  | TYR | B | 314 | 39.782 | 56.536 | 15.859 | 1.00 | 12.61 |
| ATOM | 4245 | C    | TYR | B | 314 | 37.039 | 59.950 | 17.610 | 1.00 | 14.42 |
| ATOM | 4246 | O    | TYR | B | 314 | 38.039 | 60.564 | 17.960 | 1.00 | 17.54 |
| ATOM | 4247 | N    | LEU | B | 315 | 35.844 | 60.531 | 17.546 | 1.00 | 13.41 |
| ATOM | 4248 | CA   | LEU | B | 315 | 35.651 | 61.942 | 17.904 | 1.00 | 15.02 |
| ATOM | 4249 | CB   | LEU | B | 315 | 34.181 | 62.331 | 17.777 | 1.00 | 13.22 |
| ATOM | 4250 | CG   | LEU | B | 315 | 33.465 | 62.203 | 16.442 | 1.00 | 11.72 |
| ATOM | 4251 | CD1  | LEU | B | 315 | 32.011 | 62.568 | 16.657 | 1.00 | 13.04 |
| ATOM | 4252 | CD2  | LEU | B | 315 | 34.079 | 63.107 | 15.397 | 1.00 | 11.32 |
| ATOM | 4253 | C    | LEU | B | 315 | 36.115 | 62.305 | 19.318 | 1.00 | 16.92 |
| ATOM | 4254 | O    | LEU | B | 315 | 35.769 | 61.635 | 20.290 | 1.00 | 24.05 |
| ATOM | 4255 | N    | ALA | B | 316 | 36.884 | 63.379 | 19.431 | 1.00 | 15.91 |
| ATOM | 4256 | CA   | ALA | B | 316 | 37.336 | 63.860 | 20.736 | 1.00 | 13.63 |
| ATOM | 4257 | CB   | ALA | B | 316 | 38.520 | 64.778 | 20.569 | 1.00 | 18.24 |
| ATOM | 4258 | C    | ALA | B | 316 | 36.218 | 64.593 | 21.458 | 1.00 | 10.27 |
| ATOM | 4259 | O    | ALA | B | 316 | 35.422 | 65.282 | 20.835 | 1.00 | 9.45  |
| ATOM | 4260 | N    | PRO | B | 317 | 36.160 | 64.447 | 22.773 | 1.00 | 7.68  |
| ATOM | 4261 | CA   | PRO | B | 317 | 35.129 | 65.088 | 23.589 | 1.00 | 6.85  |
| ATOM | 4262 | CB   | PRO | B | 317 | 35.786 | 65.107 | 24.968 | 1.00 | 5.83  |
| ATOM | 4263 | CG   | PRO | B | 317 | 36.494 | 63.810 | 25.004 | 1.00 | 5.99  |
| ATOM | 4264 | CD   | PRO | B | 317 | 37.051 | 63.619 | 23.602 | 1.00 | 8.16  |
| ATOM | 4265 | C    | PRO | B | 317 | 34.709 | 66.494 | 23.148 | 1.00 | 7.55  |
| ATOM | 4266 | O    | PRO | B | 317 | 33.518 | 66.797 | 23.125 | 1.00 | 9.06  |
| ATOM | 4267 | N    | GLU | B | 318 | 35.671 | 67.331 | 22.790 | 1.00 | 9.59  |
| ATOM | 4268 | CA   | GLU | B | 318 | 35.407 | 68.735 | 22.491 | 1.00 | 8.77  |
| ATOM | 4269 | CB   | GLU | B | 318 | 36.685 | 69.557 | 22.670 | 1.00 | 9.97  |
| ATOM | 4270 | CG   | GLU | B | 318 | 37.744 | 69.279 | 21.616 | 1.00 | 13.10 |
| ATOM | 4271 | CD   | GLU | B | 318 | 38.691 | 68.154 | 21.987 | 1.00 | 15.50 |
| ATOM | 4272 | OE1  | GLU | B | 318 | 38.287 | 67.204 | 22.693 | 1.00 | 18.20 |
| ATOM | 4273 | OE2  | GLU | B | 318 | 39.859 | 68.219 | 21.563 | 1.00 | 18.63 |
| ATOM | 4274 | C    | GLU | B | 318 | 34.794 | 68.949 | 21.100 | 1.00 | 8.79  |
| ATOM | 4275 | O    | GLU | B | 318 | 34.173 | 69.968 | 20.844 | 1.00 | 13.25 |
| ATOM | 4276 | N    | VAL | B | 319 | 34.965 | 67.989 | 20.203 | 1.00 | 8.20  |
| ATOM | 4277 | CA   | VAL | B | 319 | 34.271 | 68.007 | 18.921 | 1.00 | 6.16  |
| ATOM | 4278 | CB   | VAL | B | 319 | 34.911 | 67.000 | 17.951 | 1.00 | 8.45  |
| ATOM | 4279 | CG1  | VAL | B | 319 | 34.131 | 66.891 | 16.651 | 1.00 | 10.62 |
| ATOM | 4280 | CG2  | VAL | B | 319 | 36.346 | 67.392 | 17.670 | 1.00 | 9.41  |
| ATOM | 4281 | C    | VAL | B | 319 | 32.776 | 67.709 | 19.126 | 1.00 | 6.05  |
| ATOM | 4282 | O    | VAL | B | 319 | 31.955 | 68.019 | 18.266 | 1.00 | 6.41  |
| ATOM | 4283 | N    | LEU | B | 320 | 32.434 | 67.124 | 20.274 | 1.00 | 5.83  |
| ATOM | 4284 | CA   | LEU | B | 320 | 31.042 | 66.902 | 20.662 | 1.00 | 8.71  |
| ATOM | 4285 | CB   | LEU | B | 320 | 30.870 | 65.509 | 21.274 | 1.00 | 2.79  |
| ATOM | 4286 | CG   | LEU | B | 320 | 31.159 | 64.281 | 20.416 | 1.00 | 2.34  |
| ATOM | 4287 | CD1  | LEU | B | 320 | 31.272 | 63.091 | 21.304 | 1.00 | 3.00  |
| ATOM | 4288 | CD2  | LEU | B | 320 | 30.097 | 64.025 | 19.351 | 1.00 | 2.90  |
| ATOM | 4289 | C    | LEU | B | 320 | 30.519 | 67.971 | 21.638 | 1.00 | 15.55 |
| ATOM | 4290 | O    | LEU | B | 320 | 29.320 | 68.021 | 21.950 | 1.00 | 16.84 |
| ATOM | 4291 | N    | GLU | B | 321 | 31.422 | 68.835 | 22.094 | 1.00 | 22.42 |
| ATOM | 4292 | CA   | GLU | B | 321 | 31.134 | 69.770 | 23.173 | 1.00 | 29.74 |
| ATOM | 4293 | CB   | GLU | B | 321 | 31.607 | 69.153 | 24.484 | 1.00 | 31.35 |

FIGURE 3 (Cont.)

| | A | B | C | D | E | F | G | H | I | J |
|---|---|---|---|---|---|---|---|---|---|---|
| ATOM | 4294 | CG | GLU | B | 321 | 30.506 | 68.427 | 25.219 | 1.00 | 37.27 |
| ATOM | 4295 | CD | GLU | B | 321 | 29.942 | 69.265 | 26.344 | 1.00 | 42.49 |
| ATOM | 4296 | OE1 | GLU | B | 321 | 30.754 | 69.695 | 27.198 | 1.00 | 45.23 |
| ATOM | 4297 | OE2 | GLU | B | 321 | 28.704 | 69.500 | 26.373 | 1.00 | 42.64 |
| ATOM | 4298 | C | GLU | B | 321 | 31.757 | 71.166 | 22.961 | 1.00 | 34.59 |
| ATOM | 4299 | O | GLU | B | 321 | 32.983 | 71.326 | 22.919 | 1.00 | 37.16 |
| ATOM | 4300 | N | ASP | B | 322 | 30.903 | 72.180 | 22.853 | 1.00 | 37.44 |
| ATOM | 4301 | CA | ASP | B | 322 | 31.328 | 73.535 | 22.470 | 1.00 | 40.65 |
| ATOM | 4302 | CB | ASP | B | 322 | 32.434 | 74.099 | 23.389 | 1.00 | 41.61 |
| ATOM | 4303 | CG | ASP | B | 322 | 32.130 | 75.525 | 23.879 | 1.00 | 42.71 |
| ATOM | 4304 | OD1 | ASP | B | 322 | 32.293 | 75.783 | 25.093 | 1.00 | 42.32 |
| ATOM | 4305 | OD2 | ASP | B | 322 | 31.729 | 76.450 | 23.129 | 1.00 | 41.67 |
| ATOM | 4306 | C | ASP | B | 322 | 31.730 | 73.613 | 20.989 | 1.00 | 40.63 |
| ATOM | 4307 | O | ASP | B | 322 | 32.306 | 72.666 | 20.425 | 1.00 | 38.23 |
| ATOM | 4308 | N | ASN | B | 323 | 31.423 | 74.761 | 20.379 | 1.00 | 39.51 |
| ATOM | 4309 | CA | ASN | B | 323 | 31.488 | 74.928 | 18.925 | 1.00 | 37.84 |
| ATOM | 4310 | CB | ASN | B | 323 | 30.424 | 75.925 | 18.436 | 1.00 | 36.86 |
| ATOM | 4311 | CG | ASN | B | 323 | 29.498 | 76.400 | 19.548 | 1.00 | 37.44 |
| ATOM | 4312 | OD1 | ASN | B | 323 | 29.400 | 77.599 | 19.811 | 1.00 | 38.17 |
| ATOM | 4313 | ND2 | ASN | B | 323 | 28.806 | 75.464 | 20.195 | 1.00 | 36.47 |
| ATOM | 4314 | C | ASN | B | 323 | 32.875 | 75.285 | 18.374 | 1.00 | 36.80 |
| ATOM | 4315 | O | ASN | B | 323 | 32.981 | 75.908 | 17.309 | 1.00 | 37.57 |
| ATOM | 4316 | N | ASP | B | 324 | 33.927 | 74.871 | 19.088 | 1.00 | 33.06 |
| ATOM | 4317 | CA | ASP | B | 324 | 35.310 | 75.170 | 18.710 | 1.00 | 28.72 |
| ATOM | 4318 | CB | ASP | B | 324 | 35.715 | 76.549 | 19.232 | 1.00 | 31.13 |
| ATOM | 4319 | CG | ASP | B | 324 | 35.333 | 76.753 | 20.692 | 1.00 | 34.59 |
| ATOM | 4320 | OD1 | ASP | B | 324 | 34.356 | 77.493 | 20.960 | 1.00 | 36.64 |
| ATOM | 4321 | OD2 | ASP | B | 324 | 35.947 | 76.207 | 21.637 | 1.00 | 34.29 |
| ATOM | 4322 | C | ASP | B | 324 | 36.273 | 74.118 | 19.249 | 1.00 | 24.49 |
| ATOM | 4323 | O | ASP | B | 324 | 36.165 | 73.703 | 20.397 | 1.00 | 24.39 |
| ATOM | 4324 | N | TYR | B | 325 | 37.213 | 73.689 | 18.416 | 1.00 | 20.24 |
| ATOM | 4325 | CA | TYR | B | 325 | 38.232 | 72.740 | 18.836 | 1.00 | 17.31 |
| ATOM | 4326 | CB | TYR | B | 325 | 37.781 | 71.306 | 18.600 | 1.00 | 14.75 |
| ATOM | 4327 | CG | TYR | B | 325 | 37.466 | 70.927 | 17.162 | 1.00 | 14.79 |
| ATOM | 4328 | CD1 | TYR | B | 325 | 38.457 | 70.459 | 16.296 | 1.00 | 13.00 |
| ATOM | 4329 | CE1 | TYR | B | 325 | 38.154 | 70.076 | 14.990 | 1.00 | 11.33 |
| ATOM | 4330 | CZ | TYR | B | 325 | 36.846 | 70.157 | 14.544 | 1.00 | 13.15 |
| ATOM | 4331 | OH | TYR | B | 325 | 36.516 | 69.796 | 13.263 | 1.00 | 14.91 |
| ATOM | 4332 | CE2 | TYR | B | 325 | 35.848 | 70.609 | 15.379 | 1.00 | 14.41 |
| ATOM | 4333 | CD2 | TYR | B | 325 | 36.160 | 70.984 | 16.684 | 1.00 | 16.48 |
| ATOM | 4334 | C | TYR | B | 325 | 39.561 | 72.982 | 18.151 | 1.00 | 19.20 |
| ATOM | 4335 | O | TYR | B | 325 | 39.608 | 73.477 | 17.027 | 1.00 | 19.57 |
| ATOM | 4336 | N | GLY | B | 326 | 40.637 | 72.604 | 18.835 | 1.00 | 21.72 |
| ATOM | 4337 | CA | GLY | B | 326 | 41.986 | 72.881 | 18.375 | 1.00 | 21.26 |
| ATOM | 4338 | C | GLY | B | 326 | 42.671 | 71.717 | 17.690 | 1.00 | 20.47 |
| ATOM | 4339 | O | GLY | B | 326 | 42.047 | 70.708 | 17.356 | 1.00 | 17.47 |
| ATOM | 4340 | N | ARG | B | 327 | 43.973 | 71.869 | 17.477 | 1.00 | 20.74 |
| ATOM | 4341 | CA | ARG | B | 327 | 44.757 | 70.855 | 16.790 | 1.00 | 21.31 |
| ATOM | 4342 | CB | ARG | B | 327 | 46.113 | 71.423 | 16.379 | 1.00 | 23.72 |
| ATOM | 4343 | CG | ARG | B | 327 | 47.076 | 71.692 | 17.522 | 1.00 | 25.99 |
| ATOM | 4344 | CD | ARG | B | 327 | 48.529 | 71.470 | 17.131 | 1.00 | 28.60 |
| ATOM | 4345 | NE | ARG | B | 327 | 49.411 | 72.567 | 17.530 | 1.00 | 30.02 |

FIGURE 3 (Cont.)

| | A | B | C | D | E | F | G | H | I | J |
|---|---|---|---|---|---|---|---|---|---|---|
| ATOM | 4346 | CZ | ARG | B | 327 | 49.394 | 73.793 | 17.011 | 1.00 | 30.86 |
| ATOM | 4347 | NH1 | ARG | B | 327 | 48.528 | 74.131 | 16.056 | 1.00 | 31.23 |
| ATOM | 4348 | NH2 | ARG | B | 327 | 50.250 | 74.696 | 17.460 | 1.00 | 31.52 |
| ATOM | 4349 | C | ARG | B | 327 | 44.937 | 69.639 | 17.681 | 1.00 | 21.21 |
| ATOM | 4350 | O | ARG | B | 327 | 45.363 | 68.578 | 17.233 | 1.00 | 23.48 |
| ATOM | 4351 | N | ALA | B | 328 | 44.591 | 69.807 | 18.950 | 1.00 | 19.99 |
| ATOM | 4352 | CA | ALA | B | 328 | 44.769 | 68.775 | 19.953 | 1.00 | 17.18 |
| ATOM | 4353 | CB | ALA | B | 328 | 44.415 | 69.336 | 21.306 | 1.00 | 20.38 |
| ATOM | 4354 | C | ALA | B | 328 | 43.934 | 67.536 | 19.650 | 1.00 | 15.73 |
| ATOM | 4355 | O | ALA | B | 328 | 44.257 | 66.439 | 20.093 | 1.00 | 14.96 |
| ATOM | 4356 | N | VAL | B | 329 | 42.868 | 67.724 | 18.879 | 1.00 | 16.23 |
| ATOM | 4357 | CA | VAL | B | 329 | 41.957 | 66.641 | 18.495 | 1.00 | 16.29 |
| ATOM | 4358 | CB | VAL | B | 329 | 40.745 | 67.162 | 17.657 | 1.00 | 16.98 |
| ATOM | 4359 | CG1 | VAL | B | 329 | 40.216 | 68.462 | 18.227 | 1.00 | 17.33 |
| ATOM | 4360 | CG2 | VAL | B | 329 | 41.102 | 67.317 | 16.175 | 1.00 | 14.80 |
| ATOM | 4361 | C | VAL | B | 329 | 42.654 | 65.523 | 17.730 | 1.00 | 14.37 |
| ATOM | 4362 | O | VAL | B | 329 | 42.164 | 64.396 | 17.685 | 1.00 | 13.77 |
| ATOM | 4363 | N | ASP | B | 330 | 43.786 | 65.859 | 17.122 | 1.00 | 14.35 |
| ATOM | 4364 | CA | ASP | B | 330 | 44.592 | 64.902 | 16.393 | 1.00 | 14.73 |
| ATOM | 4365 | CB | ASP | B | 330 | 45.615 | 65.635 | 15.522 | 1.00 | 15.49 |
| ATOM | 4366 | CG | ASP | B | 330 | 45.235 | 65.642 | 14.045 | 1.00 | 15.11 |
| ATOM | 4367 | OD1 | ASP | B | 330 | 44.370 | 64.825 | 13.644 | 1.00 | 14.60 |
| ATOM | 4368 | OD2 | ASP | B | 330 | 45.759 | 66.424 | 13.218 | 1.00 | 12.82 |
| ATOM | 4369 | C | ASP | B | 330 | 45.278 | 63.942 | 17.369 | 1.00 | 14.54 |
| ATOM | 4370 | O | ASP | B | 330 | 45.361 | 62.738 | 17.112 | 1.00 | 11.53 |
| ATOM | 4371 | N | TRP | B | 331 | 45.744 | 64.470 | 18.498 | 1.00 | 16.03 |
| ATOM | 4372 | CA | TRP | B | 331 | 46.370 | 63.634 | 19.526 | 1.00 | 16.64 |
| ATOM | 4373 | CB | TRP | B | 331 | 47.178 | 64.474 | 20.505 | 1.00 | 19.05 |
| ATOM | 4374 | CG | TRP | B | 331 | 48.239 | 65.261 | 19.819 | 1.00 | 21.93 |
| ATOM | 4375 | CD1 | TRP | B | 331 | 48.493 | 66.578 | 19.977 | 1.00 | 20.70 |
| ATOM | 4376 | NE1 | TRP | B | 331 | 49.538 | 66.954 | 19.170 | 1.00 | 24.97 |
| ATOM | 4377 | CE2 | TRP | B | 331 | 49.978 | 65.865 | 18.464 | 1.00 | 25.95 |
| ATOM | 4378 | CD2 | TRP | B | 331 | 49.183 | 64.777 | 18.847 | 1.00 | 24.32 |
| ATOM | 4379 | CE3 | TRP | B | 331 | 49.445 | 63.524 | 18.270 | 1.00 | 26.14 |
| ATOM | 4380 | CZ3 | TRP | B | 331 | 50.475 | 63.410 | 17.338 | 1.00 | 25.95 |
| ATOM | 4381 | CH2 | TRP | B | 331 | 51.242 | 64.511 | 16.980 | 1.00 | 27.19 |
| ATOM | 4382 | CZ2 | TRP | B | 331 | 51.012 | 65.748 | 17.527 | 1.00 | 28.48 |
| ATOM | 4383 | C | TRP | B | 331 | 45.381 | 62.761 | 20.269 | 1.00 | 16.30 |
| ATOM | 4384 | O | TRP | B | 331 | 45.772 | 61.710 | 20.798 | 1.00 | 15.84 |
| ATOM | 4385 | N | TRP | B | 332 | 44.113 | 63.201 | 20.304 | 1.00 | 15.15 |
| ATOM | 4386 | CA | TRP | B | 332 | 43.020 | 62.388 | 20.826 | 1.00 | 11.35 |
| ATOM | 4387 | CB | TRP | B | 332 | 41.688 | 63.141 | 20.890 | 1.00 | 8.48 |
| ATOM | 4388 | CG | TRP | B | 332 | 40.585 | 62.189 | 21.238 | 1.00 | 10.41 |
| ATOM | 4389 | CD1 | TRP | B | 332 | 39.854 | 61.432 | 20.372 | 1.00 | 12.65 |
| ATOM | 4390 | NE1 | TRP | B | 332 | 38.965 | 60.636 | 21.057 | 1.00 | 15.47 |
| ATOM | 4391 | CE2 | TRP | B | 332 | 39.125 | 60.849 | 22.402 | 1.00 | 14.32 |
| ATOM | 4392 | CD2 | TRP | B | 332 | 40.140 | 61.823 | 22.555 | 1.00 | 12.86 |
| ATOM | 4393 | CE3 | TRP | B | 332 | 40.495 | 62.219 | 23.857 | 1.00 | 10.28 |
| ATOM | 4394 | CZ3 | TRP | B | 332 | 39.837 | 61.655 | 24.929 | 1.00 | 6.42 |
| ATOM | 4395 | CH2 | TRP | B | 332 | 38.839 | 60.691 | 24.741 | 1.00 | 8.73 |
| ATOM | 4396 | CZ2 | TRP | B | 332 | 38.467 | 60.274 | 23.492 | 1.00 | 11.29 |
| ATOM | 4397 | C | TRP | B | 332 | 42.881 | 61.180 | 19.920 | 1.00 | 12.52 |

FIGURE 3 (Cont.)

|      | A    | B   | C   | D | E   | F      | G      | H      | I    | J     |
|------|------|-----|-----|---|-----|--------|--------|--------|------|-------|
| ATOM | 4398 | O   | TRP | B | 332 | 42.926 | 60.038 | 20.380 | 1.00 | 14.93 |
| ATOM | 4399 | N   | GLY | B | 333 | 42.727 | 61.445 | 18.627 | 1.00 | 12.63 |
| ATOM | 4400 | CA  | GLY | B | 333 | 42.637 | 60.401 | 17.622 | 1.00 | 13.28 |
| ATOM | 4401 | C   | GLY | B | 333 | 43.767 | 59.399 | 17.732 | 1.00 | 12.19 |
| ATOM | 4402 | O   | GLY | B | 333 | 43.528 | 58.195 | 17.818 | 1.00 | 12.55 |
| ATOM | 4403 | N   | LEU | B | 334 | 44.996 | 59.908 | 17.756 | 1.00 | 13.12 |
| ATOM | 4404 | CA  | LEU | B | 334 | 46.190 | 59.076 | 17.876 | 1.00 | 13.17 |
| ATOM | 4405 | CB  | LEU | B | 334 | 47.444 | 59.937 | 18.012 | 1.00 | 11.84 |
| ATOM | 4406 | CG  | LEU | B | 334 | 48.625 | 59.104 | 18.486 | 1.00 | 12.18 |
| ATOM | 4407 | CD1 | LEU | B | 334 | 49.242 | 58.340 | 17.335 | 1.00 | 12.00 |
| ATOM | 4408 | CD2 | LEU | B | 334 | 49.640 | 59.960 | 19.186 | 1.00 | 15.03 |
| ATOM | 4409 | C   | LEU | B | 334 | 46.091 | 58.120 | 19.054 | 1.00 | 13.54 |
| ATOM | 4410 | O   | LEU | B | 334 | 46.466 | 56.949 | 18.944 | 1.00 | 16.15 |
| ATOM | 4411 | N   | GLY | B | 335 | 45.576 | 58.623 | 20.172 | 1.00 | 11.75 |
| ATOM | 4412 | CA  | GLY | B | 335 | 45.335 | 57.799 | 21.348 | 1.00 | 13.08 |
| ATOM | 4413 | C   | GLY | B | 335 | 44.339 | 56.666 | 21.156 | 1.00 | 8.84  |
| ATOM | 4414 | O   | GLY | B | 335 | 44.521 | 55.570 | 21.669 | 1.00 | 7.86  |
| ATOM | 4415 | N   | VAL | B | 336 | 43.283 | 56.934 | 20.409 | 1.00 | 7.01  |
| ATOM | 4416 | CA  | VAL | B | 336 | 42.305 | 55.909 | 20.115 | 1.00 | 6.97  |
| ATOM | 4417 | CB  | VAL | B | 336 | 41.063 | 56.504 | 19.467 | 1.00 | 3.69  |
| ATOM | 4418 | CG1 | VAL | B | 336 | 39.947 | 55.473 | 19.397 | 1.00 | 2.00  |
| ATOM | 4419 | CG2 | VAL | B | 336 | 40.614 | 57.707 | 20.271 | 1.00 | 3.64  |
| ATOM | 4420 | C   | VAL | B | 336 | 42.911 | 54.811 | 19.253 | 1.00 | 8.87  |
| ATOM | 4421 | O   | VAL | B | 336 | 42.619 | 53.632 | 19.450 | 1.00 | 12.62 |
| ATOM | 4422 | N   | VAL | B | 337 | 43.781 | 55.193 | 18.326 | 1.00 | 11.54 |
| ATOM | 4423 | CA  | VAL | B | 337 | 44.434 | 54.224 | 17.440 | 1.00 | 14.78 |
| ATOM | 4424 | CB  | VAL | B | 337 | 45.204 | 54.926 | 16.304 | 1.00 | 13.08 |
| ATOM | 4425 | CG1 | VAL | B | 337 | 46.202 | 53.991 | 15.671 | 1.00 | 13.68 |
| ATOM | 4426 | CG2 | VAL | B | 337 | 44.240 | 55.443 | 15.258 | 1.00 | 14.21 |
| ATOM | 4427 | C   | VAL | B | 337 | 45.372 | 53.298 | 18.226 | 1.00 | 17.27 |
| ATOM | 4428 | O   | VAL | B | 337 | 45.317 | 52.066 | 18.087 | 1.00 | 17.10 |
| ATOM | 4429 | N   | MET | B | 338 | 46.215 | 53.899 | 19.059 | 1.00 | 16.78 |
| ATOM | 4430 | CA  | MET | B | 338 | 47.142 | 53.147 | 19.892 | 1.00 | 16.49 |
| ATOM | 4431 | CB  | MET | B | 338 | 48.058 | 54.108 | 20.634 | 1.00 | 18.95 |
| ATOM | 4432 | CG  | MET | B | 338 | 48.762 | 55.066 | 19.737 | 1.00 | 20.97 |
| ATOM | 4433 | SD  | MET | B | 338 | 50.500 | 54.742 | 19.695 | 1.00 | 24.33 |
| ATOM | 4434 | CE  | MET | B | 338 | 51.093 | 56.371 | 20.031 | 1.00 | 23.99 |
| ATOM | 4435 | C   | MET | B | 338 | 46.410 | 52.235 | 20.883 | 1.00 | 15.00 |
| ATOM | 4436 | O   | MET | B | 338 | 46.736 | 51.057 | 20.986 | 1.00 | 14.57 |
| ATOM | 4437 | N   | TYR | B | 339 | 45.424 | 52.787 | 21.596 | 1.00 | 12.04 |
| ATOM | 4438 | CA  | TYR | B | 339 | 44.589 | 52.013 | 22.503 | 1.00 | 9.51  |
| ATOM | 4439 | CB  | TYR | B | 339 | 43.369 | 52.816 | 22.961 | 1.00 | 10.12 |
| ATOM | 4440 | CG  | TYR | B | 339 | 42.606 | 52.162 | 24.109 | 1.00 | 9.46  |
| ATOM | 4441 | CD1 | TYR | B | 339 | 41.662 | 51.186 | 23.871 | 1.00 | 10.35 |
| ATOM | 4442 | CE1 | TYR | B | 339 | 40.977 | 50.597 | 24.902 | 1.00 | 14.48 |
| ATOM | 4443 | CZ  | TYR | B | 339 | 41.228 | 50.985 | 26.207 | 1.00 | 14.68 |
| ATOM | 4444 | OH  | TYR | B | 339 | 40.541 | 50.383 | 27.249 | 1.00 | 17.45 |
| ATOM | 4445 | CE2 | TYR | B | 339 | 42.160 | 51.959 | 26.468 | 1.00 | 9.71  |
| ATOM | 4446 | CD2 | TYR | B | 339 | 42.835 | 52.538 | 25.430 | 1.00 | 9.10  |
| ATOM | 4447 | C   | TYR | B | 339 | 44.098 | 50.778 | 21.796 | 1.00 | 11.30 |
| ATOM | 4448 | O   | TYR | B | 339 | 44.179 | 49.671 | 22.338 | 1.00 | 10.56 |
| ATOM | 4449 | N   | GLU | B | 340 | 43.570 | 50.984 | 20.589 | 1.00 | 11.24 |

FIGURE 3 (Cont.)

| | A | B | C | D | E | F | G | H | I | J |
|---|---|---|---|---|---|---|---|---|---|---|
| ATOM | 4450 | CA  | GLU | B | 340 | 43.074 | 49.894 | 19.779 | 1.00 | 11.90 |
| ATOM | 4451 | CB  | GLU | B | 340 | 42.558 | 50.409 | 18.447 | 1.00 | 13.52 |
| ATOM | 4452 | CG  | GLU | B | 340 | 41.064 | 50.649 | 18.468 | 1.00 | 21.94 |
| ATOM | 4453 | CD  | GLU | B | 340 | 40.530 | 51.261 | 17.181 | 1.00 | 28.56 |
| ATOM | 4454 | OE1 | GLU | B | 340 | 40.818 | 52.461 | 16.914 | 1.00 | 29.69 |
| ATOM | 4455 | OE2 | GLU | B | 340 | 39.798 | 50.544 | 16.448 | 1.00 | 30.78 |
| ATOM | 4456 | C   | GLU | B | 340 | 44.176 | 48.873 | 19.585 | 1.00 | 12.55 |
| ATOM | 4457 | O   | GLU | B | 340 | 43.979 | 47.705 | 19.870 | 1.00 | 11.29 |
| ATOM | 4458 | N   | MET | B | 341 | 45.351 | 49.336 | 19.158 | 1.00 | 14.93 |
| ATOM | 4459 | CA  | MET | B | 341 | 46.463 | 48.458 | 18.796 | 1.00 | 14.45 |
| ATOM | 4460 | CB  | MET | B | 341 | 47.620 | 49.266 | 18.214 | 1.00 | 17.57 |
| ATOM | 4461 | CG  | MET | B | 341 | 47.322 | 49.800 | 16.823 | 1.00 | 24.76 |
| ATOM | 4462 | SD  | MET | B | 341 | 48.700 | 50.614 | 15.982 | 1.00 | 33.37 |
| ATOM | 4463 | CE  | MET | B | 341 | 49.211 | 51.892 | 17.221 | 1.00 | 31.54 |
| ATOM | 4464 | C   | MET | B | 341 | 46.937 | 47.631 | 19.964 | 1.00 | 12.78 |
| ATOM | 4465 | O   | MET | B | 341 | 47.284 | 46.476 | 19.795 | 1.00 | 13.64 |
| ATOM | 4466 | N   | MET | B | 342 | 46.919 | 48.223 | 21.151 | 1.00 | 14.31 |
| ATOM | 4467 | CA  | MET | B | 342 | 47.476 | 47.595 | 22.339 | 1.00 | 14.71 |
| ATOM | 4468 | CB  | MET | B | 342 | 48.242 | 48.619 | 23.171 | 1.00 | 15.87 |
| ATOM | 4469 | CG  | MET | B | 342 | 49.612 | 48.942 | 22.614 | 1.00 | 20.88 |
| ATOM | 4470 | SD  | MET | B | 342 | 50.417 | 50.389 | 23.361 | 1.00 | 26.64 |
| ATOM | 4471 | CE  | MET | B | 342 | 50.144 | 51.676 | 22.133 | 1.00 | 23.62 |
| ATOM | 4472 | C   | MET | B | 342 | 46.438 | 46.898 | 23.203 | 1.00 | 14.90 |
| ATOM | 4473 | O   | MET | B | 342 | 46.805 | 46.079 | 24.039 | 1.00 | 18.91 |
| ATOM | 4474 | N   | CYS | B | 343 | 45.158 | 47.210 | 23.014 | 1.00 | 13.67 |
| ATOM | 4475 | CA  | CYS | B | 343 | 44.099 | 46.584 | 23.805 | 1.00 | 15.90 |
| ATOM | 4476 | CB  | CYS | B | 343 | 43.246 | 47.629 | 24.506 | 1.00 | 19.25 |
| ATOM | 4477 | SG  | CYS | B | 343 | 44.170 | 48.738 | 25.586 | 1.00 | 26.27 |
| ATOM | 4478 | C   | CYS | B | 343 | 43.210 | 45.694 | 22.961 | 1.00 | 16.22 |
| ATOM | 4479 | O   | CYS | B | 343 | 42.646 | 44.716 | 23.449 | 1.00 | 17.19 |
| ATOM | 4480 | N   | GLY | B | 344 | 43.069 | 46.039 | 21.693 | 1.00 | 17.83 |
| ATOM | 4481 | CA  | GLY | B | 344 | 42.328 | 45.199 | 20.774 | 1.00 | 20.58 |
| ATOM | 4482 | C   | GLY | B | 344 | 40.860 | 45.542 | 20.698 | 1.00 | 20.75 |
| ATOM | 4483 | O   | GLY | B | 344 | 40.069 | 44.743 | 20.208 | 1.00 | 23.39 |
| ATOM | 4484 | N   | ARG | B | 345 | 40.506 | 46.732 | 21.180 | 1.00 | 20.83 |
| ATOM | 4485 | CA  | ARG | B | 345 | 39.122 | 47.199 | 21.242 | 1.00 | 20.70 |
| ATOM | 4486 | CB  | ARG | B | 345 | 38.356 | 46.513 | 22.397 | 1.00 | 25.58 |
| ATOM | 4487 | CG  | ARG | B | 345 | 38.384 | 47.254 | 23.749 | 1.00 | 34.42 |
| ATOM | 4488 | CD  | ARG | B | 345 | 37.400 | 46.749 | 24.845 | 1.00 | 41.97 |
| ATOM | 4489 | NE  | ARG | B | 345 | 36.058 | 46.369 | 24.369 | 1.00 | 49.37 |
| ATOM | 4490 | CZ  | ARG | B | 345 | 35.010 | 47.192 | 24.246 | 1.00 | 50.51 |
| ATOM | 4491 | NH1 | ARG | B | 345 | 35.110 | 48.486 | 24.546 | 1.00 | 48.34 |
| ATOM | 4492 | NH2 | ARG | B | 345 | 33.855 | 46.709 | 23.799 | 1.00 | 50.95 |
| ATOM | 4493 | C   | ARG | B | 345 | 39.172 | 48.709 | 21.409 | 1.00 | 16.65 |
| ATOM | 4494 | O   | ARG | B | 345 | 40.211 | 49.238 | 21.766 | 1.00 | 16.96 |
| ATOM | 4495 | N   | LEU | B | 346 | 38.072 | 49.405 | 21.137 | 1.00 | 15.86 |
| ATOM | 4496 | CA  | LEU | B | 346 | 38.032 | 50.862 | 21.315 | 1.00 | 14.17 |
| ATOM | 4497 | CB  | LEU | B | 346 | 36.859 | 51.477 | 20.553 | 1.00 | 12.87 |
| ATOM | 4498 | CG  | LEU | B | 346 | 36.834 | 51.339 | 19.031 | 1.00 | 15.21 |
| ATOM | 4499 | CD1 | LEU | B | 346 | 35.403 | 51.358 | 18.490 | 1.00 | 13.86 |
| ATOM | 4500 | CD2 | LEU | B | 346 | 37.662 | 52.438 | 18.390 | 1.00 | 15.93 |
| ATOM | 4501 | C   | LEU | B | 346 | 37.925 | 51.248 | 22.787 | 1.00 | 13.00 |

FIGURE 3 (Cont.)

| | A | B | C | D | E | F | G | H | I | J |
|---|---|---|---|---|---|---|---|---|---|---|
| ATOM | 4502 | O | LEU | B | 346 | 37.323 | 50.528 | 23.579 | 1.00 | 16.80 |
| ATOM | 4503 | N | PRO | B | 347 | 38.490 | 52.388 | 23.150 | 1.00 | 9.96 |
| ATOM | 4504 | CA | PRO | B | 347 | 38.318 | 52.940 | 24.499 | 1.00 | 11.39 |
| ATOM | 4505 | CB | PRO | B | 347 | 38.877 | 54.354 | 24.368 | 1.00 | 12.35 |
| ATOM | 4506 | CG | PRO | B | 347 | 38.956 | 54.594 | 22.852 | 1.00 | 12.98 |
| ATOM | 4507 | CD | PRO | B | 347 | 39.310 | 53.255 | 22.292 | 1.00 | 10.27 |
| ATOM | 4508 | C | PRO | B | 347 | 36.844 | 53.030 | 24.848 | 1.00 | 13.11 |
| ATOM | 4509 | O | PRO | B | 347 | 36.444 | 52.736 | 25.975 | 1.00 | 19.49 |
| ATOM | 4510 | N | PHE | B | 348 | 36.038 | 53.447 | 23.881 | 1.00 | 10.96 |
| ATOM | 4511 | CA | PHE | B | 348 | 34.601 | 53.523 | 24.067 | 1.00 | 10.59 |
| ATOM | 4512 | CB | PHE | B | 348 | 34.172 | 54.956 | 24.345 | 1.00 | 8.94 |
| ATOM | 4513 | CG | PHE | B | 348 | 35.185 | 55.751 | 25.091 | 1.00 | 8.20 |
| ATOM | 4514 | CD1 | PHE | B | 348 | 35.200 | 55.745 | 26.492 | 1.00 | 8.19 |
| ATOM | 4515 | CE1 | PHE | B | 348 | 36.147 | 56.488 | 27.212 | 1.00 | 3.43 |
| ATOM | 4516 | CZ | PHE | B | 348 | 37.083 | 57.231 | 26.527 | 1.00 | 6.33 |
| ATOM | 4517 | CE2 | PHE | B | 348 | 37.075 | 57.240 | 25.106 | 1.00 | 8.52 |
| ATOM | 4518 | CD2 | PHE | B | 348 | 36.132 | 56.501 | 24.407 | 1.00 | 6.05 |
| ATOM | 4519 | C | PHE | B | 348 | 33.897 | 52.997 | 22.827 | 1.00 | 11.72 |
| ATOM | 4520 | O | PHE | B | 348 | 34.343 | 53.240 | 21.700 | 1.00 | 9.50 |
| ATOM | 4521 | N | TYR | B | 349 | 32.806 | 52.263 | 23.036 | 1.00 | 12.19 |
| ATOM | 4522 | CA | TYR | B | 349 | 32.048 | 51.724 | 21.922 | 1.00 | 14.74 |
| ATOM | 4523 | CB | TYR | B | 349 | 32.625 | 50.403 | 21.414 | 1.00 | 17.05 |
| ATOM | 4524 | CG | TYR | B | 349 | 31.803 | 49.839 | 20.286 | 1.00 | 19.31 |
| ATOM | 4525 | CD1 | TYR | B | 349 | 31.926 | 50.339 | 18.978 | 1.00 | 18.91 |
| ATOM | 4526 | CE1 | TYR | B | 349 | 31.154 | 49.837 | 17.940 | 1.00 | 20.17 |
| ATOM | 4527 | CZ | TYR | B | 349 | 30.230 | 48.829 | 18.216 | 1.00 | 24.26 |
| ATOM | 4528 | OH | TYR | B | 349 | 29.431 | 48.296 | 17.226 | 1.00 | 27.02 |
| ATOM | 4529 | CE2 | TYR | B | 349 | 30.087 | 48.332 | 19.505 | 1.00 | 25.00 |
| ATOM | 4530 | CD2 | TYR | B | 349 | 30.872 | 48.839 | 20.530 | 1.00 | 21.89 |
| ATOM | 4531 | C | TYR | B | 349 | 30.593 | 51.506 | 22.229 | 1.00 | 16.51 |
| ATOM | 4532 | O | TYR | B | 349 | 30.246 | 50.827 | 23.197 | 1.00 | 21.93 |
| ATOM | 4533 | N | ASN | B | 350 | 29.749 | 52.081 | 21.380 | 1.00 | 14.72 |
| ATOM | 4534 | CA | ASN | B | 350 | 28.396 | 51.587 | 21.203 | 1.00 | 10.73 |
| ATOM | 4535 | CB | ASN | B | 350 | 27.354 | 52.415 | 21.954 | 1.00 | 8.13 |
| ATOM | 4536 | CG | ASN | B | 350 | 26.196 | 51.559 | 22.455 | 1.00 | 7.47 |
| ATOM | 4537 | OD1 | ASN | B | 350 | 25.112 | 52.048 | 22.687 | 1.00 | 8.42 |
| ATOM | 4538 | ND2 | ASN | B | 350 | 26.436 | 50.269 | 22.622 | 1.00 | 7.62 |
| ATOM | 4539 | C | ASN | B | 350 | 28.052 | 51.508 | 19.741 | 1.00 | 9.35 |
| ATOM | 4540 | O | ASN | B | 350 | 28.652 | 52.195 | 18.917 | 1.00 | 12.88 |
| ATOM | 4541 | N | GLN | B | 351 | 27.107 | 50.635 | 19.424 | 1.00 | 8.29 |
| ATOM | 4542 | CA | GLN | B | 351 | 26.494 | 50.611 | 18.112 | 1.00 | 6.68 |
| ATOM | 4543 | CB | GLN | B | 351 | 25.756 | 49.303 | 17.912 | 1.00 | 4.08 |
| ATOM | 4544 | CG | GLN | B | 351 | 24.810 | 48.977 | 19.030 | 1.00 | 3.89 |
| ATOM | 4545 | CD | GLN | B | 351 | 25.262 | 47.789 | 19.822 | 1.00 | 9.19 |
| ATOM | 4546 | OE1 | GLN | B | 351 | 26.462 | 47.553 | 19.966 | 1.00 | 13.80 |
| ATOM | 4547 | NE2 | GLN | B | 351 | 24.308 | 47.026 | 20.342 | 1.00 | 11.36 |
| ATOM | 4548 | C | GLN | B | 351 | 25.516 | 51.771 | 18.046 | 1.00 | 7.52 |
| ATOM | 4549 | O | GLN | B | 351 | 25.179 | 52.264 | 16.961 | 1.00 | 7.56 |
| ATOM | 4550 | N | ASP | B | 352 | 25.051 | 52.195 | 19.218 | 1.00 | 6.61 |
| ATOM | 4551 | CA | ASP | B | 352 | 24.173 | 53.335 | 19.299 | 1.00 | 9.50 |
| ATOM | 4552 | CB | ASP | B | 352 | 23.289 | 53.259 | 20.536 | 1.00 | 11.10 |
| ATOM | 4553 | CG | ASP | B | 352 | 22.119 | 54.201 | 20.464 | 1.00 | 13.77 |

FIGURE 3 (Cont.)

| | A | B | C | D | E | F | G | H | I | J |
|---|---|---|---|---|---|---|---|---|---|---|
| ATOM | 4554 | OD1 | ASP | B | 352 | 22.331 | 55.377 | 20.104 | 1.00 | 16.69 |
| ATOM | 4555 | OD2 | ASP | B | 352 | 20.949 | 53.856 | 20.730 | 1.00 | 14.97 |
| ATOM | 4556 | C | ASP | B | 352 | 25.045 | 54.559 | 19.345 | 1.00 | 12.58 |
| ATOM | 4557 | O | ASP | B | 352 | 25.754 | 54.791 | 20.322 | 1.00 | 15.52 |
| ATOM | 4558 | N | HIS | B | 353 | 25.005 | 55.337 | 18.271 | 1.00 | 16.44 |
| ATOM | 4559 | CA | HIS | B | 353 | 25.826 | 56.536 | 18.168 | 1.00 | 17.21 |
| ATOM | 4560 | CB | HIS | B | 353 | 25.611 | 57.218 | 16.808 | 1.00 | 17.29 |
| ATOM | 4561 | CG | HIS | B | 353 | 26.403 | 56.619 | 15.686 | 1.00 | 17.09 |
| ATOM | 4562 | ND1 | HIS | B | 353 | 26.140 | 56.899 | 14.363 | 1.00 | 16.55 |
| ATOM | 4563 | CE1 | HIS | B | 353 | 26.996 | 56.247 | 13.594 | 1.00 | 18.31 |
| ATOM | 4564 | NE2 | HIS | B | 353 | 27.806 | 55.551 | 14.371 | 1.00 | 19.70 |
| ATOM | 4565 | CD2 | HIS | B | 353 | 27.460 | 55.769 | 15.685 | 1.00 | 20.09 |
| ATOM | 4566 | C | HIS | B | 353 | 25.519 | 57.505 | 19.321 | 1.00 | 17.84 |
| ATOM | 4567 | O | HIS | B | 353 | 26.379 | 58.271 | 19.733 | 1.00 | 18.70 |
| ATOM | 4568 | N | GLU | B | 354 | 24.299 | 57.464 | 19.850 | 1.00 | 19.74 |
| ATOM | 4569 | CA | GLU | B | 354 | 23.924 | 58.387 | 20.922 | 1.00 | 21.64 |
| ATOM | 4570 | CB | GLU | B | 354 | 22.413 | 58.534 | 21.047 | 1.00 | 25.66 |
| ATOM | 4571 | CG | GLU | B | 354 | 21.976 | 59.977 | 21.223 | 1.00 | 31.74 |
| ATOM | 4572 | CD | GLU | B | 354 | 20.700 | 60.097 | 22.028 | 1.00 | 36.15 |
| ATOM | 4573 | OE1 | GLU | B | 354 | 19.634 | 59.685 | 21.517 | 1.00 | 38.49 |
| ATOM | 4574 | OE2 | GLU | B | 354 | 20.762 | 60.601 | 23.172 | 1.00 | 38.35 |
| ATOM | 4575 | C | GLU | B | 354 | 24.521 | 58.002 | 22.258 | 1.00 | 18.94 |
| ATOM | 4576 | O | GLU | B | 354 | 24.861 | 58.877 | 23.057 | 1.00 | 18.67 |
| ATOM | 4577 | N | LYS | B | 355 | 24.639 | 56.693 | 22.488 | 1.00 | 15.94 |
| ATOM | 4578 | CA | LYS | B | 355 | 25.325 | 56.160 | 23.666 | 1.00 | 12.64 |
| ATOM | 4579 | CB | LYS | B | 355 | 24.972 | 54.693 | 23.910 | 1.00 | 12.00 |
| ATOM | 4580 | CG | LYS | B | 355 | 23.482 | 54.416 | 24.082 | 1.00 | 13.23 |
| ATOM | 4581 | CD | LYS | B | 355 | 23.238 | 53.296 | 25.082 | 1.00 | 12.88 |
| ATOM | 4582 | CE | LYS | B | 355 | 21.773 | 52.947 | 25.162 | 1.00 | 14.30 |
| ATOM | 4583 | NZ | LYS | B | 355 | 20.897 | 54.166 | 25.168 | 1.00 | 18.50 |
| ATOM | 4584 | C | LYS | B | 355 | 26.831 | 56.312 | 23.530 | 1.00 | 10.38 |
| ATOM | 4585 | O | LYS | B | 355 | 27.497 | 56.748 | 24.471 | 1.00 | 11.67 |
| ATOM | 4586 | N | LEU | B | 356 | 27.367 | 55.964 | 22.361 | 1.00 | 7.01 |
| ATOM | 4587 | CA | LEU | B | 356 | 28.799 | 56.108 | 22.107 | 1.00 | 6.20 |
| ATOM | 4588 | CB | LEU | B | 356 | 29.118 | 55.777 | 20.659 | 1.00 | 3.91 |
| ATOM | 4589 | CG | LEU | B | 356 | 30.481 | 56.212 | 20.142 | 1.00 | 3.82 |
| ATOM | 4590 | CD1 | LEU | B | 356 | 31.558 | 55.270 | 20.631 | 1.00 | 3.20 |
| ATOM | 4591 | CD2 | LEU | B | 356 | 30.459 | 56.251 | 18.640 | 1.00 | 5.15 |
| ATOM | 4592 | C | LEU | B | 356 | 29.334 | 57.500 | 22.489 | 1.00 | 8.29 |
| ATOM | 4593 | O | LEU | B | 356 | 30.388 | 57.622 | 23.121 | 1.00 | 10.05 |
| ATOM | 4594 | N | PHE | B | 357 | 28.591 | 58.536 | 22.119 | 1.00 | 9.67 |
| ATOM | 4595 | CA | PHE | B | 357 | 28.896 | 59.900 | 22.530 | 1.00 | 11.05 |
| ATOM | 4596 | CB | PHE | B | 357 | 28.038 | 60.895 | 21.766 | 1.00 | 8.33 |
| ATOM | 4597 | CG | PHE | B | 357 | 28.314 | 60.894 | 20.312 | 1.00 | 6.93 |
| ATOM | 4598 | CD1 | PHE | B | 357 | 27.342 | 61.274 | 19.405 | 1.00 | 2.51 |
| ATOM | 4599 | CE1 | PHE | B | 357 | 27.601 | 61.259 | 18.037 | 1.00 | 2.00 |
| ATOM | 4600 | CZ | PHE | B | 357 | 28.840 | 60.860 | 17.562 | 1.00 | 2.83 |
| ATOM | 4601 | CE2 | PHE | B | 357 | 29.825 | 60.466 | 18.460 | 1.00 | 9.60 |
| ATOM | 4602 | CD2 | PHE | B | 357 | 29.558 | 60.474 | 19.836 | 1.00 | 8.40 |
| ATOM | 4603 | C | PHE | B | 357 | 28.782 | 60.127 | 24.029 | 1.00 | 14.12 |
| ATOM | 4604 | O | PHE | B | 357 | 29.632 | 60.812 | 24.593 | 1.00 | 16.62 |
| ATOM | 4605 | N | GLU | B | 358 | 27.762 | 59.556 | 24.676 | 1.00 | 15.51 |

FIGURE 3 (Cont.)

|      | A    | B    | C   | D | E   | F      | G      | H      | I    | J     |
|------|------|------|-----|---|-----|--------|--------|--------|------|-------|
| ATOM | 4606 | CA   | GLU | B | 358 | 27.695 | 59.586 | 26.145 | 1.00 | 20.01 |
| ATOM | 4607 | CB   | GLU | B | 358 | 26.482 | 58.807 | 26.704 | 1.00 | 25.52 |
| ATOM | 4608 | CG   | GLU | B | 358 | 26.433 | 58.673 | 28.230 | 1.00 | 34.33 |
| ATOM | 4609 | CD   | GLU | B | 358 | 25.306 | 59.482 | 28.893 | 1.00 | 43.08 |
| ATOM | 4610 | OE1  | GLU | B | 358 | 25.499 | 60.698 | 29.159 | 1.00 | 46.52 |
| ATOM | 4611 | OE2  | GLU | B | 358 | 24.221 | 58.907 | 29.177 | 1.00 | 45.48 |
| ATOM | 4612 | C    | GLU | B | 358 | 29.013 | 59.040 | 26.700 | 1.00 | 18.83 |
| ATOM | 4613 | O    | GLU | B | 358 | 29.654 | 59.683 | 27.526 | 1.00 | 18.81 |
| ATOM | 4614 | N    | LEU | B | 359 | 29.435 | 57.880 | 26.206 | 1.00 | 15.04 |
| ATOM | 4615 | CA   | LEU | B | 359 | 30.674 | 57.283 | 26.658 | 1.00 | 12.45 |
| ATOM | 4616 | CB   | LEU | B | 359 | 30.892 | 55.946 | 25.972 | 1.00 | 11.34 |
| ATOM | 4617 | CG   | LEU | B | 359 | 29.887 | 54.846 | 26.281 | 1.00 | 9.03  |
| ATOM | 4618 | CD1  | LEU | B | 359 | 30.314 | 53.574 | 25.557 | 1.00 | 8.31  |
| ATOM | 4619 | CD2  | LEU | B | 359 | 29.799 | 54.621 | 27.766 | 1.00 | 9.77  |
| ATOM | 4620 | C    | LEU | B | 359 | 31.879 | 58.210 | 26.458 | 1.00 | 14.30 |
| ATOM | 4621 | O    | LEU | B | 359 | 32.547 | 58.549 | 27.437 | 1.00 | 14.39 |
| ATOM | 4622 | N    | ILE | B | 360 | 32.140 | 58.634 | 25.213 | 1.00 | 13.76 |
| ATOM | 4623 | CA   | ILE | B | 360 | 33.250 | 59.557 | 24.914 | 1.00 | 11.97 |
| ATOM | 4624 | CB   | ILE | B | 360 | 33.255 | 60.031 | 23.426 | 1.00 | 8.94  |
| ATOM | 4625 | CG1  | ILE | B | 360 | 33.975 | 59.010 | 22.561 | 1.00 | 10.03 |
| ATOM | 4626 | CD1  | ILE | B | 360 | 33.231 | 58.611 | 21.354 | 1.00 | 9.82  |
| ATOM | 4627 | CG2  | ILE | B | 360 | 33.990 | 61.364 | 23.251 | 1.00 | 2.23  |
| ATOM | 4628 | C    | ILE | B | 360 | 33.328 | 60.750 | 25.872 | 1.00 | 14.69 |
| ATOM | 4629 | O    | ILE | B | 360 | 34.425 | 61.081 | 26.316 | 1.00 | 19.53 |
| ATOM | 4630 | N    | LEU | B | 361 | 32.194 | 61.381 | 26.199 | 1.00 | 10.03 |
| ATOM | 4631 | CA   | LEU | B | 361 | 32.198 | 62.498 | 27.158 | 1.00 | 7.39  |
| ATOM | 4632 | CB   | LEU | B | 361 | 31.152 | 63.556 | 26.806 | 1.00 | 8.80  |
| ATOM | 4633 | CG   | LEU | B | 361 | 30.569 | 63.740 | 25.412 | 1.00 | 9.05  |
| ATOM | 4634 | CD1  | LEU | B | 361 | 29.076 | 64.082 | 25.488 | 1.00 | 5.64  |
| ATOM | 4635 | CD2  | LEU | B | 361 | 31.338 | 64.829 | 24.719 | 1.00 | 10.40 |
| ATOM | 4636 | C    | LEU | B | 361 | 32.046 | 62.150 | 28.652 | 1.00 | 6.86  |
| ATOM | 4637 | O    | LEU | B | 361 | 32.473 | 62.917 | 29.502 | 1.00 | 5.61  |
| ATOM | 4638 | N    | MET | B | 362 | 31.447 | 61.012 | 28.979 | 1.00 | 9.11  |
| ATOM | 4639 | CA   | MET | B | 362 | 31.179 | 60.689 | 30.386 | 1.00 | 13.18 |
| ATOM | 4640 | CB   | MET | B | 362 | 29.692 | 60.362 | 30.616 | 1.00 | 19.25 |
| ATOM | 4641 | CG   | MET | B | 362 | 28.734 | 61.501 | 30.348 | 1.00 | 21.48 |
| ATOM | 4642 | SD   | MET | B | 362 | 29.268 | 62.998 | 31.149 | 1.00 | 26.74 |
| ATOM | 4643 | CE   | MET | B | 362 | 29.231 | 64.193 | 29.771 | 1.00 | 28.98 |
| ATOM | 4644 | C    | MET | B | 362 | 32.051 | 59.607 | 31.040 | 1.00 | 12.57 |
| ATOM | 4645 | O    | MET | B | 362 | 32.486 | 59.793 | 32.182 | 1.00 | 10.93 |
| ATOM | 4646 | N    | GLU | B | 363 | 32.269 | 58.478 | 30.354 | 1.00 | 13.09 |
| ATOM | 4647 | CA   | GLU | B | 363 | 33.051 | 57.371 | 30.927 | 1.00 | 16.46 |
| ATOM | 4648 | CB   | GLU | B | 363 | 32.879 | 56.050 | 30.164 | 1.00 | 20.77 |
| ATOM | 4649 | CG   | GLU | B | 363 | 33.637 | 54.888 | 30.816 | 1.00 | 27.84 |
| ATOM | 4650 | CD   | GLU | B | 363 | 33.685 | 53.621 | 29.967 | 1.00 | 34.76 |
| ATOM | 4651 | OE1  | GLU | B | 363 | 34.755 | 53.331 | 29.373 | 1.00 | 38.61 |
| ATOM | 4652 | OE2  | GLU | B | 363 | 32.659 | 52.898 | 29.898 | 1.00 | 37.60 |
| ATOM | 4653 | C    | GLU | B | 363 | 34.517 | 57.719 | 30.955 | 1.00 | 15.96 |
| ATOM | 4654 | O    | GLU | B | 363 | 35.063 | 58.213 | 29.976 | 1.00 | 18.32 |
| ATOM | 4655 | N    | GLU | B | 364 | 35.167 | 57.461 | 32.076 | 1.00 | 16.91 |
| ATOM | 4656 | CA   | GLU | B | 364 | 36.591 | 57.706 | 32.128 | 1.00 | 17.56 |
| ATOM | 4657 | CB   | GLU | B | 364 | 37.032 | 58.251 | 33.479 | 1.00 | 19.72 |

FIGURE 3 (Cont.)

|   | A | B | C | D | E | F | G | H | I | J |
|---|---|---|---|---|---|---|---|---|---|---|
| ATOM | 4658 | CG | GLU | B | 364 | 37.214 | 57.225 | 34.563 | 1.00 | 22.39 |
| ATOM | 4659 | CD | GLU | B | 364 | 38.290 | 57.662 | 35.515 | 1.00 | 28.14 |
| ATOM | 4660 | OE1 | GLU | B | 364 | 37.954 | 58.422 | 36.462 | 1.00 | 29.82 |
| ATOM | 4661 | OE2 | GLU | B | 364 | 39.465 | 57.267 | 35.289 | 1.00 | 29.69 |
| ATOM | 4662 | C | GLU | B | 364 | 37.306 | 56.434 | 31.744 | 1.00 | 15.21 |
| ATOM | 4663 | O | GLU | B | 364 | 36.823 | 55.330 | 32.008 | 1.00 | 14.26 |
| ATOM | 4664 | N | ILE | B | 365 | 38.450 | 56.621 | 31.095 | 1.00 | 14.13 |
| ATOM | 4665 | CA | ILE | B | 365 | 39.155 | 55.563 | 30.391 | 1.00 | 10.52 |
| ATOM | 4666 | CB | ILE | B | 365 | 40.318 | 56.166 | 29.578 | 1.00 | 8.59 |
| ATOM | 4667 | CG1 | ILE | B | 365 | 41.045 | 55.081 | 28.793 | 1.00 | 11.25 |
| ATOM | 4668 | CD1 | ILE | B | 365 | 40.713 | 55.089 | 27.299 | 1.00 | 14.08 |
| ATOM | 4669 | CG2 | ILE | B | 365 | 41.260 | 56.968 | 30.456 | 1.00 | 12.05 |
| ATOM | 4670 | C | ILE | B | 365 | 39.593 | 54.414 | 31.297 | 1.00 | 12.16 |
| ATOM | 4671 | O | ILE | B | 365 | 39.985 | 54.617 | 32.456 | 1.00 | 14.78 |
| ATOM | 4672 | N | ARG | B | 366 | 39.469 | 53.202 | 30.768 | 1.00 | 9.13 |
| ATOM | 4673 | CA | ARG | B | 366 | 39.806 | 52.001 | 31.511 | 1.00 | 5.91 |
| ATOM | 4674 | CB | ARG | B | 366 | 38.569 | 51.141 | 31.728 | 1.00 | 6.72 |
| ATOM | 4675 | CG | ARG | B | 366 | 37.302 | 51.699 | 31.175 | 1.00 | 5.57 |
| ATOM | 4676 | CD | ARG | B | 366 | 36.192 | 51.744 | 32.196 | 1.00 | 7.28 |
| ATOM | 4677 | NE | ARG | B | 366 | 35.486 | 50.467 | 32.368 | 1.00 | 8.60 |
| ATOM | 4678 | CZ | ARG | B | 366 | 34.907 | 49.731 | 31.404 | 1.00 | 7.70 |
| ATOM | 4679 | NH1 | ARG | B | 366 | 34.934 | 50.083 | 30.118 | 1.00 | 2.00 |
| ATOM | 4680 | NH2 | ARG | B | 366 | 34.288 | 48.610 | 31.745 | 1.00 | 9.51 |
| ATOM | 4681 | C | ARG | B | 366 | 40.837 | 51.215 | 30.732 | 1.00 | 5.29 |
| ATOM | 4682 | O | ARG | B | 366 | 40.873 | 51.272 | 29.515 | 1.00 | 11.26 |
| ATOM | 4683 | N | PHE | B | 367 | 41.686 | 50.478 | 31.416 | 1.00 | 2.51 |
| ATOM | 4684 | CA | PHE | B | 367 | 42.754 | 49.811 | 30.712 | 1.00 | 2.34 |
| ATOM | 4685 | CB | PHE | B | 367 | 44.106 | 50.462 | 30.991 | 1.00 | 2.00 |
| ATOM | 4686 | CG | PHE | B | 367 | 44.214 | 51.848 | 30.478 | 1.00 | 2.00 |
| ATOM | 4687 | CD1 | PHE | B | 367 | 44.468 | 52.081 | 29.148 | 1.00 | 2.00 |
| ATOM | 4688 | CE1 | PHE | B | 367 | 44.546 | 53.385 | 28.662 | 1.00 | 4.02 |
| ATOM | 4689 | CZ | PHE | B | 367 | 44.374 | 54.462 | 29.522 | 1.00 | 2.28 |
| ATOM | 4690 | CE2 | PHE | B | 367 | 44.116 | 54.229 | 30.855 | 1.00 | 2.00 |
| ATOM | 4691 | CD2 | PHE | B | 367 | 44.041 | 52.929 | 31.325 | 1.00 | 2.00 |
| ATOM | 4692 | C | PHE | B | 367 | 42.768 | 48.426 | 31.227 | 1.00 | 5.34 |
| ATOM | 4693 | O | PHE | B | 367 | 42.487 | 48.215 | 32.399 | 1.00 | 7.97 |
| ATOM | 4694 | N | PRO | B | 368 | 43.078 | 47.478 | 30.351 | 1.00 | 5.96 |
| ATOM | 4695 | CA | PRO | B | 368 | 43.335 | 46.112 | 30.778 | 1.00 | 4.44 |
| ATOM | 4696 | CB | PRO | B | 368 | 43.612 | 45.374 | 29.472 | 1.00 | 2.39 |
| ATOM | 4697 | CG | PRO | B | 368 | 43.928 | 46.403 | 28.494 | 1.00 | 6.08 |
| ATOM | 4698 | CD | PRO | B | 368 | 43.208 | 47.644 | 28.895 | 1.00 | 7.37 |
| ATOM | 4699 | C | PRO | B | 368 | 44.566 | 46.145 | 31.663 | 1.00 | 7.59 |
| ATOM | 4700 | O | PRO | B | 368 | 45.464 | 46.958 | 31.426 | 1.00 | 6.91 |
| ATOM | 4701 | N | ARG | B | 369 | 44.581 | 45.294 | 32.689 | 1.00 | 10.71 |
| ATOM | 4702 | CA | ARG | B | 369 | 45.707 | 45.186 | 33.612 | 1.00 | 9.32 |
| ATOM | 4703 | CB | ARG | B | 369 | 45.340 | 44.264 | 34.772 | 1.00 | 7.65 |
| ATOM | 4704 | CG | ARG | B | 369 | 45.497 | 44.895 | 36.139 | 1.00 | 8.23 |
| ATOM | 4705 | CD | ARG | B | 369 | 44.554 | 44.322 | 37.165 | 1.00 | 7.83 |
| ATOM | 4706 | NE | ARG | B | 369 | 45.152 | 43.956 | 38.456 | 1.00 | 8.74 |
| ATOM | 4707 | CZ | ARG | B | 369 | 45.855 | 42.849 | 38.698 | 1.00 | 12.73 |
| ATOM | 4708 | NH1 | ARG | B | 369 | 46.135 | 41.971 | 37.728 | 1.00 | 14.60 |
| ATOM | 4709 | NH2 | ARG | B | 369 | 46.289 | 42.615 | 39.931 | 1.00 | 14.63 |

FIGURE 3 (Cont.)

|  | A | B | C | D | E | F | G | H | I | J |
|---|---|---|---|---|---|---|---|---|---|---|
| ATOM | 4710 | C | ARG | B | 369 | 46.993 | 44.703 | 32.923 | 1.00 | 9.65 |
| ATOM | 4711 | O | ARG | B | 369 | 48.081 | 44.809 | 33.497 | 1.00 | 12.90 |
| ATOM | 4712 | N | THR | B | 370 | 46.859 | 44.209 | 31.692 | 1.00 | 7.86 |
| ATOM | 4713 | CA | THR | B | 370 | 47.973 | 43.637 | 30.940 | 1.00 | 8.09 |
| ATOM | 4714 | CB | THR | B | 370 | 47.504 | 42.487 | 29.984 | 1.00 | 9.51 |
| ATOM | 4715 | OG1 | THR | B | 370 | 46.387 | 42.904 | 29.171 | 1.00 | 5.06 |
| ATOM | 4716 | CG2 | THR | B | 370 | 46.999 | 41.280 | 30.799 | 1.00 | 10.09 |
| ATOM | 4717 | C | THR | B | 370 | 48.795 | 44.662 | 30.174 | 1.00 | 7.49 |
| ATOM | 4718 | O | THR | B | 370 | 49.795 | 44.313 | 29.555 | 1.00 | 11.12 |
| ATOM | 4719 | N | LEU | B | 371 | 48.382 | 45.920 | 30.207 | 1.00 | 5.89 |
| ATOM | 4720 | CA | LEU | B | 371 | 49.158 | 46.976 | 29.572 | 1.00 | 3.75 |
| ATOM | 4721 | CB | LEU | B | 371 | 48.312 | 48.244 | 29.414 | 1.00 | 2.08 |
| ATOM | 4722 | CG | LEU | B | 371 | 48.408 | 49.011 | 28.099 | 1.00 | 2.00 |
| ATOM | 4723 | CD1 | LEU | B | 371 | 48.424 | 48.045 | 26.930 | 1.00 | 3.65 |
| ATOM | 4724 | CD2 | LEU | B | 371 | 47.262 | 50.006 | 27.969 | 1.00 | 2.00 |
| ATOM | 4725 | C | LEU | B | 371 | 50.394 | 47.294 | 30.393 | 1.00 | 2.00 |
| ATOM | 4726 | O | LEU | B | 371 | 50.367 | 47.226 | 31.617 | 1.00 | 2.00 |
| ATOM | 4727 | N | GLY | B | 372 | 51.475 | 47.651 | 29.715 | 1.00 | 4.05 |
| ATOM | 4728 | CA | GLY | B | 372 | 52.622 | 48.248 | 30.382 | 1.00 | 10.07 |
| ATOM | 4729 | C | GLY | B | 372 | 52.296 | 49.531 | 31.155 | 1.00 | 10.20 |
| ATOM | 4730 | O | GLY | B | 372 | 51.306 | 50.198 | 30.849 | 1.00 | 11.60 |
| ATOM | 4731 | N | PRO | B | 373 | 53.101 | 49.859 | 32.170 | 1.00 | 8.83 |
| ATOM | 4732 | CA | PRO | B | 373 | 53.008 | 51.151 | 32.866 | 1.00 | 6.22 |
| ATOM | 4733 | CB | PRO | B | 373 | 54.124 | 51.065 | 33.904 | 1.00 | 9.46 |
| ATOM | 4734 | CG | PRO | B | 373 | 54.246 | 49.590 | 34.164 | 1.00 | 11.59 |
| ATOM | 4735 | CD | PRO | B | 373 | 54.118 | 48.985 | 32.786 | 1.00 | 10.95 |
| ATOM | 4736 | C | PRO | B | 373 | 53.198 | 52.369 | 31.980 | 1.00 | 4.47 |
| ATOM | 4737 | O | PRO | B | 373 | 52.409 | 53.293 | 32.116 | 1.00 | 2.95 |
| ATOM | 4738 | N | GLU | B | 374 | 54.188 | 52.379 | 31.094 | 1.00 | 8.26 |
| ATOM | 4739 | CA | GLU | B | 374 | 54.384 | 53.531 | 30.205 | 1.00 | 15.16 |
| ATOM | 4740 | CB | GLU | B | 374 | 55.856 | 53.696 | 29.779 | 1.00 | 19.85 |
| ATOM | 4741 | CG | GLU | B | 374 | 56.445 | 52.567 | 28.952 | 1.00 | 28.64 |
| ATOM | 4742 | CD | GLU | B | 374 | 56.644 | 51.299 | 29.761 | 1.00 | 35.84 |
| ATOM | 4743 | OE1 | GLU | B | 374 | 55.647 | 50.533 | 29.884 | 1.00 | 38.81 |
| ATOM | 4744 | OE2 | GLU | B | 374 | 57.779 | 51.072 | 30.274 | 1.00 | 37.08 |
| ATOM | 4745 | C | GLU | B | 374 | 53.417 | 53.566 | 29.006 | 1.00 | 17.35 |
| ATOM | 4746 | O | GLU | B | 374 | 53.197 | 54.617 | 28.395 | 1.00 | 17.20 |
| ATOM | 4747 | N | ALA | B | 375 | 52.827 | 52.419 | 28.678 | 1.00 | 19.32 |
| ATOM | 4748 | CA | ALA | B | 375 | 51.747 | 52.390 | 27.690 | 1.00 | 17.24 |
| ATOM | 4749 | CB | ALA | B | 375 | 51.422 | 50.967 | 27.302 | 1.00 | 17.75 |
| ATOM | 4750 | C | ALA | B | 375 | 50.527 | 53.078 | 28.280 | 1.00 | 14.03 |
| ATOM | 4751 | O | ALA | B | 375 | 50.039 | 54.083 | 27.745 | 1.00 | 10.60 |
| ATOM | 4752 | N | LYS | B | 376 | 50.062 | 52.526 | 29.400 | 1.00 | 13.22 |
| ATOM | 4753 | CA | LYS | B | 376 | 48.987 | 53.102 | 30.193 | 1.00 | 13.09 |
| ATOM | 4754 | CB | LYS | B | 376 | 48.994 | 52.491 | 31.588 | 1.00 | 11.06 |
| ATOM | 4755 | CG | LYS | B | 376 | 47.690 | 51.889 | 32.046 | 1.00 | 14.10 |
| ATOM | 4756 | CD | LYS | B | 376 | 47.913 | 50.530 | 32.781 | 1.00 | 20.14 |
| ATOM | 4757 | CE | LYS | B | 376 | 48.319 | 50.678 | 34.268 | 1.00 | 23.68 |
| ATOM | 4758 | NZ | LYS | B | 376 | 47.313 | 51.417 | 35.125 | 1.00 | 27.68 |
| ATOM | 4759 | C | LYS | B | 376 | 49.163 | 54.619 | 30.294 | 1.00 | 15.09 |
| ATOM | 4760 | O | LYS | B | 376 | 48.200 | 55.371 | 30.124 | 1.00 | 16.30 |
| ATOM | 4761 | N | SER | B | 377 | 50.393 | 55.067 | 30.551 | 1.00 | 12.63 |

FIGURE 3 (Cont.)

| | A | B | C | D | E | F | G | H | I | J |
|---|---|---|---|---|---|---|---|---|---|---|
| ATOM | 4762 | CA | SER | B | 377 | 50.630 | 56.484 | 30.777 | 1.00 | 12.31 |
| ATOM | 4763 | CB | SER | B | 377 | 51.964 | 56.739 | 31.470 | 1.00 | 13.61 |
| ATOM | 4764 | OG | SER | B | 377 | 52.032 | 58.090 | 31.891 | 1.00 | 16.33 |
| ATOM | 4765 | C | SER | B | 377 | 50.536 | 57.324 | 29.512 | 1.00 | 13.11 |
| ATOM | 4766 | O | SER | B | 377 | 50.140 | 58.483 | 29.585 | 1.00 | 17.27 |
| ATOM | 4767 | N | LEU | B | 378 | 50.904 | 56.766 | 28.361 | 1.00 | 10.26 |
| ATOM | 4768 | CA | LEU | B | 378 | 50.834 | 57.541 | 27.125 | 1.00 | 5.76 |
| ATOM | 4769 | CB | LEU | B | 378 | 51.666 | 56.915 | 26.016 | 1.00 | 3.43 |
| ATOM | 4770 | CG | LEU | B | 378 | 51.365 | 57.364 | 24.592 | 1.00 | 2.00 |
| ATOM | 4771 | CD1 | LEU | B | 378 | 52.178 | 58.586 | 24.259 | 1.00 | 2.00 |
| ATOM | 4772 | CD2 | LEU | B | 378 | 51.668 | 56.229 | 23.624 | 1.00 | 2.00 |
| ATOM | 4773 | C | LEU | B | 378 | 49.400 | 57.674 | 26.690 | 1.00 | 6.60 |
| ATOM | 4774 | O | LEU | B | 378 | 48.993 | 58.736 | 26.249 | 1.00 | 5.97 |
| ATOM | 4775 | N | LEU | B | 379 | 48.647 | 56.581 | 26.821 | 1.00 | 9.04 |
| ATOM | 4776 | CA | LEU | B | 379 | 47.233 | 56.552 | 26.465 | 1.00 | 9.66 |
| ATOM | 4777 | CB | LEU | B | 379 | 46.706 | 55.131 | 26.535 | 1.00 | 4.19 |
| ATOM | 4778 | CG | LEU | B | 379 | 47.225 | 54.242 | 25.418 | 1.00 | 5.73 |
| ATOM | 4779 | CD1 | LEU | B | 379 | 46.522 | 52.896 | 25.475 | 1.00 | 6.27 |
| ATOM | 4780 | CD2 | LEU | B | 379 | 47.040 | 54.891 | 24.058 | 1.00 | 2.59 |
| ATOM | 4781 | C | LEU | B | 379 | 46.410 | 57.464 | 27.368 | 1.00 | 12.95 |
| ATOM | 4782 | O | LEU | B | 379 | 45.664 | 58.311 | 26.889 | 1.00 | 13.92 |
| ATOM | 4783 | N | SER | B | 380 | 46.577 | 57.292 | 28.676 | 1.00 | 15.75 |
| ATOM | 4784 | CA | SER | B | 380 | 45.855 | 58.063 | 29.667 | 1.00 | 14.56 |
| ATOM | 4785 | CB | SER | B | 380 | 46.265 | 57.643 | 31.086 | 1.00 | 14.01 |
| ATOM | 4786 | OG | SER | B | 380 | 45.185 | 57.754 | 32.013 | 1.00 | 16.66 |
| ATOM | 4787 | C | SER | B | 380 | 46.121 | 59.535 | 29.436 | 1.00 | 15.10 |
| ATOM | 4788 | O | SER | B | 380 | 45.247 | 60.362 | 29.664 | 1.00 | 22.62 |
| ATOM | 4789 | N | GLY | B | 381 | 47.316 | 59.856 | 28.954 | 1.00 | 13.67 |
| ATOM | 4790 | CA | GLY | B | 381 | 47.686 | 61.236 | 28.677 | 1.00 | 14.15 |
| ATOM | 4791 | C | GLY | B | 381 | 47.106 | 61.752 | 27.371 | 1.00 | 12.27 |
| ATOM | 4792 | O | GLY | B | 381 | 46.678 | 62.892 | 27.301 | 1.00 | 10.44 |
| ATOM | 4793 | N | LEU | B | 382 | 47.100 | 60.902 | 26.342 | 1.00 | 13.78 |
| ATOM | 4794 | CA | LEU | B | 382 | 46.567 | 61.240 | 25.021 | 1.00 | 12.68 |
| ATOM | 4795 | CB | LEU | B | 382 | 46.985 | 60.191 | 23.994 | 1.00 | 8.24 |
| ATOM | 4796 | CG | LEU | B | 382 | 48.429 | 60.232 | 23.498 | 1.00 | 8.35 |
| ATOM | 4797 | CD1 | LEU | B | 382 | 48.751 | 58.945 | 22.793 | 1.00 | 7.85 |
| ATOM | 4798 | CD2 | LEU | B | 382 | 48.698 | 61.420 | 22.589 | 1.00 | 7.40 |
| ATOM | 4799 | C | LEU | B | 382 | 45.048 | 61.315 | 25.040 | 1.00 | 16.94 |
| ATOM | 4800 | O | LEU | B | 382 | 44.440 | 62.066 | 24.262 | 1.00 | 18.77 |
| ATOM | 4801 | N | LEU | B | 383 | 44.438 | 60.525 | 25.925 | 1.00 | 15.76 |
| ATOM | 4802 | CA | LEU | B | 383 | 42.989 | 60.442 | 26.003 | 1.00 | 10.53 |
| ATOM | 4803 | CB | LEU | B | 383 | 42.510 | 58.984 | 25.989 | 1.00 | 4.96 |
| ATOM | 4804 | CG | LEU | B | 383 | 42.782 | 58.220 | 24.688 | 1.00 | 4.47 |
| ATOM | 4805 | CD1 | LEU | B | 383 | 42.371 | 56.776 | 24.794 | 1.00 | 3.93 |
| ATOM | 4806 | CD2 | LEU | B | 383 | 42.075 | 58.855 | 23.509 | 1.00 | 7.12 |
| ATOM | 4807 | C | LEU | B | 383 | 42.427 | 61.232 | 27.174 | 1.00 | 12.02 |
| ATOM | 4808 | O | LEU | B | 383 | 41.405 | 60.865 | 27.757 | 1.00 | 18.13 |
| ATOM | 4809 | N | LYS | B | 384 | 43.079 | 62.338 | 27.508 | 1.00 | 12.50 |
| ATOM | 4810 | CA | LYS | B | 384 | 42.471 | 63.280 | 28.440 | 1.00 | 14.64 |
| ATOM | 4811 | CB | LYS | B | 384 | 43.492 | 64.277 | 28.988 | 1.00 | 13.39 |
| ATOM | 4812 | CG | LYS | B | 384 | 44.655 | 63.614 | 29.726 | 1.00 | 14.50 |
| ATOM | 4813 | CD | LYS | B | 384 | 44.620 | 63.850 | 31.223 | 1.00 | 14.30 |

FIGURE 3 (Cont.)

| | A | B | C | D | E | F | G | H | I | J |
|---|---|---|---|---|---|---|---|---|---|---|
| ATOM | 4814 | CE  | LYS | B | 384 | 45.682 | 63.023 | 31.912 | 1.00 | 16.78 |
| ATOM | 4815 | NZ  | LYS | B | 384 | 45.266 | 62.620 | 33.293 | 1.00 | 20.83 |
| ATOM | 4816 | C   | LYS | B | 384 | 41.360 | 63.988 | 27.683 | 1.00 | 14.59 |
| ATOM | 4817 | O   | LYS | B | 384 | 41.557 | 64.409 | 26.539 | 1.00 | 17.07 |
| ATOM | 4818 | N   | LYS | B | 385 | 40.188 | 64.081 | 28.300 | 1.00 | 10.54 |
| ATOM | 4819 | CA  | LYS | B | 385 | 39.030 | 64.653 | 27.627 | 1.00 | 8.68 |
| ATOM | 4820 | CB  | LYS | B | 385 | 37.760 | 64.407 | 28.424 | 1.00 | 7.45 |
| ATOM | 4821 | CG  | LYS | B | 385 | 37.541 | 62.968 | 28.768 | 1.00 | 6.96 |
| ATOM | 4822 | CD  | LYS | B | 385 | 36.219 | 62.770 | 29.471 | 1.00 | 6.99 |
| ATOM | 4823 | CE  | LYS | B | 385 | 35.535 | 61.488 | 29.002 | 1.00 | 7.08 |
| ATOM | 4824 | NZ  | LYS | B | 385 | 36.465 | 60.334 | 28.757 | 1.00 | 12.14 |
| ATOM | 4825 | C   | LYS | B | 385 | 39.192 | 66.136 | 27.373 | 1.00 | 10.15 |
| ATOM | 4826 | O   | LYS | B | 385 | 38.705 | 66.646 | 26.368 | 1.00 | 11.63 |
| ATOM | 4827 | N   | ASP | B | 386 | 39.865 | 66.820 | 28.294 | 1.00 | 13.93 |
| ATOM | 4828 | CA  | ASP | B | 386 | 40.107 | 68.256 | 28.183 | 1.00 | 17.29 |
| ATOM | 4829 | CB  | ASP | B | 386 | 40.223 | 68.908 | 29.567 | 1.00 | 20.29 |
| ATOM | 4830 | CG  | ASP | B | 386 | 40.597 | 70.391 | 29.499 | 1.00 | 24.52 |
| ATOM | 4831 | OD1 | ASP | B | 386 | 40.218 | 71.086 | 28.529 | 1.00 | 26.37 |
| ATOM | 4832 | OD2 | ASP | B | 386 | 41.264 | 70.959 | 30.388 | 1.00 | 28.24 |
| ATOM | 4833 | C   | ASP | B | 386 | 41.370 | 68.498 | 27.374 | 1.00 | 17.08 |
| ATOM | 4834 | O   | ASP | B | 386 | 42.453 | 68.078 | 27.782 | 1.00 | 19.50 |
| ATOM | 4835 | N   | PRO | B | 387 | 41.229 | 69.183 | 26.239 | 1.00 | 16.08 |
| ATOM | 4836 | CA  | PRO | B | 387 | 42.343 | 69.409 | 25.310 | 1.00 | 16.17 |
| ATOM | 4837 | CB  | PRO | B | 387 | 41.679 | 70.145 | 24.153 | 1.00 | 15.02 |
| ATOM | 4838 | CG  | PRO | B | 387 | 40.237 | 69.897 | 24.320 | 1.00 | 15.37 |
| ATOM | 4839 | CD  | PRO | B | 387 | 39.984 | 69.808 | 25.765 | 1.00 | 15.21 |
| ATOM | 4840 | C   | PRO | B | 387 | 43.455 | 70.273 | 25.913 | 1.00 | 19.24 |
| ATOM | 4841 | O   | PRO | B | 387 | 44.620 | 70.136 | 25.536 | 1.00 | 21.57 |
| ATOM | 4842 | N   | LYS | B | 388 | 43.097 | 71.146 | 26.850 | 1.00 | 19.81 |
| ATOM | 4843 | CA  | LYS | B | 388 | 44.083 | 71.940 | 27.576 | 1.00 | 19.31 |
| ATOM | 4844 | CB  | LYS | B | 388 | 43.370 | 73.006 | 28.423 | 1.00 | 18.17 |
| ATOM | 4845 | CG  | LYS | B | 388 | 43.081 | 74.312 | 27.659 | 1.00 | 17.80 |
| ATOM | 4846 | CD  | LYS | B | 388 | 41.592 | 74.639 | 27.590 | 1.00 | 15.83 |
| ATOM | 4847 | CE  | LYS | B | 388 | 41.261 | 75.859 | 28.447 | 1.00 | 14.50 |
| ATOM | 4848 | NZ  | LYS | B | 388 | 40.561 | 76.927 | 27.686 | 1.00 | 11.38 |
| ATOM | 4849 | C   | LYS | B | 388 | 45.017 | 71.061 | 28.435 | 1.00 | 19.41 |
| ATOM | 4850 | O   | LYS | B | 388 | 46.099 | 71.496 | 28.832 | 1.00 | 20.21 |
| ATOM | 4851 | N   | GLN | B | 389 | 44.601 | 69.815 | 28.672 | 1.00 | 18.15 |
| ATOM | 4852 | CA  | GLN | B | 389 | 45.263 | 68.886 | 29.590 | 1.00 | 17.02 |
| ATOM | 4853 | CB  | GLN | B | 389 | 44.245 | 68.447 | 30.641 | 1.00 | 18.88 |
| ATOM | 4854 | CG  | GLN | B | 389 | 44.681 | 68.522 | 32.090 | 1.00 | 21.45 |
| ATOM | 4855 | CD  | GLN | B | 389 | 43.571 | 68.045 | 33.041 | 1.00 | 24.71 |
| ATOM | 4856 | OE1 | GLN | B | 389 | 43.223 | 66.850 | 33.082 | 1.00 | 24.94 |
| ATOM | 4857 | NE2 | GLN | B | 389 | 43.016 | 68.978 | 33.803 | 1.00 | 25.49 |
| ATOM | 4858 | C   | GLN | B | 389 | 45.808 | 67.642 | 28.861 | 1.00 | 15.29 |
| ATOM | 4859 | O   | GLN | B | 389 | 46.562 | 66.846 | 29.431 | 1.00 | 15.31 |
| ATOM | 4860 | N   | ARG | B | 390 | 45.421 | 67.487 | 27.601 | 1.00 | 11.99 |
| ATOM | 4861 | CA  | ARG | B | 390 | 45.751 | 66.310 | 26.813 | 1.00 | 9.96 |
| ATOM | 4862 | CB  | ARG | B | 390 | 44.740 | 66.169 | 25.665 | 1.00 | 9.74 |
| ATOM | 4863 | CG  | ARG | B | 390 | 45.088 | 65.125 | 24.615 | 1.00 | 8.49 |
| ATOM | 4864 | CD  | ARG | B | 390 | 44.015 | 64.894 | 23.545 | 1.00 | 11.21 |
| ATOM | 4865 | NE  | ARG | B | 390 | 42.637 | 65.098 | 24.006 | 1.00 | 11.27 |

FIGURE 3 (Cont.)

| | A | B | C | D | E | F | G | H | I | J |
|---|---|---|---|---|---|---|---|---|---|---|
| ATOM | 4866 | CZ | ARG | B | 390 | 41.776 | 65.975 | 23.469 | 1.00 | 8.19 |
| ATOM | 4867 | NH1 | ARG | B | 390 | 42.138 | 66.737 | 22.443 | 1.00 | 2.92 |
| ATOM | 4868 | NH2 | ARG | B | 390 | 40.546 | 66.088 | 23.962 | 1.00 | 5.78 |
| ATOM | 4869 | C | ARG | B | 390 | 47.149 | 66.396 | 26.243 | 1.00 | 10.43 |
| ATOM | 4870 | O | ARG | B | 390 | 47.363 | 67.108 | 25.272 | 1.00 | 15.15 |
| ATOM | 4871 | N | LEU | B | 391 | 48.093 | 65.679 | 26.843 | 1.00 | 10.19 |
| ATOM | 4872 | CA | LEU | B | 391 | 49.427 | 65.465 | 26.259 | 1.00 | 13.75 |
| ATOM | 4873 | CB | LEU | B | 391 | 49.815 | 63.996 | 26.479 | 1.00 | 16.72 |
| ATOM | 4874 | CG | LEU | B | 391 | 51.137 | 63.373 | 26.021 | 1.00 | 18.33 |
| ATOM | 4875 | CD1 | LEU | B | 391 | 52.191 | 63.456 | 27.101 | 1.00 | 20.44 |
| ATOM | 4876 | CD2 | LEU | B | 391 | 50.897 | 61.932 | 25.685 | 1.00 | 18.53 |
| ATOM | 4877 | C | LEU | B | 391 | 49.516 | 65.840 | 24.760 | 1.00 | 14.90 |
| ATOM | 4878 | O | LEU | B | 391 | 49.199 | 65.037 | 23.900 | 1.00 | 14.10 |
| ATOM | 4879 | N | GLY | B | 392 | 49.927 | 67.070 | 24.462 | 1.00 | 18.54 |
| ATOM | 4880 | CA | GLY | B | 392 | 49.930 | 67.581 | 23.097 | 1.00 | 24.37 |
| ATOM | 4881 | C | GLY | B | 392 | 49.313 | 68.974 | 22.907 | 1.00 | 31.50 |
| ATOM | 4882 | O | GLY | B | 392 | 49.559 | 69.654 | 21.884 | 1.00 | 34.64 |
| ATOM | 4883 | N | GLY | B | 393 | 48.519 | 69.413 | 23.884 | 1.00 | 30.41 |
| ATOM | 4884 | CA | GLY | B | 393 | 47.796 | 70.666 | 23.770 | 1.00 | 32.56 |
| ATOM | 4885 | C | GLY | B | 393 | 48.485 | 71.868 | 24.398 | 1.00 | 36.15 |
| ATOM | 4886 | O | GLY | B | 393 | 47.810 | 72.783 | 24.898 | 1.00 | 38.26 |
| ATOM | 4887 | N | GLY | B | 394 | 49.819 | 71.874 | 24.382 | 1.00 | 34.80 |
| ATOM | 4888 | CA | GLY | B | 394 | 50.585 | 72.995 | 24.911 | 1.00 | 33.76 |
| ATOM | 4889 | C | GLY | B | 394 | 51.272 | 73.725 | 23.780 | 1.00 | 31.88 |
| ATOM | 4890 | O | GLY | B | 394 | 50.974 | 73.453 | 22.612 | 1.00 | 31.26 |
| ATOM | 4891 | N | SER | B | 395 | 52.181 | 74.645 | 24.107 | 1.00 | 28.79 |
| ATOM | 4892 | CA | SER | B | 395 | 53.032 | 75.239 | 23.082 | 1.00 | 27.08 |
| ATOM | 4893 | CB | SER | B | 395 | 54.147 | 76.067 | 23.715 | 1.00 | 25.22 |
| ATOM | 4894 | OG | SER | B | 395 | 53.618 | 77.146 | 24.455 | 1.00 | 26.24 |
| ATOM | 4895 | C | SER | B | 395 | 53.640 | 74.118 | 22.233 | 1.00 | 27.61 |
| ATOM | 4896 | O | SER | B | 395 | 53.434 | 74.049 | 21.018 | 1.00 | 23.10 |
| ATOM | 4897 | N | GLU | B | 396 | 54.327 | 73.211 | 22.925 | 1.00 | 30.57 |
| ATOM | 4898 | CA | GLU | B | 396 | 55.229 | 72.206 | 22.350 | 1.00 | 33.83 |
| ATOM | 4899 | CB | GLU | B | 396 | 55.884 | 71.416 | 23.494 | 1.00 | 37.99 |
| ATOM | 4900 | CG | GLU | B | 396 | 54.890 | 70.647 | 24.368 | 1.00 | 42.84 |
| ATOM | 4901 | CD | GLU | B | 396 | 55.072 | 70.859 | 25.869 | 1.00 | 44.81 |
| ATOM | 4902 | OE1 | GLU | B | 396 | 56.219 | 70.772 | 26.373 | 1.00 | 45.53 |
| ATOM | 4903 | OE2 | GLU | B | 396 | 54.049 | 71.091 | 26.554 | 1.00 | 46.06 |
| ATOM | 4904 | C | GLU | B | 396 | 54.671 | 71.243 | 21.279 | 1.00 | 33.27 |
| ATOM | 4905 | O | GLU | B | 396 | 55.419 | 70.797 | 20.406 | 1.00 | 31.56 |
| ATOM | 4906 | N | ASP | B | 397 | 53.381 | 70.908 | 21.360 | 1.00 | 34.54 |
| ATOM | 4907 | CA | ASP | B | 397 | 52.720 | 70.014 | 20.393 | 1.00 | 31.74 |
| ATOM | 4908 | CB | ASP | B | 397 | 52.781 | 70.602 | 18.971 | 1.00 | 33.35 |
| ATOM | 4909 | CG | ASP | B | 397 | 51.819 | 69.931 | 18.025 | 1.00 | 33.30 |
| ATOM | 4910 | OD1 | ASP | B | 397 | 50.704 | 69.613 | 18.475 | 1.00 | 33.64 |
| ATOM | 4911 | OD2 | ASP | B | 397 | 52.092 | 69.666 | 16.835 | 1.00 | 33.13 |
| ATOM | 4912 | C | ASP | B | 397 | 53.271 | 68.581 | 20.410 | 1.00 | 29.56 |
| ATOM | 4913 | O | ASP | B | 397 | 53.436 | 67.990 | 21.475 | 1.00 | 28.58 |
| ATOM | 4914 | N | ALA | B | 398 | 53.560 | 68.046 | 19.223 | 1.00 | 28.18 |
| ATOM | 4915 | CA | ALA | B | 398 | 54.031 | 66.676 | 19.033 | 1.00 | 25.89 |
| ATOM | 4916 | CB | ALA | B | 398 | 54.292 | 66.418 | 17.563 | 1.00 | 24.12 |
| ATOM | 4917 | C | ALA | B | 398 | 55.274 | 66.356 | 19.853 | 1.00 | 26.09 |

FIGURE 3 (Cont.)

| | A | B | C | D | E | F | G | H | I | J |
|---|---|---|---|---|---|---|---|---|---|---|
| ATOM | 4918 | O | ALA | B | 398 | 55.518 | 65.190 | 20.188 | 1.00 | 26.79 |
| ATOM | 4919 | N | LYS | B | 399 | 56.052 | 67.394 | 20.158 | 1.00 | 25.13 |
| ATOM | 4920 | CA | LYS | B | 399 | 57.205 | 67.296 | 21.048 | 1.00 | 26.19 |
| ATOM | 4921 | CB | LYS | B | 399 | 57.720 | 68.699 | 21.393 | 1.00 | 28.61 |
| ATOM | 4922 | CG | LYS | B | 399 | 59.237 | 68.870 | 21.379 | 1.00 | 30.31 |
| ATOM | 4923 | CD | LYS | B | 399 | 59.646 | 70.184 | 20.692 | 1.00 | 32.29 |
| ATOM | 4924 | CE | LYS | B | 399 | 59.984 | 71.289 | 21.704 | 1.00 | 33.00 |
| ATOM | 4925 | NZ | LYS | B | 399 | 60.789 | 72.398 | 21.105 | 1.00 | 29.82 |
| ATOM | 4926 | C | LYS | B | 399 | 56.836 | 66.547 | 22.332 | 1.00 | 25.79 |
| ATOM | 4927 | O | LYS | B | 399 | 57.478 | 65.554 | 22.683 | 1.00 | 25.48 |
| ATOM | 4928 | N | GLU | B | 400 | 55.785 | 67.026 | 23.006 | 1.00 | 25.55 |
| ATOM | 4929 | CA | GLU | B | 400 | 55.288 | 66.464 | 24.272 | 1.00 | 24.77 |
| ATOM | 4930 | CB | GLU | B | 400 | 53.938 | 67.106 | 24.653 | 1.00 | 26.39 |
| ATOM | 4931 | CG | GLU | B | 400 | 53.779 | 67.510 | 26.119 | 1.00 | 26.89 |
| ATOM | 4932 | CD | GLU | B | 400 | 52.510 | 68.318 | 26.383 | 1.00 | 28.74 |
| ATOM | 4933 | OE1 | GLU | B | 400 | 52.146 | 69.188 | 25.554 | 1.00 | 28.39 |
| ATOM | 4934 | OE2 | GLU | B | 400 | 51.868 | 68.083 | 27.429 | 1.00 | 29.74 |
| ATOM | 4935 | C | GLU | B | 400 | 55.137 | 64.944 | 24.207 | 1.00 | 22.68 |
| ATOM | 4936 | O | GLU | B | 400 | 55.404 | 64.251 | 25.193 | 1.00 | 22.99 |
| ATOM | 4937 | N | ILE | B | 401 | 54.712 | 64.451 | 23.040 | 1.00 | 17.70 |
| ATOM | 4938 | CA | ILE | B | 401 | 54.475 | 63.033 | 22.812 | 1.00 | 13.94 |
| ATOM | 4939 | CB | ILE | B | 401 | 53.459 | 62.847 | 21.666 | 1.00 | 14.15 |
| ATOM | 4940 | CG1 | ILE | B | 401 | 52.048 | 62.898 | 22.224 | 1.00 | 14.04 |
| ATOM | 4941 | CD1 | ILE | B | 401 | 51.276 | 64.043 | 21.696 | 1.00 | 18.56 |
| ATOM | 4942 | CG2 | ILE | B | 401 | 53.648 | 61.526 | 20.929 | 1.00 | 13.92 |
| ATOM | 4943 | C | ILE | B | 401 | 55.769 | 62.280 | 22.544 | 1.00 | 12.44 |
| ATOM | 4944 | O | ILE | B | 401 | 55.936 | 61.143 | 22.985 | 1.00 | 11.72 |
| ATOM | 4945 | N | MET | B | 402 | 56.684 | 62.915 | 21.824 | 1.00 | 12.24 |
| ATOM | 4946 | CA | MET | B | 402 | 57.963 | 62.297 | 21.500 | 1.00 | 10.51 |
| ATOM | 4947 | CB | MET | B | 402 | 58.660 | 63.105 | 20.421 | 1.00 | 10.94 |
| ATOM | 4948 | CG | MET | B | 402 | 57.900 | 63.111 | 19.108 | 1.00 | 13.95 |
| ATOM | 4949 | SD | MET | B | 402 | 58.341 | 64.408 | 17.917 | 1.00 | 20.12 |
| ATOM | 4950 | CE | MET | B | 402 | 59.970 | 65.037 | 18.520 | 1.00 | 19.55 |
| ATOM | 4951 | C | MET | B | 402 | 58.841 | 62.146 | 22.740 | 1.00 | 10.46 |
| ATOM | 4952 | O | MET | B | 402 | 59.511 | 61.131 | 22.907 | 1.00 | 10.50 |
| ATOM | 4953 | N | GLN | B | 403 | 58.808 | 63.142 | 23.622 | 1.00 | 10.83 |
| ATOM | 4954 | CA | GLN | B | 403 | 59.545 | 63.088 | 24.884 | 1.00 | 13.29 |
| ATOM | 4955 | CB | GLN | B | 403 | 59.663 | 64.484 | 25.505 | 1.00 | 14.52 |
| ATOM | 4956 | CG | GLN | B | 403 | 60.672 | 65.434 | 24.871 | 1.00 | 14.98 |
| ATOM | 4957 | CD | GLN | B | 403 | 60.516 | 66.858 | 25.405 | 1.00 | 17.09 |
| ATOM | 4958 | OE1 | GLN | B | 403 | 61.496 | 67.598 | 25.527 | 1.00 | 17.64 |
| ATOM | 4959 | NE2 | GLN | B | 403 | 59.281 | 67.238 | 25.739 | 1.00 | 18.02 |
| ATOM | 4960 | C | GLN | B | 403 | 58.926 | 62.139 | 25.926 | 1.00 | 14.85 |
| ATOM | 4961 | O | GLN | B | 403 | 59.525 | 61.921 | 26.987 | 1.00 | 18.25 |
| ATOM | 4962 | N | HIS | B | 404 | 57.738 | 61.596 | 25.640 | 1.00 | 14.60 |
| ATOM | 4963 | CA | HIS | B | 404 | 57.031 | 60.689 | 26.560 | 1.00 | 12.42 |
| ATOM | 4964 | CB | HIS | B | 404 | 55.643 | 60.357 | 26.034 | 1.00 | 10.49 |
| ATOM | 4965 | CG | HIS | B | 404 | 54.775 | 59.698 | 27.049 | 1.00 | 11.74 |
| ATOM | 4966 | ND1 | HIS | B | 404 | 54.853 | 58.353 | 27.328 | 1.00 | 12.95 |
| ATOM | 4967 | CE1 | HIS | B | 404 | 53.992 | 58.051 | 28.283 | 1.00 | 12.88 |
| ATOM | 4968 | NE2 | HIS | B | 404 | 53.361 | 59.154 | 28.638 | 1.00 | 13.64 |
| ATOM | 4969 | CD2 | HIS | B | 404 | 53.835 | 60.200 | 27.882 | 1.00 | 14.30 |

FIGURE 3 (Cont.)

| | A | B | C | D | E | F | G | H | I | J |
|---|---|---|---|---|---|---|---|---|---|---|
| ATOM | 4970 | C | HIS | B | 404 | 57.789 | 59.388 | 26.774 | 1.00 | 14.58 |
| ATOM | 4971 | O | HIS | B | 404 | 58.390 | 58.863 | 25.826 | 1.00 | 17.22 |
| ATOM | 4972 | N | ARG | B | 405 | 57.748 | 58.865 | 28.007 | 1.00 | 13.51 |
| ATOM | 4973 | CA | ARG | B | 405 | 58.546 | 57.683 | 28.391 | 1.00 | 10.40 |
| ATOM | 4974 | CB | ARG | B | 405 | 58.389 | 57.332 | 29.881 | 1.00 | 12.61 |
| ATOM | 4975 | CG | ARG | B | 405 | 57.022 | 57.631 | 30.492 | 1.00 | 20.03 |
| ATOM | 4976 | CD | ARG | B | 405 | 57.012 | 57.588 | 32.012 | 1.00 | 24.92 |
| ATOM | 4977 | NE | ARG | B | 405 | 55.825 | 56.948 | 32.594 | 1.00 | 28.15 |
| ATOM | 4978 | CZ | ARG | B | 405 | 55.850 | 55.860 | 33.379 | 1.00 | 31.85 |
| ATOM | 4979 | NH1 | ARG | B | 405 | 57.002 | 55.249 | 33.675 | 1.00 | 33.78 |
| ATOM | 4980 | NH2 | ARG | B | 405 | 54.714 | 55.376 | 33.878 | 1.00 | 30.85 |
| ATOM | 4981 | C | ARG | B | 405 | 58.326 | 56.448 | 27.502 | 1.00 | 7.63 |
| ATOM | 4982 | O | ARG | B | 405 | 59.227 | 55.625 | 27.338 | 1.00 | 8.53 |
| ATOM | 4983 | N | PHE | B | 406 | 57.138 | 56.338 | 26.919 | 1.00 | 4.12 |
| ATOM | 4984 | CA | PHE | B | 406 | 56.826 | 55.287 | 25.960 | 1.00 | 4.46 |
| ATOM | 4985 | CB | PHE | B | 406 | 55.369 | 55.413 | 25.536 | 1.00 | 6.67 |
| ATOM | 4986 | CG | PHE | B | 406 | 54.887 | 54.276 | 24.708 | 1.00 | 8.77 |
| ATOM | 4987 | CD1 | PHE | B | 406 | 54.590 | 53.049 | 25.294 | 1.00 | 9.17 |
| ATOM | 4988 | CE1 | PHE | B | 406 | 54.152 | 51.992 | 24.529 | 1.00 | 8.37 |
| ATOM | 4989 | CZ | PHE | B | 406 | 54.007 | 52.156 | 23.155 | 1.00 | 10.53 |
| ATOM | 4990 | CE2 | PHE | B | 406 | 54.293 | 53.374 | 22.566 | 1.00 | 9.98 |
| ATOM | 4991 | CD2 | PHE | B | 406 | 54.736 | 54.424 | 23.342 | 1.00 | 9.27 |
| ATOM | 4992 | C | PHE | B | 406 | 57.754 | 55.239 | 24.721 | 1.00 | 3.43 |
| ATOM | 4993 | O | PHE | B | 406 | 58.218 | 54.158 | 24.326 | 1.00 | 2.00 |
| ATOM | 4994 | N | PHE | B | 407 | 58.009 | 56.404 | 24.116 | 1.00 | 3.91 |
| ATOM | 4995 | CA | PHE | B | 407 | 59.014 | 56.549 | 23.042 | 1.00 | 5.09 |
| ATOM | 4996 | CB | PHE | B | 407 | 58.597 | 57.639 | 22.054 | 1.00 | 2.46 |
| ATOM | 4997 | CG | PHE | B | 407 | 57.241 | 57.449 | 21.470 | 1.00 | 2.00 |
| ATOM | 4998 | CD1 | PHE | B | 407 | 56.246 | 58.389 | 21.700 | 1.00 | 2.00 |
| ATOM | 4999 | CE1 | PHE | B | 407 | 54.978 | 58.231 | 21.160 | 1.00 | 2.00 |
| ATOM | 5000 | CZ | PHE | B | 407 | 54.704 | 57.125 | 20.363 | 1.00 | 2.00 |
| ATOM | 5001 | CE2 | PHE | B | 407 | 55.695 | 56.176 | 20.119 | 1.00 | 2.00 |
| ATOM | 5002 | CD2 | PHE | B | 407 | 56.961 | 56.350 | 20.669 | 1.00 | 2.00 |
| ATOM | 5003 | C | PHE | B | 407 | 60.444 | 56.845 | 23.566 | 1.00 | 5.86 |
| ATOM | 5004 | O | PHE | B | 407 | 61.052 | 57.870 | 23.233 | 1.00 | 3.30 |
| ATOM | 5005 | N | ALA | B | 408 | 60.973 | 55.927 | 24.371 | 1.00 | 7.79 |
| ATOM | 5006 | CA | ALA | B | 408 | 62.213 | 56.151 | 25.096 | 1.00 | 6.36 |
| ATOM | 5007 | CB | ALA | B | 408 | 62.287 | 55.232 | 26.301 | 1.00 | 2.74 |
| ATOM | 5008 | C | ALA | B | 408 | 63.442 | 55.980 | 24.201 | 1.00 | 10.98 |
| ATOM | 5009 | O | ALA | B | 408 | 64.261 | 56.907 | 24.059 | 1.00 | 13.54 |
| ATOM | 5010 | N | GLY | B | 409 | 63.579 | 54.803 | 23.597 | 1.00 | 12.32 |
| ATOM | 5011 | CA | GLY | B | 409 | 64.721 | 54.540 | 22.733 | 1.00 | 14.00 |
| ATOM | 5012 | C | GLY | B | 409 | 64.699 | 55.293 | 21.410 | 1.00 | 13.20 |
| ATOM | 5013 | O | GLY | B | 409 | 65.740 | 55.666 | 20.881 | 1.00 | 10.72 |
| ATOM | 5014 | N | ILE | B | 410 | 63.495 | 55.523 | 20.892 | 1.00 | 15.38 |
| ATOM | 5015 | CA | ILE | B | 410 | 63.283 | 56.052 | 19.546 | 1.00 | 12.78 |
| ATOM | 5016 | CB | ILE | B | 410 | 61.771 | 56.350 | 19.316 | 1.00 | 11.06 |
| ATOM | 5017 | CG1 | ILE | B | 410 | 60.890 | 55.231 | 19.900 | 1.00 | 7.10 |
| ATOM | 5018 | CD1 | ILE | B | 410 | 60.914 | 53.925 | 19.123 | 1.00 | 6.62 |
| ATOM | 5019 | CG2 | ILE | B | 410 | 61.480 | 56.627 | 17.830 | 1.00 | 10.25 |
| ATOM | 5020 | C | ILE | B | 410 | 64.111 | 57.294 | 19.262 | 1.00 | 11.66 |
| ATOM | 5021 | O | ILE | B | 410 | 64.120 | 58.231 | 20.058 | 1.00 | 10.41 |

FIGURE 3 (Cont.)

| | A | B | C | D | E | F | G | H | I | J |
|---|---|---|---|---|---|---|---|---|---|---|
| ATOM | 5022 | N | VAL | B | 411 | 64.818 | 57.275 | 18.136 | 1.00 | 11.48 |
| ATOM | 5023 | CA | VAL | B | 411 | 65.432 | 58.482 | 17.609 | 1.00 | 13.15 |
| ATOM | 5024 | CB | VAL | B | 411 | 66.853 | 58.254 | 17.122 | 1.00 | 14.89 |
| ATOM | 5025 | CG1 | VAL | B | 411 | 67.651 | 59.547 | 17.257 | 1.00 | 15.43 |
| ATOM | 5026 | CG2 | VAL | B | 411 | 67.508 | 57.106 | 17.890 | 1.00 | 15.87 |
| ATOM | 5027 | C | VAL | B | 411 | 64.560 | 59.009 | 16.472 | 1.00 | 14.19 |
| ATOM | 5028 | O | VAL | B | 411 | 64.385 | 58.353 | 15.440 | 1.00 | 12.26 |
| ATOM | 5029 | N | TRP | B | 412 | 64.021 | 60.208 | 16.679 | 1.00 | 15.19 |
| ATOM | 5030 | CA | TRP | B | 412 | 62.891 | 60.710 | 15.901 | 1.00 | 12.24 |
| ATOM | 5031 | CB | TRP | B | 412 | 62.198 | 61.846 | 16.649 | 1.00 | 8.88 |
| ATOM | 5032 | CG | TRP | B | 412 | 61.381 | 61.304 | 17.776 | 1.00 | 11.18 |
| ATOM | 5033 | CD1 | TRP | B | 412 | 61.698 | 61.317 | 19.107 | 1.00 | 13.52 |
| ATOM | 5034 | NE1 | TRP | B | 412 | 60.713 | 60.695 | 19.839 | 1.00 | 11.73 |
| ATOM | 5035 | CE2 | TRP | B | 412 | 59.734 | 60.261 | 18.987 | 1.00 | 9.95 |
| ATOM | 5036 | CD2 | TRP | B | 412 | 60.126 | 60.616 | 17.676 | 1.00 | 10.83 |
| ATOM | 5037 | CE3 | TRP | B | 412 | 59.282 | 60.278 | 16.610 | 1.00 | 10.98 |
| ATOM | 5038 | CZ3 | TRP | B | 412 | 58.108 | 59.610 | 16.879 | 1.00 | 12.18 |
| ATOM | 5039 | CH2 | TRP | B | 412 | 57.752 | 59.266 | 18.196 | 1.00 | 11.83 |
| ATOM | 5040 | CZ2 | TRP | B | 412 | 58.548 | 59.592 | 19.258 | 1.00 | 9.24 |
| ATOM | 5041 | C | TRP | B | 412 | 63.260 | 61.095 | 14.487 | 1.00 | 14.58 |
| ATOM | 5042 | O | TRP | B | 412 | 62.387 | 61.208 | 13.618 | 1.00 | 18.36 |
| ATOM | 5043 | N | GLN | B | 413 | 64.559 | 61.287 | 14.270 | 1.00 | 15.20 |
| ATOM | 5044 | CA | GLN | B | 413 | 65.117 | 61.552 | 12.953 | 1.00 | 14.61 |
| ATOM | 5045 | CB | GLN | B | 413 | 66.468 | 62.236 | 13.108 | 1.00 | 13.94 |
| ATOM | 5046 | CG | GLN | B | 413 | 66.982 | 62.876 | 11.849 | 1.00 | 15.29 |
| ATOM | 5047 | CD | GLN | B | 413 | 67.083 | 64.366 | 11.983 | 1.00 | 16.22 |
| ATOM | 5048 | OE1 | GLN | B | 413 | 66.084 | 65.075 | 11.839 | 1.00 | 16.22 |
| ATOM | 5049 | NE2 | GLN | B | 413 | 68.286 | 64.855 | 12.276 | 1.00 | 16.10 |
| ATOM | 5050 | C | GLN | B | 413 | 65.278 | 60.251 | 12.162 | 1.00 | 15.48 |
| ATOM | 5051 | O | GLN | B | 413 | 65.277 | 60.263 | 10.925 | 1.00 | 13.68 |
| ATOM | 5052 | N | HIS | B | 414 | 65.409 | 59.142 | 12.897 | 1.00 | 17.36 |
| ATOM | 5053 | CA | HIS | B | 414 | 65.685 | 57.816 | 12.337 | 1.00 | 17.09 |
| ATOM | 5054 | CB | HIS | B | 414 | 66.286 | 56.896 | 13.407 | 1.00 | 18.65 |
| ATOM | 5055 | CG | HIS | B | 414 | 67.776 | 56.791 | 13.357 | 1.00 | 19.06 |
| ATOM | 5056 | ND1 | HIS | B | 414 | 68.550 | 57.516 | 12.477 | 1.00 | 19.59 |
| ATOM | 5057 | CE1 | HIS | B | 414 | 69.822 | 57.217 | 12.664 | 1.00 | 21.56 |
| ATOM | 5058 | NE2 | HIS | B | 414 | 69.901 | 56.325 | 13.635 | 1.00 | 21.97 |
| ATOM | 5059 | CD2 | HIS | B | 414 | 68.635 | 56.043 | 14.087 | 1.00 | 19.80 |
| ATOM | 5060 | C | HIS | B | 414 | 64.411 | 57.185 | 11.831 | 1.00 | 16.07 |
| ATOM | 5061 | O | HIS | B | 414 | 64.361 | 56.673 | 10.708 | 1.00 | 13.91 |
| ATOM | 5062 | N | VAL | B | 415 | 63.387 | 57.218 | 12.686 | 1.00 | 17.18 |
| ATOM | 5063 | CA | VAL | B | 415 | 62.065 | 56.688 | 12.359 | 1.00 | 18.84 |
| ATOM | 5064 | CB | VAL | B | 415 | 61.112 | 56.666 | 13.615 | 1.00 | 16.46 |
| ATOM | 5065 | CG1 | VAL | B | 415 | 60.902 | 58.053 | 14.205 | 1.00 | 15.76 |
| ATOM | 5066 | CG2 | VAL | B | 415 | 59.785 | 56.014 | 13.292 | 1.00 | 16.70 |
| ATOM | 5067 | C | VAL | B | 415 | 61.511 | 57.475 | 11.162 | 1.00 | 19.55 |
| ATOM | 5068 | O | VAL | B | 415 | 60.721 | 56.961 | 10.372 | 1.00 | 20.16 |
| ATOM | 5069 | N | TYR | B | 416 | 61.983 | 58.711 | 11.034 | 1.00 | 18.88 |
| ATOM | 5070 | CA | TYR | B | 416 | 61.687 | 59.574 | 9.909 | 1.00 | 19.82 |
| ATOM | 5071 | CB | TYR | B | 416 | 62.009 | 61.017 | 10.301 | 1.00 | 19.35 |
| ATOM | 5072 | CG | TYR | B | 416 | 61.923 | 62.030 | 9.186 | 1.00 | 19.92 |
| ATOM | 5073 | CD1 | TYR | B | 416 | 60.794 | 62.826 | 9.038 | 1.00 | 20.41 |

FIGURE 3 (Cont.)

|      | A    | B    | C   | D | E   | F      | G      | H      | I    | J     |
|------|------|------|-----|---|-----|--------|--------|--------|------|-------|
| ATOM | 5074 | CE1  | TYR | B | 416 | 60.709 | 63.763 | 8.027  | 1.00 | 22.09 |
| ATOM | 5075 | CZ   | TYR | B | 416 | 61.769 | 63.921 | 7.152  | 1.00 | 21.94 |
| ATOM | 5076 | OH   | TYR | B | 416 | 61.682 | 64.856 | 6.147  | 1.00 | 23.42 |
| ATOM | 5077 | CE2  | TYR | B | 416 | 62.908 | 63.146 | 7.280  | 1.00 | 20.65 |
| ATOM | 5078 | CD2  | TYR | B | 416 | 62.983 | 62.212 | 8.295  | 1.00 | 19.84 |
| ATOM | 5079 | C    | TYR | B | 416 | 62.496 | 59.141 | 8.683  | 1.00 | 21.72 |
| ATOM | 5080 | O    | TYR | B | 416 | 62.001 | 59.165 | 7.551  | 1.00 | 22.60 |
| ATOM | 5081 | N    | GLU | B | 417 | 63.742 | 58.741 | 8.908  | 1.00 | 22.98 |
| ATOM | 5082 | CA   | GLU | B | 417 | 64.603 | 58.311 | 7.811  | 1.00 | 22.62 |
| ATOM | 5083 | CB   | GLU | B | 417 | 66.068 | 58.324 | 8.237  | 1.00 | 24.32 |
| ATOM | 5084 | CG   | GLU | B | 417 | 66.875 | 59.467 | 7.647  | 1.00 | 27.05 |
| ATOM | 5085 | CD   | GLU | B | 417 | 67.910 | 60.000 | 8.619  | 1.00 | 27.56 |
| ATOM | 5086 | OE1  | GLU | B | 417 | 68.980 | 59.366 | 8.747  | 1.00 | 28.27 |
| ATOM | 5087 | OE2  | GLU | B | 417 | 67.649 | 61.045 | 9.257  | 1.00 | 26.82 |
| ATOM | 5088 | C    | GLU | B | 417 | 64.222 | 56.926 | 7.311  | 1.00 | 20.94 |
| ATOM | 5089 | O    | GLU | B | 417 | 64.955 | 56.341 | 6.510  | 1.00 | 21.26 |
| ATOM | 5090 | N    | LYS | B | 418 | 63.079 | 56.417 | 7.781  | 1.00 | 17.81 |
| ATOM | 5091 | CA   | LYS | B | 418 | 62.594 | 55.080 | 7.437  | 1.00 | 17.59 |
| ATOM | 5092 | CB   | LYS | B | 418 | 62.250 | 55.008 | 5.944  | 1.00 | 19.32 |
| ATOM | 5093 | CG   | LYS | B | 418 | 60.805 | 54.677 | 5.610  | 1.00 | 20.49 |
| ATOM | 5094 | CD   | LYS | B | 418 | 60.502 | 55.018 | 4.145  | 1.00 | 22.68 |
| ATOM | 5095 | CE   | LYS | B | 418 | 60.147 | 53.778 | 3.326  | 1.00 | 23.26 |
| ATOM | 5096 | NZ   | LYS | B | 418 | 58.767 | 53.874 | 2.753  | 1.00 | 24.01 |
| ATOM | 5097 | C    | LYS | B | 418 | 63.622 | 54.002 | 7.818  | 1.00 | 18.01 |
| ATOM | 5098 | O    | LYS | B | 418 | 63.679 | 52.932 | 7.206  | 1.00 | 16.37 |
| ATOM | 5099 | N    | LYS | B | 419 | 64.433 | 54.299 | 8.833  | 1.00 | 20.05 |
| ATOM | 5100 | CA   | LYS | B | 419 | 65.495 | 53.399 | 9.286  | 1.00 | 21.58 |
| ATOM | 5101 | CB   | LYS | B | 419 | 66.681 | 54.203 | 9.836  | 1.00 | 21.79 |
| ATOM | 5102 | CG   | LYS | B | 419 | 67.940 | 54.115 | 8.979  | 1.00 | 22.28 |
| ATOM | 5103 | CD   | LYS | B | 419 | 68.717 | 55.425 | 8.986  | 1.00 | 22.60 |
| ATOM | 5104 | CE   | LYS | B | 419 | 70.096 | 55.251 | 8.368  | 1.00 | 23.58 |
| ATOM | 5105 | NZ   | LYS | B | 419 | 70.137 | 55.659 | 6.932  | 1.00 | 24.30 |
| ATOM | 5106 | C    | LYS | B | 419 | 65.014 | 52.362 | 10.312 | 1.00 | 21.62 |
| ATOM | 5107 | O    | LYS | B | 419 | 65.506 | 51.238 | 10.340 | 1.00 | 21.99 |
| ATOM | 5108 | N    | LEU | B | 420 | 64.055 | 52.741 | 11.149 | 1.00 | 23.01 |
| ATOM | 5109 | CA   | LEU | B | 420 | 63.474 | 51.825 | 12.127 | 1.00 | 25.14 |
| ATOM | 5110 | CB   | LEU | B | 420 | 62.361 | 52.522 | 12.929 | 1.00 | 25.31 |
| ATOM | 5111 | CG   | LEU | B | 420 | 62.550 | 52.506 | 14.454 | 1.00 | 24.73 |
| ATOM | 5112 | CD1  | LEU | B | 420 | 63.098 | 53.835 | 14.988 | 1.00 | 22.15 |
| ATOM | 5113 | CD2  | LEU | B | 420 | 61.264 | 52.114 | 15.173 | 1.00 | 24.48 |
| ATOM | 5114 | C    | LEU | B | 420 | 62.934 | 50.588 | 11.422 | 1.00 | 25.34 |
| ATOM | 5115 | O    | LEU | B | 420 | 62.066 | 50.696 | 10.557 | 1.00 | 25.10 |
| ATOM | 5116 | N    | SER | B | 421 | 63.464 | 49.419 | 11.775 | 1.00 | 27.17 |
| ATOM | 5117 | CA   | SER | B | 421 | 63.070 | 48.175 | 11.107 | 1.00 | 28.65 |
| ATOM | 5118 | CB   | SER | B | 421 | 64.083 | 47.039 | 11.359 | 1.00 | 28.35 |
| ATOM | 5119 | OG   | SER | B | 421 | 63.958 | 46.485 | 12.656 | 1.00 | 28.20 |
| ATOM | 5120 | C    | SER | B | 421 | 61.645 | 47.780 | 11.499 | 1.00 | 27.57 |
| ATOM | 5121 | O    | SER | B | 421 | 61.312 | 47.795 | 12.685 | 1.00 | 28.53 |
| ATOM | 5122 | N    | PRO | B | 422 | 60.814 | 47.443 | 10.506 | 1.00 | 26.68 |
| ATOM | 5123 | CA   | PRO | B | 422 | 59.390 | 47.170 | 10.731 | 1.00 | 26.88 |
| ATOM | 5124 | CB   | PRO | B | 422 | 58.807 | 47.156 | 9.314  | 1.00 | 25.64 |
| ATOM | 5125 | CG   | PRO | B | 422 | 59.912 | 46.735 | 8.466  | 1.00 | 26.93 |

FIGURE 3 (Cont.)

| | A | B | C | D | E | F | G | H | I | J |
|---|---|---|---|---|---|---|---|---|---|---|
| ATOM | 5126 | CD | PRO | B | 422 | 61.174 | 47.271 | 9.089 | 1.00 | 27.56 |
| ATOM | 5127 | C | PRO | B | 422 | 59.181 | 45.822 | 11.398 | 1.00 | 26.38 |
| ATOM | 5128 | O | PRO | B | 422 | 60.054 | 44.966 | 11.277 | 1.00 | 27.83 |
| ATOM | 5129 | N | PRO | B | 423 | 58.069 | 45.640 | 12.104 | 1.00 | 26.23 |
| ATOM | 5130 | CA | PRO | B | 423 | 57.780 | 44.361 | 12.752 | 1.00 | 25.52 |
| ATOM | 5131 | CB | PRO | B | 423 | 56.851 | 44.761 | 13.907 | 1.00 | 27.42 |
| ATOM | 5132 | CG | PRO | B | 423 | 56.675 | 46.269 | 13.789 | 1.00 | 27.18 |
| ATOM | 5133 | CD | PRO | B | 423 | 57.012 | 46.630 | 12.377 | 1.00 | 27.44 |
| ATOM | 5134 | C | PRO | B | 423 | 57.080 | 43.378 | 11.815 | 1.00 | 23.99 |
| ATOM | 5135 | O | PRO | B | 423 | 56.980 | 42.200 | 12.164 | 1.00 | 22.27 |
| ATOM | 5136 | N | PHE | B | 424 | 56.624 | 43.847 | 10.652 | 1.00 | 23.26 |
| ATOM | 5137 | CA | PHE | B | 424 | 55.876 | 43.010 | 9.720 | 1.00 | 23.60 |
| ATOM | 5138 | CB | PHE | B | 424 | 54.377 | 43.165 | 9.975 | 1.00 | 23.98 |
| ATOM | 5139 | CG | PHE | B | 424 | 53.514 | 42.363 | 9.043 | 1.00 | 24.92 |
| ATOM | 5140 | CD1 | PHE | B | 424 | 53.419 | 40.978 | 9.174 | 1.00 | 26.27 |
| ATOM | 5141 | CE1 | PHE | B | 424 | 52.611 | 40.230 | 8.312 | 1.00 | 27.70 |
| ATOM | 5142 | CZ | PHE | B | 424 | 51.888 | 40.876 | 7.305 | 1.00 | 27.16 |
| ATOM | 5143 | CE2 | PHE | B | 424 | 51.976 | 42.262 | 7.169 | 1.00 | 25.21 |
| ATOM | 5144 | CD2 | PHE | B | 424 | 52.783 | 42.996 | 8.039 | 1.00 | 25.24 |
| ATOM | 5145 | C | PHE | B | 424 | 56.181 | 43.354 | 8.271 | 1.00 | 25.35 |
| ATOM | 5146 | O | PHE | B | 424 | 56.035 | 44.510 | 7.863 | 1.00 | 29.58 |
| ATOM | 5147 | N | LYS | B | 425 | 56.589 | 42.349 | 7.495 | 1.00 | 23.66 |
| ATOM | 5148 | CA | LYS | B | 425 | 56.860 | 42.520 | 6.066 | 1.00 | 21.08 |
| ATOM | 5149 | CB | LYS | B | 425 | 58.184 | 41.848 | 5.681 | 1.00 | 21.73 |
| ATOM | 5150 | CG | LYS | B | 425 | 59.366 | 42.803 | 5.539 | 1.00 | 23.54 |
| ATOM | 5151 | CD | LYS | B | 425 | 60.451 | 42.527 | 6.586 | 1.00 | 24.10 |
| ATOM | 5152 | CE | LYS | B | 425 | 61.829 | 42.962 | 6.093 | 1.00 | 23.74 |
| ATOM | 5153 | NZ | LYS | B | 425 | 62.735 | 41.797 | 5.865 | 1.00 | 21.37 |
| ATOM | 5154 | C | LYS | B | 425 | 55.715 | 41.945 | 5.230 | 1.00 | 19.06 |
| ATOM | 5155 | O | LYS | B | 425 | 55.531 | 40.731 | 5.199 | 1.00 | 18.70 |
| ATOM | 5156 | N | PRO | B | 426 | 54.930 | 42.813 | 4.585 | 1.00 | 18.34 |
| ATOM | 5157 | CA | PRO | B | 426 | 53.874 | 42.381 | 3.649 | 1.00 | 19.77 |
| ATOM | 5158 | CB | PRO | B | 426 | 53.444 | 43.697 | 2.986 | 1.00 | 17.71 |
| ATOM | 5159 | CG | PRO | B | 426 | 53.747 | 44.750 | 4.004 | 1.00 | 15.19 |
| ATOM | 5160 | CD | PRO | B | 426 | 54.961 | 44.281 | 4.742 | 1.00 | 15.73 |
| ATOM | 5161 | C | PRO | B | 426 | 54.331 | 41.341 | 2.593 | 1.00 | 22.96 |
| ATOM | 5162 | O | PRO | B | 426 | 55.115 | 41.654 | 1.691 | 1.00 | 23.51 |
| ATOM | 5163 | N | GLN | B | 427 | 53.821 | 40.113 | 2.714 | 1.00 | 26.14 |
| ATOM | 5164 | CA | GLN | B | 427 | 54.267 | 38.970 | 1.898 | 1.00 | 27.11 |
| ATOM | 5165 | CB | GLN | B | 427 | 54.142 | 37.662 | 2.701 | 1.00 | 28.14 |
| ATOM | 5166 | CG | GLN | B | 427 | 54.950 | 37.626 | 3.993 | 1.00 | 28.44 |
| ATOM | 5167 | CD | GLN | B | 427 | 56.389 | 37.204 | 3.769 | 1.00 | 28.57 |
| ATOM | 5168 | OE1 | GLN | B | 427 | 56.768 | 36.090 | 4.122 | 1.00 | 29.24 |
| ATOM | 5169 | NE2 | GLN | B | 427 | 57.193 | 38.089 | 3.181 | 1.00 | 28.25 |
| ATOM | 5170 | C | GLN | B | 427 | 53.508 | 38.837 | 0.575 | 1.00 | 26.04 |
| ATOM | 5171 | O | GLN | B | 427 | 52.528 | 38.093 | 0.481 | 1.00 | 26.48 |
| ATOM | 5172 | N | VAL | B | 428 | 53.976 | 39.535 | -0.452 | 1.00 | 24.39 |
| ATOM | 5173 | CA | VAL | B | 428 | 53.219 | 39.633 | -1.704 | 1.00 | 24.67 |
| ATOM | 5174 | CB | VAL | B | 428 | 53.196 | 41.090 | -2.248 | 1.00 | 25.65 |
| ATOM | 5175 | CG1 | VAL | B | 428 | 51.960 | 41.831 | -1.738 | 1.00 | 23.03 |
| ATOM | 5176 | CG2 | VAL | B | 428 | 54.493 | 41.843 | -1.891 | 1.00 | 25.75 |
| ATOM | 5177 | C | VAL | B | 428 | 53.632 | 38.636 | -2.810 | 1.00 | 22.99 |

FIGURE 3 (Cont.)

| | A | B | C | D | E | F | G | H | I | J |
|---|---|---|---|---|---|---|---|---|---|---|
| ATOM | 5178 | O | VAL | B | 428 | 54.816 | 38.474 | -3.108 | 1.00 | 19.93 |
| ATOM | 5179 | N | THR | B | 429 | 52.631 | 37.986 | -3.406 | 1.00 | 23.47 |
| ATOM | 5180 | CA | THR | B | 429 | 52.818 | 37.047 | -4.518 | 1.00 | 25.62 |
| ATOM | 5181 | CB | THR | B | 429 | 51.512 | 36.236 | -4.793 | 1.00 | 26.66 |
| ATOM | 5182 | OG1 | THR | B | 429 | 50.799 | 36.016 | -3.571 | 1.00 | 27.48 |
| ATOM | 5183 | CG2 | THR | B | 429 | 51.830 | 34.814 | -5.282 | 1.00 | 27.23 |
| ATOM | 5184 | C | THR | B | 429 | 53.227 | 37.774 | -5.799 | 1.00 | 25.59 |
| ATOM | 5185 | O | THR | B | 429 | 53.974 | 37.237 | -6.628 | 1.00 | 25.49 |
| ATOM | 5186 | N | SER | B | 430 | 52.722 | 38.996 | -5.947 | 1.00 | 23.73 |
| ATOM | 5187 | CA | SER | B | 430 | 52.862 | 39.774 | -7.167 | 1.00 | 22.72 |
| ATOM | 5188 | CB | SER | B | 430 | 51.972 | 39.185 | -8.267 | 1.00 | 22.21 |
| ATOM | 5189 | OG | SER | B | 430 | 50.801 | 38.583 | -7.729 | 1.00 | 20.01 |
| ATOM | 5190 | C | SER | B | 430 | 52.427 | 41.195 | -6.857 | 1.00 | 23.87 |
| ATOM | 5191 | O | SER | B | 430 | 51.927 | 41.461 | -5.763 | 1.00 | 26.31 |
| ATOM | 5192 | N | GLU | B | 431 | 52.611 | 42.107 | -7.809 | 1.00 | 24.94 |
| ATOM | 5193 | CA | GLU | B | 431 | 52.092 | 43.469 | -7.673 | 1.00 | 26.95 |
| ATOM | 5194 | CB | GLU | B | 431 | 52.757 | 44.415 | -8.681 | 1.00 | 27.82 |
| ATOM | 5195 | CG | GLU | B | 431 | 53.923 | 45.231 | -8.130 | 1.00 | 29.51 |
| ATOM | 5196 | CD | GLU | B | 431 | 53.575 | 46.036 | -6.881 | 1.00 | 32.06 |
| ATOM | 5197 | OE1 | GLU | B | 431 | 52.469 | 46.622 | -6.803 | 1.00 | 31.83 |
| ATOM | 5198 | OE2 | GLU | B | 431 | 54.422 | 46.089 | -5.963 | 1.00 | 34.08 |
| ATOM | 5199 | C | GLU | B | 431 | 50.554 | 43.513 | -7.792 | 1.00 | 27.31 |
| ATOM | 5200 | O | GLU | B | 431 | 49.890 | 44.300 | -7.102 | 1.00 | 25.43 |
| ATOM | 5201 | N | THR | B | 432 | 50.009 | 42.650 | -8.655 | 1.00 | 27.75 |
| ATOM | 5202 | CA | THR | B | 432 | 48.560 | 42.483 | -8.833 | 1.00 | 28.12 |
| ATOM | 5203 | CB | THR | B | 432 | 48.242 | 41.547 | -10.043 | 1.00 | 26.38 |
| ATOM | 5204 | OG1 | THR | B | 432 | 46.950 | 40.950 | -9.879 | 1.00 | 24.96 |
| ATOM | 5205 | CG2 | THR | B | 432 | 49.166 | 40.336 | -10.079 | 1.00 | 25.65 |
| ATOM | 5206 | C | THR | B | 432 | 47.873 | 41.969 | -7.564 | 1.00 | 31.24 |
| ATOM | 5207 | O | THR | B | 432 | 46.702 | 42.269 | -7.321 | 1.00 | 32.54 |
| ATOM | 5208 | N | ASP | B | 433 | 48.617 | 41.204 | -6.765 | 1.00 | 33.27 |
| ATOM | 5209 | CA | ASP | B | 433 | 48.101 | 40.545 | -5.562 | 1.00 | 33.19 |
| ATOM | 5210 | CB | ASP | B | 433 | 49.185 | 39.648 | -4.941 | 1.00 | 34.60 |
| ATOM | 5211 | CG | ASP | B | 433 | 48.750 | 39.003 | -3.627 | 1.00 | 34.90 |
| ATOM | 5212 | OD1 | ASP | B | 433 | 47.606 | 38.503 | -3.533 | 1.00 | 34.60 |
| ATOM | 5213 | OD2 | ASP | B | 433 | 49.503 | 38.942 | -2.633 | 1.00 | 35.87 |
| ATOM | 5214 | C | ASP | B | 433 | 47.573 | 41.527 | -4.525 | 1.00 | 31.69 |
| ATOM | 5215 | O | ASP | B | 433 | 48.231 | 42.527 | -4.220 | 1.00 | 32.62 |
| ATOM | 5216 | N | THR | B | 434 | 46.377 | 41.224 | -4.009 | 1.00 | 29.61 |
| ATOM | 5217 | CA | THR | B | 434 | 45.724 | 41.985 | -2.938 | 1.00 | 26.44 |
| ATOM | 5218 | CB | THR | B | 434 | 44.499 | 42.765 | -3.469 | 1.00 | 26.60 |
| ATOM | 5219 | OG1 | THR | B | 434 | 43.625 | 41.870 | -4.171 | 1.00 | 25.46 |
| ATOM | 5220 | CG2 | THR | B | 434 | 44.910 | 43.789 | -4.517 | 1.00 | 27.63 |
| ATOM | 5221 | C | THR | B | 434 | 45.268 | 41.052 | -1.818 | 1.00 | 23.17 |
| ATOM | 5222 | O | THR | B | 434 | 44.095 | 41.046 | -1.438 | 1.00 | 22.16 |
| ATOM | 5223 | N | ARG | B | 435 | 46.200 | 40.269 | -1.288 | 1.00 | 19.68 |
| ATOM | 5224 | CA | ARG | B | 435 | 45.875 | 39.314 | -0.240 | 1.00 | 16.54 |
| ATOM | 5225 | CB | ARG | B | 435 | 46.998 | 38.285 | -0.068 | 1.00 | 15.91 |
| ATOM | 5226 | CG | ARG | B | 435 | 48.318 | 38.848 | 0.455 | 1.00 | 13.16 |
| ATOM | 5227 | CD | ARG | B | 435 | 49.323 | 37.785 | 0.902 | 1.00 | 11.43 |
| ATOM | 5228 | NE | ARG | B | 435 | 49.741 | 36.901 | -0.190 | 1.00 | 7.98 |
| ATOM | 5229 | CZ | ARG | B | 435 | 49.522 | 35.590 | -0.222 | 1.00 | 5.39 |

FIGURE 3 (Cont.)

| | A | B | C | D | E | F | G | H | I | J |
|---|---|---|---|---|---|---|---|---|---|---|
| ATOM | 5230 | NH1 | ARG | B | 435 | 48.889 | 34.988 | 0.776 | 1.00 | 5.35 |
| ATOM | 5231 | NH2 | ARG | B | 435 | 49.934 | 34.876 | -1.254 | 1.00 | 2.69 |
| ATOM | 5232 | C | ARG | B | 435 | 45.590 | 40.015 | 1.076 | 1.00 | 14.84 |
| ATOM | 5233 | O | ARG | B | 435 | 45.149 | 39.376 | 2.039 | 1.00 | 13.40 |
| ATOM | 5234 | N | TYR | B | 436 | 45.833 | 41.327 | 1.099 | 1.00 | 13.90 |
| ATOM | 5235 | CA | TYR | B | 436 | 45.738 | 42.123 | 2.326 | 1.00 | 14.53 |
| ATOM | 5236 | CB | TYR | B | 436 | 47.078 | 42.813 | 2.626 | 1.00 | 13.11 |
| ATOM | 5237 | CG | TYR | B | 436 | 48.158 | 41.852 | 3.066 | 1.00 | 12.11 |
| ATOM | 5238 | CD1 | TYR | B | 436 | 49.367 | 41.769 | 2.378 | 1.00 | 12.28 |
| ATOM | 5239 | CE1 | TYR | B | 436 | 50.370 | 40.877 | 2.775 | 1.00 | 14.02 |
| ATOM | 5240 | CZ | TYR | B | 436 | 50.160 | 40.045 | 3.872 | 1.00 | 16.17 |
| ATOM | 5241 | OH | TYR | B | 436 | 51.142 | 39.150 | 4.273 | 1.00 | 17.21 |
| ATOM | 5242 | CE2 | TYR | B | 436 | 48.956 | 40.108 | 4.569 | 1.00 | 15.73 |
| ATOM | 5243 | CD2 | TYR | B | 436 | 47.965 | 41.012 | 4.163 | 1.00 | 12.55 |
| ATOM | 5244 | C | TYR | B | 436 | 44.577 | 43.124 | 2.325 | 1.00 | 13.84 |
| ATOM | 5245 | O | TYR | B | 436 | 44.577 | 44.113 | 3.067 | 1.00 | 14.05 |
| ATOM | 5246 | N | PHE | B | 437 | 43.580 | 42.858 | 1.494 | 1.00 | 11.60 |
| ATOM | 5247 | CA | PHE | B | 437 | 42.395 | 43.696 | 1.466 | 1.00 | 10.70 |
| ATOM | 5248 | CB | PHE | B | 437 | 42.306 | 44.458 | 0.144 | 1.00 | 7.31 |
| ATOM | 5249 | CG | PHE | B | 437 | 43.381 | 45.490 | -0.028 | 1.00 | 3.62 |
| ATOM | 5250 | CD1 | PHE | B | 437 | 44.699 | 45.114 | -0.267 | 1.00 | 3.17 |
| ATOM | 5251 | CE1 | PHE | B | 437 | 45.692 | 46.060 | -0.417 | 1.00 | 2.75 |
| ATOM | 5252 | CZ | PHE | B | 437 | 45.378 | 47.406 | -0.333 | 1.00 | 2.75 |
| ATOM | 5253 | CE2 | PHE | B | 437 | 44.071 | 47.795 | -0.099 | 1.00 | 3.29 |
| ATOM | 5254 | CD2 | PHE | B | 437 | 43.079 | 46.834 | 0.051 | 1.00 | 3.22 |
| ATOM | 5255 | C | PHE | B | 437 | 41.187 | 42.809 | 1.677 | 1.00 | 13.08 |
| ATOM | 5256 | O | PHE | B | 437 | 41.191 | 41.653 | 1.251 | 1.00 | 12.09 |
| ATOM | 5257 | N | ASP | B | 438 | 40.167 | 43.351 | 2.343 | 1.00 | 17.43 |
| ATOM | 5258 | CA | ASP | B | 438 | 38.947 | 42.611 | 2.681 | 1.00 | 21.30 |
| ATOM | 5259 | CB | ASP | B | 438 | 37.924 | 43.546 | 3.342 | 1.00 | 22.82 |
| ATOM | 5260 | CG | ASP | B | 438 | 37.892 | 43.411 | 4.868 | 1.00 | 25.30 |
| ATOM | 5261 | OD1 | ASP | B | 438 | 37.062 | 42.623 | 5.374 | 1.00 | 24.74 |
| ATOM | 5262 | OD2 | ASP | B | 438 | 38.641 | 44.059 | 5.642 | 1.00 | 27.09 |
| ATOM | 5263 | C | ASP | B | 438 | 38.337 | 41.890 | 1.462 | 1.00 | 23.31 |
| ATOM | 5264 | O | ASP | B | 438 | 38.342 | 42.420 | 0.341 | 1.00 | 25.71 |
| ATOM | 5265 | N | GLU | B | 439 | 37.828 | 40.678 | 1.688 | 1.00 | 22.87 |
| ATOM | 5266 | CA | GLU | B | 439 | 37.253 | 39.855 | 0.618 | 1.00 | 21.87 |
| ATOM | 5267 | CB | GLU | B | 439 | 37.118 | 38.395 | 1.073 | 1.00 | 25.82 |
| ATOM | 5268 | CG | GLU | B | 439 | 38.448 | 37.664 | 1.249 | 1.00 | 29.83 |
| ATOM | 5269 | CD | GLU | B | 439 | 38.590 | 36.446 | 0.344 | 1.00 | 31.99 |
| ATOM | 5270 | OE1 | GLU | B | 439 | 38.059 | 35.368 | 0.710 | 1.00 | 33.40 |
| ATOM | 5271 | OE2 | GLU | B | 439 | 39.236 | 36.561 | -0.728 | 1.00 | 31.67 |
| ATOM | 5272 | C | GLU | B | 439 | 35.912 | 40.399 | 0.109 | 1.00 | 18.60 |
| ATOM | 5273 | O | GLU | B | 439 | 35.424 | 39.989 | -0.942 | 1.00 | 17.16 |
| ATOM | 5274 | N | GLU | B | 440 | 35.335 | 41.329 | 0.864 | 1.00 | 16.37 |
| ATOM | 5275 | CA | GLU | B | 440 | 34.090 | 41.994 | 0.499 | 1.00 | 15.13 |
| ATOM | 5276 | CB | GLU | B | 440 | 33.507 | 42.691 | 1.729 | 1.00 | 17.49 |
| ATOM | 5277 | CG | GLU | B | 440 | 32.078 | 42.286 | 2.061 | 1.00 | 20.88 |
| ATOM | 5278 | CD | GLU | B | 440 | 31.132 | 43.472 | 2.151 | 1.00 | 22.30 |
| ATOM | 5279 | OE1 | GLU | B | 440 | 30.007 | 43.297 | 2.681 | 1.00 | 23.27 |
| ATOM | 5280 | OE2 | GLU | B | 440 | 31.511 | 44.576 | 1.690 | 1.00 | 21.80 |
| ATOM | 5281 | C | GLU | B | 440 | 34.287 | 43.009 | -0.630 | 1.00 | 12.48 |

FIGURE 3 (Cont.)

|      | A    | B    | C   | D | E   | F      | G      | H       | I    | J     |
|------|------|------|-----|---|-----|--------|--------|---------|------|-------|
| ATOM | 5282 | O    | GLU | B | 440 | 33.327 | 43.430 | -1.278  | 1.00 | 11.09 |
| ATOM | 5283 | N    | PHE | B | 441 | 35.536 | 43.399 | -0.853  | 1.00 | 10.88 |
| ATOM | 5284 | CA   | PHE | B | 441 | 35.872 | 44.406 | -1.844  | 1.00 | 12.26 |
| ATOM | 5285 | CB   | PHE | B | 441 | 36.781 | 45.457 | -1.226  | 1.00 | 11.29 |
| ATOM | 5286 | CG   | PHE | B | 441 | 36.157 | 46.211 | -0.106  | 1.00 | 11.12 |
| ATOM | 5287 | CD1  | PHE | B | 441 | 36.829 | 46.357 | 1.102   | 1.00 | 9.74  |
| ATOM | 5288 | CE1  | PHE | B | 441 | 36.261 | 47.067 | 2.148   | 1.00 | 9.36  |
| ATOM | 5289 | CZ   | PHE | B | 441 | 35.002 | 47.637 | 1.996   | 1.00 | 9.86  |
| ATOM | 5290 | CE2  | PHE | B | 441 | 34.317 | 47.500 | 0.792   | 1.00 | 11.80 |
| ATOM | 5291 | CD2  | PHE | B | 441 | 34.898 | 46.793 | -0.256  | 1.00 | 11.95 |
| ATOM | 5292 | C    | PHE | B | 441 | 36.590 | 43.786 | -3.024  | 1.00 | 15.98 |
| ATOM | 5293 | O    | PHE | B | 441 | 36.371 | 44.176 | -4.175  | 1.00 | 17.64 |
| ATOM | 5294 | N    | THR | B | 442 | 37.458 | 42.822 | -2.727  | 1.00 | 17.76 |
| ATOM | 5295 | CA   | THR | B | 442 | 38.251 | 42.141 | -3.749  | 1.00 | 18.76 |
| ATOM | 5296 | CB   | THR | B | 442 | 39.442 | 41.384 | -3.101  | 1.00 | 19.03 |
| ATOM | 5297 | OG1  | THR | B | 442 | 39.062 | 40.872 | -1.817  | 1.00 | 18.53 |
| ATOM | 5298 | CG2  | THR | B | 442 | 40.564 | 42.360 | -2.764  | 1.00 | 17.88 |
| ATOM | 5299 | C    | THR | B | 442 | 37.433 | 41.225 | -4.682  | 1.00 | 18.00 |
| ATOM | 5300 | O    | THR | B | 442 | 37.894 | 40.892 | -5.771  | 1.00 | 16.80 |
| ATOM | 5301 | N    | ALA | B | 443 | 36.222 | 40.851 | -4.262  | 1.00 | 18.77 |
| ATOM | 5302 | CA   | ALA | B | 443 | 35.349 | 39.947 | -5.022  | 1.00 | 21.39 |
| ATOM | 5303 | CB   | ALA | B | 443 | 34.304 | 39.322 | -4.103  | 1.00 | 19.73 |
| ATOM | 5304 | C    | ALA | B | 443 | 34.676 | 40.549 | -6.278  | 1.00 | 24.55 |
| ATOM | 5305 | O    | ALA | B | 443 | 34.258 | 39.800 | -7.172  | 1.00 | 24.41 |
| ATOM | 5306 | N    | GLN | B | 444 | 34.572 | 41.882 | -6.342  | 1.00 | 26.42 |
| ATOM | 5307 | CA   | GLN | B | 444 | 34.003 | 42.582 | -7.508  | 1.00 | 27.26 |
| ATOM | 5308 | CB   | GLN | B | 444 | 33.185 | 43.801 | -7.072  | 1.00 | 27.50 |
| ATOM | 5309 | CG   | GLN | B | 444 | 31.918 | 43.477 | -6.295  | 1.00 | 28.15 |
| ATOM | 5310 | CD   | GLN | B | 444 | 31.930 | 44.059 | -4.889  | 1.00 | 27.86 |
| ATOM | 5311 | OE1  | GLN | B | 444 | 32.020 | 43.319 | -3.910  | 1.00 | 28.20 |
| ATOM | 5312 | NE2  | GLN | B | 444 | 31.835 | 45.383 | -4.787  | 1.00 | 26.99 |
| ATOM | 5313 | C    | GLN | B | 444 | 35.097 | 43.034 | -8.476  | 1.00 | 27.45 |
| ATOM | 5314 | O    | GLN | B | 444 | 36.141 | 43.536 | -8.043  | 1.00 | 28.23 |
| ATOM | 5315 | N    | SER | B | 445 | 34.850 | 42.868 | -9.777  | 1.00 | 26.55 |
| ATOM | 5316 | CA   | SER | B | 445 | 35.858 | 43.163 | -10.806 | 1.00 | 26.44 |
| ATOM | 5317 | CB   | SER | B | 445 | 36.364 | 41.865 | -11.476 | 1.00 | 26.62 |
| ATOM | 5318 | OG   | SER | B | 445 | 35.613 | 41.499 | -12.627 | 1.00 | 25.91 |
| ATOM | 5319 | C    | SER | B | 445 | 35.421 | 44.225 | -11.837 | 1.00 | 26.45 |
| ATOM | 5320 | O    | SER | B | 445 | 34.723 | 45.183 | -11.484 | 1.00 | 24.53 |
| ATOM | 5321 | N    | ILE | B | 446 | 35.845 | 44.032 | -13.092 | 1.00 | 27.50 |
| ATOM | 5322 | CA   | ILE | B | 446 | 35.634 | 44.967 | -14.213 | 1.00 | 28.51 |
| ATOM | 5323 | CB   | ILE | B | 446 | 35.826 | 44.252 | -15.605 | 1.00 | 27.94 |
| ATOM | 5324 | CG1  | ILE | B | 446 | 35.045 | 42.928 | -15.678 | 1.00 | 27.10 |
| ATOM | 5325 | CD1  | ILE | B | 446 | 34.396 | 42.649 | -17.025 | 1.00 | 24.40 |
| ATOM | 5326 | CG2  | ILE | B | 446 | 37.315 | 44.045 | -15.921 | 1.00 | 27.20 |
| ATOM | 5327 | C    | ILE | B | 446 | 34.302 | 45.730 | -14.180 | 1.00 | 29.49 |
| ATOM | 5328 | O    | ILE | B | 446 | 34.236 | 46.877 | -13.724 | 1.00 | 29.43 |
| TER  | 5328 |      | ILE | B | 446 |        |        |         |      |       |
| ATOM | 5329 | N    | PRO | B | 468 | 28.648 | 70.365 | -13.352 | 1.00 | 31.71 |
| ATOM | 5330 | CA   | PRO | B | 468 | 29.552 | 71.059 | -12.428 | 1.00 | 32.09 |
| ATOM | 5331 | CB   | PRO | B | 468 | 29.122 | 70.516 | -11.064 | 1.00 | 31.84 |
| ATOM | 5332 | CG   | PRO | B | 468 | 27.659 | 70.217 | -11.231 | 1.00 | 31.61 |

FIGURE 3 (Cont.)

| | A | B | C | D | E | F | G | H | I | J |
|---|---|---|---|---|---|---|---|---|---|---|
| ATOM | 5333 | CD | PRO | B | 468 | 27.470 | 69.805 | -12.665 | 1.00 | 31.40 |
| ATOM | 5334 | C | PRO | B | 468 | 31.032 | 70.745 | -12.700 | 1.00 | 32.65 |
| ATOM | 5335 | O | PRO | B | 468 | 31.418 | 69.576 | -12.672 | 1.00 | 32.18 |
| ATOM | 5336 | N | HIS | B | 469 | 31.834 | 71.782 | -12.961 | 1.00 | 33.78 |
| ATOM | 5337 | CA | HIS | B | 469 | 33.271 | 71.642 | -13.246 | 1.00 | 34.47 |
| ATOM | 5338 | CB | HIS | B | 469 | 33.570 | 72.008 | -14.718 | 1.00 | 31.97 |
| ATOM | 5339 | CG | HIS | B | 469 | 35.035 | 72.104 | -15.052 | 1.00 | 29.73 |
| ATOM | 5340 | ND1 | HIS | B | 469 | 35.813 | 71.000 | -15.334 | 1.00 | 28.12 |
| ATOM | 5341 | CE1 | HIS | B | 469 | 37.049 | 71.387 | -15.598 | 1.00 | 26.57 |
| ATOM | 5342 | NE2 | HIS | B | 469 | 37.101 | 72.703 | -15.505 | 1.00 | 26.50 |
| ATOM | 5343 | CD2 | HIS | B | 469 | 35.854 | 73.177 | -15.171 | 1.00 | 28.51 |
| ATOM | 5344 | C | HIS | B | 469 | 34.124 | 72.493 | -12.294 | 1.00 | 36.18 |
| ATOM | 5345 | O | HIS | B | 469 | 33.944 | 73.714 | -12.216 | 1.00 | 37.23 |
| ATOM | 5346 | N | PHE | B | 470 | 35.043 | 71.842 | -11.577 | 1.00 | 36.97 |
| ATOM | 5347 | CA | PHE | B | 470 | 36.012 | 72.541 | -10.731 | 1.00 | 39.54 |
| ATOM | 5348 | CB | PHE | B | 470 | 36.027 | 71.976 | -9.305 | 1.00 | 41.74 |
| ATOM | 5349 | CG | PHE | B | 470 | 34.868 | 72.423 | -8.458 | 1.00 | 43.68 |
| ATOM | 5350 | CD1 | PHE | B | 470 | 34.532 | 73.779 | -8.356 | 1.00 | 44.66 |
| ATOM | 5351 | CE1 | PHE | B | 470 | 33.449 | 74.195 | -7.573 | 1.00 | 45.09 |
| ATOM | 5352 | CZ | PHE | B | 470 | 32.695 | 73.246 | -6.882 | 1.00 | 45.24 |
| ATOM | 5353 | CE2 | PHE | B | 470 | 33.026 | 71.887 | -6.978 | 1.00 | 44.68 |
| ATOM | 5354 | CD2 | PHE | B | 470 | 34.109 | 71.487 | -7.759 | 1.00 | 43.87 |
| ATOM | 5355 | C | PHE | B | 470 | 37.413 | 72.467 | -11.329 | 1.00 | 40.38 |
| ATOM | 5356 | O | PHE | B | 470 | 38.033 | 71.402 | -11.325 | 1.00 | 40.25 |
| ATOM | 5357 | N | PRO | B | 471 | 37.913 | 73.593 | -11.840 | 1.00 | 41.82 |
| ATOM | 5358 | CA | PRO | B | 471 | 39.256 | 73.635 | -12.434 | 1.00 | 42.33 |
| ATOM | 5359 | CB | PRO | B | 471 | 39.234 | 74.926 | -13.278 | 1.00 | 42.58 |
| ATOM | 5360 | CG | PRO | B | 471 | 37.822 | 75.471 | -13.172 | 1.00 | 42.27 |
| ATOM | 5361 | CD | PRO | B | 471 | 37.249 | 74.908 | -11.902 | 1.00 | 42.34 |
| ATOM | 5362 | C | PRO | B | 471 | 40.353 | 73.686 | -11.360 | 1.00 | 41.63 |
| ATOM | 5363 | O | PRO | B | 471 | 40.039 | 73.631 | -10.163 | 1.00 | 40.81 |
| ATOM | 5364 | N | GLN | B | 472 | 41.614 | 73.775 | -11.795 | 1.00 | 40.44 |
| ATOM | 5365 | CA | GLN | B | 472 | 42.779 | 73.849 | -10.901 | 1.00 | 38.23 |
| ATOM | 5366 | CB | GLN | B | 472 | 42.937 | 75.259 | -10.317 | 1.00 | 38.18 |
| ATOM | 5367 | CG | GLN | B | 472 | 43.468 | 76.279 | -11.318 | 1.00 | 37.65 |
| ATOM | 5368 | CD | GLN | B | 472 | 42.414 | 77.287 | -11.739 | 1.00 | 37.19 |
| ATOM | 5369 | OE1 | GLN | B | 472 | 41.639 | 77.036 | -12.661 | 1.00 | 36.62 |
| ATOM | 5370 | NE2 | GLN | B | 472 | 42.386 | 78.429 | -11.067 | 1.00 | 37.32 |
| ATOM | 5371 | C | GLN | B | 472 | 42.727 | 72.780 | -9.806 | 1.00 | 36.56 |
| ATOM | 5372 | O | GLN | B | 472 | 43.102 | 73.009 | -8.652 | 1.00 | 35.16 |
| ATOM | 5373 | N | PHE | B | 473 | 42.241 | 71.612 | -10.210 | 1.00 | 35.67 |
| ATOM | 5374 | CA | PHE | B | 473 | 42.162 | 70.427 | -9.375 | 1.00 | 34.75 |
| ATOM | 5375 | CB | PHE | B | 473 | 40.706 | 69.924 | -9.341 | 1.00 | 35.20 |
| ATOM | 5376 | CG | PHE | B | 473 | 40.540 | 68.501 | -8.859 | 1.00 | 34.87 |
| ATOM | 5377 | CD1 | PHE | B | 473 | 40.363 | 68.226 | -7.509 | 1.00 | 34.27 |
| ATOM | 5378 | CE1 | PHE | B | 473 | 40.197 | 66.916 | -7.064 | 1.00 | 33.72 |
| ATOM | 5379 | CZ | PHE | B | 473 | 40.198 | 65.865 | -7.974 | 1.00 | 33.78 |
| ATOM | 5380 | CE2 | PHE | B | 473 | 40.363 | 66.126 | -9.324 | 1.00 | 34.17 |
| ATOM | 5381 | CD2 | PHE | B | 473 | 40.523 | 67.439 | -9.764 | 1.00 | 34.81 |
| ATOM | 5382 | C | PHE | B | 473 | 43.125 | 69.393 | -9.967 | 1.00 | 34.07 |
| ATOM | 5383 | O | PHE | B | 473 | 43.790 | 68.666 | -9.231 | 1.00 | 35.52 |
| ATOM | 5384 | N | ASP | B | 474 | 43.209 | 69.357 | -11.297 | 1.00 | 31.78 |

FIGURE 3 (Cont.)

|  | A | B | C | D | E | F | G | H | I | J |
|---|---|---|---|---|---|---|---|---|---|---|
| ATOM | 5385 | CA | ASP | B | 474 | 44.097 | 68.439 | -12.005 | 1.00 | 30.92 |
| ATOM | 5386 | CB | ASP | B | 474 | 43.791 | 68.433 | -13.501 | 1.00 | 32.01 |
| ATOM | 5387 | CG | ASP | B | 474 | 42.376 | 68.864 | -13.803 | 1.00 | 33.67 |
| ATOM | 5388 | OD1 | ASP | B | 474 | 41.548 | 67.991 | -14.132 | 1.00 | 34.24 |
| ATOM | 5389 | OD2 | ASP | B | 474 | 41.996 | 70.053 | -13.725 | 1.00 | 34.34 |
| ATOM | 5390 | C | ASP | B | 474 | 45.563 | 68.784 | -11.782 | 1.00 | 30.71 |
| ATOM | 5391 | O | ASP | B | 474 | 45.956 | 69.951 | -11.846 | 1.00 | 29.55 |
| ATOM | 5392 | N | TYR | B | 475 | 46.357 | 67.749 | -11.518 | 1.00 | 31.26 |
| ATOM | 5393 | CA | TYR | B | 475 | 47.787 | 67.879 | -11.246 | 1.00 | 30.94 |
| ATOM | 5394 | CB | TYR | B | 475 | 48.010 | 68.210 | -9.760 | 1.00 | 30.19 |
| ATOM | 5395 | CG | TYR | B | 475 | 49.106 | 67.394 | -9.111 | 1.00 | 29.86 |
| ATOM | 5396 | CD1 | TYR | B | 475 | 50.344 | 67.962 | -8.827 | 1.00 | 29.95 |
| ATOM | 5397 | CE1 | TYR | B | 475 | 51.360 | 67.210 | -8.251 | 1.00 | 29.34 |
| ATOM | 5398 | CZ | TYR | B | 475 | 51.139 | 65.875 | -7.963 | 1.00 | 28.52 |
| ATOM | 5399 | OH | TYR | B | 475 | 52.136 | 65.127 | -7.392 | 1.00 | 29.27 |
| ATOM | 5400 | CE2 | TYR | B | 475 | 49.922 | 65.285 | -8.243 | 1.00 | 28.61 |
| ATOM | 5401 | CD2 | TYR | B | 475 | 48.913 | 66.042 | -8.808 | 1.00 | 29.15 |
| ATOM | 5402 | C | TYR | B | 475 | 48.549 | 66.595 | -11.637 | 1.00 | 31.37 |
| ATOM | 5403 | O | TYR | B | 475 | 47.954 | 65.511 | -11.717 | 1.00 | 30.37 |
| ATOM | 5404 | N | SER | B | 476 | 49.859 | 66.730 | -11.874 | 1.00 | 31.87 |
| ATOM | 5405 | CA | SER | B | 476 | 50.764 | 65.582 | -12.042 | 1.00 | 31.69 |
| ATOM | 5406 | CB | SER | B | 476 | 50.757 | 65.089 | -13.491 | 1.00 | 31.24 |
| ATOM | 5407 | OG | SER | B | 476 | 49.672 | 64.202 | -13.700 | 1.00 | 31.01 |
| ATOM | 5408 | C | SER | B | 476 | 52.200 | 65.865 | -11.563 | 1.00 | 31.81 |
| ATOM | 5409 | O | SER | B | 476 | 52.584 | 67.026 | -11.379 | 1.00 | 31.72 |
| ATOM | 5410 | N | ALA | B | 477 | 52.981 | 64.799 | -11.364 | 1.00 | 31.55 |
| ATOM | 5411 | CA | ALA | B | 477 | 54.346 | 64.902 | -10.833 | 1.00 | 32.22 |
| ATOM | 5412 | CB | ALA | B | 477 | 54.406 | 64.316 | -9.422 | 1.00 | 32.63 |
| ATOM | 5413 | C | ALA | B | 477 | 55.408 | 64.248 | -11.728 | 1.00 | 32.51 |
| ATOM | 5414 | O | ALA | B | 477 | 55.221 | 64.122 | -12.939 | 1.00 | 33.28 |
| ATOM | 5415 | N | SER | B | 478 | 56.526 | 63.850 | -11.120 | 1.00 | 32.63 |
| ATOM | 5416 | CA | SER | B | 478 | 57.600 | 63.153 | -11.821 | 1.00 | 32.96 |
| ATOM | 5417 | CB | SER | B | 478 | 58.605 | 64.154 | -12.393 | 1.00 | 32.47 |
| ATOM | 5418 | OG | SER | B | 478 | 59.359 | 63.564 | -13.437 | 1.00 | 32.85 |
| ATOM | 5419 | C | SER | B | 478 | 58.305 | 62.158 | -10.898 | 1.00 | 33.82 |
| ATOM | 5420 | O | SER | B | 478 | 59.219 | 61.441 | -11.313 | 1.00 | 34.50 |
| TER Peptide B | | | | | | | | | | |
| ATOM | 5421 | N | GLY | B | 3 | 36.231 | 42.092 | 16.828 | 1.00 | 77.87 |
| ATOM | 5422 | CA | GLY | B | 3 | 35.401 | 42.391 | 15.627 | 1.00 | 77.15 |
| ATOM | 5423 | C | GLY | B | 3 | 35.352 | 43.871 | 15.292 | 1.00 | 74.66 |
| ATOM | 5424 | O | GLY | B | 3 | 36.306 | 44.419 | 14.743 | 1.00 | 76.35 |
| ATOM | 5425 | N | ARG | B | 4 | 34.229 | 44.501 | 15.626 | 1.00 | 71.60 |
| ATOM | 5426 | CA | ARG | B | 4 | 33.958 | 45.920 | 15.361 | 1.00 | 70.81 |
| ATOM | 5427 | CB | ARG | B | 4 | 34.880 | 46.840 | 16.177 | 1.00 | 68.89 |
| ATOM | 5428 | CG | ARG | B | 4 | 35.299 | 48.145 | 15.535 | 1.00 | 67.82 |
| ATOM | 5429 | CD | ARG | B | 4 | 36.807 | 48.232 | 15.413 | 1.00 | 69.37 |
| ATOM | 5430 | NE | ARG | B | 4 | 37.335 | 49.547 | 15.065 | 1.00 | 69.01 |
| ATOM | 5431 | CZ | ARG | B | 4 | 37.226 | 50.115 | 13.867 | 1.00 | 69.46 |
| ATOM | 5432 | NH1 | ARG | B | 4 | 36.573 | 49.505 | 12.884 | 1.00 | 66.67 |
| ATOM | 5433 | NH2 | ARG | B | 4 | 37.766 | 51.308 | 13.653 | 1.00 | 70.36 |
| ATOM | 5434 | C | ARG | B | 4 | 33.901 | 46.257 | 13.863 | 1.00 | 73.54 |
| ATOM | 5435 | O | ARG | B | 4 | 34.876 | 46.061 | 13.126 | 1.00 | 73.45 |

FIGURE 3 (Cont.)

| | A | B | C | D | E | F | G | H | I | J |
|---|---|---|---|---|---|---|---|---|---|---|
| ATOM | 5436 | N   | PRO | B | 5  | 32.740 | 46.754 | 13.426 | 1.00 | 74.33 |
| ATOM | 5437 | CA  | PRO | B | 5  | 32.453 | 46.937 | 11.999 | 1.00 | 73.21 |
| ATOM | 5438 | CB  | PRO | B | 5  | 30.985 | 47.379 | 12.001 | 1.00 | 74.87 |
| ATOM | 5439 | CG  | PRO | B | 5  | 30.791 | 48.025 | 13.333 | 1.00 | 74.29 |
| ATOM | 5440 | CD  | PRO | B | 5  | 31.614 | 47.200 | 14.269 | 1.00 | 73.53 |
| ATOM | 5441 | C   | PRO | B | 5  | 33.313 | 48.032 | 11.405 | 1.00 | 71.42 |
| ATOM | 5442 | O   | PRO | B | 5  | 33.799 | 48.865 | 12.168 | 1.00 | 72.08 |
| ATOM | 5443 | N   | ARG | B | 6  | 33.497 | 48.023 | 10.084 | 1.00 | 70.45 |
| ATOM | 5444 | CA  | ARG | B | 6  | 34.164 | 49.122 |  9.392 | 1.00 | 69.90 |
| ATOM | 5445 | CB  | ARG | B | 6  | 34.160 | 48.902 |  7.877 | 1.00 | 71.75 |
| ATOM | 5446 | CG  | ARG | B | 6  | 35.329 | 48.069 |  7.363 | 1.00 | 75.17 |
| ATOM | 5447 | CD  | ARG | B | 6  | 35.588 | 48.186 |  5.858 | 1.00 | 78.38 |
| ATOM | 5448 | NE  | ARG | B | 6  | 36.777 | 48.986 |  5.521 | 1.00 | 81.20 |
| ATOM | 5449 | CZ  | ARG | B | 6  | 36.758 | 50.271 |  5.128 | 1.00 | 82.44 |
| ATOM | 5450 | NH1 | ARG | B | 6  | 35.614 | 50.944 |  5.029 | 1.00 | 82.43 |
| ATOM | 5451 | NH2 | ARG | B | 6  | 37.894 | 50.893 |  4.837 | 1.00 | 81.60 |
| ATOM | 5452 | C   | ARG | B | 6  | 33.468 | 50.430 |  9.763 | 1.00 | 68.05 |
| ATOM | 5453 | O   | ARG | B | 6  | 32.248 | 50.528 |  9.718 | 1.00 | 64.87 |
| ATOM | 5454 | N   | THR | B | 7  | 34.249 | 51.418 | 10.177 | 1.00 | 69.96 |
| ATOM | 5455 | CA  | THR | B | 7  | 33.681 | 52.676 | 10.641 | 1.00 | 75.31 |
| ATOM | 5456 | CB  | THR | B | 7  | 34.371 | 53.180 | 11.937 | 1.00 | 78.86 |
| ATOM | 5457 | OG1 | THR | B | 7  | 35.759 | 53.446 | 11.691 | 1.00 | 81.18 |
| ATOM | 5458 | CG2 | THR | B | 7  | 34.386 | 52.102 | 13.023 | 1.00 | 79.41 |
| ATOM | 5459 | C   | THR | B | 7  | 33.772 | 53.725 |  9.547 | 1.00 | 75.83 |
| ATOM | 5460 | O   | THR | B | 7  | 34.782 | 53.815 |  8.849 | 1.00 | 77.51 |
| ATOM | 5461 | N   | THR | B | 8  | 32.713 | 54.516 |  9.411 | 1.00 | 75.65 |
| ATOM | 5462 | CA  | THR | B | 8  | 32.593 | 55.466 |  8.314 | 1.00 | 75.25 |
| ATOM | 5463 | CB  | THR | B | 8  | 31.315 | 55.177 |  7.534 | 1.00 | 77.85 |
| ATOM | 5464 | OG1 | THR | B | 8  | 31.376 | 53.832 |  7.041 | 1.00 | 81.44 |
| ATOM | 5465 | CG2 | THR | B | 8  | 31.237 | 56.020 |  6.256 | 1.00 | 80.03 |
| ATOM | 5466 | C   | THR | B | 8  | 32.619 | 56.905 |  8.801 | 1.00 | 73.48 |
| ATOM | 5467 | O   | THR | B | 8  | 32.054 | 57.236 |  9.839 | 1.00 | 76.37 |
| ATOM | 5468 | N   | SER | B | 9  | 33.287 | 57.757 |  8.041 | 1.00 | 69.64 |
| ATOM | 5469 | CA  | SER | B | 9  | 33.400 | 59.154 |  8.400 | 1.00 | 68.59 |
| ATOM | 5470 | CB  | SER | B | 9  | 34.571 | 59.780 |  7.659 | 1.00 | 71.13 |
| ATOM | 5471 | OG  | SER | B | 9  | 34.367 | 59.686 |  6.265 | 1.00 | 71.72 |
| ATOM | 5472 | C   | SER | B | 9  | 32.120 | 59.912 |  8.077 | 1.00 | 66.52 |
| ATOM | 5473 | O   | SER | B | 9  | 31.226 | 59.391 |  7.417 | 1.00 | 66.44 |
| ATOM | 5474 | N   | PHE | B | 10 | 32.045 | 61.146 |  8.556 | 1.00 | 63.50 |
| ATOM | 5475 | CA  | PHE | B | 10 | 30.918 | 62.013 |  8.293 | 1.00 | 64.59 |
| ATOM | 5476 | CB  | PHE | B | 10 | 29.815 | 61.795 |  9.333 | 1.00 | 62.46 |
| ATOM | 5477 | CG  | PHE | B | 10 | 30.143 | 62.359 | 10.674 | 1.00 | 61.36 |
| ATOM | 5478 | CD1 | PHE | B | 10 | 29.911 | 63.697 | 10.956 | 1.00 | 60.08 |
| ATOM | 5479 | CE1 | PHE | B | 10 | 30.240 | 64.235 | 12.202 | 1.00 | 62.01 |
| ATOM | 5480 | CZ  | PHE | B | 10 | 30.800 | 63.428 | 13.183 | 1.00 | 62.27 |
| ATOM | 5481 | CE2 | PHE | B | 10 | 31.038 | 62.083 | 12.914 | 1.00 | 62.88 |
| ATOM | 5482 | CD2 | PHE | B | 10 | 30.713 | 61.557 | 11.658 | 1.00 | 63.57 |
| ATOM | 5483 | C   | PHE | B | 10 | 31.402 | 63.448 |  8.369 | 1.00 | 69.31 |
| ATOM | 5484 | O   | PHE | B | 10 | 32.478 | 63.719 |  8.915 | 1.00 | 71.93 |
| ATOM | 5485 | N   | ALA | B | 11 | 30.596 | 64.356 |  7.819 | 1.00 | 72.01 |
| ATOM | 5486 | CA  | ALA | B | 11 | 30.762 | 65.791 |  8.000 | 1.00 | 71.64 |
| ATOM | 5487 | CB  | ALA | B | 11 | 31.710 | 66.335 |  6.964 | 1.00 | 71.14 |

FIGURE 3 (Cont.)

|      | A    | B    | C   | D | E   | F      | G      | H      | I    | J     |
|------|------|------|-----|---|-----|--------|--------|--------|------|-------|
| ATOM | 5488 | C    | ALA | B | 11  | 29.387 | 66.454 | 7.888  | 1.00 | 74.07 |
| ATOM | 5489 | O    | ALA | B | 11  | 28.549 | 66.015 | 7.085  | 1.00 | 73.91 |
| ATOM | 5490 | N    | GLU | B | 12  | 29.138 | 67.466 | 8.723  | 1.00 | 75.99 |
| ATOM | 5491 | CA   | GLU | B | 12  | 27.940 | 68.308 | 8.598  | 1.00 | 81.61 |
| ATOM | 5492 | CB   | GLU | B | 12  | 26.760 | 67.837 | 9.473  | 1.00 | 85.80 |
| ATOM | 5493 | CG   | GLU | B | 12  | 26.862 | 66.434 | 10.062 | 1.00 | 93.38 |
| ATOM | 5494 | CD   | GLU | B | 12  | 25.640 | 65.554 | 9.792  | 1.00 | 97.62 |
| ATOM | 5495 | OE1  | GLU | B | 12  | 25.403 | 65.186 | 8.608  | 1.00 | 97.70 |
| ATOM | 5496 | OE2  | GLU | B | 12  | 24.932 | 65.206 | 10.774 | 1.00 | 98.65 |
| ATOM | 5497 | C    | GLU | B | 12  | 28.273 | 69.764 | 8.909  | 1.00 | 82.88 |
| ATOM | 5498 | O    | GLU | B | 12  | 28.527 | 70.150 | 10.057 | 1.00 | 82.74 |
| ATOM | 5499 | OXT  | GLU | B | 12  | 28.297 | 70.587 | 7.996  | 1.00 | 84.03 |
| TER  |      |      |     |   |     |        |        |        |      |       |
| ATOM | 5500 | O1A  | ANP | B | 490 | 40.736 | 56.269 | 0.517  | 1.00 | 65.98 |
| ATOM | 5501 | PA   | ANP | B | 490 | 39.476 | 56.089 | 1.472  | 1.00 | 61.95 |
| ATOM | 5502 | O2A  | ANP | B | 490 | 39.897 | 56.090 | 3.006  | 1.00 | 66.24 |
| ATOM | 5503 | O3A  | ANP | B | 490 | 38.388 | 57.226 | 1.183  | 1.00 | 61.27 |
| ATOM | 5504 | PB   | ANP | B | 490 | 37.100 | 57.408 | 2.117  | 1.00 | 62.59 |
| ATOM | 5505 | O1B  | ANP | B | 490 | 35.992 | 56.356 | 1.692  | 1.00 | 63.01 |
| ATOM | 5506 | O2B  | ANP | B | 490 | 36.529 | 58.891 | 1.975  | 1.00 | 63.56 |
| ATOM | 5507 | N3B  | ANP | B | 490 | 37.450 | 57.086 | 3.790  | 1.00 | 64.14 |
| ATOM | 5508 | PG   | ANP | B | 490 | 36.137 | 57.418 | 4.889  | 1.00 | 64.32 |
| ATOM | 5509 | O3G  | ANP | B | 490 | 34.807 | 56.669 | 4.445  | 1.00 | 65.34 |
| ATOM | 5510 | O2G  | ANP | B | 490 | 36.496 | 56.934 | 6.358  | 1.00 | 65.52 |
| ATOM | 5511 | O1G  | ANP | B | 490 | 35.951 | 58.991 | 4.823  | 1.00 | 65.40 |
| ATOM | 5512 | O5*  | ANP | B | 490 | 38.751 | 54.712 | 1.172  | 1.00 | 61.60 |
| ATOM | 5513 | C5*  | ANP | B | 490 | 38.712 | 53.784 | 2.243  | 1.00 | 61.27 |
| ATOM | 5514 | C4*  | ANP | B | 490 | 39.627 | 52.630 | 1.896  | 1.00 | 58.60 |
| ATOM | 5515 | O4*  | ANP | B | 490 | 40.314 | 52.868 | 0.674  | 1.00 | 54.17 |
| ATOM | 5516 | C1*  | ANP | B | 490 | 41.505 | 52.094 | 0.707  | 1.00 | 59.26 |
| ATOM | 5517 | C2*  | ANP | B | 490 | 41.778 | 51.721 | 2.162  | 1.00 | 59.70 |
| ATOM | 5518 | O2*  | ANP | B | 490 | 41.700 | 50.315 | 2.367  | 1.00 | 59.84 |
| ATOM | 5519 | C3*  | ANP | B | 490 | 40.693 | 52.410 | 2.947  | 1.00 | 59.23 |
| ATOM | 5520 | O3*  | ANP | B | 490 | 40.222 | 51.570 | 3.987  | 1.00 | 60.77 |
| ATOM | 5521 | N9   | ANP | B | 490 | 42.621 | 52.930 | 0.219  | 1.00 | 60.78 |
| ATOM | 5522 | C8   | ANP | B | 490 | 42.693 | 54.283 | 0.151  | 1.00 | 60.89 |
| ATOM | 5523 | N7   | ANP | B | 490 | 43.885 | 54.735 | -0.350 | 1.00 | 59.27 |
| ATOM | 5524 | C5   | ANP | B | 490 | 44.614 | 53.641 | -0.610 | 1.00 | 59.75 |
| ATOM | 5525 | C6   | ANP | B | 490 | 45.948 | 53.278 | -1.145 | 1.00 | 61.98 |
| ATOM | 5526 | N6   | ANP | B | 490 | 46.816 | 54.237 | -1.535 | 1.00 | 63.69 |
| ATOM | 5527 | C4   | ANP | B | 490 | 43.781 | 52.513 | -0.231 | 1.00 | 60.40 |
| ATOM | 5528 | N3   | ANP | B | 490 | 44.220 | 51.151 | -0.368 | 1.00 | 62.24 |
| ATOM | 5529 | C2   | ANP | B | 490 | 45.459 | 50.958 | -0.871 | 1.00 | 66.35 |
| ATOM | 5530 | N1   | ANP | B | 490 | 46.289 | 51.968 | -1.239 | 1.00 | 64.75 |
| ATOM | 5531 | MN   | MN  | B | 491 | 38.911 | 56.563 | 5.142  | 1.00 | 59.48 |
| ATOM | 5532 | MN   | MN  | B | 492 | 37.513 | 60.211 | 4.000  | 1.00 | 70.66 |
| TER  |      |      |     |   |     |        |        |        |      |       |
| ATOM | 5533 | O    | HOH | B | 500 | 56.696 | 41.781 | 18.932 | 1.00 | 33.51 |
| ATOM | 5534 | O    | HOH | B | 501 | 35.997 | 61.332 | 33.177 | 1.00 | 37.49 |
| ATOM | 5535 | O    | HOH | B | 502 | 39.275 | 47.725 | 17.172 | 1.00 | 24.72 |
| ATOM | 5536 | O    | HOH | B | 503 | 36.156 | 54.959 | 20.848 | 1.00 | 26.79 |
| ATOM | 5537 | O    | HOH | B | 504 | 33.232 | 51.144 | 26.038 | 1.00 | 26.58 |

FIGURE 3 (Cont.)

|   | A | B | C | D | E | F | G | H | I | J |
|---|---|---|---|---|---|---|---|---|---|---|
| ATOM | 5538 | O | HOH | B | 505 | 35.734 | 56.074 | 38.054 | 1.00 | 41.80 |
| ATOM | 5539 | O | HOH | B | 506 | 50.924 | 58.731 | 34.338 | 1.00 | 7.07 |
| ATOM | 5540 | O | HOH | B | 507 | 40.791 | 64.735 | 30.804 | 1.00 | 47.25 |
| ATOM | 5541 | O | HOH | B | 508 | -0.883 | -4.548 | 23.859 | 1.00 | 31.17 |
| ATOM | 5542 | O | HOH | B | 509 | 9.604 | -5.253 | 44.274 | 1.00 | 31.40 |
| ATOM | 5543 | O | HOH | B | 510 | 8.342 | -14.502 | 50.113 | 1.00 | 48.29 |
| ATOM | 5544 | O | HOH | B | 511 | 0.427 | -11.693 | 32.465 | 1.00 | 40.80 |
| ATOM | 5545 | O | HOH | B | 512 | -5.380 | -4.103 | 45.084 | 1.00 | 41.45 |
| ATOM | 5546 | O | HOH | B | 513 | -12.592 | 16.204 | 51.921 | 1.00 | 30.04 |
| ATOM | 5547 | O | HOH | B | 514 | -12.237 | 10.744 | 55.180 | 1.00 | 28.58 |
| ATOM | 5548 | O | HOH | B | 515 | 57.986 | 48.033 | 27.056 | 1.00 | 42.67 |
| ATOM | 5549 | O | HOH | B | 516 | 56.656 | 47.677 | 30.807 | 1.00 | 33.50 |
| ATOM | 5550 | O | HOH | B | 517 | 31.789 | 70.556 | 16.103 | 1.00 | 42.31 |
| ATOM | 5551 | O | HOH | B | 518 | 29.791 | 54.625 | 12.185 | 1.00 | 50.25 |

SEQUENCE LISTING

```
<160> NUMBER OF SEQ ID NOS: 6

<210> SEQ ID NO 1
<211> LENGTH: 480
<212> TYPE: PRT
<213> ORGANISM: Homo sapiens
<220> FEATURE:
<221> NAME/KEY: MISC_FEATURE
<223> OTHER INFORMATION: Amino acid sequence for full-length human wild
      type AKT1

<400> SEQUENCE: 1

Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80
```

Thr Thr Val Ile Glu Arg Thr Phe His Val Glu Thr Pro Glu Glu Arg
                    85                  90                  95

Glu Glu Trp Thr Thr Ala Ile Gln Thr Val Ala Asp Gly Leu Lys Lys
                100                 105                 110

Gln Glu Glu Glu Met Asp Phe Arg Ser Gly Ser Pro Ser Asp Asn
            115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
                180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
                260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
                340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
    370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
                420                 425                 430

Thr Asp Thr Arg Tyr Phe Asp Glu Glu Phe Thr Ala Gln Met Ile Thr
        435                 440                 445

Ile Thr Pro Pro Asp Gln Asp Ser Met Glu Cys Val Asp Ser Glu
    450                 455                 460

Arg Arg Pro His Phe Pro Gln Phe Ser Tyr Ser Ala Ser Ser Thr Ala
465                 470                 475                 480

<210> SEQ ID NO 2
<211> LENGTH: 1032
<212> TYPE: DNA

<213> ORGANISM: Homo sapiens
<220> FEATURE:
<221> NAME/KEY: misc_feature
<223> OTHER INFORMATION: Human cDNA sequence encoding residues 138-480
      of AKT1

<400> SEQUENCE: 2

```
ctggccaagc ccaagcaccg cgtgaccatg aacgagtttg agtacctgaa gctgctgggc      60
aagggcactt tcggcaaggt gatcctggtg aaggagaagg ccacaggccg ctactacgcc     120
atgaagatcc tcaagaagga agtcatcgtg gccaaggacg aggtggccca cactcacc      180
gagaaccgcg tcctgcagaa ctccaggcac cccttcctca cagccctgaa gtactctttc     240
cagacccacg accgcctctg ctttgtcatg gagtacgcca acgggggcga gctgttcttc     300
cacctgtccc gggaacgtgt gttctccgag accgggccc gcttctatgg cgctgagatt     360
gtgtcagccc tggactacct gcactcggag aagaacgtgg tgtaccggga cctcaagctg     420
gagaacctca tgctggacaa ggacgggcac attaagatca cagacttcgg gctgtgcaag     480
gaggggatca aggacggtgc caccatgaag acctttttgcg gcacacctga gtacctggcc     540
cccgaggtgc tggaggacaa tgactacggc cgtgcagtgg actggtgggg gctgggcgtg     600
gtcatgtacg agatgatgtg cggtcgcctg cccttctaca accaggacca tgagaagctt     660
tttgagctca tcctcatgga ggagatccgc ttcccgcgca cgcttggtcc cgaggccaag     720
tccttgcttt cagggctgct caagaaggac cccaagcaga ggcttggcgg gggctccgag     780
gacgccaagg agatcatgca gcatcgcttc tttgccggta tcgtgtggca gcacgtgtac     840
gagaagaagc tcagcccacc cttcaagccc caggtcacgt cggagactga caccaggtat     900
tttgatgagg agttcacggc ccagatgatc accatcacac cacctgacca agatgacagc     960
atggagtgtg tggacagcga gcgcaggccc cacttccccc agttctccta ctcggccagc    1020
agcacggcct ga                                                         1032
```

<210> SEQ ID NO 3
<211> LENGTH: 370
<212> TYPE: PRT
<213> ORGANISM: Artificial
<220> FEATURE:
<223> OTHER INFORMATION: Amino acid sequence for residues 138-480 of
      AKT1 with a N-terminal 6x-histidine tag, spacer region and rTEV
      cleavage site

<400> SEQUENCE: 3

```
Met Ser Tyr Tyr His His His His His His Asp Tyr Asp Ile Pro Thr
1               5                  10                  15

Thr Glu Asn Leu Tyr Phe Gln Gly Ala Met Gly Ser Leu Ala Lys Pro
            20                  25                  30

Lys His Arg Val Thr Met Asn Glu Phe Glu Tyr Leu Lys Leu Leu Gly
        35                  40                  45

Lys Gly Thr Phe Gly Lys Val Ile Leu Val Lys Glu Lys Ala Thr Gly
    50                  55                  60

Arg Tyr Tyr Ala Met Lys Ile Leu Lys Lys Glu Val Ile Val Ala Lys
65                  70                  75                  80

Asp Glu Val Ala His Thr Leu Thr Glu Asn Arg Val Leu Gln Asn Ser
                85                  90                  95

Arg His Pro Phe Leu Thr Ala Leu Lys Tyr Ser Phe Gln Thr His Asp
            100                 105                 110

Arg Leu Cys Phe Val Met Glu Tyr Ala Asn Gly Gly Glu Leu Phe Phe
        115                 120                 125
```

His Leu Ser Arg Glu Arg Val Phe Ser Glu Asp Arg Ala Arg Phe Tyr
            130                 135                 140
Gly Ala Glu Ile Val Ser Ala Leu Asp Tyr Leu His Ser Arg Asp Val
145                 150                 155                 160
Val Tyr Arg Asp Leu Lys Leu Glu Asn Leu Met Leu Asp Lys Asp Gly
                165                 170                 175
His Ile Lys Ile Thr Asp Phe Gly Leu Cys Lys Glu Gly Ile Lys Asp
            180                 185                 190
Gly Ala Thr Met Lys Thr Phe Cys Gly Thr Pro Glu Tyr Leu Ala Pro
        195                 200                 205
Glu Val Leu Glu Asp Asn Asp Tyr Gly Arg Ala Val Asp Trp Trp Gly
    210                 215                 220
Leu Gly Val Val Met Tyr Glu Met Met Cys Gly Arg Leu Pro Phe Tyr
225                 230                 235                 240
Asn Gln Asp His Glu Lys Leu Phe Glu Leu Ile Leu Met Glu Glu Ile
                245                 250                 255
Arg Phe Pro Arg Thr Leu Gly Pro Glu Ala Lys Ser Leu Leu Ser Gly
            260                 265                 270
Leu Leu Lys Lys Asp Pro Lys Gln Arg Leu Gly Gly Gly Ser Glu Asp
        275                 280                 285
Ala Lys Glu Ile Met Gln His Arg Phe Phe Ala Gly Ile Val Trp Gln
    290                 295                 300
His Val Tyr Glu Lys Lys Leu Ser Pro Pro Phe Lys Pro Gln Val Thr
305                 310                 315                 320
Ser Glu Thr Asp Thr Arg Tyr Phe Asp Glu Glu Phe Thr Ala Gln Ser
                325                 330                 335
Ile Thr Ile Thr Pro Pro Asp Gln Asp Asp Ser Met Glu Cys Val Asp
            340                 345                 350
Ser Glu Arg Arg Pro His Phe Pro Gln Phe Asp Tyr Ser Ala Ser Ser
        355                 360                 365
Thr Ala
    370

<210> SEQ ID NO 4
<211> LENGTH: 1014
<212> TYPE: DNA
<213> ORGANISM: Artificial
<220> FEATURE:
<223> OTHER INFORMATION: cDNA sequence encoding SEQ ID NO:5

<400> SEQUENCE: 4
cgcgtgacca tgaacgagtt tgagtacctg aagctgctgg caagggcac tttcggcaag      60
gtgatcctgg tgaaggagaa ggccacaggc cgctactacg ccatgaagat cctcaagaag    120
gaagtcatcg tggccaagga cgaggtggcc cacacactca ccgagaaccg cgtcctgcag    180
aactccaggc acccttcct cacagccctg aagtactctt tccagaccca cgaccgcctc    240
tgctttgtca tggagtacgc caacggggc gagctgttct tccacctgtc ccgggaacgt    300
gtgttctccg aggaccgggc cgcttctat ggcgctgaga ttgtgtcagc cctggactac    360
ctgcactcgg agaagaacgt gatgtaccgg gacctcaagc tggagaacct catgctggac    420
aaggacgggc acattaagat cacagacttc gggctgtgca aggagggat caaggacggt    480
gccaccatga agacctttg cggcacacct gagtacctgg ccccgaggt gctggaggac    540
aatgactacg gccgtgcagt ggactggtgg gggctgggcg tggtcatgta cgagatgatg    600

-continued

```
tgcggtcgcc tgcccttcta caaccaggac catgagaagc ttttgagct catcctcatg    660 gaggagatcc gcttcccgcg cacgcttggt cccgaggcca gtccttgct ttcagggctg    720 ctcaagaagg accccaagca gaggcttggc gggggctccg aggacgccaa ggagatcatg    780
cagcatcgct tctttgccgg tatcgtgtgg cagcacgtgt acgagaagaa gctcagccca    840
cccttcaagc cccaggtcac gtcggagact gacaccaggt attttgatga ggagttcacg    900
gcccagatga tcaccatcac accacctgac caagatgaca gcatggagtg tgtggacagc    960
gagcgcgagg agcaggaaat gttcagagat tttgactaca ttgctgattg gtga         1014
```

<210> SEQ ID NO 5
<211> LENGTH: 365
<212> TYPE: PRT
<213> ORGANISM: Artificial
<220> FEATURE:
<223> OTHER INFORMATION: Amino acid sequence with a N-terminal
6x-histidine tag, spacer region, rTEV cleavage site, and a
C-terminal PIFTIDE

<400> SEQUENCE: 5

```
Met Ser Tyr Tyr His His His His His His Asp Tyr Asp Ile Pro Thr
1               5                   10                  15

Thr Glu Asn Leu Tyr Phe Gln Gly Ala Met Gly Ser Arg Val Thr Met
                20                  25                  30

Asn Glu Phe Glu Tyr Leu Lys Leu Leu Gly Lys Gly Thr Phe Gly Lys
            35                  40                  45

Val Ile Leu Val Lys Glu Lys Ala Thr Gly Arg Tyr Tyr Ala Met Lys
        50                  55                  60

Ile Leu Lys Lys Glu Val Ile Val Ala Lys Asp Glu Val Ala His Thr
65                  70                  75                  80

Leu Thr Glu Asn Arg Val Leu Gln Asn Ser Arg His Pro Phe Leu Thr
                85                  90                  95

Ala Leu Lys Tyr Ser Phe Gln Thr His Asp Arg Leu Cys Phe Val Met
            100                 105                 110

Glu Tyr Ala Asn Gly Gly Glu Leu Phe Phe His Leu Ser Arg Glu Arg
        115                 120                 125

Val Phe Ser Glu Asp Arg Ala Arg Phe Tyr Gly Ala Glu Ile Val Ser
    130                 135                 140

Ala Leu Asp Tyr Leu His Ser Glu Lys Asn Val Val Tyr Arg Asp Leu
145                 150                 155                 160

Lys Leu Glu Asn Leu Met Leu Asp Lys Asp Gly His Ile Lys Ile Thr
                165                 170                 175

Asp Phe Gly Leu Cys Lys Glu Gly Ile Lys Asp Gly Ala Thr Met Lys
            180                 185                 190

Thr Phe Cys Gly Thr Pro Glu Tyr Leu Ala Pro Glu Val Leu Glu Asp
        195                 200                 205

Asn Asp Tyr Gly Arg Ala Val Asp Trp Trp Gly Leu Gly Val Val Met
    210                 215                 220

Tyr Glu Met Met Cys Gly Arg Leu Pro Phe Tyr Asn Gln Asp His Glu
225                 230                 235                 240

Lys Leu Phe Glu Leu Ile Leu Met Glu Glu Ile Arg Phe Pro Arg Thr
                245                 250                 255

Leu Gly Pro Glu Ala Lys Ser Leu Leu Ser Gly Leu Leu Lys Lys Asp
            260                 265                 270

Pro Lys Gln Arg Leu Gly Gly Gly Ser Glu Asp Ala Lys Glu Ile Met
        275                 280                 285
```

```
                                    -continued

Gln His Arg Phe Phe Ala Gly Ile Val Trp Gln His Val Tyr Glu Lys
    290                 295                 300

Lys Leu Ser Pro Pro Phe Lys Pro Gln Val Thr Ser Glu Thr Asp Thr
305                 310                 315                 320

Arg Tyr Phe Asp Glu Glu Phe Thr Ala Gln Met Ile Thr Ile Thr Pro
                325                 330                 335

Pro Asp Gln Asp Asp Ser Met Glu Cys Val Asp Ser Glu Arg Glu Glu
                340                 345                 350

Gln Glu Met Phe Arg Asp Phe Asp Tyr Ile Ala Asp Trp
        355                 360                 365

<210> SEQ ID NO 6
<211> LENGTH: 10
<212> TYPE: PRT
<213> ORGANISM: Artificial
<220> FEATURE:
<223> OTHER INFORMATION: Synthetic

<400> SEQUENCE: 6

Gly Arg Pro Arg Thr Thr Ser Phe Ala Glu
1               5                   10
```

CRYSTALLIZATION OF PROTEIN KINASE Bα/AKT1

FIELD OF THE INVENTION

The present invention relates to a member of a family of Serine/Threonine protein kinases and more specifically to a particular protein kinase known as Protein Kinase Bα/AKT1 (AKT1). Provided are AKT1 in crystalline form, methods of forming crystals comprising AKT1, methods of using crystals comprising AKT1, a crystal structure of AKT1, and methods of using the crystal structure.

BACKGROUND OF THE INVENTION

A general approach to designing inhibitors that are selective for a given protein is to determine how a putative inhibitor interacts with a three dimensional structure of that protein. For this reason it is useful to obtain the protein in crystalline form and perform X-ray diffraction techniques to determine the protein's three-dimensional structure coordinates. Various methods for preparing crystalline proteins are known in the art.

Once protein crystals are produced, crystallographic data can be generated using the crystals to provide useful structural information that assists in the design of small molecules that bind to the active site of the protein and inhibit the protein's activity in vivo. If the protein is crystallized as a complex with a ligand, one can determine both the shape of the protein's binding pocket when bound to the ligand, as well as the amino acid residues that are capable of close contact with the ligand. By knowing the shape and amino acid residues comprised in the binding pocket, one may design new ligands that will interact favorably with the protein. With such structural information, available computational methods may be used to predict how strong the ligand binding interaction will be. Such methods aid in the design of inhibitors that bind strongly, as well as selectively to the protein. A need thus exists for proteins in crystalline form.

SUMMARY OF THE INVENTION

The present invention is directed to crystals comprising AKT1 and particularly crystals comprising AKT1 that have sufficient size and quality to obtain useful information about the structural properties of AKT1 and molecules or complexes that may associate with AKT1.

In one embodiment, a composition is provided that comprises a protein in crystalline form wherein at least a portion of the protein has 55%, 65%, 75%, 85%, 90%, 95%, 97%, 99% or greater identity with residues 29 to 370 of SEQ. ID No. 3.

In another embodiment, a composition is provided that comprises a protein in crystalline form wherein at least a portion of the protein has 55%, 65%, 75%, 85%, 90%, 95%, 97%, 99% or greater identity with residues 29 to 350 of SEQ. ID No. 5.

In one variation, the protein has activity characteristic of AKT1. For example, the protein may optionally be inhibited by inhibitors of wild type AKT1. The protein crystal may also diffract X-rays for a determination of structure coordinates to a resolution of 4 Å, 3.5 Å, 3.0 Å or less.

In one variation, the protein crystal has a crystal lattice in a C2 space group. The protein crystal may also have a crystal lattice having unit cell dimensions, +/−5%, of a=153.000 Å, b=79.597 Å, c=103.363 Å, α=90.00, β=123.16, γ=90.00 degrees.

In another variation, the protein crystal has a crystal lattice in a P1 space group. The protein crystal may also have a crystal lattice having unit cell dimensions, +/−5%, of a=44.045 Å, b=45.247 Å, c=101.445 Å, α=88.41, β=78.93, γ=72.99 degrees.

The present invention is also directed to crystallizing AKT1. The present invention is also directed to the conditions useful for crystallizing AKT1. It should be recognized that a wide variety of crystallization methods can be used in combination with the crystallization conditions to form crystals comprising AKT1 including, but not limited to, vapor diffusion, batch, dialysis, and other methods of contacting the protein solution for the purpose of crystallization.

In one embodiment, a method is provided for forming crystals of a protein comprising: forming a crystallization volume comprising: a protein wherein at least a portion of the protein has 55%, 65%, 75%, 85%, 90%, 95%, 97%, 99% or greater identity with residues 29 to 370 of SEQ. ID No. 3; and storing the crystallization volume under conditions suitable for crystal formation.

In another embodiment, a method is provided for forming crystals of a protein comprising: forming a crystallization volume comprising: a protein wherein at least a portion of the protein has 55%, 65%, 75%, 85%, 90%, 95%, 97%, 99% or greater identity with residues 29 to 350 of SEQ. ID No. 5; and storing the crystallization volume under conditions suitable for crystal formation.

In one variation, the crystallization volume comprises the protein, a two-fold molar excess of a GSK3β substrate peptide (SEQ ID NO:6), a nucleotide or nucleotide analog such as adenosine-5'-[(β,γ)-imido]triphosphate (AMPPNP), a two-fold molar excess of $MnCl_2$, and crystallization solutions comprising 19% polyethylene glycol 3350, 0.20M potassium chloride and 0.1 M N-[2-Hydroxyethyl]piperazine-N'-[2-ethanesulfonic acid](HEPES), pH7.5.

The method may optionally further comprise forming a protein crystal that has a crystal lattice in a C2 space group. The method also optionally further comprises forming a protein crystal that has a crystal lattice having unit cell dimensions, +/−5%, of a=153.000 Å, b=79.597 Å, c=103.363 Å, α=90.00, β=123.16, γ=90.00 degrees. The invention also relates to protein crystals formed by these methods.

In another variation, the crystallization volume comprises the protein, a two-fold molar excess of a GSK3β substrate peptide (GRPRTTSFAE) (SEQ ID NO:6), a nucleotide or nucleotide analog such as adenosine-5'-[(β,γ)-imido]triphosphate (AMPPNP), a two-fold molar excess of $MnCl_2$, and crystallization solutions comprising 13% polyethylene glycol 3350, 0.20M ammonium sulfate and 0.1M N-[2-Hydroxyethyl]piperazine-N'-[2-ethanesulfonic acid](HEPES), pH 7.5.

The method may optionally further comprise forming a protein crystal that has a crystal lattice in a P1 space group. The method also optionally further comprises forming a protein crystal that has a crystal lattice having unit cell dimensions, +/−5%, of a=44.045 Å, b=45.247 Å, c=101.445 Å, α=88.41, β=78.93, γ=72.99 degrees. The invention also relates to protein crystals formed by these methods.

The present invention is also directed to a composition comprising an isolated protein that comprises or consists of one or more of the protein sequence(s) of AKT1 taught herein for crystallizing AKT1. The present invention is also directed to a composition comprising an isolated nucleic acid molecule that comprises or consists of the nucleotides for expressing the protein sequence of AKT1 taught herein for crystallizing AKT1.

The present invention is also directed to an expression vector that may be used to express the isolated proteins taught herein for crystallizing AKT1. In one variation, the expression vector comprises a promoter that promotes expression of the isolated protein.

The present invention is also directed to a cell line transformed or transfected by an isolated nucleic acid molecule or expression vector of the present invention.

The present invention is also directed to structure coordinates for AKT1 as well as structure coordinates that are comparatively similar to these structure coordinates. It is noted that these comparatively similar structure coordinates may encompass proteins with similar sequences and/or structures, such as other protein kinases. For example, machine-readable data storage media is provided having data storage material encoded with machine-readable data that comprises structure coordinates that are comparatively similar to the structure coordinates of AKT1. The present invention is also directed to a machine readable data storage medium having data storage material encoded with machine readable data, which, when read by an appropriate machine, can display a three dimensional representation of all or a portion of a structure of AKT1 or a model that is comparatively similar to the structure of all or a portion of AKT1.

Various embodiments of machine readable data storage medium are provided that comprise data storage material encoded with machine readable data. The machine readable data comprises: structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1. The amino acids being overlayed and compared need not be identical when the RMSD calculation is performed on alpha carbons and main chain atoms but the amino acids being overlayed and compared must have identical side chains when the RMSD calculation is performed on all non-hydrogen atoms.

For example, in one embodiment where the comparison is based on the 4 Angstrom set of amino acid residues (Column 1) and is based on superimposing alpha-carbon atoms (Column 2), the structure coordinates may have a root mean square deviation equal to or less than 0.22 when compared to the structure coordinates of FIG. 3.

TABLE 1

| AA RESIDUES TO USE TO PERFORM RMSD COMPARISON | PORTION OF EACH AA RESIDUE USED TO PERFORM RMSD COMPARISON | RMSD VALUE LESS THAN OR EQUAL TO | | |
|---|---|---|---|---|
| Table 2 (4 Angstrom set) | alpha-carbon atoms[1] | 0.22 | 0.14 | 0.11 |
|  | main-chain atoms[1] | 0.25 | 0.16 | 0.12 |
|  | all non-hydrogen[2] | 0.27 | 0.18 | 0.13 |
| Table 3 (7 Angstrom set) | alpha-carbon atoms[1] | 0.25 | 0.17 | 0.13 |
|  | main-chain atoms[1] | 0.29 | 0.19 | 0.14 |
|  | all non-hydrogen[2] | 0.34 | 0.22 | 0.17 |
| Table 4 (10 Angstrom set) | alpha-carbon atoms[1] | 0.30 | 0.20 | 0.15 |
|  | main-chain atoms[1] | 0.31 | 0.21 | 0.16 |
|  | all non-hydrogen[2] | 0.40 | 0.26 | 0.20 |

TABLE 1-continued

| AA RESIDUES TO USE TO PERFORM RMSD COMPARISON | PORTION OF EACH AA RESIDUE USED TO PERFORM RMSD COMPARISON | RMSD VALUE LESS THAN OR EQUAL TO | | |
|---|---|---|---|---|
| Residues 138 to 480 of SEQ. ID No. 1 | alpha-carbon atoms[1] | 0.40 | 0.26 | 0.21 |
|  | main-chain atoms[1] | 0.40 | 0.27 | 0.20 |
|  | all non-hydrogen[2] | 0.66 | 0.44 | 0.33 |

[1] the RMSD computed between the atoms of all amino acids that are common to both the target and the reference in the aligned and superposed structure. The amino acids need not be identical.
[2] the RMSD computed only between identical amino acids, which are common to both the target and the reference in the aligned and superposed structure.

The present invention is also directed to a three-dimensional structure of all or a portion of AKT1. This three-dimensional structure may be used to identify binding sites, to provide mutants having desirable binding properties, and ultimately, to design, characterize, or identify ligands capable of interacting with AKT1. Ligands that interact with AKT1 may be any type of atom, compound, protein or chemical group that binds to or otherwise associates with the protein. Examples of types of ligands include natural substrates for AKT1, inhibitors of AKT1, and heavy atoms. The inhibitors of AKT1 may optionally be used as drugs to treat therapeutic indications by modifying the in vivo activity of AKT1.

In various embodiments, methods are provided for displaying a three dimensional representation of a structure of a protein comprising:

taking machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1;

computing a three dimensional representation of a structure based on the structure coordinates; and displaying the three dimensional representation.

The present invention is also directed to a method for solving a three-dimensional crystal structure of a target protein using the structure of AKT1.

In various embodiments, computational methods are provided comprising:

taking machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1;

computing phases based on the structural coordinates;

computing an electron density map based on the computed phases; and determining a three-dimensional crystal structure based on the computed electron density map.

In various embodiments, computational methods are provided comprising: taking an X-ray diffraction pattern of a crystal of the target protein; and computing a three-dimensional electron density map from the X-ray diffraction pattern by molecular replacement, wherein structure coordinates used as a molecular replacement model comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1.

These methods may optionally further comprise determining a three-dimensional crystal structure based upon the computed three-dimensional electron density map.

The present invention is also directed to using a crystal structure of AKT1, in particular the structure coordinates of AKT1 and the surface contour defined by them, in methods for screening, designing, or optimizing molecules or other chemical entities that interact with and preferably inhibit AKT1.

One skilled in the art will appreciate the numerous uses of the inventions described herein, particularly in the areas of drug design, screening and optimization of drug candidates, as well as in determining additional unknown crystal structures. For example, a further aspect of the present invention relates to using a three-dimensional crystal structure of all or a portion of AKT1 and/or its structure coordinates to evaluate the ability of entities to associate with AKT1. The entities may be any entity that may function as a ligand and thus may be any type of atom, compound, protein (such as antibodies) or chemical group that can bind to or otherwise associate with a protein.

In various embodiments, methods are provided for evaluating a potential of an entity to associate with a protein comprising:

creating a computer model of a protein structure using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1;

performing a fitting operation between the entity and the computer model; and analyzing results of the fitting operation to quantify an association between the entity and the model.

In other embodiments, methods are provided for identifying entities that can associate with a protein comprising:

generating a three-dimensional structure of a protein using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1;

employing the three-dimensional structure to design or select an entity that can associate with the protein; and contacting the entity with a protein wherein at least a portion of the protein has 55%, 65%, 75%, 85%, 90%, 95%, 97%, 99% or greater identity with residues 29 to 370 of SEQ. ID No. 3.

In still other embodiments, methods are provided for identifying entities that can associate with a protein comprising:

generating a three-dimensional structure of a protein using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1;

employing the three-dimensional structure to design or select an entity that can associate with the protein; and contacting the entity with a protein wherein at least a portion of the protein has 55%, 65%, 75%, 85%, 90%, 95%, 97%, 99% or greater identity with residues 29 to 350 of SEQ. ID No. 5.

In other embodiments, methods are provided for identifying entities that can associate with a protein comprising:

generating a three-dimensional structure of a protein using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1; and employing the three-dimensional structure to design or select an entity that can associate with the protein.

In other embodiments, methods are provided for identifying entities that can associate with a protein comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1);

employing the computer model to design or select an entity that can associate with the protein; and contacting the entity with a protein wherein at least a portion of the protein has 55%, 65%, 75%, 85%, 90%, 95%, 97%, 99% or greater identity with residues 29 to 370 of SEQ. ID No. 3.

In yet other embodiments, methods are provided for identifying entities that can associate with a protein comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1);

employing the computer model to design or select an entity that can associate with the protein; and contacting the entity with a protein wherein at least a portion of the protein has 55%, 65%, 75%, 85%, 90%, 95%, 97%, 99% or greater identity with residues 29 to 350 of SEQ. ID No. 5.

In other embodiments, methods are provided for identifying entities that can associate with a protein comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1); and employing the computer model to design or select an entity that can associate with the protein.

In other embodiments, methods are provided for evaluating the ability of an entity to associate with a protein, the methods comprising:

constructing a computer model defined by structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1;

selecting an entity to be evaluated by a method selected from the group consisting of (i) assembling molecular fragments into the entity, (ii) selecting an entity from a small molecule database, (iii) de novo ligand design of the entity, and (iv) modifying a known ligand for AKT1, or a portion thereof;

performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

In other embodiments, methods are provided for evaluating the ability of an entity to associate with a protein, the methods comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1);

selecting an entity to be evaluated by a method selected from the group consisting of (i) assembling molecular fragments into the entity, (ii) selecting an entity from a small molecule database, (iii) de novo ligand design of the entity, and (iv) modifying a known ligand for AKT1, or a portion thereof;

performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

In regard to each of these embodiments, the protein may optionally have activity characteristic of AKT1. For example, the protein may optionally be inhibited by inhibitors of wild type AKT1.

In another embodiment, a method is provided for identifying an entity that associates with a protein comprising: taking structure coordinates from diffraction data obtained from a crystal of a protein wherein at least a portion of the protein has 55%, 65%, 75%, 85%, 90%, 95%, 97%, 99% or greater identity with residues 29 to 370 of SEQ. ID No. 3; and performing rational drug design using a three dimensional structure that is based on the obtained structure coordinates.

In another embodiment, a method is provided for identifying an entity that associates with a protein comprising: taking structure coordinates from diffraction data obtained from a crystal of a protein wherein at least a portion of the protein has 55%, 65%, 75%, 85%, 90%, 95%, 97%, 99% or greater identity with residues 29 to 350 of SEQ. ID No. 5; and performing rational drug design using a three dimensional structure that is based on the obtained structure coordinates.

The protein crystals may optionally have a crystal lattice with a C2 space group and unit cell dimensions, +/−5%, of a=153.000 Å, b=79.597 Å, c=103.363 Å, α=90.00, β=123.16, γ=90.00 degrees.

The protein crystals may optionally have a crystal lattice with a P1 space group and unit cell dimensions, +/−5%, of a=44.045 Å, b=45.247 Å, c=101.445 Å, α=88.41, β=78.93, γ=72.99 degrees.

The method may optionally further comprise selecting one or more entities based on rational drug design and contacting the selected entities with the protein. The method may also optionally further comprise measuring an activity of the protein when contacted with the one or more entities. The method also may optionally further comprise comparing activity of the protein in the presence of and in the absence of the one or more entities; and selecting entities where activity of the protein changes depending upon whether a particular entity is present. The method also may optionally further comprise contacting cells expressing the protein with the one or more entities and detecting a change in a phenotype of the cells when a particular entity is present.

BRIEF DESCRIPTION OF THE FIGURES

FIG. 1 illustrates SEQ. ID Nos. 1, 2, 3, 4 and 5 referred to in this application.

FIG. 3 lists sets of atomic structure coordinates for AKT1 as derived by X-ray crystallography from a crystal that comprises the protein of SEQ ID NO:3 (the numbering of the amino acid residues is according to SEQ ID NO:1). The following abbreviations are used in FIG. 3: "X, Y, Z" crystallographically define the atomic position of the element measured: "B" is a thermal factor that measures movement of the atom around its atomic center; and "Occ" is an occupancy factor that refers to the fraction of the molecules in which each atom occupies the position specified by the coordinates (a value of "1" indicates that each atom has the same conformation, i.e., the same position, in all molecules of the crystal).

DETAILED DESCRIPTION OF THE INVENTION

Figure 2A:
FIG. 2A illustrates crystals of AKT1 corresponding to SEQ. ID No. 3, having a crystal lattice in a C2 space group and unit cell dimensions, +/−5%, of a=153.000 Å, b=79.597 Å, c=103.363 Å, α=90.00, β=123.16, γ=90.00 degrees.

The present invention relates to a member of a family of serine/threonine protein kinases and more specifically to a particular protein kinase known as Protein Kinase Bα/AKT1 (AKT1). Provided is AKT1 in crystalline form, methods of forming crystals comprising AKT1, methods of using crystals comprising AKT1, a crystal structure of AKT1, and methods of using the crystal structure.

In describing protein structure and function herein, reference is made to amino acids comprising the protein. The amino acids may also be referred to by their conventional abbreviations; A=Ala=Alanine; T=Thr=Threonine; V=Val=Valine; C=Cys=Cysteine; L=Leu=Leucine; Y=Tyr=Tyrosine; I=Ile=Isoleucine; N=Asn=Asparagine; P=Pro=Proline; Q=Gln=Glutamine; F=Phe=Phenylalanine; D=Asp=Aspartic Acid; W=Trp=Tryptophan; E=Glu=Glutamic Acid; M=Met=Methionine; K=Lys=Lysine; G=Gly=Glycine; R=Arg=Arginine; S=Ser=Serine; and H=His=Histidine.

1. AKT1

The AKT or protein Kinase B (PKB) family of serine/threonine protein kinases is comprised of 3 highly homologous members, AKT1/PKBα, AKT2/PKBβ and AKT3/PKBγ. The family of AKT proteins are involved in signal transduction pathways that regulate cellular processes including apoptosis, proliferation, differentiation and metabolism. Expression of AKT family members have been found to be altered in many human malignant carcinomas including gastric, breast, prostate, ovarian and pancreatic. AKT1 is the cellular homolog for the viral oncogene (v-AKT) that causes leukemia in mice, whereas AKT1 is overexpressed in 20% of gastric adenocarcinomas (Staal, S. P. (1987) Proc. Natl. Acad. Sci. U. S. A. 84, 5034-5037). The AKT proteins are activated via the phosphatidylinositol 3-kinase (PI-3K) second messenger system. PI-3K generates polyphosphatidylinositides with a 3'-phosphate. The AKT proteins interact with 3'-phosphorylated phosphoinositides through their pleckstrin homology domains, which targets them to the cellular membrane where they become phosphorylated on two specific residues. For AKT1, these residues are Thr 308, within the P-loop of the protein kinase domain, and Ser 473, within the C-terminal hydrophobic motif. These phosphorylation events relieve the intracellular inhibition of AKT1 resulting in active kinase. Mutation of either of these residues to alanine inactivates AKT1, whereas substitution of these residues with aspartic acid results in partially active kinase independent of the PI-3K second messenger (Alessi, D. R., Andjelkovic, M., Caudwell, B., Cron, P., Morrice, N., Cohen, P. and Hemmings, B. A. (1996) EMBO J. 15, 6541-6551)

In one embodiment, AKT1 comprises a form of AKT1 comprising residues 138 to 480 containing the kinase domains and the C-terminal hydrophobic motif, set forth herein as SEQ. ID No. 3 that is derived from the wild-type full-length AKT1 protein (GenBank Accession Number NM_005163; Staal, S. P. (1987), "Molecular cloning of the akt oncogene and its human homologues Akt1 and Akt2: amplification of AKT1 in a primary human gastric adenocarcinoma Proc. Natl. Acad. Sci. U.S.A. 84, 5034-5037).

In another embodiment, AKT1 comprises residues 29 to 350 of SEQ. ID No. 5 which comprises the kinase domains of wild-type AKT1, with an engineered C-terminus in which the natural hydrophobic motif has been replaced with an engineered sequence (PIFtide).

It should be recognized that the invention may be readily extended to various variants of wild-type AKT1 and variants of fragments thereof. In another embodiment, AKT1 comprises a sequence wherein at least a portion of the sequence has 55%, 65%, 75%, 85%, 90%, 95%, 97%, 99% or greater identity with SEQ. ID No. 1.

It is also noted that the above sequences of AKT1 are also intended to encompass isoforms, mutants and fusion proteins of these sequences. Example of fusion proteins are provided by SEQ. ID No. 3 and SEQ. ID No. 5, which include a 6 residue N-terminal tag (6 residues are histidine) and a rTev cleavage site that may be used to facilitate purification of the protein.

With the crystal structure provided herein, it is now known where amino acid residues are positioned in the structure. As a result, the impact of different substitutions can be more easily predicted and understood.

For example, based on the crystal structure, applicants have determined that the AKT1 amino acids shown in Table 2 encompass a 4-Angstrom radius around the AKT1 active site and thus are likely to interact with any active site inhibitor of AKT1. Applicants have also determined that the amino acids of Table 3 encompass a 7-Angstrom radius around the AKT1 active site. Further it has been determined that the amino acids of Table 4 encompass a 10-Angstrom radius around the AKT1 active site. It is noted that there is one AKT1 molecule in the asymmetric unit, referred to as chain A. Structural coordinates appear in FIG. 3. It is noted that the sequence and structure of the residues in the active site may also be conserved and hence pertinent to other AKT1 variants and homologs.

One or more of the sets of amino acids set forth in the tables is preferably conserved in a variant of AKT1. Hence, AKT1 may optionally comprise a sequence wherein at least a portion of the sequence has 55%, 65%, 75%, 85%, 90%, 95%, 97%, 99% or greater identity with any one of the above sequences (e.g., all of SEQ. ID No. 1; residues 29 to 370 of SEQ. ID No. 3; or residues 29 to 350 of SEQ. ID No. 5) where at least the residues shown in Tables 2, 3, and/or 4 are conserved with the exception of 0, 1, 2, 3, or 4 residues. It should be recognized that one might optionally vary some of the binding site residues in order to determine the effect such changes have on structure or activity.

TABLE 2

Amino Acids encompassed by a 4-Angstrom radius around the AKT1 active site (SEQ ID NO:1).

| | | |
|---|---|---|
| LEU 156 | GLY 157 | GLY 159 |
| GLY 162 | VAL 164 | ALA 177 |
| LYS 179 | THR 211 | MET 227 |
| GLU 228 | TYR 229 | ALA 230 |
| GLU 234 | ASP 274 | LYS 276 |
| GLU 278 | ASN 279 | MET 281 |
| THR 291 | ASP 292 | PHE 438 |

TABLE 3

Amino Acids encompassed by a 7-Angstrom radius around the AKT1 active site (SEQ ID NO:1).

| | | |
|---|---|---|
| LEU 156 | GLY 157 | GLY 159 |
| GLY 162 | VAL 164 | ALA 177 |
| LYS 179 | THR 211 | MET 227 |
| GLU 228 | TYR 229 | ALA 230 |
| GLU 234 | ASP 274 | LYS 276 |
| GLU 278 | ASN 279 | MET 281 |
| THR 291 | ASP 292 | PHE 438 |
| THR 160 | PHE 161 | LYS 163 |
| ILE 165 | TYR 176 | MET 178 |
| LEU 181 | GLU 198 | ALA 212 |
| ASN 231 | GLY 232 | GLY 233 |
| TYR 272 | LEU 282 | LYS 289 |
| PHE 293 | GLY 294 | LEU 295 |

TABLE 3-continued

Amino Acids encompassed by a 7-Angstrom radius around the AKT1 active site (SEQ ID NO:1).

| | | |
|---|---|---|
| THR 312 | TYR 437 | PHE 442 |
| LYS 158 | | |

TABLE 4

Amino Acids encompassed by a 10-Angstrom radius around the AKT1 active site (SEQ ID NO:1).

| | | |
|---|---|---|
| LEU 156 | GLY 157 | GLY 159 |
| GLY 162 | VAL 164 | ALA 177 |
| LYS 179 | THR 211 | MET 227 |
| GLU 228 | TYR 229 | ALA 230 |
| GLU 234 | ASP 274 | LYS 276 |
| GLU 278 | ASN 279 | MET 281 |
| THR 291 | ASP 292 | PHE 438 |
| THR 160 | PHE 161 | LYS 163 |
| ILE 165 | TYR 176 | MET 178 |
| LEU 181 | GLU 198 | ALA 212 |
| ASN 231 | GLY 232 | GLY 233 |
| TYR 272 | LEU 282 | LYS 289 |
| PHE 293 | GLY 294 | LEU 295 |
| THR 312 | TYR 437 | PHE 442 |
| LYS 154 | LEU 155 | LEU 166 |
| VAL 167 | TYR 175 | ILE 180 |
| VAL 185 | ILE 186 | GLU 191 |
| HIS 194 | THR 195 | LEU 202 |
| LEU 210 | LEU 213 | LYS 214 |
| PHE 225 | VAL 226 | LEU 235 |
| PHE 236 | PHE 237 | HIS 238 |
| ARG 273 | LEU 275 | LEU 277 |
| LEU 280 | ASP 283 | LYS 284 |
| ILE 290 | CYS 296 | CYS 310 |
| GLY 311 | PRO 313 | TYR 315 |
| GLU 432 | ASP 434 | THR 435 |
| ASP 439 | THR 443 | TRP 480 |
| LYS 158 | | |

With the benefit of the crystal structure and guidance provided by Tables 2, 3 and 4, a wide variety of AKT1 variants (e.g., insertions, deletions, substitutions, etc.) that fall within the above specified identity ranges may be designed and manufactured utilizing recombinant DNA techniques well known to those skilled in the art, particularly in view of the knowledge of the crystal structure provided herein. These modifications can be used in a number of combinations to produce the variants. The present invention is useful for crystallizing and then solving the structure of the range of variants of AKT1.

Variants of AKT1 may be insertional variants in which one or more amino acid residues are introduced into a predetermined site in the AKT1 sequence. For instance, insertional variants can be fusions of heterologous proteins or polypeptides to the amino or carboxyl terminus of the subunits.

Variants of AKT1 also may be substitutional variants in which at least one residue has been removed and a different residue inserted in its place. Non-natural amino acids (i.e., amino acids not normally found in native proteins), as well as isosteric analogs (amino acid or otherwise), may optionally be employed in substitutional variants. Examples of suitable substitutions are well known in the art, such as Glu→Asp, Asp→Glu, Ser→Cys, and Cys→Ser for example.

Another class of variants is deletional variants, which are characterized by the removal of one or more amino acid residues from the AKT1 sequence.

Other variants may be produced by chemically modifying amino acids of the native protein (e.g., diethylpyrocarbonate treatment that modifies histidine residues). Preferred are chemical modifications that are specific for certain amino acid side chains. Specificity may also be achieved by blocking other side chains with antibodies directed to the side chains to be protected. Chemical modification includes such reactions as oxidation, reduction, amidation, deamidation, or substitution with bulky groups such as polysaccharides or polyethylene glycol.

Exemplary modifications include the modification of lysinyl and amino terminal residues by reaction with succinic or other carboxylic acid anhydrides. Modification with these agents has the effect of reversing the charge of the lysinyl residues. Other suitable reagents for modifying amino-containing residues include imidoesters such as methyl picolinimidate; pyridoxal phosphate; pyridoxal chloroborohydride; trinitrobenzenesulfonic acid; O-methylisourea; 2,4-pentanedione; transaminase catalyzed reaction with glyoxylate; and N-hydroxysuccinamide esters of polyethylene glycol or other bulky substitutions.

Arginyl residues may be modified by reaction with a number of reagents, including phenylglyoxal; 2,3-butanedione; 1,2-cyclohexanedione; and ninhydrin. Modification of arginine residues requires that the reaction be performed in alkaline conditions because of the high $pK_a$ of the guanidine functional group. Furthermore, these reagents may react with the groups of lysine as well as the arginine epsilon-amino group.

Tyrosyl residues may also be modified to introduce spectral labels into tyrosyl residues by reaction with aromatic diazonium compounds or tetranitromethane, forming 0-acetyl tyrosyl species and 3-nitro derivatives, respectively. Tyrosyl residues may also be iodinated using $^{125}I$ or $^{131}I$ to prepare labeled proteins for use in radioimmunoassays.

Carboxyl side groups (aspartyl or glutamyl) may be selectively modified by reaction with carbodiimides or they may be converted to asparaginyl and glutaminyl residues by reaction with ammonium ions. Conversely, asparaginyl and glutaminyl residues may be deamidated to the corresponding aspartyl or glutamyl residues, respectively, under mildly acidic conditions. Either form of these residues falls within the scope of this invention.

Other modifications that may be formed include the hydroxylation of proline and lysine, phosphorylation of hydroxyl groups of seryl or threonyl groups of lysine, arginine and histidine side chains (T. E. Creighton, *Proteins: Structure and Molecular Properties*, W.H. Freeman & Co., San Francisco, pp. 79-86, 1983), acetylation of the N-terminal amine and amidation of any C-terminal carboxyl group.

As can be seen, modifications of the nucleic sequence encoding AKT1 may be accomplished by a variety of well-known techniques, such as site-directed mutagenesis (see, Gillman and Smith, *Gene* 8:81-97 (1979) and Roberts, S. et al., *Nature* 328:731-734 (1987)). When modifications are made, these modifications may optionally be evaluated for their affect on a variety of different properties including, for example, solubility, crystallizability and a modification to the protein's structure and activity.

In one variation, the variant and/or fragment of wild-type AKT1 is functional in the sense that the resulting protein is capable of associating with at least one same chemical entity that is also capable of selectively associating with a protein comprising the wild-type AKT1 (e.g., residues 138 to 480 of SEQ. ID No. 1, residues 29 to 370 of SEQ. ID No. 3, or residues 29 to 350 of SEQ. ID No. 5) since this common associative ability evidences that at least a portion of the native structure has been conserved.

It is noted that the activity of the native protein need not necessarily be conserved. Rather, amino acid substitutions, additions or deletions that interfere with native activity but which do not significantly alter the three-dimensional structure of the domain are specifically contemplated by the invention. Crystals comprising such variants of AKT1, and the atomic structure coordinates obtained therefrom, can be used to identify compounds that bind to the native domain. These compounds may affect the activity of the native domain.

Amino acid substitutions, deletions and additions that do not significantly interfere with the three-dimensional structure of AKT1 will depend, in part, on the region where the substitution, addition or deletion occurs in the crystal structure. These modifications to the protein can now be made far more intelligently with the crystal structure information provided herein. In highly variable regions of the molecule, non-conservative substitutions as well as conservative substitutions may be tolerated without significantly disrupting the three-dimensional structure of the molecule. In highly conserved regions, or regions containing significant secondary structure, conservative amino acid substitutions are preferred.

Conservative amino acid substitutions are well known in the art, and include substitutions made on the basis of similarity in polarity, charge, solubility, hydrophobicity, hydrophilicity and/or the amphipathic nature of the amino acid residues involved. For example, negatively charged amino acids include aspartic acid and glutamic acid; positively charged amino acids include lysine and arginine; and amino acids with uncharged polar head groups having similar hydrophilicity values include the following: leucine; isoleucine; valine; glycine; alanine; asparagine; glutamine; serine; threonine; phenylalanine; and tyrosine. Other conservative amino acid substitutions are well known in the art.

It should be understood that the protein may be produced in whole or in part by chemical synthesis. As a result, the selection of amino acids available for substitution or addition is not limited to the genetically encoded amino acids. Indeed, mutants may optionally contain non-genetically encoded amino acids. Conservative amino acid substitutions for many of the commonly known non-genetically encoded amino acids are well known in the art. Conservative substitutions for other amino acids can be determined based on their physical properties as compared to the properties of the genetically encoded amino acids.

In some instances, it may be particularly advantageous or convenient to substitute, delete and/or add amino acid residues in order to provide convenient cloning sites in cDNA encoding the polypeptide, to aid in purification of the polypeptide, etc. Such substitutions, deletions and/or additions which do not substantially alter the three dimensional structure of AKT1 will be apparent to those having skills in the art, particularly in view of the three dimensional structure of AKT1 provided herein.

2. Cloning, Expression and Purification of AKT1

The gene encoding AKT1 can be isolated from RNA, cDNA or cDNA libraries. In this case, the portion of the gene encoding amino acid residues 138 to 480 of SEQ. ID No. 1, corresponding to the kinase domains of AKT1, was isolated and is shown as SEQ. ID No. 2. In addition, the portion of the gene encoding amino acid residues 29 to 350 of SEQ. ID No. 5, corresponding to the kinase domains of an engineered AKT1, was also isolated and is shown as SEQ. ID No. 4.

Construction of expression vectors and recombinant proteins from the DNA sequence encoding AKT1 may be performed by various methods well known in the art. For example, these techniques may be performed according to Sambrook et al., Molecular Cloning-A Laboratory Manual, Cold Spring Harbor, N.Y. (1989), and Kriegler, M., Gene Transfer and Expression, A Laboratory Manual, Stockton Press, New York (1990).

A variety of expression systems and hosts may be used for the expression of AKT1. Example 1 provides one such expression system.

Once expressed, purification steps are employed to produce AKT1 in a relatively homogeneous state. In general, a higher purity solution of a protein increases the likelihood that the protein will crystallize. Typical purification methods include the use of centrifugation, partial fractionation, using salt or organic compounds, dialysis, conventional column chromatography (such as ion exchange, molecular sizing chromatography, etc.), high performance liquid chromatography (HPLC), and gel electrophoresis methods (see, e.g., Deutcher, "Guide to Protein Purification" in Methods in Enzymology (1990), Academic Press, Berkeley, Calif.).

AKT1 may optionally be affinity labeled during cloning, preferably with a N-terminal six-histidine tag and rTev cleavage site, in order to facilitate purification. With the use of an affinity label, it is possible to perform a one-step purification process on a purification column that has a unique affinity for the label. The affinity label may be optionally removed after purification. These and other purification methods are known and will be apparent to one of skill in the art.

3. Crystallization & Crystals Comprising AKT1

One aspect of the present invention relates to methods for forming crystals comprising AKT1 as well as crystals comprising AKT1.

In one embodiment, a method for forming crystals comprising AKT1 is provided comprising forming a crystallization volume comprising AKT1, one or more precipitants, optionally a buffer, optionally a monovalent and/or divalent salt and optionally an organic solvent; and storing the crystallization volume under conditions suitable for crystal formation.

In yet another embodiment, a method for forming crystals comprising AKT1 is provided comprising forming a crystallization volume comprising AKT1 in solution comprising the components shown in Table 5; and storing the crystallization volume under conditions suitable for crystal formation.

TABLE 5

Precipitant 5-50% w/v of precipitant wherein the precipitant comprises one or more members of the group consisting of PEG MME having a molecular weight range between 1000-10000, PEG having a molecular weight range between 100-10000, and 0.02-2.0 M Sodium, potassium or ammonium phosphate or sulfate.

pH pH 4-10. Buffers that may be used include, but are not limited to tris, bicine, phosphate, cacodylate, acetate, citrate, HEPES, PIPES, MES and combinations thereof.

Additives

Optionally 0.05 to 2.5 M additives wherein the additives comprise a monovalent and/or divalent salt (for example, ammonium, potassium, sodium, lithium, magnesium, calcium, and the like)

TABLE 5-continued

Protein Concentration 1 mg/ml-50 mg/ml

Temperature

1° C.-25° C.

In yet another embodiment, a method for forming crystals comprising AKT1 is provided comprising forming a crystallization volume comprising AKT1; introducing crystals comprising AKT1 as nucleation sites; and storing the crystallization volume under conditions suitable for crystal formation.

Crystallization experiments may optionally be performed in volumes commonly used in the art, for example typically 15, 10, 5, 2 microliters or less. It is noted that the crystallization volume optionally has a volume of less than 1 microliter, optionally 500, 250, 150, 100, 50 or less nanoliters.

It is also noted that crystallization may be performed by any crystallization method including, but not limited to batch, dialysis and vapor diffusion (e.g., sitting drop and hanging drop) methods. Micro, macro and/or streak seeding of crystals may also be performed to facilitate crystallization.

It should be understood that forming crystals comprising AKT1 and crystals comprising AKT1 according to the invention are not intended to be limited to the wild type, full length AKT1 shown in SEQ. ID No. 1 and fragments comprising residues 29 to 370 of SEQ. ID No. 3 or residues 29 to 350 of SEQ. ID No. 5. Rather, it should be recognized that the invention may be extended to various other fragments and variants of wild-type AKT1 as described above.

It should also be understood that forming crystals comprising AKT1 and crystals comprising AKT1 according to the invention may be such that AKT1 is optionally complexed with one or more ligands and one or more copies of the same ligand. The ligand used to form the complex may be any ligand capable of binding to AKT1. In one variation, the ligand is a natural substrate. In another variation, the ligand is an inhibitor.

In one particular embodiment, AKT1 crystals have a crystal lattice in the C2 space group. AKT1 crystals may also optionally have unit cell dimensions, +/−5%, of a=153.000 Å, b=79.597 Å, c=103.363 Å, $\alpha$=90.00, $\beta$=123.16, $\gamma$=90.00 degrees. AKT1 crystals also preferably are capable of diffracting X-rays for determination of atomic coordinates to a resolution of 4 Å, 3.5 Å, 3.0 Å or better.

In another embodiment, AKT1 crystals have a crystal lattice in the P1 space group. AKT1 crystals may also optionally have unit cell dimensions, +/−5%, of a=44.045 Å, b=45.247 Å, c=101.445 Å, $\alpha$=88.41, $\beta$=78.93, $\gamma$=72.99 degrees. AKT1 crystals also preferably are capable of diffracting X-rays for determination of atomic coordinates to a resolution of 4 Å, 3.5 Å, 3.0 Åor better.

Crystals comprising AKT1 may be formed by a variety of different methods known in the art. For example, crystallizations may be performed by batch, dialysis, and vapor diffusion (sitting drop and hanging drop) methods. A detailed description of basic protein crystallization setups may be found in McRee, D., *Practical Protein Crystallography*, 2$^{nd}$ Ed. (1999), Academic Press Inc. Further descriptions regarding performing crystallization experiments are provided in Stevens et al. (2000) *Curr. Opin. Struct. Biol.*: 10(5):558-63, and U.S. Pat. Nos. 6,296,673; 5,419,278; and 5,096,676.

In one variation, crystals comprising AKT1 are formed by mixing substantially pure AKT1 with an aqueous buffer containing a precipitant at a concentration just below a concentration necessary to precipitate the protein. One suitable precipitant for crystallizing AKT1 is polyethylene glycol (PEG), which combines some of the characteristics of the salts and other organic precipitants (see, for example, Ward et al., *J. Mol. Biol.* 98:161, 1975, and McPherson, *J. Biol. Chem.* 251:6300, 1976).

During a crystallization experiment, water is removed by diffusion or evaporation to increase the concentration of the precipitant, thus creating precipitating conditions for the protein. In one particular variation, crystals are grown by vapor diffusion in hanging drops or sitting drops. According to these methods, a protein/precipitant solution is formed and then allowed to equilibrate in a closed container with a larger aqueous reservoir having a precipitant concentration for producing crystals. The protein/precipitant solution continues to equilibrate until crystals grow.

By performing submicroliter volume sized crystallization experiments, as detailed in U.S. Pat. No. 6,296,673, effective crystallization conditions for forming crystals of a AKT1 complex were obtained. In order to accomplish this, systematic broad screen crystallization trials were performed on an AKT1 complex using the sitting drop technique. In each experiment, a 100 nL mixture of AKT1 complex and precipitant was placed on a platform positioned over a well containing 100 µL of the precipitating solution. Precipitate and crystal formation was detected in the sitting drops. Fine screening was then carried out for those crystallization conditions that appeared to produce precipitate and/or crystal in the drops.

Figure 2B:
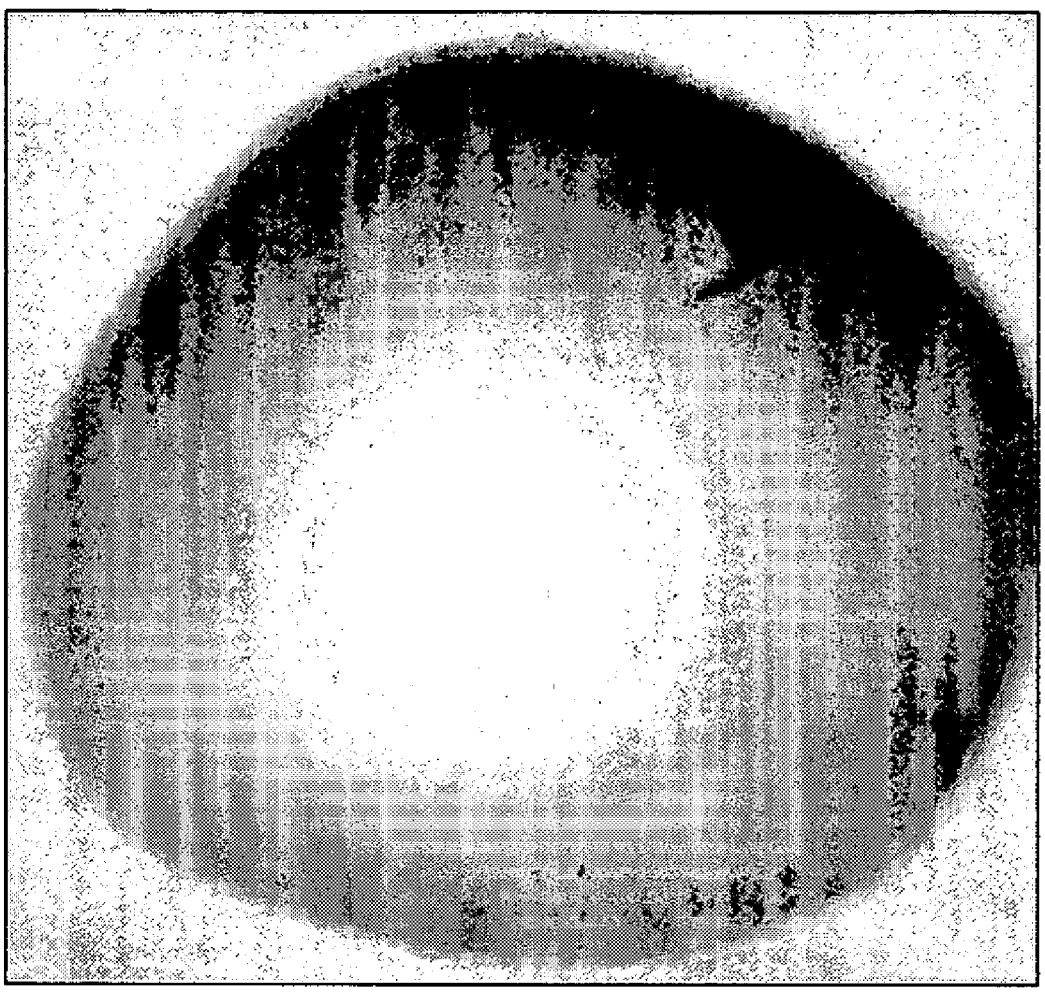
FIG. 2B illustrates a crystal of AKT1 corresponding to SEQ. ID No. 5, having a crystal lattice in a P1 space group and unit cell dimensions, +/−5%, a=44.045 Å, b=45.247 Å, c=101.445 Å, α=88.41, β=78.93, γ=72.99 degrees.

Based on the crystallization experiments that were performed, a thorough understanding of how different crystallization conditions affect AKT1 crystallization was obtained. Based on this understanding, a series of crystallization conditions were identified that may be used to form crystals comprising AKT1. These conditions are summarized in Table 5. A particular example of crystallization conditions that may be used to form diffraction quality crystals of the AKT1 complex is detailed in Example 2. FIGS. 2A and 2B illustrate crystals of the AKT1 complex formed using the crystallization conditions provided in Table 5.

One skilled in the art will recognize that the crystallization conditions provided in Table 5 and Example 2 can be varied and still yield protein crystals comprising AKT1. For example, it is noted that variations on the crystallization conditions described herein can be readily determined by taking the conditions provided in Table 5 and performing fine screens around those conditions by varying the type and concentration of the components in order to determine additional suitable conditions for crystallizing AKT1, variants of AKT1, and ligand complexes thereof.

Crystals comprising AKT1 have a wide range of uses. For example, now that crystals comprising AKT1 have been produced, it is noted that crystallizations may be performed using such crystals as a nucleation site within a concentrated protein solution. According to this variation, a concentrated protein solution is prepared and crystalline material (microcrystals) is used to 'seed' the protein solution to assist nucleation for crystal growth. If the concentrations of the protein and any precipitants are optimal for crystal growth, the seed crystal will provide a nucleation site around which a larger crystal forms. Given the ability to form crystals comprising AKT1 according to the present invention, the crystals so formed can be used by this crystallization technique to initiate crystal growth of other AKT1 comprising crystals, including AKT1 complexed with other ligands.

As will be described herein in greater detail, crystals may also be used to perform X-ray or neutron diffraction analysis in order to determine the three-dimensional structure of AKT1 and, in particular, to assist in the identification of its active site. Knowledge of the binding site region allows rational design and construction of ligands including inhibitors. Crystallization and structural determination of AKT1 mutants having altered bioactivity allows the evaluation of whether such changes are caused by general structure deformation or by side chain alterations at the substitution site.

4. X-Ray Data Collection and Structure Determination

Crystals comprising AKT1 may be obtained as described above in Section 3. As described herein, these crystals may then be used to perform X-ray data collection and for structure determination.

In one embodiment, described in Example 2, crystals of AKT1 were obtained where AKT1 has the sequence of residues shown in SEQ. ID No. 3. These particular crystals were used to determine the three dimensional structure of AKT1. However, it is noted that other crystals comprising AKT1 including different AKT1 variants, fragments, and complexes thereof may also be used. In particular, crystals of AKT1 having the sequence of residues shown in SEQ. ID No. 5 were also obtained, as described below.

Diffraction data were collected from cryocooled crystals (100K) of AKT1 at the Advanced Light Source (ALS) beam line 5.0.3 using an ADSC Quantum CCD detector. The diffraction pattern of the AKT1 crystals displayed symmetry consistent with space group C2 with unit cell dimensions a=153.000 Å, b=79.597 Å, c=103.363 Å, $\alpha$=90.00, $\beta$=123.16, $\gamma$=90.00 degrees (+/−5%). Data were collected and integrated to 3.15 Å with the HKL2000 program package (Otwinowski, Z. and Minor, W., *Meth. Enzymol.* 276: 307 (1997)).

In another embodiment, crystals of AKT1 were obtained where AKT1 has the sequence of residues shown in SEQ. ID No. 5. These particular crystals also were used to determine the three dimensional structure of AKT1. However, it is noted that other crystals comprising AKT1 including different AKT1 variants, fragments, and complexes thereof may also be used. In particular, crystals of AKT1 having the sequence of residues shown in SEQ. ID No. 3 were also obtained, as described above.

Diffraction data were collected from cryocooled crystals (100K) of AKT1 at the Advanced Light Source (ALS) beam line 5.0.3 using an ADSC Quantum CCD detector. The diffraction pattern of the AKT1 crystals displayed symmetry consistent with space group P1 with unit cell dimensions=44.045 Å, b=45.247 Å, c=101.445 Å, $\alpha$=88.41, $\beta$=78.93, $\gamma$=72.99 degrees (+/−5%). Data were collected and integrated to 2.25 Å with the HKL2000 program package (Otwinowski, Z. and Minor, W., *Meth. Enzymol.* 276:307 (1997)).

The structure solution for AKT1 in the space group C2 with unit cell dimensions a=153.000 Å, b=79.597 Å, c=103.363 Å, $\alpha$=90.00, $\beta$=123.16, $\gamma$=90.00 degrees (+/−5%) was obtained by the molecular replacement method using the program AMoRE (Navaza, J. *Acta Crystallogr. A*50:157 (1994)), with the coordinates for AKT2 kinase (Yang, J., et al., *Nature: Struct. Biol.* 9:940 (2002); PDB code 1O6K) used as a search model. Using data in the resolution range 15.0 to 3.5 Å, the correct solutions were obtained yielding a correlation coefficient of 0.600 and an R-value of 0.389.

All subsequent crystallographic calculations were performed using the CCP4 program package (Collaborative Computational Project, N. The CCP4 Suite: Programs for Protein Crystallography. *Acta Crystallogr.* D50, 760-763 (1994)). The molecular replacement solutions were subjected to rigid body refinement followed by restrained least-squares refinement using the maximum likelihood method as implemented in REFMAC (Murshudov, G. N., Vagin, A. A. and Dodson E. J. *Acta Crystallogr* D53:240 (1997)). The initial refinement resulted in an R-value of 0.250 and an $R_{free}$ value of 0.334 from which differences between the AKT1 structure and the molecular replacement model could be discerned. Multiple rounds of manual fitting of the AKT1 sequence and ordered regions not present in the initial model were performed with Xfit (McRee, D. E., *J. Struct. Biol.* 125:156 (1999)). Manual fitting was interspersed with restrained least-squares refinement in REFMAC against data from 15.0 to 3.15 Å. All stages of refinement were carried with bulk solvent corrections and anisotropic scaling, and excluded 5% of $R_{free}$ reflections for cross-validation. The data collections and data refinement statistics are given in Table 6.

TABLE 6A

| Crystal data | | |
|---|---|---|
| Space group | | C2 |
| Unit cell dimensions | | a = 153.000Å |
| | | b = 79.597Å |
| | | c = 103.363Å |
| | | α = 90.00° |
| | | β = 123.16° |
| | | γ = 90.00° |
| Data collection | | |
| X-ray source | | ALS BL 5.0.3 |
| Wavelength [Å] | | 1.00 |
| Resolution [Å] | | 3.15 |
| Observations (unique) | | 17948 |
| Redundancy | | 3.14 |
| Completeness | overall (outer shell) | 98.6 (99.0)% |
| I/σ(I) | overall (outer shell) | 8.5 (2.1) |
| $R_{symm}^1$ | overall (outer shell) | 0.102 (.506) |
| Refinement | | |
| Reflections used | | 16835 |
| R-factor | | 20.43% |
| $R_{free}$ | | 27.85% |
| r.m.s bonds | | 0.010Å |
| r.m.s angles | | 1.40° |

During structure determination, where the unit cell dimensions were a=153.000 Å, b=79.597 Å, c=103.363 Å, α=90.00, β=123.16, γ=90.00 degrees, it was realized that the asymmetric unit comprised two AKT1 molecules. Structure coordinates were determined for this complex and the resultant set of structural coordinates from the refinement are presented in FIG. 3. It is noted that the sequence of the structure coordinates presented in FIG. 3 differ in some regards from the sequence shown in SEQ ID No. 3. Structure coordinates are not reported for the residues 138, and 449-461 in molecule A and residues 138-140, and 447-467 in molecule B because the electron density obtained was insufficient to identify their position.

The structure solution for AKT1 in the space group P1 with unit cell dimensions a=44.045 Å, b=45.247 Å, c=101.445 Å, α88.41, β=78.93, γ=72.99 degrees (+/−5%) was obtained by the molecular replacement method using the program AMoRE (Navaza, J. *Acta Crystallogr. A*50: 157 (1994)), with the coordinates for AKT2 kinase (Yang, J., et al., *Nature: Struct. Biol.* 9:940 (2002); PDB code 1O6K) used as a search model. Using data in the resolution range 15.0 to 3.5 Å, the correct solutions were obtained yielding a correlation coefficient of 0.435 and an R-value of 0.409. All subsequent crystallographic calculations were performed using the CCP4 program package (Collaborative Computational Project, N. The CCP4 Suite: Programs for Protein Crystallography. *Acta Crystallogr.* D50, 760-763 (1994)). The molecular replacement solutions were subjected to rigid body refinement followed by restrained least-squares refinement using the maximum likelihood method as implemented in REFMAC (Murshudov, G. N., Vagin, A. A. and Dodson E. J. *Acta Crystallogr* D53:240 (1997)). The initial refinement resulted in an R-value of 0.236 and an $R_{free}$ value of 0.313 from which differences between the AKT1 structure and the molecular replacement model could be discerned. Multiple rounds of manual fitting of the AKT1 sequence and ordered regions not present in the initial model were performed with Xfit (McRee, D. E., *J. Struct. Biol.* 125:156 (1999)). Manual fitting was interspersed with restrained least-squares refinement in REFMAC against data from 30.0 to 2.25 Å. All stages of refinement were carried with bulk solvent corrections and anisotropic scaling, and excluded 5% of $R_{free}$ reflections for cross-validation. The data collection and data refinement statistics are given in Table 6B.

TABLE 6B

| Crystal data | | |
|---|---|---|
| Space group | | P1 |
| Unit cell dimensions | | a = 44.045Å |
| | | b = 45.2477Å |
| | | c = 101.445Å |
| | | α = 88.41° |
| | | β = 78.93° |
| | | γ = 72.99° |
| Data collection | | |
| X-ray source | | ALS BL 5.0.3 |
| Wavelength [Å] | | 1.00 |
| Resolution [Å] | | 2.25 |
| Observations (unique) | | 33469 |
| Redundancy | | 3.68 |
| Completeness | overall (outer shell) | 95.7 (93.0)% |
| I/σ(I) | overall (outer shell) | 15.5 (2.6) |
| $R_{symm}^1$ | overall (outer shell) | 0.074 (.463) |
| Refinement | | |
| Reflections used | | 31663 |
| R-factor | | 21.69% |
| $R_{free}$ | | 27.91% |
| r.m.s bonds | | 0.013Å |
| r.m.s angles | | 1.33° |

During structure determination, where the unit cell dimensions were a=44.045 Å, b=45.247 Å, c=101.445 Å, α=88.41, β=78.93, γ=72.99 degrees, it was realized that the asymmetric unit comprised two AKT1 molecules.

Those of skill in the art understand that a set of structure coordinates (such as those in FIG. 3) for a protein or a protein-complex or a portion thereof, is a relative set of points that define a shape in three dimensions. Thus, it is possible that an entirely different set of structure coordinates could define a similar or identical shape. Moreover, slight variations in the individual coordinates may have little effect on overall shape. In terms of binding pockets, these variations would not be expected to significantly alter the nature of ligands that could associate with those pockets. The term "binding pocket" as used herein refers to a region of the protein that, as a result of its shape, favorably associates with a ligand.

These variations in coordinates may be generated because of mathematical manipulations of the AKT1 structure coordinates. For example, the sets of structure coordinates shown in FIG. 3 could be manipulated by crystallographic permutations of the structure coordinates, fractionalization of the structure coordinates, application of a rotation matrix, integer additions or subtractions to sets of the structure coordinates, inversion of the structure coordinates or any combination of the above.

Alternatively, modifications in the crystal structure due to mutations, additions, substitutions, and/or deletions of amino acids or other changes in any of the components that make up the crystal could also account for variations in structure coordinates. If such variations are within an acceptable standard error as compared to the original coordinates, the resulting three-dimensional shape should be considered to be the same. Thus, for example, a ligand that binds to the active site binding pocket of AKT1 would also be expected to bind to another binding pocket whose structure coordinates defined a shape that fell within the acceptable error.

Various computational methods may be used to determine whether a particular protein or a portion thereof (referred to here as the "target protein"), typically the binding pocket, has a high degree of three-dimensional spatial similarity to another protein (referred to here as the "reference protein") against which the target protein is being compared.

The process of comparing a target protein structure to a reference protein structure may generally be divided into three steps: 1) defining the equivalent residues and/or atoms for the target and reference proteins, 2) performing a fitting operation between the proteins; and 3) analyzing the results. These steps are described in more detail below. All structure comparisons reported herein and the structure comparisons claimed are intended to be based on the particular comparison procedure described below.

Equivalent residues or atoms can be determined based upon an alignment of primary sequences of the proteins, an alignment of their structural domains or as a combination of both. Sequence alignments generally implement the dynamic programming algorithm of Needleman and Wunsch [*J. Mol. Biol.* 48: 442-453, 1970]. For the purpose of this invention the sequence alignment was performed using the publicly available software program MOE (Chemical Computing Group Inc.) package version 2002.3. When using the MOE program, alignment was performed in the sequence editor window using the ALIGN option utilizing the following program parameters: Initial pairwise Build-up: ON, Substitution Matrix: Blosum62, Round Robin: ON, Gap Start: 7, Gap Extend: 1, Iterative Refinement: ON, Build-up: TREE-BASED, Secondary Structure: NONE, Structural Alignment: ENABLED, Gap Start: 1, Gap Extend: 0.1

Once aligned, a rigid body fitting operation is performed where the structure for the target protein is translated and rotated to obtain an optimum fit relative to the structure of the reference protein. The fitting operation uses an algorithm that computes the optimum translation and rotation to be applied to the moving structure, such that the root mean square deviation of the fit over the specified pairs of equivalent atoms is an absolute minimum. For the purpose of fitting operations made herein, the publicly available software program MOE (Chemical Computing Group Inc.) v. 2002.3 was used.

The results from this process are typically reported as an RMSD value between two sets of atoms. The term "root mean square deviation" means the square root of the arithmetic mean of the squares of deviations. It is a way to express the deviation or variation from a trend or object. As used herein, an RMSD value refers to a calculated value based on variations in the atomic coordinates of a target protein from the atomic coordinates of a reference protein or portions of thereof. The structure coordinates for AKT1, provided in FIG. 3, are used as the reference protein in these calculations.

The same set of atoms was used for initial fitting of the structures and for computing root mean square deviation values. For example, if a root mean square deviation (RMSD) between Cα atoms of two proteins is needed, the proteins in question should be superposed only on the Cα atoms and not on any other set of atoms. Similarly, if an RMSD calculation for all atoms is required, the superposition of two structures should be performed on all atoms.

Based on a review of protein structures deposited in the Protein Databank (PDB), 1O6L was identified as having the smallest RMSD values relative to the structure coordinates described in Table 6B provided herein. Table 7 below provides a series of RMSD values that were calculated by the above described process using the structure coordinates in FIG. 3 as the reference protein and the structure coordinates from PDB code: 1O6L (Human Protein Kinase Bβ, AKT2) as the target protein.

TABLE 7

| AA RESIDUES USED TO PERFORM RMSD COMPARISON WITH PDB:1VR2 | PORTION OF EACH AA RESIDUE USED TO PERFORM RMSD COMPARISON WITH PDB:1O6L | RMSD [Å] |
| --- | --- | --- |
| Table 2 | alpha-carbon atoms[1] | 0.43 |
| (4 Angstrom set) | main-chain atoms[1] | 0.49 |
|  | all non-hydrogen[2] | 0.53 |
| Table 3 | alpha-carbon atoms[1] | 0.50 |
| (7 Angstrom set) | main-chain atoms[1] | 0.57 |
|  | all non-hydrogen[2] | 0.67 |
| Table 4 | alpha-carbon atoms[1] | 0.59 |
| (10 Angstrom set) | main-chain atoms[1] | 0.62 |
|  | all non-hydrogen[2] | 0.79 |
| 138 to 480 of | alpha-carbon atoms[1] | 0.79 |
| SEQ. ID No. 1 | main-chain atoms[1] | 0.80 |
|  | all non-hydrogen[2] | 1.32 |

[1] the RMSD computed between the atoms of all amino acids that are common to both the target and the reference in the aligned and superposed structure. The amino acids need not be identical.
[2] the RMSD computed only between identical amino acids, which are common to both the target and the reference in the aligned and superposed structure.

It is noted that mutants and variants of AKT1, as well as other protein kinases, are likely to have similar structures despite having different sequences. For example, the binding pockets of these related proteins are likely to have similar contours. Accordingly, it should be recognized that the structure coordinates and binding pocket models provided herein have utility for these other related proteins.

Accordingly, in one embodiment, the invention relates to data, computer readable media comprising data, and uses of the data where the data comprises all or a portion of the structure coordinates shown in FIG. 3 or structure coordinates having a root mean square deviation (RMSD) equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1.

As noted, there are many different ways to express the surface contours of the AKT1 structure other than by using the structure coordinates provided in FIG. 3. Accordingly, it is noted that the present invention is also directed to any data, computer readable media comprising data, and uses of the data where the data defines a computer model for a protein binding pocket, at least a portion of the computer model having a surface contour that has a root mean square deviation equal to or less than a given RMSD value specified in Columns 3,4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1).

5. AKT1 Structure

The present invention is also directed to a three-dimensional crystal structure of AKT1. This crystal structure may be used to identify binding sites, to provide mutants having desirable binding properties, and ultimately, to design, characterize, or identify ligands that interact with AKT1 as well as other structurally similar proteins.

The three-dimensional crystal structure of AKT1 may be generated, as is known in the art, from the structure coordinates shown in FIG. 3 and similar such coordinates.

During the course of structure solution, it became evident that the crystals of AKT1 of the present invention contained two AKT1 molecules in the asymmetric unit. For crystals in space group C2 comprising AKT1 corresponding to SEQ ID NO:3, the final refined coordinates include amino acid residues 139-448, 462-481 in molecule A. and residues 141-446. 468-478 in molecule B (FIG. 3). Structure coordinates are not reported for residues 138, 449-461, in molecule A and residues 138-140, 447-467, in molecule B because the electron density obtained was insufficient to identify their position. The final coordinate set additionally includes two 10 residue GSK3β substrate peptide (SEQ ID NO:6) moieties, 38 solvent molecules modeled as water, two AMPPNP ligands, and four manganese metal ions.

Figure 4A:
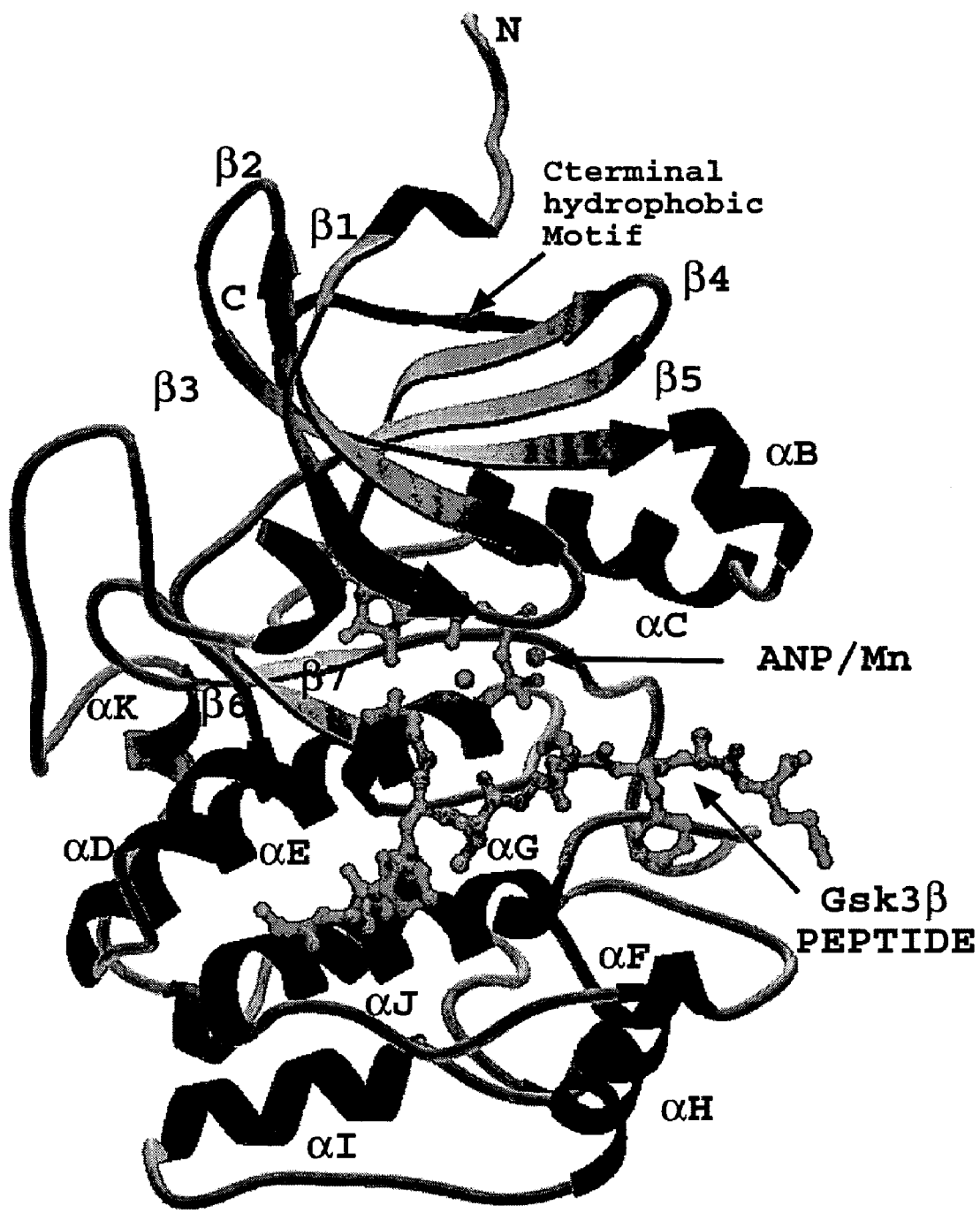
FIG. 4A illustrates a ribbon diagram overview of the structures of AKT1 from SEQ. ID No. 3, highlighting secondary structural elements of the protein.
Figure 4B:
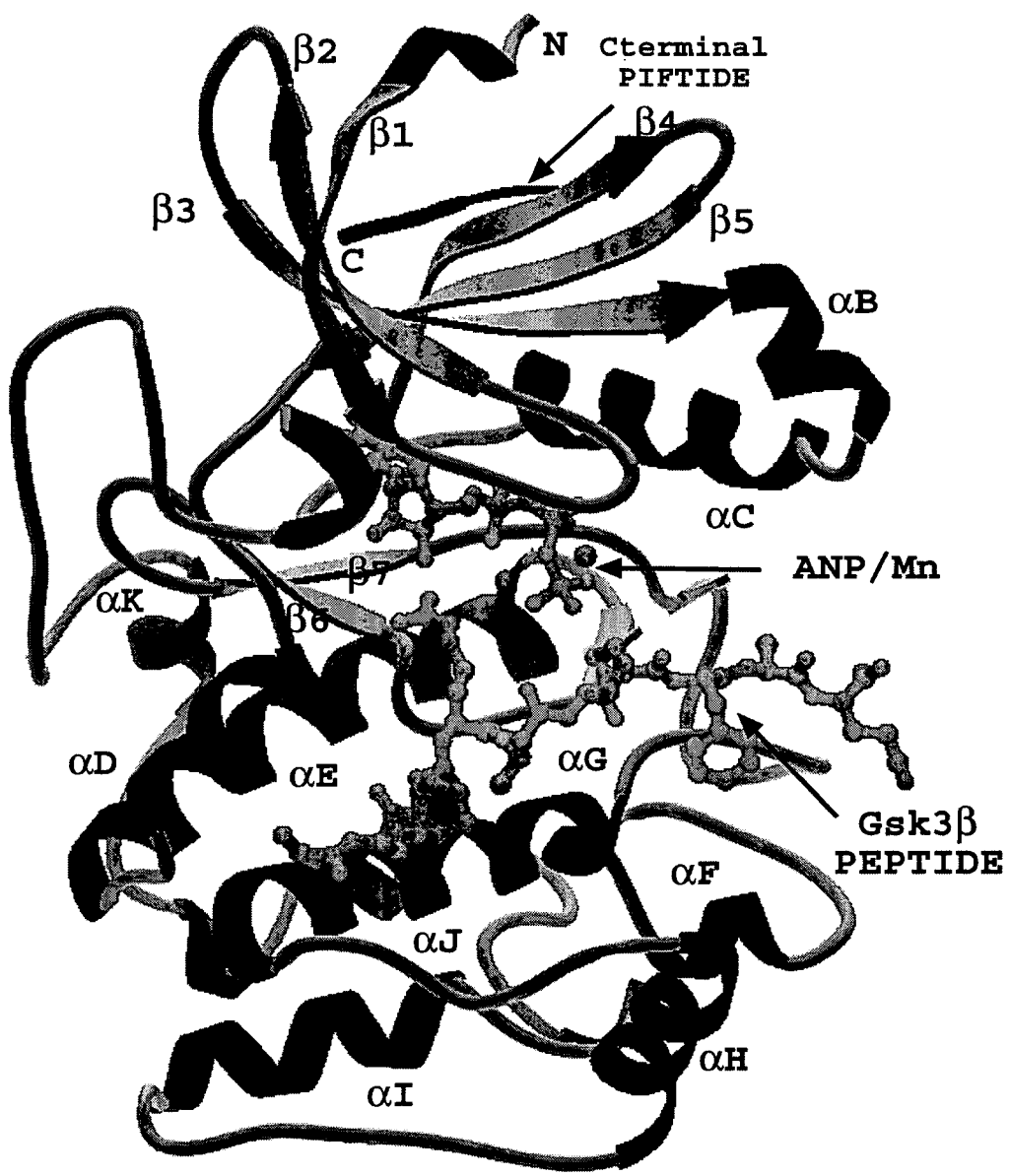
FIG. 4B illustrates a ribbon diagram overview of the structures of AKT1 from SEQ. ID No. 5, highlighting secondary structural elements of the protein.

FIGS. 4A and 4B illustrate ribbon diagram overviews of the structures of AKT1 from SEQ. ID Nos. 3 and 5, respectively, highlighting the secondary structural elements of the protein. As can be seen, the structure exhibits bilobal architecture typical of protein kinase catalytic domains. The smaller N-terminal lobe contains a five-stranded anti-parallel β-sheet (β1-β5) and a critical α-helix (αC). The C-terminal lobe contains two short β-strands (β6 and β7) and eight α-helices (αD-αK).

Kinases show considerable variability in the relative orientation of the N and C lobes, in the position and orientation of the αC helix, and in the conformation of the activation loop. This relative orientation of the N- and C-terminal lobes is important in kinase function. A catalytically active conformation is generally a closed structure in which the two lobes clamp together bringing conserved residues into catalytically optimal positions. In particular, in the active conformation, the αC helix becomes parallel with the cleft between the lobes and makes tertiary contacts with the C-lobe. In the inactive conformation, observed in several unphosphorylated kinase structures, the two lobes are spaced apart at a much higher angle and the αC helix is rotated away from the C-lobe.

For AKT1, the activation segment (also known as the activation loop) comprising residues 294-316 is fully ordered in molecules A and B in both the C2 and P1 crystal forms.

6. AKT1 Active Site and Ligand Interaction

The terms "binding site" or "binding pocket", as used herein, refer to a region of a protein that, as a result of its shape, favorably associates with a ligand or substrate. The term "AKT1-like binding pocket" refers to a portion of a molecule or molecular complex whose shape is sufficiently similar to the AKT1 binding pockets as to bind common ligands. This commonality of shape may be quantitatively defined based on a comparison to a reference point, that reference point being the structure coordinates provided herein. For example, the commonality of shape may be quantitatively defined based on a root mean square deviation (RMSD) from the structure coordinates of the backbone atoms of the amino acids that make up the binding pockets in AKT1 (as set forth in FIG. 3).

The "active site binding pockets" or "active site" of AKT1 refers to the area on the surface of AKT1 where the substrate binds.

Figure 5:
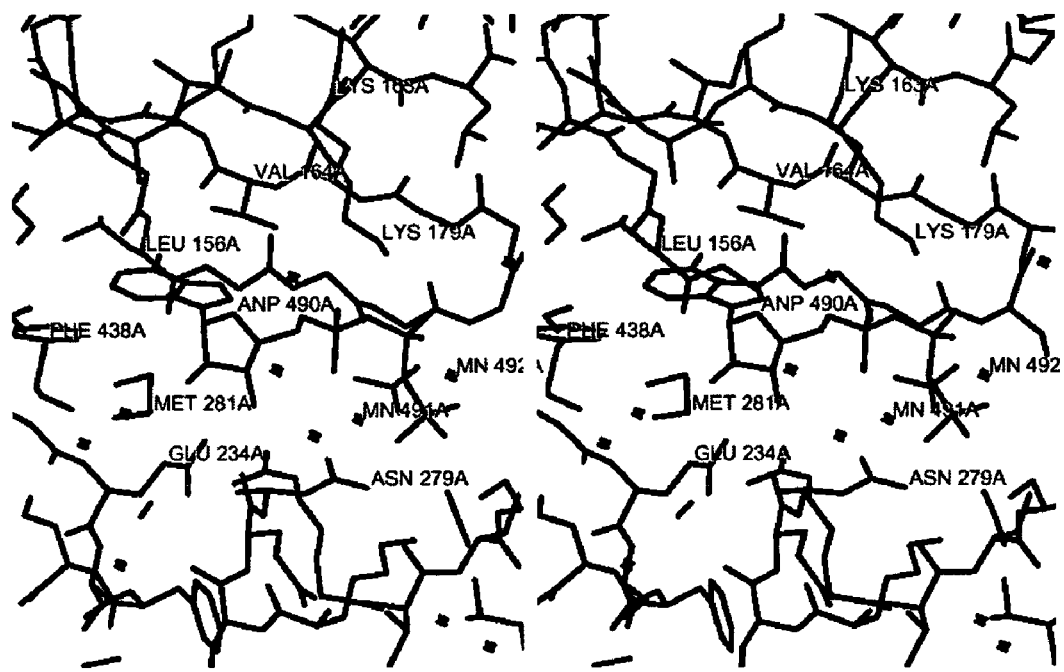
FIG. 5 illustrates the nucleotide binding site of AKT1 (SEQ ID NO:1) based on the determined crystal structure for the molecule in the asymmetric unit corresponding to the coordinates shown in FIG. 3.

FIG. 5 illustrates the ATP binding site of AKT1 based on the determined crystal structure for the molecule in the asymmetric unit corresponding to the structure coordinates shown in FIG. 3. The catalytic site for ATP is located at the interface of the two lobes (FIG. 5).

The ATP binding site of protein kinases is a primary target for the design of small molecule inhibitors. The ATP binding site appears well conserved among protein kinases and involves residues protruding from the β1-β2-β3 sheet, helix C, the loop region linking β5 and the C-lobe, the catalytic loop, and the loop linking the C-lobe with the hydrophobic motif. The structure of the ATP binding pocket in the AKT1 complex shows considerable sequence variability with other kinases, which is reflective of diversity among kinase subfamilies. The ATP binding cleft shows subtle differences in ATP site architecture that may be explored to confer specificity of inhibition.

In resolving the crystal structure of AKT1, Applicants determined that AKT1 amino acids shown in Table 2 (above) are encompassed within a 4-Angstrom radius around the AKT1 active site and therefore are likely close enough to interact with an active site inhibitor of AKT1. Applicants have also determined that the amino acids shown in Table 3 (above) are encompassed within a 7-Angstrom radius around the AKT1 active site. Further, the amino acids shown in Table 4 (above) are encompassed within a 10-Angstrom radius around the AKT1 active site. Due to their proximity to the active site, the amino acids in the 4, 7, and/or 10 Angstrom sets are preferably conserved in variants of AKT1. While it is desirable to largely conserve these residues, it should be recognized however that variants may also involve varying 1, 2, 3, 4 or more of the residues set forth in Tables 2, 3 and 4 in order, for example, to evaluate the roles these amino acids play in the binding pocket.

With the knowledge of the AKT1 crystal structure provided herein, Applicants are able to know the contour of an AKT1 binding pocket based on the relative positioning of the 4, 7, and/or 10 Angstroms sets of amino acids. Again, it is noted that it may be desirable to form variants where 1, 2, 3, 4 or more of the residues set forth in Tables 2, 3 and 4 are varied in order to evaluate the roles these amino acids play in the binding pocket. Accordingly, any set of structure coordinates for a protein from any source shall be considered within the scope of the present invention if the structure coordinates have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1.

Accordingly, in various embodiments, the invention relates to data, computer readable media comprising data, and uses of the data where the data comprises structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1.

As noted above, there are many different ways to express the surface contours of the AKT1 structure other than by using the structure coordinates provided in FIG. 3. Accordingly, it is noted that the present invention is also directed to any data, computer readable media comprising data, and uses of the data where the data defines a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1).

It will be readily apparent to those of skill in the art that the numbering of amino acids in other isoforms of AKT1 may be different than that set forth for AKT1. Corresponding amino acids in other isoforms of AKT1 are easily identified by visual inspection of the amino acid sequences or by using commercially available homology software programs, as further described below.

7. System For Displaying the Three Dimensional Structure of AKT1

The present invention is also directed to machine-readable data storage media having data storage material encoded with machine-readable data that comprises structure coordinates for AKT1. The present invention is also directed to a machine readable data storage media having data storage material encoded with machine readable data, which, when read by an appropriate machine, can display a three dimensional representation of a structure of AKT1.

All or a portion of the AKT1 coordinate data shown in FIG. 3, when used in conjunction with a computer programmed with software to translate those coordinates into the three-dimensional structure of AKT1 may be used for a variety of purposes, especially for purposes relating to drug discovery. Software for generating three-dimensional graphical representations are known and commercially available. The ready use of the coordinate data requires that it be stored in a computer-readable format. Thus, in accordance with the present invention, data capable of being displayed as the three-dimensional structure of AKT1 and/or portions thereof and/or their structurally similar variants may be stored in a machine-readable storage medium, which is capable of displaying a graphical three-dimensional representation of the structure.

For example, in various embodiments, a computer is provided for producing a three-dimensional representation of at least an AKT1-like binding pocket, the computer comprising:

machine readable data storage medium comprising a data storage material encoded with machine-readable data, the machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1;

a working memory for storing instructions for processing the machine-readable data;

a central-processing unit coupled to the working memory and to the machine-readable data storage medium, for processing the machine-readable data into the three-dimensional representation; and an output hardware coupled to the central processing unit, for receiving the three dimensional representation.

Another embodiment of this invention provides a machine-readable data storage medium, comprising a data storage material encoded with machine readable data which, when used by a machine programmed with instructions for using said data, displays a graphical three-dimensional representation comprising AKT1 or a portion or variant thereof.

In various variations, the machine readable data comprises data for representing a protein based on structure coordinates where the structure coordinates have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1.

According to another embodiment, the machine-readable data storage medium comprises a data storage material encoded with a first set of machine readable data which comprises the Fourier transform of structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1, and which, when using a machine programmed with instructions for using said data, can be combined with a second set of machine readable data comprising the X-ray diffraction pattern of another molecule or molecular complex to determine at least a portion of the structure coordinates corresponding to the second set of machine readable data. For example, the Fourier transform of the structure coordinates set forth in FIG. 3 may be used to determine at least a portion of the structure coordinates of other AKT1-like enzymes, and isoforms of AKT1.

Optionally, a computer system is provided in combination with the machine-readable data storage medium provided herein. In one embodiment, the computer system comprises a working memory for storing instructions for processing the machine-readable data; a processing unit coupled to the working memory and to the machine-readable data storage medium, for processing the machine-readable data into the three-dimensional representation; and an output hardware coupled to the processing unit, for receiving the three-dimensional representation.

Figure 6:
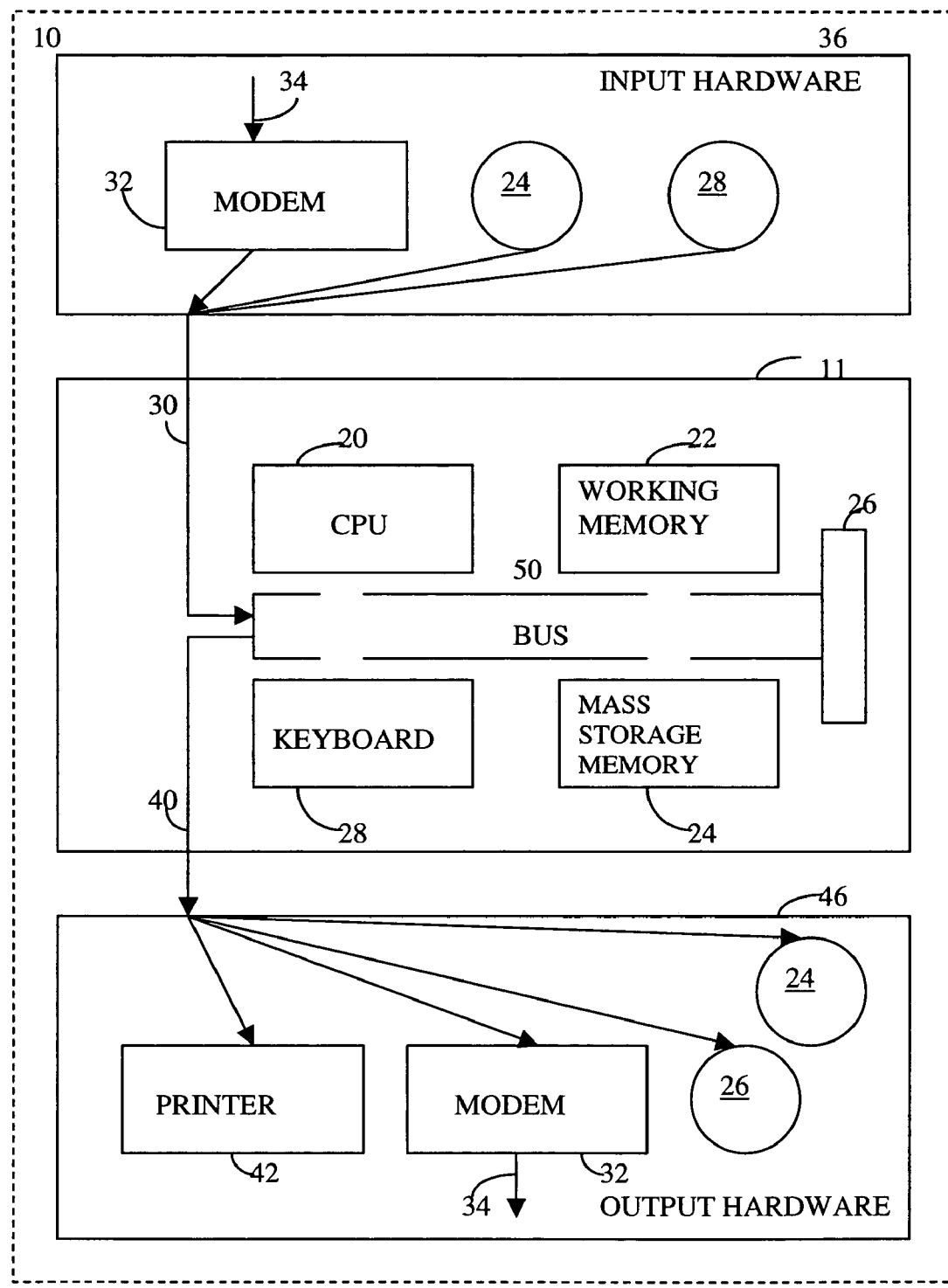
FIG. 6 illustrates a system that may be used to carry out instructions for displaying a crystal structure of AKT1 SEQ ID NO:1) encoded on a storage medium.

FIG. 6 illustrates an example of a computer system that may be used in combination with storage media according to the present invention. As illustrated, the computer system 10 includes a computer 11 comprising a central processing unit ("CPU") 20, a working memory 22 which may be, e.g., RAM (random-access memory) or "core" memory, mass storage memory 24 (such as one or more disk drives or CD-ROM drives), one or more cathode-ray tube ("CRT") display terminals 26, one or more keyboards 28, one or more input lines 30, and one or more output lines 40, all of which are interconnected by a conventional bi-directional system bus 50.

Input hardware 36, coupled to computer 11 by input lines 30, may be implemented in a variety of ways. For example, machine-readable data of this invention may be inputted via the use of a modem or modems 32 connected by a telephone line or dedicated data line 34. Alternatively or additionally, the input hardware 36 may comprise CD-ROM drives or disk drives 24. In conjunction with display terminal 26, keyboard 28 may also be used as an input device.

Conventional devices, coupled to computer 11 by output lines 40, may similarly implement output hardware 46. By way of example, output hardware 46 may include CRT display terminal 26 for displaying a graphical representation of a binding pocket of this invention using a program such as MOE as described herein. Output hardware might also include a printer 42, so that hard copy output may be produced, or a disk drive 24, to store system output for later use.

In operation, CPU 20 coordinates the use of the various input and output devices 36, 46; coordinates data accesses from mass storage 24 and accesses to and from working memory 22; and determines the sequence of data processing steps. A number of programs may be used to process the machine-readable data of this invention. Such programs are discussed in reference to using the three dimensional structure of AKT1 described herein.

The storage medium encoded with machine-readable data according to the present invention can be any conventional data storage device known in the art. For example, the storage medium can be a conventional floppy diskette or hard disk. The storage medium can also be an optically readable data storage medium, such as a CD-ROM or a DVD-ROM, or a rewritable medium such as a magneto-optical disk that is optically readable and magneto-optically writable.

8. Uses of the Three Dimensional Structure of AKT1

The three-dimensional crystal structure of the present invention may be used to identify AKT1 binding sites, be used as a molecular replacement model to solve the structure of unknown crystallized proteins, to design mutants having desirable binding properties, and ultimately, to design, characterize, and identify entities capable of interacting with AKT1 and other structurally similar proteins as well as other uses that would be recognized by one of ordinary skill in the art. Such entities may be chemical entities or proteins. The term "chemical entity," as used herein, refers to chemical compounds, complexes of at least two chemical compounds, and fragments of such compounds.

The AKT1 structure coordinates provided herein are useful for screening and identifying drugs that inhibit AKT1 and other structurally similar proteins. For example, the structure encoded by the data may be computationally evaluated for its ability to associate with putative substrates or ligands. Such compounds that associate with AKT1 may inhibit AKT1, and are potential drug candidates. Additionally or alternatively, the structure encoded by the data may be displayed in a graphical three-dimensional representation on a computer screen. This allows visual inspection of the structure, as well as visual inspection of the structure's association with the compounds.

Thus, according to another embodiment of the present invention, a method is provided for evaluating the potential of an entity to associate with AKT1 or a fragment or variant thereof by using all or a portion of the structure coordinates provided in FIG. 3 or functional equivalents thereof. A method is also provided for evaluating the potential of an entity to associate with AKT1 or a fragment or variant thereof by using structure coordinates similar to all or a portion of the structure coordinates provided in FIG. 3 or functional equivalents thereof.

The method may optionally comprise the steps of: creating a computer model of all or a portion of a protein structure (e.g., a binding pocket) using structure coordinates according to the present invention; performing a fitting operation between the entity and the computer model; and analyzing the results of the fitting operation to quantify the association between the entity and the model. The portion of the protein structure used optionally comprises all of the amino acids listed in Tables 2, 3 and 4 that are present in the structure coordinates being used.

It is noted that the computer model may not necessarily directly use the structure coordinates. Rather, a computer model can be formed that defines a surface contour that is the same or similar to the surface contour defined by the structure coordinates.

The structure coordinates provided herein can also be utilized in a method for identifying a ligand (e.g., entities capable of associating with a protein) of a protein comprising an AKT1-like binding pocket. One embodiment of the method comprises: using all or a portion of the structure coordinates provided herein to generate a three-dimensional structure of an AKT1-like binding pocket; employing the three-dimensional structure to design or select a potential ligand; synthesizing the potential ligand; and contacting the synthesized potential ligand with a protein comprising an AKT1-like binding pocket to determine the ability of the potential ligand to interact with the protein. According to this method, the structure coordinates used may have a root mean square deviation equal to or less than the RMSD values specified in Columns 3, 4 or 5 of Table 1 when compared to the structure coordinates of FIG. 3 according to the RMSD calculation method set forth herein, provided that the portion of amino acid residues specified in Column 2 of Table 1 of each set of structure coordinates are superimposed and the root mean square deviation is calculated based only on those amino acid residues in the structure coordinates that are also present in the portion of the protein specified in Column 1 of Table 1. The portion of the protein structure used optionally comprises all of the amino acids listed in Tables 2, 3, and/or 4 that are present.

As noted previously, the three-dimensional structure of an AKT1-like binding pocket need not be generated directly from structure coordinates. Rather, a computer model can be formed that defines a surface contour that is the same or similar to the surface contour defined by the structure coordinates.

A method is also provided for evaluating the ability of an entity, such as a compound or a protein to associate with an AKT1-like binding pocket, the method comprising: constructing a computer model of a binding pocket defined by structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1; selecting an entity to be evaluated by a method selected from the group consisting of (i) assembling molecular fragments into the entity, (ii) selecting an entity from a small molecule database, (iii) de novo ligand design of the entity, and (iv) modifying a known ligand for AKT1, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

The computer model of a binding pocket used in this embodiment need not be generated directly from structure coordinates. Rather, a computer model can be formed that defines a surface contour that is the same or similar to the surface contour defined by the structure coordinates.

Also according to the method, the method may further include synthesizing the entity and contacting a protein having an AKT1-like binding pocket with the synthesized entity.

With the structure provided herein, the present invention for the first time permits the use of molecular design techniques to identify, select or design potential inhibitors of AKT1, based on the structure of an AKT1-like binding pocket. Such a predictive model is valuable in light of the high costs associated with the preparation and testing of the many diverse compounds that may possibly bind to the AKT1 protein.

According to this invention, a potential AKT1 inhibitor may now be evaluated for its ability to bind an AKT1-like binding pocket prior to its actual synthesis and testing. If a proposed entity is predicted to have insufficient interaction or association with the binding pocket, preparation and testing of the entity can be obviated. However, if the computer modeling indicates a strong interaction, the entity may then be obtained and tested for its ability to bind.

A potential inhibitor of an AKT1-like binding pocket may be computationally evaluated using a series of steps in which chemical entities or fragments are screened and selected for their ability to associate with the AKT1-like binding pockets.

One skilled in the art may use one of several methods to screen entities (whether chemical or protein) for their ability to associate with an AKT1-like binding pocket. This process may begin by visual inspection of, for example, an AKT1-like binding pocket on a computer screen based on the AKT1 structure coordinates in FIG. 3 or other coordinates which define a similar shape generated from the machine-readable storage medium. Selected fragments or chemical entities may then be positioned in a variety of orientations, or docked, within that binding pocket as defined above. Docking may be accomplished using software such as Quanta and Sybyl, followed by energy minimization and molecular dynamics with standard molecular mechanics force fields, such as CHARMM and AMBER.

Specialized computer programs may also assist in the process of selecting entities. These include: GRID (P. J. Goodford, "A Computational Procedure for Determining Energetically Favorable Binding Sites on Biologically Important Macromolecules", J. Med. Chem., 28, pp. 849-857 (1985)) available from Oxford University, Oxford, UK; MCSS (A. Miranker et al., "Functionality Maps of Binding Sites: A Multiple Copy Simultaneous Search Method." Proteins: Structure, Function and Genetics, 11, pp. 29-34 (1991)) available from Molecular Simulations, San Diego, Calif.; AUTODOCK (D. S. Goodsell et al., "Automated Docking of Substrates to Proteins by Simulated Annealing", Proteins: Structure, Function, and Genetics, 8, pp. 195-202 (1990)) available from Scripps Research Institute, La Jolla, Calif.; and DOCK (I. D. Kuntz et al., "A Geometric Approach to Macromolecule-Ligand Interactions", J. Mol. Biol., 161, pp. 269-288 (1982)) available from University of California, San Francisco, Calif.

Once suitable entities have been selected, they can be designed or assembled. Assembly may be preceded by visual inspection of the relationship of the fragments to each other on the three-dimensional image displayed on a computer screen in relation to the structure coordinates of AKT1. This may then be followed by manual model building using software such as MOE, QUANTA or Sybyl [Tripos Associates, St. Louis, Mo].

Useful programs to aid one of skill in the art in connecting the individual chemical entities or fragments include: CAVEAT (P. A. Bartlett et al, "CAVEAT: A Program to Facilitate the Structure-Derived Design of Biologically Active Molecules", in "Molecular Recognition in Chemical and Biological Problems", Special Pub., Royal Chem. Soc., 78, pp. 182-196 (1989); G. Lauri and P. A. Bartlett, "CAVEAT: a Program to Facilitate the Design of Organic Molecules", J. Comput. Aided Mol. Des., 8, pp. 51-66 (1994)) available from the University of California, Berkeley, Calif.; 3D Database systems such as ISIS (MDL Information Systems, San Leandro, Calif.) reviewed in Y. C. Martin, "3D Database Searching in Drug Design", J. Med. Chem., 35, pp. 2145-2154 (1992); and HOOK (M. B. Eisen et al, "HOOK: A Program for Finding Novel Molecular Architectures that Satisfy the Chemical and Steric Requirements of a Macromolecule Binding Site", Proteins: Struct., Funct., Genet., 19, pp. 199-221 (1994)) available from Molecular Simulations, San Diego, Calif.

Instead of proceeding to build an inhibitor of an AKT1-like binding pocket in a step-wise fashion one fragment or entity at a time as described above, inhibitory or other AKT1 binding compounds may be designed as a whole or "de novo" using either an empty binding site or optionally including some portion(s) of a known inhibitor(s). There are many de novo ligand design methods including: LUDI (H.-J. Bohm, "The Computer Program LUDI: A New Method for the De Novo Design of Enzyme Inhibitors", J. Comp. Aid. Molec. Design, 6, pp. 61-78 (1992)) available from Molecular Simulations Incorporated, San Diego, Calif.; LEGEND (Y. Nishibata et al., Tetrahedron, 47, p. 8985 (1991)) available from Molecular Simulations Incorporated, San Diego, Calif.; LEAPFROG available from Tripos Associates, St. Louis, Mo.; and SPROUT (V. Gillet et al., "SPROUT: A Program for Structure Generation)", J. Comput. Aided Mol. Design, 7, pp. 127-153 (1993)) available from the University of Leeds, UK.

Other molecular modeling techniques may also be employed in accordance with this invention (see, e.g., Cohen et al., "Molecular Modeling Software and Methods for Medicinal Chemistry, J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modern Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994)).

Once an entity has been designed or selected, for example, by the above methods, the efficiency with which that entity may bind to an AKT1 binding pocket may be tested and optimized by computational evaluation. For example, an effective AKT1 binding pocket inhibitor preferably demonstrates a relatively small difference in energy between its bound and free states (i.e., a small deformation energy of binding). Thus, the most efficient AKT1 binding pocket inhibitors should preferably be designed with deformation energy of binding of not greater than about 10 kcal/mole, and more preferably, not greater than 7 kcal/mole. AKT1 binding pocket inhibitors may interact with the binding pocket in more than one of multiple conformations that are similar in overall binding energy. In those cases, the deformation energy of binding is taken to be the difference between the energy of the free entity and the average energy of the conformations observed when the inhibitor binds to the protein.

An entity designed or selected as binding to an AKT1 binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. COPYRGT.1995); AMBER, version 4.1 (P. A. Kollman, University of California at San Francisco, COPYRGT 1995); QUANTA/CHARMM (Molecular Simulations, Inc., San Diego, Calif. COPYRGT. 1995); Insight II/Discover (Molecular Simulations, Inc., San Diego, Calif. COPYRGT.1995); DelPhi (Molecular Simulations, Inc., San Diego, Calif. COPYRGT.1995); and AMSOL (Quantum Chemistry Program Exchange, Indiana University). These programs may be implemented, for instance, using a Silicon Graphics workstation such as an Indigo$^2$ with "IMPACT" graphics. Other hardware systems and software packages will be known to those skilled in the art.

Another approach provided by this invention, is the computational screening of small molecule databases for chemical entities or compounds that can bind in whole, or in part, to an AKT1 binding pocket. In this screening, the quality of fit of such entities to the binding site may be judged either by shape complementarities or by estimated interaction energy [E. C. Meng et al., J. Comp. Chem., 13, 505-524 (1992)].

According to another embodiment, the invention provides compounds that associate with an AKT1-like binding pocket produced or identified by various methods set forth above.

The structure coordinates set forth in FIG. 3 can also be used to aid in obtaining structural information about another crystallized molecule or molecular complex. This may be achieved by any of a number of well-known techniques, including molecular replacement.

For example, a method is also provided for utilizing molecular replacement to obtain structural information about a protein whose structure is unknown comprising the steps of: generating an X-ray diffraction pattern of a crystal of the protein whose structure is unknown; generating a three-dimensional electron density map of the protein whose structure is unknown from the X-ray diffraction pattern by using at least a portion of the structure coordinates set forth in FIG. 3 as a molecular replacement model.

By using molecular replacement, all or part of the structure coordinates of the AKT1 provided by this invention (and set forth in FIG. 3) can be used to determine the structure of another crystallized molecule or molecular complex more quickly and efficiently than attempting an ab initio structure determination. One particular use includes use with other structurally similar proteins. Molecular replacement provides an accurate estimation of the phases for an unknown structure. Phases are a factor in equations used to solve crystal structures that cannot be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of AKT1 according to FIG. 3 within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex [E. Lattman, "Use of the Rotation and Translation Functions", in Meth. Enzymol., 115, pp. 55-77 (1985); M. G. Rossmann, ed., "The Molecular Replacement Method", Int. Sci. Rev. Ser., No. 13, Gordon & Breach, New York (1972)].

The structure of any portion of any crystallized molecule or molecular complex that is sufficiently homologous to any portion of AKT1 can be resolved by this method.

In one embodiment, the method of molecular replacement is utilized to obtain structural information about the present invention and any other AKT1-like molecule. The structure coordinates of AKT1, as provided by this invention, are particularly useful in solving the structure of other isoforms of AKT1 or AKT1 complexes.

The structure coordinates of AKT1 as provided by this invention are useful in solving the structure of AKT1 variants that have amino acid substitutions, additions and/or deletions (referred to collectively as "AKT1 mutants", as compared to naturally occurring AKT1). These AKT1 mutants may optionally be crystallized in co-complex with a ligand, such as an inhibitor, substrate analogue or a suicide substrate. The crystal structures of a series of such complexes may then be solved by molecular replacement and compared with that of AKT1. Potential sites for modification within the various binding sites of the enzyme may thus be identified. This information provides an additional tool for determining the most efficient binding interactions such as, for example, increased hydrophobic interactions, between AKT1 and a ligand. It is noted that the ligand may be the protein's natural ligand or may be a potential agonist or antagonist of a protein.

All of the complexes referred to above may be studied using well-known X-ray diffraction techniques and may be refined versus 1.5-3 Å resolution X-ray data to an R value of about 0.22 or less using computer software, such as X-PLOR [Yale University, COPYRIGHT.1992, distributed by Molecular Simulations, Inc.; see, e.g., Blundell & Johnson, supra; Meth. Enzymol., Vol. 114 & 115, H. W. Wyckoff et al., eds., Academic Press (1985)]. This information may thus be used to optimize known AKT1 inhibitors, and more importantly, to design new AKT1 inhibitors.

The structure coordinates described above may also be used to derive the dihedral angles, phi and psi, that define the conformation of the amino acids in the protein backbone. As will be understood by those skilled in the art, the $phi_n$ angle refers to the rotation around the bond between the alpha-carbon and the nitrogen, and the $Psi_n$ angle refers to the rotation around the bond between the carbonyl carbon and the alpha-carbon. The subscript "n" identifies the amino acid whose conformation is being described [for a general reference, see Blundell and Johnson, Protein Crystallography, Academic Press, London, 1976].

9. Uses of the Crystal and Diffraction Pattern of AKT1

Crystals, crystallization conditions and the diffraction pattern of AKT1 that can be generated from the crystals also have a range of uses. One particular use relates to screening entities that are not known ligands of AKT1 for their ability to bind to AKT1. For example, with the availability of crystallization conditions, crystals and diffraction patterns of AKT1 provided according to the present invention, it is possible to take a crystal of AKT1; expose the crystal to one or more entities that may be a ligand of AKT1; and determine whether a ligand/AKT1 complex is formed. The crystals of AKT1 may be exposed to potential ligands by various methods, including but not limited to, soaking a crystal in a solution of one or more potential ligands or co-crystallizing AKT1 in the presence of one or more potential ligands. Given the structure coordinates provided herein, once a ligand complex is formed, the structure coordinates can be used as a model in molecular replacement in order to determine the structure of the ligand complex.

Once one or more ligands are identified, structural information from the ligand/AKT1 complex(es) may be used to design new ligands that bind tighter, bind more specifically, have better biological activity or have better safety profiles than known ligands.

In one embodiment, a method is provided for identifying a ligand that binds to AKT1 comprising: (a) attempting to crystallize a protein that comprises a sequence wherein at least a portion of the sequence has 55%, 65%, 75%, 85%, 90%, 95%, 97%, 99% or greater identity with residues 138-480 of SEQ. ID No. 1 in the presence of one or more entities; (b) if crystals of the protein are obtained in step (a), obtaining an X-ray diffraction pattern of the protein crystal; and (c) determining whether a ligand/protein complex was formed by comparing an X-ray diffraction pattern of a crystal of the protein formed in the absence of the one or more entities to the crystal formed in the presence of the one or more entities.

In another embodiment, a method is provided for identifying a ligand that binds to AKT1 comprising: (a) attempting to crystallize a protein that comprises a sequence wherein at least a portion of the sequence has 55%, 65%, 75%, 85%, 90%, 95%, 97%, 99% or greater identity with SEQ. ID No. 3 in the presence of one or more entities; (b) if crystals of the protein are obtained in step (a), obtaining an X-ray diffraction pattern of the protein crystal; and (c) determining whether a ligand/protein complex was formed by comparing an X-ray diffraction pattern of a crystal of the protein formed in the absence of the one or more entities to the crystal formed in the presence of the one or more entities.

In yet another embodiment, a method is provided for identifying a ligand that binds to AKT1 comprising: (a) attempting to crystallize a protein that comprises a sequence wherein at least a portion of the sequence has 55%, 65%, 75%, 85%, 90%, 95%, 97%, 99% or greater identity with SEQ. ID No. 5 in the presence of one or more entities; (b) if crystals of the protein are obtained in step (a), obtaining an X-ray diffraction pattern of the protein crystal; and (c) determining whether a ligand/protein complex was formed by comparing an X-ray diffraction pattern of a crystal of the protein formed in the absence of the one or more entities to the crystal formed in the presence of the one or more entities.

In one embodiment, a method is provided for identifying a ligand that binds to AKT1 comprising: soaking a crystal of a protein wherein at least a portion of the protein has 55%, 65%, 75%, 85%, 90%, 95%, 97%, 99% or greater identity with residues 138-380 of SEQ. ID No. 1 with one or more entities; determining whether a ligand/protein complex was formed by comparing an X-ray diffraction pattern of a crystal of the protein that has not been soaked with the one or more entities to the crystal that has been soaked with the one or more entities. Optionally, the method may further comprise converting the diffraction patterns into electron density maps using phases of the protein crystal and comparing the electron density maps.

In another embodiment, a method is provided for identifying a ligand that binds to AKT1 comprising: soaking a crystal of a protein wherein at least a portion of the protein has 55%, 65%, 75%, 85%, 90%, 95%, 97%, 99% or greater identity with SEQ. ID No. 3 with one or more entities; determining whether a ligand/protein complex was formed by comparing an X-ray diffraction pattern of a crystal of the protein that has not been soaked with the one or more entities to the crystal that has been soaked with the one or more entities. Optionally, the method may further comprise converting the diffraction patterns into electron density maps using phases of the protein crystal and comparing the electron density maps.

In yet another embodiment, a method is provided for identifying a ligand that binds to AKT1 comprising: soaking a crystal of a protein wherein at least a portion of the protein has 55%, 65%, 75%, 85%, 90%, 95%, 97%, 99% or greater identity with SEQ. ID No. 5 with one or more entities; determining whether a ligand/protein complex was formed by comparing an X-ray diffraction pattern of a crystal of the protein that has not been soaked with the one or more entities to the crystal that has been soaked with the one or more entities. Optionally, the method may further comprise converting the diffraction patterns into electron density maps using phases of the protein crystal and comparing the electron density maps.

Libraries of "shape-diverse" compounds may optionally be used to allow direct identification of the ligand-receptor complex even when the ligand is exposed as part of a mixture. According to this variation, the need for time-consuming de-convolution of a hit from the mixture is avoided. More specifically, the calculated electron density function reveals the binding event, identifies the bound compound and provides a detailed 3-D structure of the ligand-receptor complex. Once a hit is found, one may optionally also screen a number of analogs or derivatives of the hit for tighter binding or better biological activity by traditional screening methods. The hit and information about the structure of the target may also be used to develop analogs or derivatives with tighter binding or better biological activity. It is noted that the ligand-AKT1 complex may optionally be exposed to additional iterations of potential ligands so that two or more hits can be linked together to make a more potent ligand. Screening for potential ligands by co-crystallization and/or soaking is further described in U.S. Pat. No. 6,297,021, which is incorporated herein by reference.

EXAMPLES

Example 1

Expression and Purification of AKT1

This example describes cloning, expression and purification of AKT1. It should be noted that a variety of other expression systems and hosts are also suitable for the expression of AKT1, as would be readily appreciated by one of skill in the art.

The portion of the gene encoding residues 138-480 of SEQ ID NO:1 (SEQ ID NO:2), which corresponds to the catalytic domain of human AKT1, was cloned into a modified pFastBacHTb vector (also known as pSXB1). In order to facilitate protein expression several site-directed mutations were introduced into the catalytic domain of human AKT1 including Met446 to Ser (M446S), and the replacement of a loop containing Glu 267-Lys 268-Asn 269 with two residues Arg267 and Asp268. In addition this construct contained a phosphomimetic Aspartic acid mutation of a hydrophobic motif serine residue (S473D). Expression from this vector produced the recombinant AKT1 catalytic domain with a 6x-histidine tag at the N-terminus followed by a rTEV protease cleavage sequence to facilitate tag removal (the excised 6x-Histidine tag and rTev cleavage site sequences are underlined in SEQ ID NO:3). Recombinant baculovirus genomic DNAs incorporating the AKT1 catalytic domain cDNA sequences were generated by transposition using the BAC-TO-BAC® Baculovirus Expression system (Invitrogen). Infectious viral particles were obtained by transfection of a 2 ml adherent culture of Spodoptera frugiperda Sf9 insect cells with the recombinant viral genomic DNA. Growth in ESF 921 protein free medium (Expression Systems) was for 3 days at 27° C. The resulting Passage 0 viral supernatant was used to obtain Passage 1 high titer viral stock (HTS) by infection of a 30 ml adherent culture of Spodoptera frugiperda Sf9 insect cells grown under similar conditions. Passage 1 HTS was used in turn to infect a 100 ml suspension culture of Spodoptera frugiperda Sf9 insect cells in order to generate Passage 2 HTS.

Passage 2 HTS was used to infect a 5-liter culture of Spodoptera frugiperda Sf9 insect cells (at a density of approx. $3\times10^6$ cells/ml) in a 10 liter Wave BioReactor grown in ESF-921 serum-free medium at a multiplicity of infection (moi) of approximately 5 (empirical value based on usual HTS viral counts). Cell growth/infection proceeded for two days after which time the cells were pelleted by centrifugation and the cell pellet stored at −80° C. until required. Frozen cell pellets from two such 5-liter cultures were removed from the −80° C. freezer and each suspended in 150 ml of Lysis Buffer (50 mM Tris-HCl, pH 7.9, 200 mM NaCl, 0.25 mM TCEP, 1 mM PMSF and 2 'Complete-EDTA' Roche Protease Inhibitor tablets). The suspensions were stirred for 45 min at 4° C. followed by centrifugation at 7,000 g for 1 h. To each supernatant was added 8 ml of a 50% slurry of PROBOND® (InVitrogen) nickel-chelating) resin that had been equilibrated in Lysis Buffer without protease inhibitors. The suspensions were mixed for 90 min followed by centrifugation at 640 g for 5 min. The supernatants were discarded and the resin pellets washed three times with 50 mM potassium phosphate, pH 7.9, 400 mM NaCl, 0.25 mM TCEP and 1 µg/ml leupeptin. Each resin sample was transferred to an OMN1 chromatography column (10 cm×1.5 cm diameter) at 4° C. and washed with 50 column volumes of 50 mM potassium phosphate, pH 7.9, 400 mM NaCl, 20 mM imidazole-HCl, pH 7.9, 0.25 mM TCEP and 1 µg/mL, leupeptin. The columns were subsequently washed with 5 column volumes of 50 mM Tris-HCl, pH 7.9, 400 mM NaCl, 0.25 mM TCEP and 1 µg/mL leupeptin. Target elution was effected by the addition of 50 mM Tris-HCl, pH 7.9, 400 mM NaCl, 200 mM imidazole-HCl, pH 7.9, 0.25 mM TCEP, 1 µg/mL leupeptin. The eluates were pooled and the polyhistidine purification tag removed by cleavage overnight with 100 µg/mL TEV protease during dialysis against 50 mM Tris-HCl, pH 7.9, 400 mM NaCl, 20 mM imidazole-HCl, pH 7.9, 0.25 mM TCEP and 1 µg/mL leupeptin at 4° C. The TEV-treated sample was passed by gravity flow through an 8 ml bed volume of ProBond chelating resin charged with Ni that had been equilibrated in 50 mM Tris-HCl, pH 7.9, 400 mM NaCl, 20 mM imidazole-HCl, pH 7.9, 0.25 mM TCEP and 1 µg mL leupeptin at 4° C. The unbound flow-through material was concentrated using VIVASPIN® centrifugal concentrators (ultrafiltration spin columns) (Sartorius AG). The purified protein was a mixture of unphosphorylated and monophosphorylated (~39933 (+0P) and 40013 (+1P)) species as determined by Mass Spectrograph (MS) analysis and had the correct molecular mass (~39,000) as determined by Mass Spectrograph (MS) analysis. This mixture of phosphorylated forms of AKT1 was then specifically phosphorylated on Thr-308 by treatment with a 1/50 molar ratio of PDK1 kinase in the presence of 5 mM ATP and 10 mM $MgCl_2$. Following 120 minute incubation with PDK1, AKT1 was converted into a mixture of mono and double phosphorylated proteins and the phosphorylation reaction was stopped by addition of 40 mM EDTA. The protein was dialyzed overnight against 50 mM Tris-HCl buffer, pH 7.6, 200 mM NaCl, 0.25 M TCEP. Following overnight dialysis, AKT1 was concentrated to approximately 10 mg/ml and diluted 4-fold in 50 mM Tris-HCl buffer, pH 7.6, 0.25 M TCEP to reduce the salt concentration prior to loading on an anion exchange column. The diluted sample was applied to a PROS-HQ™ anion exchange column (Applied Biosystems) and eluted with 0-500 mM NaCl gradient over 48 fractions. Fractions containing double phosphorylated protein were pooled and diluted 10-fold with 25 mM Tris-HCl buffer, pH 7.6. 250 mM NaCl, 5 mM DTT and 0.1 mM EDTA. Following two ten-fold dilution buffer-exchanges, the purified AKT1 was concentrated to 17.9 mg/ml with a total volume of 0.120 ml (2.2 mg purified AKT1). The purified protein had the correct molecular mass (~40096+2P) as determined by Mass Spectrograph (MS) analysis, was monomeric by analytical size-exclusion chromatography (SEC) and exhibited a major band by sodium-dodecyl-sulfate polyacrylamide gel electrophoresis (SDS-PAGE) analyses.

The cDNA sequence encoding residues 29 to 350 of SEQ. ID No. 5 (SEQ. ID No. 4), which corresponds to the catalytic domain of engineered AKT1, was expressed, and the resultant protein purified, in an analogous manner to that described above for the protein produced from SEQ. ID No. 2.

Example 2

Crystallization of AKT1

This example describes the crystallization of AKT1. It is noted that the precise crystallization conditions used may be further varied, for example by performing a fine screen based on these crystallization conditions.

AKT1 protein samples (corresponding to SEQ ID NO:3) that had been treated with PDK1 kinase to phosphorylate the activation loop residue Thr 308, were incubated with 0.6 mM GSK3β substrate peptide (SEQ ID NO:6), 3 mM of the non-hydrolysable ATP analog AMPPNP and 6 mM MnCl$_2$ before setting crystallization trials. Crystals were obtained after an extensive and broad screen of conditions, followed by optimization. Diffraction quality crystals were grown in 100 nl sitting droplets using the vapor diffusion method. 50 nl comprising the AKT1-peptide-AMPPNP complex (18 mg/ml) was mixed with 50 nL from a reservoir solution (100 µl) comprising: 13% PEG 3350; 0.2M ammonium sulfate; and 0.1M HEPES buffer pH=7.5. The resulting solution was incubated over a period of two weeks at 4° C. Crystals typically appeared after 3-5 days and grew to a maximum size within 7-10 days. Single crystals were transferred, briefly, into a cryoprotecting solution containing the reservoir solution supplemented with 25% v/v ethylene glycol. Crystals were then flash frozen by immersion in liquid nitrogen and then stored under liquid nitrogen. Crystals of the AKT1 complex produced as described are illustrated in FIG. 2A.

For AKT1 protein samples comprising SEQ.ID NO:5 that had been similarly treated with PDK1 kinase and incubated with 0.6 mM GSK3β substrate peptide (SEQ ID NO:6), 3 mM AMPPNP and 6 mM MnCl$_2$ diffraction quality crystals were grown in 100 nl sitting droplets using the vapor diffusion method. 50 nl comprising the AKT1-peptide-AMPPNP complex (13 mg/ml)) was mixed with 50 nL from a reservoir solution (100 µl) comprising: 19% PEG 3350; 0.2M potassium chloride; and 0.1M HEPES buffer pH=7.5. The resulting solution was incubated over a period of two weeks at 4° C. and single crystals transferred to a cryoprotecting solution containing the reservoir solution supplemented with 25% v/v ethylene glycol prior to flash freezing in liquid nitrogen. Crystals of the AKT1 complex produced as described are illustrated in FIG. 2B.

While the present invention is disclosed with reference to certain embodiments and examples detailed above, it is to be understood that these embodiments and examples are intended to be illustrative rather than limiting, as it is contemplated that modifications will readily occur to skilled in the art, which modifications are intended to be within the scope of the invention and the appended claims. All patents, patent applications, papers, and books cited in this application are incorporated herein in their entirety.

We claim:

1. An isolated non-crystalline protein consisting of SEQ ID NO:3.

2. A non-crystalline protein consisting of SEQ ID NO:3.

3. A non-crystalline mutant protein consisting of residues 138-480 of SEQ ID NO: 1, wherein said mutant protein contains the mutation of M446S and S473D, and the substitution of residues E267-K268 N269 with K267-D268.

4. An isolated non-crystalline mutant protein consisting of residues 138-480 of SEQ ID NO: 1, wherein said mutant protein contains the mutation of M446S and S473D, and the substitution of residues E267-K268-N269 with K267-D268.

* * * * *